US012378276B2

(12) United States Patent
Shi et al.

(10) Patent No.: US 12,378,276 B2
(45) Date of Patent: Aug. 5, 2025

(54) CONVERGENT LIQUID PHASE SYNTHESES OF OLIGONUCLEOTIDES

(71) Applicants: BIOGEN MA INC., Cambridge, MA (US); AJINOMOTO CO., INC., Tokyo (JP)

(72) Inventors: Xianglin Shi, Cambridge, MA (US); William F. Kiesman, Cambridge, MA (US); Firoz Antia, Cambridge, MA (US); Yannick Fillon, Cambridge, MA (US); Xuan Zhou, Cambridge, MA (US); Wuming Yan, Cambridge, MA (US); Hong Jiang, Cambridge, MA (US); Hien Nguyen, Cambridge, MA (US); Robert S. Gronke, Cambridge, MA (US); Taisuke Ichimaru, Kawasaki (JP); Takuya Hamagaki, Kawasaki (JP); Daisuke Takahashi, Kawasaki (JP)

(73) Assignees: BIOGEN MA INC., Cambridge, MA (US); AJINOMOTO CO., INC, Tokyo (JP)

(*) Notice: Subject to any disclaimer, the term of this patent is extended or adjusted under 35 U.S.C. 154(b) by 866 days.

(21) Appl. No.: 17/608,802

(22) PCT Filed: May 8, 2020

(86) PCT No.: PCT/US2020/032070
§ 371 (c)(1),
(2) Date: Nov. 4, 2021

(87) PCT Pub. No.: WO2020/227618
PCT Pub. Date: Nov. 12, 2020

(65) Prior Publication Data
US 2022/0348602 A1    Nov. 3, 2022

Related U.S. Application Data

(60) Provisional application No. 62/845,160, filed on May 8, 2019.

(51) Int. Cl.
C07H 1/02    (2006.01)
C07H 21/02    (2006.01)

(52) U.S. Cl.
CPC .............. C07H 1/02 (2013.01); C07H 21/02 (2013.01)

(58) Field of Classification Search
None
See application file for complete search history.

(56) References Cited

U.S. PATENT DOCUMENTS 5,510,476 A    4/1996    Ravikumar et al.
8,980,853 B2    3/2015    Bennett et al.

2012/0184724 A1*    7/2012    Sierzchala ............ C07B 59/005
536/25.31
2013/0267697 A1    10/2013    Hirai et al.
2018/0291056 A1    10/2018    Yamashita et al.

FOREIGN PATENT DOCUMENTS

| AU | 1357300 A | 3/2000 |
| AU | 738032 B2 | 9/2001 |
| CN | 104114569 A | 10/2014 |
| EP | 0558749 A1 | 9/1993 |
| EP | 2711370 A1 | 3/2014 |
| EP | 2857412 A1 | 4/2015 |
| EP | 3263579 A1 | 1/2018 |
| EP | 3398955 A1 | 11/2018 |
| EP | 3398965 A1 | 11/2018 |
| JP | 5548852 B2 | 12/2010 |
| JP | 5705512 B2 | 4/2015 |
| RU | 2572826 C2 | 1/2016 |
| WO | 1992/08729 A1 | 5/1992 |
| WO | 2007/002390 A2 | 1/2007 |
| WO | 2010/064146 A2 | 6/2010 |
| WO | 2010/148249 A1 | 12/2010 |
| WO | 2015/153800 A2 | 10/2015 |
| WO | 2018/203574 A1 | 11/2018 |

OTHER PUBLICATIONS

Hayakawa, Tetrahedron 57 (2001) 8823-8826. (Year: 2001).*
Bonora et al., A Liquid-Phase Process Suitable for Large-Scale Synthesis of Phosphorothioate Oligonucleotides. Org Proc Res Dev. 2000;4(3):225-231.
Chen et al., Convergent Solution Phase Synthesis of Chimeric Oligonucleotides by a 2+2 and 3+3 Phosphoramidite Strategy. Australian Journal of Chemistry. Feb. 26, 2010;63(2):227-235.
Herdering et al., Phosphoramidites of Chiral (Rp) and (Sp)-Configurated d(T[P-180]-A): Synthesis, Configurational Assignment, and Use as Dimer Blocks in Oligonucleotide Synthesis. Helvetica Chimica Acta. Dec. 18, 1985;68(8):2119-2127.
Wamoto et al., Control of phosphorothioate stereochemistry substantially increases the efficacy of antisense bligonucleotides. Nat Biotechnol. Sep. 2017;35(9):845-851.
Kim et al., Liquid-phase RNA synthesis by using alkyl-chain-soluble support. Chem Euro J. Jun. 24, 2013;19(26):8615-20.
Knouse et al., Unlocking P(V): Reagents for chiral phosphorothioate synthesis. Science. Sep. 21, 2018;361(6408):1234-1238.
Mcmurray et al., The synthesis of phosphopeptides. Biopolymers. 2001;60(1):3-31.
Wilk et al., The 4-[n-methyl-n-(2,2,2,-trifluoroacetyl)amino]butyl Group as an Alternative to the 2-Cyanoethyl Group for Phosphate Protection in the Synthesis of Olugodeoxyribonucleotides. J Org Chem. 1999;64(20):7515-7522.

(Continued)

*Primary Examiner* — Layla D Berry
(74) *Attorney, Agent, or Firm* — McCarter & English, LLP; Xin Zhang

(57) ABSTRACT

The present disclosure describes a convergent liquid phase process for manufacturing oligonucleotides by coupling two or more oligonucleotide fragments, each of which have two or more nucleotides. Also provided by the present disclosure are reaction steps involved the convergent liquid phase process.

17 Claims, 43 Drawing Sheets
Specification includes a Sequence Listing.

(56) References Cited

OTHER PUBLICATIONS

International Search Report and Written Opinion for Application No. PCT/US2020/032070, dated Dec. 11, 2020, 19 pages.
De Bernardini et al., 58. Nucleosides and Nucleotides. Part 21. Synthesis of a Tridecanucleoside Dodecaphosphate Incorporating the Unnatural Base 2(1H)-Pyridone1). Helvetica Chimica Acta. 1983;66:639-651.
Kierzek et al., Selective N-Deacylation of N,O-Protected Nucleosides by Zinc Bromide. Tetrahedron Letters. 1981;22(33):3761-4.
Title: "Selective N-Deacylation of N,O-Protected Nucleosides by Zinc Bromide" Publication: Tetrahedron Letters, vol. 22, No. 38, pp. 3761-3764, 1981 Author: R. Kierzek et al. Date: 1981 Language: English.
EP Third Party Observation EP Patent Application No. 20729413.3 (EP Counterpart to the '802 application) Country or Patent Office: EP Date: Sep. 14, 2022 Language: English.
Sato, Kakusaniyaku gosei kisokoza dai 1 kai origonukureotido gosei. Basic lecture about synthesis of nucleic acid drugs, 1st lecture, synthesis of oligonucleotides. Wako Junyaku Jiho. 2018;86(1):14-15.
Sato, Kakusaniyaku gosei kisokoza dai 2 kai origonukureotido gosei niokeru hogo-datsuhogo. Basic lecture about synthesis of nucleic acid drugs, 2nd lecture, protection-deprotection in synthesis of oligonucleotides. Wako Junyaku Jiho. 2018;86(2):22-23.
Sato, Kakusaniyaku gosei kisokoza dai 3 kai origonukureotido gosei niokeru kappuringu hanno. Basic lecture about synthesis of nucleic acid drugs, 3rd lecture, coupling reaction in synthesis of oligonucleotides. Wako Junyaku Jiho. 2018;86(3):18-19.
Sato, Kakusaniyaku gosei kisokoza dai 4 kai origonukureotido gosei niokeru kyappingu oyobi sanka-ryuka hanno. Basic lecture about synthesis of nucleic acid drugs, 4th lecture, capping and oxidation-sulfuration reaction in synthesis of oligonucleotides. Wako Junyaku Jiho. 2018:86(4):12-13.
Wang et al., Protection Groups in RNA Synthesis. Youji Huaxue. 1994;14:242-258.
Yu et al., Synthesis of 5-alkynyl-2'-deoxyuridines and their incorporation into oligonucleotides. Chinese Journal of Medicinal Chemistry. Oct. 3, 2002;12(4):254-257.
Japanese Third Party Observation for Application No. 2021-565931, dated May 9, 2024, 13 pages.

\* cited by examiner

SEQUENCE LISTING

<160> NUMBER OF SEQ ID NOS: 17

<210> SEQ ID NO 1
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 1
tcactttcat aatgctgg                                                    18

<210> SEQ ID NO 2
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 2
caggatacat ttctacagct                                                  20

<210> SEQ ID NO 3
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 3
cgactatacg cgcaatatgg                                                  20

<210> SEQ ID NO 4
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 4
cgacuatacg cgcaauaugg                                                  20

<210> SEQ ID NO 5
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 5
cgactatacg cgcaatatgg                                                  20

<210> SEQ ID NO 6
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 6
cgacuatacg cgcaauaugg                                        20

<210> SEQ ID NO 7
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 7
cgacuatacg cgcaauaugg                                        20

<210> SEQ ID NO 8
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 8
guuuucatca atatcugcaa                                        20

<210> SEQ ID NO 9
<211> LENGTH: 18
<212> TYPE: DNA
<213> ORGANISM: Artificial Sequence
<220> FEATURE:
<221> NAME/KEY: source
<223> OTHER INFORMATION: /note="Description of Artificial Sequence: Synthetic oligonucleotide"
<220> FEATURE:
<221> NAME/KEY: source
<223> OTHER INFORMATION: /note="Description of Combined DNA/RNA Molecule: Synthetic oligonucleotide"

<400> SEQUENCE: 9
ccguuttctt accacccu                                          18

<210> SEQ ID NO 10
<211> LENGTH: 10
<212> TYPE: DNA
<213> ORGANISM: Artificial Sequence
<220> FEATURE:

```
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 10
guuuuttgtt                                                          10

<210> SEQ ID NO 11
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 11
acagatattt ttgtt                                                    15

<210> SEQ ID NO 12
<211> LENGTH: 10
<212> TYPE: RNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 12
guuuuugcaa                                                          10

<210> SEQ ID NO 13
<211> LENGTH: 10
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 13
ttaccacccu                                                          10

<210> SEQ ID NO 14
<211> LENGTH: 14
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 14
uttcttacca cccu                                                     14

<210> SEQ ID NO 15
<211> LENGTH: 10
```

```
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"

<400> SEQUENCE: 15
acagatattt                                                          10

<210> SEQ ID NO 16
<211> LENGTH: 11
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 16
aatatcugca a                                                        11

<210> SEQ ID NO 17
<211> LENGTH: 15
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic oligonucleotide"
<220> FEATURE:
<221> NAME/KEY: source
<223> OTHER INFORMATION: /note="Description of Combined DNA/RNA
      Molecule: Synthetic oligonucleotide"

<400> SEQUENCE: 17
catcaatatc ugcaa                                                    15
```

CONVERGENT LIQUID PHASE SYNTHESES OF OLIGONUCLEOTIDES

RELATED APPLICATIONS

This application is a 35 U.S.C. § 371 national stage filing of International Application No. PCT/US2020/032070, filed on May 8, 2020, which claims the benefit of the filing date, under 35 U.S.C. § 119(e), of U.S. Provisional Application No. 62/845,160, filed on May 8, 2019. The entire contents of which each of the aforementioned applications are incorporated herein by reference.

SEQUENCE LISTING

The instant application contains a Sequence Listing which has been submitted electronically in ASCII format and is hereby incorporated by reference in its entirety. Said ASCII copy, created on Jul. 16, 2020, is named 123429-05220_SL.txt and is 5,911 bytes in size.

BACKGROUND

Oligonucleotides are short DNA or RNA oligomers that can be chemically synthesized for a wide range of applications. Recent developments in utilizing synthetic oligonucleotides as therapeutic agents have increased demand for synthetic methods that can produce oligonucleotides in large quantities with high efficiency and purity.

Traditionally, oligonucleotides are synthesized by a solid phase automated synthesizer utilizing phosphoramidite chemistry, limited to a scale of less than 2 moles. Thus, the solid phase synthesis is insufficient for the production of materials needed for clinical development and commercialization of oligonucleotide drugs in large indications. In addition, the solid phase synthesis often requires the use of excess reagents and consequently increases the cost associated with the production of the target oligonucleotides.

Hence, there is a need for a robust method for synthesizing oligonucleotides that is suitable for large scale manufacturing process with high efficiency and purity.

SUMMARY OF THE INVENTION

The present disclosure describes a convergent liquid phase process for manufacturing oligonucleotides by coupling two or more (e.g., three, four, five, six, etc.) oligonucleotide fragments, each of which have two or more (e.g., three, four, five, six, etc.) nucleotides. It is surprisingly found that the convergent liquid phase process of the present disclosure can be used to synthesize protected oligonucleotides with high purity without the need of purification by chromatography (e.g., column chromatography), which renders the process suitable for use as a large-scale manufacturing process. After deprotection and standard downstream purification, high purity ASO oligonucleotides suitable for therapeutic uses can be obtained. Also provided by the present disclosure are reaction steps involved the convergent liquid phase process.

DETAILED DESCRIPTION

Figure 1:
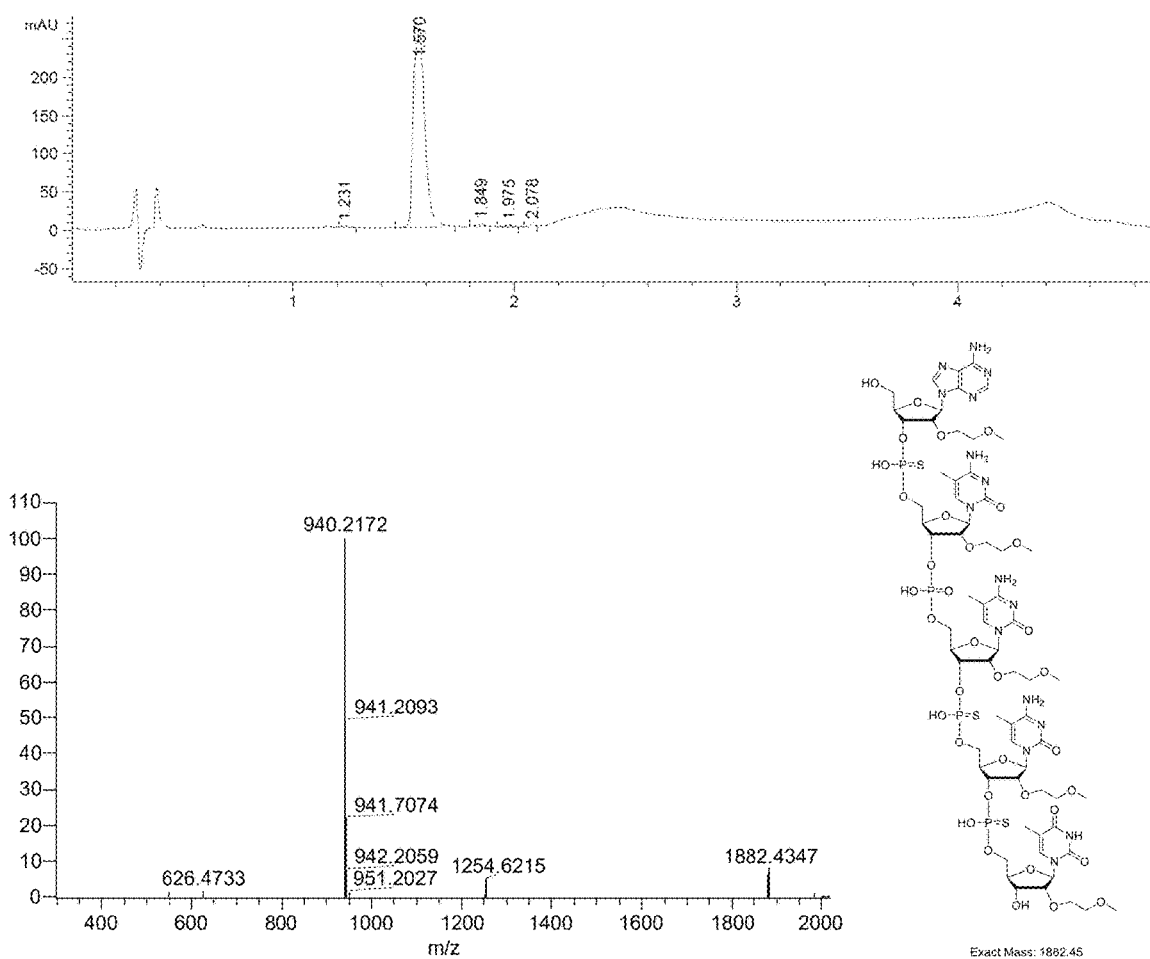
FIG. 1 shows reverse phase HPLC and MS of compound 1-7-a obtained after ammonolysis of product compound 1-7.

The inventors of the present disclosure for the first time developed a convergent liquid phase process for preparing target oligonucleotides. Surprisingly, the convergent liquid phase process can produce protected target oligonucleotides on a large-scale with high purity without the need for chromatographic purification from the assembly of oligonucleotide fragments. The convergent liquid phase process can produce target oligonucleotides by elongation in the direction from the 3'-terminal to the 5'-terminal (i.e., 3'-5' elongation) or from the 5'-terminal to the 3'-terminal (i.e., 5'-3' elongation). The present disclosure also provides methods of selective deprotection of 3'-hydroxyl protecting group that do not affect other sensitive groups to minimize the generation of side products. The inventors of the present disclosure discovered that the presence of water in the detritylation reaction can lead to deamination side reactions (e.g., deamination of cytosine or 5-methylcytosine or their derivatives commonly used in oligonucleotide synthesis). To reduce or prevent the formation of the deamination side product(s), the reaction conditions to control and minimize water level have been developed to minimize deamination during the detritylation step. In addition, it was also discovered that the use of a cation scavenger (e.g., RSH) in the detritylation reaction facilitates the completion of the detritylation reaction (i.e., the reaction goes into completion more readily). The presence of the cation scavenger also makes the reaction less prone to reverse detritylation (i.e., the DMT protection group being added back on the deprotected 5'-OH group). It has also been demonstrated that phosphitylation of the 3'-hydroxyl group can be carried out in liquid phase without purification by chromatography. Oligonucleotide fragments with four or five nucleotides have been successfully synthesized and coupled to fully protected target oligonucleotides in liquid phase using the methods of the present disclosure. Generally, the liquid phase processes described in the present disclosure can be used to synthesize large quantities of the desired protected nucleotide or oligonucleotide products without chromatographic purification. After deprotection and standard downstream purification, high purity ASO oligonucleotides suitable for therapeutic uses are obtained.

Definitions

The term "nucleobase" means the heterocyclic base portion of a nucleoside. Nucleobases may be naturally occurring or may be modified. In certain embodiments, a nucleobase may comprise any atom or group of atoms capable of hydrogen bonding to a nucleobase of another nucleic acid. In particular, the nucleobase is a heterocyclic base, typically purines and pyrimidines. In addition to "unmodified" or "natural" nucleobases such as the purine nucleobases adenine (A) and guanine (G), and the pyrimidine nucleobases thymine (T), cytosine (C) and uracil (U), many modified nucleobases or nucleobase mimetics known to those skilled in the art are amenable to incorporation into the compounds synthesized by the method described herein. In certain embodiments, a modified nucleobase is a nucleobase that is fairly similar in structure to the parent nucleobase, such as for example a 7-deaza purine, a 5-methyl cytosine, or a G-clamp. In certain embodiments, nucleobase mimetic include more complicated structures, such as for example a tricyclic phenoxazine nucleobase mimetic. Methods for preparation of the above noted modified nucleobases are well known to those skilled in the art.

The term "nucleoside" means a compound comprising a heterocyclic base moiety and a sugar moiety, which can be modified at the 2'-end.

The term "nucleotide" means a nucleoside comprising a phosphate or thiophosphate or dithiophosphate linking group.

The term "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

As used herein, "target oligonucleotide" refers to the oligonucleotide product that can be prepared by the convergent liquid phase process of the present disclosure. In certain embodiments, the target oligonucleotide comprises at least 10 or at least 15 nucleotides. In certain embodiments, the target oligonucleotide has 10 to 500, 15 to 500, 15 to 200, 15 to 100, 15 to 50, 15 to 40, 15 to 30 or 16 to 30 nucleotides.

As used herein, "convergent synthesis" refers to synthetic process for making a target oligonucleotide, wherein two or more oligonucleotide fragments are assembled from either the 5'-3' direction or the 3'-5' direction.

As used herein, "oligonucleotide fragments" refers to short oligonucleotides that are assembled to make the target oligonucleotide. In certain embodiments, the oligonucleotide fragment has 3 to 10, 3 to 8, 3 to 6 or 4 to 6 nucleotides. In certain embodiments, the oligonucleotide fragment has 4 or 5 nucleotides.

The term "internucleoside linkage" means a covalent linkage between adjacent nucleosides of an oligonucleotide.

The term "gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions.

As used herein, the term "alkyl" refers to a fully saturated branched or unbranched hydrocarbon moiety. Preferably the alkyl comprises 1 to 20 carbon atoms, more preferably 1 to 16 carbon atoms, 1 to 10 carbon atoms, 1 to 6 carbon atoms, or 1 to 4 carbon atoms. In some embodiments, an alkyl comprises from 6 to 20 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, or n-decyl.

The term "aryl" refers to monocyclic, bicyclic or tricyclic aromatic hydrocarbon groups having from 6 to 14 carbon atoms in the ring portion. In one embodiment, the term aryl refers to monocyclic and bicyclic aromatic hydrocarbon groups having from 6 to 10 carbon atoms. Representative examples of aryl groups include phenyl, naphthyl, fluorenyl, and anthracenyl.

The term "aryl" also refers to a bicyclic or tricyclic group in which at least one ring is aromatic and is fused to one or two non-aromatic hydrocarbon ring(s). Nonlimiting examples include tetrahydronaphthalene, dihydronaphthalenyl and indanyl.

Optional substituents for both the alkyl or aryl groups are, in each occurrence, independently selected from $C_{1-6}$alkyl, $C_{2-6}$alkenyl, $C_{2-6}$alkynyl, 3- to 7-membered carbocyclyl, 3- to 7-membered heterocyclyl, halo, —CN, —C(O)$R^a$, —C(O)$_2R^a$, —C(O)N($R^a$)$_2$, —O$R^a$, —N($R^a$)$_2$, —N($R^a$)C(O)$R^a$, —N($R^a$)N($R^a$)$_2$, —NO$_2$, —N($R^a$)C(O)$_2R^a$, —N($R^a$)C(O)N($R^a$)$_2$, —N($R^a$)S(O)$_2R^a$, —S$R^a$, —S(O)$R^a$, —S(O)$_2R^a$, —S(O)N($R^a$)$_2$, and —S(O)$_2$N($R^a$)$_2$; and $R^a$ in each occurrence is independently selected from H, $C_{1-6}$alkyl, 3- to 6-membered monocyclic carbocyclyl, and 3- to 6-membered monocyclic heterocyclyl.

As used herein, the term "carbocyclyl" refers to saturated or unsaturated monocyclic or bicyclic hydrocarbon groups of 3-7 carbon atoms, 3-6, or 5-7 carbon atoms. The term "carbocyclyl" encompasses cycloalkyl groups and aromatic groups. The term "cycloalkyl" refers to completely saturated monocyclic or bicyclic hydrocarbon groups of 3-7 carbon atoms, 3-6 carbon atoms, or 5-7 carbon atoms. Exemplary monocyclic carbocyclyl groups include, but are not limited to, cyclopropyl, cyclobutyl, cyclopentyl, cyclohexyl, cycloheptyl, cyclopropenyl, cyclobutenyl, cyclopenentyl, cyclohexenyl, cycloheptenyl, cyclobutadienyl, cyclopentadienyl, cyclohexadienyl, cycloheptadienyl, phenyl and cycloheptatrienyl. Exemplary bicyclic carbocyclyl groups include bicyclo[2.1.1]hexyl, bicyclo[2.2.1]heptyl, bicyclo[2.2.1]heptenyl, tricyclo[2.2.1.0$^{2,6}$]heptanyl, 6,6-dimethylbicyclo[3.1.1]heptyl, or 2,6,6-trimethylbicyclo[3.1.1]heptyl, spiro[2.2]pentanyl, and spiro[3.3]heptanyl.

The term "bridged ring system," as used herein, is a ring system that has a carbocyclyl or heterocyclyl ring wherein two non-adjacent atoms of the ring are connected (bridged) by one or more (preferably from one to three) atoms selected from C, N, O, or S. A bridged ring system may have from 6-7 ring members.

The term "spiro ring system," as used herein, is a ring system that has two rings each of which are independently selected from a carbocyclyl or a heterocyclyl, wherein the two ring structures having one ring atom in common. Spiro ring systems have from 5 to 7 ring members.

As used herein, the term "heterocyclyl" refers to a saturated or unsaturated, monocyclic or bicyclic (e.g., bridged or spiro ring systems) ring system which has from 3- to 7-ring members, or in particular 3- to 6-ring members or 5- to 7-ring members, at least one of which is a heteroatom, and up to 4 (e.g., 1, 2, 3, or 4) of which may be heteroatoms, wherein the heteroatoms are independently selected from O, S and N, and wherein C can be oxidized (e.g., C(O)), N can be oxidized (e.g., N(O)) or quaternized, and S can be optionally oxidized to sulfoxide and sulfone. Unsaturated heterocyclic rings include heteroaryl rings. As used herein, the term "heteroaryl" refers to an aromatic 5 or 6 membered monocyclic ring system, having 1 to 4 heteroatoms independently selected from O, S and N, and wherein N can be oxidized (e.g., N(O)) or quaternized, and S can be optionally oxidized to sulfoxide and sulfone. In one embodiment, a heterocyclyl is a 3- to 7-membered saturated monocyclic or a 3- to 6-membered saturated monocyclic or a 5- to 7-membered saturated monocyclic ring. In one embodiment, a heterocyclyl is a 3- to 7-membered monocyclic or a 3- to 6-membered monocyclic or a 5- to 7-membered monocyclic ring. In another embodiment, a heterocyclyl is a 6 or –7-membered bicyclic ring. The heterocyclyl group can be attached at a heteroatom or a carbon atom. Examples of heterocyclyls include aziridinyl, oxiranyl, thiiranyl, oxaziridinyl, dioxiranyl, azetidinyl, oxetanyl, thietanyl, pyrrolidinyl, tetrahydrofuranyl, thiolanyl, imidazolidinyl, pyrazolidinyl, oxazolidinyl, isoxazolidinyl, thiazolidinyl, isothiazolidinyl, dioxolanyl, dithiolanyl, oxathiolanyl, piperidinyl, tetrahydropyranyl, thianyl, piperazinyl, morpholinyl, thiomorpholinyl, dioxanyl, dithianyl, trioxanyl, trithianyl, azepanyl, oxepanyl, thiepanyl, dihydrofuranyl, imidazolinyl, dihydropyranyl, and heteroaryl rings including azirinyl, oxirenyl, thiiranyl, diazirinyl, azetyl, oxetyl, thietyl, pyrrolyl, furanyl, thiophenyl (or thienyl), imidazolyl, pyrazolyl, oxazolyl, isoxazolyl, thiazolyl, isothiazolyl, furazanyl, oxadiazolyl, thiadiazolyl, dithiazolyl, triazolyl, tetrazolyl, pyridinyl, pyranyl, thiopyranyl, pyrazinyl, pyrimidinyl, pyridazinyl, oxazinyl, thiazinyl, dioxinyl, dithiinyl, oxathianyl, triazinyl, tetrazinyl, azepinyl, oxepinyl, thiepinyl, diazepinyl, and thiazepinyl and the like. Examples of bicyclic heterocyclic ring systems include 3-azabicyclo[3.1.0]hexanyl, 3-azabicyclo[3.1.1]heptanyl, 2-azaspiro[3.3]heptanyl, 2-oxa-6-azaspiro[3.3]heptanyl, and 5-azaspiro[2.3]hexanyl.

"Halogen" or "halo" may be fluoro, chloro, bromo or iodo.

As used herein the term "substantially anhydrous" refers to a water content of approximately 1000 parts per million (ppm) or less, preferably 500 ppm or less, more preferably 100 ppm or less. The water content is between 500-1000 ppm, between 100-500 ppm, between 50-100 ppm or less than 50 ppm. The organic solution or solvent is made substantially anhydrous by using drying agents or through azeotropic removal of water (azeotropic distillation).

As used herein the term "drying agent" refers to a chemical reagent used to remove water from an organic solvent or an organic compound, or a solution of organic compounds. Any suitable drying agents can be used. Exemplary drying agents include, but are not limited to, calcium chloride, potassium chloride, sodium sulfate, calcium sulfate, magnesium sulfate or molecular sieves. In some embodiments, molecular sieves are 3 Å or 4 Å.

As used herein, a "hydroxyl protecting group" refers to a group that is suitable for protecting a hydroxyl group, —OH, from reacting with other reagents. Examples of hydroxyl protecting groups can be found in Greene, T W et al., Protective Groups in Organic Synthesis, 4$^{th}$ Ed., John Wiley and Sons (2007).

In certain embodiments, the hydroxyl protecting groups can be selected from, for example, acetyl (Ac); benzoyl (Bz); benzyl (Bn); β-methoxyethoxymethyl ether (MEM); methoxymethyl ether (MOM); methoxytrityl [(4-methoxyphenyl)diphenylmethyl, MMT); p-methoxybenzyl ether (PMB); methylthiomethyl ether; pivaloyl (Piv); tetrahydropyranyl (THP); tetrahydrofuran (THF); silyl ether (including, but not limited to, trimethylsilyl (TMS), tert-butyldiphenylsilyl (TBDPS), tert-butyldimethylsilyl (TBDMS), tri-iso-propylsilyloxymethyl (TOM), and triisopropylsilyl (TIPS) ethers); methyl ethers, and ethoxyethyl ethers (EE).

In certain embodiments, the hydroxyl protecting group protects the 3'-hydroxyl of a nucleoside (referred to as 3'-hydroxyl protecting group). In certain embodiments, the 3'-hydroxyl protecting groups include a silyl hydroxyl protecting group, such as trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl tri(trimethylsilyl)silyl, t-butylmethoxyphenylsilyl, and t-butoxydiphenylsilyl. In certain embodiments, the 3'-hydroxyl protecting group is TBDPS. In certain embodiments, the 3'-hydroxyl protecting group is a large hydrophobic protecting group (LHPG), such as those described herein.

In certain embodiments, the hydroxyl protecting group protects the 5'-hydroxyl of a nucleoside (referred to as 5'-hydroxyl protecting group). Exemplary 5'-hydroxyl groups include, but are not limited to those as described herein (e.g., $R^{15}$ in any of the aspects or embodiments). In a specific embodiment, 5'-hydoxyl protecting group is an acid-labile 4,4'-dimethoxytrityl (or bis-(4-methoxyphenyl) phenylmethyl) (DMT or DMTr) protecting group. In certain embodiments, the 5'-hydroxyl protecting group is a large hydrophobic protecting group (LHPG), such as those described herein.

As used herein, the term "azeotropic distillation" refers to removal of water from an organic solution or solvent by distillation using a material separation agent. A material separation agent includes, but is not limited to, benzene, toluene.

As used herein, "selective precipitation" refers to a purification method that separates the desired product from one or more impurities in a solution by adding the solution to a solvent that precipitates out the product; while leaving the one or more impurities in the solution. Alternatively, the solvent can be added to the solution comprising the crude product and the one or more impurities to precipitate out the product. In certain embodiments, the desired compound or oligonucleotide of the present disclosure comprises a hydrophobic group (e.g., hydrophobic 3'-hydroxyl protecting group or hydrophobic 5'-hydroxyl protecting group (e.g., LHPG group described herein)) and the addition of a polar solvent (e.g. $CH_3CN$) into the solution containing the compound or oligonucleotide and one or more impurities to precipitate out the desired oligonucleotide. In certain embodiments, the desired compound or oligonucleotide of the present disclosure can be purified by adding a co-solvent or solvent mixture (e.g., heptane, tert-butylmethylether (TBME or MBTE), heptane/MBTE mixture (e.g. a heptane/MBTE mixture with volume ratio of heptane to MBTE in the range of 20:1 to 1:20, 9:1 to 1:9, or 4:1 to 1:4, or a heptane/MBTE mixture with heptane to MBTE volume ratio of 9:1, 4:1, 2:1, 1:1, 2:5, 1:2, 1:4 or 1:9) to a solution comprising the crude product and the one or more impurities in an organic solvent (e.g., dichloromethane (DCM) or ethylacetate (EtOAc)) to precipitate out the product. Alternatively, the solution comprising the crude product and the one or more impurities can be added to the non-polar or less polar solvent or solvent mixture to precipitate out the product. Suitable co-solvent can be determined based on the hydrophobicity of the product. In certain embodiments, the co-solvent is less polar than the organic solvent the product is dissolved in.

As used herein, "extraction" refers to a purification method that separates the desired product from one or more impurities in a solution by contacting the solution with a solvent that the product is soluble in; while the one or more impurities are insoluble. Alternatively, the solution containing the product and one or more impurities can be contacted with a solvent that the one or more impurities are soluble in; while the product is insoluble. In certain embodiments, the solution (e.g., a reaction mixture or a solution of crude product) containing the product and one or more impurities in an organic solvent (e.g., DCM, EtOAc or THF) or an organic solvent mixture can be contacted (extracted or washed) with water or an aqueous solution (e.g., $NaHCO_3$/$H_2O$ solution or $NaCl/H_2O$ solution) to remove hydrophilic impurities.

As used herein the term "strong acid" refers to an acid that dissociates completely in solutions as shown below:

S represents a solvent molecule. Exemplary strong acid includes, but are not limited to, HCl, HBr, HI, triflic acid, perchloric acid, $CCl_3COOH$, $CHCl_2COOH$ and $CH_2ClCOOH$. In certain embodiments, the strong acid is a strong organic acid, such as $CF_3COOH$, $CHCl_2COOH$ and $CH_2ClCOOH$.

As used herein the term "base" refers to a substance that can produce hydroxide ion ($OH^-$) in water solutions or a substance that can donate a pair of nonbonding electrons. Exemplary bases include, but are not limited to, alkaline hydroxide, alkaline earth hydroxide, alkylamines (e.g., tert-butylamine, sec-butylamine, trimethylamine, triethylamine, diisopropylethylamine, 2-methylpropan-2-amine), 8-diazabicyclo[5.4.0]undec-7-ene (DBU), imidazole, N-methylimidazole, pyridine and 3-picoline.

As used herein, the term "salt" refers to an organic or inorganic salt of a compound, nucleotide or oligonucleotide described herein. In certain embodiments, the salt is a pharmaceutically acceptable salt thereof. The phrase "pharmaceutically acceptable" indicates that the substance or composition must be compatible chemically and/or toxicologically, with the other ingredients comprising a formulation, and/or the mammal being treated therewith. In certain embodiments, the salt of the compound, nucleotide or oligonucleotide described herein is a sodium salt, a potassium salt or an ammonium salt. In certain embodiments, the salt is a sodium salt or ammonium salt.

Methods of the Present Disclosure

I. Fragment Synthesis:

The process described herein involves a stepwise addition of nucleotides in liquid (solution) phase, to form the desired oligonucleotide fragments. In certain embodiments, each nucleotide addition involves at least three reactions (coupling, sulfurization or oxidation, and deprotection) to add the nucleotide to the growing oligonucleotide. First, the 5' end of a first nucleoside is coupled to the 3' end of a second nucleotide to form a dimer. Then the dimer is sulfurized or oxidized form a phosphothioate (i.e., a P=S bond) or a phosphodiester (i.e., a P=O bond). The 5'-hydroxyl group of the second nucleotide is then deprotected and the process is repeated to add the next nucleoside.

a. 5'-Deprotection Reactions:

In a first aspect, the present disclosure provides a deprotection method of removing 5'-hydroxyl protecting group on a nucleotide, a nucleoside or an oligonucleotide. In one embodiment, the deprotection method is a detritylation method for removing a 5'-trityl group. It is discovered that when the detritylation reaction is carried out under anhydrous or substantially anhydrous conditions, significant reduction of side reactions (e.g., deamination of nucleobase cytosine or 5-methylcytosine or their derivatives commonly used for oligonucleotide synthesis) can be achieved (see Example 3). The present detritylation method also involves the addition of a cation scavenger to facilitate the completion of the reaction. As a result, the product with high purity can be obtained without the need of chromatography (e.g., column chromatography). Water level of the detritylation reaction can be controlled by the use of drying agent (e.g., molecular sieves), azeoptropic distillation or other suitable methods known in the art. Alternatively, solvents, acids, and other reagents used in the detritylation reaction, substrates to be subjected to detritylation reaction, and the reaction vessel can be dried to meet the residual water levels prior to use for the detritylation reaction.

A first embodiment of the first aspect is a liquid phase process for preparing a compound of formula (AII$^a$):

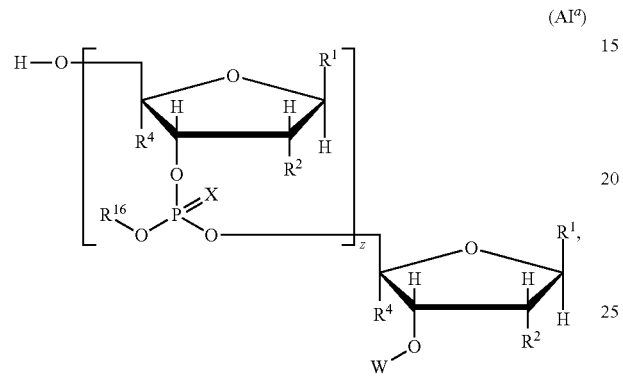
(AI$^a$)

or a salt thereof, comprising deprotecting a compound of formula (AII$^a$):

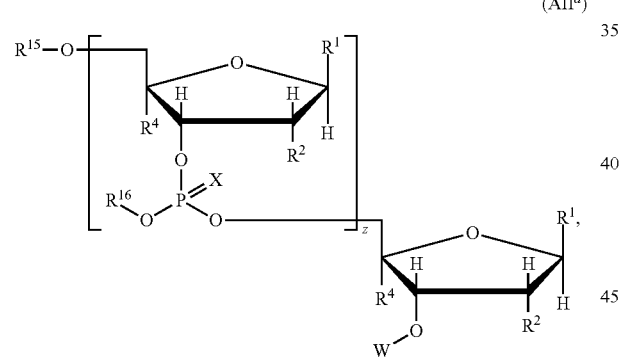
(AII$^a$)

or a salt thereof, wherein the deprotection reaction is carried out in a solution that is anhydrous or substantially anhydrous and wherein:

$R^1$, for each occurrence, is independently a nucleobase, wherein the NH$_2$ of the nucleobase, if present, is protected by an amine protecting group;

$R^2$, for each occurrence, is independently selected from the group consisting of H, halo, and C$_{1-6}$alkoxy optionally substituted with C$_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently C$_{1-6}$alkyl group, C$_{2-6}$alkenyl group, phenyl or benzyl group, each of which is optionally substituted with —CN, —NO$_2$ or halogen; or $R^{16}$ is

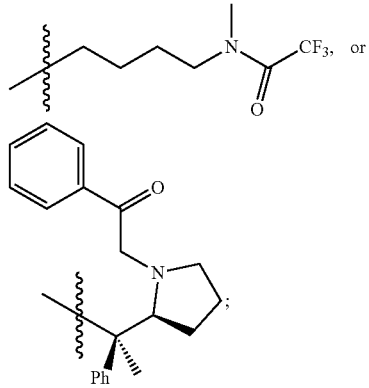

z is 0 or an integer from 1 to 200;

X, for each occurrence, is independently O or S;

W is H, Y or Z;

Y is a hydrophobic hydroxyl protecting group containing an alkyl chain; and

Z is a hydroxyl protecting group.

The first embodiment of the first aspect also includes a liquid phase process for preparing a compound of formula (AI):

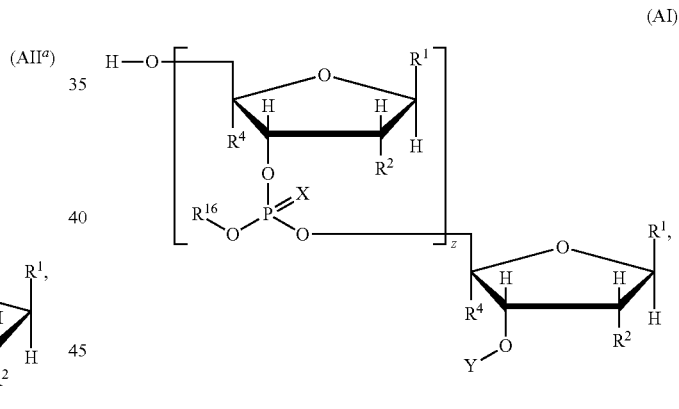
(AI)

or a salt thereof, comprising deprotecting a compound of formula (AII):

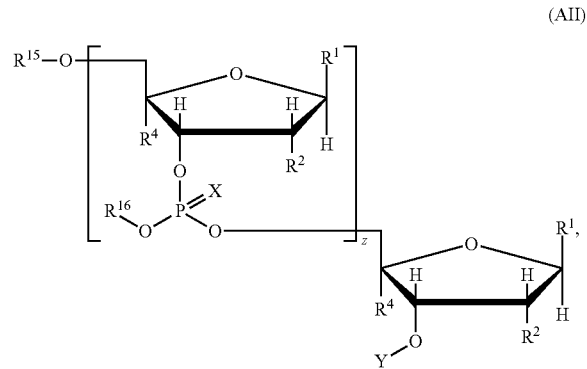
(AII)

or a salt thereof, wherein the deprotection reaction is carried out in a solution that is anhydrous or substantially anhydrous and wherein the variables are as defined above for formulae (AI$^a$) and (AII$^a$).

Also included in the first embodiment is a liquid phase process for preparing a compound of formula (AI'):

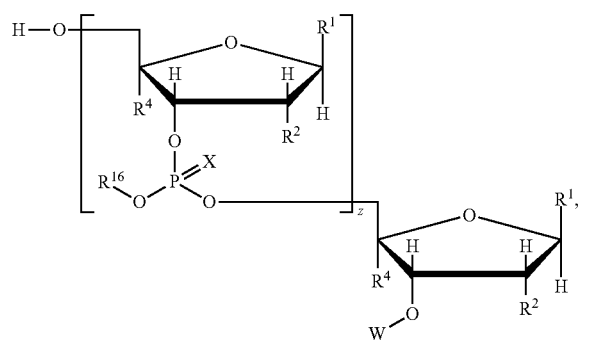

(AI')

or a salt thereof, comprising deprotecting a compound of formula (AII'):

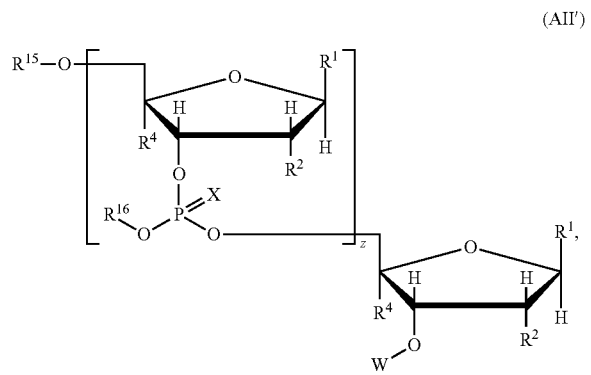

(AII')

or a salt thereof, wherein the deprotection reaction is carried out in a solution that is anhydrous or substantially anhydrous and wherein W is H or Z; Z is a silyl hydroxyl protecting group; and the remaining variables are as defined above for formulae (AI$^a$) and (AII$^a$).

In a specific embodiment, R$^{16}$ is one of the following:

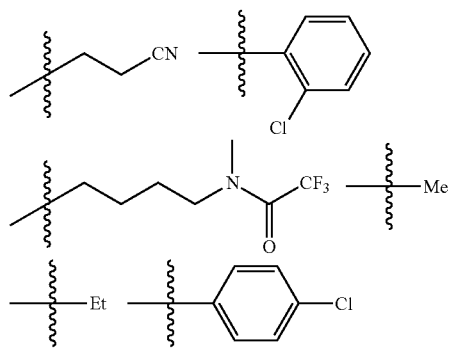

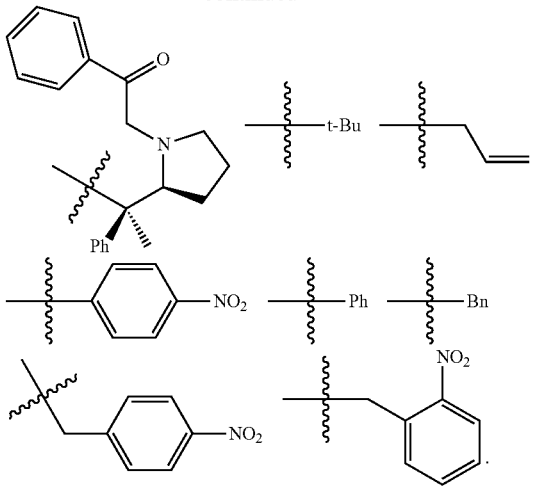

See *Nat Biotechnol.* 2017 September; 35(9):845-851; *J. Org. Chem.* 1999, 64, 7515-7522; *Biopolymers* (*Peptide Science*), 2001, 60, 3, each of which is incorporated herein by reference.

In a second embodiment, the deprotection reaction is carried out in the presence of a drying agent. Any suitable drying agents can be used in the deprotection reaction. In some embodiments, the drying agent is selected from calcium chloride, potassium chloride, sodium sulfate, calcium sulfate, magnesium sulfate and molecular sieves.

In a third embodiment, the drying agent used in the second embodiment is molecular sieves.

In a fourth embodiment, the size of molecular sieves of the third embodiment is 3 Å or 4 Å. In a preferred embodiment, the size of molecular sieves is 3 Å.

In a fifth embodiment, the anhydrous or substantially anhydrous solution for the deprotection reaction is obtained by removing water using azeotropic distillation prior to the deprotection reaction.

Alternatively, solvents, acids or acid solutions, and other reagents or solutions comprising the reagents to be used in the detritylation reaction, substrates or substrate solutions to be subjected to detritylation reaction, and the reaction vessel can be dried individually or combined prior to the detritylation reaction.

In a sixth embodiment, the deprotection reaction is carried out in the presence of a scavenger selected from a cation scavenger comprising a —SH group, a silane scavenger (such as HSiPh$_3$, HSiBu$_3$, triisopropylsilane etc.), siloxane, polystyrene, furan, pyrrole and indole.

In a specific embodiment, the deprotection reaction is carried out in the presence of a scavenger selected from 1-dodecanethiol, cyclohexanethiol, 1-octanethiol, triisopropylsilane, indole, 2,3-dimethylfuran, diphenylsilane, 2-mercaptoimidazole, diphenylmethylsilane, phenylsilane, 5-methoxyindole, methylphenylsilane, chlorodimethylsilane, 1,1,3,3-tetramethyldisiloxane, 1-thioglycerol, triphenylsilane, tert-butyldimethylsilane, butylsilane, methyldiethoxysilane, 1,1,3,3,5,5-hexamethyltrisiloxane, hexylsilane, (mercaptomethyl)polystyrene, or dimethylphenylsilane.

In a seventh embodiment, the cation scavenger of sixth embodiment is a compound of formula RSH, wherein R is an alkyl, a cycloalkyl, a heterocycloalkyl, an aryl or a heteroaryl group, each of which is optionally substituted.

In an eighth embodiment, the RSH group of the seventh embodiment is $CH_3(CH_2)_5SH$, $CH_3(CH_2)_{11}SH$, cyclohexanethiol (CySH), or $CH_3CH_2OC(=O)CH_2CH_2SH$.

A ninth embodiment of the present disclosure is a process as described in any one of the first to eighth embodiments, wherein $R^{15}$ is a 4,4'-dimethoxytrityl (DMT) group.

In a tenth embodiment, the deprotection reaction is carried out by reacting the compound of formula (AII) with a detritylation reagent. Any suitable detritylation reagent can be used.

In an eleventh embodiment, the detritylation reagent of the tenth embodiment is a strong organic acid.

In a twelfth embodiment, the detritylation reagent is selected from $CF_3COOH$, $CCl_3COOH$, $CHCl_2COOH$, $CH_2ClCOOH$, $H_3PO_4$, methanesulfonic acid (MSA), benzenesulfonic acid (BSA), $CClF_2COOH$, $CHF_2COOH$, $PhSO_2H$ (phenylsulfonic acid) etc. In a preferred embodiment, the detritylation reagent is $CH_2ClCOOH$. In another specific embodiment, the detritylation reagent is $CF_3COOH$. In yet another specific embodiment, the detritylation reagent is $CHC_{1-2}COOH$.

In certain embodiments, the detritylation reagent is citric acid. In certain embodiments, the detritylation reagent is saturated citric acid solution.

A thirteenth embodiment of the first aspect is a process as described in any one of the above disclosed embodiments, wherein W is Z.

In a fourteenth embodiment, the Z group is a silyl hydroxyl protecting group. Exemplary silyl protecting groups include, but are not limited to, trimethylsilyl, triethylsilyl, triisopropylsilyl, dimethylisopropylsilyl, diethylisopropylsilyl, dimethylthexylsilyl, t-butyldimethylsilyl, t-butyldiphenylsilyl, tribenzylsilyl, tri-p-xylylsilyl, triphenylsilyl, diphenylmethylsilyl, di-t-butylmethylsilyl tri (trimethylsilyl)silyl, t-butylmethoxyphenylsilyl, and t-butoxydiphenylsilyl.

In a fifteenth embodiment, the silyl hydroxyl protecting group of the fourteenth embodiment is selected from TBDPS, TBoDPS and TBDAS.

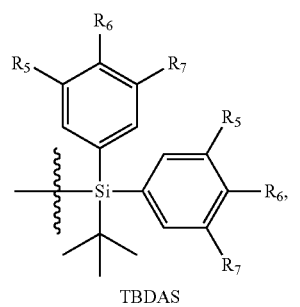

TBDPS

TBoDPS

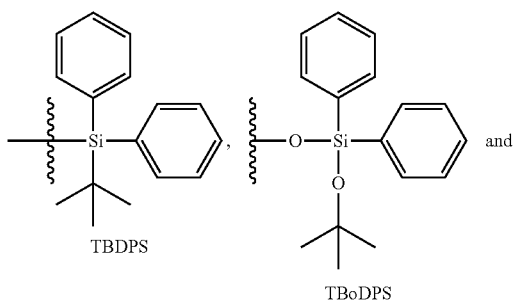

TBDAS wherein $R_5$, $R_6$ and $R_7$ are each independently H, $C_{1-30}$alkyl, or $C_{1-30}$alkoxy.

In a sixteenth embodiment, the silyl protecting group of the fourteenth embodiment is:

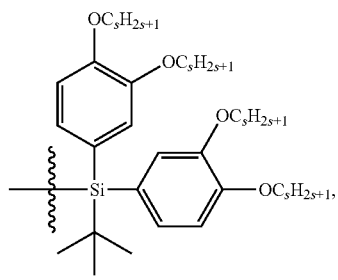

wherein s is an integer from 1 to 30.

In a seventeenth embodiment, Z group of the fourteenth embodiment is TBDPS.

An eighteenth embodiment discloses a process as described in any one of the first to twelfth embodiments, wherein W is Y represented by the following formula:

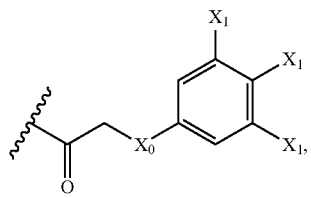

wherein $X_0$ is $C_{1-10}$alkyl, wherein one or more $CH_2$ groups are independently replaced with $C(O)$, $C(O)NH_2$, cycloalkyl or heterocyclyl group; and $X_1$ is $C_{1-25}$alkyl or $C_{1-25}$alkoxy. In a specific embodiment, Y is represented by the following formula:

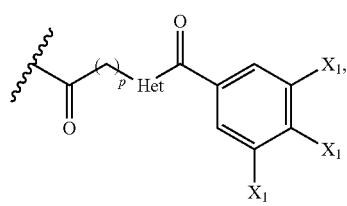

wherein p is an integer from 1 to 10; Het is a saturated heterocycle; and the remaining variables are as described above. In a more specific embodiment, Het is piperazine.

In a nineteenth embodiment, Y of the eighteenth embodiment is represented by the following formula:

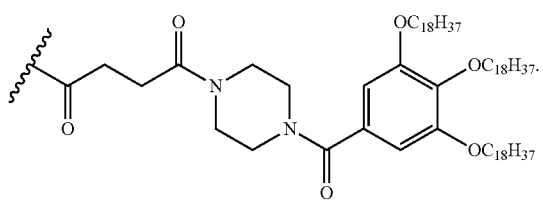

A twentieth embodiment discloses a process described in any one of the first to nineteenth embodiments, wherein the compound of formula (AI) or (AI') or a salt thereof is not purified by chromatography (e.g., column chromatography).

A twenty-first embodiment discloses a process described in first to twentieth embodiments, wherein the compound of formula (AI) or (AI') or a salt thereof is purified by selective precipitation and/or extraction. In certain embodiment, the compound of formula (AI) or a salt thereof is purified by selective precipitation. In certain embodiments, the selective precipitation the compound of formula (AI) or a salt thereof can be achieved by adding acetonitrile to a solution of the crude product in DCM. Alternatively, the solution of the crude product can be added to acetonitrile to precipitate out the desired product.

In certain embodiments, the compound of formula (AI') or a salt thereof is purified by selective precipitation. In certain embodiments, the compound of formula (AI') or a salt thereof is purified by extraction a solution comprising the compound of formula (AI') or a salt thereof in an organic solvent (MBTE, EtOAc, heptane/MBTE mixture, DCM, etc.) with an aqueous solution (e.g., NaHCO$_3$/H$_2$O or NaCl/H$_2$O) in addition to selective precipitation. In certain embodiments, the extraction is carried out before selective precipitation. Alternatively, the extraction is carried out after selective precipitation. In certain embodiments, the selective precipitation of the compound of formula (AI') or a salt thereof can be achieved by adding heptane or a heptane/MBTE mixture to a solution of the crude product in DCM or EtOAc. Alternatively, the solution of the crude product can be added to heptane or a heptane/MBTE mixture to precipitate out the desired product. A heptane/MBTE mixture with a suitable volume ratio (e.g., a volume ratio described herein) can be used.

In some embodiments, for the processes of the first aspect or any embodiments described there (e.g., the process described in any one of the first to the twenty-first embodiments), z is 1 to 150, 1 to 100, 1 to 50, 1 to 20, 1 to 10 or 1 to 5.

In some embodiments, for the processes the first aspect or any embodiments described there (e.g., the process described in any one of the first to the twenty-first embodiments), $R^{16}$, for each occurrence, is independently $C_{1-6}$alkyl group, $C_{2-6}$alkenyl group, phenyl or benzyl group, each of which is optionally substituted with —CN, —NO$_2$ or halogen; or $R^{16}$ is

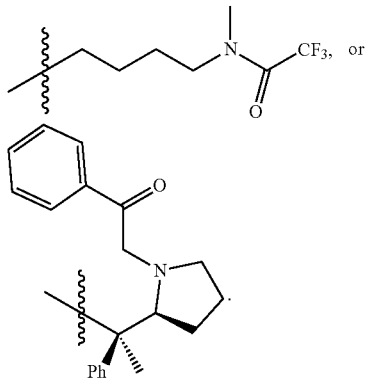

In a specific embodiment, $R^{16}$ is one of the following:

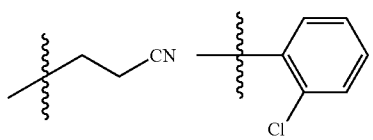

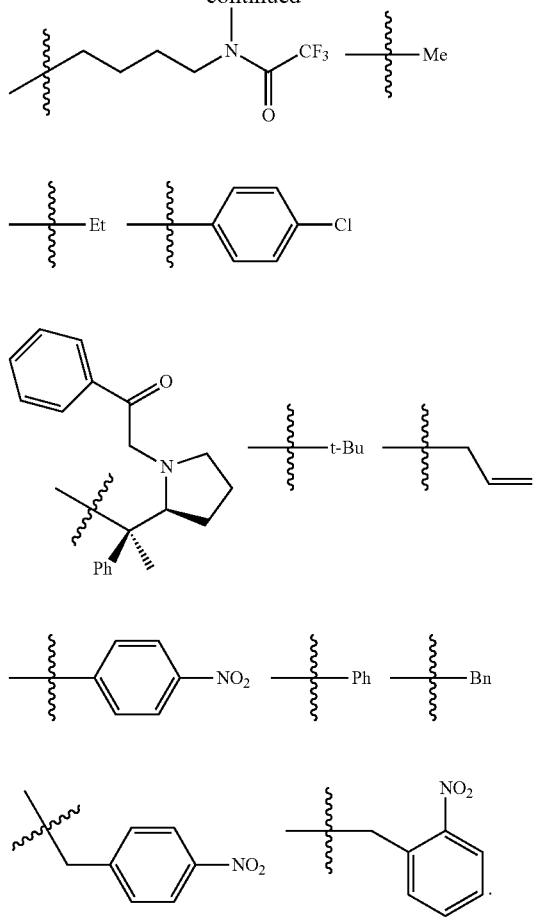

In some embodiments, for the processes the first aspect or any embodiments described there (e.g., the process described in any one of the first to the twenty-first embodiments):

each $R^2$ is independently selected from H, halogen or $C_{1-4}$alkoxy optionally substituted with $C_{1-4}$alkoxy;

$R^4$ is H; and $R^{16}$ is —CH$_2$CH$_2$CN.

In a specific embodiment, $R^2$ is —OCH$_2$CH$_2$OMe.

b. 3'-Deprotection Reactions:

In a second aspect, the present disclosure describes a liquid phase deprotection method of removing a 3'-hydroxyl protecting group on oligonucleotide. In one embodiment, the deprotection method is a desilylation process. It is discovered that the desilylation process of the present disclosure can selectively remove the silyl protecting group of the 3'-hydroxyl group without affecting other sensitive groups on the oligonucleotide, such as the 5'-trityl group, various protecting groups of the nucleobases (e.g., benzoyl or isobutyryl group), cyanoethyl and —OCH$_2$CH$_2$OMe (also known as methoxyethyl (MOE)) groups.

In a twenty-second embodiment, the second aspect of the present disclosure relates to a liquid phase process for preparing a compound of formula (BI):

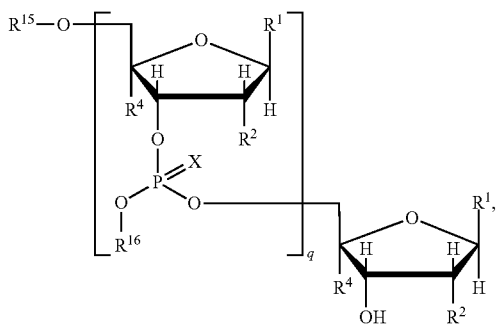

(BI)

or a salt thereof, comprising deprotecting a compound of formula (BII):

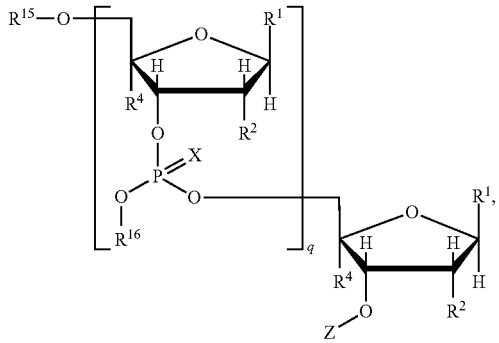

(BII)

or a salt thereof, to form the compound of formula (BI), or a salt thereof, wherein:

- $R^1$, for each occurrence, is independently a nucleobase, wherein the $NH_2$ of the nucleobase, if present, is protected by an amine protecting group;
- $R^2$, for each occurrence, is independently selected from the group consisting of H, halo, and $C_{1-6}$alkoxy optionally substituted with $C_{1-6}$alkoxy;
- $R^4$, for each occurrence, is independently H or forms a ring with the alkoxy group of $R^2$;
- $R^{15}$ is a hydroxyl protecting group;
- $R^{16}$, for each occurrence, is independently $C_{1-6}$alkyl group, $C_{2-6}$alkenyl group, phenyl or benzyl group, each of which is optionally substituted with —CN, —$NO_2$ or halogen; or
- $R^{16}$ is

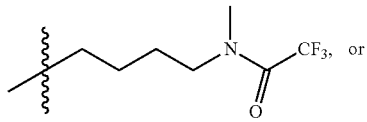

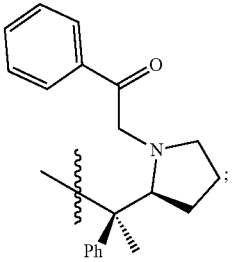

q is an integer from 1 to 200;
X, for each occurrence, is independently O or S; and
Z is a hydroxyl protecting group (e.g., a silyl hydroxyl protecting group).

In a twenty-third embodiment, the second aspect of the present disclosure relates to a liquid phase process for preparing a compound of formula (B2I):

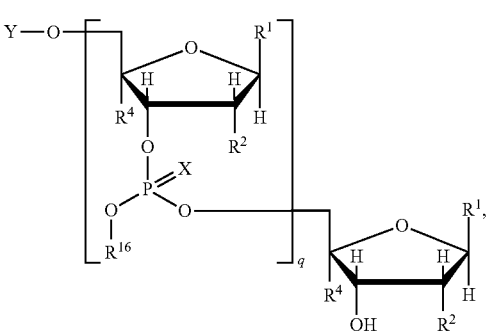

(B2I)

or a salt thereof, comprising deprotecting a compound of formula (B2I I):

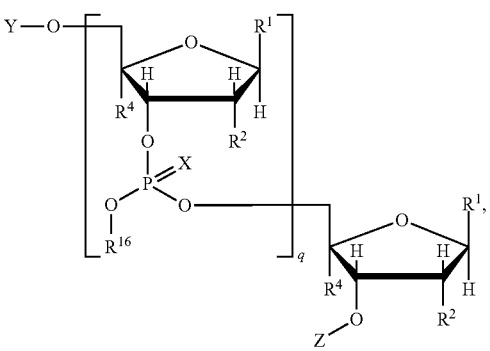

(B2II)

or a salt thereof, to form the compound of formula (B2I) or a salt thereof, wherein:

- $R^1$, for each occurrence, is independently a nucleobase, wherein the $NH_2$ of the nucleobase, if present, is protected by an amine protecting group;
- $R^2$, for each occurrence, is independently selected from the group consisting of H, halo, and $C_{1-6}$alkoxy optionally substituted with $C_{1-6}$alkoxy;
- $R^4$, for each occurrence, is independently H or forms a ring with the alkoxy group of $R^2$;

$R^{16}$, for each occurrence, is independently $C_{1-6}$alkyl group, $C_{2-6}$alkenyl group, phenyl or benzyl group, each of which is optionally substituted with —CN, —NO$_2$ or halogen; or $R^{16}$ is

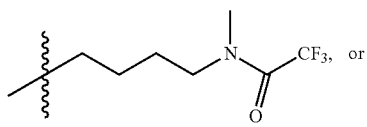

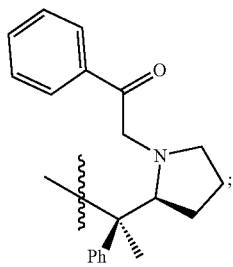

q is an integer from 1 to 200;

X, for each occurrence, is independently O or S;

Y is a hydrophobic hydroxyl protecting group containing an alkyl chain; and

Z is a hydroxyl protecting group.

In a twenty-fourth embodiment, Y of the twenty-third embodiment is represented by the following formula:

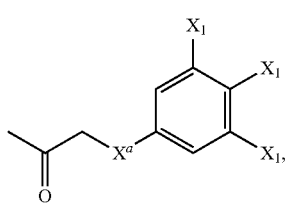

wherein $X^a$ is $C_{1-10}$alkyl, wherein one or more CH$_2$ groups are independently replaced with C(O), C(O)NH$_2$, cycloalkyl or $C_{1-6}$heterocylcyl group; and X1 is $C_{1-25}$alkyl or $C_{1-25}$alkoxy. In a specific embodiment, Y is represented by the following formula:

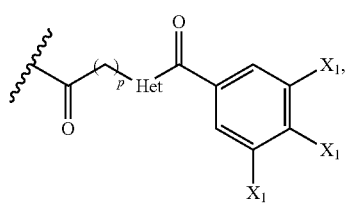

wherein p is an integer from 1 to 10; Het is a saturated heterocycle; and the remaining variables are as described above. In a more specific embodiment, Het is piperazine.

In a twenty-fifth embodiment, Y of the twenty-third embodiment is represented by the following formula:

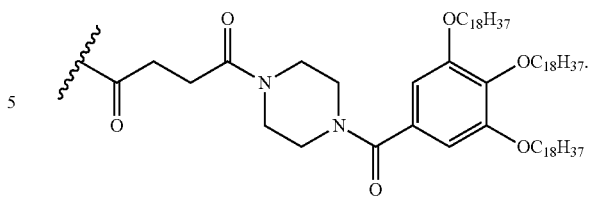

In a twenty-sixth embodiment, the deprotection reaction is carried out by reacting the compound of formula (BII) or (B2II) or a salt thereof with HF in the presence of a base.

In a twenty-seventh embodiment, the base in twenty-sixth embodiment is imidazole or pyridine, wherein imidazole or pyridine are optionally substituted.

A twenty-eighth embodiment discloses a process described in any one of the twenty-second to twenty-seventh embodiments, wherein excess amount of base relative to HF is used.

In a twenty-ninth embodiment, the deprotection reaction is carried out by reacting the compound of formula (BII) or (B2II) or a salt thereof with HF in the presence of pyridine and imidazole.

In a thirtieth embodiment, the molar ratio of imidazole to HF of the twenty-ninth embodiment is in the range of 1.1:1 to 5:1. In some embodiments, the molar ratio of imidazole to HF is in the range of 1.1:1 to 3:1, 1.5:1 to 3:1, or 1.5:1 to 2.5:1.

In a thirty-first embodiment, the molar ratio of imidazole to HF in the thirtieth embodiment is 2:1.

In a thirty-second embodiment, for the process described in any of the twenty-ninth to thirty first embodiments, the molar ratio of pyridine to HF is in the range 1.1:1 to 20:1. In some embodiments, the molar ratio of pyridine to HF is in the range of 5:1 to 20:1 or 5:1 to 15:1. In a specific embodiment, the molar ratio of pyridine to HF is 10:1.

A thirty-third embodiment discloses a process described in any one of the twenty-second to thirty-second embodiments, wherein Z is a silyl hydroxyl protecting group. In certain embodiments, the silyl protecting groups include, but are not limited to, those described above in the fourteenth embodiment.

In a thirty-fourth embodiment, the silyl hydroxyl protecting group is TBDPS, ToBDPS or TBDAS as described in the fifteenth, sixteenth or seventeenth embodiment. In certain embodiments, the silyl hydroxyl protecting group is TBDPS.

In certain embodiments, the deprotection reaction described above (e.g., in any one of the twenty-third to thirty-fourth embodiments) is carried out in a suitable organic solvent, e.g., THF.

A thirty-fifth embodiment discloses a process described in any one of the twenty-second to thirty-fourth embodiments, wherein the compound of formula (BI) or (B2I) or a salt thereof is not purified by chromatography (e.g., column chromatography).

In a thirty-sixth embodiment, the compound of formula (BI) or (B2I) or a salt thereof is purified by selective precipitation and/or extraction. In certain embodiment, the compound of formula (B2I) or a salt thereof is purified by selective precipitation. In certain embodiments, the selective precipitation the compound of formula (B2I) or a salt thereof can be achieved by adding acetonitrile to a solution of the crude product in DCM. Alternatively, the solution of the crude product can be added to acetonitrile to precipitate out the desired product.

In certain embodiments, the compound of formula (BI) or a salt thereof is purified by selective precipitation. In certain embodiments, the compound of formula (BI) or a salt thereof is purified by extraction a solution comprising the compound of formula (BI) or a salt thereof in an organic solvent (MBTE, EtOAc, heptane/MBTE mixture, DCM, etc.) with an aqueous solution (e.g., NaHCO$_3$/H$_2$O or NaCl/H$_2$O) in addition to selective precipitation. In certain embodiments, the extraction is carried out before selective precipitation. Alternatively, the extraction is carried out after selective precipitation. In certain embodiments, the selective precipitation of the compound of formula (BI) or a salt thereof can be achieved by adding heptane or a heptane/MBTE mixture to a solution of the crude product in DCM or EtOAc. Alternatively, the solution of the crude product can be added to heptane or a heptane/MBTE mixture to precipitate out the desired product. A heptane/MBTE mixture with a suitable volume ratio (e.g., a volume ratio described herein) can be used.

In some embodiments, for the process described in the second aspect or any embodiments described therein (e.g. the twenty-second, twenty-sixth to thirty-sixth embodiment), $R^{15}$ is 4,4'-dimethoxytrityl (DMT) group.

In some embodiments, for the process described in the second aspect or any embodiments described therein (e.g. the twenty-second to thirty-sixth embodiments), each $R^2$ is independently selected from H or C$_{1-4}$alkoxy optionally substituted with C$_{1-4}$alkoxy; $R^4$ is H; and $R^{16}$ is —CH$_2$CH$_2$CN.

In some embodiments, for the process described in the second aspect or any embodiments described therein (e.g. the twenty-second, twenty-sixth to thirty-sixth embodiment), each $R^2$ is independently selected from H, halo, or C$_{1-4}$alkoxy optionally substituted with C$_{1-4}$alkoxy; $R^4$ is H; $R^{15}$ is 4,4'-dimethoxytrityl; and $R^{16}$ is —CH$_2$CH$_2$CN. In a specific embodiment, $R^2$ is MOE.

In some embodiments, for the process described in the second aspect or any embodiments described therein (e.g. the twenty-second to thirty-sixth embodiments), each $R^2$ is independently selected from H, halo (e.g., F), or C$_{1-4}$alkoxy optionally substituted with C$_{1-4}$alkoxy; $R^4$ is H; and
  $R^{16}$ is —CH$_2$CH$_2$CN. In a specific embodiment, $R^2$ is —OCH$_2$CH$_2$OCH$_3$ (MOE).

c. Phosphitylation Reactions

A third aspect of the present disclosure provides a liquid phase phosphitylation method of an oligonucleotide described herein. The method comprises reacting the 3'-OH group with a phosphordiamidite or H-phosphonate (HO)P(O)H. The phosphitylation methods of the present disclosure can be used to synthesize oligonucleotide fragments with 3 or more nucleotides with high purity without chromatographic purification.

A thirty-seventh embodiment discloses a liquid process for preparing a compound of formula (CI) or (CI'):

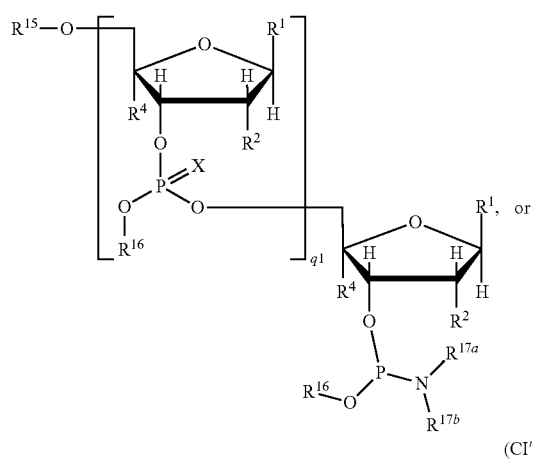

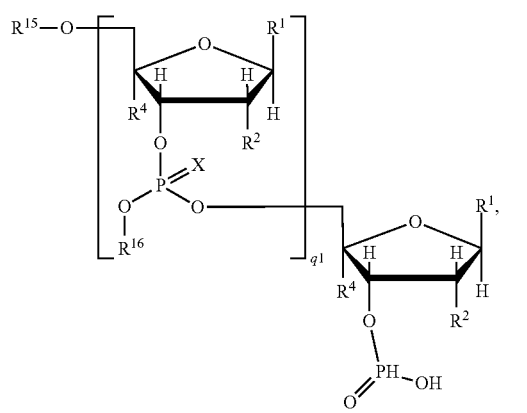

or a salt thereof, comprising reacting a compound of formula (CII):

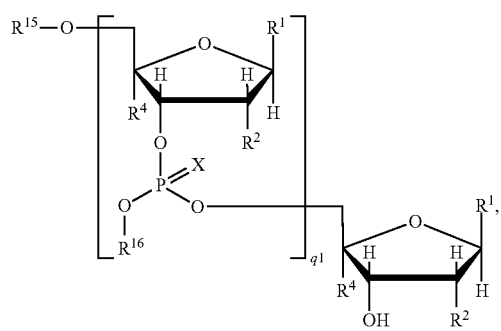

or a salt thereof, with a phosphordiamidite (R$^{16}$O)P(NR$^{17a}$R$^{17b}$)$_2$ or H-phosphonate (HO)P(O)H to form the compound of formula (CI) or (CI'), respectively, wherein:
  $R^1$, for each occurrence, is independently a nucleobase, wherein the NH$_2$ of the nucleobase, if present, is protected by an amine protecting group;
  $R^2$, for each occurrence, is independently selected from the group consisting of H, halo, and C$_{1-6}$alkoxy optionally substituted with halogen or C$_{1-6}$alkoxy;
  $R^4$, for each occurrence, is independently H or forms a ring with the alkoxy group of $R^2$;

$R^{15}$ is a hydroxyl protecting group;

$R^{16}$, for each occurrence, is independently $C_{1-6}$alkyl group, $C_{2-6}$alkenyl group, phenyl or benzyl group, each of which is optionally substituted with —CN, —NO$_2$ or halogen; or $R^{16}$ is

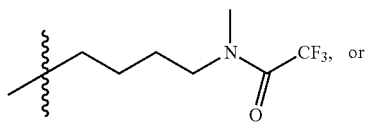

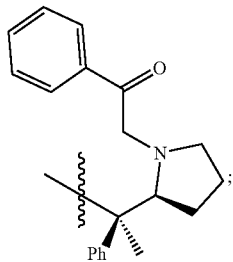

$R^{17a}$ and $R^{17b}$ are independently $C_{1-6}$alkyl q1 is an integer from 2 to 200;

X, for each occurrence, is independently O or S; and

Z is a silyl hydroxyl protecting group.

A thirty-eighth embodiment discloses a liquid process for preparing a compound of formula (C2I):

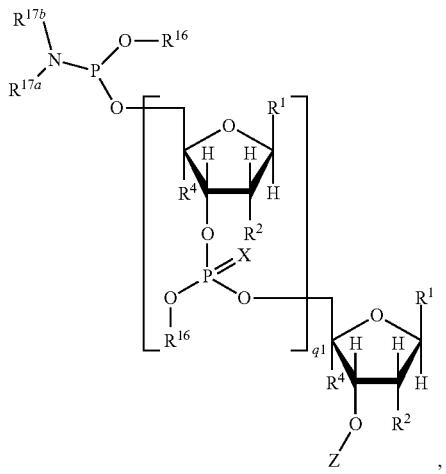

(C2I)

or a salt thereof, comprising reacting a compound of formula (C2II):

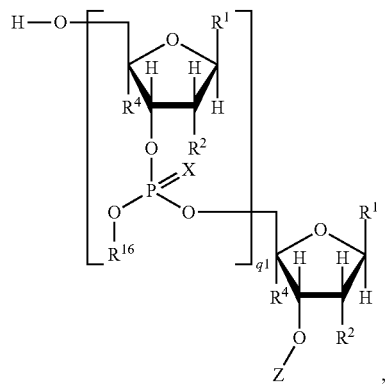

(C2II)

or a salt thereof, with a phosphordiamidite $(R^{16}O)P(NR^{17a}R^{17b})_2$ to form the compound of formula (C2I), or a salt thereof, wherein:

$R^1$, for each occurrence, is independently a nucleobase, wherein the NH$_2$ of the nucleobase, if present, is protected by an amine protecting group;

$R^2$, for each occurrence, is independently selected from the group consisting of H, halo, and $C_{1-6}$alkoxy optionally substituted with halogen or $C_{1-6}$alkoxy;

$R^4$, for each occurrence, is independently H or forms a ring with the alkoxy group of $R^2$;

$R^{16}$, for each occurrence, is independently $C_{1-6}$alkyl group, $C_{2-6}$alkenyl group, phenyl or benzyl group, each of which is optionally substituted with —CN, —NO$_2$ or halogen; or $R^{16}$ is

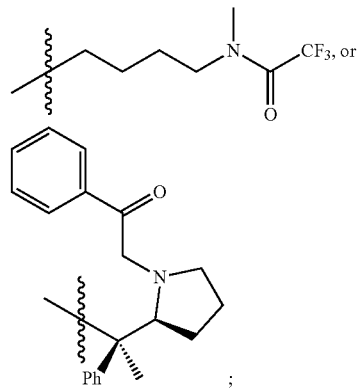

$R^{17a}$ and $R^{17b}$ are independently $C_{1-6}$alkyl q1 is an integer from 2 to 200;

X, for each occurrence, is independently O or S; and

Z is a silyl hydroxyl protecting group.

In some embodiments, for the process described in the thirty-eighth embodiment, each $R^2$ is independently selected from H, F, or $C_{1-4}$alkoxy optionally substituted with $C_{1-4}$alkoxy; $R^4$ is H; $R^{16}$ is —CH$_2$CH$_2$CN; $R^{17a}$ and $R^{17b}$ are independently $C_{1-6}$alkyl; and Z is a silyl hydroxyl protecting group described herein. In some embodiments, Z is selected from TBDPS, TBoDPS and TBDAS. In a specific embodiment, $R^2$ is H, $R^4$ is H; $R^{16}$ is —CH$_2$CH$_2$CN; $R^{17a}$ and $R^{17b}$ are both —CH(CH$_3$)$_2$; and Z is TBDPS. In another specific embodiment, $R^2$ is MOE, $R^4$ is H; $R^{16}$ is —CH$_2$CH$_2$CN; $R^{17a}$ and $R^{17b}$ are both —CH(CH$_3$)$_2$; and Z is TBDPS.

A thirty-ninth embodiment discloses a process described in the third aspect or any embodiments described therein (e.g. thirty-seventh or thirty-eighth embodiment), wherein the reaction is carried out in the presence of an activator. As used herein, an activator is a chemical reagent that facilitates the reaction between the phosphordiamidite or H-phosphonate and 3'-hydroxyl group of oligonucleotide (e.g., compound of formula (CII) or (C2II)). Exemplary activators include, but are not limited to, the following reagents:

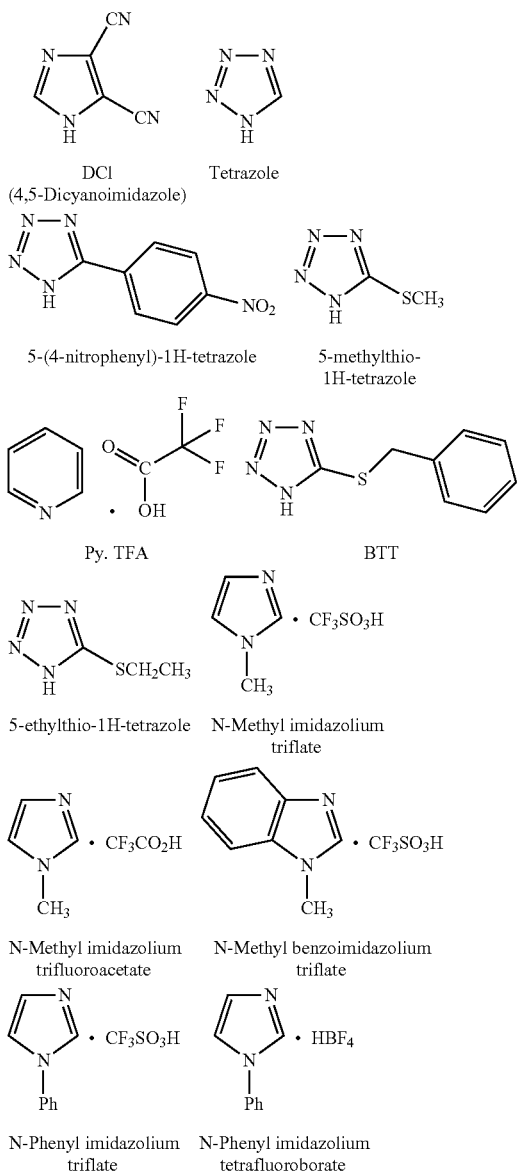

In a fortieth embodiment, the present disclosure provides a process as described in thirty-ninth embodiment, wherein the activator is pyridine trifluoroacetate (Py•TFA) or N-methylimidazolium triflate.

A forty-first embodiment discloses a process described in any one of the thirty-fourth to thirty-sixth embodiments, wherein the compound of formula (CI), (CI') or (C2I) is not purified by chromatography (e.g., column chromatography).

A forty-second embodiment discloses a process described in any one of the thirty-fourth to thirty-sixth embodiments, wherein the compound of formula (CI), (CI') or (C2I) or a salt thereof is purified by selective precipitation and/or extraction. In certain embodiments, the compound of formula (CI), (CI') or (C2I) or a salt thereof is purified by selective precipitation. In certain embodiments, the compound of formula (CI), (CI') or (C2I) or a salt thereof is purified by extraction a solution comprising the compound of formula (CI), (CI') or (C2I) or a salt thereof in an organic solvent (MBTE, EtOAc, heptane/MBTE mixture, DCM, etc.) with an aqueous solution (e.g., NaHCO$_3$/H$_2$O or NaCl/H$_2$O) in addition to selective precipitation. In certain embodiments, the extraction is carried out before selective precipitation. Alternatively, the extraction is carried out after selective precipitation. In certain embodiments, the selective precipitation of the compound of formula (CI), (CI') or (C2I) or a salt thereof can be achieved by adding heptane or a heptane/MBTE mixture to a solution of the crude product in DCM or EtOAc. Alternatively, the solution of the crude product can be added to heptane or a heptane/MBTE mixture to precipitate out the desired product. A heptane/MBTE mixture with a suitable volume ratio (e.g., a volume ratio described herein) can be used.

In some embodiments, for the process described in the third aspect or any embodiments described therein (e.g., the thirty-seventh embodiment), the variables for formula (CI), (CI') or (CII) are as defined below:

each $R^2$ is independently selected from H, F, or $C_{1-4}$alkoxy optionally substituted with $C_{1-4}$alkoxy;

$R^4$ is H;

$R^{15}$ is 4,4'-dimethoxytrityl;

$R^{16}$ is —CH$_2$CH$_2$CN; and $R^{17a}$ and $R^{17b}$ are independently $C_{1-6}$alkyl.

In a specific embodiment, $R^2$ is MOE. In another specific embodiment, $R^2$ is H; $R^4$ is H; $R^{16}$ is —CH$_2$CH$_2$CN; and $R^{17a}$ and $R^{17b}$ are both —CH(CH$_3$)$_2$. In another specific embodiment, $R^2$ is MOE, $R^4$ is H; $R^{16}$ is —CH$_2$CH$_2$CN; and $R^{17a}$ and $R^{17b}$ are both —CH(CH$_3$)$_2$.

A forty-third embodiment discloses a liquid process for preparing a compound of formula (CI'):

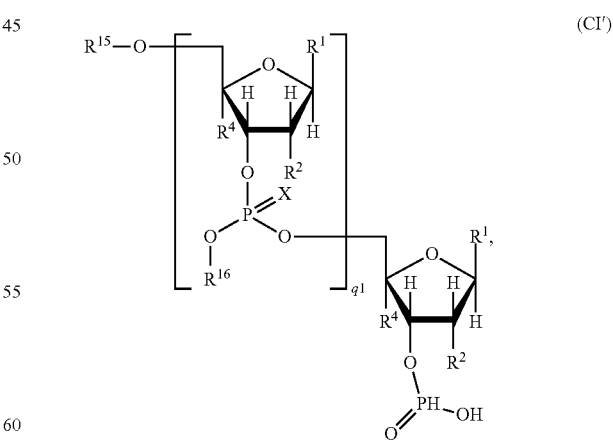

or a salt thereof, comprising the steps of:

1) reacting the compound of formula (CI'A):

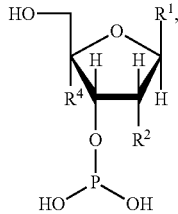
(CI'A)

or a salt thereof,
with a compound of formula (AI):

(AI)

or a salt thereof, to form a compound of formula (CI'B):

(CI'B)

or a salt thereof; and 3) sulfurizing or oxidizing the compound of formula (CI'B), or a salt thereof, with a sulfurization or oxidation agent to form a compound of formula (CI'C):

(CI'C)

or a salt thereof;

4) deprotecting the compound of formula (CI'C), or a salt thereof to form a compound of formula (CI'D):

(CI'D)

or a salt thereof;

5) starting with the compound of formula (CI'D), repeating steps 1), 2) 3) and 4) for q1-3 times, followed by repeating steps 1), 2) and 3) to yield the fragment of formula (CI'), or a salt thereof, wherein:

$R^1$, for each occurrence, is independently a nucleobase, wherein the $NH_2$ of the nucleobase, if present, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group (e.g., DMT group);

$R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

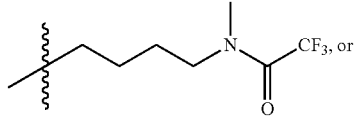

-continued

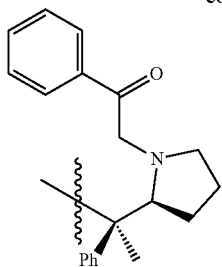

$R^{17a}$ and $R^{17b}$ are independently $C_{1-6}$alkyl;

q1 is an integer from 2 to 200; and

X, for each occurrence, is independently O or S.

A forty-fourth embodiment discloses a liquid phase process for preparing an oligonucleotide of formula ($CI^c$):

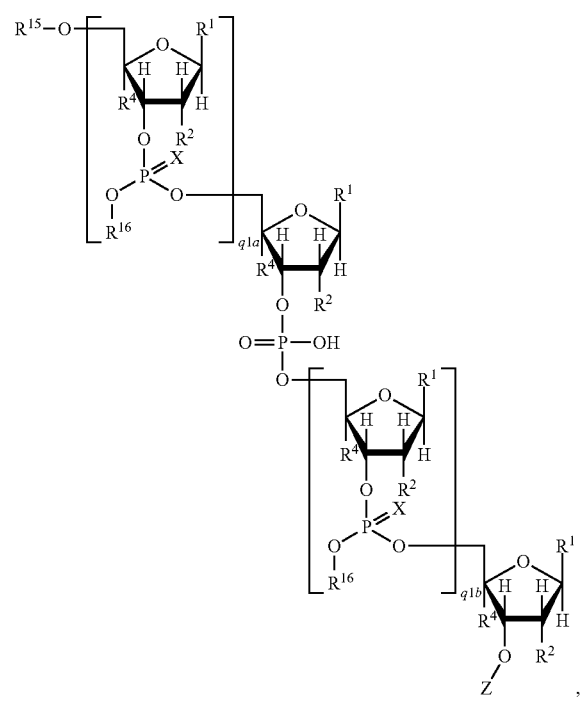

(CI$^c$)

or a salt thereof, comprising coupling an oligonucleotide fragment of formula ($CI^a$):

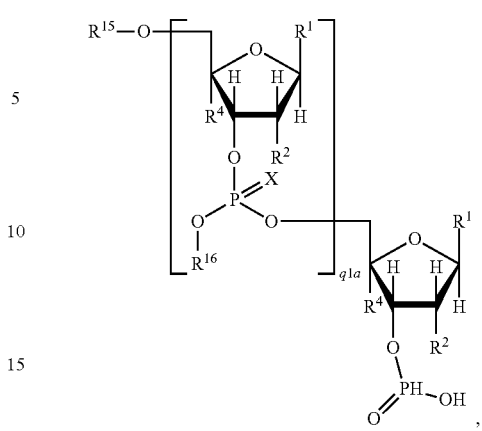

or a salt thereof, with an oligonucleotide fragment of formula ($CI^b$):

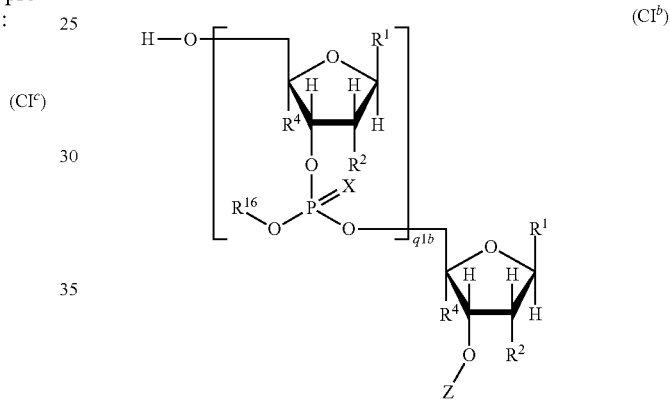

(CI$^b$)

or a salt thereof, to form the oligonucleotide of formula ($CI^c$) or a salt thereof, wherein:

$R^1$, for each occurrence, is independently a nucleobase, wherein the $NH_2$ of the nucleobase, if present, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

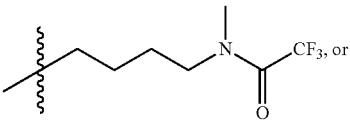

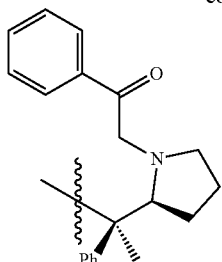

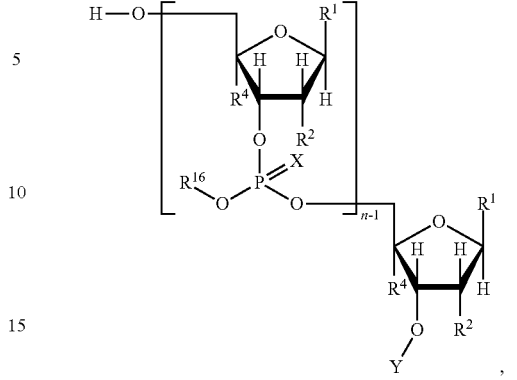

q1a is an integer from 2 to 20;

q1b is an integer from 2 to 20;

X, for each occurrence, is independently O or S; and

Z is hydroxyl protecting group.

In certain embodiments, the coupling reaction of the forty-fourth embodiment is carried out in the presence of an acyl chloride. In a specific embodiment, the coupling reaction between the oligonucleotide of formula (CI$^a$) and the oligonucleotide of formula (CI$^b$) is carried out in the presence of pivaloyl chloride. In another specific embodiment, the coupling reaction is carried out in the presence of pivaloyl chloride and a base (e.g., pyridine).

In certain embodiments, for the process described in the forty-third or forty-fourth embodiment, no chromatography is used for purifying the reaction product of any one of reaction steps described therein. In certain embodiments, the reaction product of any one of reaction steps described therein is purified by selective precipitation and/or extraction as described herein (e.g., as described in the twenty-first, thirty-five or forty-second embodiment).

d. Syntheses of 3'-Oligonucleotide Fragments

In a fourth aspect, the present disclosure describes a liquid phase process of preparing an oligonucleotide fragment bearing a hydrophobic hydroxyl protecting group at the 3'-end (referred herein as the "3'-fragment"). It is surprisingly discovered that the methods of the present disclosure for synthesizing the 3'-fragment can be used to prepare an oligonucleotide fragment having 3 to 20 (e.g., 3 to 10, 3 to 8, 3 to 5 or 4 to 5) nucleotides with high purity without chromatographic purification. In some embodiments, a hydrophobic 3'-hydroxyl protecting group is used, which facilitates the separation of the oligonucleotide fragment product by selective precipitation. In some embodiments, the liquid phase process comprises (1) 5'-OH deprotection step, (2) coupling step, and (3) oxidation or sulfurization step, wherein the steps (1), (2) and (3) are repeated until the desired number of nucleotides are linked together to form the 3'-oligonucleotide fragment.

A forty-fifth embodiment discloses a liquid phase process for preparing an oligonucleotide fragment of formula (I), or a salt thereof, comprising the steps of:

1) deprotecting a compound of formula (I'A):

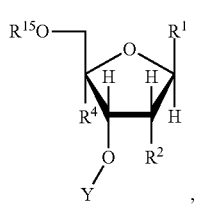

or a salt thereof, to form a compound of formula (IA):

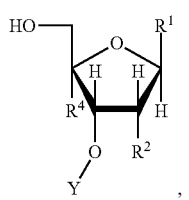

or a salt thereof;

2) reacting the compound of formula (IA), or a salt thereof, with a compound of formula (AI):

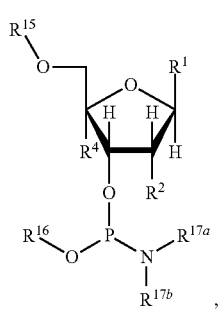

or a salt thereof, to form a compound of formula (IB):

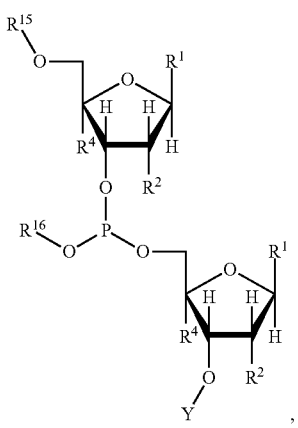

or a salt thereof; and 3) sulfurizing or oxidizing the compound of formula (IB), or a salt thereof, with a sulfurization or oxidation agent to form a compound of formula (IC):

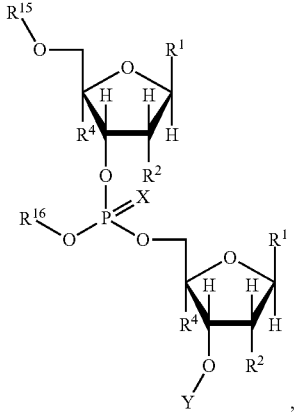

or a salt thereof;

4) deprotecting the compound of formula (IC), or a salt thereof to form a compound of formula (ID):

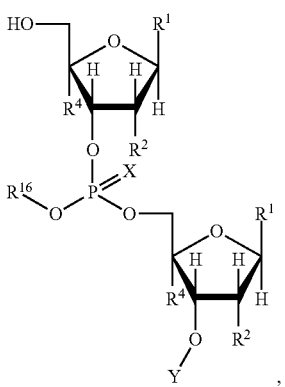

or a salt thereof;

5) starting with the compound of formula (ID), repeating steps 2), 3) and 4) for n−2 times to yield the fragment of formula (I), or a salt thereof, wherein:

$R^1$, for each occurrence, is independently a nucleobase, wherein the $NH_2$ of the nucleobase, if present, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

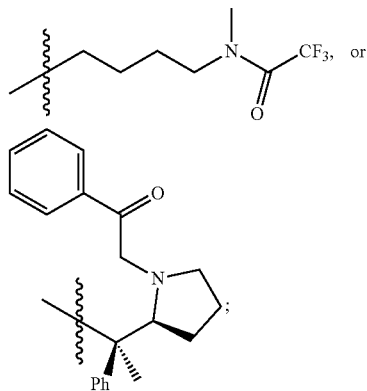

$R^{17a}$ and $R^{17b}$ are independently $C_{1-6}$alkyl;

n is an integer from 2 to 20;

X, for each occurrence, is independently O or S;

Y is a hydrophobic hydroxyl protecting group containing an alkyl chain.

A forty-sixth embodiment discloses a process described in forty-fifth embodiment, wherein the fragment for formula (I) is not purified by chromatography (e.g., column chromatography).

A forty-seventh embodiment discloses a process described in forty-fifth or forty-sixth embodiment, wherein the fragment of formula (I) is purified by selective precipitation and/or extraction. In certain embodiments, the fragment of formula (I) is purified by selective precipitation. In a specific embodiment, the fragment of formula (I) is purified by adding $CH_3CN$ to the reaction mixture containing the crude product, followed by filtration to isolate the fragment product.

A forty-eighth embodiment discloses a process described in the forty-fifth, forty-sixth or forty-seventh embodiment, wherein no chromatography (e.g., column chromatography) is used for purifying the reaction product of any one of steps 1), 2), 3) and 4).

A forty-ninth embodiment discloses a process described in any one of the forty-fifth to forty-eighth embodiments, wherein the reaction product of any one of steps 1), 2), 3) and 4) is purified by selective precipitation (e.g., as described in the twenty-first, thirty-five or forty-second embodiment).

In a fiftieth embodiment, for the processes described in any one of the forty-fifth to forty-ninth embodiments, Y is represented by the following formula:

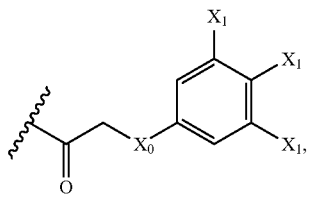

wherein $X_0$ is $C_{1-10}$alkyl, wherein one or more $CH_2$ groups are independently replaced with C(O), C(O)NH$_2$, cycloalkyl or heterocyclyl group; and $X_1$ is $C_{1-25}$alkyl or $C_{1-25}$alkoxy. In a specific embodiment, Y is represented by the following formula:

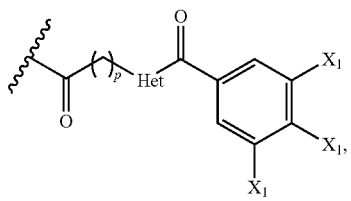

wherein p is an integer from 1 to 10; Het is a saturated heterocycle; and the remaining variables are as described above. In a more specific embodiment, Het is piperazine.

A fifty-first embodiment discloses a process described in any one of the forty-fifth to forty-ninth embodiments, wherein Y is:

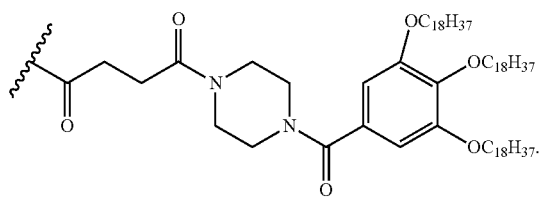

In certain embodiments, for the process described in the fourth aspect or any embodiments describe therein (e.g., the forty-fifth to fifty-first embodiments), the deprotection reactions of step 1) and/or step 4) are carried out as described in the first aspect or any embodiments described therein (e.g., the second to twelfth embodiments).

In certain embodiments, for the process described in the fourth aspect or any embodiments describe therein (e.g., the forty-fifth to fifty-first embodiments), the coupling reaction of step 2) can be carried out in the presence of an activator described herein (e.g. activators described in the thirty-ninth embodiment). In certain embodiments, the activator is 4,5-dicyanoimidazole (DCI) or 5-ethylthio-11H-tetrazole (ETT).

In certain embodiments, for the process described in the fourth aspect or any embodiments describe therein (e.g., forty-fifth to fifty-first embodiments), the sulfurization reaction of step 3) is carried out using a sulfurizing agent, such as 3-amino-1,2,4-dithiazole-5-thione (xanthane hydride or ADTT), 3-(N,N-dimethylamino-methylidene)amino)-3H-1,2,4-dithiazole (DDTT), phenylacetyl disulfide (PADS), 3H-1,2-benzodithiol-3-one 1,1-dioxide (Beaucage Reagent), or phenyl-3H-1,2,4-dithiazol-3-one (POS). In a specific embodiment, the sulfurizing agent is DDTT. In a specific embodiment, the sulfurizing agent is xanthane hydride. In certain embodiments, the sulfurization reaction is carried out in the presence of a base as described herein. In certain embodiments, the base is pyridine or imidazole. In certain embodiments, the sulfurization reaction of step 3) is carried out in the presence of DDTT and 4,5-dicyanoimidazole (DCI).

In certain embodiments, for the process described in the fourth aspect or any embodiments describe therein (e.g., forty-fifth to fifty-first embodiments), the oxidation reaction of step 3) is carried out by using standard oxidizing agents known in the literature. Exemplary oxidizing agent include, but are not limited to, tert-butylhydroperoxide (t-BuOOH), (1S)-(+)-(10-camphorsulfonyl)oxaziridine (CSO), $I_2$, and iodine-pyridine-water oxidizer solution. In a specific embodiment, the oxidizing agent is t-BuOOH.

e. Synthesis of 5'-Oligonucleotide Fragments

In a fifth aspect, the present disclosure describes a liquid phase process of preparing an oligonucleotide fragment (5'-fragment) having a phosphoramidite group that can be coupled with the 3'-fragment described above. It is surprisingly discovered that the methods of the present disclosure for preparing 5'-fragments can be used to synthesize an oligonucleotide fragment having 3 to 20 (e.g., 3 to 10, 3 to 8, 3 to 5 or 4 to 5) nucleotides with high purity without chromatographic purification. In some embodiments, the methods involve selective deprotection of 3'-hydroxyl protecting group. In some embodiments, the liquid phase process comprises (1) 5'-OH deprotection step, (2) coupling step, and (3) oxidization or sulfurization step, wherein the steps (1), (2) and (3) are repeated until the desired number of nucleotides are linked together to form the 5'-oligonucleotide fragment.

A fifty-second embodiment discloses a liquid phase process for preparing an oligonucleotide fragment of formula (II),

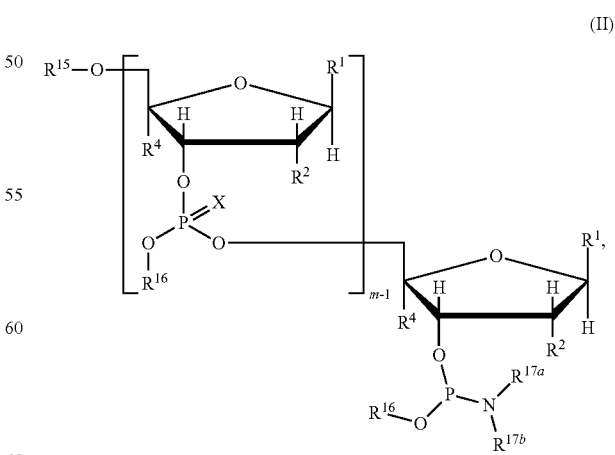

or a salt thereof, comprising the steps of:
1') deprotecting a compound of formula (IIA'):

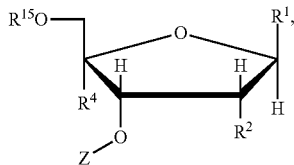

or a salt thereof, to form a compound of formula (IIA):

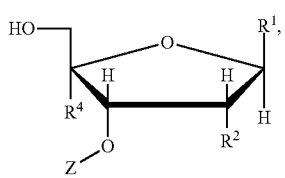

or a salt thereof;
2') reacting a compound of formula (IIA), or a salt thereof, with a compound of formula (A2):

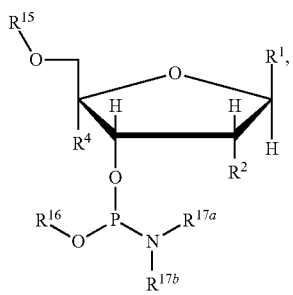

or a salt thereof, to form a compound of formula (IIB):

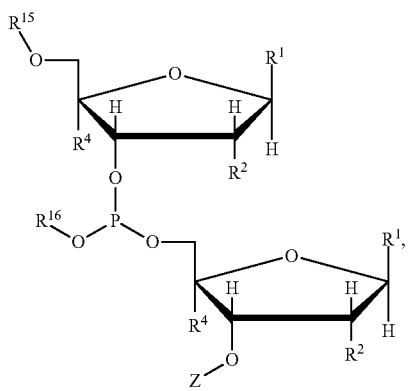

or a salt thereof; and
3') sulfurizing or oxidizing the compound of formula (IIB), or a salt thereof, with a sulfurization or oxidation agent to form a compound of formula (IIC):

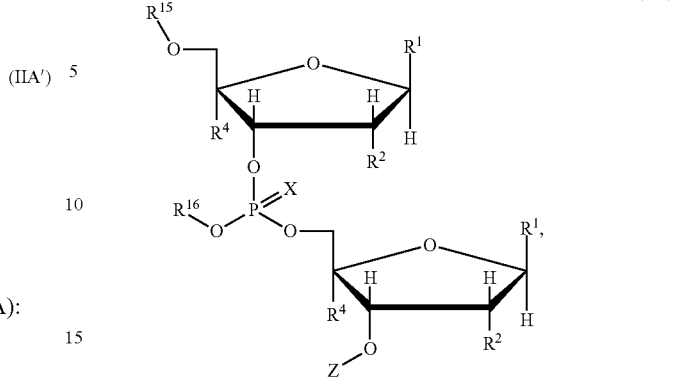

or a salt thereof,
4') deprotecting the compound of formula (IIC), or a salt thereof, to form a compound of formula (IID):

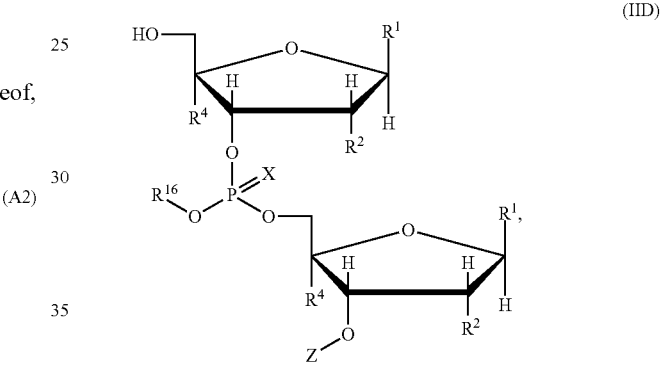

or a salt thereof;
5') when m is 3, starting with the compound of formula (IID), or a salt thereof, repeating step 2') and step 3') to form a compound of formula (IIE) or a salt thereof, or when m is greater than 3, starting with the compound of formula (IID), or a salt thereof, repeating the steps 2'), 3') and 4') for m−3 times, followed by step 2') and step 3') to from a compound of formula (IIE):

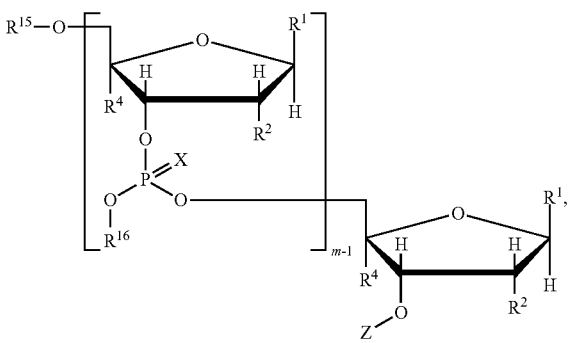

or a salt thereof;
6') deprotecting the compound of formula (IIE) or a salt thereof, to form a compound of formula (IIF):

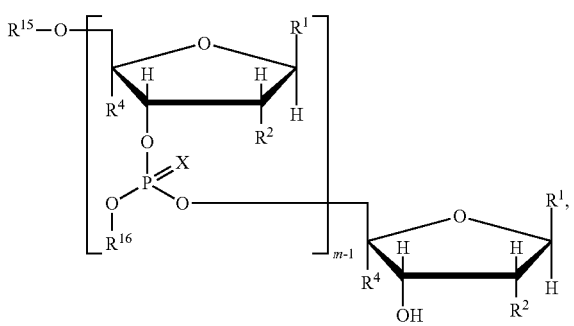

(IIF)

or a salt thereof; and

7') reacting the compound of formula (IIF), or a salt thereof, with a phosphordiamidite $(R^{16}O)P(NR^{17a}R^{17b})_2$ to yield the fragment of formula (II), or a salt thereof:

wherein:

$R^1$, for each occurrence, is independently a nucleobase, wherein the $NH_2$ of the nucleobase, if present, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group; $R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

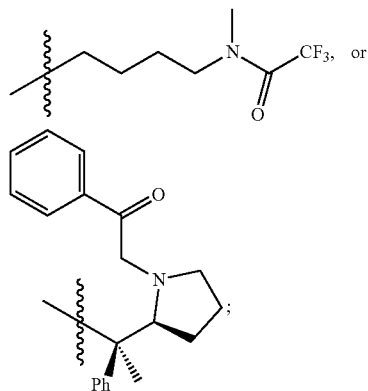

$R^{17a}$ and $R^{17b}$ are independently $C_{1-6}$alkyl;

m is an integer from 2 to 20;

X, for each occurrence, is independently O or S; and

Z is a hydroxyl silyl protecting group.

In a fifty-third embodiment, for the process described in the fifty-second embodiment, the fragment of formula (II) is not purified by chromatography (e.g. column chromatography).

A fifty-fourth embodiment discloses a process as described in the fifty-second or fifty-third embodiment, wherein the fragment of formula (II) is purified by extraction and/or selective precipitation as described herein (e.g., as described in twenty-first, thirty-five or forty-second embodiments).

A fifty-fifth embodiment discloses a process as described in fifty-second to fifty-fourth embodiments, wherein no chromatography is used for purifying the reaction product of any one of steps 1'), 2'), 3'), 4'), 5'), 6') and 7').

A fifty-sixth embodiment discloses a process as described in the fifty-second to fifty-fifth embodiments, wherein the reaction product of any one of steps 1'), 2') 3'), 4'), 5'), 6') and 7') is purified by extraction and/or selective precipitation as described herein (e.g., as described in twenty-first, thirty-five or forty-second embodiments).

In some embodiments, the deprotection reactions of step 1') and step 4') are carried out as described in the first aspect or any embodiments described therein (e.g., any one of the second to twelfth embodiments).

In some embodiments, the coupling reaction of step 2') is carried out as described in the fourth aspect. In certain embodiments, the coupling reaction is carried out in the presence of an activator described herein (e.g. activators described in the thirty-ninth embodiment). In certain embodiments, the activator is 4,5-dicyanoimidazole (DCI) or 5-ethylthio-1H-tetrazole (ETT).

In some embodiments, the sulfurization or oxidation reaction of step 3') is carried out as described in the fourth aspect.

In some embodiments, the deprotection reaction of step 6') is carried out as described in the second aspect or any embodiments described therein (e.g., any one of the twenty-sixth to thirty-fourth embodiments).

In some embodiments, the phosphitylation reaction of step 7') is carried out as described in the third aspect or any embodiments described therein (e.g., any one of the thirty ninth to forty-second embodiments).

II. Synthesis of Target Oligonucleotides i) 3'-5' elongation:

In a sixth aspect, the present disclosure describes a liquid phase convergent synthesis of target oligonucleotides, wherein the target oligonucleotide is assembled in the direction of the 3'-terminal to the 5'-terminal (3'-5' direction). It has been demonstrated that the convergent liquid phase process of the present disclosure is successfully used to synthesize target oligonucleotides in large quantities. In addition, high purity protected target oligonucleotide can be obtained by the methods of the present disclosure without chromatographic purification.

In certain embodiments, the convergent liquid phase process described herein involves step by step addition of oligonucleotide fragments in liquid (solution) phase to synthesize the target oligonucleotide. For example, 5-mer and 4-mer fragments are coupled first to synthesize a 9-mer fragment which is further reacted with another 5-mer fragment to synthesize 14-mer oligonucleotide. The 14-mer oligonucleotide can be further coupled with another fragment until the desired length of the target oligonucleotide is obtained. In certain embodiments, a 5-mer fragment having a 3'-hydrophobic hydroxyl protecting group (3'-LHPG) (3'-end fragment) is first coupled with 5-mer fragment to form a 10-mer fragment having 3'-LHPG group, which is then further reacted with a 4-mer fragment to form a 14-mer fragment, which is in turn coupled with another 4-mer fragment to form the target 18-mer oligonucleotide. In certain embodiments, the 3'-end fragment having n nucleotides (e.g. 5-mer fragment) is synthesized by coupling a single nucleotide having the 3'-LHPG group with a fragment having n−1 nucleotides (e.g., 4-mer fragment).

A fifty-seventh embodiment discloses a convergent liquid phase process for preparing a target oligonucleotide comprising the steps of:

a) coupling an oligonucleotide fragment of formula (I):
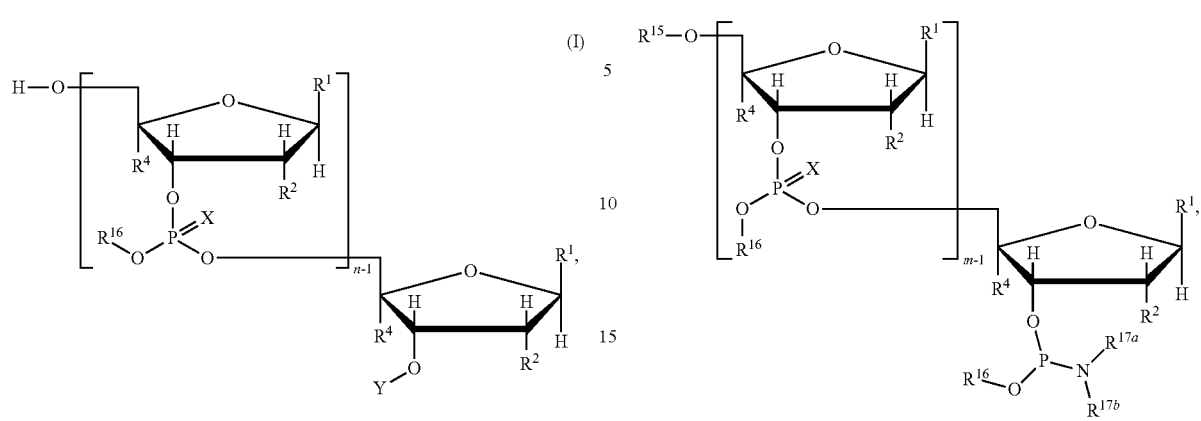
or a salt thereof, with an oligonucleotide fragment of formula (I):
or a salt thereof, in a solution to form an oligonucleotide of formula (III):
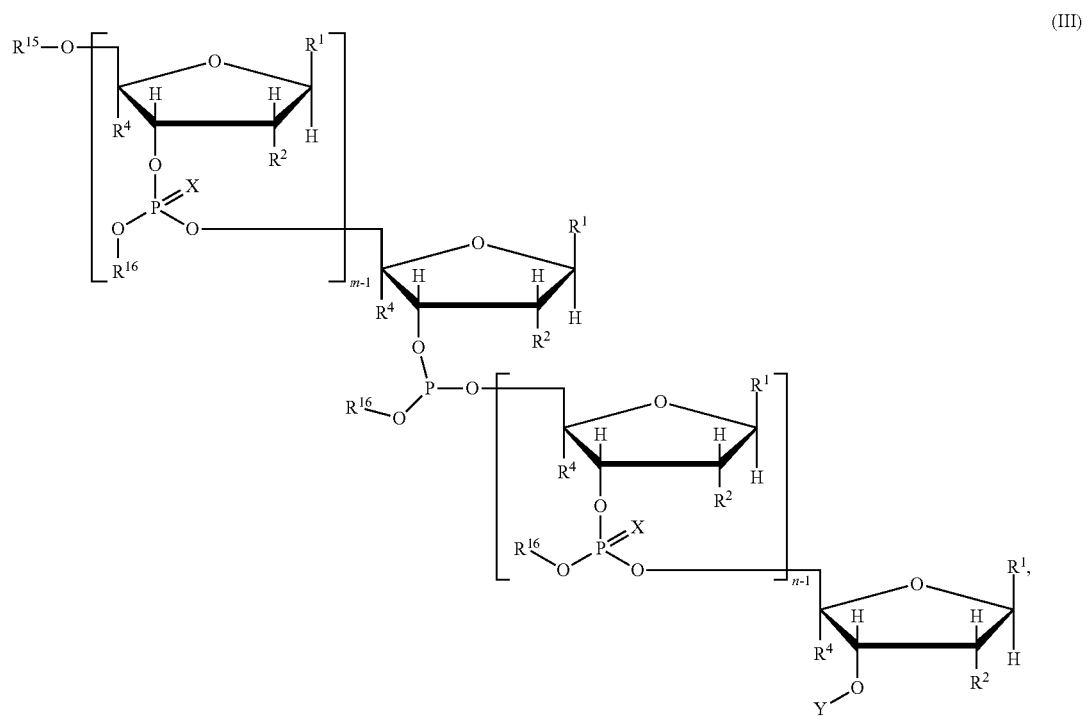
or a salt thereof; and b) sulfurizing or oxidizing the oligonucleotide of formula (III), or a salt thereof, to form an oligonucleotide of formula (IV):

$R^{17a}$ and $R^{17b}$ are independently $C_{1-6}$alkyl;
n is an integer from 2 to 200;
m is an integer from 2 to 20

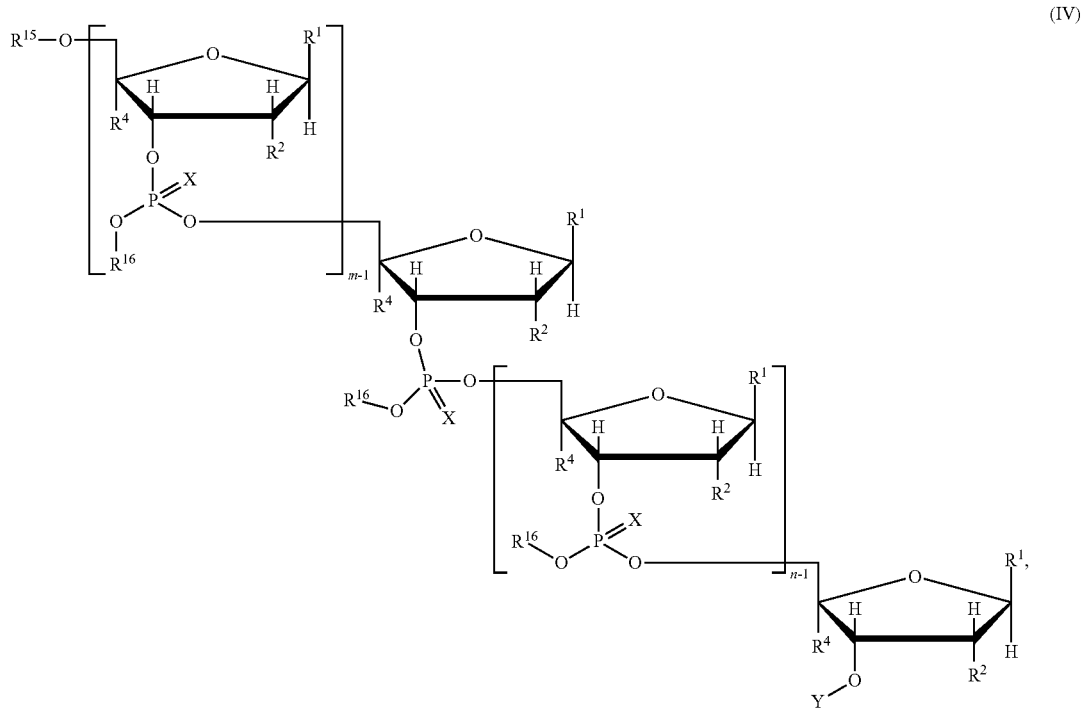

(IV)

or a salt thereof, wherein:

$R^1$, for each occurrence, is independently a nucleobase, wherein the $NH_2$ of the nucleobase, if present, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

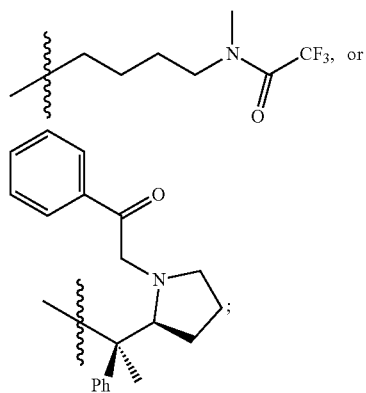

X, for each occurrence, is independently O or S;

Y is a hydrophobic hydroxyl protecting group containing an alkyl chain.

Also included in the fifty-seventh embodiment is a convergent liquid phase process for preparing a target oligonucleotide comprising the steps of: a) coupling an oligonucleotide fragment of formula (I):

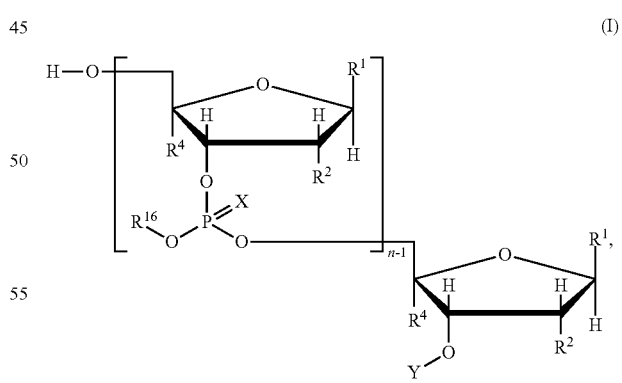

(I)

or a salt thereof, with an oligonucleotide fragment of formula ($II^a$):

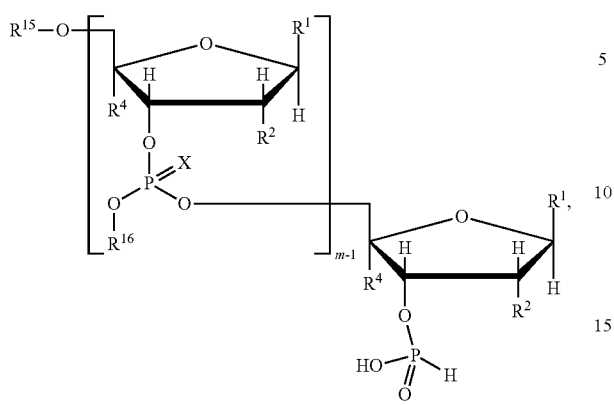

(II$^a$)

or a salt thereof, in a solution to form an oligonucleotide of formula (III'):

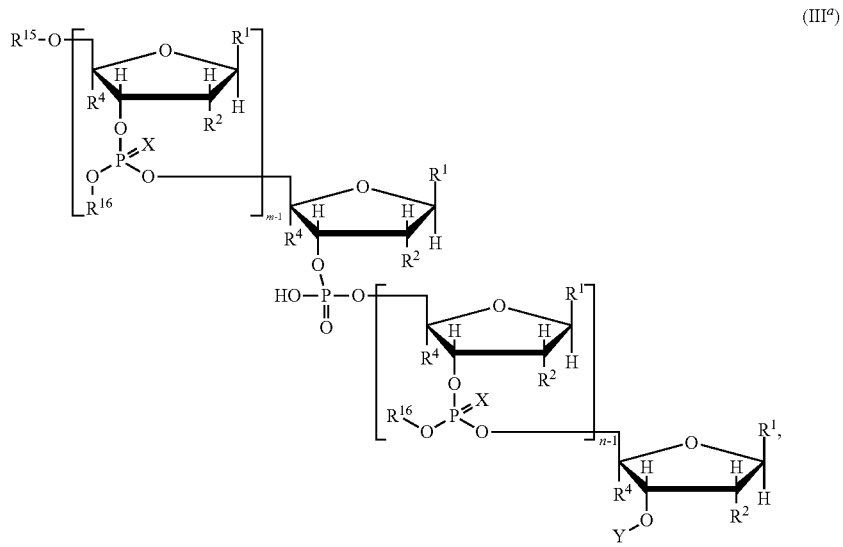

(III$^a$)

or a salt thereof; wherein:

$R^1$, for each occurrence, is independently a nucleobase, wherein the NH$_2$ of the nucleobase, if present, is protected by an amine protecting group;

$R^2$, for each occurrence, is independently selected from the group consisting of H, halo, and C$_{1-6}$alkoxy optionally substituted with C$_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently C$_{1-6}$alkyl group, C$_{2-6}$alkenyl group, phenyl or benzyl group, each of which is optionally substituted with —CN, —NO$_2$ or halogen; or $R^{16}$ is

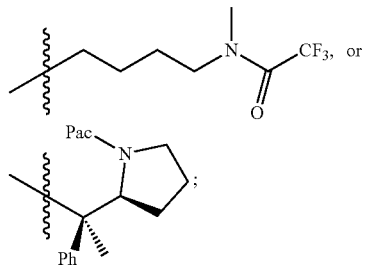

n is an integer from 2 to 200;

m is an integer from 2 to 20

X, for each occurrence, is independently O or S;

Y is a hydrophobic hydroxyl protecting group containing an alkyl chain.

A fifty-eighth embodiment discloses a process described in the fifty-seventh embodiment, wherein the fragment of formula (I) can be synthesized by coupling a nucleotide of formula (Ia1):

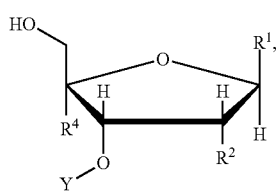

(Ia1)

or a salt thereof, with an oligonucleotide fragment of formula (Ia2):

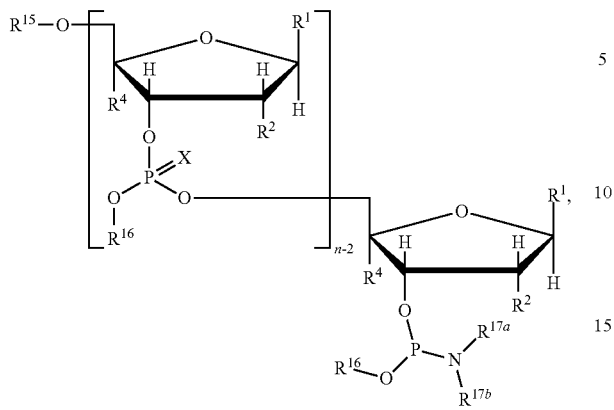

(Ia2)

or a salt thereof, in a solution to form the oligonucleotide fragment of formula (I) or a salt thereof.

In certain embodiments, for the process described in the fifty-eighth embodiment, n is an integer from 3 to 20. In a specific embodiment, n is 3 to 6. In another specific embodiment, n is 5.

In certain embodiments, for the process described in the fifty-eighth embodiment, the fragment (I) is not purified by chromatography. In another embodiment, the fragment (I) is purified by selective precipitation and/or extraction (e.g. as described in forty-sixth and forty-seventh embodiments).

A fifty-ninth embodiment discloses a process as described in the fifty-seventh or fifty-eighth embodiment, further comprising step c) of deprotecting the oligonucleotide of formula (IV), or a salt thereof, to form an oligonucleotide of formula (V):

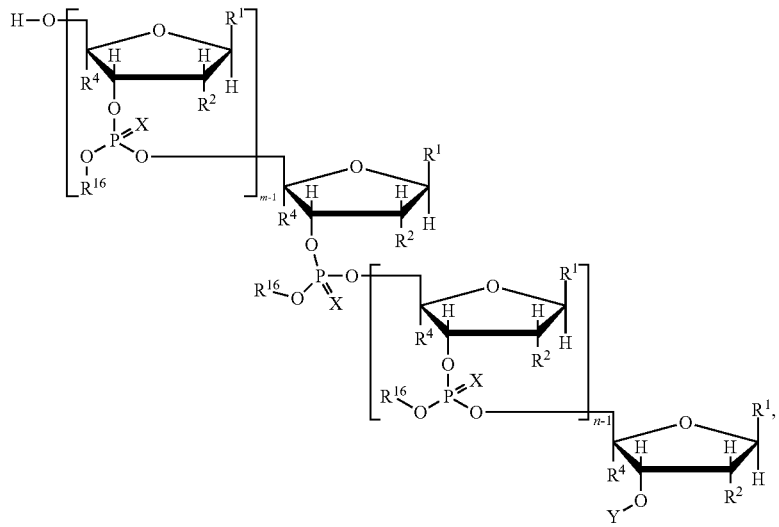

(V)

or a salt thereof.

Also provided in the fifty-ninth embodiment is a process as described in the fifty-seventh or fifty-eighth embodiment, further comprising step b) of deprotecting the oligonucleotide of formula (III$^a$), or a salt thereof, to form an oligonucleotide of formula (V$^a$):

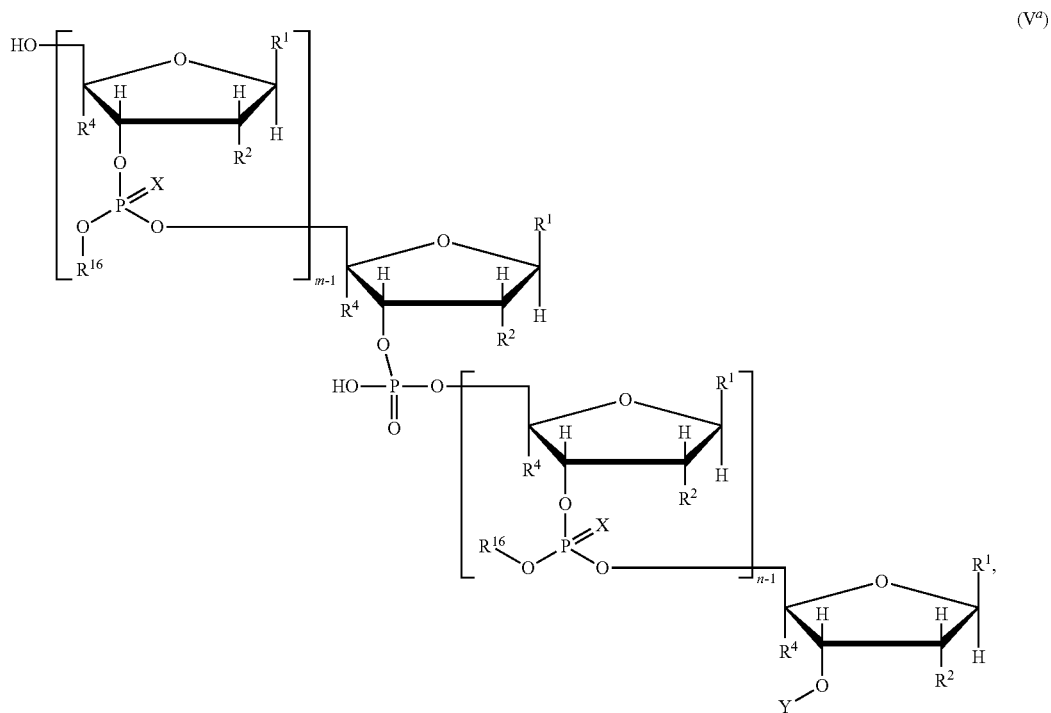
(V$^a$)
or a salt thereof.
A sixtieth embodiment discloses a process described in the fifty-ninth embodiment, further comprising: d) coupling the oligonucleotide of formula (V), or a salt thereof, with an oligonucleotide fragment of formula (II'):
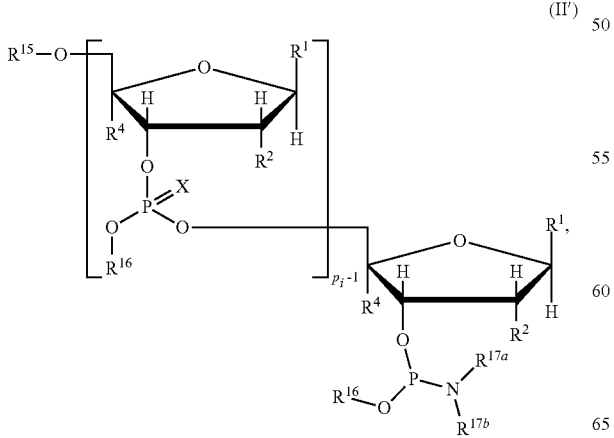
(II')

or a salt thereof to form an oligonucleotide of formula (VI):
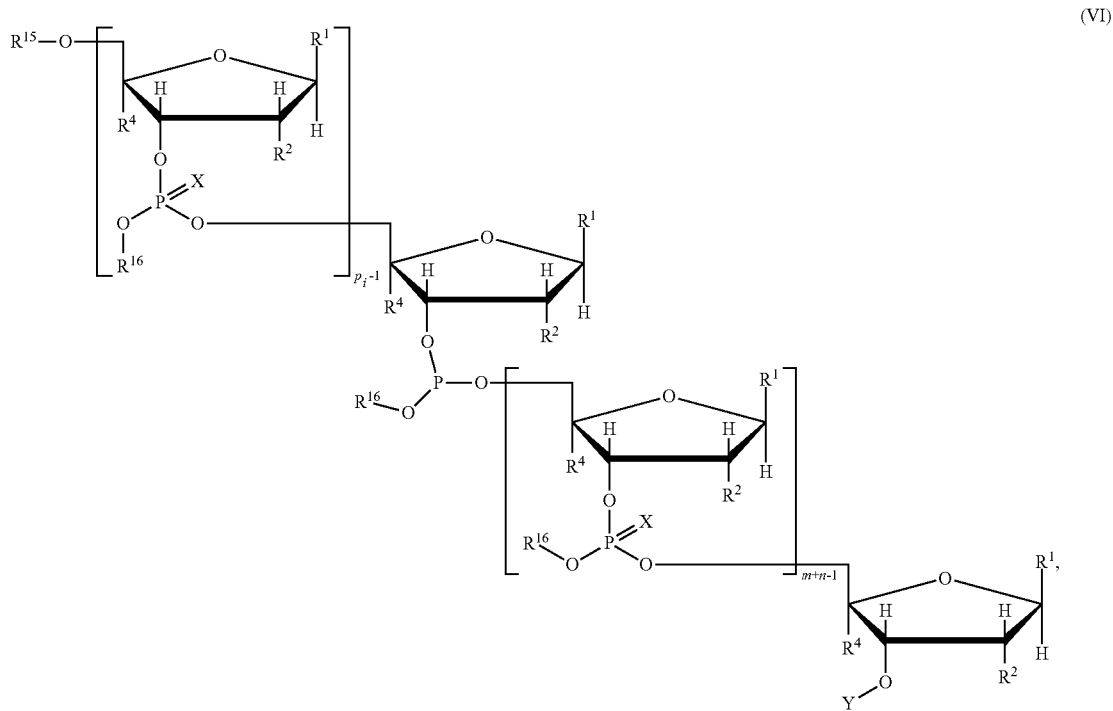
or a salt thereof,
e) sulfurizing or oxidizing the oligonucleotide of formula (VI) to form an oligonucleotide of formula (VII):
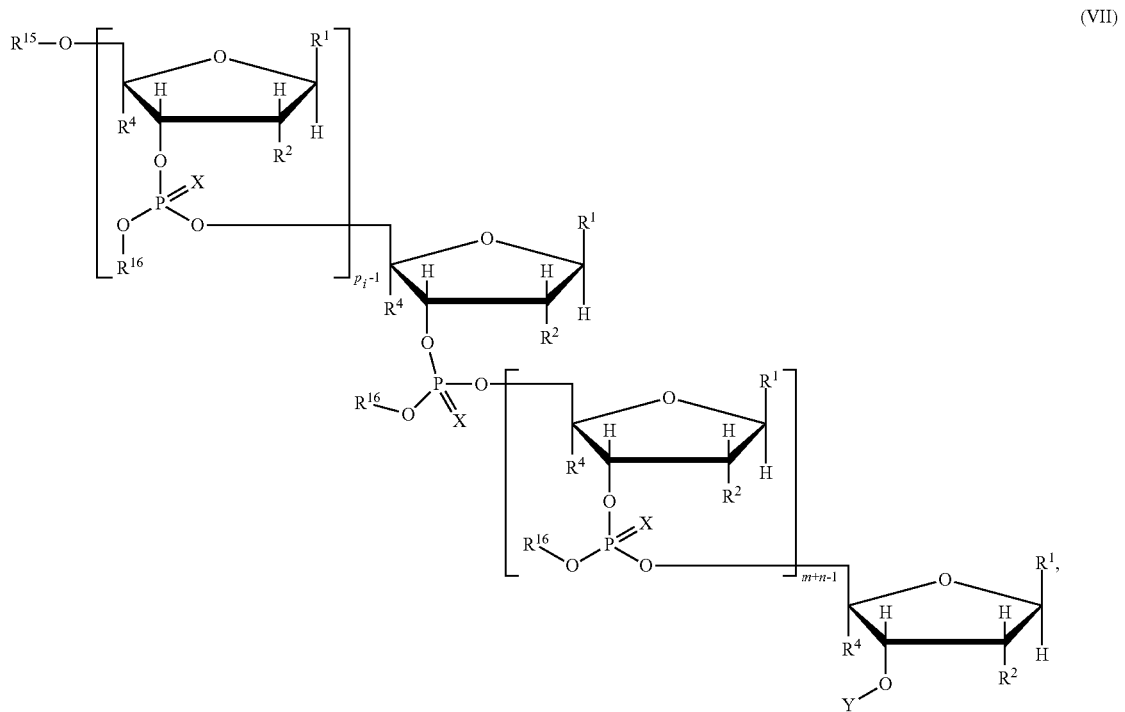
or a salt thereof, f) deprotecting the oligonucleotide of formula (VII), or a salt thereof, to form an oligonucleotide of formula (VIII):

(VIII)

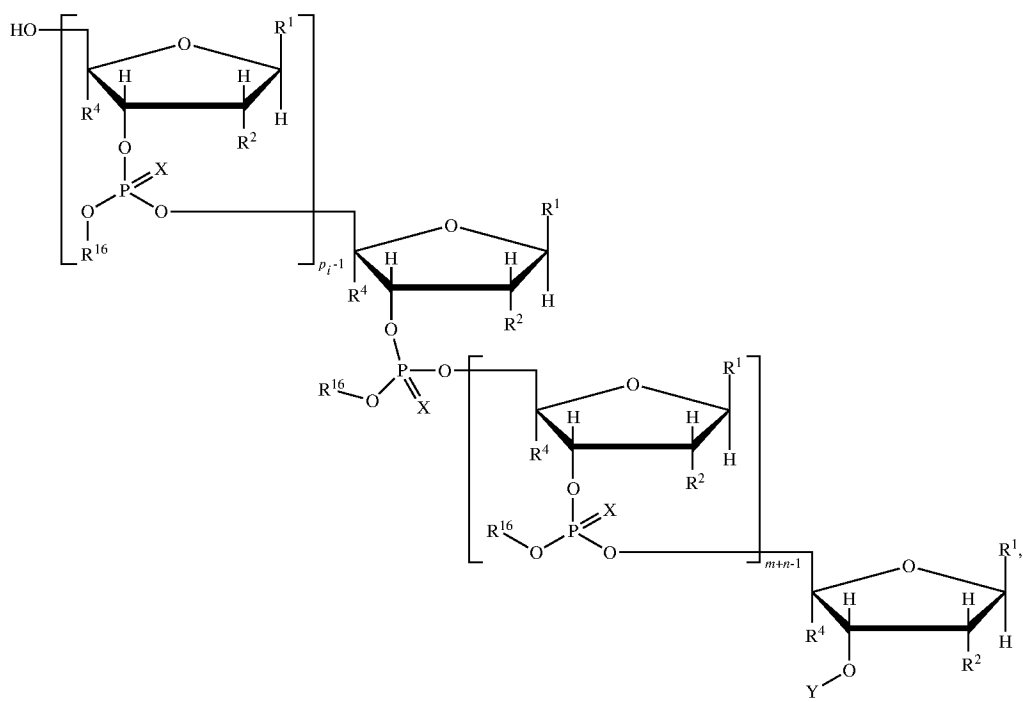

or a salt thereof, g) repeating the steps of d), e) and f) for r−1 times followed by repeating the steps of d) and e) to form an oligonucleotide of formula (IX):

(IX)

or a salt thereof wherein:

r is an integer from 1 to 50;

$p_i$, for each occurrence, is independently an integer from 2 to 20, i is an integer from 1 to r; and $$p_{total} = \sum_{i=1}^{r} p_i.$$

A sixty-first embodiment discloses a process as described in sixtieth embodiment, wherein r is 2 and the oligonucleotide of formula (IX) is represented by formula (X):

(X)

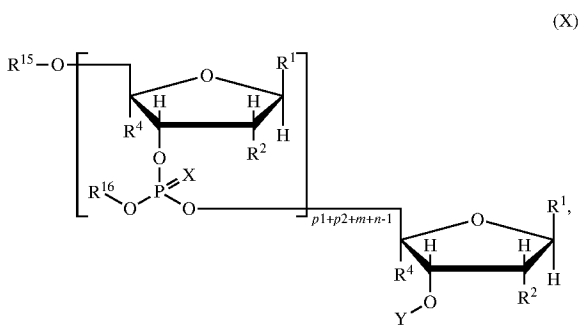

wherein p1 and p2 are each independently an integer from 2 to 20. In certain embodiments, m, n, p1 and p2 are each independently an integer from 3 to 10, 3 to 6 or 4 to 6. In certain embodiments, m, n, p1 and p2 are each independently 4 or 5. In certain embodiments, m and n are both 5; and p1 and p2 are both 4.

A sixty-second embodiment discloses a process described in the fifty-seventh to sixty-first embodiments, wherein no chromatography (e.g. column chromatography) is used for purifying the reaction product of any one of steps a), b), c), d), e), f) and g).

A sixty-third embodiment discloses a process described in fifty-seventh to sixty-second embodiments, wherein the reaction product of any one of steps a), b), c), d), e), f) and g) is purified by extraction and/or selective precipitation as described herein (e.g. as described in the twenty-first, thirty-five, forty-two, forty-sixth and forty-seventh embodiments).

In certain embodiments, the process described in the sixtieth to sixty-third embodiments, the process further comprises the step of:

h1) deprotecting oligonucleotide (IX) or (X) to form oligonucleotide of formula (IXA) or (XA):

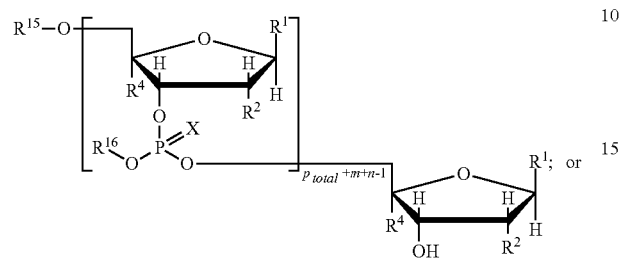

(IXA)

or a salt thereof.

In certain embodiments, the process described in the sixtieth to sixty-third embodiments, the process further comprises the step of:

h1) deprotecting oligonucleotide (IX) or (X) or a salt thereof to form oligonucleotide of formula (IXA) or (XA):

(IXA)

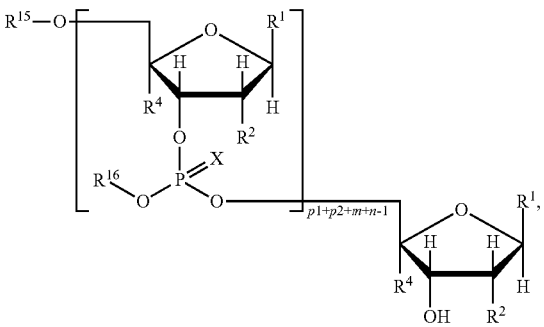

(XA)

or a salt thereof;

h2) deprotecting oligonucleotide (IXA) or (XA) or a salt thereof to form oligonucleotide of formula (IXB) or (XB):

(IXB)

(XB)

or a salt thereof.

In certain embodiments, for step hi) described above, the oligonucleotide of formula (IXA) or (XA) is obtained by reacting the oligonucleotide of formula (IX) or (X) with NH$_4$OH. In certain embodiments, treatment with NH$_4$OH also removes other protecting group in the oligonucleotides, such as protecting groups in any nucleobases (e.g., the NH$_2$ protecting group on a nucleobase). In certain embodiments, treatment with NH$_4$OH results in oligonucleotides of formula (IXA) or (XA) or a salt thereof, wherein $R^1$, for each occurrence, is independently a nucleobase, wherein the NH$_2$ of the nucleobase, if present, is unprotected.

In sixty-fourth embodiment, the process described in the sixtieth to sixty-third embodiments, wherein when $R^{16}$ is —CH$_2$CH$_2$CN, deprotecting the oligonucleotide (IX) or (X) or a salt thereof forms an oligonucleotide of formula (IXAb) or (XAb):

(IXAb)

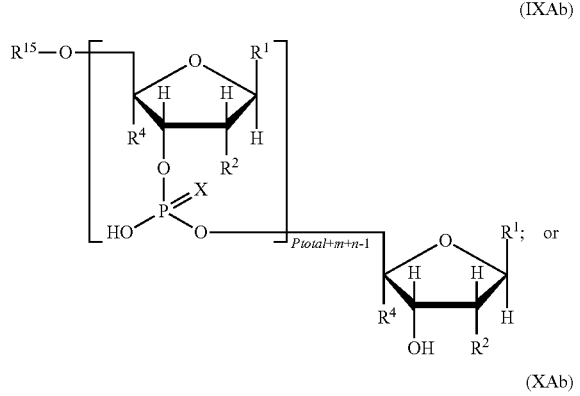

(XAb)

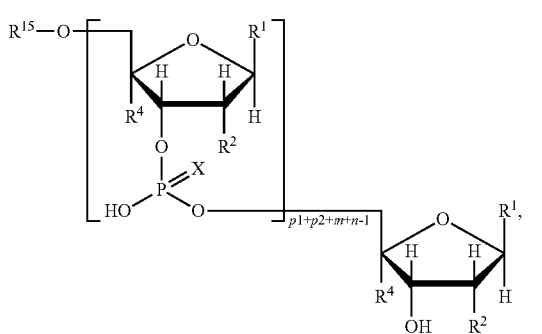

or a salt thereof. In certain embodiments, the deprotection reaction is carried out by reacting the oligonucleotide (IX) or (X) or a salt thereof with NH$_4$OH to form the oligonucleotide of formula (IXAb) or (XAb). In certain embodiments, treatment with NH$_4$OH also removes other protecting group in the oligonucleotides, such as protecting groups in any nucleobases (e.g., the NH$_2$ protecting group on a nucleobase). In certain embodiments, treatment with NH$_4$OH results in oligonucleotides of formula (IXAb) or (XAb) or a salt thereof, wherein R$^1$, for each occurrence, is independently a nucleobase, wherein the NH$_2$ of the nucleobase, if present, is unprotected.

In certain embodiments, in the process described in sixty-fourth embodiment, the process further comprises the step of:
deprotecting the oligonucleotide (IXAb) or (XAb) or a salt thereof to form an oligonucleotide of formula (IXBa) or (XBa):

(IXBa)

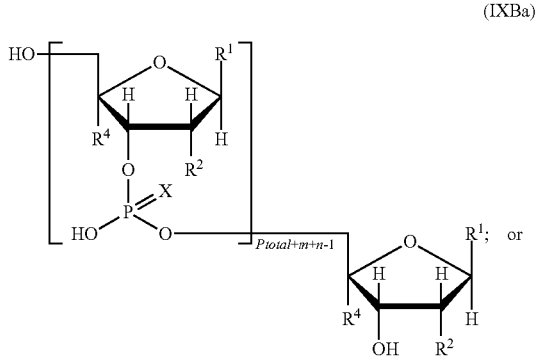

(XBa)

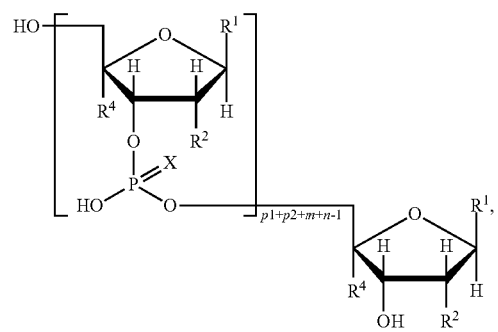

or a salt thereof. In certain embodiments, the oligonucleotide (IXA) or (XA) is reacted with citric acid to form the oligonucleotide of formula (IXBa) or (XBa).

In sixty-fifth embodiment, in the process described in the sixtieth to sixty-third embodiments, wherein R$^{16}$ is —CH$_2$CH$_2$CN, the process further comprises the step of:
h1) deprotecting the oligonucleotide (IX) or (X) to form an oligonucleotide of formula (IXAa) or (XAa):

(IXAa)

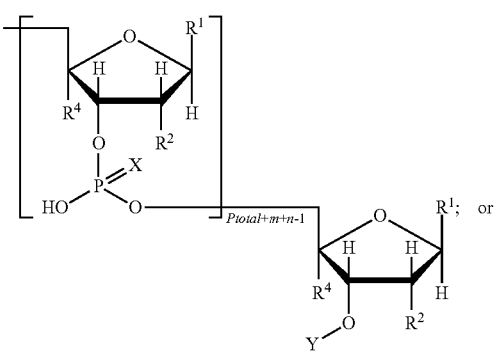

(XAa)

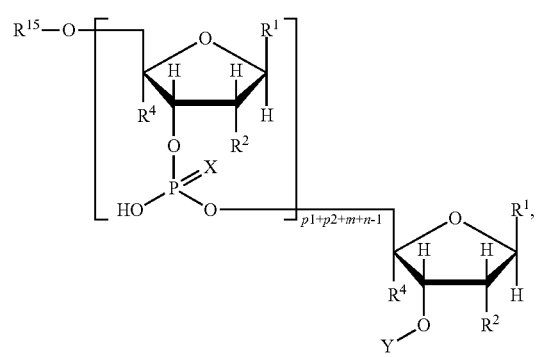

or a salt thereof.

In certain embodiments, in the process of sixty-fifth embodiment, the deprotection reaction is carried out by reacting the oligonucleotide (IX) or (X) or a salt thereof with a base. In certain embodiments, the base is selected from 1,8-diazabicyclo[5.4.0]undec-7-ene, alkylamine (e.g., tert-butylamine, sec-butylamine, diisopropylethylamine, trimethylamine) and other suitable organic bases.

A sixty-sixth embodiment discloses a process described in sixty-fifth embodiment, wherein the method further comprises the step of deprotecting the oligonucleotide (IXAa) or (XAa) or a salt thereof to form an oligonucleotide of formula (IXAb) or (XAb):

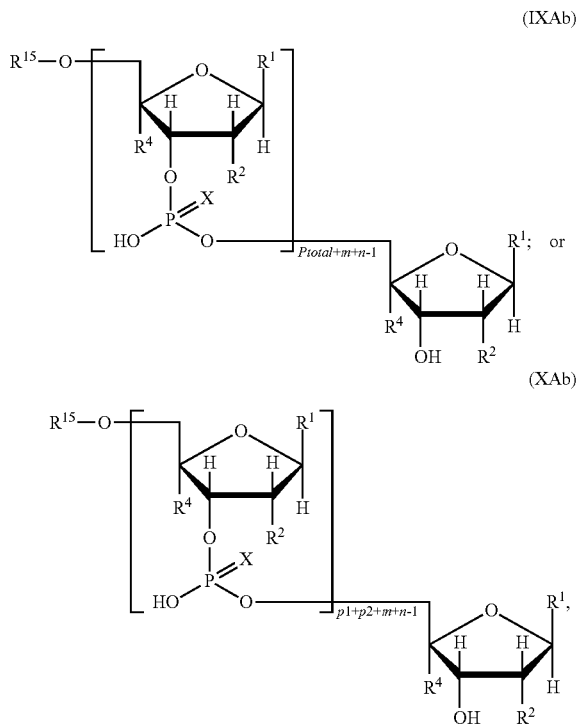

or a salt thereof.

In certain embodiments, in the process described in sixty-sixth embodiment, the deprotection of the oligonucleotide (IXAa) or (XAa) or a salt thereof is carried out by reacting the oligonucleotide (IXAa) or (XAa) or a salt thereof with NH$_4$OH. In certain embodiments, treatment with NH$_4$OH also removes other protecting group in the oligonucleotides, such as protecting groups in any nucleobases (e.g., the NH$_2$ protecting group on a nucleobase). In certain embodiments, treatment with NH$_4$OH results in oligonucleotides of formula (IXAb) or (XAb) or a salt thereof, wherein R$^1$, for each occurrence, is independently a nucleobase, wherein the NH$_2$ of the nucleobase, if present, is unprotected.

In certain embodiments, the oligonucleotide (IXAb) or (XAb) or a salt thereof can further react with a deprotecting reagent (e.g., de-tritylation reagent) to form the oligonucleotide of formula (IXBa) or (XBa) or a salt thereof.

In one embodiment, for processes described in the sixth aspect or any embodiments described therein (e.g., the fifty-seventh to sixty-sixth embodiments), Y is:

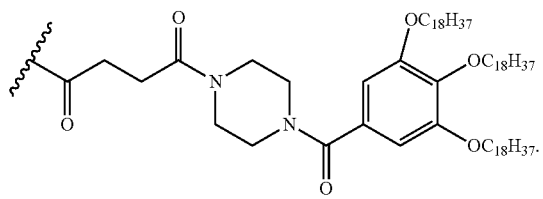

In certain embodiments, the oligonucleotide of formula (IXA) or (XA) obtained from step h1) or the oligonucleotide of formula (IXAb) or (XAb) is purified by depth filtration. In one embodiment, the reaction mixture of step h1) is diluted with ammonium sulfate solution before being subjected to depth filtration. Dilution with ammonium sulfate may prevent the oligonucleotide from sticking to the filter.

In certain embodiments, the concentration for the ammonium sulfate solution is between 100 mM and 5M, between 500 mM and 2M, between 500 mM and 1500 mM, or between 1000 mM and 1200 mM.

Any suitable depth filters can be used for depth filtration. As used herein, the term "depth filter" refers to filters that use a porous filtration medium to retain particles through the medium, rather than just on the surface of the medium. These filters are commonly used when the fluid to be filtered contains a high load of particles because, relative to other types of filters, they can retain a large mass of particles before becoming clogged. It is surprisingly found that depth filtration can efficiently remove the by-product LHPG-OH (e.g. Y—OH) from the reaction mixture before subjecting the mixture to HIC purification.

In certain embodiments, depth filters comprises a filter aid, such as diatomaceous earth, cellulose, polyacrylic fiber and silica, and activated carbon.

In certain embodiments, the oligonucleotide of formula (IXA), (IXAb), (XA) or (XAb) obtained from step h1) is purified by depth filtration followed by hydrophobic interaction chromatography (HIC).

In certain embodiment, for step h2) described above, the oligonucleotide of formula (IXA), (IXAa), (IXAb), (XA), (XAa) or (XAb) is reacted with a detritylation reagent described herein to form the oligonucleotide of formula (IXB), (IXBa), (XB) or (XBa). In one embodiment, the detritylation reagent is an organic acid. In one embodiment, the organic acid is acetic acid or citric acid. In a specific embodiment, the detritylation reagent is citric acid. In one embodiment, R$^{15}$ in formula (IXA), (IXAa), (IXAb), (XA), (XAa) or (XAb) is a 4,4'-dimethoxytrityl group. In certain embodiments, the detritylation reaction of step h2) is carried out in an aqueous solution.

In certain embodiment, the oligonucleotide of formula (IXB), (IXBa), (XB) or (XBa) obtained from step h2) is purified by anion exchange chromatography.

A sixty-seventh embodiment discloses a process described in fifty-seventh to sixty-sixth embodiments, wherein the fragment (I) is obtained by:

1) deprotecting a compound of formula (I'A):

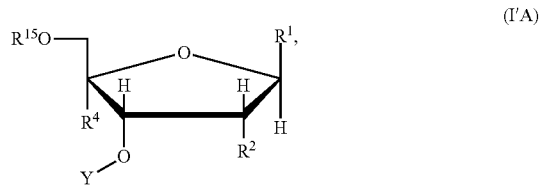

or a salt thereof, to form a compound of formula (IA):

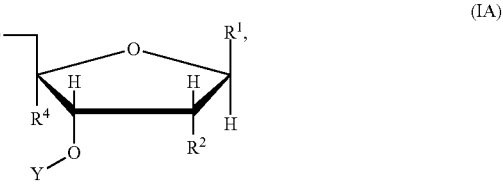

or a salt thereof;

2) reacting the compound of formula (IA), or a salt thereof, with a compound of formula (A1):

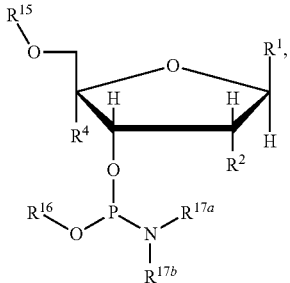

(A1)

or a salt thereof, to form a compound of formula (IB):

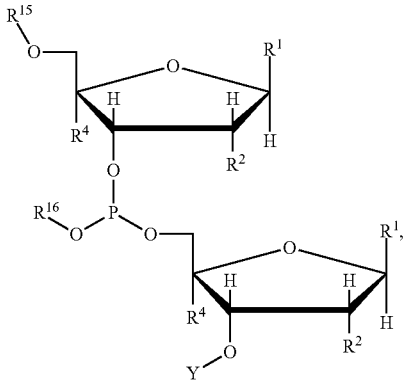

(IB)

or a salt thereof; and 3) sulfurizing or oxidizing the compound of formula (IB), or a salt thereof, with a sulfurization or oxidation agent to form a compound of formula (IC):

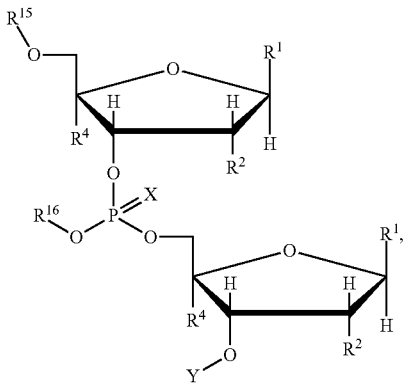

(IC)

or a salt thereof;

4) deprotecting the compound of formula (IC), or a salt thereof to form a compound of formula (ID):

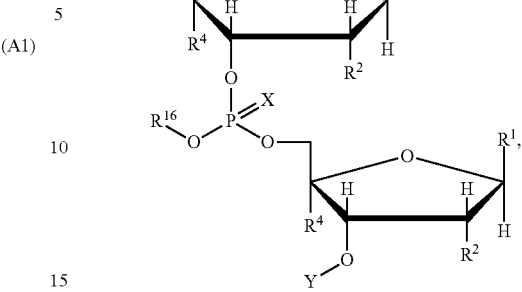

(ID)

or a salt thereof;

5) starting with the compound of formula (ID), repeating steps 2) 3) and 4) for n–2 times to yield the fragment of formula (I), or a salt thereof.

A sixty-eighth embodiment discloses a process described in the sixty-seven embodiments, wherein no chromatography (e.g., column chromatography) is used for purifying the reaction product of any one of steps 1), 2), 3), 4) and 5).

A sixty-ninth embodiment discloses a process described in the sixty-seven or sixty-eighth embodiment, wherein the reaction product of any one of steps 1), 2), 3), 4) and 5) is purified by extraction and/or selective precipitation as described herein (e.g., as describe in the twenty-first, thirty-five, forty-two, forty-sixth or forty-seventh embodiments).

A seventieth embodiment discloses a process described in the fifty-seventh to sixty-ninth embodiments, wherein Y is represented by the following formula:

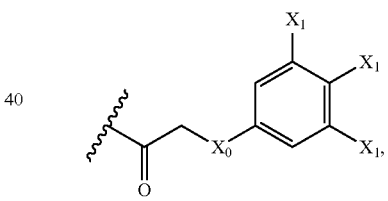

wherein $X_0$ is $C_{1-10}$alkyl, wherein one or more $CH_2$ groups are independently replaced with C(O), C(O)NH$_2$, cycloalkyl or heterocyclyl group; and $X_1$ is $C_{1-25}$alkyl or $C_{1-25}$alkoxy. In a specific embodiment, Y is represented by the following formula:

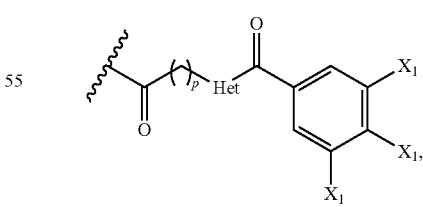

wherein p is an integer from 1 to 10; Het is a saturated heterocycle; and the remaining variables are as described above. In a more specific embodiment, Het is piperazine.

A seventy-first embodiment discloses a process described in the fifty-seventh to sixty-ninth embodiments, wherein Y is:

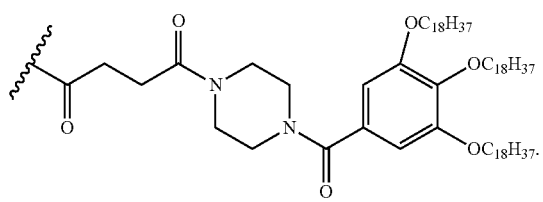

A seventy-second embodiment discloses a process described in fifty-seventh to seventy-first embodiments, wherein the fragment of formula (II) is obtained by:

1') deprotecting a compound of formula (IIA'):

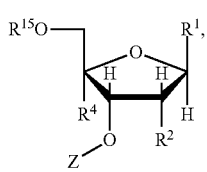
(IIA')

or a salt thereof, to form a compound of formula (IIA):

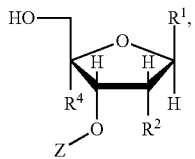
(IIA)

or a salt thereof;

2') reacting a compound of formula (IIA), or a salt thereof, with a compound of formula (A2):

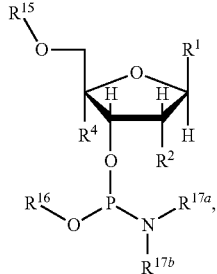
(A2)

or a salt thereof, to form a compound of formula (IIB):

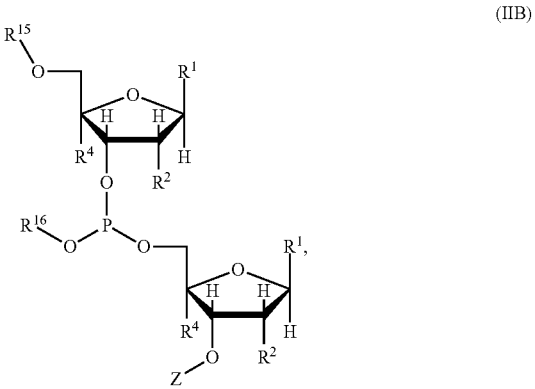
(IIB)

or a salt thereof; and

3') sulfurizing or oxidizing the compound of formula (IIB), or a salt thereof, with a sulfurization or oxidation agent to form a compound of formula (IIC):

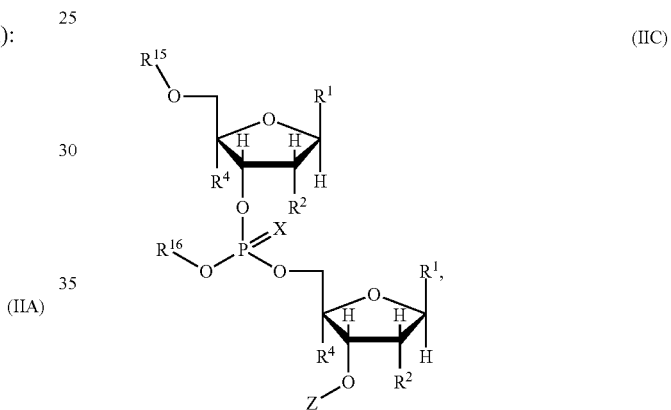
(IIC)

or a salt thereof,

4') deprotecting the compound of formula (IIC), or a salt thereof, to form a compound of formula (IID):

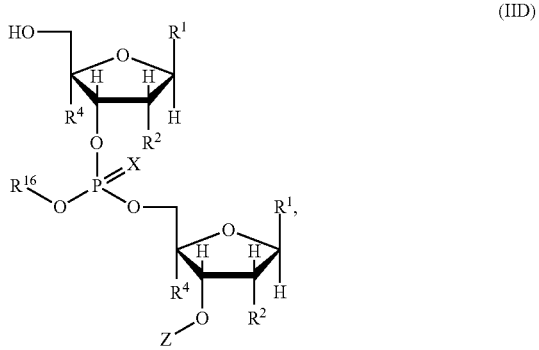
(IID)

or a salt thereof;

5') when m is 3, starting with the compound of formula (IID), or a salt thereof, repeating step 2') and step 3') to form a compound of formula (IIE) or a salt thereof, or when m is greater than 3, starting with the compound of formula (IID), or a salt thereof, repeating the steps 2'), 3') and 4') for m−3 times, followed by step 2') and step 3') to from a compound of formula (IIE):

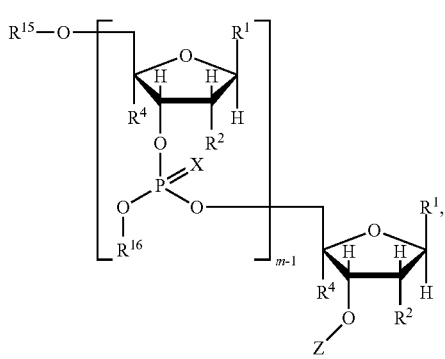

(IIE)

or a salt thereof;

6') deprotecting the compound of formula (IIE), or a salt thereof, to form a compound of formula (IIF):

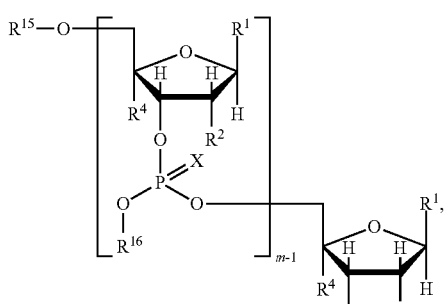

(IIF)

or a salt thereof; and

7') reacting the compound of formula (IIF), or a salt thereof, with a phosphordiamidite $(R^{16}O)P(NR^{17a}R^{17b})_2$ to yield the fragment of formula (II), or a salt thereof, wherein Z is a hydroxyl protecting group.

A seventy-third embodiment discloses a process described in seventy-second embodiment, wherein the fragment of formula (II) is not purified by chromatography before reacting with fragment of formula (I).

A seventy-fourth embodiment discloses a process described in seventy-second or seventy-third embodiment, wherein the reaction product of any one of steps 1'), 2'), 3'), 4'), 5'), 6') and 7') is purified by extraction and/or selective precipitation (e.g., as described in the twenty-first, thirty-five, forty-two, forty-sixth or forty-seventh embodiment).

A seventy-fifth embodiment discloses a process described in fifty-ninth to seventy-fourth embodiment, wherein the fragment of formula (II') is prepared by:

1") deprotecting a compound of formula (II'A'):

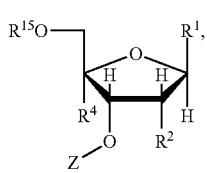

(II'A')

or a salt thereof, to form a compound of formula (II'A):

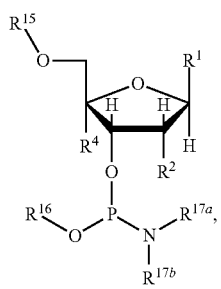

(II'A)

or a salt thereof,

2") reacting a compound of formula (II'A), or a salt thereof, with a compound of formula (A2):

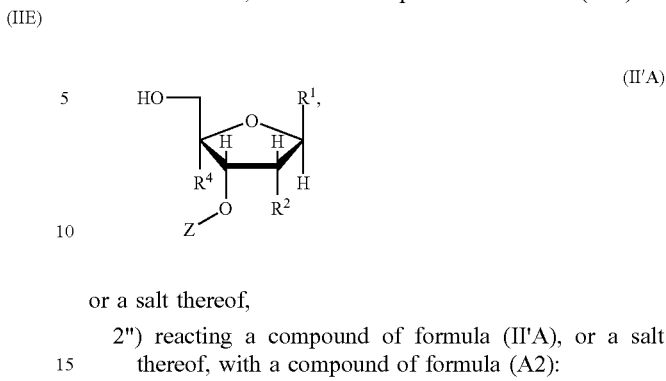

(A2)

or a salt thereof, to form a compound of formula (II'B):

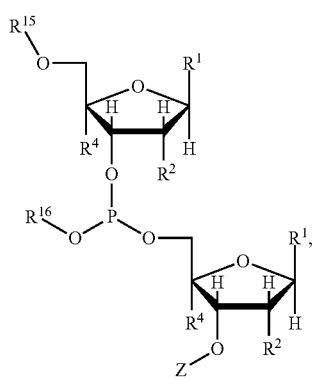

(II'B)

or a salt thereof; and

3") sulfurizing or oxidizing the compound of formula (II'B), or a salt thereof, with a sulfurization or oxidation agent to form a compound of formula (II'C):

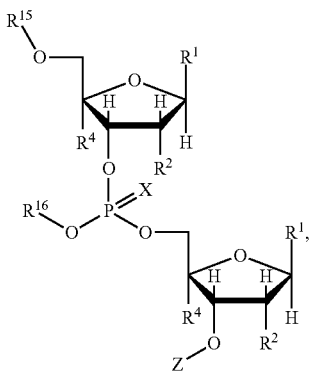

or a salt thereof,

4") deprotecting the compound of formula (II'C), or a salt thereof, to form a compound of formula (II'D):

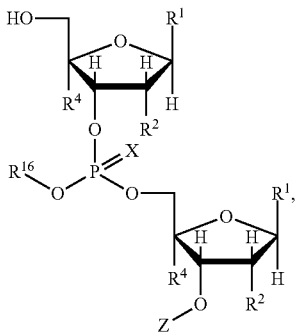

or a salt thereof;

5") starting with the compound of formula (II'D), or a salt thereof, repeating the steps 1'), 2') and 3') for $p_i$-2 times, followed by step 1') and step 2') to from a compound of formula (II'E):

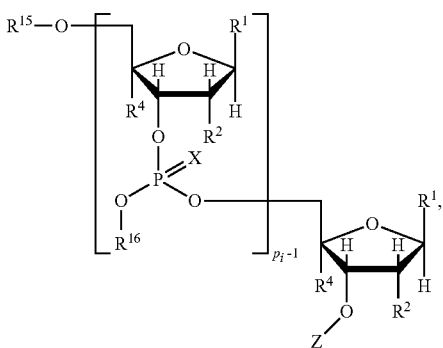

or a salt thereof;

6") deprotecting the compound of formula (II'E), or a salt thereof, to form a compound of formula (II'F):

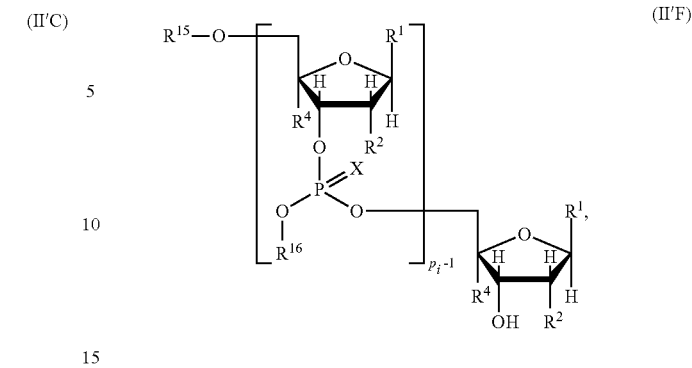

or a salt thereof;

7") reacting the compound of formula (II'F), or a salt thereof, with a phosphordiamidite $(R^{16}O)P(NR^{17a}R^{17b})_2$ to yield the fragment of formula (II'), or a salt thereof, wherein Z is a hydroxyl protecting group.

A seventy-sixth embodiment discloses a process described in the seventy-fifth embodiment, wherein the fragment of formula (II') is not purified by chromatography (column chromatography) before reacting with oligonucleotide of formula (V).

A seventy-seventh embodiment discloses a process described in the seventy-fifth or seventy-sixth embodiment, wherein the reaction product of any one of steps 1"), 2"), 3"), 4"), 5"), 6") and 7") is purified by extraction and/or selective precipitation as described herein (e.g., as described in the twenty-first, thirty-five, forty-two, forty-sixth or forty-seventh embodiment).

A seventy-eighth embodiment discloses a process of any one of the fifty-seventh to seventy-seventh embodiments, wherein n is 3, 4, 5 or 6.

A seventy-ninth embodiment discloses a process of any one of the fifty-seventh to seventy-eighth embodiments, wherein m is 3, 4, 5 or 6.

An eightieth embodiment discloses a process of any one of fifty-ninth to seventy-ninth embodiments, wherein $p_i$, for each occurrence, is independently 3, 4, 5 or 6.

An eighty-first embodiment discloses a process of any one of sixtieth to seventy-ninth embodiments, wherein p1 and p2 are each independently 3, 4, 5, or 6.

An eighty-second embodiment discloses a process of any one of sixtieth to eighty-first embodiments, wherein r is 1, 2, 3, 4, 5 or 6.

In some embodiments, the deprotection reactions of steps c), f, 1), 4), 1'), 4'), 1") and 4") or de-tritylation reactions are carried out as described in the first aspect or any embodiments described therein (e.g., the second to twelfth embodiments).

In some embodiments, the coupling reactions of steps a), d), 2), 2') and 2") can be carried out by adding an activator to the organic solution containing 3'-OH protected nucleotide fragment and 5'-OH protected phosphamidite or phosphonate fragment.

In some embodiments, the sulfurization reactions of steps b), e), 3), 3') and 3") can be carried out by using sulfurizing agents (e.g. 3-amino-1,2,4-dithiazole-5-thione (XH or ADTT), 3-(N,N-dimethylamino-methylidene)amino)-3H-1,2,4-dithiazole (DDTT), phenylacetyl disulfide (PADS), 3H-1,2-benzodithiol-3-one 1,1-dioxide (Beaucage Reagent), or phenyl-3H-1,2,4-dithiazol-3-one (POS). In a specific embodiment, the sulfurizing agent is DDTT. In certain embodiments, the base is pyridine or imidazole.

In certain embodiments, the oxidation reactions of steps b), e), 3), 3') and 3") can be carried out by using standard oxidizing agents known in the literature. Exemplary oxidizing agents include, but are not limited to. tert-butylhydroperoxide (t-BuOOH), (1S)-(+)-(10-camphorsulfonyl)oxaziridine (CSO), $I_2$, and iodine-pyridine-water oxidizer solution. In a specific embodiment, the oxidizing agent is t-BuOOH.

In some embodiments, the deprotection reaction of step 6') or 6") is as described in the second aspect or any embodiments described therein (e.g., the twenty-third to thirty-first embodiments).

In some embodiments, the phosphitylation reaction of step 7') or 7") is as described in the third aspect or any embodiments described therein (e.g., thirty-fifth to thirty-eighth embodiments).

II) 5'-3' Elongation:

In a seventh aspect, the present disclosure describes a liquid phase convergent synthesis of target oligonucleotides, wherein the target oligonucleotide is assembled in the direction of the 5'-terminal to the 3'-terminal (5'-3' direction). It has been demonstrated that the convergent liquid phase process of the present disclosure in 5'-3' direction is successfully used to synthesize target oligonucleotides. In addition, high purity protected target oligonucleotide can be obtained by the methods of the present disclosure without chromatographic purification.

In certain embodiments, the convergent liquid phase process described herein involves step by step addition of oligonucleotide fragments in liquid (solution) phase to synthesize the target oligonucleotide. For example, a 5-mer fragment having a 5'-hydrophobic hydroxyl protecting group (5'-LHPG) (5'-end fragment) is first coupled with 5-mer fragment to form a 10-mer fragment having 5'-LHPG group, which is then further reacted with another 5-mer fragment to form a 15-mer oligonucleotide. In certain embodiments, the 5'-end fragment having n nucleotides (e.g. 5-mer fragment) is synthesized by coupling a single nucleotide having the 5'-LHPG group with a fragment having n–1 nucleotides (e.g., 4-mer fragment).

An eighty-third embodiment discloses a convergent liquid phase process for preparing a target oligonucleotide comprising the steps of:

a) coupling an oligonucleotide fragment of formula (II2):

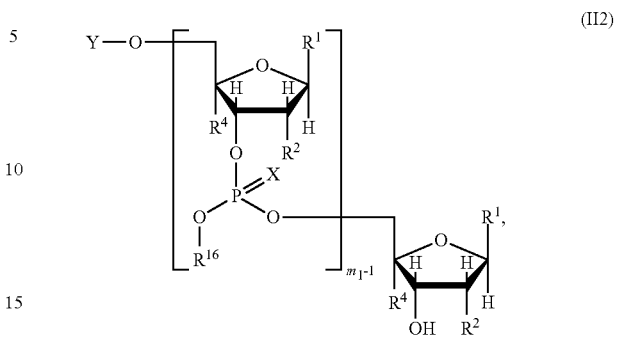

or a salt thereof, with an oligonucleotide fragment of formula (I2):

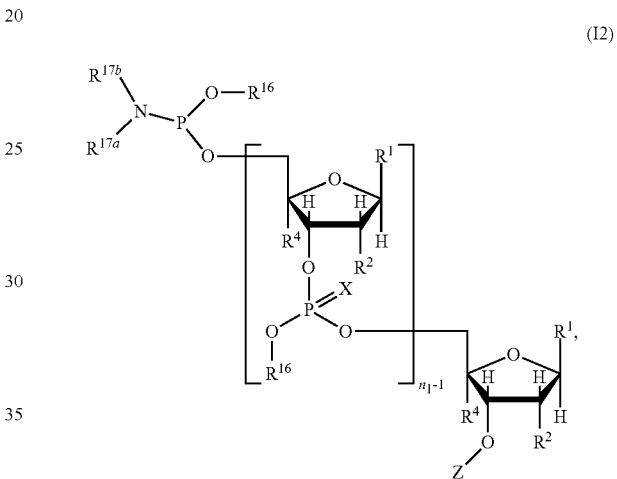

or a salt thereof, in a solution to form an oligonucleotide of formula (III2):

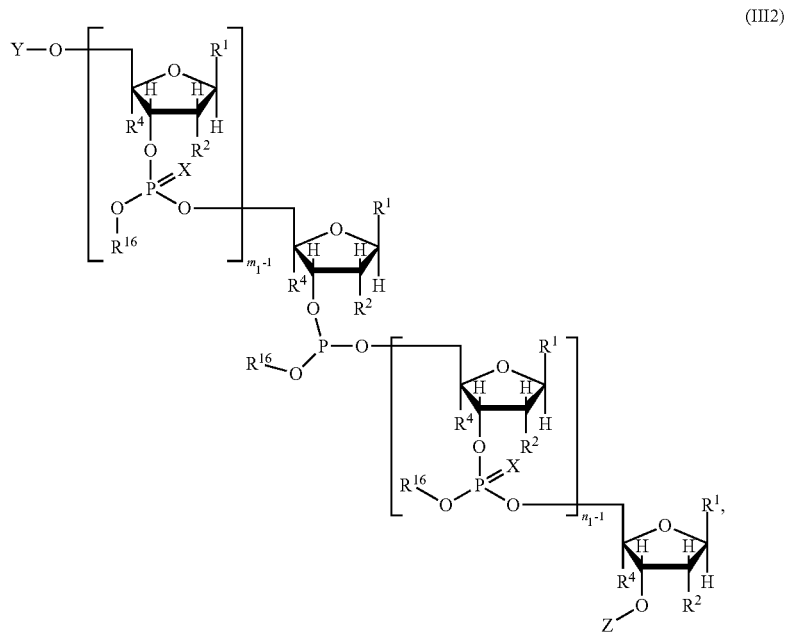

or a salt thereof; and
b) sulfurizing or oxidizing the oligonucleotide of formula (III2), or a salt thereof, to form an oligonucleotide of formula (IV2):

X, for each occurrence, is independently O or S;
Y is a hydrophobic hydroxyl protecting group containing an alkyl chain;
Z is a silyl hydroxyl protecting group.

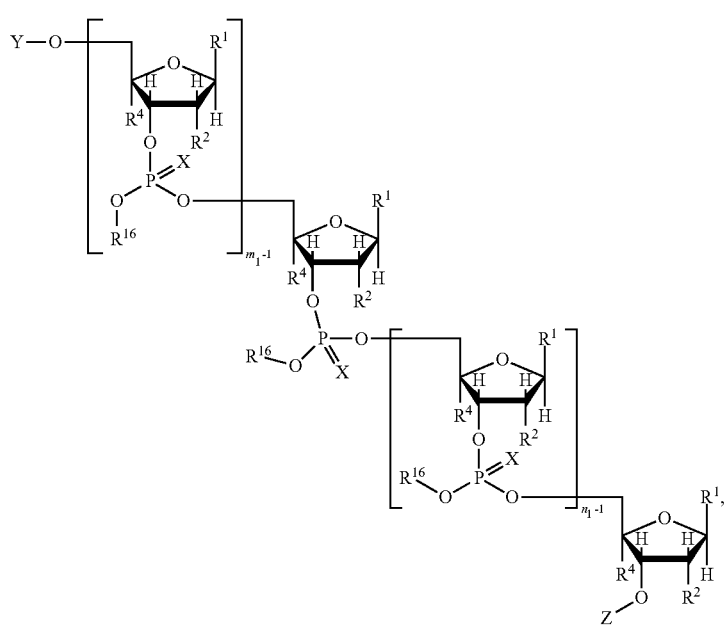

(IV2)

or a salt thereof, wherein:
- $R^1$, for each occurrence, is independently a nucleobase, wherein the $NH_2$ of the nucleobase, if present, is protected by an amine protecting group;
- $R^2$, for each occurrence, is independently selected from the group consisting of H, halo, and $C_{1-6}$alkoxy optionally substituted with $C_{1-6}$alkoxy;
- $R^4$, for each occurrence, is independently H or forms a ring with the alkoxy group of $R^2$;
- $R^{16}$, for each occurrence, is independently $C_{1-6}$alkyl group, $C_{2-6}$alkenyl group, phenyl or benzyl group, each of which is optionally substituted with —CN, —$NO_2$ or halogen; or
- $R^{16}$ is

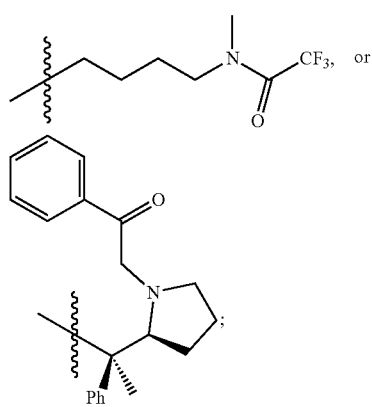

$R^{17a}$ and $R^{17b}$ are independently $C_{1-6}$alkyl;
$n_1$ is an integer from 2 to 20;
$m_1$ is an integer from 2 to 200;

An eighty-fourth embodiment discloses a process described in eighty-third embodiment, wherein fragment (II2) is prepared by:
ia) coupling nucleotide of formula (II2a1):

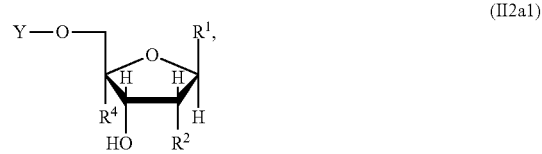

(II2a1)

or a salt thereof, with an oligonucleotide fragment of formula (II2a2):

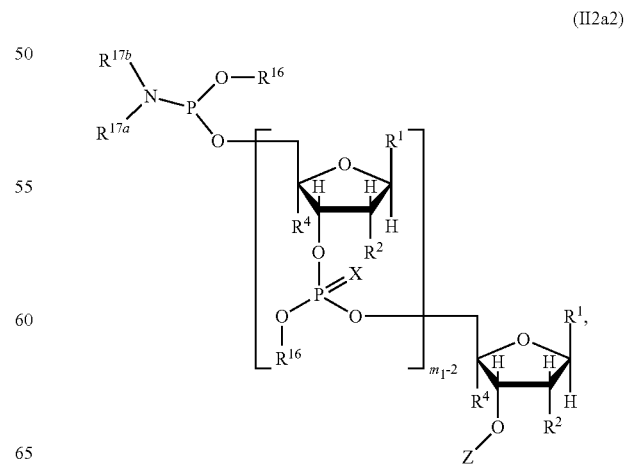

(II2a2)

or a salt thereof, in a solution to form an oligonucleotide of formula (II2a3):

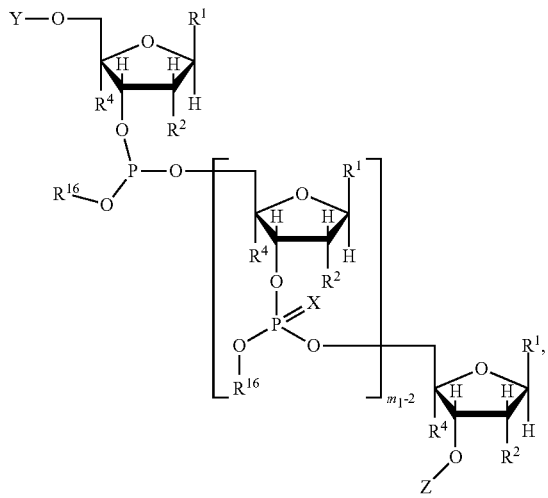
(II2a3)

or a salt thereof;
  iia) sulfurizing or oxidizing the oligonucleotide of formula (II2a3) or a salt thereof to from an oligonucleotide of formula (II2a4):

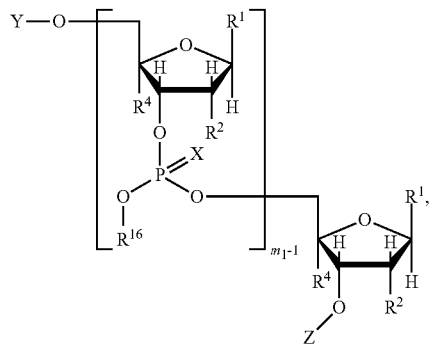
(II2a4)

or a salt thereof;
  iia) deprotecting the oligonucleotide of formula (II2a4) or a salt thereof to form the oligonucleotide of formula (II2) or a salt thereof.

An eighty-fifth embodiment discloses a process described in eighty-fourth embodiment, wherein fragment (II2a2) is obtained by reacting an oligonucleotide of formula (II2a5):

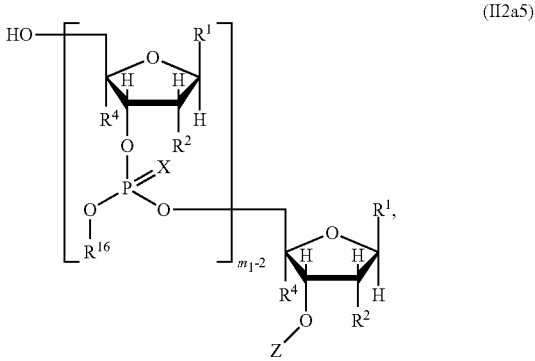
(II2a5)

or a salt thereof, with a phosphordiamidite $(R^{16}O)P(NR^{17a}R^{17b})_2$ to form the compound of (II2a2).

An eighty-sixth embodiment discloses a process described in eighty-fifth embodiment, wherein the oligonucleotide of formula (II2a3) is obtained by:
  iA) deprotecting a compound of formula (II2A'):

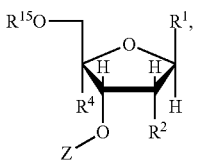
(II2A')

or a salt thereof, to form a compound of formula (II2A):

(II2A)
HO—[sugar with $R^1$, $R^4$, $R^2$, Z—O]

or a salt thereof;
  iiA) reacting a compound of formula (II2A), or a salt thereof, with a compound of formula (A12):

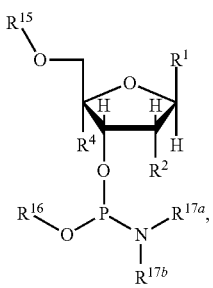
(A12)

or a salt thereof, to form a compound of formula (II2B):

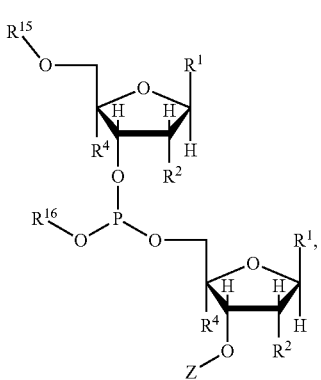
(II2B)

or a salt thereof; and iiiA) sulfurizing or oxidizing the compound of formula (II2B), or a salt thereof, with a sulfurization or oxidation agent to form a compound of formula (II2C):

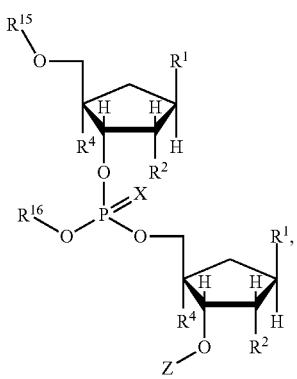
(II2C)

or a salt thereof, ivA) deprotecting the compound of formula (II2C), or a salt thereof, to form a compound of formula (IID):

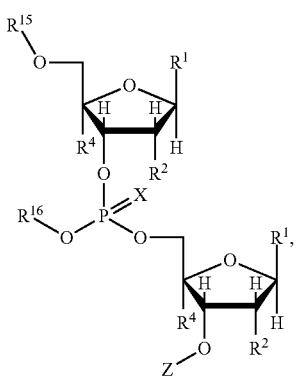
(II2D)

or a salt thereof;

vA) when $m_1$ is greater than 3, starting from the compound of formula (IID), repeating the steps of ii), iii) and iv) for mi-3 times to from the compound of formula (II2a3) or a salt thereof.

In certain embodiments, the process disclosed in any of the eighty-fourth to eighty-sixth embodiments, $m_1$ is an integer from 3 to 20. In a specific embodiment, $m_1$ is an 3 to 6. In another specific embodiment, $m_1$ is 4. In yet another specific embodiment, $m_1$ is 5.

An eighty-seventh embodiment discloses a process as described in the seventh aspect or any of the eighty-third to eighty-sixth embodiments, wherein fragment (I2) is obtained by reacting an oligonucleotide of formula (I2a1):

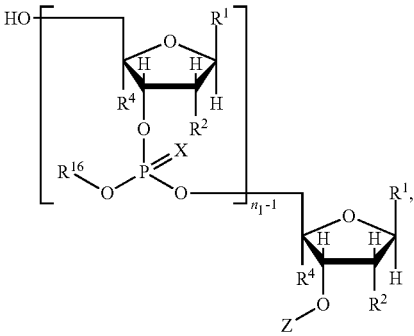

or a salt thereof, with a phosphordiamidite $(R^{16}O)P(NR^{17a}R^{17b})_2$ to form the fragment of formula (I2).

An eighty-eighth embodiment discloses a process as described in eighty-seventh embodiment, wherein the oligonucleotide of formula (I2a1) is obtained by:

i') deprotecting a compound of formula (I2A'):

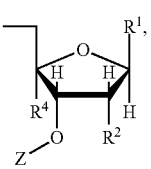
(I2A')

or a salt thereof, to form a compound of formula (I2A):

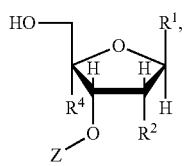
(I2A)

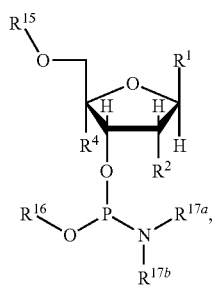
(A11)

or a salt thereof;

ii') reacting a compound of formula (I2A), or a salt thereof, with a compound of formula (A11):

or a salt thereof, to form a compound of formula (I2B):

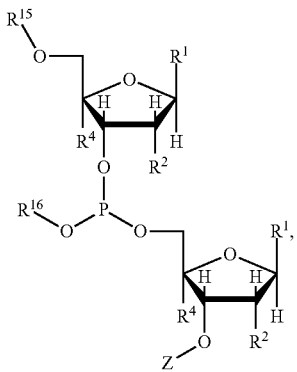
(I2B)

or a salt thereof; and iii') sulfurizing or oxidizing the compound of formula (I2B), or a salt thereof, with a sulfurization or oxidation agent to form a compound of formula (I2C):

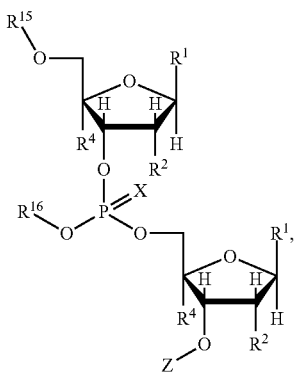
(I2C)

or a salt thereof, iv') deprotecting the compound of formula (I2C), or a salt thereof, to form a compound of formula (I2D):

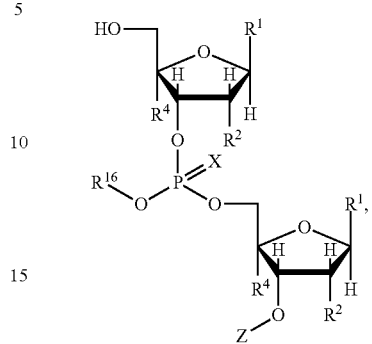
(I2D)

or a salt thereof;

v') when $n_1$ is greater than 2, starting from compound of formula (I2D), repeating the steps of ii'), iii') and iv') for $n_1-2$ times to form the compound of formula (I2a1) or a salt thereof.

An eighty-ninth embodiment discloses a process as described in the eighty-third to eighty-eighth embodiments, further comprising, further comprising step c) of deprotecting the oligonucleotide of formula (IV2), or a salt thereof, to form an oligonucleotide of formula (V2):

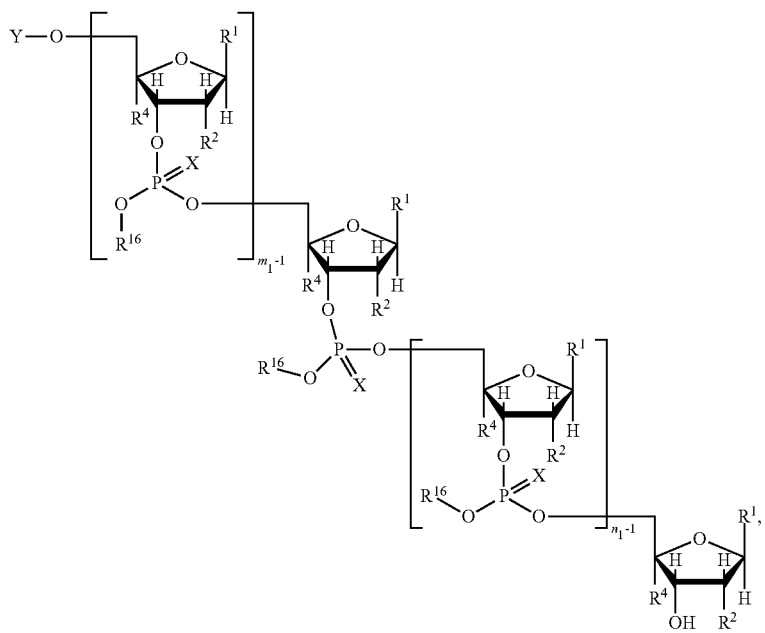
(V2)

or a salt thereof.

A ninetieth embodiment discloses a process as described in the eighty-ninth embodiment, further comprising:

d) coupling the oligonucleotide of formula (V2), or a salt thereof, with an oligonucleotide fragment of formula (I12'):

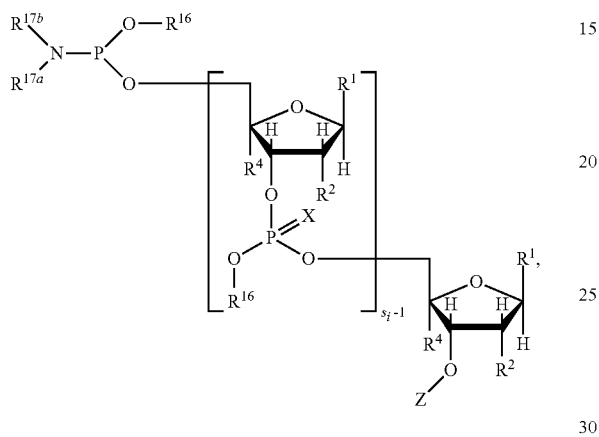

(II2')

or a salt thereof to form an oligonucleotide of formula (VI2):

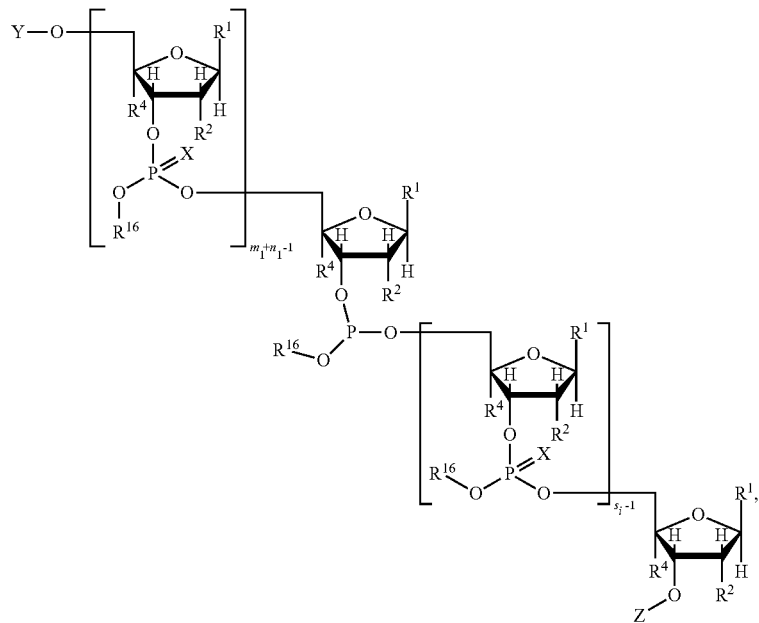

(VI2)

or a salt thereof, e) sulfurizing or oxidizing the oligonucleotide of formula (VI2) to form an oligonucleotide of formula (VI12):

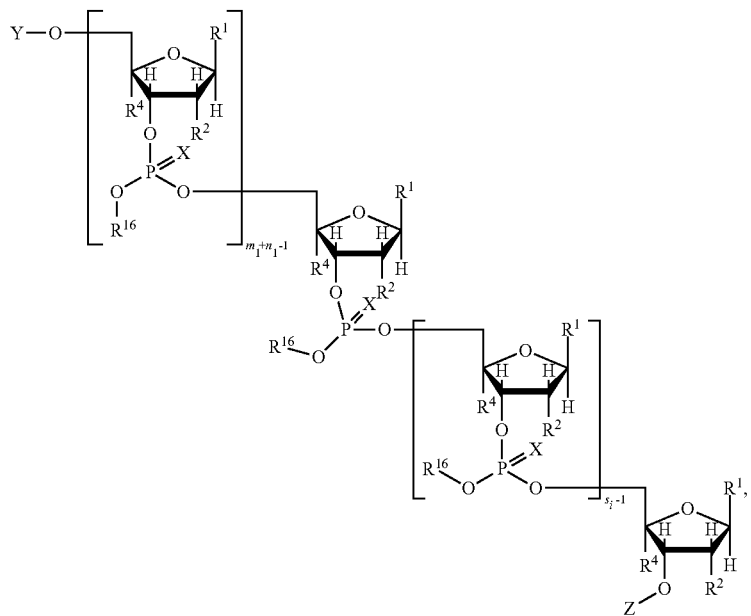
(VII2)
or a salt thereof,
  f) deprotecting the oligonucleotide of formula (VII2), or a salt thereof, to form an oligonucleotide of formula (VIII2):
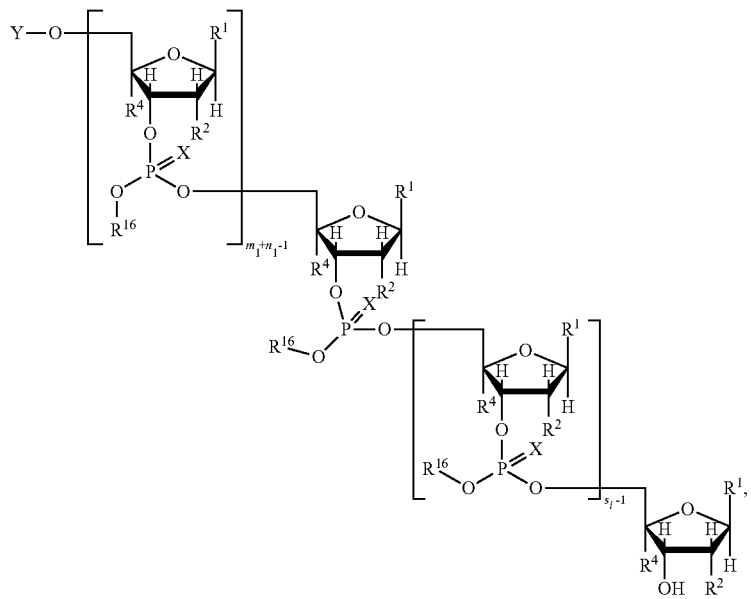
(VIII2)
or a salt thereof,
  g) repeating the steps of d), e) and f) for $r_1-1$ times followed by repeating the steps of d) and e) to form an oligonucleotide of formula (IX2):

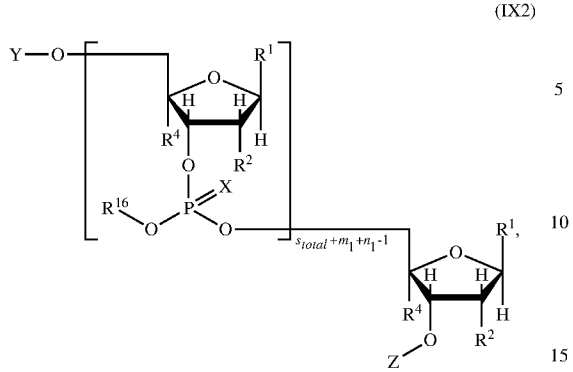

(IX2)

or a salt thereof
wherein:
  $r_1$ is an integer from 1 to 50;
  $s_i$, for each occurrence, is independently an integer from 2 to 20,
  i is an integer from 1 to $r_1$; and $$S_{total} = \sum_{i=1}^{r_1} s_i ..$$

A ninety-first embodiment discloses a process as described in the ninetieth embodiment, wherein $r_1$ is 2 and the oligonucleotide of formula (IX2) is represented by formula (X2):

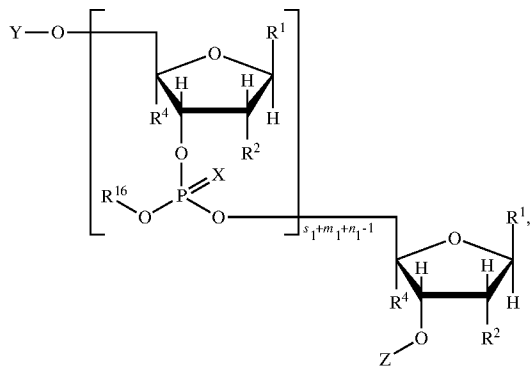

(X2)

or a salt thereof, wherein s1 and s2 are each independently an integer from 2 to 20.

A ninety-second embodiment discloses a process as described in the ninetieth embodiment, wherein r1 is 1 and the oligonucleotide of formula (IX2) is represented by formula (X2'):

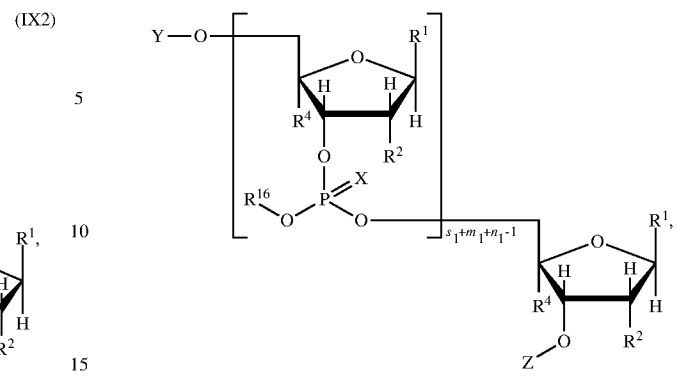

or a salt thereof, wherein s1 is an integer from 2 to 20.

In certain embodiments, for the process of the ninety-first or ninety-second embodiment, s1, s2, m1 and n1 are each independently an integer from 3 to 10, 3 to 6 or 4 to 6. In certain embodiments, s1, s2, m1 and n1 are each independently 4 or 5.

A ninety-third embodiment discloses a process as described in the ninetieth, ninety-first or ninety-second embodiment, wherein the oligonucleotide fragment of formula (I12') is obtained by reacting an oligonucleotide of formula (II2a1'):

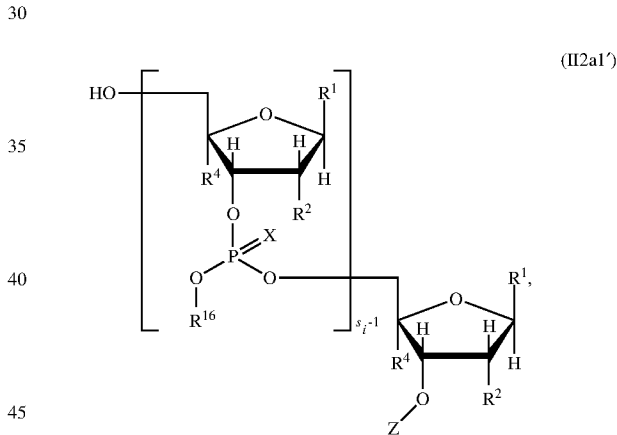

(II2a1')

or a salt thereof,
with a phosphordiamidite $(R^{16}O)P(NR^{17a}R^{17}n)_2$ to form the fragment of formula (II2') or a salt thereof.

A ninety-fourth embodiment discloses a process as described in the ninety-third embodiment, wherein the oligonucleotide of formula (II2a1') is obtained by:
  i'') deprotecting a compound of formula (II'2A'):

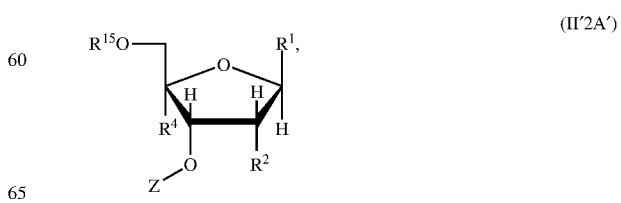

(II'2A')

or a salt thereof, to form a compound of formula (II'2A):

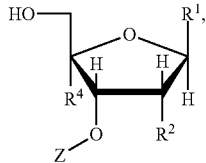
(II'2A)

or a salt thereof;

ii") reacting a compound of formula (II'2A), or a salt thereof, with a compound of formula (A12'):

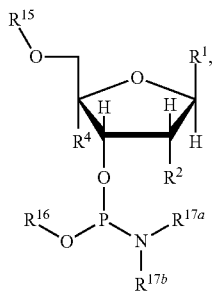
(A12')

or a salt thereof, to form a compound of formula (II'2B):

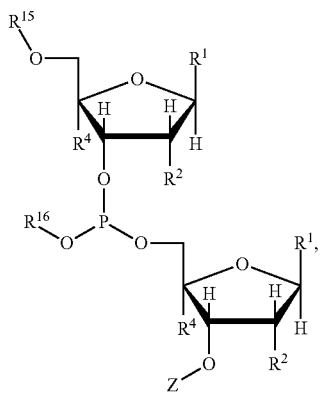
(II'2B)

or a salt thereof; and iii") sulfurizing or oxidizing the compound of formula (II'2B), or a salt thereof, with a sulfurization or oxidation agent to form a compound of formula (II'2C):

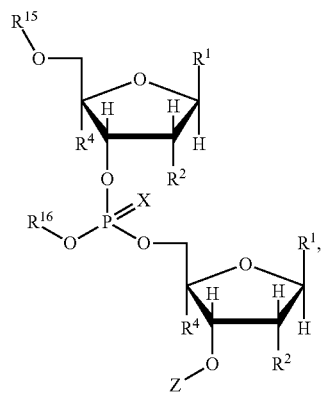
(II'2C)

or a salt thereof, iv") deprotecting the compound of formula (II'2C), or a salt thereof, to form a compound of formula (II'2D):

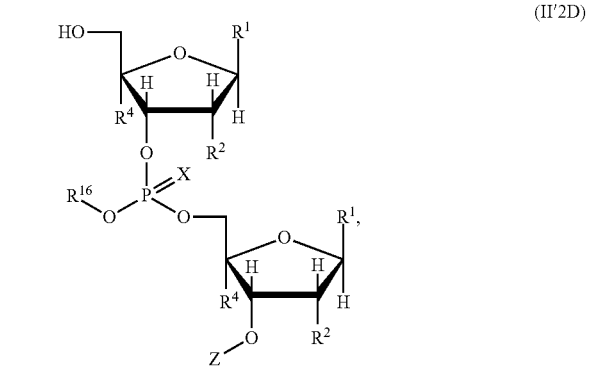
(II'2D)

or a salt thereof;

v") when $s_i$ is greater than 2, starting from the compound of (II'2D), repeating the steps of ii"), iii") and iv") for $s_i$-2 times to from the compound of formula (II2a1') or a salt thereof.

A ninety-fifth embodiment discloses a process as described in the eighty-third to ninety-fourth embodiments, wherein no chromatography is used for purifying the reaction product of any one of steps a), b), c), d), e), f) and g).

A ninety-sixth embodiment discloses a process as described in the eighty-third to ninety-fourth embodiments, wherein the reaction product of any one of steps a), b), c), d), e), f) and g) is purified by extraction and/or selective precipitation as described herein (e.g., as described in the twenty-first, thirty-five, forty-two, forty-sixth or forty-seventh embodiment).

A ninety-seventh embodiment discloses a process as described in the ninetieth to ninety-sixth embodiments, wherein the method further comprises deprotecting the oligonucleotide of formula of (IX2), (X2) or (X2') or a salt thereof to form the oligonucleotide of formula (IX2A), (X2A) or (X2A') or a salt thereof:

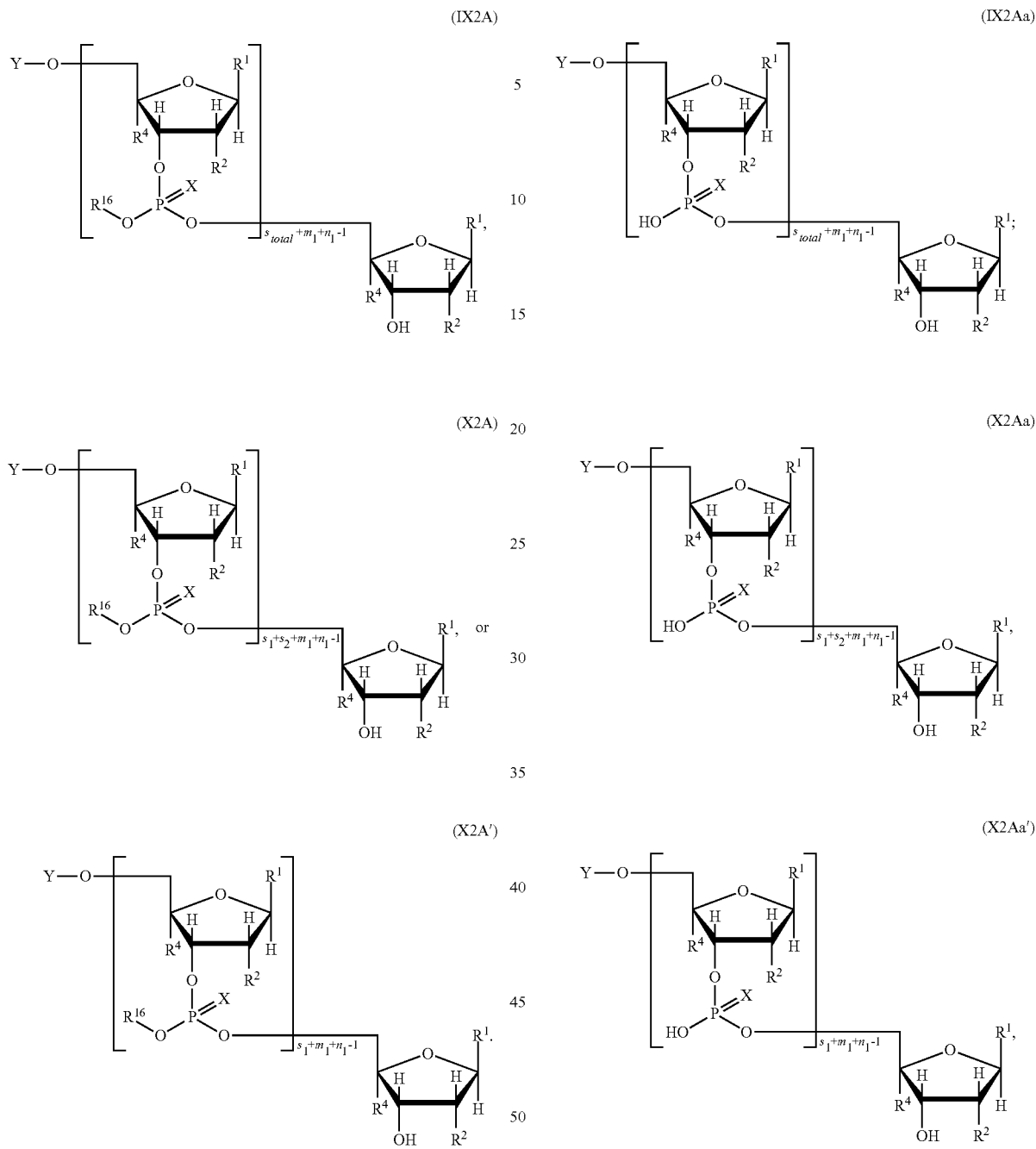

In certain embodiments, the Z is group in formula (IX2), (X2) or (X2') is selected from TBDPS, ToBDPS and TBDAS. In certain embodiments, the deprotection reaction is carried out as described in the second aspect or any embodiments described therein (e.g., in the twenty-sixth to thirty-second embodiments).

A ninety-eighth embodiment discloses a process as described in any of the eighty-third to ninety-seventh embodiments, wherein, when $R^{16}$ is —$CH_2CH_2CN$, the process further comprises the step of:

h1) deprotecting the oligonucleotide (IX2A), (X2A) or (X2A') or a salt thereof to form an oligonucleotide of formula (IX2Aa), (X2Aa) or (X2Aa'):

or a salt thereof.

A ninety-ninth embodiment discloses a process as described in the ninety-eighth embodiment, wherein the deprotection reaction is carried out by reacting the oligonucleotide (IX2A), (X2A) or (X2A') or a salt thereof with a base. In some embodiments, the base is selected from 1,8-diazabicyclo[5.4.0]undec-7-ene, alkylamine (e.g., tert-butylamine, sec-butylamine, diisopropylethylamine and triethylamine) and other suitable organic base.

A $100^{th}$ embodiment discloses a process as described in the ninety-eighth or ninety-ninth embodiment, wherein the method further comprises the step of deprotecting the oligonucleotide (IX2Aa), (X2Aa) or (X2Aa') or a salt thereof to form an oligonucleotide of formula (IX2B), (X2B) or (X2B'):

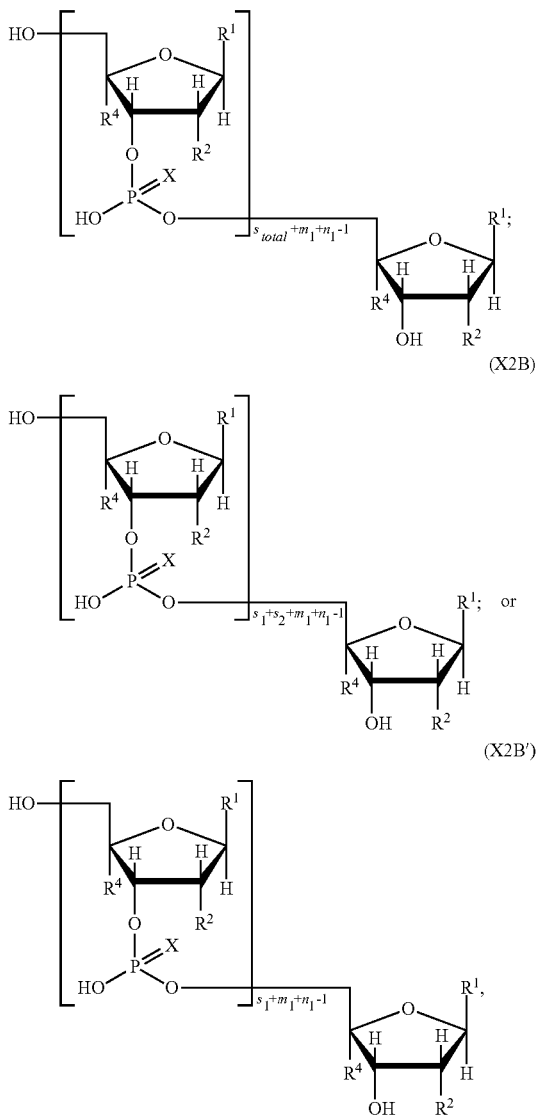

or a salt thereof.

A 101$^{st}$ embodiment discloses a process as described in the 100$^{th}$ embodiment, wherein the deprotection is carried out by reacting the oligonucleotide (IX2Aa) or (X2Aa) or a salt thereof with NH$_4$OH. In certain embodiments, treatment with NH$_4$OH also removes other protecting group in the oligonucleotides, such as protecting groups in any nucleobases (e.g., the NH$_2$ protecting group on a nucleobase). In certain embodiments, treatment with NH$_4$OH results in oligonucleotides of formula (IX2B), (X2B) or (X2B') or a salt thereof, wherein R$^1$, for each occurrence, is independently a nucleobase, wherein the NH$_2$ of the nucleobase, if present, is unprotected.

A 102$^{nd}$ embodiment discloses a process as described in any one of the eighty-third to 101$^{st}$ embodiments, wherein n$_1$ is 3, 4, 5 or 6.

A 103$^{rd}$ embodiment discloses a process as described in any one of the ninetieth to 101$^{st}$ embodiments, wherein s$_i$, for each occurrence, is independently 3, 4, 5 or 6.

A 104$^{th}$ embodiment discloses a process as described in any one of the ninety-first to 101$^{st}$ embodiments, wherein s$_1$ and s$_2$ ae each independently 3, 4, 5 or 6.

A 105$^{th}$ embodiment discloses a process as described in any one of the eighty-third to 101$^{st}$ embodiments, wherein r$_1$ is 1, 2, 3, 4, 5 or 6.

A 106$^{th}$ embodiment discloses a process as described in any one of the first to 105$^{th}$ embodiments, wherein all of the P=X groups in the compound or oligonucleotide are P=S.

A 107$^{th}$ embodiment discloses a process as described in any one of the first to 105$^{th}$ embodiments, wherein all of the P=X groups in the compound or oligonucleotide are P=O.

A 108$^{th}$ embodiment discloses a process as described in any one of the first to 105$^{th}$ embodiments, wherein greater than 10%, 20%, 30%, 40%, 50%, 60%, 70%, 80% or 90% of the P=X groups in the compound or oligonucleotide are P=S.

A 109$^{th}$ embodiment discloses a process as described in any one of the first to 105$^{th}$ embodiments, wherein 10-90%, 20-80%, 30-70% or 40-60% of the P=X groups in the compound or oligonucleotide are P=S.

A 110$^{th}$ embodiment discloses a process as described in any one of the first to 105$^{th}$ embodiments, wherein 10-90%, 20-80%, 30-70% or 40-60% of the P=X groups in the compound or oligonucleotide are P=O.

In some embodiments, the deprotection reactions of steps iia), step c) and f) of any of the eighty fourth to ninetieth embodiments, and of the ninety-sixth embodiment can be carried out as described in the first aspect or any embodiments described therein (e.g. twenty-sixth to thirty-fourth embodiments)

In some embodiments, the deprotection step of iA), ivA), i'), iv'), i") and iv") of the seventh aspect can be carried out as described in the first aspect or any embodiments described therein (e.g., the second to twelfth embodiments).

In some embodiments, the coupling reactions of steps a), ia), ii), iiA), ii'), d) and ii") can be carried out by adding an activator to the organic solution containing 3'-OH protected nucleotide fragment and 5'-OH protected phosphamidite or phosphonate fragment.

In some embodiments, the sulfurization reactions of steps b), iii), iiiA), iii') e) and iii") can be carried out by using sulfurizing agents (e.g. 3-amino-1,2,4-dithiazole-5-thione (XH or ADTT), 3-(N,N-dimethylamino-methylidene) amino)-3H-1,2,4-dithiazole (DDTT), phenylacetyl disulfide (PADS), 3H-1,2-benzodithiol-3-one 1,1-dioxide (Beaucage Reagent), or phenyl-3H-1,2,4-dithiazol-3-one (POS). In a specific embodiment, the sulfurizing agent is DDTT. In certain embodiments, the base is pyridine or imidazole.

In certain embodiments, the oxidation reactions of steps b), iii), iiiA), iii') e) and iii") can be carried out by using standard oxidizing agents known in the literature. Exemplary oxidizing agents include, but are not limited to. tert-butylhydroperoxide (t-BuOOH), (1S)-(+)-(10-camphorsulfonyl)oxaziridine (CSO), I$_2$, and iodine-pyridine-water oxidizer solution. In a specific embodiment, the oxidizing agent is t-BuOOH.

In some embodiments, the phosphitylation reaction of eighty-fifth, eighty-seventh and ninety-second embodiments can be carried out as described in the third aspect or any embodiments described therein (e.g., thirty-ninth to forty-second embodiments).

In one embodiment, Y is:

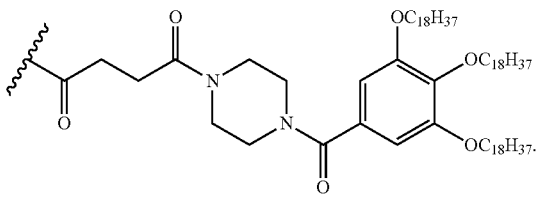

In certain embodiments, the oligonucleotide of formula (IX2B), (X2B) or (X2B') obtained from the deprotection reaction is purified by depth filtration. In one embodiment, the reaction mixture of the deprotection reaction is diluted with ammonium sulfate solution before being subjected to depth filtration. Dilution with ammonium sulfate may prevent the oligonucleotide from sticking to the filter.

In certain embodiments, the concentration for the ammonium sulfate solution is between 100 mM and 5M, between 500 mM and 2M, between 500 mM and 1500 mM, or between 1000 mM and 1200 mM.

Any suitable depth filters can be used for depth filtration, e.g., suitable depth filters described herein.

In certain embodiments, the oligonucleotide of formula (IX2A), (IX2Aa), (IX2Aa'), (X2A), (X2A'), (X2Aa), (X2Aa'), (X2B) or (X2B') can be purified by depth filtration followed by hydrophobic interaction chromatography (HIC).

In certain embodiments, any of the reactions described in the first to eighth aspects or any embodiments described therein (e.g., the first to $135^{th}$ embodiments) can be carried out in a suitable solvent or a mixture of suitable solvents. In certain embodiments, the reactions can be carried out in a suitable organic solvent or a mixture of suitable organic solvents. Exemplary organic solvents can be used in the present disclosure include, but are not limited to, dichloromethane (DCM), acetonitrile (ACN), tetrahydrofuran (THF), acetone, 2-methyltetrahydrofuran, methyl tert-butyl ether, ethyl acetate, etc.

In certain embodiments, any of the reactions described in the first to eighth aspects or any embodiments described therein (e.g., the first to $135^{th}$ embodiments) can be carried out at a suitable temperature. In certain embodiments, the reaction is carried out at room temperature. In certain embodiment, the reaction is carried out at a temperature between 20° C. and 30° C. In certain embodiments, the reaction is carried out at a temperature between −10° C. and 10° C., between −5° C. and 5° C. In certain embodiments, the reaction is carried out at 25±2° C. In certain embodiments, the reaction is carried out at 0±2° C.

A $111^{th}$ embodiment discloses a process of any one of the embodiments described herein (e.g., the first to $135^{th}$ embodiments), wherein the nucleobase is selected from the group consisting of cytosine, guanine, adenine, thymine, uracil, hypoxanthine, xanthine, 7-methylguanine, 5,6-dihydrouracil, 5-methylcytosine, and 5-hydroxymethylcytosine, wherein the $NH_2$ group of the nucleobase, if present, is protected by PhCO—, $CH_3CO$—, iPrCO—, $Me_2N$—CH=, or $Me_2N$—CMe=.

A $112^{th}$ embodiment discloses a process of any one of the embodiments described herein (e.g., the first to $135^{th}$ embodiments), wherein $R^1$ is selected from the group consisting of cytosine, guanine, adenine, thymine, uracil, and 5-methylcytosine, wherein the $NH_2$ group of the nucleobase, if present, is protected by PhCO—, $CH_3CO$—, iPrCO—, $Me_2N$—CH=, or $Me_2N$—CMe=.

A $113^{th}$ embodiment discloses a process of any one of the embodiments described herein (e.g., the first to $135^{th}$ embodiments), wherein: each $R^2$ is independently selected from the group consisting of H, F, and $C_{1-4}$alkoxy optionally substituted with $C_{1-4}$alkoxy; each $R^4$ is independently H or forms a ring with the alkoxy group of $R^2$, wherein the ring is a 5 or 6-membered ring optionally substituted with 1 to 3 $C_{1-4}$ alkyl groups;
$R^{16}$ is —$CH_2CH_2CN$; and
$R^{17a}$ and $R^{17b}$ are independently $C_{1-4}$alkyl.

In a specific embodiment, the process is a process described in the $113^{th}$ embodiment, wherein:
each $R^2$ is independently H or —$OCH_2CH_2OMe$;
each $R^4$ is H;
$R^{16}$ is —$CH_2CH_2CN$; and
$R^{17a}$ and $R^{17b}$ are both —$CH(CH_3)_2$.

A $114^{th}$ embodiment discloses a process described in any one of the fifty-first to $135^{th}$ embodiments, wherein the target oligonucleotide is an anti-sense oligonucleotide comprising 16 to 30 nucleotides.

A $115^{th}$ embodiment discloses a process described in the $114^{th}$ embodiment, wherein the anti-sense oligonucleotide comprises modified RNA only.

A $116^{th}$ embodiment discloses a process described the $114^{th}$ embodiment, wherein the anti-sense oligonucleotide comprises DNA and modified RNA.

A $117^{th}$ embodiment discloses a process described in the one $114^{th}$ embodiment, wherein the anti-sense oligonucleotide is a gapmer.

A $118^{th}$ embodiment discloses a process described the one hundred-fourteenth embodiment, wherein the anti-sense oligonucleotide comprises DNA only.

In certain embodiments, the target oligonucleotide describe herein having 5'-DMT group (represented by $R^{15}$) is purified by chromatography (e.g., hydrophobic interaction chromatography (HIC)), followed by detritylation reaction to remove the 5'-DMT group.

III. Synthesis of Oligonucleotide with Chiral Phosphorothioate Linkage

In an eighth aspect, the present disclosure describes liquid phase processes for the synthesis of stereospecific oligonucleotides using a P(V)—PSI reagent (K. W. Knouse, J. N. deGruyter, M. A. Schmidt, et al. Science, Vol. 361, Issue 6408, pp 1234-1238 (2018)). Linearly synthesized oligonucleotide fragments can be combined using liquid phase convergent synthesis methods described herein to yield stereoselective target oligonucleotides (e.g., antisense oligonucleotides (ASOs)).

A $119^{th}$ embodiment discloses a liquid phase process for preparing an oligonucleotide of formula (PI1) or (PI2),

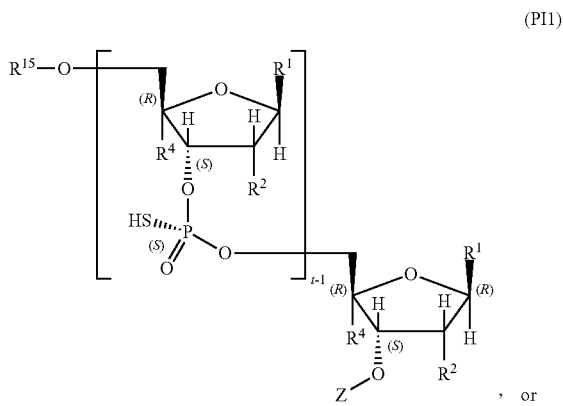

(PI1)

, or

-continued
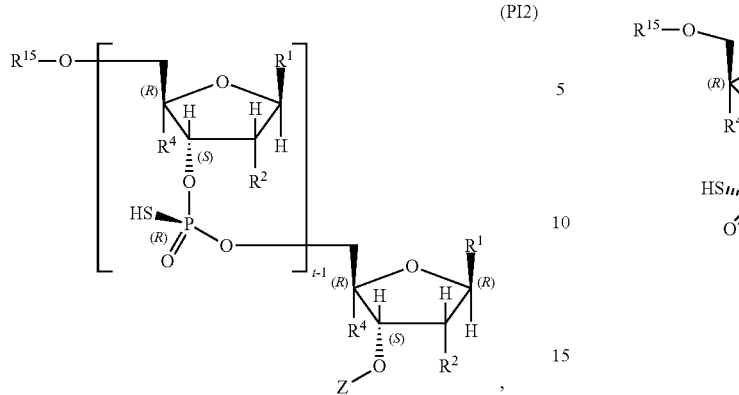
(PI2)
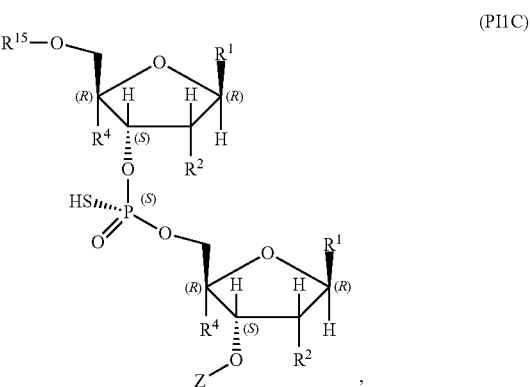
(PI1C)
or a salt thereof, comprising the steps of:
1) coupling a compound of formula (PIB):
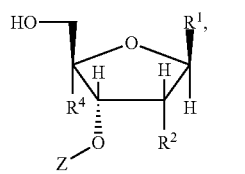
(PIB)
or a salt thereof, with a compound of formula (PI1A) or (PI2A):
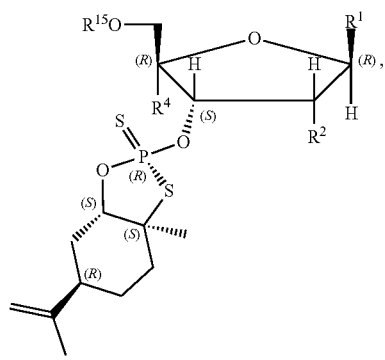
(PI1A)
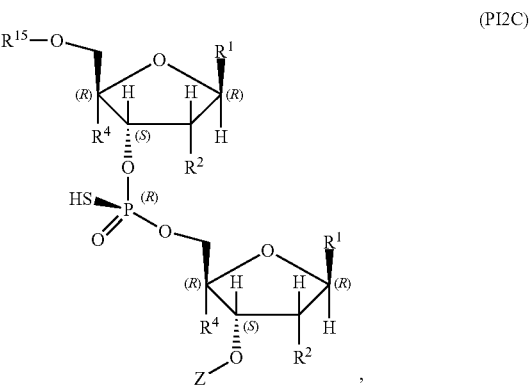
(PI2C)
or a salt thereof;
2) deprotecting the compound of formula (PI1C) or (PI2C), or a salt thereof to form a compound of formula (PI1D) or (PI2D):
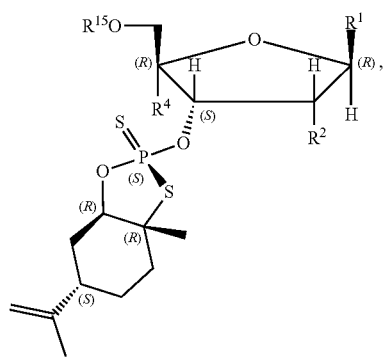
(PI2A)
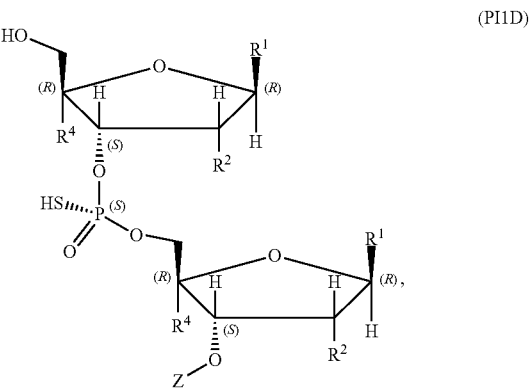
(PI1D)
or a salt thereof, to form a compound of formula (PI1C) or (PI2C):

-continued (PI2D)

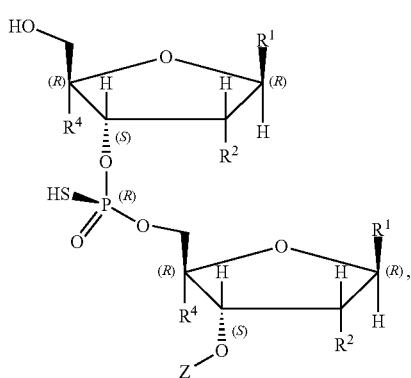

or a salt thereof;

3) starting with the compound of formula (PI1D) or (PI2D) or a salt thereof, repeating steps 1) and 2) for t−3 times, followed by step 1) to yield the formula (PI'), or a salt thereof, wherein:

$R^1$, for each occurrence, is independently a nucleobase, wherein the $NH_2$ of the nucleobase, if present, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group;

t is an integer from 3 to 20; and

Z is a silyl hydroxyl protecting group.

In a 120$^{th}$ embodiment, for the process described in the 119$^{th}$ embodiment, the compound of formula (PI1A) is prepared by reacting a compound of formula (PIA1):

(PIA1)

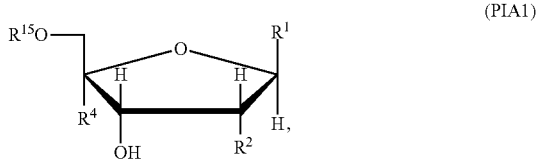

or a salt thereof, with a compound of formula (1):

(1)

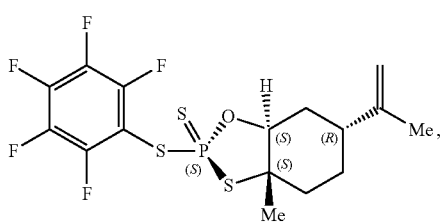

to form the compound of formula (PI1A) or a salt thereof; and the compound of formula (PI2A) is prepared by reacting the compound of formula (PIA1) or a salt thereof with a compound of formula (2):

(2)

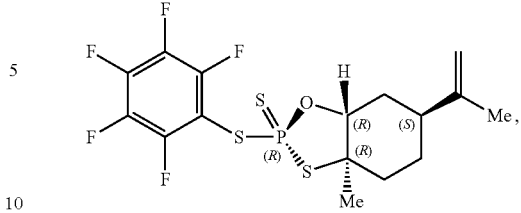

to form the compound of formula (PI2A) or a salt thereof.

A 121$^{st}$ embodiment discloses a process as described in the process of 119$^{th}$ or 120$^{th}$ embodiment, wherein the fragment of formula (PIB) is prepared by deprotecting a compound of formula (PIB1)

(PIB1)

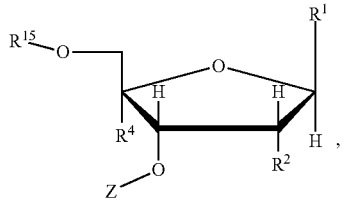

Z o(PIB1), or a salt thereof.

A 122$^{nd}$ embodiment discloses a process as described in the process of the 119$^{th}$, 120$^{th}$ or 121$^{st}$ embodiment, wherein the coupling reaction of step 1) is carried out in the presence of a base. In certain embodiments, the base is selected from 8-diazabicyclo[5.4.0]undec-7-ene (DBU), alkylamine (e.g., tert-butylamine, sec-butylamine, diisopropylethylamine, trimethylamine, triethylamine, 2-methylpropan-2-amine etc.) and other suitable organic bases. In a specific embodiment, the base is DBU.

In certain embodiments, the coupling reaction of step 1) is carried out in an anhydrous or substantially anhydrous solution in the presence of a base. In certain embodiments, the anhydrous or substantially anhydrous solution is obtained by removing water using azeotropic distillation prior to the reaction. In certain embodiments, the anhydrous or substantially anhydrous solution is obtained by the addition of a drying agent.

A 123$^{rd}$ embodiment discloses a process as described in the process of 122$^{nd}$ embodiment, wherein the coupling reaction is carried out in presence of a base and a drying agent. Any suitable drying agent can be used. In some embodiments, the drying agent is selected for calcium chloride, potassium chloride, sodium sulfate, calcium sulfate, magnesium sulfate and molecular sieves. In a specific embodiment, the drying agent is molecular sieves.

In certain embodiments, the base is DBU and the drying agent is molecular sieves. In a specific embodiment, the size of molecular sieves is 3A.

A 124$^{th}$ embodiment discloses a process as described in any one of the 119$^{th}$ to 121$^{st}$ embodiments, wherein the deprotection reaction is carried out by reacting the compound with a detritylation reagent. In certain embodiments, the detritylation reagent is an organic acid. In certain embodiments, the detritylation reagent is $CF_3COOH$, $CCl_3COOH$, $CHCl_2COOH$, $CH_2ClCOOH$, citric acid, methanesulfonic acid, benzenesulfonic acid, $CClF_2COOH$, $CHF_2COOH$, or $PhSO_2H$. In a specific embodiment, the detritylation reagent is $CHCl_2COOH$. In another preferred embodiment, the detritylation reagent is citric acid.

A 125$^{th}$ embodiment discloses a process as described in any one of the 119$^{th}$ embodiment to 124$^{th}$ embodiment, wherein $R^{15}$ is a 4,4'-dimethoxytrityl group.

A 126$^{th}$ embodiment discloses a process as described in any one of the 120$^{th}$ to 125$^{th}$ embodiments, wherein the reaction between the compound of formula (PIA1) and the compound of formula (1) or (2) is carried out in an anhydrous or substantially anhydrous solution in the presence of a base.

In certain embodiments, the anhydrous or substantially anhydrous solution is obtained by removing water using azeotropic distillation prior to the reaction. In certain embodiments, the anhydrous or substantially anhydrous solution is obtained by the addition of a drying agent.

In certain embodiments, the base is selected from 1,8-diazabicyclo[5.4.0]undec-7-ene (DBU), alkylamine (e.g., tert-butylamine, sec-butylamine, diisopropylethylamine, trimethylamine, triethylamine etc.) and other suitable organic bases. In a specific embodiment, the base is DBU.

A 127th embodiment discloses a process as described in any one of the 119th to 126h embodiments, wherein the process further comprises deprotecting the oligonucleotide of formula (PI1) or (PI2) or a salt thereof to form an oligonucleotide of formula (PI1') or (PI2'):

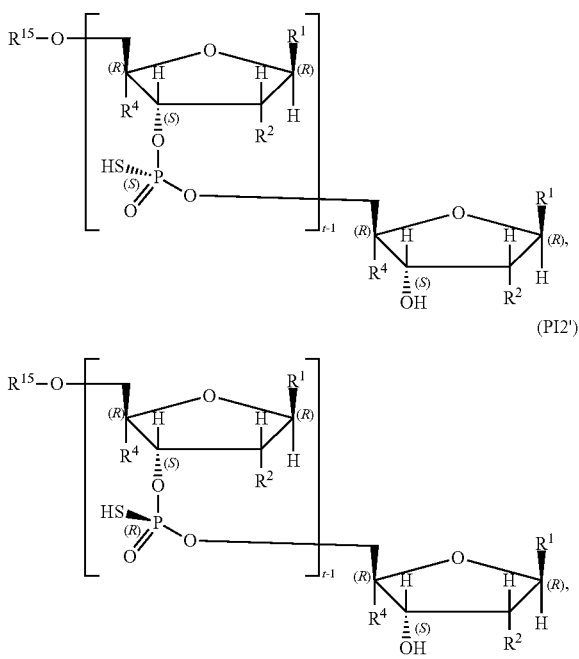

or a salt thereof.

A 128th embodiment discloses a process as described in the 127th embodiment, wherein the silyl protecting group is selected from TBDPS, TBoDPS and TBDAS.

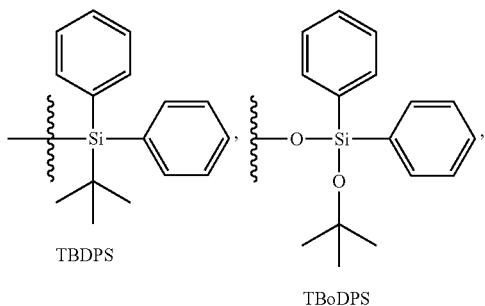

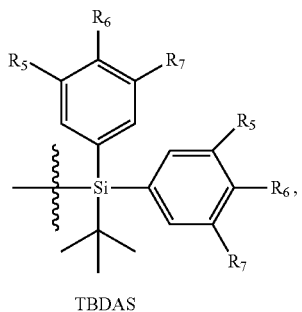

wherein $R_5$, $R_6$ and $R_7$ are each independently H, $C_{1-30}$alkyl, or $C_{1-30}$alkoxy. In a specific embodiment, Z is TBDPS.

A 129th embodiment discloses a process as described in the 128th embodiment, wherein the deprotection reaction is reaction is carried out by reaction the oligonucleotide of formula (PI1) or (PI2) or a salt thereof desilylation reagent (e.g., as described in the second aspect or any embodiments described therein). In certain embodiments, the disilylation reagent is tetra-n-butylammonium fluoride (TEAF).

A 130th embodiment discloses a process as described in any one of the 119th to 129th embodiments, wherein: each $R^2$ is independently selected from H, F, or $C_{1-4}$alkoxy optionally substituted with $C_{1-4}$alkoxy; and $R^4$ is H. In a specific embodiment, $R^2$ is H. In another specific embodiment, $R^2$ is —OCH$_2$CH$_2$OCH$_3$.

A 131st embodiment discloses a process as described in any one of the 119th to 130th embodiments, wherein the compound of formula (PI1A), (PI2A) (PIB), (PI1C), (PI2C), (PI1D), (PI2D), (PI1), (PI2), (PI1') and/or (PI2') are purified by column chromatography.

The present disclosure also provides a convergent liquid phase process for preparing an oligonucleotide, wherein at least a portion of the phosphorothiolate linkages in the oligonucleotide is diastereospecific phosphorothiolate.

A 132nd embodiment discloses a convergent liquid phase process for preparing an oligonucleotide comprising the steps of coupling an oligonucleotide fragment of formula (P1F1) or (P2F2):

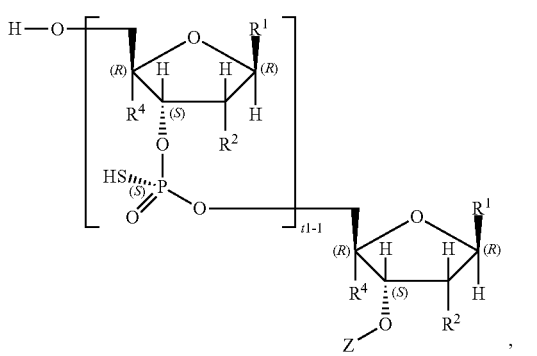

-continued
(P2F1)
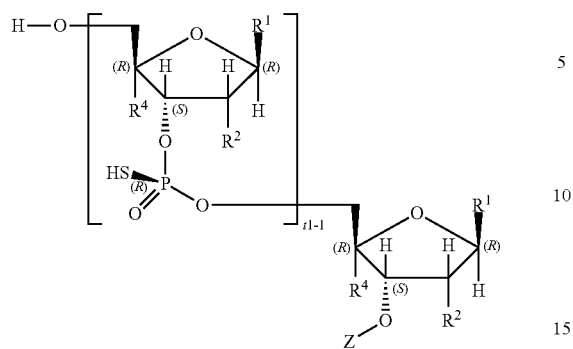
or a salt thereof, with an oligonucleotide of formula (P1F2) or (P2F2):
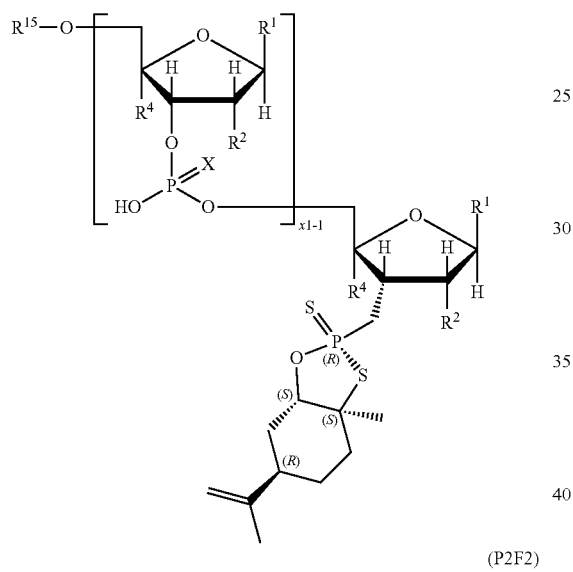
(P2F2)
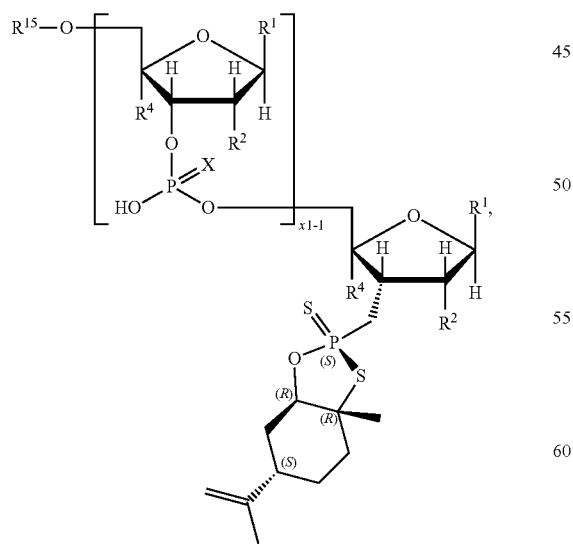
or a salt thereof, to form the oligonucleotide of formula (PIII1) or (PIII2):

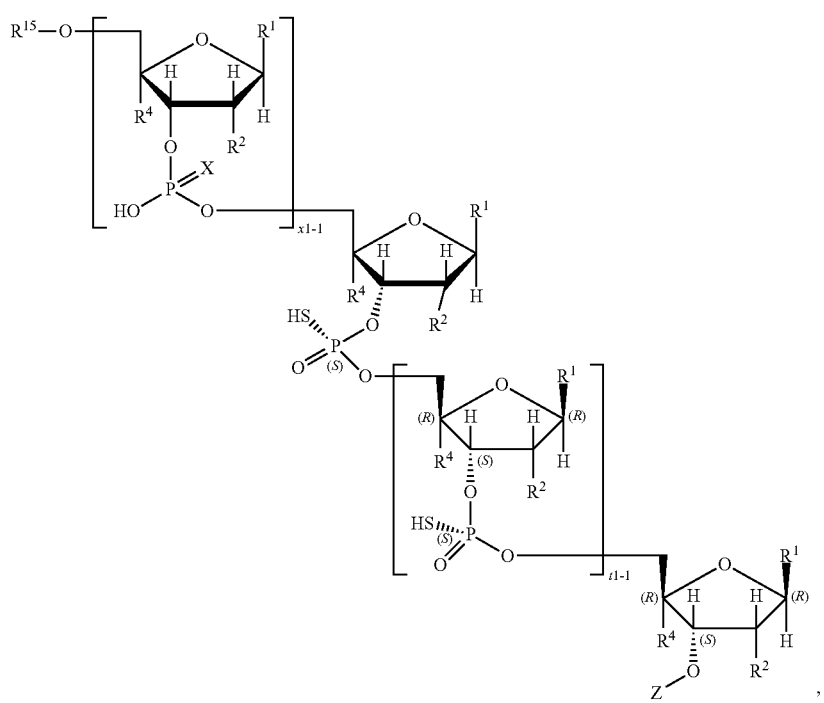
(PIII1)
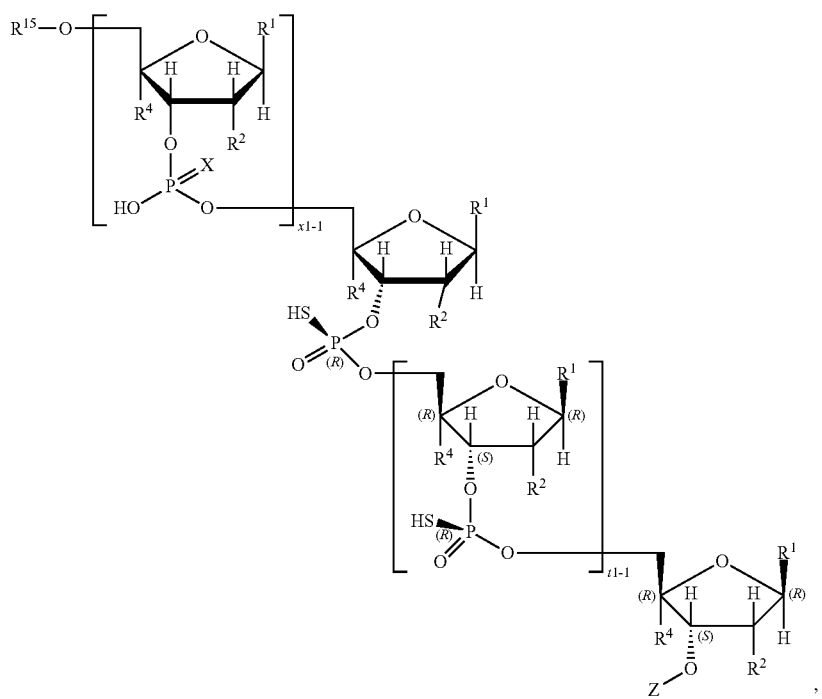
(PIII2)

or a salt thereof, wherein:

R¹, for each occurrence, is independently a nucleobase, wherein the $NH_2$ of the nucleobase, if present, is protected by an amine protecting group;

R², for each occurrence, is independently selected from the group consisting of H, halo, and $C_{1-6}$alkoxy optionally substituted with $C_{1-6}$alkoxy;

R⁴, for each occurrence, is independently H or forms a ring with the alkoxy group of R²;

R¹⁵ is a hydroxyl protecting group;

X, for each occurrence, is independently O or S;

t1 is an integer from 3 to 20;

x1 is an integer from 3 to 20; and

Z is a silyl hydroxyl protecting group.

Specifically, the oligonucleotide of formula (PIII1) or a salt thereof is formed by the coupling reaction between the an oligonucleotide fragment of formula (P1F1) or a salt thereof and the oligonucleotide of formula (P1F2) or a salt thereof. Similarly, the oligonucleotide of formula (PIII2) or a salt thereof is formed by the coupling reaction between the an oligonucleotide fragment of formula (P2F1) or a salt thereof and the oligonucleotide of formula (P2F2) or a salt thereof In certain embodiments, the oligonucleotide of formula (PIII1) or (PIII2) or a salt thereof is purified by chromatography.

A 133$^{rd}$ embodiment discloses a convergent liquid phase process for preparing an oligonucleotide comprising the steps of coupling an oligonucleotide fragment of formula (P1F3) or (P2F3):

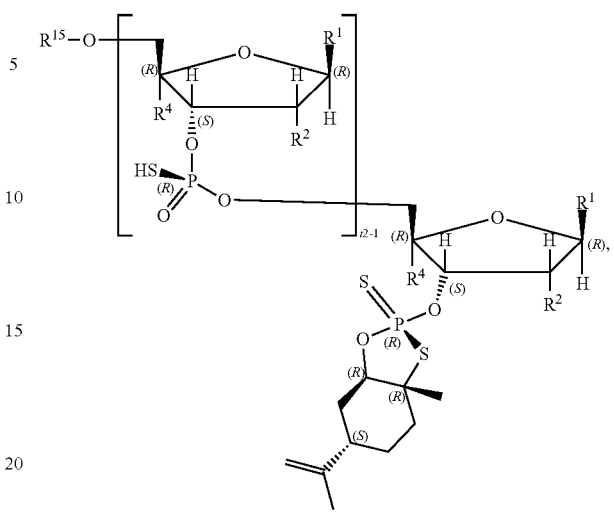

(P2F3)

or a salt thereof, with an oligonucleotide fragment of formula (PF4):

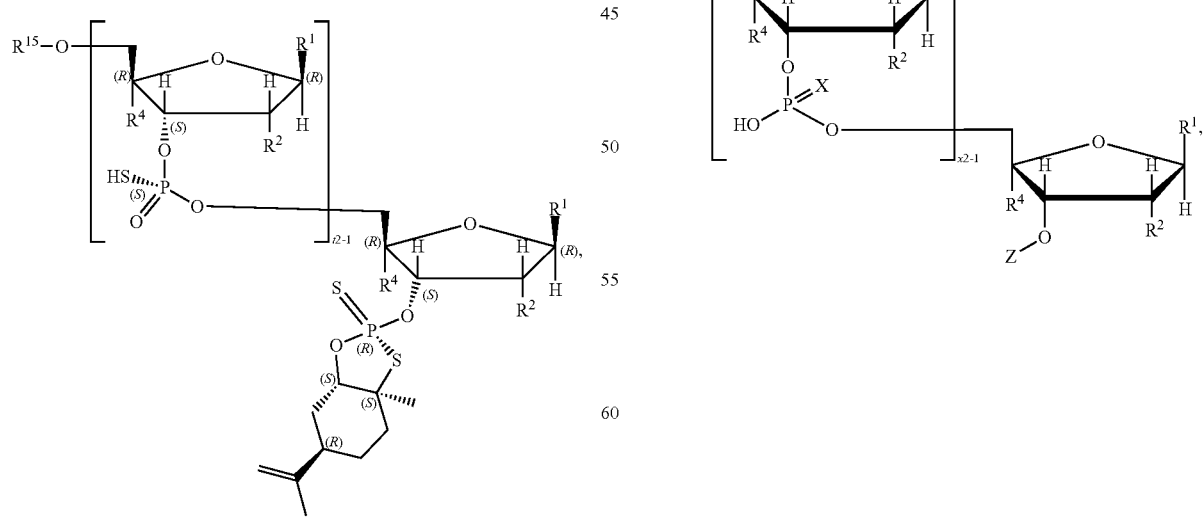

or a salt thereof, to form an oligonucleotide of formula (PIV1) or (PIV2):

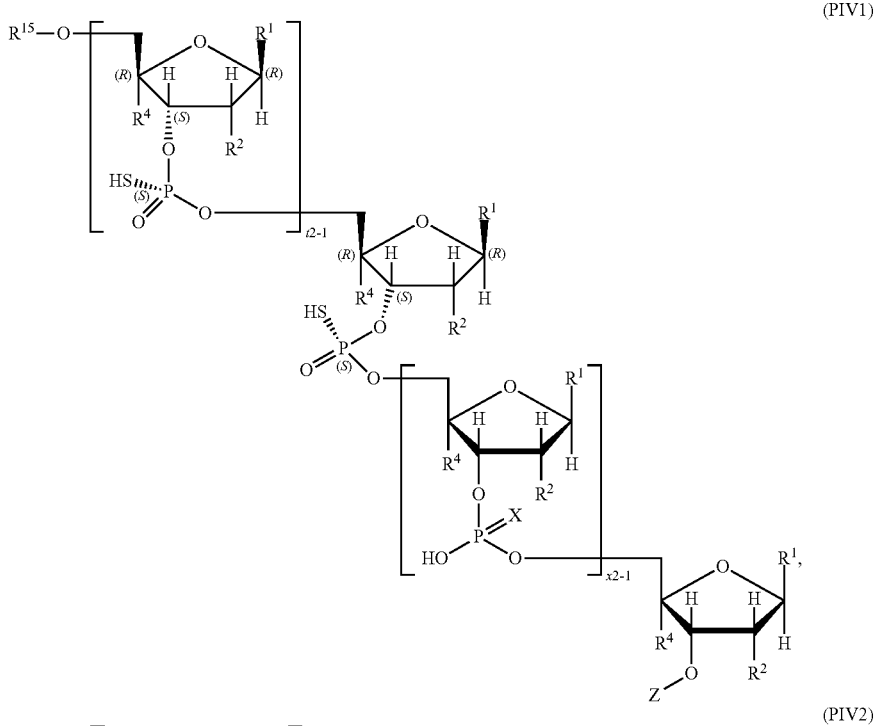

(PIV1)

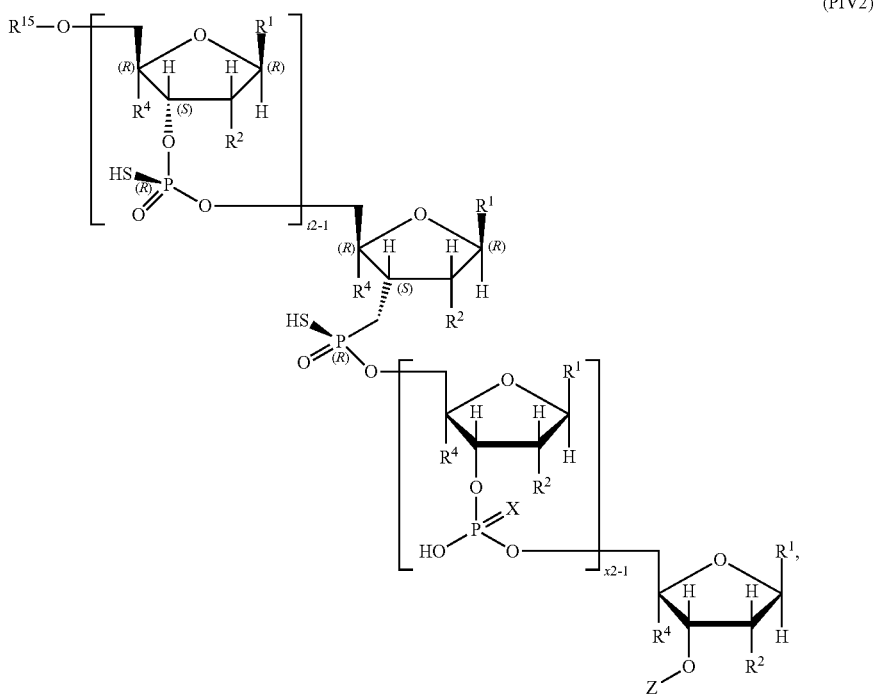

(PIV2)

or a salt thereof, wherein:

- $R^1$, for each occurrence, is independently a nucleobase, wherein the $NH_2$ of the nucleobase, if present, is protected by an amine protecting group;
- $R^2$, for each occurrence, is independently selected from the group consisting of H, halo, and $C_{1-6}$alkoxy optionally substituted with $C_{1-6}$alkoxy;
- $R^4$, for each occurrence, is independently H or forms a ring with the alkoxy group of $R^2$;
- $R^{15}$ is a hydroxyl protecting group;
- X, for each occurrence, is independently O or S
- t2 is an integer from 3 to 20;
- x2 is an integer from 3 to 20; and
- Z is a silyl hydroxyl protecting group.

Specifically, the oligonucleotide of formula (PIV1) or a salt thereof is formed by the coupling reaction of the oligonucleotide fragment of formula (P1F3) or a salt thereof with the oligonucleotide fragment of formula (PF4) or salt thereof. Similarly, the oligonucleotide of formula (PIV2) or a salt thereof is formed by the coupling reaction of the oligonucleotide fragment of formula (P2F3) or a salt thereof with the oligonucleotide fragment of formula (PF4) or salt thereof In certain embodiments, the oligonucleotide of formula (PIV1) or (PIV2) or a salt thereof is purified by chromatography.

A 134th embodiment discloses a process as described in the 133rd embodiment, wherein the process further comprises the step of:
a) deprotecting the oligonucleotide of formula (PIV1) or (PIV2) or a salt thereof to form an oligonucleotide of formula (PIV1') or (PIV2'):

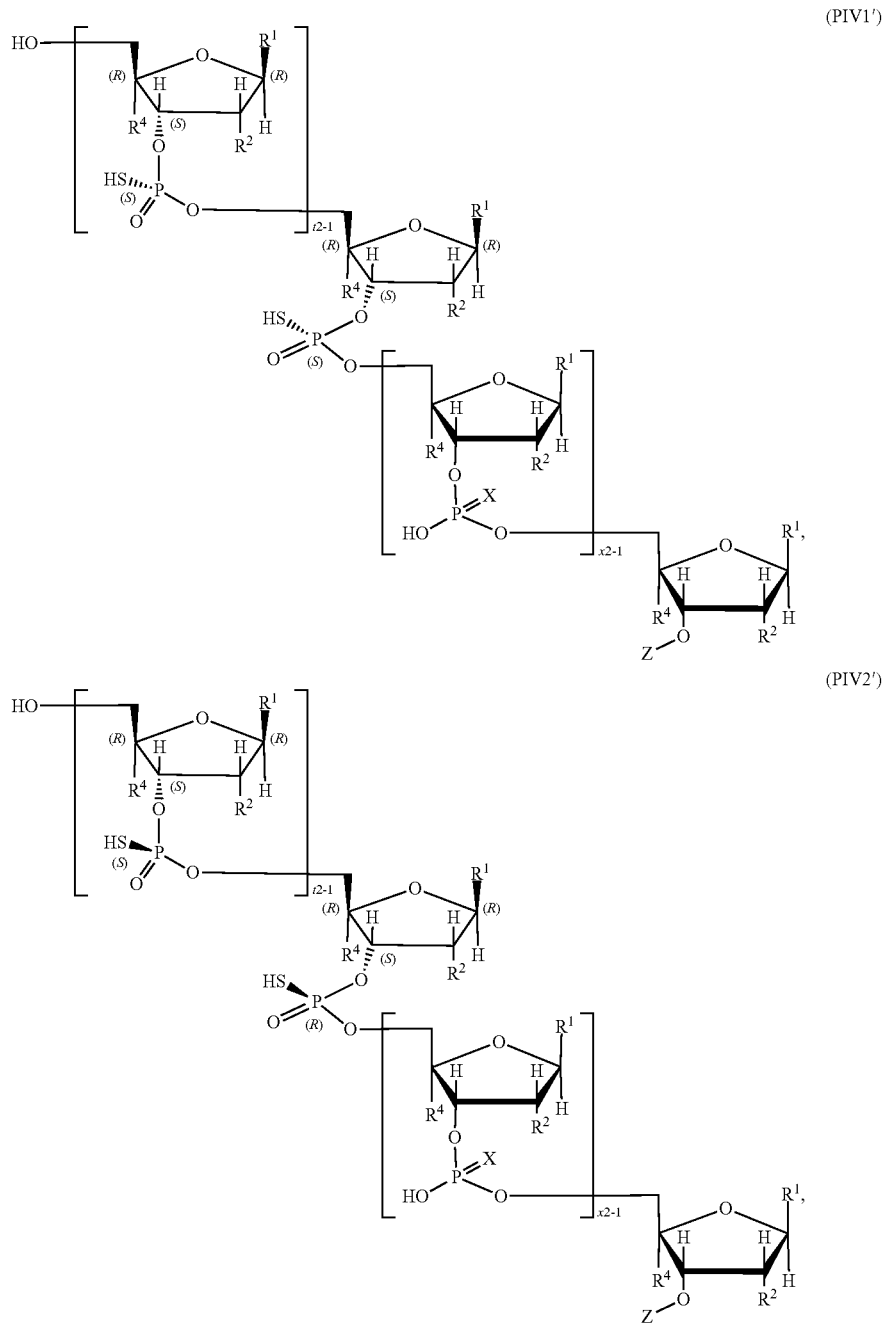

or a salt thereof; and b) coupling the oligonucleotide of formula (PIV1') or (PIV2') or a salt thereof with an oligonucleotide fragment of formula (P1F5) or (P2F5):
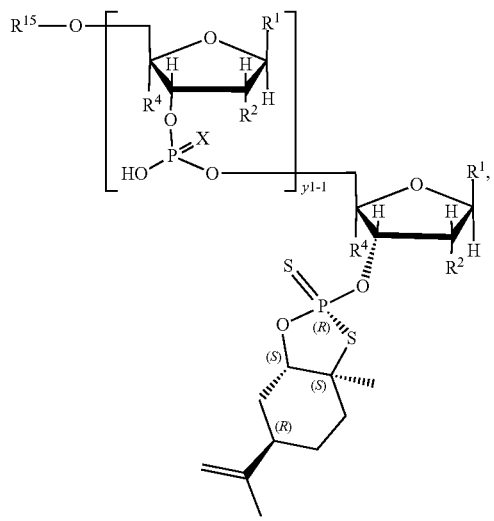
(P1F5)
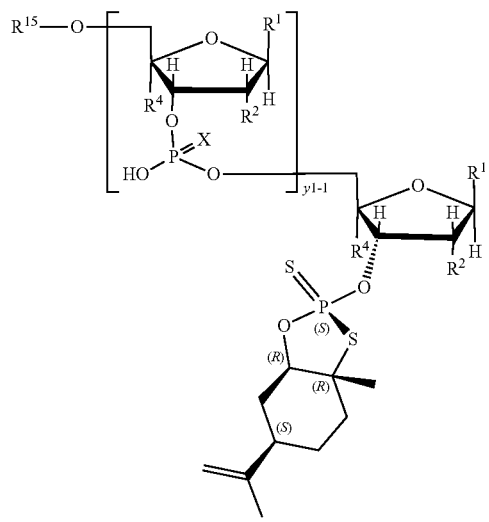
(P2F5)
or a salt thereof, to form an oligonucleotide of formula (PV1) or (PV2):
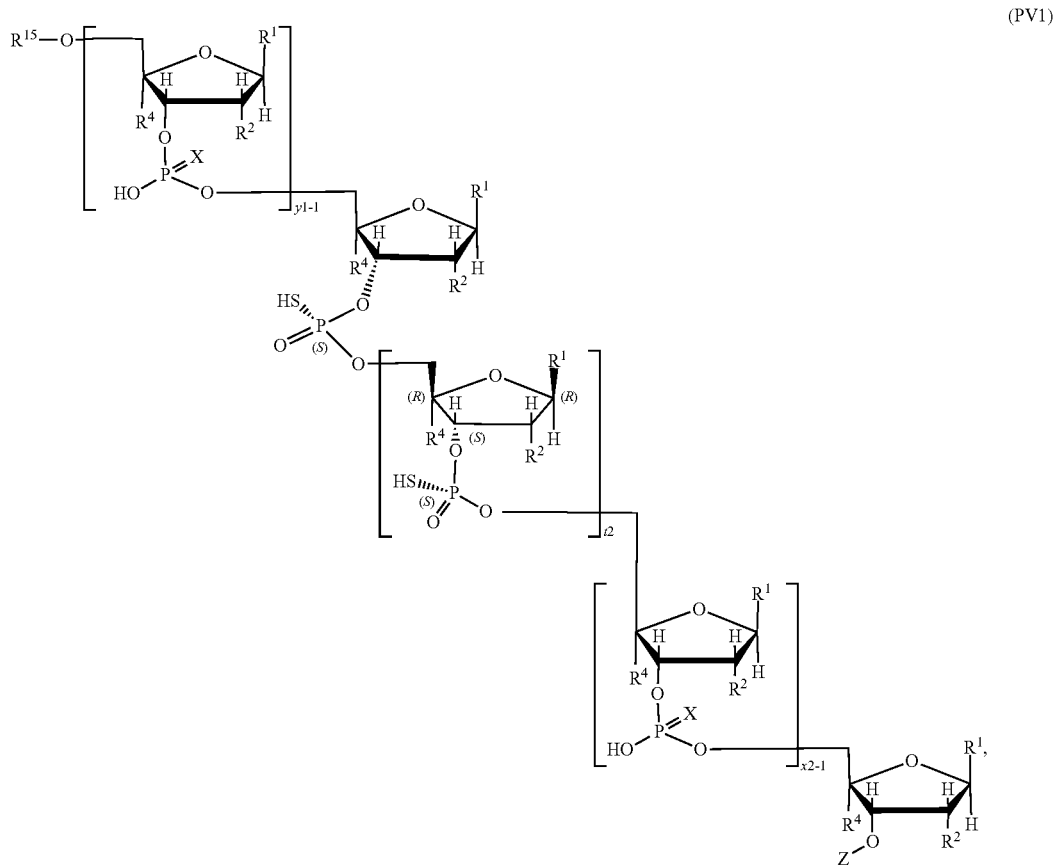
(PV1)

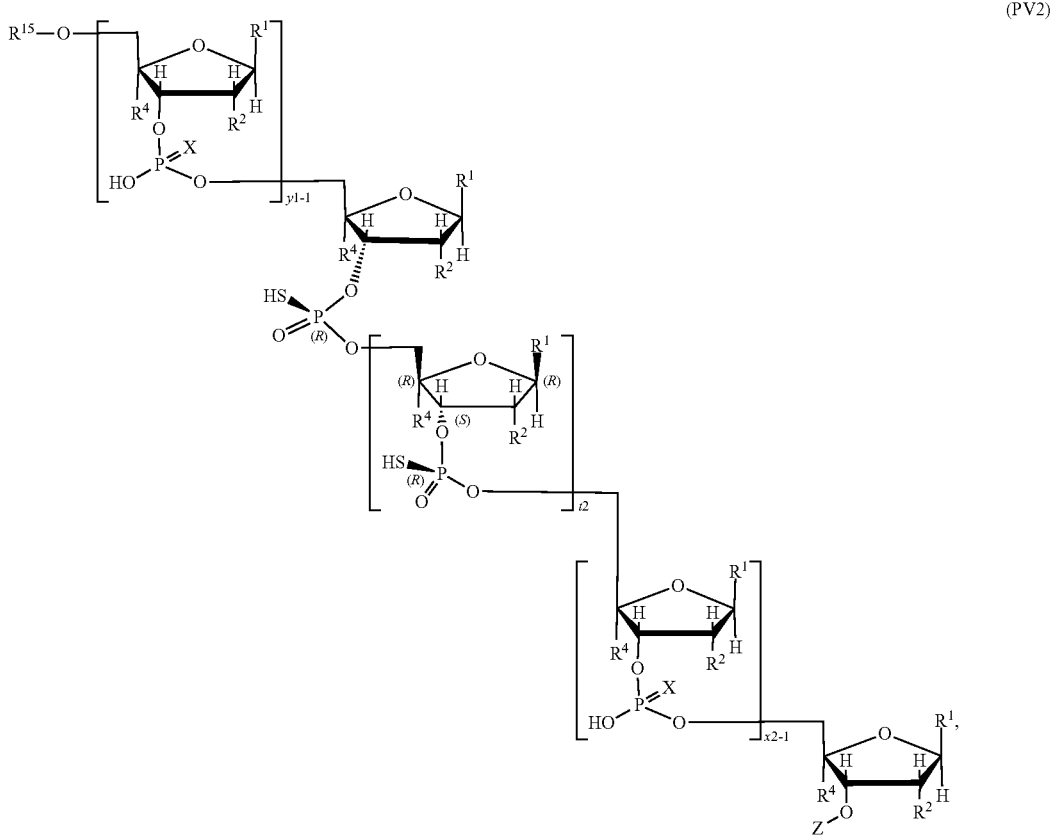

or a salt thereof, wherein y1 is an integer from 3 to 20.

Specifically, the oligonucleotide of formula (PV1) or salt thereof is formed by coupling reaction of the oligonucleotide of formula (PIV1') or a salt thereof with the oligonucleotide fragment of formula (P1F5) or a salt thereof. Similarly, the oligonucleotide of formula (PV2) or salt thereof is formed by coupling reaction of the oligonucleotide of formula (PIV2') or a salt thereof with the oligonucleotide fragment of formula (P2F5) or a salt thereof.

In certain embodiments, the oligonucleotide of formula (PIV1') or (PIV2') or a salt thereof and/or the oligonucleotide of formula (PV1) or (PV2) or a salt thereof are purified by chromatography.

In certain embodiment, the oligonucleotide fragment of formula (P1F5) or (P2F5) or a salt thereof is prepared by reacting an oligonucleotide fragment of formula (PF5a):

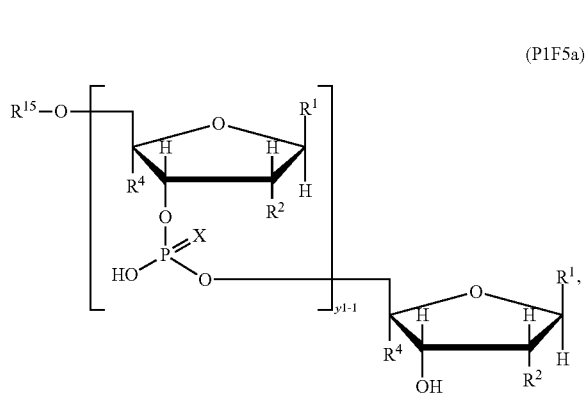

or a salt thereof with the PSI reagent (i.e., compound of formula (1) or (2) or a salt thereof).

In certain embodiments, the oligonucleotide of formula (PF5a) or a salt thereof is prepared by reacting an oligonucleotide of formula (PF5b):

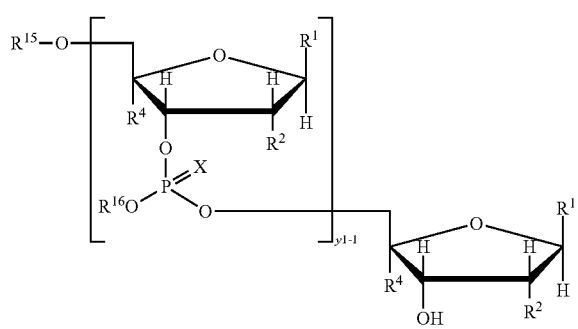

or a salt thereof, with a base, wherein $R^{16}$ is —$CH_2CH_2CN$. In certain embodiments, the base is selected from DBU, alkylamine (e.g., tert-butylamine, sec-butylamine, diisopropylethylamine, trimethylamine, triethylamine, 2-methylpropan-2-amine etc.) and other suitable organic bases. In a specific embodiment, the base is triethylamine or 2-methylpropan-2-amine. In another specific embodiment, the base is triethylamine.

A 135$^{th}$ embodiment discloses a process as described in the 133$^{rd}$ embodiment, wherein the process further comprises the steps of:

a) deprotecting the oligonucleotide of formula (PIV1) or (PIV2) or a salt thereof to form an oligonucleotide of formula (PIV1') or (PIV2'):

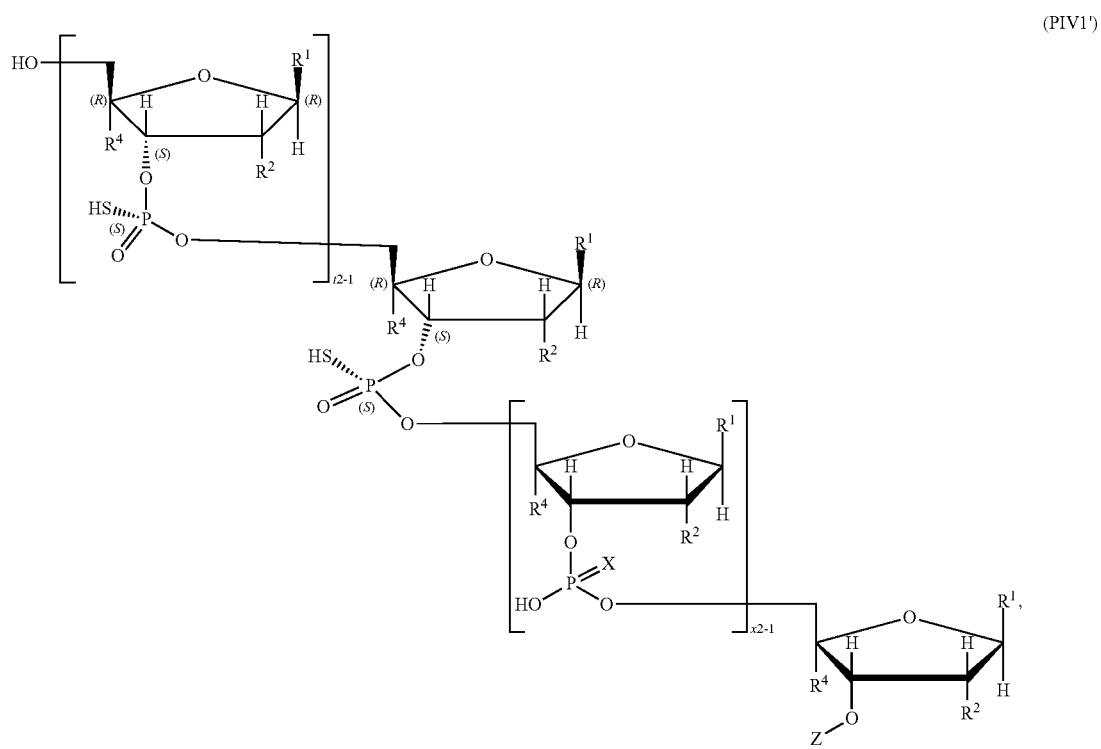

(PIV1')

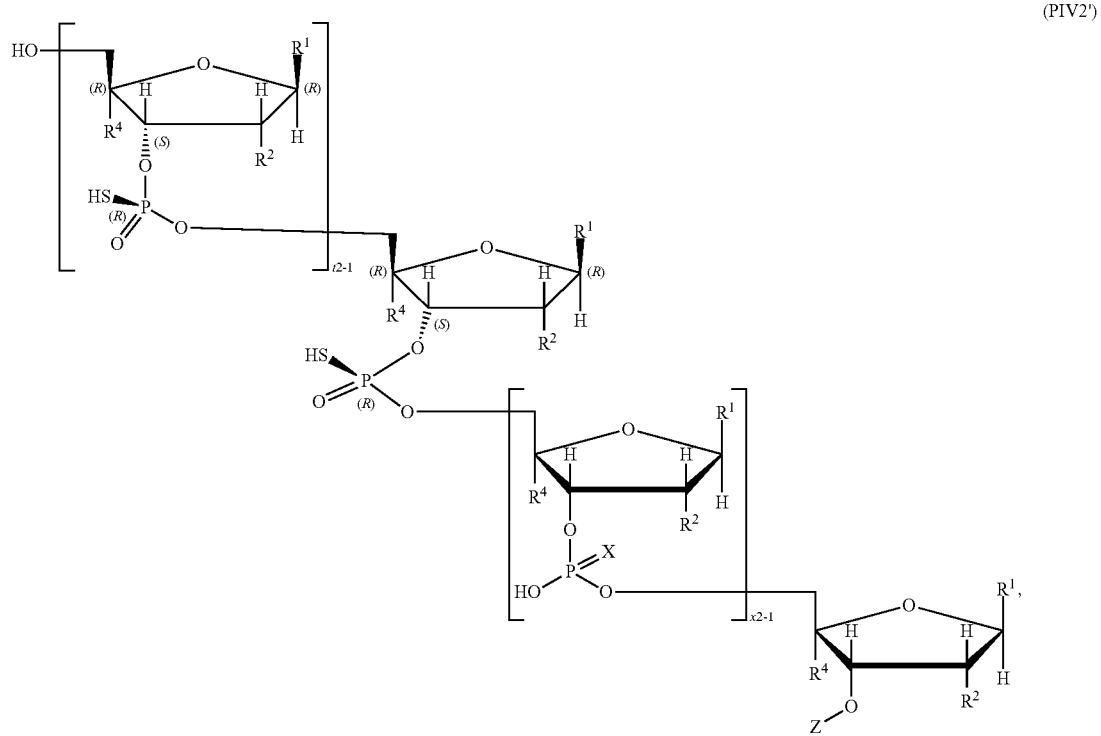
(PIV2')
or a salt thereof;
b) coupling the oligonucleotide of formula (PIV1') or (PIV2') or a salt thereof with an oligonucleotide fragment of formula (PIF6) or (P2F6):
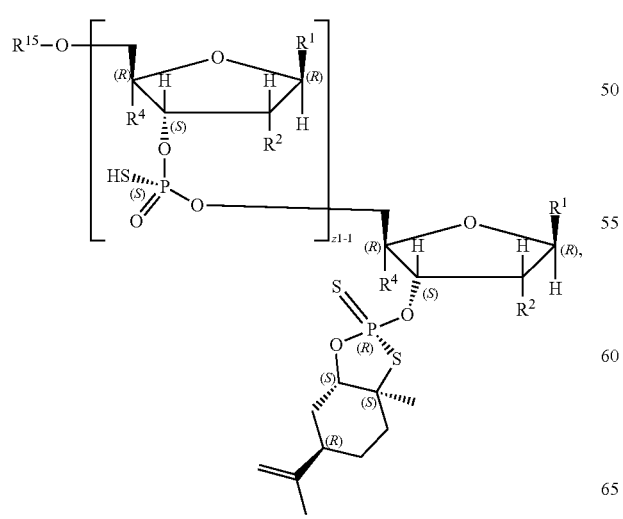
(P1F6)
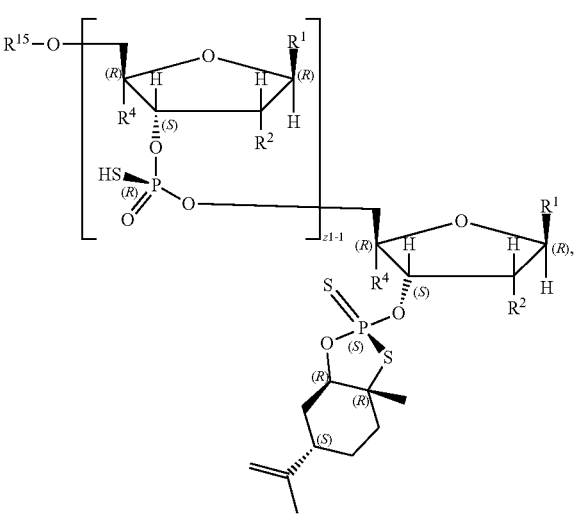
(P2F6)
or a salt thereof, to form an oligonucleotide of formula (PVI1) or (PVI2):

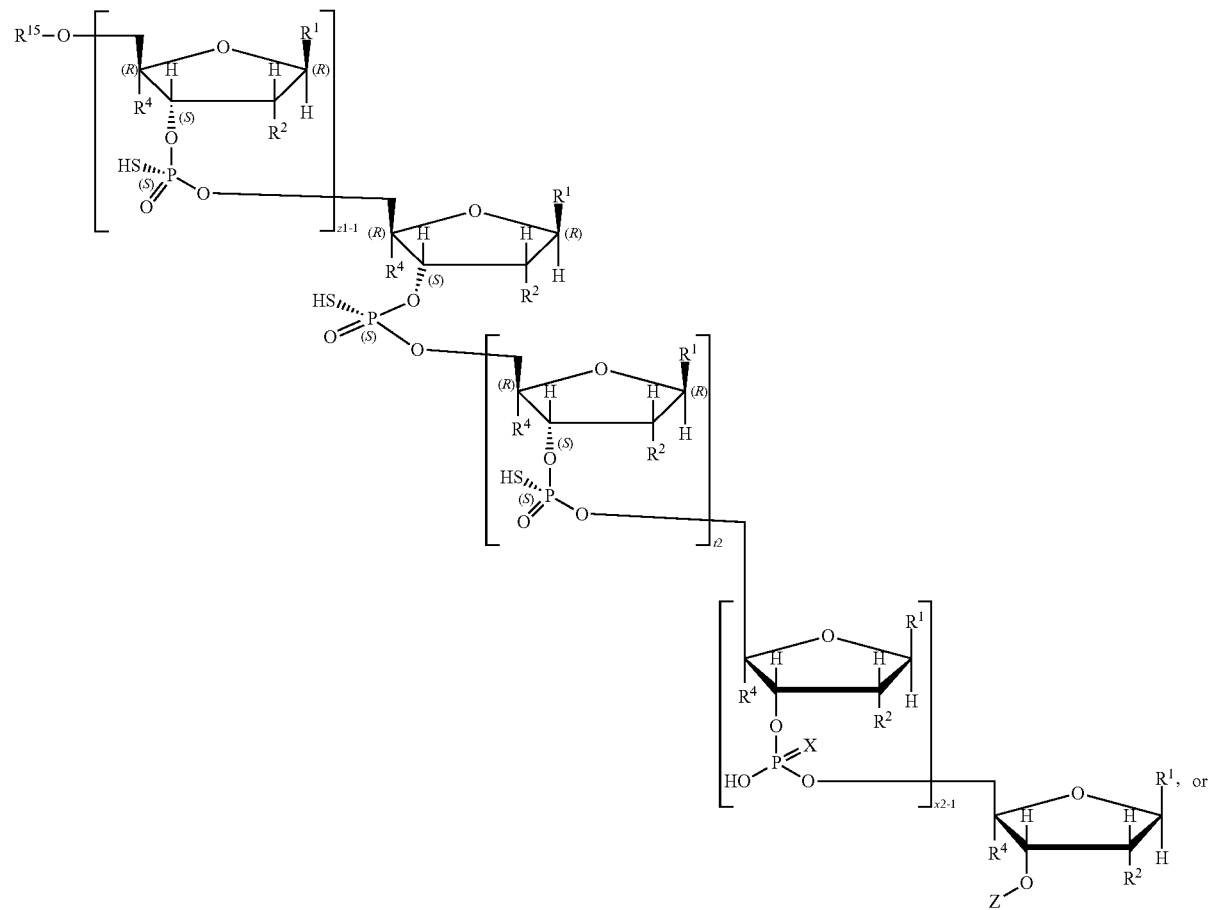

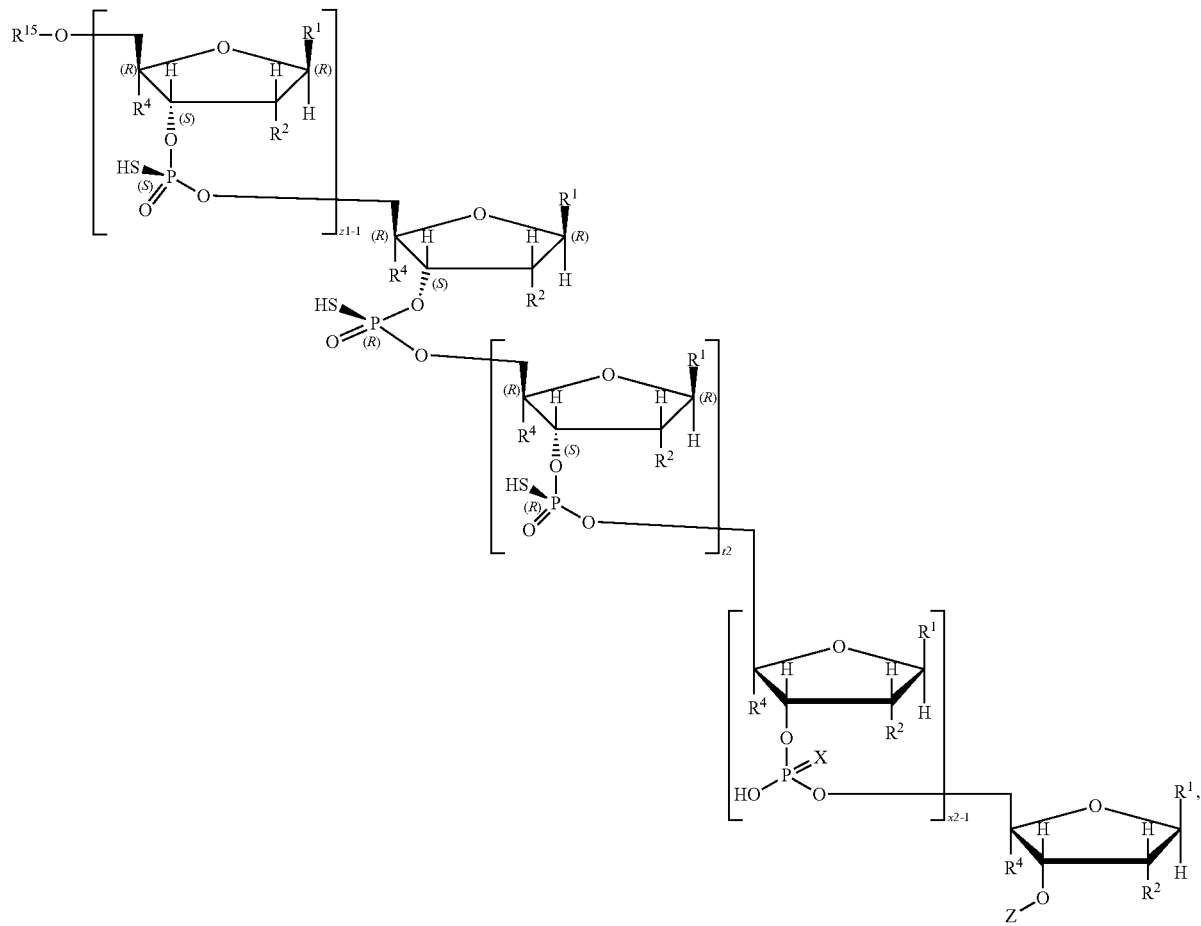
(PVI2)
or a salt thereof;
c) deprotecting the oligonucleotide of formula (PVI1) or (PIV2) or a salt thereof to form an oligonucleotide of (PVI1') or (PVI2'):

(PVI1')
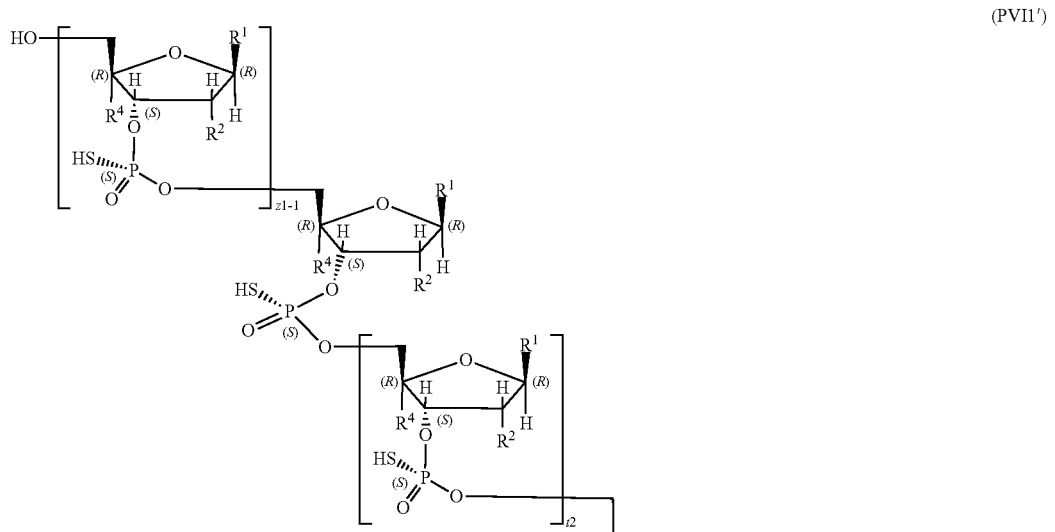
(PVI2')
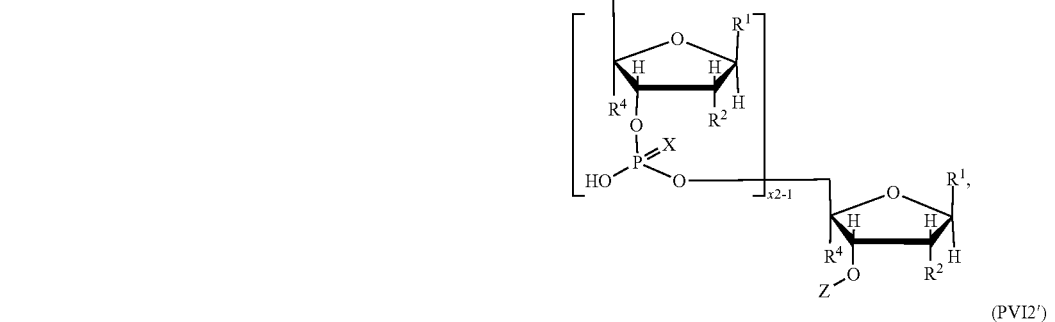
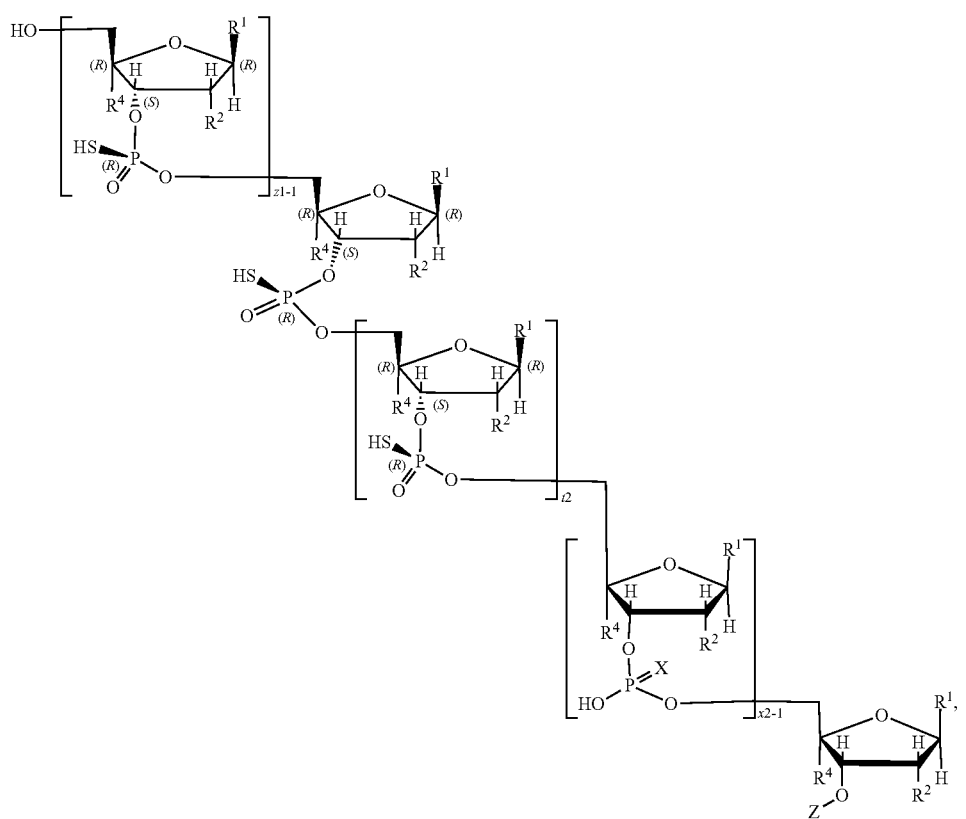
or a salt thereof, c) coupling the oligonucleotide of formula (PVI1') or (PVI2') or a salt thereof with an oligonucleotide fragment of formula (P1F5) or (P2F5)
(P1F5)
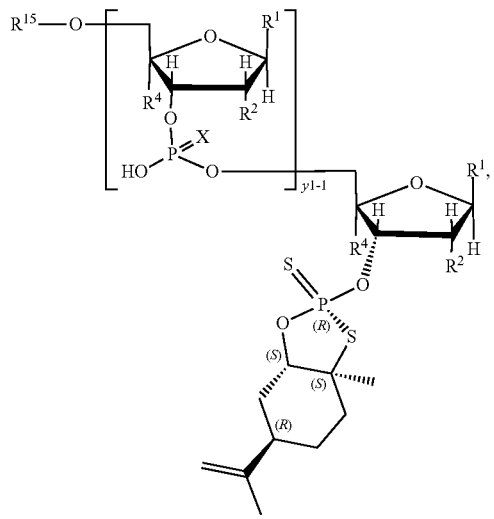
(P2F5)
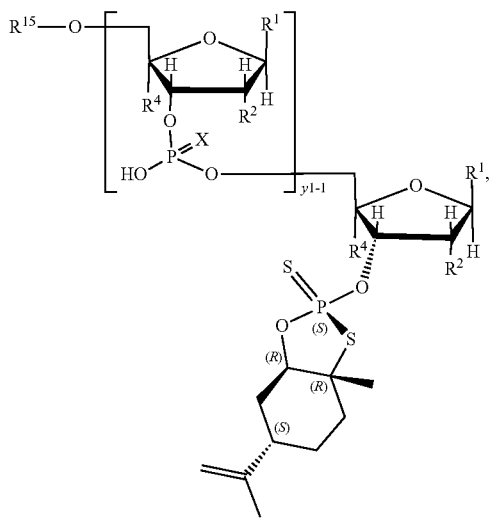
or a salt thereof, to form an oligonucleotide of formula (PVII1) or (PVII2):
(PVII1)
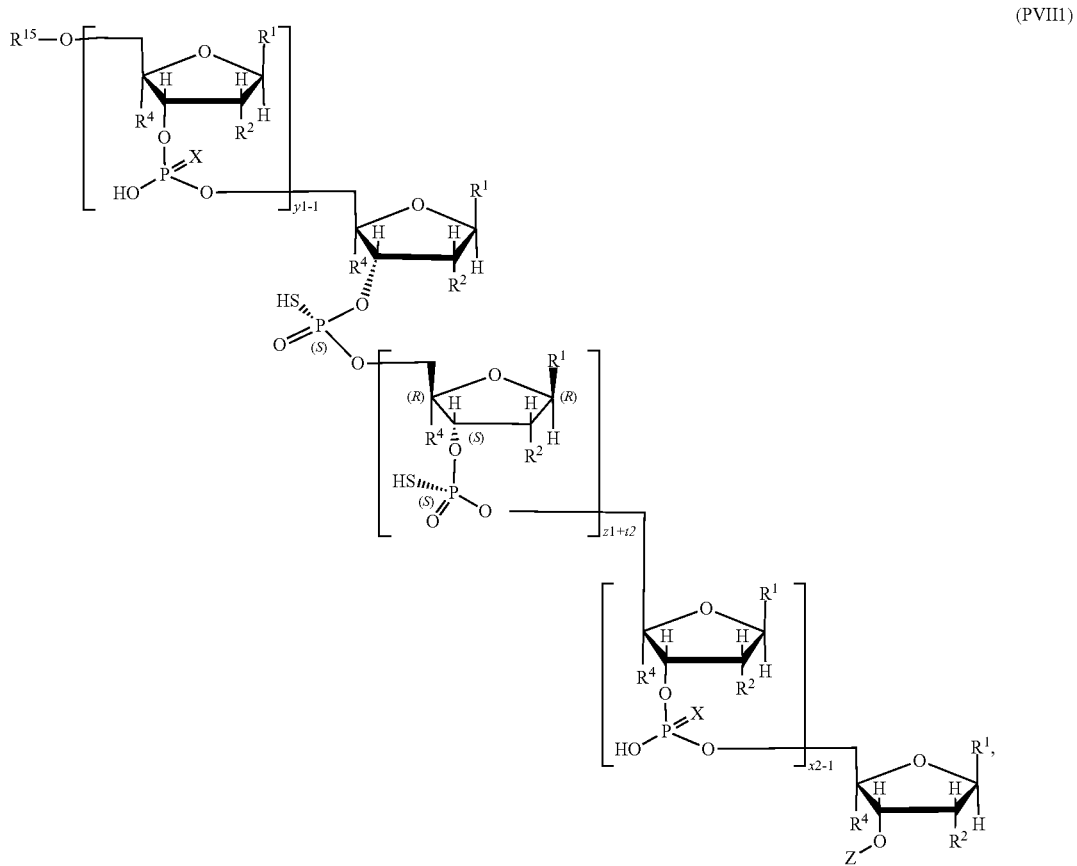

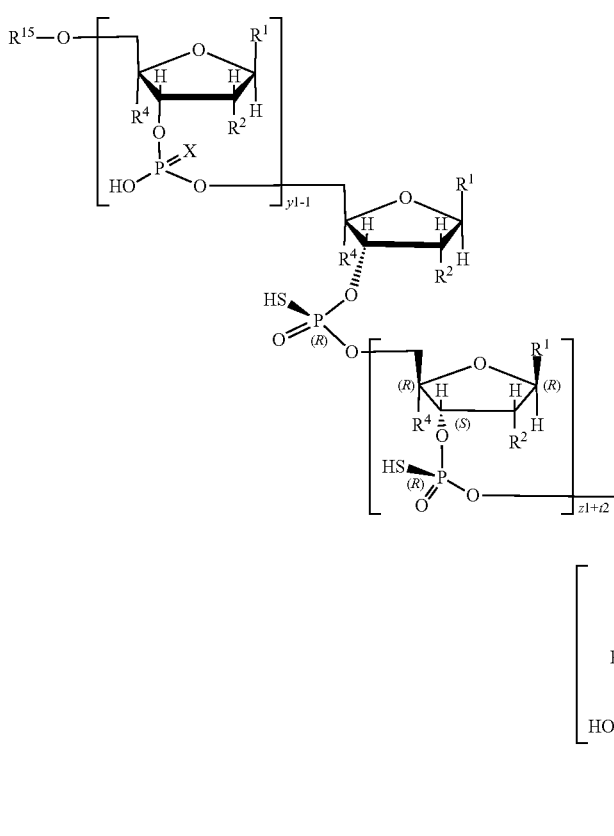

(PVII2)

or a salt thereof, wherein y1 is an integer from 3 to 20; and z1 is an integer from 3 to 20.

Specifically, the oligonucleotide of formula (PVI1) or a salt thereof is formed by coupling reaction of the oligonucleotide of formula (PIV1') or a salt thereof with the oligonucleotide fragment of formula (P1F6) or a salt thereof and the oligonucleotide of formula (PVII1) or a salt thereof is formed by coupling reaction of the oligonucleotide of formula (PVI1') or a salt thereof with the oligonucleotide fragment of formula (P1F5) or a salt thereof. Similarly, the oligonucleotide of formula (PVI2) or a salt thereof is formed by coupling reaction of the oligonucleotide of formula (PIV2') or a salt thereof with the oligonucleotide fragment of formula (P2F6) or a salt thereof and the oligonucleotide of formula (PVII2) or a salt thereof is formed by coupling reaction of the oligonucleotide of formula (PVI2') or a salt thereof with the oligonucleotide fragment of formula (P2F5) or a salt thereof.

In certain embodiments, any one of the oligonucleotide of formulae (PIV1'), (PIV2'), (PVI1), (PVI2), (PVI1'), (PVI2'), (PVII1) and (PVII2) or a salt thereof is purified by chromatography.

In certain embodiments, the coupling reaction described in the any one of the $132^{nd}$ to $135^{th}$ embodiments is carried out as described in the $122^{nd}$ or $123^{rd}$ embodiment. In a specific embodiment, the coupling reaction is carried out in the presence of a base. In another specific embodiment, the coupling reaction is carried out in the presence of a base and a drying agent. In yet another specific embodiment, the coupling reaction is carried out in the presence of DBU and molecular sieves.

In certain embodiments, the deprotection reaction described any one of the $132^{nd}$ to $135^{th}$ embodiments is carried out as describe in the $124^{th}$ embodiment.

In certain embodiments, the process disclosed herein involves preparation of following oligonucleotides:

1. ASO 1 (BIIB 058) (SEQ ID NO: 1), an 18-mer phosphorothioate oligonucleotide, in which each riboligonucleotide includes methoxy-ethyl (MoE) at the 2' position.
2. ASO 2 (BIIB 067) (SEQ ID NO: 2), a 5-10-5 gapmer phosphothioester and phosphodiester mixed backbone oligonucleotide. The central block of a gapmer is 10 deoxy ribonucleotides, which is flanked by blocks of 2'-MoE ribonucleotides.
3. Phosphorothioate oligonucleotides A, B, C, D, and E as shown in Table 2, below.
4. ASO 8 (SEQ ID NO:8), a 4-8-6 gapmer phosphothioester and phosphodiester mixed backbone oligonucleotide. The central block of a gapmer is 8 deoxy ribonucleotides, which is flanked by blocks of 2'-MoE ribonucleotides.

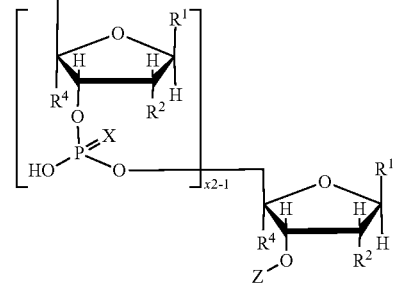

5. ASO 9 (SEQ ID NO:9), a 5-8-5 gapmer phosphothioester and phosphodiester mixed backbone oligonucleotide. The central block of the gapmer is 8 deoxy ribonucleotides, which is flanked by blocks of 2'-MoE ribonucleotides.

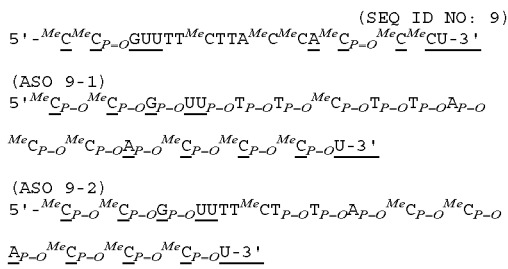

(ASO 9-1)
5'-$^{Me}$C$_{P=O}$$^{Me}$C$_{P=O}$G$_{P=O}$UU$_{P=O}$T$_{P=O}$T$_{P=O}$$^{Me}$C$_{P=O}$T$_{P=O}$T$_{P=O}$A$_{P=O}$ $^{Me}$C$_{P=O}$$^{Me}$C$_{P=O}$A$_{P=O}$$^{Me}$C$_{P=O}$$^{Me}$C$_{P=O}$$^{Me}$C$_{P=O}$U-3'

(ASO 9-2)
5'-$^{Me}$C$_{P=O}$$^{Me}$C$_{P=O}$G$_{P=O}$UUTT$^{Me}$CT$_{P=O}$T$_{P=O}$A$_{P=O}$$^{Me}$C$_{P=O}$$^{Me}$C$_{P=O}$

A$_{P=O}$$^{Me}$C$_{P=O}$$^{Me}$C$_{P=O}$$^{Me}$C$_{P=O}$U-3' wherein: underline: MOE ribonucleotide
P=O: phosphodiester
any others: phosphothioester

TABLE 1

Phosphorothioate oligonucleotides A, B, C, D, and E

| Code | Sequence Type | Oligonucleotide Sequence with modified bases |
|---|---|---|
| A | Fully DNA sequence | $^{Me}$CGA$^{Me}$CT ATA$^{Me}$CG$^{Me}$CG$^{Me}$CAA TATGG ASO 3 (SEQ ID NO: 3) |
| B | 5-10-5 gapmer The central block of a gapmer is 10 deoxy ribonucleotides, which is flanked by blocks of 2'-OMe ribonucleotides. | $^{Me}$CGA$^{Me}$CU ATA$^{Me}$CG$^{Me}$CG$^{Me}$CAA UAUGG ASO 4 (SEQ ID NO: 4) |
| C | 5-10-5 gapmer The central block of a gapmer is 10 deoxy ribonucleotides, which is flanked by blocks of 2'-MoE ribonucleotides. | $^{Me}$CGA$^{Me}$CT ATA$^{Me}$CG$^{Me}$CG$^{Me}$CAA TATGG ASO 5 (SEQ ID NO: 5) |
| D | 5-10-5 gapmer The central block of a gapmer is 10 deoxy ribonucleotides, which is flanked by blocks of cEt ribonucleotides. | $^{Me}$CGA$^{Me}$CU ATA$^{Me}$CG$^{Me}$CG$^{Me}$CAA UAUGG ASO 6 (SEQ ID NO: 6) |
| E | 5-10-5 gapmer The central block of a gapmer is 10 deoxy ribonucleotides, which is flanked by blocks of 2'-Fluoro ribonucleotides. | CGACU ATA$^{Me}$CG$^{Me}$CG$^{Me}$CAA UAUGG ASO 7 (SEQ ID NO: 7) |

In certain embodiments, the target anti-sense oligonucleotide is a phosphorothioate oligonucleotide having a sequence of (from 5' to 3')

TCACTTTCATAATGCTGG, (SEQ ID NO: 1)

wherein each internucleoside linkage of the oligonucleotide is a phosphorothioate linkage, each nucleoside of the oligonucleotide is a 2'-O-methoxyethyl (MOE) nucleoside, and each cytosine is a 5-methylcytosine. SEQ ID NO: 1 is also known as BIIB058, and is described in WO2007/002390, WO2010/148249, and U.S. Pat. No. 8,980,853, the teaching of each are herein incorporated by reference.

In certain embodiments, the sequence of the anti-sense oligonucleotide is a 5-10-5 MOE gapmer, having a sequence of (from 5' to 3')

CAGGATACATTTCTACAGCT, (SEQ ID NO: 2)

wherein each of nucleosides 1-5 and 16-20 are 2'-O-methoxyethylribose modified nucleosides, and each of nucleosides 6-15 are 2'-deoxynucleosides, wherein the internucleoside linkages between nucleosides 2 to 3, 4 to 5, 16 to 17, and 18 to 19 are phosphodiester linkages and the internucleoside linkages between nucleosides 1 to 2, 3 to 4, 5 to 6, 6 to 7, 7 to 8, 8 to 9, 9 to 10, 10 to 11, 11 to 12, 12 to 13, 13 to 14, 14 to 15, 15 to 16, 17 to 18, and 19 to 20 are phosphorothioate linkages, and wherein each cytosine is a 5'-methylcytosine. SEQ ID NO:2 is described by the following chemical notation: mCes Aeo Ges Geo Aes Tds Ads mCds Ads Tds Tds Tds mCds Tds Ads mCeo Aes Geo mCes Te; wherein,
A=an adenine,
mC=a 5'-methylcytosine
G=a guanine,
T=a thymine,
e=a 2'-O-methoxyethylribose modified sugar,
d=a 2'-deoxyribose sugar,
s=a phosphorothioate internucleoside linkage, and
o=a phosphodiester internucleoside linkage.
SEQ ID NO: 2 is as known as BIIB067 or ISIS 666853 and is described in WO2015153800, the teachings of which are incorporated herein by reference.

In certain embodiments, the process is as described in any of the above embodiments, or any of the aspects thereof, wherein the anti-sense oligonucleotide is a 4-8-6 gapmer, having a sequence of (from 5' to 3'):

GUUUUCATCAATATCUGCAA (SEQ ID NO: 8)

wherein each of nucleosides 1-4 and 13-18 are 2'-O-methoxyethylribose modified nucleosides, and each of nucleosides 5-12 are 2'-deoxy ribonucleotides, wherein the internucleoside linkages between nucleosides 2 to 3, 3 to 4, 13 to 14, 14 to 15, and 15 to 16 are phosphodiester linkages and the internucleoside linkages between nucleosides 1 to 2, 4 to 5, 5 to 6, 6 to 7, 7 to 8, 8 to 9, 9 to 10, 10 to 11, 11 to 12, 12 to 13, 16 to 17 and 17 to 18 are phosphorothioate linkages, wherein each cytosine is 5-methylcytosine, and wherein the uracil is 5-methyluracil. SEQ ID NO:8 is described by the following chemical notation:

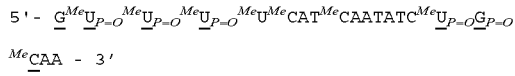

Underline=MoE ribonucleotide
G=guanine
$^{Me}$C=5-methylcytosine
T=thymine
A=adenine
$^{Me}$U=5-methyluracil (also known as thymine)
P=O=phosphodiester internucleoside linkage
Any other internucleoside linkages are phosphothioester linkage.

In certain embodiments, the process is as described in any of the above embodiments, or any of the aspects thereof, wherein the anti-sense oligonucleotide is a 5-8-5 gapmer (ASO 9), having a sequence of (from 5' to 3'):

CCGUUTTCTTACCACCCU (SEQ ID NO: 9)

wherein each of nucleosides 1-5 and 14-18 are 2'-O-methoxyethylribose modified nucleosides, and each of nucleosides 6-13 are 2'-deoxy ribonucleotides, wherein the internucleoside linkages between nucleosides 3 to 4, and 16 to 17 are phosphodiester linkages and the internucleoside linkages between nucleosides 1 to 2, 2 to 3, 4 to 5, 5 to 6, 6 to 7, 7 to 8, 8 to 9, 9 to 10, 10 to 11, 11 to 12, 12 to 13, 13 to 14, 14 to 15, 15 to 16 and 17 to 18 are phosphorothioate linkages, wherein each cytosine is 5-methylcytosine, and wherein the uracil is 5-methyluracil.

SEQ ID NO:9 is described by the following chemical notation:

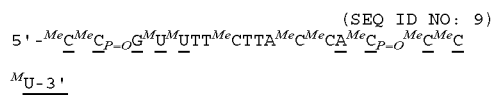

Underline=MoE ribonucleotide
G=guanine
$^{Me}$C=5-methylcytosine
T=thymine
A=adenine
$^{Me}$U=5-methyluracil (also known as thymine)
P=O=phosphodiester internucleoside linkage In certain embodiments, ASO 9 was prepared using convergent liquid phase process of oligonucleotide synthesis of present disclosure as follows:

In certain embodiments, ASO 9 was prepared using convergent liquid phase process of oligonucleotide synthesis of the present disclosure. In certain embodiments, the process involves addition of phosphoramidite at 3'-hydroxyl for the fragment DMTrO-$T_sT_sA_sC_sC_s$—OH to yield fragment DMTrO-$T_sT_sA_sC_sC_s$—OP. The fragment DMTrO-$T_sT_sA_sC_sC_s$—OP is coupled with HO-$A_sC_oC_sC_s$U-LHPG followed by sulfurization to give DMTrO-$T_sT_sA_sC_sC_sA_s$-$C_oC_sC_s$U-LHPG. This DMT-protected fragment undergoes 5'-hydroxyl deprotection (detritylation) to yield HO-$T_sT_sA_sC_sC_sA_sC_oC_sC_s$U-LHPG which is further coupled with phosphoramidite fragment DMTrO-$U_sT_sT_sC$—OP (synthesized with a method similar to DMTrO-$T_sT_sA_sC_sC_s$—OP synthesis as discussed above) followed by sulfurization to give DMTrO-$U_sT_sT_sC_sT_sT_sA_sC_sC_sA_sC_oC_sC_s$U-LHPG. This DMT-protected fragment undergoes 5'-hydroxyl deprotection (detritylation) to yield HO-$U_sT_sT_sC_sT_sT_sA_sC_sC_sA_sC_oC_sC_s$U-LHPG which is coupled with DMTrO-$C_sC_oG_sU$—OP ((synthesized with a method similar to DMTrO-$T_sT_sA_sC_sC_s$—OP synthesis as discussed above)) followed by sulfurization to give DMTrO-$C_sC_oG_sU_sU_sT_sT_sC_sT_sT_sA_sC_sC_sA_sC_oC_sC_s$U-LHPG (fully protected ASO 9). In certain embodiments, fragment HO-$A_sC_sC_sC_s$U-LHPG can be prepared by coupling HO-U-LHPG with DMTrO$A_sC_sC_s$CP, followed by sulfurization and 5'-hydroxyl deprotection (detritylation). The fragment DMTrO$A_sC_oC_s$CP can prepared by addition of phosphoramidite at 3'hydroxyl of the fragment DMTrO$A_sC_sC$—OH. As used herein, 0 is a phospodiester linkage and s is a phosphothiolate linkage.

EXEMPLIFICATION

Abbreviation
ACN=acetonitrile
DBU=8-diazabicyclo[5.4.0]undec-7-ene
DCA=CHCl$_2$COOH or dichloroacetic acid
DCM=dichloromethane
DDTT=3-(N,N-dimethylamino-methylidene)amino)-3H-1,2,4-dithiazole
DCI=4,5-dicyanoimidazole DI=
DIEA=N,N-diisopropylethylamine
DMT or DMTr=4,4'-dimethoxytrityl or bis-(4-methoxyphenyl)phenylmethyl
DMSO=dimethyl sulfoxide
EtOAc or EA=ethyl acetate
ETT=5-ethylthio-1H-tetrazole
h or hr=hour
HBTU=3-[bis(dimethylamino)methyliumyl]-3H-benzotriazol-1-oxide hexafluorophosphate
HOBt=hydroxybenzotriazole
imid=imidazole
iPrOH=isopropyl alcohol
MOE=methoxyethyl
MS=molecular sieve
MTBE or TBME=methyl tert-butyl ether
Py=pyridine
RT=retention time
TBAF=tetra-n-butylammonium fluoride
TBuAA=tributylamine acetate
TBDPSCl=tert-butyl(chloro)diphenylsilane
TCA=trichloroacetic acid
TEA=triethylamine
TEAB=tetraethylammonium bromide
TFA=trifluoroacetic acid
THF=tetrahydrofuran Example 1. Synthesis of ASO 9

A. Preparation of 3'-Fragment:
1. Synthesis of 5'-OH-ACCCU-LHPG fragment (Fragment 1)
General Procedure for Preparation of Compound 1-2

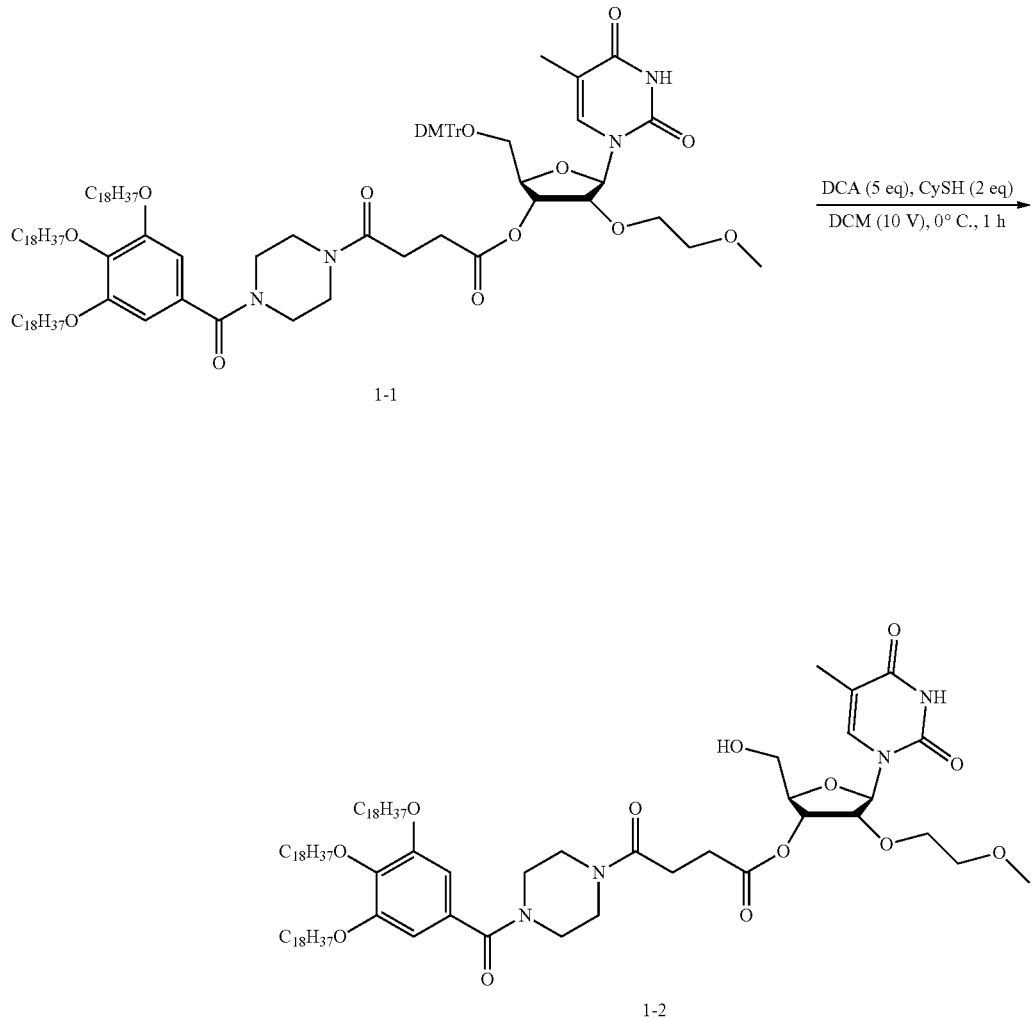

To a solution of compound 1-1 (176 g, 103 mmol, 1.00 eq) in DCM (1800 mL) was added DCA (66.8 g, 518 mmol, 42.6 mL, 5.00 eq) and CySH (24.1 g, 207 mmol, 25.3 mL, 2.00 eq) at 0° C. The mixture was stirred at 0° C. for 1 h. TLC (Dichloromethane:Ethyl acetate:Methanol=10:10:1, product Rf=0.43) indicated compound 1-1 was consumed completely and one new spot formed. The reaction was clean according to TLC. The reaction mixture was quenched by addition NaHCO$_3$ (2.50%, 2000 mL) and collected the dichloromethane (DCM) layer. Anhydrous acetonitrile (ACN) (5000 mL, 30.0 V) was added slowly at 25° C. to precipitate the product. Compound 1-2 (144 g, 103 mmol, 99.5% yield) was obtained as a white solid.

General Procedure for Preparation of Compound 1-3

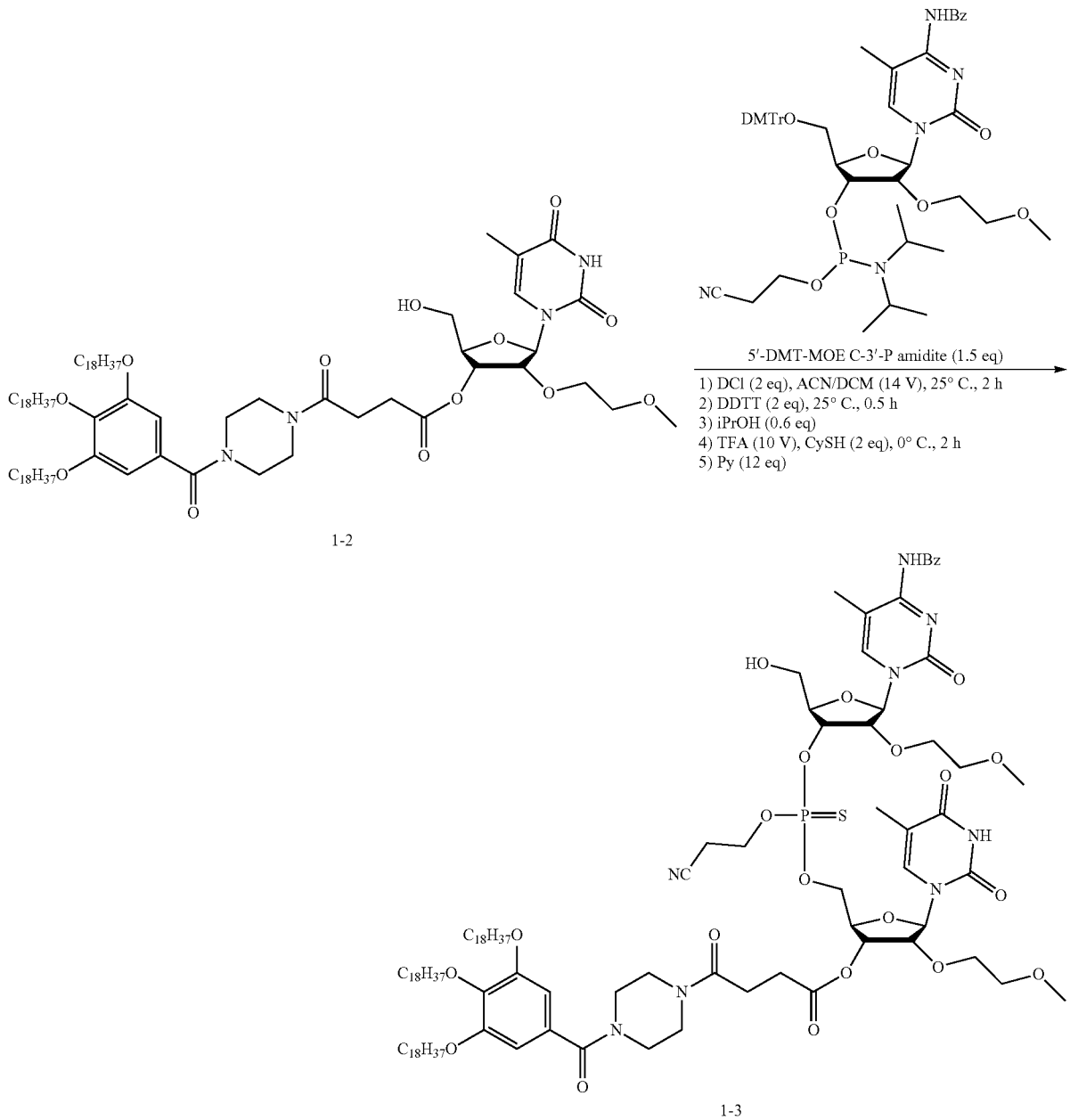

Compound 1-2 (125 g, 89.6 mmol, 1.00 eq) and 5'-DMT-MOE C-3'-P amidite (124 g, 134 mmol, 1.50 eq) co-evaporated with ACN (300 mL) and DCM (700 mL).

To a solution of compound 1-2 (125 g, 89.6 mmol, 1.00 eq) and 5'-DMT-MOE C-3'-P amidite (124 g, 134 mmol, 1.50 eq) in DCM/ACN=3:1 (1800 mL) was added molecular sieve 3A (54.0 g). The mixture was stirred at 25° C. for 1 h. The mixture was added DCI (21.1 g, 179 mmol, 2.00 eq). The mixture was stirred at 25° C. for 1 h. TLC (Dichloromethane:Ethyl acetate:Methanol=10:10:1, product Rf=0.55) indicated compound 1-2 was consumed completely and one new spot formed. The reaction was clean according to TLC.

The mixture was added DDTT (36.7 g, 178 mmol, 2.00 eq) and propan-2-ol (3.22 g, 53.6 mmol, 4.11 mL, 0.600 eq). The mixture was stirred at 25° C. for 0.5 h. TLC (Dichloromethane:Ethyl acetate:Methanol=10:10:1, product Rf=0.55) indicated one new spot formed. The reaction was clean according to TLC.

The mixture was added CySH (20.6 g, 178 mmol, 21.7 mL, 2.00 eq) and TFA (101 g, 890 mmol, 65.9 mL, 10.0 eq) at 0° C. The mixture was stirred at 0° C. for 2 h. TLC (Dichloromethane:Ethyl acetate:Methanol=10:10:1, product Rf=0.51) indicated one new spot formed. The reaction was clean according to TLC.

Pyrinde (Py) (84.4 g, 1.07 mol, 86.2 mL, 12.0 eq) was added to the mixture. Molecular sieves were removed by filtration and the solid cake was washed with DCM (500 mL). The pH value of the reaction mixture was adjusted to 6-7 with 2.5% NaHCO$_3$ aqueous (1000 mL). The combined organic layers were dried over Mg$_2$SO$_4$, filtered and concentrated. The crude was re-dissolve in DCM (450 mL) and dropped into ACN (4000 ml, 30.0 V) with vigorous stirring. Desired product was precipitated out. Compound 1-3 (173 g, 88.9 mmol, 99.9% yield) was obtained as a white solid.

General Procedure for Preparation of Compound 1-4

The mixture was added DCI (14.9 g, 126 mmol, 2.00 eq). The mixture was stirred at 25° C. for 1 h. TLC (Dichloromethane:Ethyl acetate:Methanol=10:10:1, product Rf=0.64) indicated compound 1-3 was consumed completely and one new spot formed. The reaction was clean according to TLC.

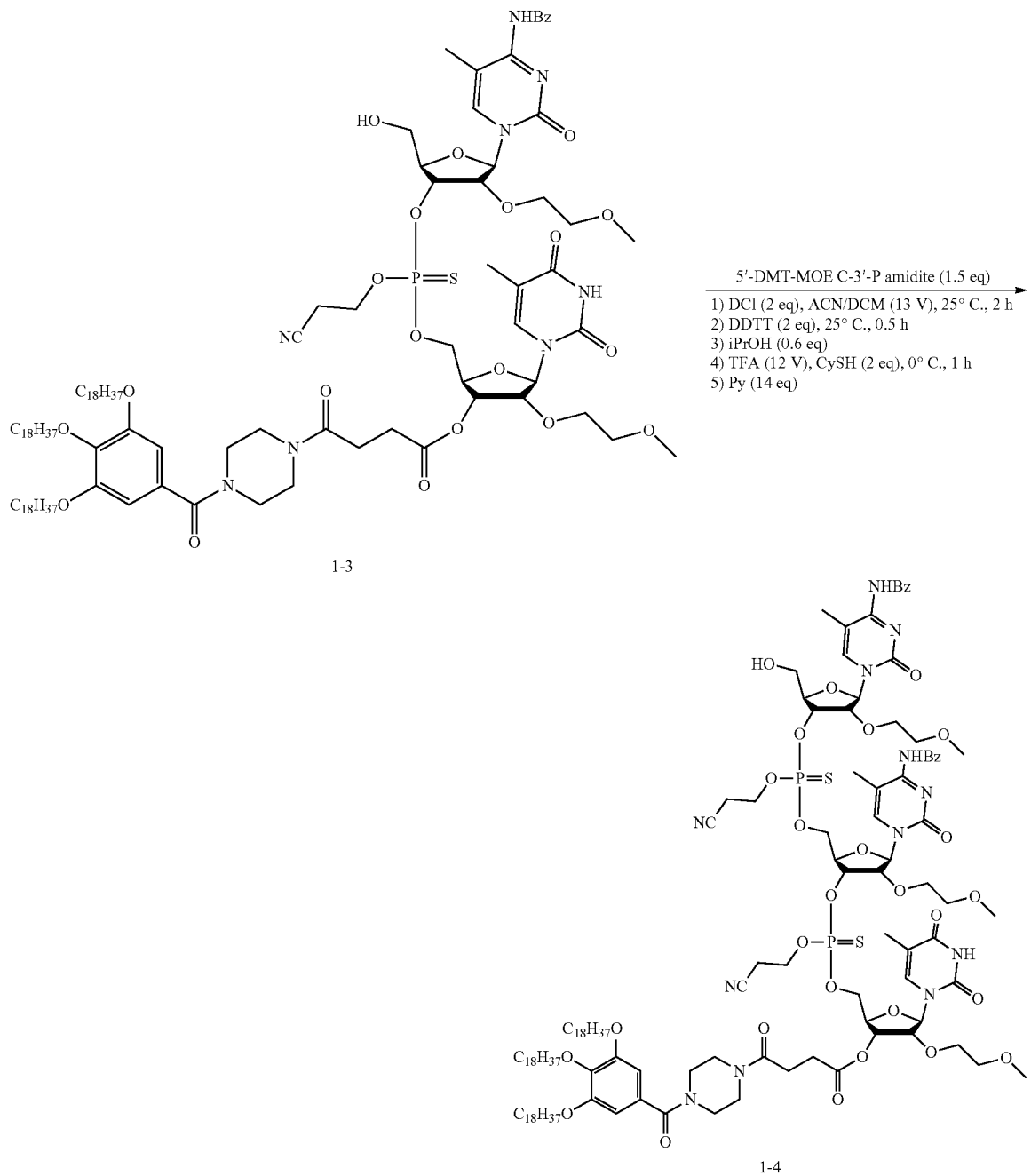

Compound 1-3 (123 g, 63.2 mmol, 1 eq) and 5'-DMT-MOE C-3'-P amidite (87.4 g, 94.8 mmol, 1.50 eq) were co-evaporated with ACN (500 mL) and DCM (1500 mL).

To a solution of compound 1-3 (123 g, 63.2 mmol, 1.00 eq) and 5'-DMT-MOE C-3'-P amidite (87.4 g, 94.8 mmol, 1.50 eq) in DCM/ACN=3:1 (1600 mL) was added molecular sieve 3A (48.0 g). The mixture was stirred at 25° C. for 1 h.

To the mixture was added DDTT (25.9 g, 126 mmol, 2.00 eq). The mixture was stirred at 25° C. for 0.5 h. The mixture was added propan-2-ol (2.28 g, 37.95 mmol, 2.91 mL, 0.6 eq) at 25° C. TLC (Dichloromethane:Ethyl acetate:Methanol=10:10:1, product Rf=0.68) indicated one new spot formed. The reaction was clean according to TLC.

To the mixture was added trifluoroacetic acid (TFA) (86.5 g, 758 mmol, 56.1 mL, 12.0 eq) and CySH (14.7 g, 126 mmol, 15.4 mL, 2.00 eq) at 0° C. The mixture was stirred at 0° C. for 1 h. TLC (Dichloromethane:Ethyl acetate:Methanol=10:10:1, product Rf=0.56) indicated one new spot formed. The reaction was clean according to TLC.

Py (70.03 g, 885.31 mmol, 71.46 mL, 14 eq) was added to the mixture. Molecular sieves were removed by filtration and the solid cake was washed with DCM (1000 mL). The pH value of the reaction mixture was adjusted to 6-7 with 2.5% NaHCO$_3$ aqueous (2000 mL). The combined organic layers were dried over Mg$_2$SO$_4$. The crude was re-dissolve in DCM (600 mL) and dropped into ACN (5000 ml, 30 V) with vigorous stirring. Desired product was precipitated out. Compound 1-4 (143 g, 57.31 mmol, 90.63% yield) was obtained as a white solid.

General Procedure for Preparation of Compound 1-5

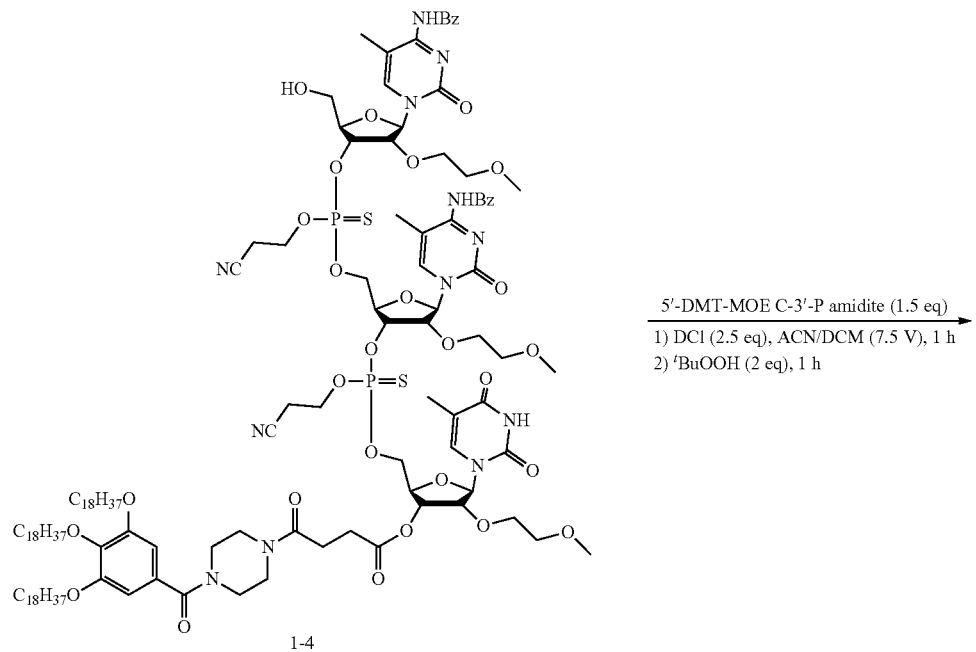

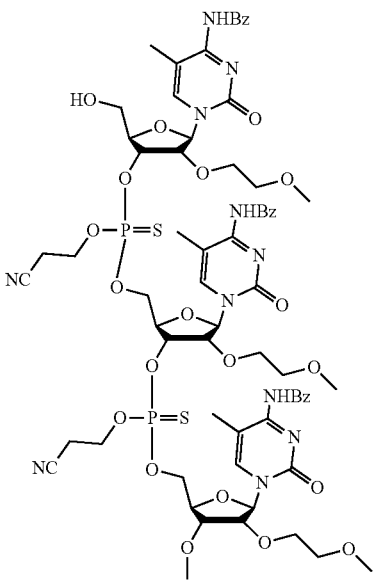

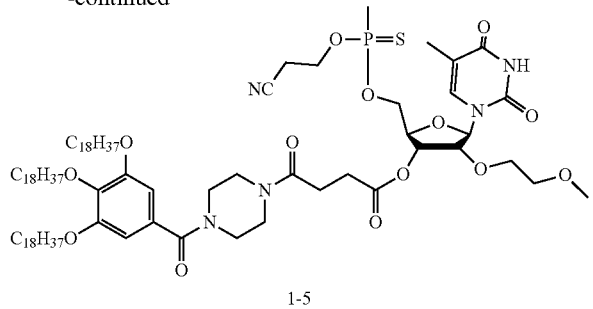

1-5

Compound 1-4 (290 g, 116 mmol, 1.00 eq) and 5'-DMT-MOE C-3'-P amidite (160 g, 174 mmol, 1.50 eq) were co-evaporated with ACN (500 mL) and DCM (1500 mL).

To a solution of compound 1-4 (290 g, 116.23 mmol, 1 eq) and 5'-DMT-MOE C-3'-P amidite (160 g, 174 mmol, 1.50 eq) in DCM/ACN=3:1 (2300 mL) was added molecular sieve 3 Å(69.0 g). The mixture was stirred at 25° C. for 1 h. The mixture was added DCI (34.3 g, 290 mmol, 2.50 eq). The mixture was stirred at 25° C. for 1 h. TLC (Dichloromethane:Ethyl acetate:Methanol=10:10:1, product Rf=0.70) indicated compound 1-4 was consumed completely and one new spot formed. The reaction was clean according to TLC.

To the mixture was added t-BuOOH (H$_2$O, 31.8 mL, 70.0% purity, 2.00 eq) and the resultant mixture was stirred at 25° C. for 1 h. TLC (Dichloromethane:Ethyl acetate:Methanol=10:10:1, product Rf=0.72) indicated one new spot formed. The reaction was clean according to TLC. Molecular sieves were removed by filtration and the solid cake was washed with DCM (1000 mL). The crude was dropped into ACN (9000 ml, 30.0 V) with vigorous stirring. Desired product was precipitated out. Compound 1-5 (386 g, 116 mmol, 99.8% yield) was obtained as a white solid.

General Procedure for Preparation of Compound 1-6

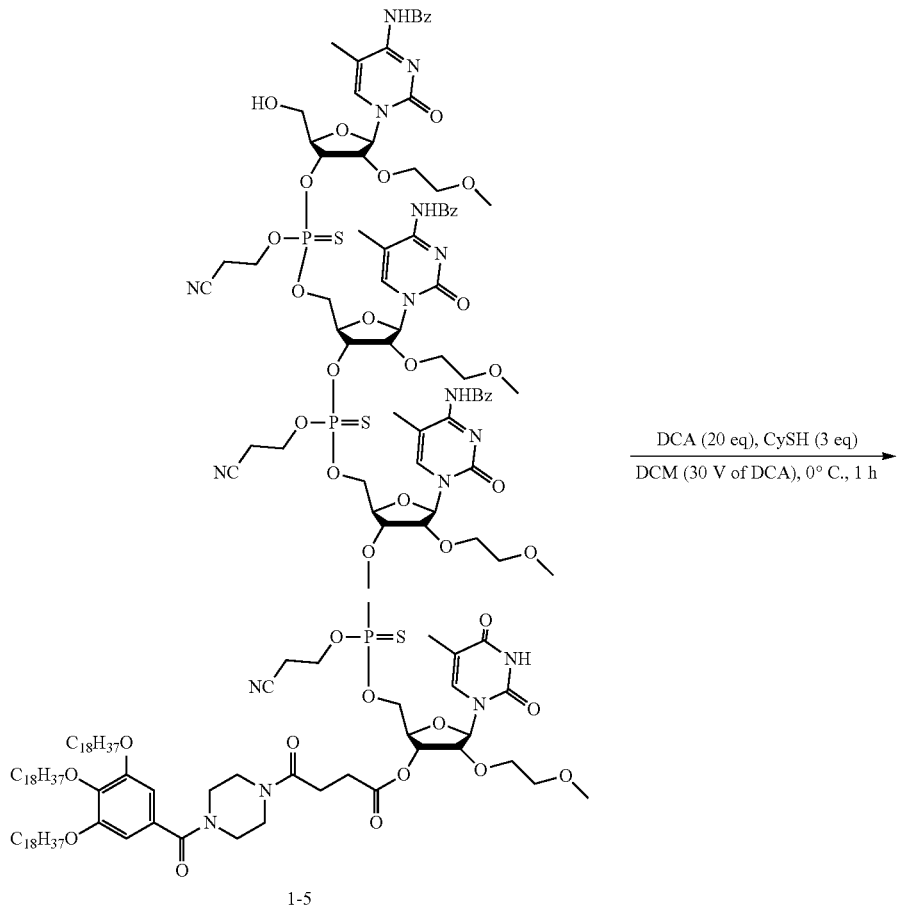

DCA (20 eq), CySH (3 eq)
DCM (30 V of DCA), 0° C., 1 h 1-5

-continued

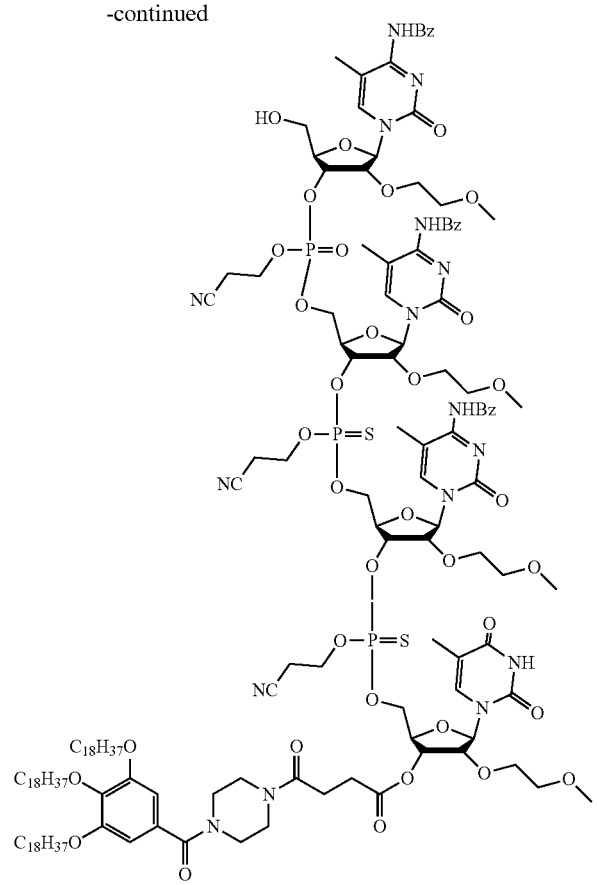

1-6

To a solution of compound 1-5 (386 g, 115 mmol, 1.00 eq) in DCM (5700 mL) was added CySH (40.3 g, 347 mmol, 42.5 mL, 3.00 eq) and dichloroacetic acid (DCA) (298 g, 2.32 mol, 190 mL, 20.0 eq) at 0° C. The mixture was stirred at 0° C. for 1 h. TLC (Dichloromethane:Ethyl acetate:Methanol=10:10:1, product Rf=0.46) indicated compound 1-5 was consumed completely and one new spot formed. The reaction was clean according to TLC. Py (201 g, 2.55 mol, 205 mL, 22.0 eq) was added to the mixture. Molecular sieves were removed by filtration and the solid cake was washed with DCM (800 mL). The pH value of the reaction mixture was adjusted to 6-7 with 2.5% NaHCO$_3$ aqueous (4000 mL). The combined organic layers were dried over Mg$_2$SO$_4$. The crude was re-dissolve in DCM (500 mL) and dropped into ACN (12000 ml, 30 V) with vigorous stirring. Desired product was precipitated out. Compound 1-6 (310 g, 102 mmol, 88.3% yield) was obtained as a white solid.

General Procedure for Preparation of Compound 1-7 (5'-OH-ACCCU-LHPG)
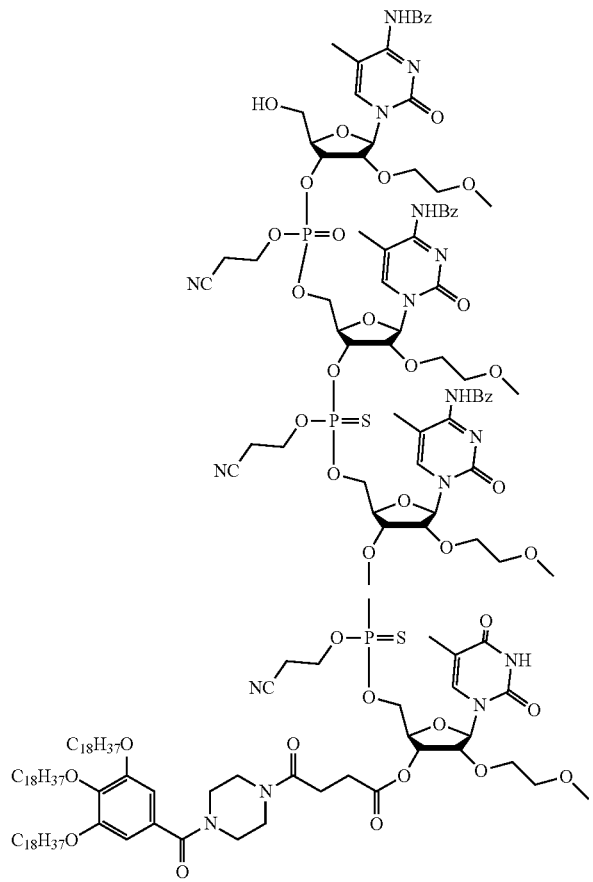
1-6
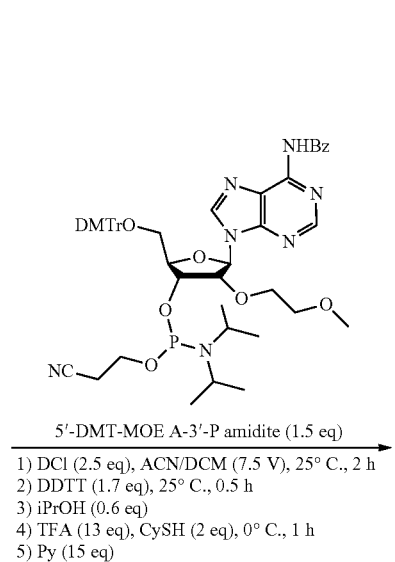
5'-DMT-MOE A-3'-P amidite (1.5 eq)
1) DCI (2.5 eq), ACN/DCM (7.5 V), 25° C., 2 h
2) DDTT (1.7 eq), 25° C., 0.5 h
3) iPrOH (0.6 eq)
4) TFA (13 eq), CySH (2 eq), 0° C., 1 h
5) Py (15 eq)
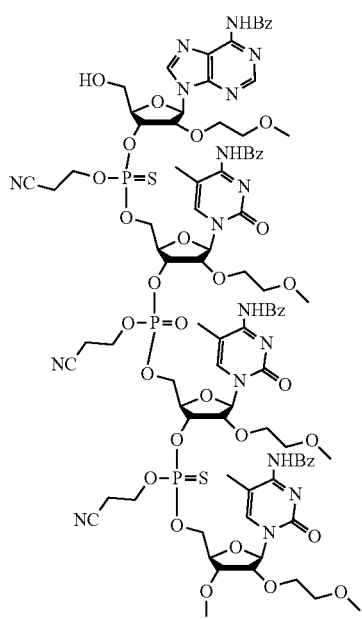

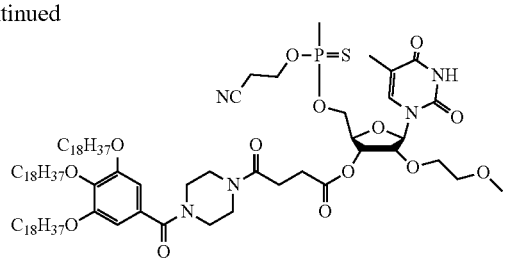

1-7

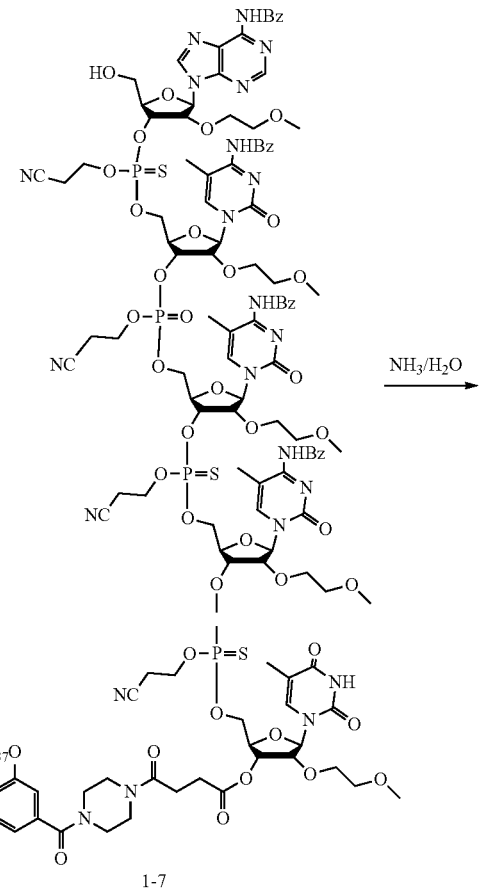

Compound 1-6 (154 g, 50.8 mmol, 1.00 eq) and 5'-DMT-MOE A-3'-P amidite (71.0 g, 76.2 mmol, 1.50 eq) were co-evaporated with ACN (500 mL) and DCM (1500 mL).

To a solution of compound 1-6 (154 g, 50.8 mmol, 1.00 eq) and 5'-DMT-MOE A-3'-P amidite (71.0 g, 76.2 mmol, 1.50 eq) in DCM/ACN=3:1 (1200 mL) was added molecular sieve 3A (36.0 g). The mixture was stirred at 25° C. for 1 h. The mixture was added DCI (15.0 g, 127 mmol, 2.50 eq). The mixture was stirred at 25° C. for 1 h. TLC (Dichloromethane:Ethyl acetate:Methanol=10:10:1, product Rf=0.57) indicated compound 1-6 was consumed completely and one new spot formed. The reaction was clean according to TLC.

The mixture was added DDTT (17.7 g, 86.3 mmol, 1.70 eq) and propan-2-ol (iPrOH) (1.83 g, 30.4 mmol, 2.33 mL, 0.600 eq). The mixture was stirred at 25° C. for 0.5 h. TLC (Dichloromethane:Ethyl acetate:Methanol=10:10:1, product Rf=0.59) indicated one new spot formed. The reaction was clean according to TLC.

To the mixture was added TFA (75.2 g, 659 mmol, 48.8 mL, 13.0 eq) and CySH (11.7 g, 101 mmol, 12.4 mL, 2.00 eq) at 0° C. The mixture was stirred at 0° C. for 1 h. TLC (Dichloromethane:Ethyl acetate:Methanol=10:10:1, product Rf=0.47) indicated one new spot formed. The reaction was clean according to TLC.

Py (58.5 g, 739 mmol, 59.7 mL, 15.0 eq) was added to the mixture. Molecular sieves were removed by filtration and the solid cake was washed with DCM (300 mL). The pH value of the reaction mixture was adjusted to 6-7 with 2.5% $NaHCO_3$ aqueous (2000 mL). The combined organic layers were dried over $Mg_2SO_4$. The crude was re-dissolve in DCM (400 mL) and dropped into ACN (4500 ml, 30.0 V) with vigorous stirring. Desired product was precipitated out. Compound 1-7 (5'-OH-ACCCU-LHPG) (169 g, 47.0 mmol, 92.7% yield) was obtained as a white solid. For HPLC and LC-MS analyses of compound 1-7, it was deprotected using ammonolysis ($NH_3/H_2O$) procedure similar to the one used for compound 1 ammonolysis disclosed below to obtain 1-7-a (5'-OH-ACCCU-OH). HPLC and LC-MS of compound 1-7-a is shown in FIG. 1.

-continued

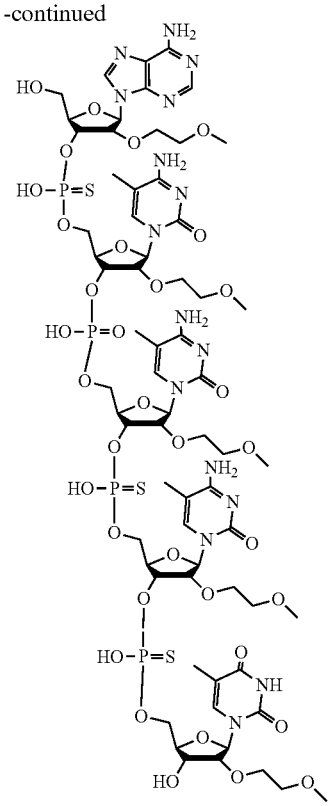

1-7a

HPLC-MS method for compound 1-7-a is described below:

Column—ACQUITY UPLC BEH Shield RP18 Column, 130 Å, 1.7 μm, 2.1 mm×150 mm;

Column temperature: 65° C.;

Mass spec scan range: 300-2000 m/z;

MS polarity: negative

Solution A: 5 mM tributylamine acetate (TBuAA) in 10% CH$_3$CN, 1 μm EDTA;

Solution B: 5 mM TBuAA in 80% CH$_3$CN, 1 μm EDTA

Gradient:

| Time min | A % | B % | Flow mL/min | Pressure bar |
|---|---|---|---|---|
| 0.00 | 84.00 | 16.00 | 0.45 | — |
| 0.50 | 84.00 | 16.00 | 0.45 | — |
| 1.50 | 84.00 | 16.00 | 0.45 | — |
| 30.0 | 68.00 | 32.00 | 0.45 | — |
| 35.0 | 15.00 | 85.00 | 0.45 | |
| 36.0 | 15.00 | 85.00 | 0.45 | |
| 37.0 | 84.00 | 16.00 | 0.45 | |
| 41.0 | 84.00 | 16.00 | 0.45 | |

2. Alternate Synthesis of 5'-OH-ACCCU-LHPG fragment (Fragment 1) Preparation of 5'-DMT-ACCC-3' OH

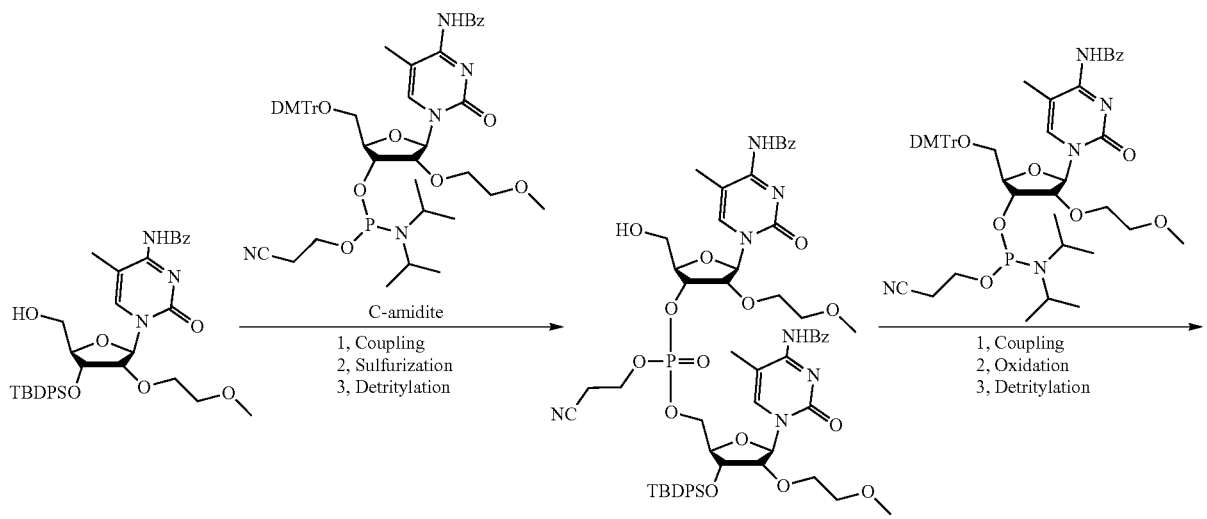

149
150
-continued
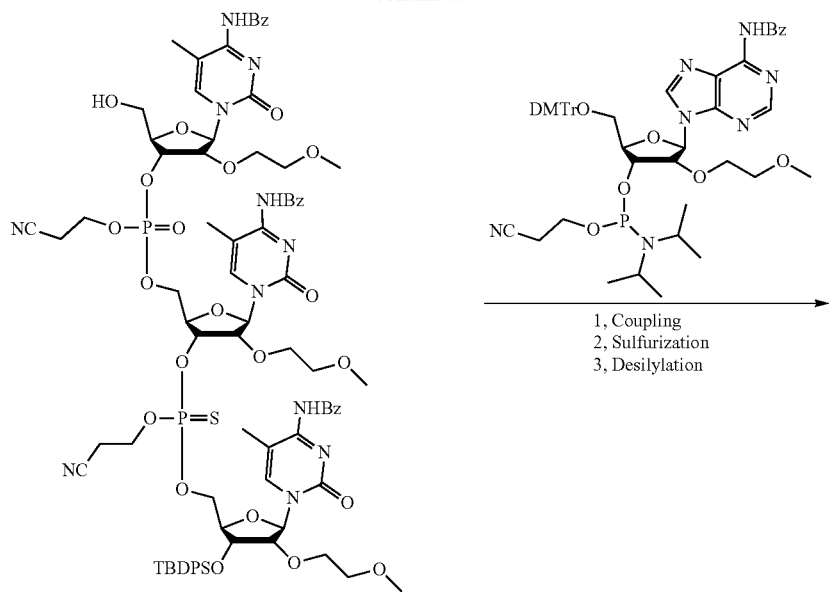
1, Coupling
2, Sulfurization
3, Desilylation
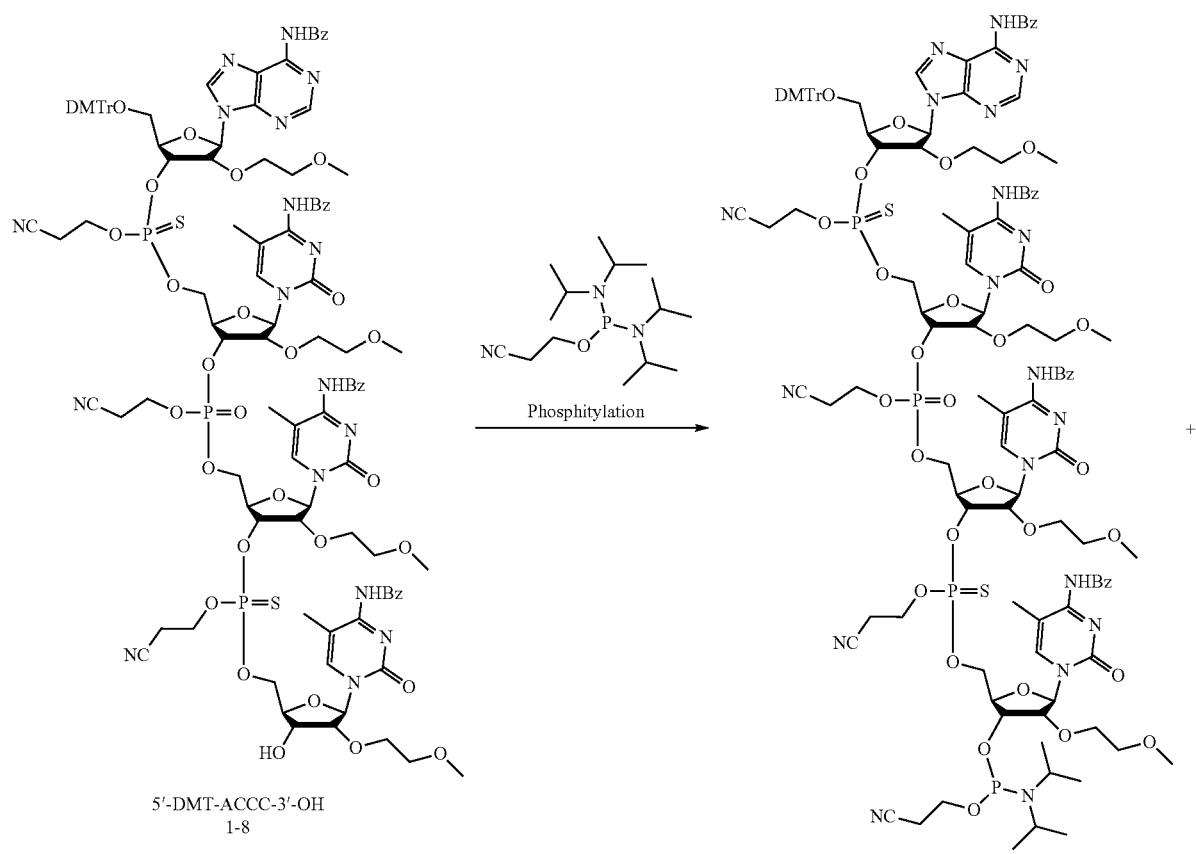

151
152
-continued
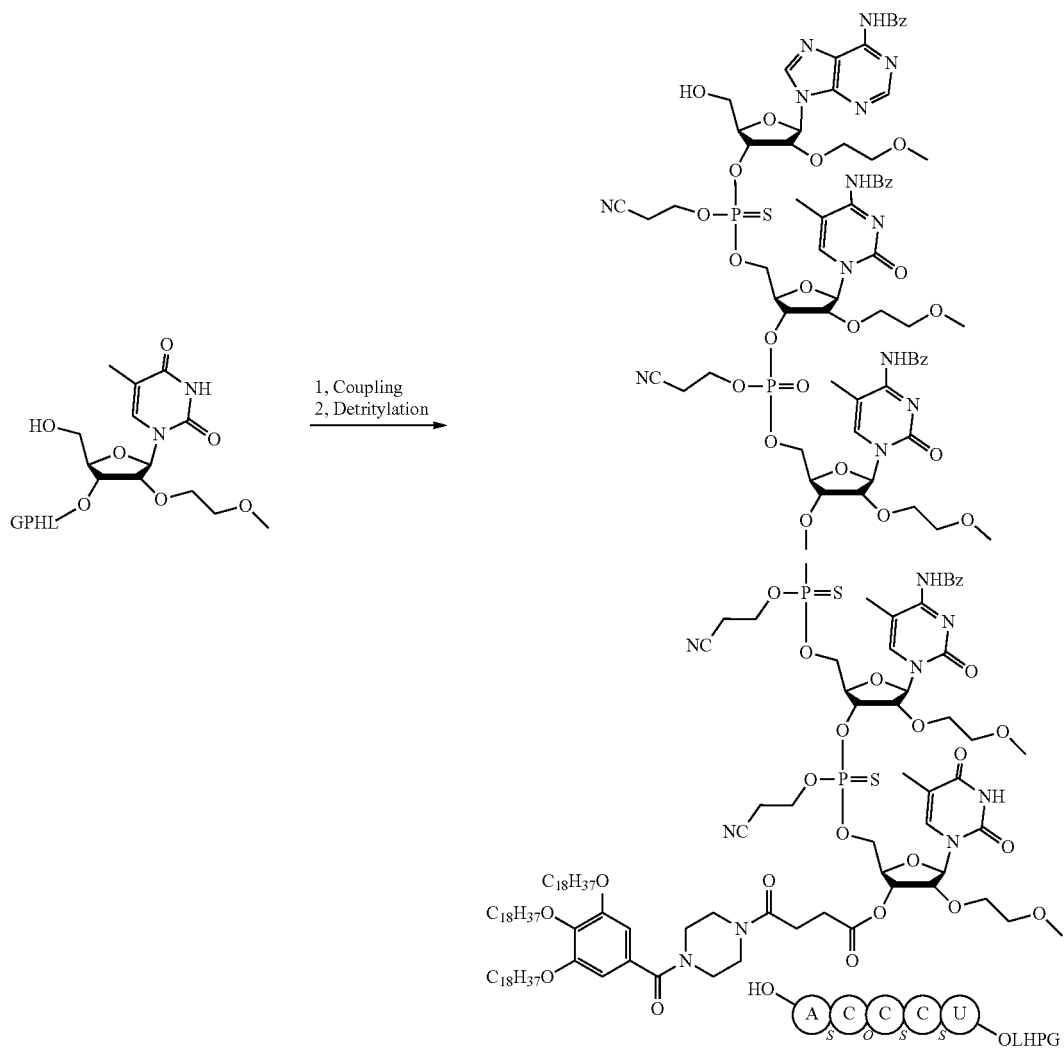

5'-DMT-ACCC-3'-OH (1-8) was prepared based on the scheme depicted above using similar procedures as described above for compound 1-3.

General Procedure for Preparation of 5'-DMT-ACCC-3'-P Amidite (1-8a)

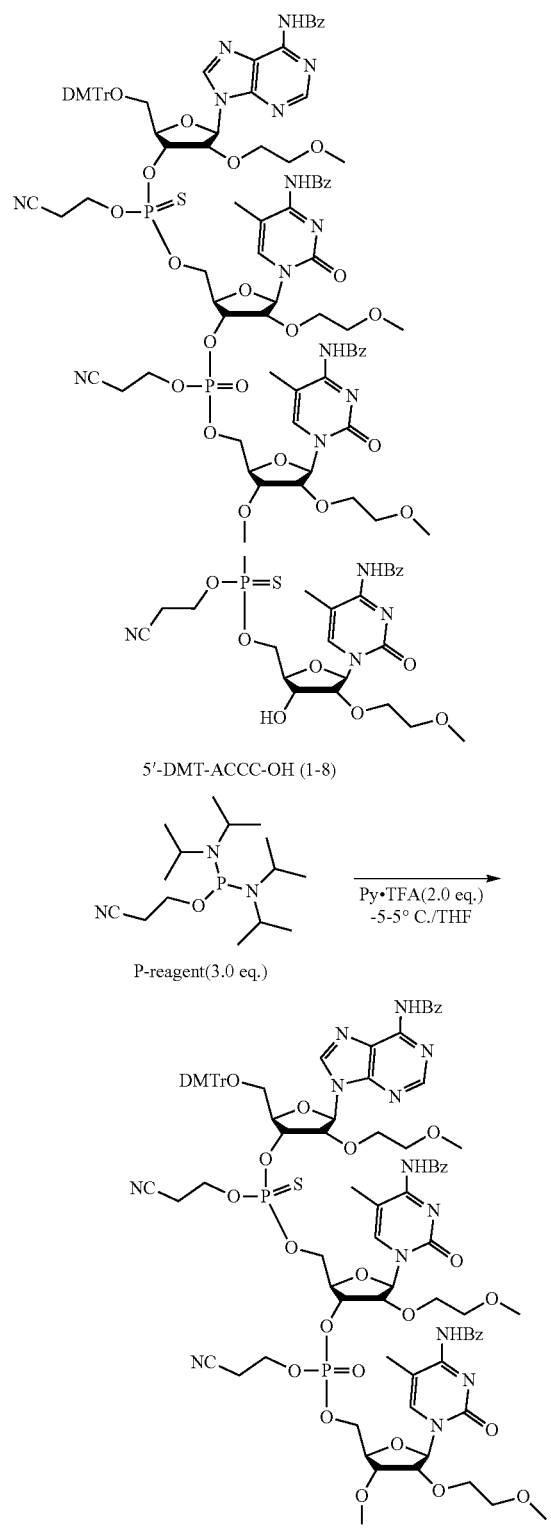

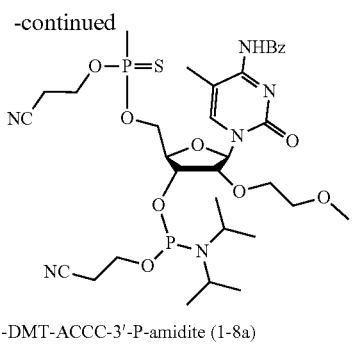

5'-DMT-ACCC-3'-P-amidite (1-8a)

5'-DMT-ACCC-3'-OH (280.0 g, 1.0 eq.) was charged in a reactor (R1) under N₂ protection. DCM (1000 mL 3.57V) was charged in the flask under N₂ protection. The compound was co-evaporated with DCM under vacuum at 25-30° C. The co-evaporation with DCM was repeated three time until the residual water level is below 0.01%. THF (1400 mL 5V) was charged into R1 under N2 protection. A sample was collected for analysis. Temperature of R1 was adjusted between −5° C. to 5° C. P-reagent (106.7 g, 2.992 eq.) was charged into R1 under N2 protection. (pyridine; 2,2,2-trifluoroacetic acid 45.7 g, 2.001 eq.) into RI under N₂ protection and the reaction mixture was stirred for 1 hour at −5° C. to 5° C.

Methyl tert-butyl ether (MTBE) (10080 mL 36V) was charged into another flask (R2) under N₂ protection. Py (70 mL 0.25V) was charged into R2 under N₂ protection. Heptane (3920 mL 14V) was charged into R1 under N₂ protection. Purge R2 with N₂ at −5° C. to 5° C. for 30 minutes. Solution from R1 was charged slowly to the solution of R2 under N₂ protection. R2 was stirred for 1 hour at −5° C. to 5° C. The reaction mixture was filtered. The cake was washed twice with a solution of MTBE:heptane (5:2, 700 mL). A sample of the filtrate was collected for analysis. The cake was dried at 25° C. to 30° C. for 24 hours to obtain 5'-DMT-ACCC-3'-P amidite 1-8a (292.3 g, Yield: 96.25%, Purity: 98%).

General Procedure for Preparation of 5'-DMT-ACCCU-3'-LHPG (1-9)

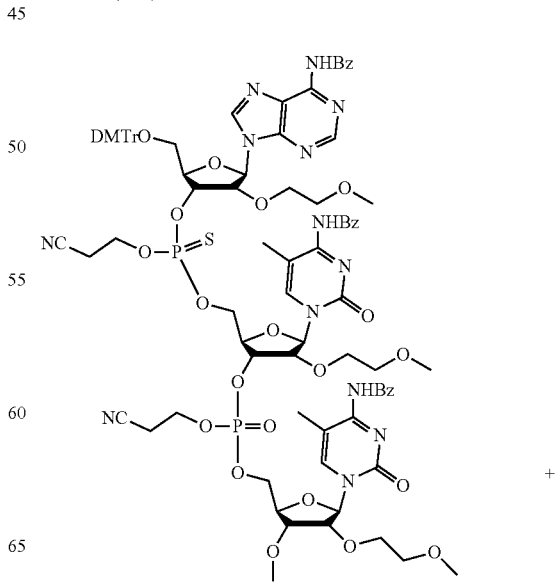

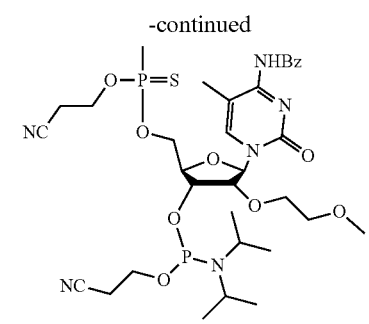

5'-DMT-ACCC-3'-P-amidite (1-8a)

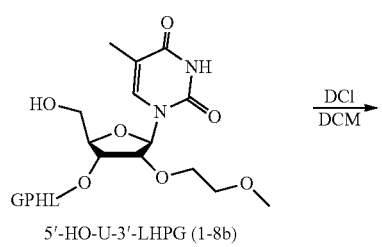

5'-HO-U-3'-LHPG (1-8b)

5'-HO-U-3'-LHPG (120.0 g) was charged to a reactor followed by molecular sieves (3 Å) (300.0 g), 5'-DMT-ACCC-P-Amidite (280.68 g, 1.27 eq.) and DCM (3000 mL, 25 V). The reaction mixture was stirred for 1 hour at 20° C.-30° C. DCI (20.33 g, 2.00 eq.) was charged into the reaction mixture and the mixture was stirred for 30 minutes at 20° C.-30° C. Sample was collected for analysis. DDTT (35.35 g, 2.0 eq.) was charged into the reaction mixture. Sample was collected for analysis. Reaction mixture was filtered, concentrated and dissolved with DCM (720 mL, 6V). DCM solution was added dropwise into a solution of ACN (9000 mL, 75 V), followed by removing most of the DCM by rotary distillation. The mixture was filtered and the cake was washed with ACN (600 mL, 10 V) twice. The wet cake was dried at 20° C.-30° C. for 16 hours to obtain 5'-DMT-ACCCU-3'-LHPG (287.15 g, 85.7% yield).

General Procedure for Preparation of 5'-OH-ACCCU-3'-LHPG (1-7)

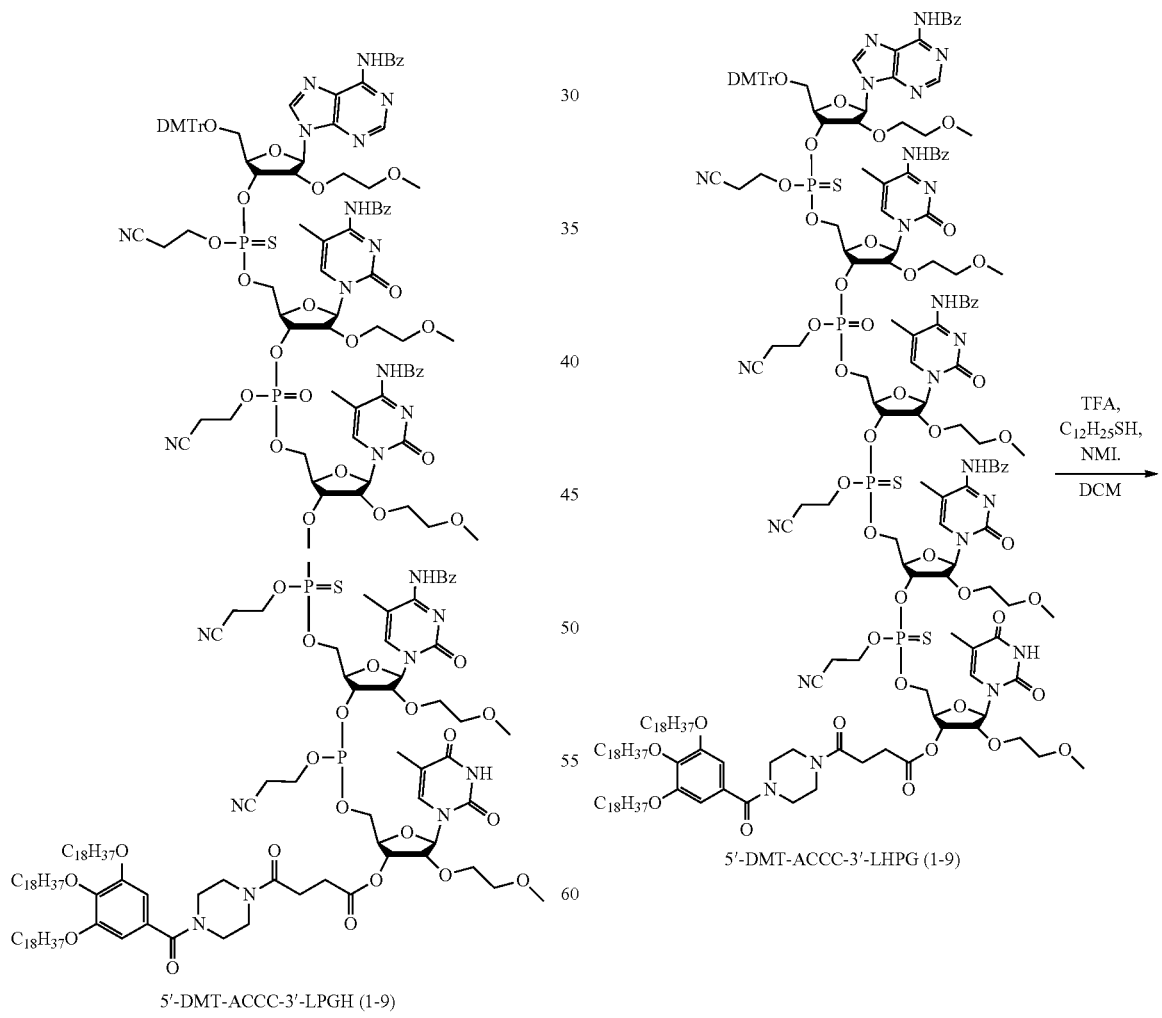

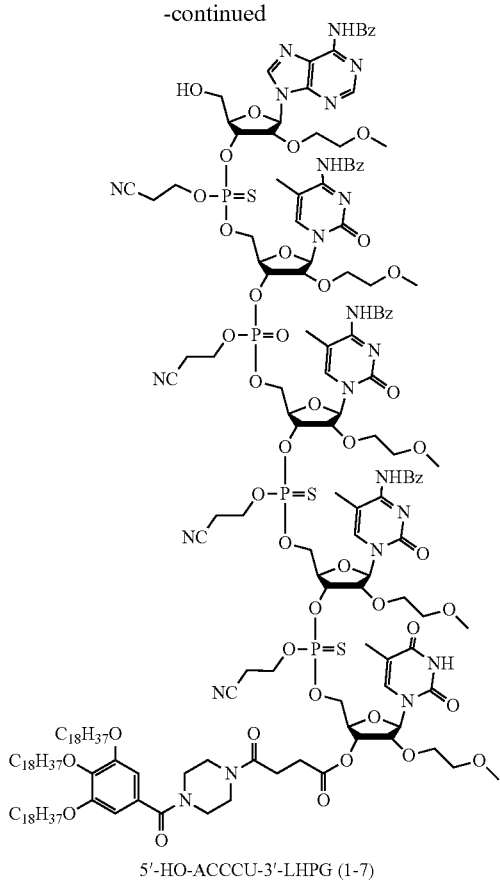

5'-HO-ACCCU-3'-LHPG (1-7)

5'-DMT-ACCCC-3'-LHPG (285.54 g), molecular sieves (3A) (142.77 g) and DCM (2855 mL, 10 V) were charged into a reactor. The reaction mixture was stirred for 1 hour at 20° C.-30° C., and the reaction temperature was adjusted to −5° C.-5° C. Dodecane-1-thiol (51.97 g, 3.5 eq.) was charged into the reactor followed by TFA (58.55 g, 7.0 eq.), and the reaction mixture was stirred for 1 hour at −5° C.-5° C. 1-methylimidazole (NMI) (54.21 g, 9.0 eq.) was charged into the reactor, and the reaction mixture was stirred for 5 minutes at 20° C.-30° C. The reaction mixture was filtered and the solution was concentrated to remove DCM. The crude product was dissolved in DCM (427.5 mL, 1.5 V), and this solution was added dropwise into a solution of ACN (8566 mL, 30 V). The resulting mixture was concentrated by removing most of DCM by rotary distillation and filtered. The cake was washed with ACN (571 mL, 4 V) twice and dried at 20° C.-30° C. to obtain compound 1-7 (239.92 g; 91.1% yield).

B. General Procedure for Preparation of 5'-Fragment:
1. Synthesis of deoxy-TTACC 5mer Fragment (Fragment 2)
General Procedure for Preparation of Compound 2-2

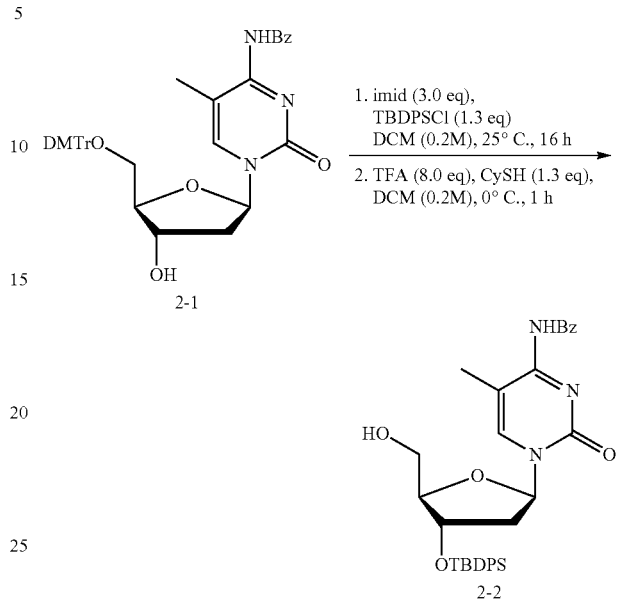

To a solution of compound 2-1 (300 g, 463 mmol, 1.00 eq) in DCM (2300 mL) was added imidazole (94.6 g, 1.39 mol, 3.00 eq) at 25° C. The mixture was light yellow homogenous solution. TBDPSCl (tert-butyl(chloro)diphenylsilane) (166 g, 602 mmol, 155 mL, 1.30 eq) was added at 25° C. The mixture was stirred at 25° C. for 12 hrs. Note: Temperature increased by 5° C. during the addition of TBDPSCl. HPLC showed reactant was consumed completely. Propan-2-ol (27.8 g, 463 mmol, 35.5 mL, 1.00 eq) was added and the mixture was stirred at 25° C. for 0.5 hr.

To the above solution was added cyclohexanethiol (70.0 g, 602 mmol, 73.7 mL, 1.30 eq) at 0° C. The mixture was stirred at 0° C. for 15 min. TFA (264.06 g, 2.32 mol, 171.47 mL, 5 eq) was added dropwise at 0° C. over a period of 45 min. The mixture was stirred at 0° C. for 1 hr. The color of solution was changed from light yellow to deep red, white solid was observed during the addition of TFA. HPLC showed the reaction completed.

The reaction mixture was poured into the $Na_2CO_3$ solution (245 g $Na_2CO_3$ in 1.5 L water), diluted with methyl tert-butyl ether (TBME or MTBE) (1.5 L) and two layers were separated. The organic layer was washed with brine (750 mL×2), dried by anhydrous $MgSO_4$ (232 g) filtered through celite and concentrated. Note that some white solid was observed during the addition of aq·$Na_2CO_3$ and the product was not precipitated out during the concentration process until evaporated to dryness to give the crude product as yellow foam solid.

The crude product was dissolved in DCM (300 mL) and loaded in a 1000 mL separation funnel. To the solvent mixture of Heptane/TBME (v/v 9:1, 3.0 L) was slowly dropped the solution of crude product from funnel to performance the precipitation process. This process took about 30 minutes. The pure product was collected as a white solid with buchner funnel, the cake of product was washed with the solvent mixture of Heptane (100 mL×2) and concentrated to dry. Compound 2-2 (235 g, 395 mmol, 85.2% yield, 98.0% purity) was obtained as a white solid.

General Procedure for Preparation of Compound 2-4

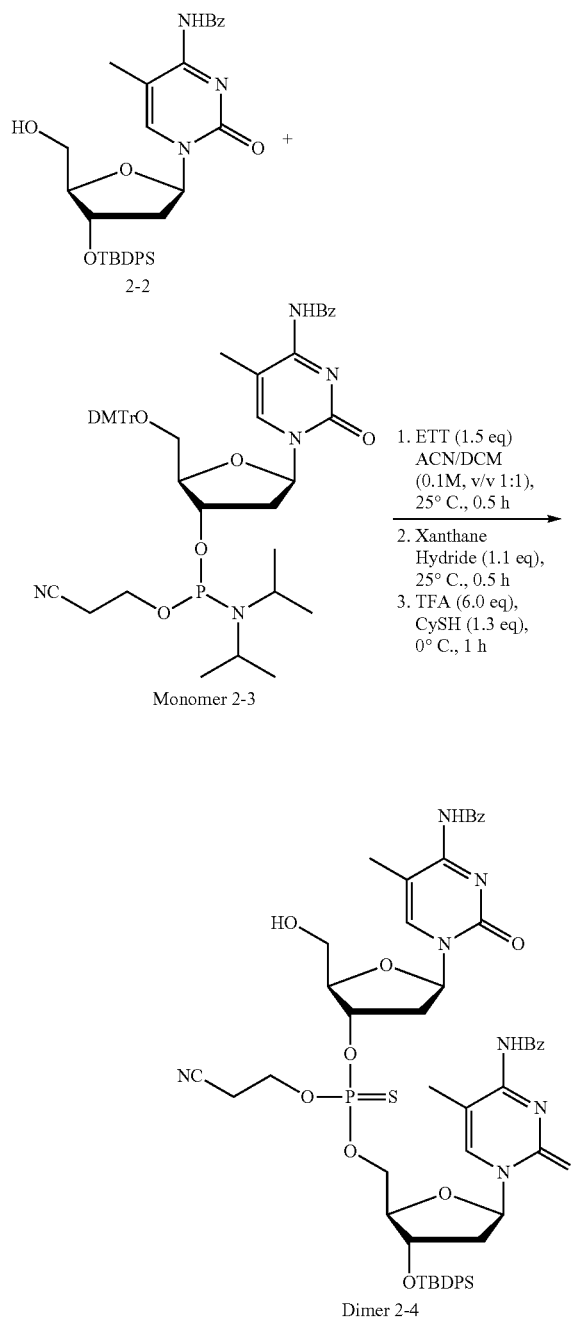

Monomer 2-3

Dimer 2-4

Compound 2-2 (10.0 g, 17.1 mmol, 1.00 eq) and compound Monomer 2-3 (17.4 g, 20.6 mmol, 1.20 eq) were co-evaporated with CH₃CN (20 mL×2) under Ar₂ in a 250 mL single-necked round bottle.

Compound 2-2 (10.0 g, 17.1 mmol, 1.00 eq) and compound Monomer 2-3 (17.4 g, 20.6 mmol, 1.20 eq) was dissolved in ACN (80 mL) and DCM (80 mL) (CH₃CN/DCM=1/1) at 25° C. ETT (3.34 g, 25.7 mmol, 1.50 eq) was added and the mixture solution was stirred at 25° C. for 30 min under Ar₂. It is important to note that Acetonitrile used in the reaction was 99.9% pure and was further dried with molecular sieves to get water content of <50 ppm. DCM used was also Anhydrous DCM. The mixture was changed from light yellow homogenous solution to light yellow cloudy. HPLC showed compound 2-2 was consumed completely.

To the above solution was added xanthane hydride (2.83 g, 18.8 mmol, 1.10 eq) at 25° C. The mixture was stirred at 25° C. for 0.5 hr. Note: The mixture was changed from light yellow homogenous solution to yellow cloudy. HPLC showed the reaction completed.

The above solution was cooled to 0° C. in ice water bath for 30 min. TFA (13.7 g, 120 mmol, 8.88 mL, 7.00 eq) was added to reaction mixture at 0° C. The mixture was stirred at 0° C. for 2.5 hrs. The color of mixture was changed from yellow cloudy to red. HPLC showed the reaction completed.

The Na₂CO₃ solution (12.7 g Na₂CO₃ in 83 mL water) was added slowly to the reaction mixture (watched for the speed of CO₂ release to avoid the bumping of reaction solution). The naturalization process was done in about 12 hrs and then all the solvents of reaction mixture were removed by rotavapor to give a milk-white water suspension of crude product.

The crude product was dissolved in the mixture solvent of EtOAc/TBME (v/v 1:3, 800 mL) and two layers were separated. The organic layer was washed with water (400 mL), brine (2×400 mL) and dried by anhydrous MgSO₄ (~42.0 g). filtered through celite and concentrated.

The crude product was dissolved in DCM (55 mL) and loaded in a 100 mL separation funnel. To the solvent mixture of Heptane/TBME (v/v 9:1, 1600 mL) was slowly added the solution of crude product from funnel to performance the precipitation process. This process took about 60 minutes. The time of quenching step was extended for 1 hr.

The pure product was collected as a white solid with buchner funnel. The cake of product was washed with the solvent mixture of Heptane(50 mL×2) and concentrated to dry. Compound Dimer 2-4 (25.5 g, 16.6 mmol, 96.6% yield, 68.2% purity) was obtained as a light yellow solid.

General Procedure for Preparation of Compound 2-6

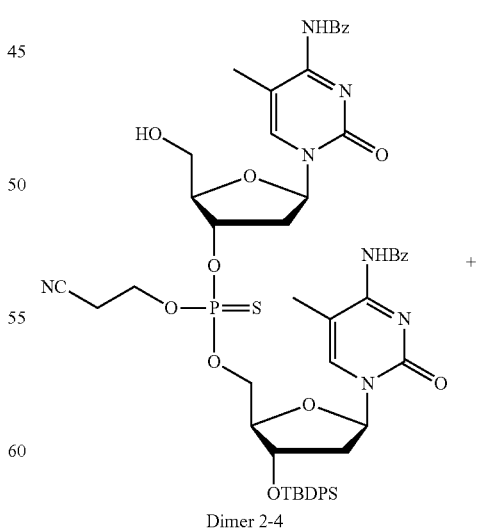

Dimer 2-4

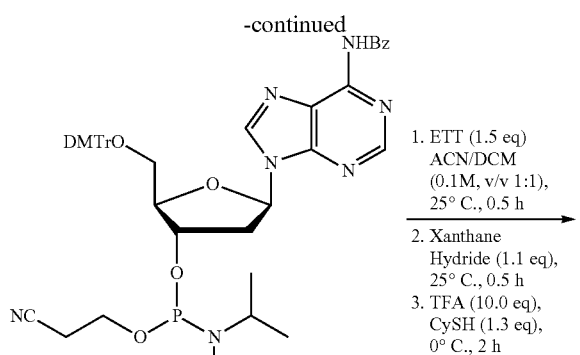

Monomer 2-5

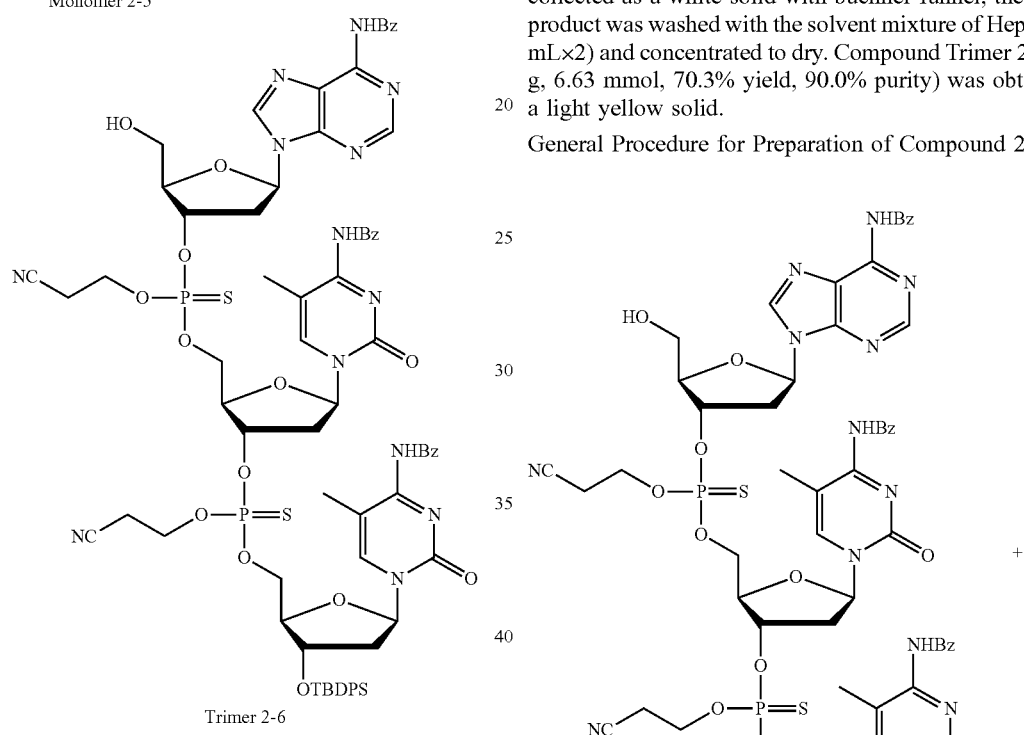

Trimer 2-6

Compound Dimer 2-4 (10.0 g, 9.43 mmol, 1.00 eq) and compound Monomer 2-5 (8.90 g, 10.4 mmol, 1.10 eq) were co-evaporated with ACN (100 mL×3) in a 500 mL singe-necked round bottle and then dissolved in ACN (30 mL) and DCM (30 mL) (CH₃CN/DCM=1/1) at 25° C. 5-ethylsulfanyl-2H-tetrazole (1.84 g, 14.2 mmol, 1.5 eq) was added at 25° C. and the mixture was stirred at 25° C. for 30 min. HPLC indicated reactant dimer 2-4 was consumed completely.

To the above solution was added 5-amino-1, 2, 4-dithiazole-3-thione (1.56 g, 10.4 mmol, 1.10 eq) at 25° C. The mixture was stirred at 25° C. for 0.5 hr. The mixture was changed from light yellow homogenous solution to yellow cloudy. HPLC showed the reaction completed.

The above solution was cooled to 0° C. TFA (6.45 g, 56.6 mmol, 4.20 mL, 6.00 eq) was added dropwise at 0° C. The mixture was stirred at 0-25° C. for 3 hr. The color of mixture was changed from yellow cloudy to orange-yellow suspension. HPLC showed the reaction completed.

The Na₂CO₃ solution (6.00 g, Na₂CO₃ in 46.6 mL water) was added slowly to the reaction mixture (watched for the speed of CO₂ release to avoid the bumping of reaction solution). The naturalization process was done in about 1 hr and then all the solvents of reaction mixture were removed by rotavapor to give a milk-white water suspension of crude product. The crude product was dissolved in the mixture solvent of EtOAc/TBME (v/v 3:1, 622 mL) and two layers were separated. The organic layer was washed with water (155 mL), brine (2×155 mL) and dried by anhydrous MgSO₄ (~15.5 g) filtered and concentrated in vacuum. Note that in this process, no yellow gel solids were precipitated out. The crude product was dissolved in DCM (70 mL) and loaded in a 100 mL separation funnel.

To the solvent of TBME (1.24 L) was slowly added the solution of crude product from funnel for the precipitation process. This process took about 1.5 h. The pure product was collected as a white solid with buchner funnel, the cake of product was washed with the solvent mixture of Heptane (50 mL×2) and concentrated to dry. Compound Trimer 2-6 (11.4 g, 6.63 mmol, 70.3% yield, 90.0% purity) was obtained as a light yellow solid.

General Procedure for Preparation of Compound 2-8

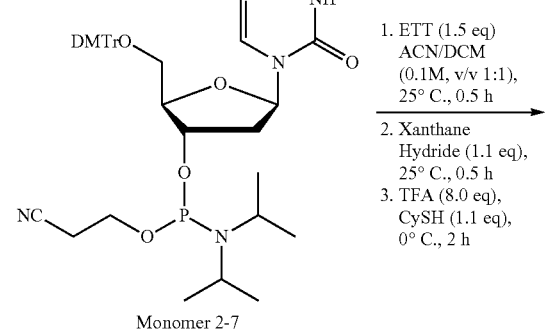

Monomer 2-7

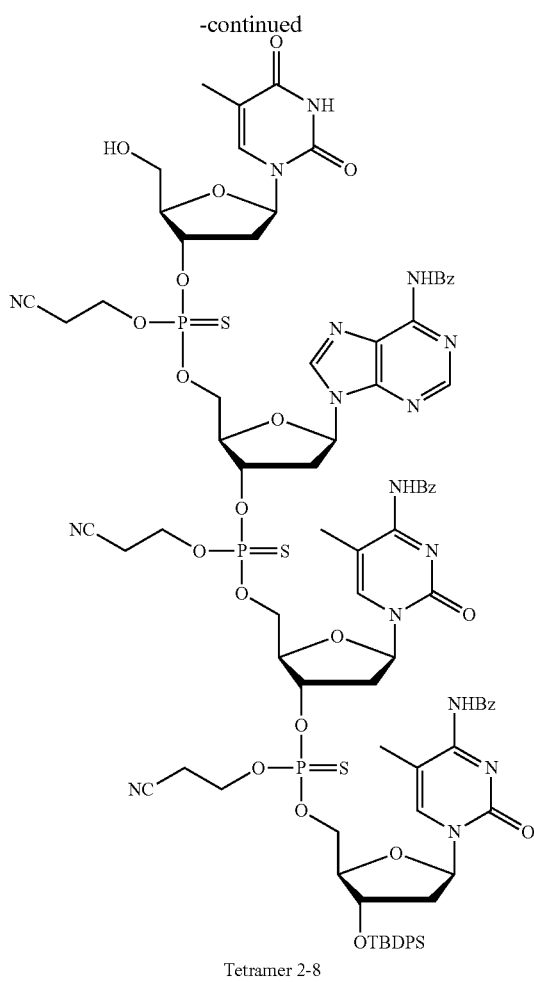

Tetramer 2-8

To a solution of compound Trimer 2-6 (4.20 g, 2.72 mmol, 1.00 eq) in CH$_3$CN (10 mL) was added Monomer 2-7 (3.03 g, 4.07 mmol, 1.50 eq) and the solution was co-evaporated with CH$_3$CN (10 mL×2) under Ar$_2$ in a 100 mL single-necked round bottle.

Compound Trimer 2-6 (4.20 g, 2.72 mmol, 1.00 eq) and Monomer 2-7 (3.03 g, 4.07 mmol, 1.50 eq) was dissolved in CH$_3$CN (12 mL) and DCM (12 mL) (CH$_3$CN/DCM=1/1) at 25° C. Molecular sieve 3 Å (4.00 g, 1.00 eq) was added and the mixture solution was stirred at 25° C. for 1 hr under Ar$_2$. 5-ethylsulfanyl-2H-tetrazole (530 mg, 4.07 mmol, 1.50 eq) was added at 25° C. The mixture was stirred at 25° C. for 0.5 hr. The mixture was changed from light yellow homogenous solution to light yellow cloudy. The reaction mixture was filtered to remove the 3 Å molecular sieves.

It is important to note that acetonitrile and DCM were both redistilled freshly. HPLC showed trimer was consumed completely.

To the above solution was added 5-amino-1, 2, 4-dithiazole-3-thione (449 mg, 2.99 mmol, 1.10 eq) at 25° C. The mixture was stirred at 25° C. for 0.5 hr. The mixture was changed from light yellow homogenous solution to yellow cloudy. HPLC showed reaction completed.

To the above mixture was added TFA (2.48 g, 21.7 mmol, 1.61 mL, 8.00 eq) dropwise at 0° C. The mixture was stirred at 0° C. for 4.5 hrs. The mixture was changed from yellow cloudy to orange-yellow suspension. HPLC showed reaction completed.

The Na$_2$CO$_3$ solution (2.88 g Na$_2$CO$_3$ in 20 mL water) was added slowly to the reaction mixture (watched for the speed of CO$_2$ release to avoid the bumping of reaction solution). The naturalization process was done in about 1 hr and then all the solvents of reaction mixture were removed by rotavapor to give a milk-white water suspension of crude product.

The crude product was dissolved in the mixture solvent of EtOAc/TBME (v/v 3:1, 260 mL) and two layers were separated. The organic layer was washed with water (64 mL), brine (2×64 mL) and dried by anhydrous MgSO$_4$ (~6.44 g) filtered through celite and concentrated.

The crude product was dissolved in DCM (28 mL) and loaded in a 100 mL separation funnel. To the solvent TBME (518 mL) was slowly dropped the solution of crude product from funnel to performance the precipitation process. This process took about 30 minutes.

The pure product was collected as a white solid with buchner funnel. The cake of product was washed with the solvent mixture of Heptane(20 mL×2) and concentrated to dry. Compound Tetramer 2-8 (4.37 g, 2.07 mmol, 76.2% yield, 91.0% purity) was obtained as a light yellow solid.

General Procedure for Preparation of Compound 2-9 (Deoxy-TTACC 5mer)

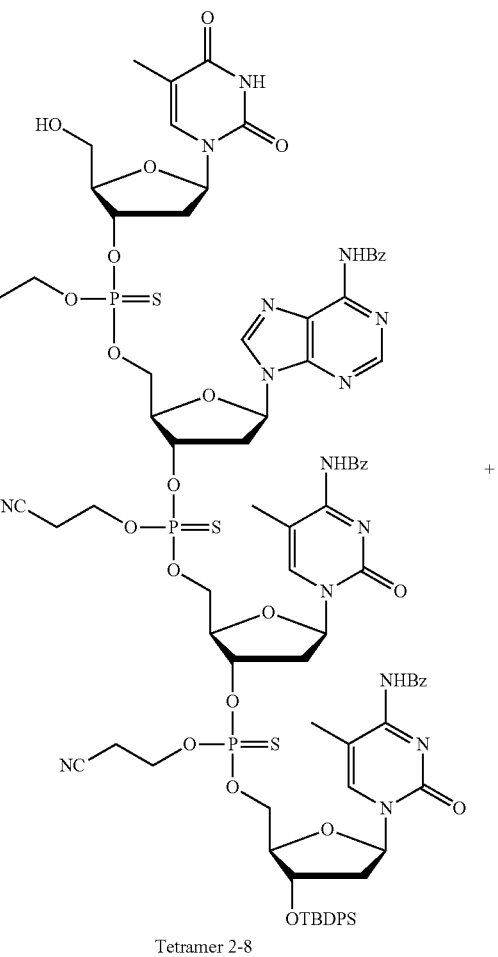

Tetramer 2-8

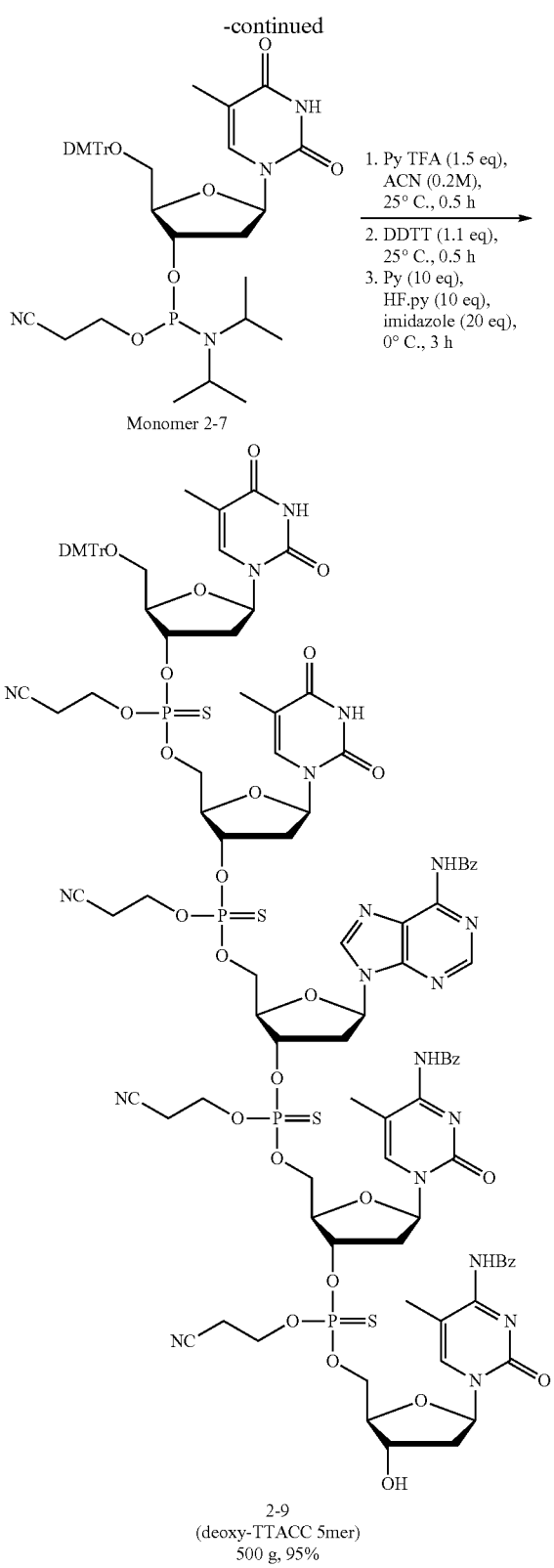

Tetramer 2-8 (120 g, 62.5 mmol, 1.00 eq) was co-evaporated with ACN (500 mL×2), then Monomer 2-7 (51.2 g, 68.8 mmol, 1.10 eq) was added and the solution was co-evaporated with ACN (500 mL×2) under $Ar_2$ in a 3 L single-necked round.

To the mixture solution of Tetramer 2-8 (120 g, 62.5 mmol, 1.00 eq) and Monomer 2-7 (51.2 g, 68.8 mmol, 1.10 eq) in ACN (485 mL) was added Molecular sieve 3A (36 g) at 25° C. The mixture was stirred at 25° C. for 1 h. Py•TFA (1 M, 93.8 mL, 1.50 eq) was added at 25° C. The resulting mixture was stirred at 25° C. for 30 min. It is important to note that Acetonitrile was redistilled freshly. HPLC indicated Tetramer 2-8 was consumed completely.

To the above mixture was added DDTT (14.1 g, 68.8 mmol, 1.10 eq) at 25° C. The mixture was stirred at 25° C. for 0.5 hr. After the completion of sulfurization, the above mixture was diluted with redistilled MeCN (480 mL) and then cooled to 0° C. Py (49.4 g, 625 mmol, 50.5 mL, 10.0 eq) was added at 0° C.

At the same time, a 1 L three-neck round bottom flask was charged with imidazole (85.1 g, 1.25 mol, 20.0 eq) and anhydrous THF (240 mL) and placed in the ice bath for 30 min. The HF (17.9 g, 625 mmol, 16.3 mL, 70% purity, 10.0 eq) was slowly added and then stirred for another 15 min (A homogeneous was obtained from this step). The solution was added to the above suspension at 0° C. by syringe pump (2 mL/min dropping rate). The mixture was stirred at 0° C. for 3 h. HPLC showed the reaction was completed.

The reaction mixture was dissolved in the EtOAc (2.8 L). The organic layer was washed with sat·aq·$NaHCO_3$ (1.4 L×2), water (1.4 L×3), brine (1.4 L) and dried by anhydrous $MgSO_4$ (~208 g) filtered and concentrated in vacuum. In this process, no yellow gel solids were precipitated out.

Figure 2:
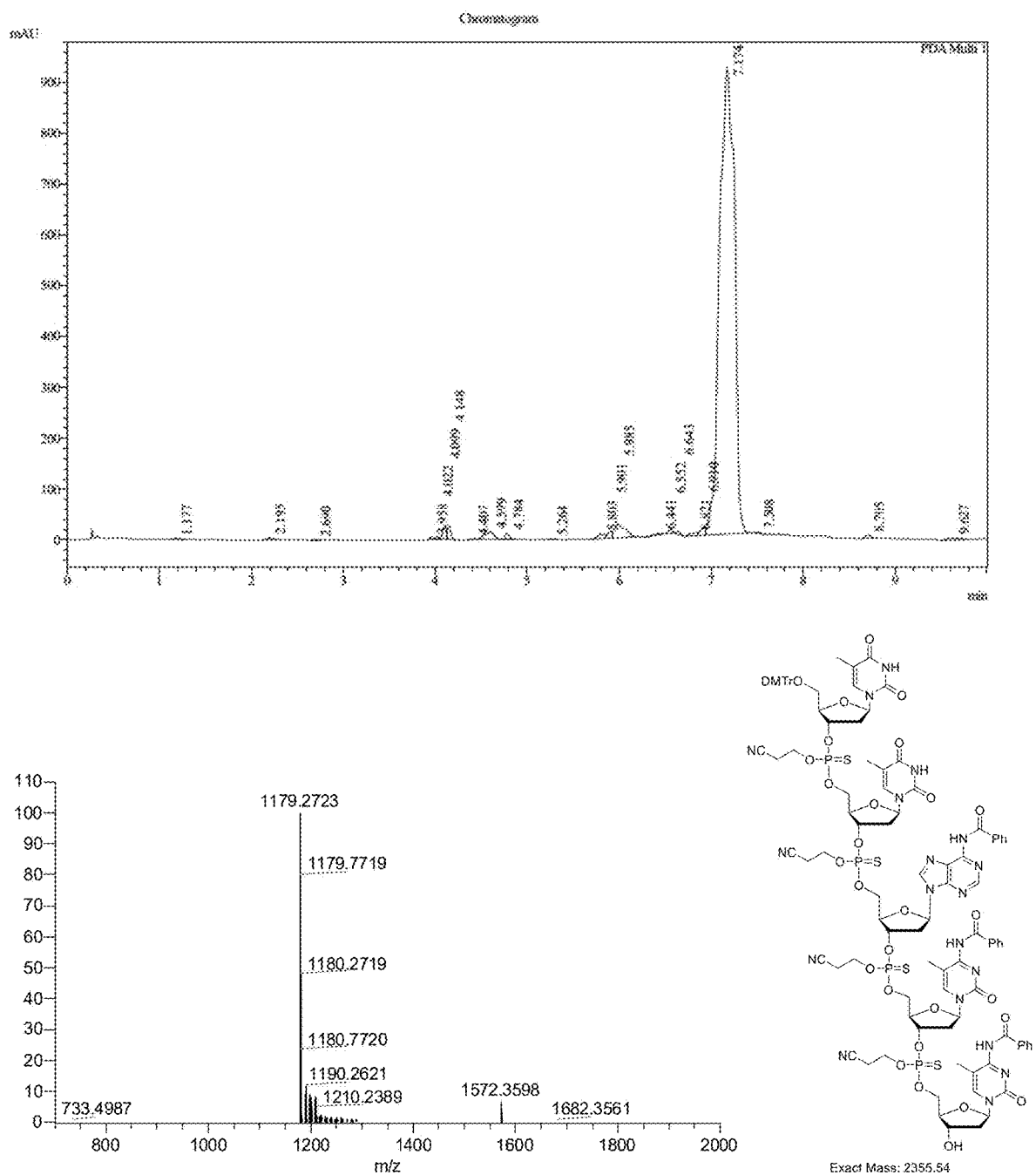
FIG. 2 shows HPLC and MS of product compound 2-9 obtained after precipitation.

The crude product was dissolved in DCM (840 mL) and ACN (240 mL) loaded in a 1 L separation funnel. To the solvent of TBME (8.5 L) was slowly added the solution of crude product from funnel to performance the precipitation process. This process took about 3 h. The pure product was collected as a white solid with buchner funnel, the cake of product was washed with the solvent mixture of TBME (1 L×2) and concentrated to dry. deoxy-TTACC 5mer (145.5 g, 57.8 mmol, 92.4% yield, 93.6% purity) was obtained as a white solid. HPLC-MS for deoxy-TTACC 5mer (2-9) with RT=7.174 min is shown in FIG. 2.

HPLC-MS method for compound 2-9:

Column: ACQUITY UPLC BEH Shield RP18 Column, 130 Å, 1.7 μm, 2.1 mm×150 mm;

Column temperature: 60° C.;

MS analysis was done on the Thermo Orbitrap Fusion with 60k resolution and mass range from 700 to 2000;

MS polarity: positive

Mobile phase A: 20 mM Ammonium Acetate in ACN: Water=25:75; Mobile phase B: acetonitrile;

Gradient:

| Time min | A % | B % | Flow mL/min | Pressure bar |
|---|---|---|---|---|
| 0.00 | 64.00 | 36.00 | 0.50 | — |
| 1.00 | 64.00 | 36.00 | 0.50 | — |
| 29.0 | 54.00 | 46.00 | 0.50 | — |
| 30.0 | 20.00 | 80.00 | 0.50 | — |
| 31.0 | 20.00 | 80.00 | 0.50 | |
| 32.0 | 64.00 | 36.00 | 0.50 | |
| 35.0 | 64.00 | 36.00 | 0.50 | |
| 36.0 | 64.00 | 36.00 | 0.50 | |

2. Synthesis of UTTC 4mer (Fragment 3)
General procedure for preparation of compound 3-2

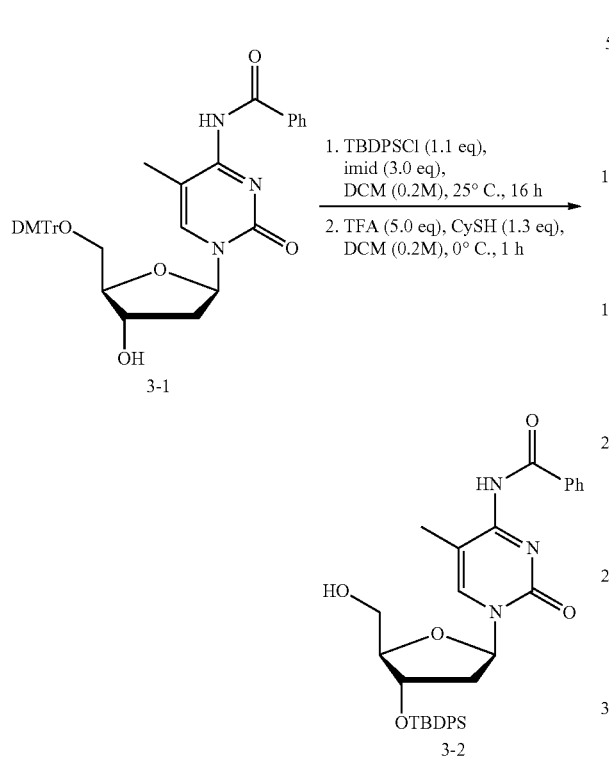

General Procedure for Preparation of Compound 3-3

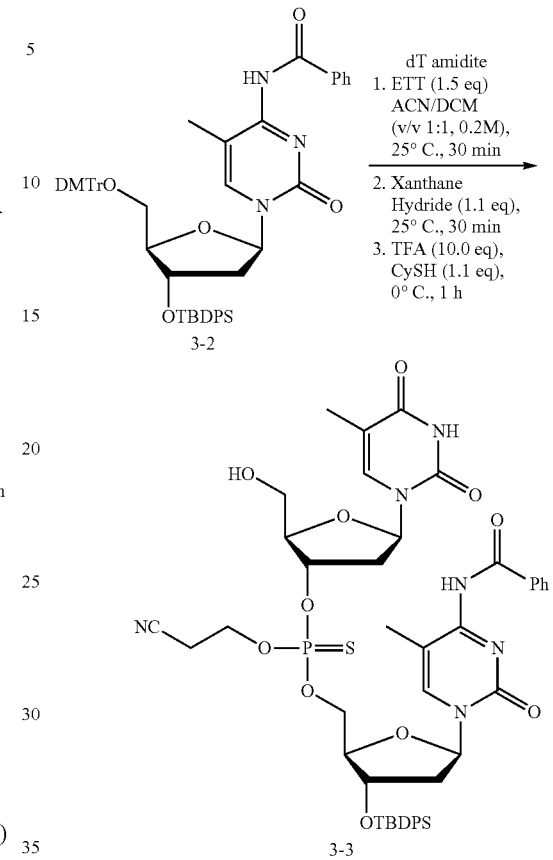

To a solution of compound 3-1 (500 g, 772 mmol, 1.00 eq) in DCM (3800 mL) was added imidazole (158 g, 2.32 mol, 3.00 eq). The TBDPSCl (276 g, 1.00 mol, 258 mL, 1.30 eq) was added. The mixture was stirred at 25° C. for 16 h. TLC (Petroleum ether/Ethyl acetate=5/1, product: Rf=0.40) indicated compound 3-1 was consumed completely. Propan-2-ol (46.4 g, 59.1 mL, 1.00 eq) was added and the mixture was stirred at 30 min.

To the above solution was added CySH (117 g, 1.00 mol, 123 mL, 1.30 eq) at 0° C. The mixture was stirred at 0° C. for 15 min. TFA (440 g, 3.86 mol, 286 mL, 5.00 eq) was added dropwise at 0° C. over a period of 30 min. The mixture was stirred at 0° C. for 1 h. HPLC showed the reaction completed. Note that the color of solution was changed from light yellow to deep red observed during the addition of TFA.

The reaction mixture was poured into the Na$_2$CO$_3$ solution (410 g Na$_2$CO$_3$ in 2.5 L water), diluted with TBME (2.5 L) and two layers were separated. The organic layer was washed with brine (1.3 L×2), dried by anhydrous MgSO$_4$ (321 g) filtered through celite and concentrated.

The crude product was dissolved in DCM (600 mL) and loaded in a 1000 mL separation funnel. To the solvent mixture of Heptane/TBME (v/v 9:1, 5.0 L) was slowly added the solution of crude product from funnel to performance the precipitation process. This process took about 30 min. The pure product was collected as a white solid with buchner funnel, the cake of product was washed with the solvent mixture of Heptane (500 mL×2) and concentrated to dry. Compound 3-2 (390 g, 660 mmol, 85.5% yield, 98.8% purity) was obtained as a white solid.

Compound 3-2 (110 g, 188 mmol, 1.00 eq) and dT amidite (168 g, 226 mmol, 1.20 eq) was co-evaporated with CH$_3$CN (1.0 L×3). The mixture was dissolved in CH$_3$CN (500 mL) and DCM (500 mL) at 25° C. 5-(Ethylthio)-1H-tetrazole (ETT) (1.67 g, 12.8 mmol, 1.50 eq) was added with stirring and the mixture solution was stirred at 25° C. for 30 min under Ar$_2$ atmosphere. Note that Acetonitrile and DCM were both redistilled freshly. HPLC indicated compound 3-2 was consumed completely. Note that dT amidite is DMT-2'-deoxythymidine-phosphoramidite:

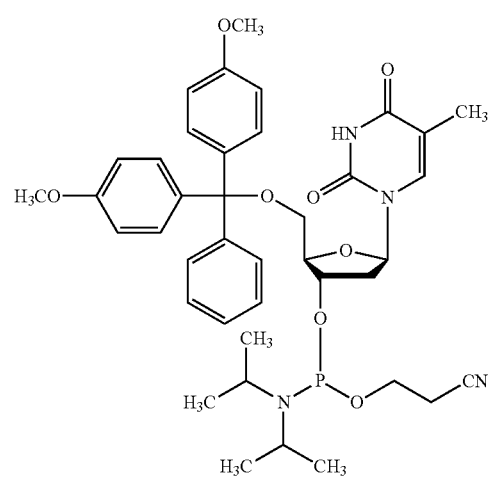

To the above solution was added Xanthane Hydride (31.1 g, 207 mmol, 1.10 eq) at 25° C. The mixture was stirred at 25° C. for 0.5 h. HPLC indicated the reaction completed.

To the above solution was cooled to 0° C. in ice water. CySH (24.1 g, 207 mmol, 25.4 mL, 1.10 eq) was added the reaction mixture at 0° C. TFA (215 g, 1.88 mol, 140 mL, 10.0 eq) was added the reaction mixture at 0° C. The mixture was stirred at 25° C. for 2 h. HPLC indicated the reaction completed. The color of mixture was changed from yellow cloudy to red.

The $Na_2CO_3$ solution (254 g, $Na_2CO_3$ in 3.4 L water) was added slowly to the reaction mixture (watched for the speed of $CO_2$ release to avoid the bumping of reaction solution). The naturalization process was done in about 1 hr and then all the solvents of reaction mixture were removed by rotavapor to give a milk-white water suspension of crude product.

Two reactions were combined here and the resulted water solution of crude product was diluted with 7.5 L MeCN (the addition of MeCN can dissolve the cake of crude product) and extracted by TBME/Heptane (3×3.4 L, v/v, 1:4) three times to remove non-polar impurities (such as CySH and DMTrSCy etc.). The water layer fraction was collected in a 3.0 L round-bottom flask and reduced pressure was applied by rotavapor to remove all MeCN to give a water solution with yellow-gel cake of crude product again.

The water solution of crude product was diluted with the mixture solvent of EtOAc/TBME (v/v=1:3, 5.1 L) (make sure no gel solid left in the solution) and two layers were separated. The organic layer was washed with DI water three times (3×2.5 L), brine (2.5 L) and dried by anhydrous $MgSO_4$ (~500 g) and condensed to dryness to yield a yellow foam of crude product which was directly used for next step without further treatment. Compound 3-3 (420 g, 330 mmol, 88.5% yield, 76.0% purity) was obtained as a light yellow solid.

General Procedure for Preparation of Compound 3-4

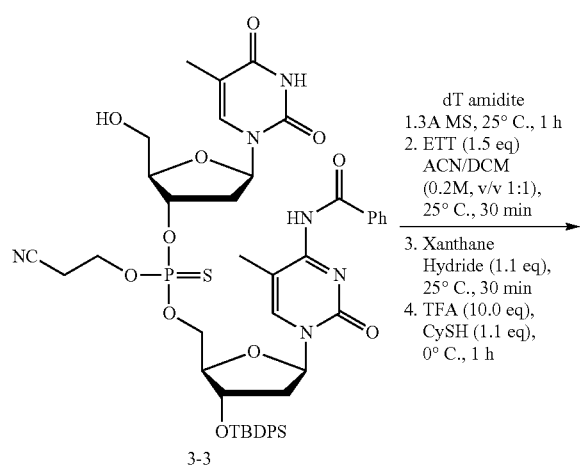

3-3

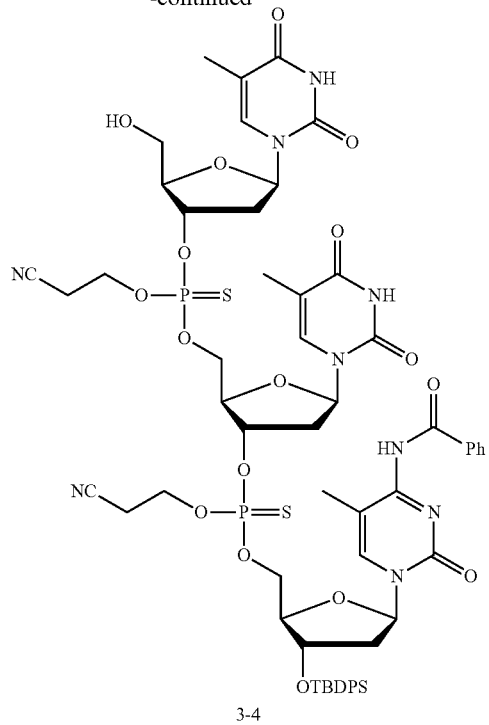

3-4

Compound 3-3 (200 g, 208 mmol, 1.00 eq) and dT amidite (186 g, 250 mmol, 1.20 eq) was co-evaporated with ACN (1.0 L×3) under $Ar_2$ in a 3 L single-necked round. The above solution in ACN (525 mL) and DCM (525 mL) was added Molecular sieve 3A (52.0 g) at 25° C. The mixture was stirred at 25° C. for 1 h. ETT (40.8 g, 313 mmol, 1.50 eq) was added at 25° C. The resulting mixture was stirred at 25° C. for 30 min. Note that Acetonitrile and DCM were both redistilled freshly. HPLC indicated compound 3-3 was consumed completely.

To the above solution was added Xanthane Hydride (34.5 g, 229 mmol, 1.10 eq) at 25° C. The mixture was stirred at 25° C. for 0.5 h. HPLC indicated the reaction completed.

To the above solution was cooled to 0° C. in ice water. CySH (26.7 g, 229 mmol, 28.1 mL, 1.10 eq) was added to the reaction mixture at 0° C. for 10 min. TFA (238 g, 2.09 mol, 154 mL, 10.0 eq) was added to the reaction mixture at 0° C. The mixture was stirred at 25° C. for 2 h. HPLC indicated the reaction completed. Note that the color of mixture was changed from yellow cloudy to red.

The $Na_2CO_3$ solution (156 g, $Na_2CO_3$ in 2100 mL water) was added slowly to the reaction mixture (watched for the speed of $CO_2$ release to avoid the bumping of reaction solution). The naturalization process was done in about 1 h and then all the solvents of reaction mixture were removed by rotavab to give a milk-white water suspension of crude product. The crude product was dissolved in the mixture solvent of EtOAc/TBME (v/v 1:2, 6400 mL) and two layers were separated. The organic layer was washed with water (3×3200 mL), brine (3200 mL) and dried by anhydrous $MgSO_4$ (~520 g) filtered and concentrated in vacuum.

Two reactions were combined here and the crude product was dissolved in DCM (1.0 L x 2) and loaded in a 1000 mL separation funnel. To the solvent of TBME/Heptane (v/v=9:1, 21 L) was slowly added the solution of crude product from funnel to performance the precipitation process. This process took about 3 h. The pure product was collected as a white solid with buchner funnel, the cake of product was washed with the solvent mixture of Heptane (800 mL×2)

and concentrated to dry. Compound 3-4 (301 g, 216 mmol, 51.8% yield, 95.8% purity) was obtained as a light yellow solid. HPLC shows Compound 2-4: RT=6.778 min.

General Procedure for Preparation of 3-5 (UTTC 4mer)

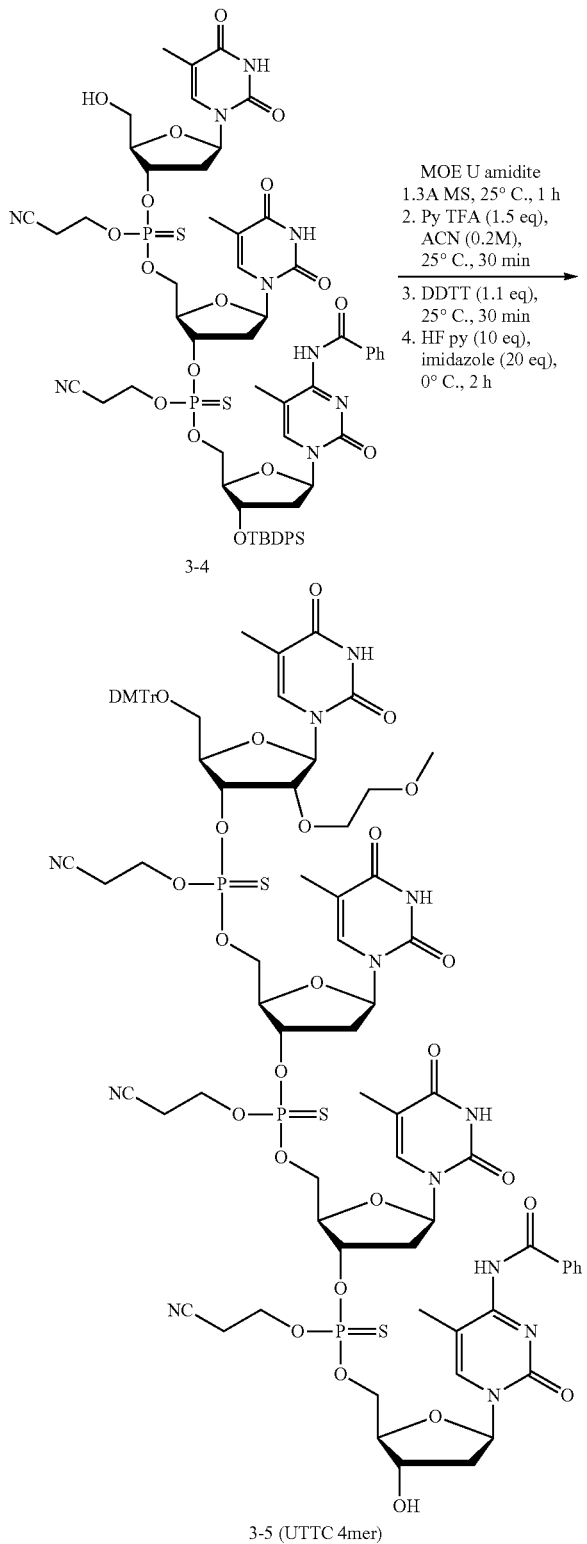

3-5 (UTTC 4mer)

Compound 3-4 (200 g, 150 mmol, 1.00 eq) and MOE U amidite (129 g, 157.85 mmol, 1.05 eq) was co-evaporated with CH₃CN (500 mL×3). To a solution of compound 3-4 (200 g, 150 mmol, 1.00 eq) and MOE U amidite (129 g, 157 mmol, 1.05 eq) in anhydrous CH₃CN (800 mL) was added Molecular sieve (MS) 3 Å (40.0 g, 150 mmol, 1.00 eq). The mixture was stirred at 25° C. for 1 h. Then the Py-TFA (1.00 M, 225 mL, 1.50 eq) was added to the mixture reaction at 25° C. The resulting mixture was stirred at 25° C. for 30 min. Note that Acetonitrile and DCM were both redistilled freshly. HPLC indicated compound 2-4 was consumed completely. Note that MOE U amidite is:

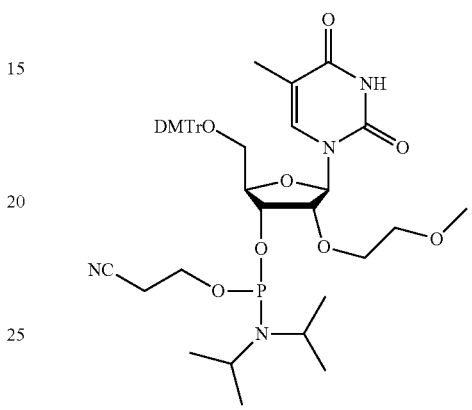

To the above solution was added DDTT (33.9 g, 165 mmol, 1.10 eq) at 25° C. The mixture was stirred at 25° C. for 0.5 h. And then the mixture cooled down to 0° C. in ice bath for 30 min. HPLC indicated the reaction completed. Note that the mixture was changed from yellow cloudy to yellow homogenous solution.

At the same time, a 1 L three-neck round bottom flask was charged with imidazole (204 g, 3.01 mol, 20.0 eq) and anhydrous THF (400 mL) and placed in the ice bath for 30 min. The HF (43.0 g, 1.50 mol, 39.1 mL, 70.0% purity, 10.0 eq) was slowly added and then stirred for another 15 min. The mixture was added to the above suspension at 0° C. for 1 h. The mixture was stirred at 0° C. for 1 h. HPLC indicated the reaction completed.

The reaction mixture was dissolved in the EtOAc (5.2 L). The organic layer was washed with sat·aq·NaHCO₃ (3.6 L×2), water (2.6 L×3), brine (2.6 L) and dried by anhydrous MgSO₄ (~440 g) filtered and concentrated in vacuum. Note that in this process, no yellow gel solids were precipitated out.

Figure 3:
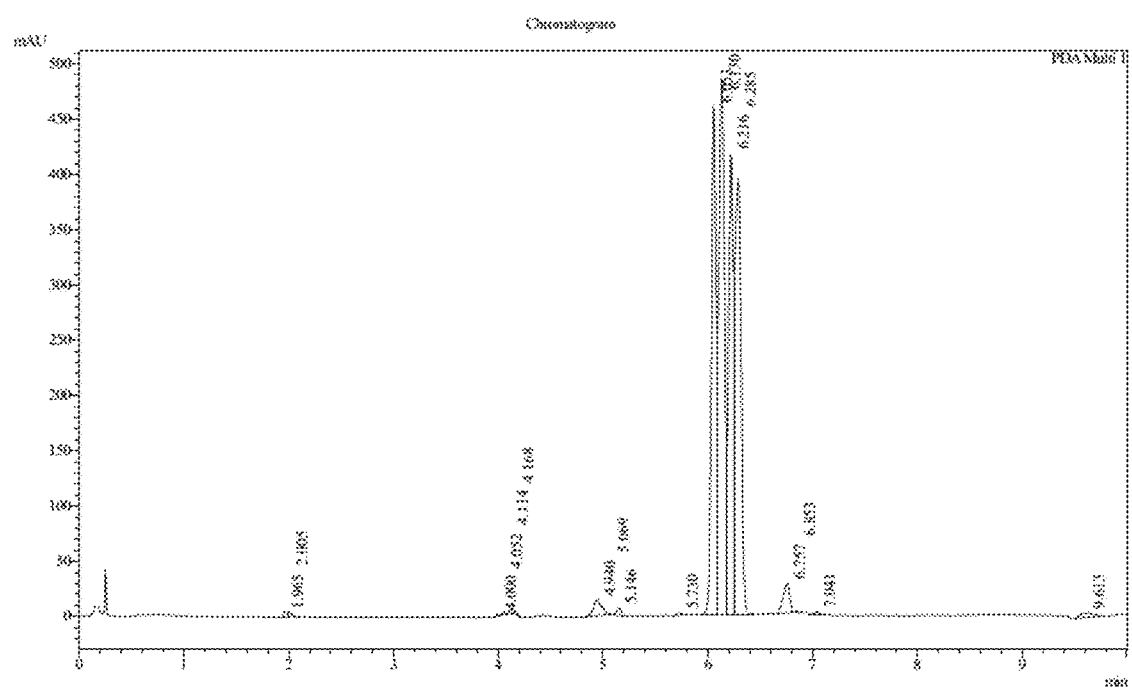
FIG. 3 shows HPLC and MS of product compound 3-5 obtained after precipitation.
Figure 3:
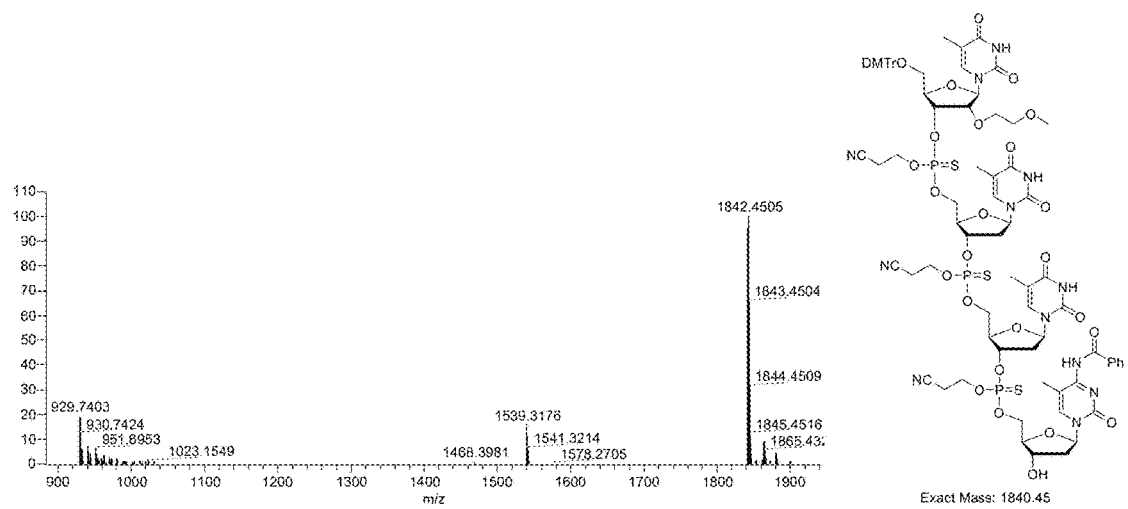

The crude product was dissolved in DCM (2.0 L) and loaded in a 1 L separation funnel. To the solvent mixture of TBME (17.6 L) was slowly added the solution of crude product from funnel to performance the precipitation process. This process took about 30 minutes. The pure product was collected as a white solid with buchner funnel, the cake of product was washed with the solvent mixture of TBME (500 mL×2) and concentrated to dry. Compound 3-5 (UTTC 4mer) (258 g, 134 mmol, 89.0% yield, 95.6% purity) was obtained as a light yellow solid. HPLC-MS for compound UTTC 4mer (3-5) is shown in FIG. 3.

HPLC-MS method for compound 3-5:
Column: ACQUITY UPLC BEH Shield RP18 Column, 130 Å, 1.7 μm, 2.1 mm×150 mm;
Column temperature: 60° C.;
MS analysis was done on the Thermo Orbitrap Fusion with 60k resolution and mass range from 300 to 2000;
MS polarity: positive;

Mobile phase A: 20 mM Ammonium Acetate in ACN:Water=25:75; Mobile phase B: acetonitrile;
Gradient:

| Time min | A % | B % | Flow mL/min | Pressure bar |
|---|---|---|---|---|
| 0.00 | 70.00 | 30.00 | 0.50 | — |
| 1.00 | 70.00 | 30.00 | 0.50 | — |
| 28.0 | 55.00 | 45.00 | 0.50 | — |
| 30.0 | 10.00 | 90.00 | 0.50 | — |
| 31.0 | 10.00 | 90.00 | 0.50 | |
| 32.0 | 70.00 | 30.00 | 0.50 | |
| 35.0 | 70.00 | 30.00 | 0.50 | |
| 36.0 | 70.00 | 30.00 | 0.50 | |

3. Synthesis of 5' DMT-MOE CCGU-OH (Fragment 4)
General Procedure for Preparation of Compound 4-2

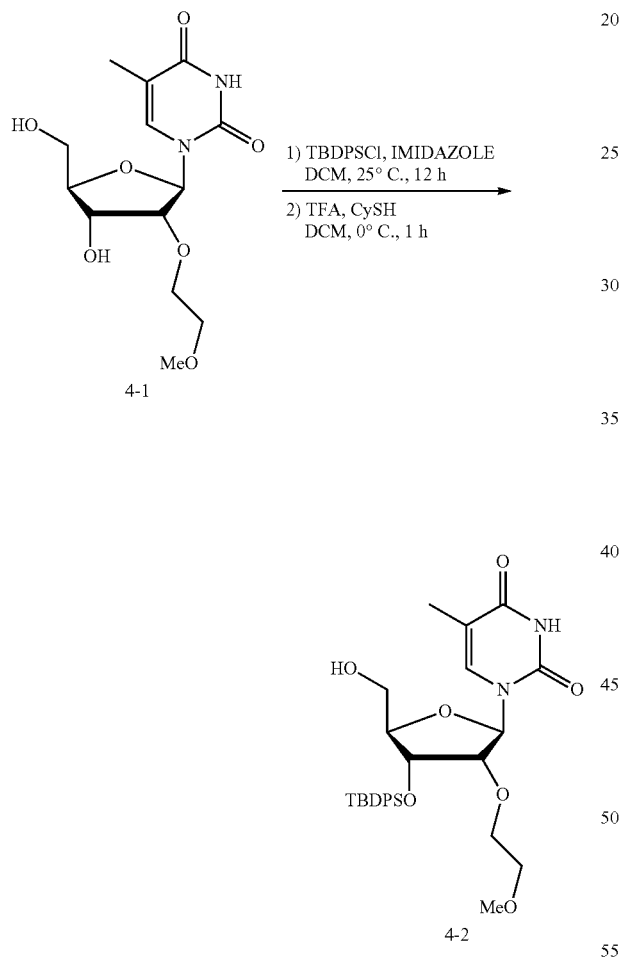

To a solution of compound 4-1 (200 g, 323 mmol) in DCM (1600 mL) was added IMIDAZOLE (66.0 g, 969 mmol) and TBDPSCl (115 g, 420 mmol, 107 mL) at 25° C. The mixture was stirred at 25° C. for 12 hr. TLC (Petroleum ether/Ethyl acetate=1/1, $R_f$=0.63 min) indicated compound 4-1 along with one major new spot with lower polarity. Propan-2-ol (19.4 g, 323 mmol, 24.7 mL) was added into the mixture and stirred at 25° C. for 0.5 h.

To a solution of the last step was added dropwise CySH (48.8 g, 420 mmol) and TFA (184 g, 1.62 mol) at 0° C. The mixture was stirred at 0° C. for 1 h. TLC (Petroleum ether/Ethyl acetate=1/1, Rf=0.50) showed the reaction was complete. The reaction mixture was quenched by addition $Na_2CO_3$ solution (185 g, 1600 mL DI $H_2O$) at 25° C., and then diluted with TBME (500 mL) and two layers were separated. The combined organic layers were washed with brine (500 mL), dried over $MgSO_4$, filtered and concentrated under reduced pressure to give a residue. The crude product compound 4-2 was dissolved in ACN (2000 mL) and DI $H_2O$ (300 mL) and extracted with Heptane/TBME (4/1, 8L, 1.6L×5). The ACN layer was diluted with DCM (3.2 L) separated the water, dried over dry $MgSO_4$, filtered and concentrated under reduced pressure to give a residue. Compound 4-2 (176 g, 98.1% yield, 95.8% purity) was obtained as a white foam.

$^1$H NMR: 400 MHz DMSO: 11.30 (s, 11H), 7.69 (m, J=6.4 Hz, 3H), 7.61 (dd, J=7.73, 1.47 Hz, 2H), 7.44 (m, 6H), 5.97 (d, J=5.87 Hz, 1H), 5.12 (t, J=4.89, 4.89 Hz, 1H), 4.31 (m, 1H), 3.9 (q, J=2.8, 2.8, 2.8 Hz, 1H), 3.76 (t, J=5.38, 5.38 Hz, 1H), 3.46 (m, 2H), 3.28 (m, 2H), 3.21 (ddd, J=12.23, 4.4, 3.13 Hz, 1H), 3.14 (s, 3H), 1.73 (s, 3H), 1.05 (s, 9H)

General Procedure for Preparation of Compound 4-4

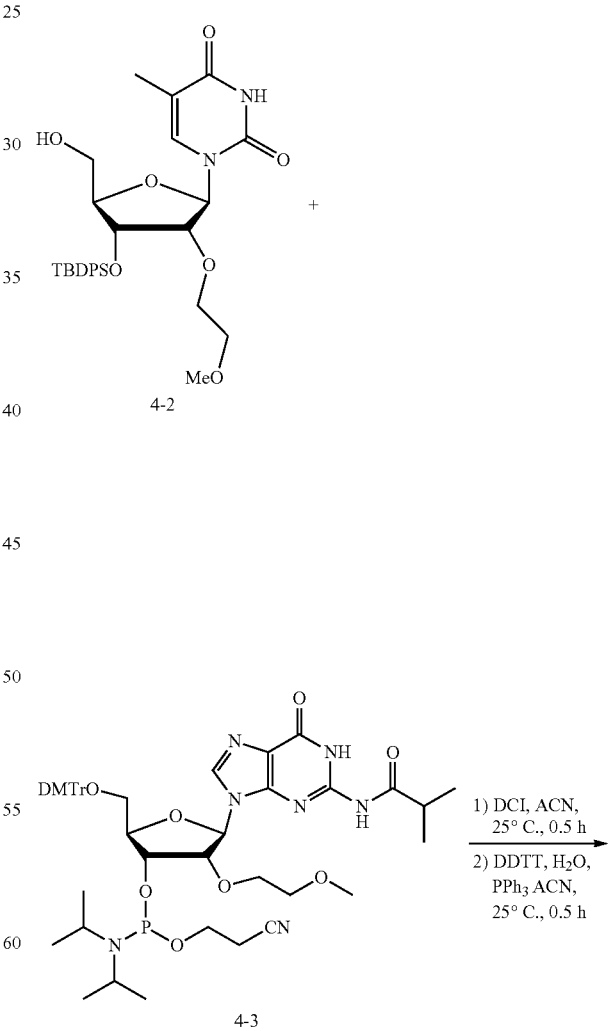

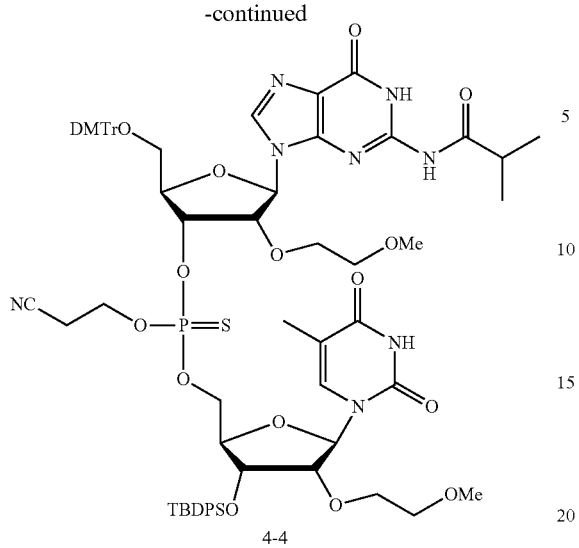

4-4

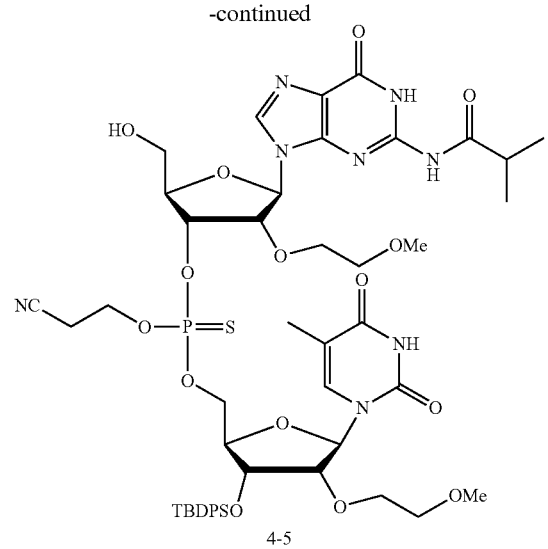

4-5

Compound 4-3 (164 g, 179 mmol) and compound 4-2 (90.5 g, 163 mmol) were co-evaporated with ACN (450 mL×3) under $Ar_2$ in a 3000 mL single-necked round bottle, and 3 Å molecular sieve (10.0 g) were added to the single-necked bottle, under $Ar_2$ pressure ACN (1000 mL) was added. The mixture was stirred at 25° C. for 1 h, and then DCI (28.9 g, 244 mmol) was added to the mixture. The mixture was stirred at 25° C. for 0.5 hr. HPLC showed the starting material was consumed completely.

After the completion of coupling reaction, DDTT (37.7 g, 183 mmol) was added to the mixture. The reaction mixture was stirred at 25° C. for 0.5 hr, and then DI $H_2O$ (0.12 mL), $PPh_3$ (4.38 g, 16.7 mmol) were added to the mixture, and the mixture was stirred at 25° C. for 0.5 hr. HPLC showed the starting material was consumed completely.

Remove most of the ACN by rotavapor, and then dilute the reaction with tBuOMe/EtOAc (3/1, 1500 mL). Yellow solid was precipitated out. Filter and wash the filtrate with DI $H_2O$ (1000 mL×2), brine (600 mL×2). The organic layer was dried and concentrated to dryness. The compound 4-4 (233.8 g, crude, 80.1% purity) was obtained as light yellow solid used into the next step without further purification.

General Procedure for Preparation of Compound 4-5

Compound 4-4 (234 g, 167 mmol) was dissolved in anhydrous DCM (1600 mL), then at 0° C. TCA (81.8 g, 501 mmol) and CySH (29.1 g, 250 mmol) were added. The mixture was stirred at 0° C. for 0.5 hr. HPLC showed the starting material was consumed completely.

The reaction was quenched by slowly add $NaHCO_3/H_2O$ (84.0 g $NaHCO_3$ in 1200 mL DI $H_2O$). The mixture was stirred vigorously for 10 min and two layers were separated. The $H_2O$ layer was extracted with DCM (600 mL), and the combined organic layer was dried and condensed to dryness. The mixture was re-dissolved in $CH_3CN$/DI $H_2O$ (2/1, 1200 mL), and the $CH_3CN/H_2O$ layer was washed by Heptane/tBuOMe (4/1, 1000 mL×5). Remove most of the $CH_3CN$ by rotavapor, and then dilute the mixture with tBuOMe/EtOAc (2/1, 1500 mL), wash the mixture with $NaHCO_3/H_2O$ (1000 mL×2, remove DCI), Brine (600 mL×2). The organic layer was dried with $MgSO_4$, filtered and concentrated to dryness. The crude product was used into the next step without further purification. The crude product compound 4-5 (180 g, 98.2% yield, 94.6% purity) was obtained as light yellow solid used into the next step without further purification.

General Procedure for Preparation of Compound 4-7

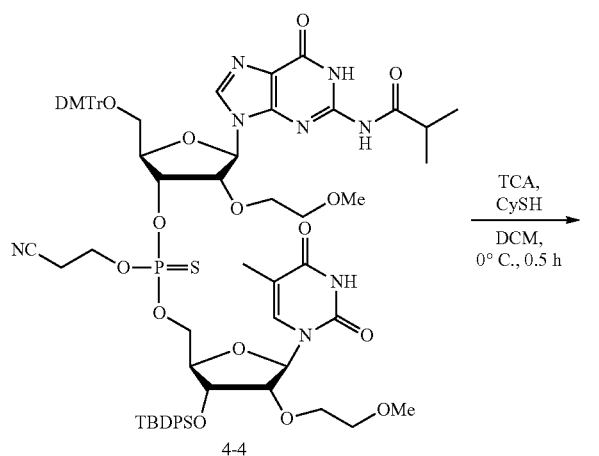

4-4

TCA, CySH

DCM, 0° C., 0.5 h

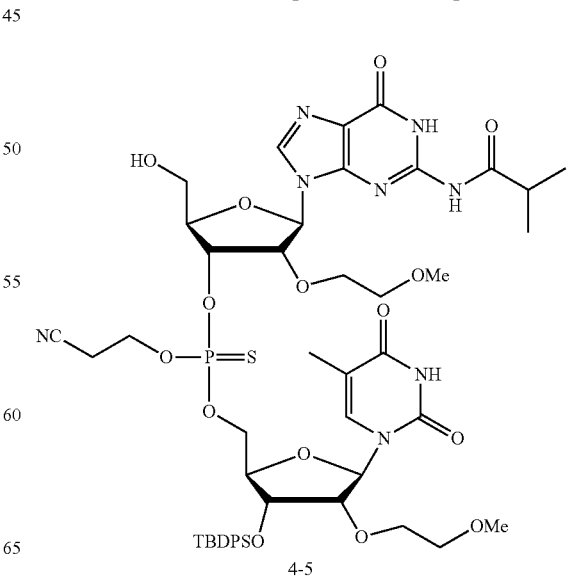

4-5

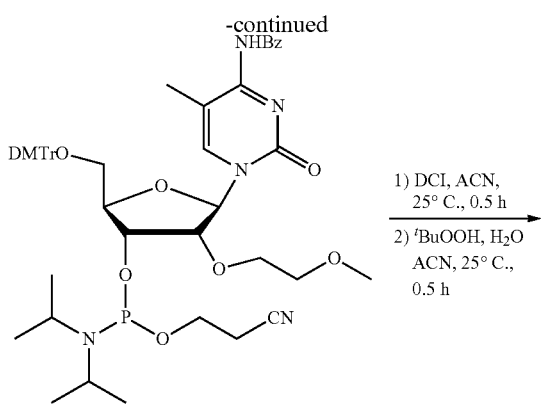

4-6

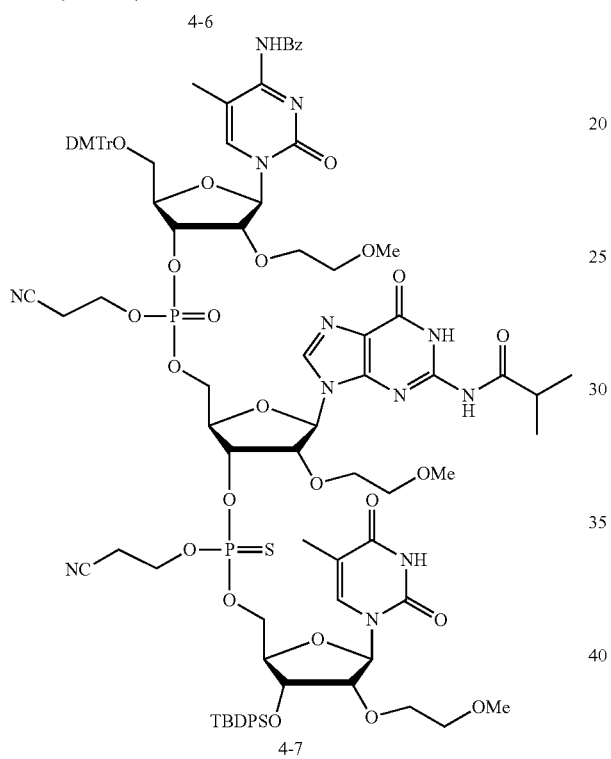

4-7

Compound 4-5 (115 g, 104 mmol) and compound 4-6 (106 g, 115 mmol) were co-evaporated with ACN (500 mL×3) under Ar₂ in a 2000 mL single-necked round bottle, and 3 Å molecular sieve (45.0 g) were added to the single-necked bottle, under Ar₂ pressure ACN (1050 mL) was added. The mixture was stirred at 25° C. for 1 hour, and then DCI (18.6 g, 157 mmol) was added to the mixture. HPLC showed the starting material was consumed completely.

After the coupling reaction finished, tBuOOH (5.5 M, 38.1 mL) and H₂O (10 mL) were added to the reaction mixture. The reaction mixture was stirred at 25° C. for 30 min. HPLC showed the starting material was consumed completely.

After the completion of oxidation, the reaction mixture was cooled down to 0° C. in ice water bath for 5 min, and the commercial grade 12 oxidation solution (628.87 mL 0.05 M in pyridine/H₂O, v/v 9:1) was added to the mixture in 20 min. The reaction mixture was stirred at 0° C. for an additional five minutes. HPLC showed the starting material was consumed completely.

The reaction mixture was poured slowly into Na₂S₂O₃/H₂O solution (Na₂S₂O₃ 33.1 g in 2300 mL H₂O) and the solution was stirred vigorously for 10 min. The mixture was then diluted with 3000 mL mixture solvent of EtOAc/tBuOMe (1/3). The organic layer was separated and washed with NaHCO₃/H₂O(2000 mL), Brine (1000 mL). The organic layer was dried and concentrated to dryness. The crude product was re-dissolve in DCM/tBuOMe (1/1, 460 mL). The crude solvent was slowly dropped to a solvent mixture of Heptane/BuOMe (2/1, 2300 mL). Desired product was precipitated out. The product was collected as a light-yellow solid after filtration, the solid cake was washed with heptanePBuOMe (1/1, 230 mL×2). The compound 7 (217 g, crude, 87.6% purity) was obtained as a light yellow solid used into the next step without further purification.

General Procedure for Preparation of Compound 4-8

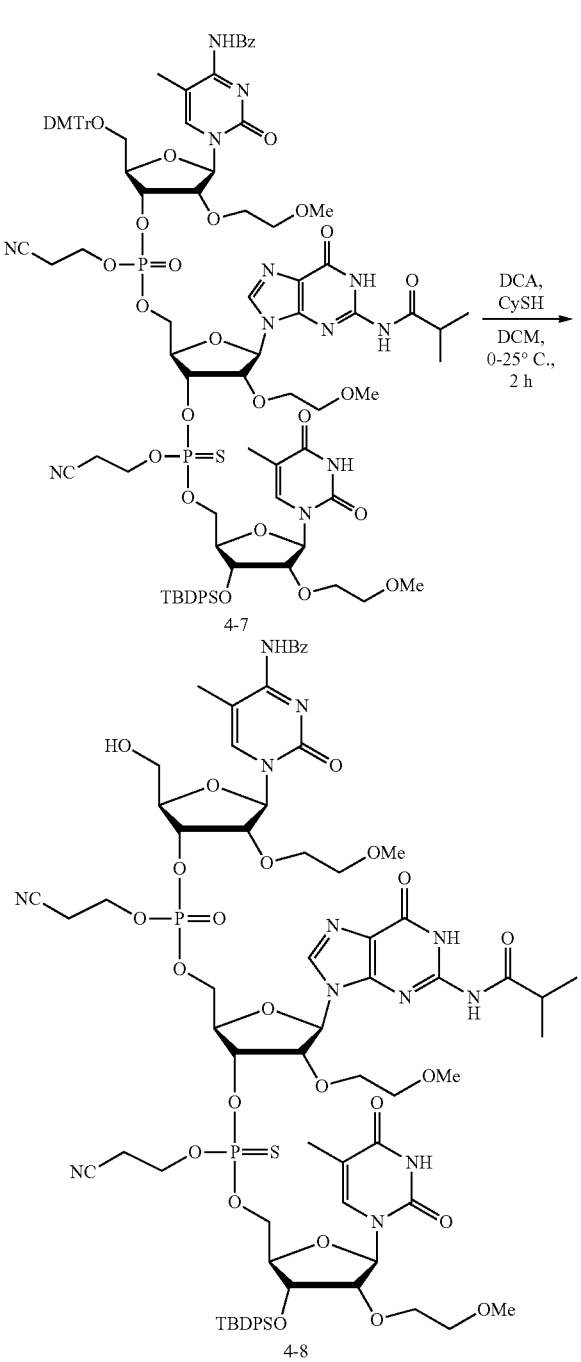

4-7

4-8

Compound 4-7 (204 g, 104 mmol) was dissolved in anhydrous DCM (2000 mL), then at 0° C. DCA (67.5 g, 524 mmol) and CySH (18.2 g, 157 mmol) were added. The mixture was warm to 25° C. and stirred for 2 h. HPLC showed the starting material was consumed completely.

The reaction was quenched by slowly add $Na_2CO_3/H_2O$ (77.4 g $Na_2CO_3$ in 1200 mL DI $H_2O$). The mixture was stirred vigorously for 10 min and two layers were separated. The $H_2O$ layer was extracted with DCM (600 mL), and the combined organic layer was dried and condensed to dryness. The mixture was re-dissolved in $CH_3CN/H_2O$ (2/1, 900 mL), and the $CH_3CN/H_2O$ layer was washed by Heptane/tBuOMe=(4/1, 800 mL×5). Remove most of the $CN_3CN$ by rotavapor, and then dilute the mixture with tBuOMe/EtOAc (1/3, 1800 mL), wash the mixture with $NaHCO_3/H_2O$ (900 mL×2), Brine (600 mL). The organic layer was dried and concentrated to dryness. The crude product was used for next step without further purification. The compound 4-8 (130 g, 75.3% yield, 92.4% purity) was obtained as light yellow solid used into the next step without further purification.

General Procedure for Preparation of 5' DMT-MOE CCGU-OH

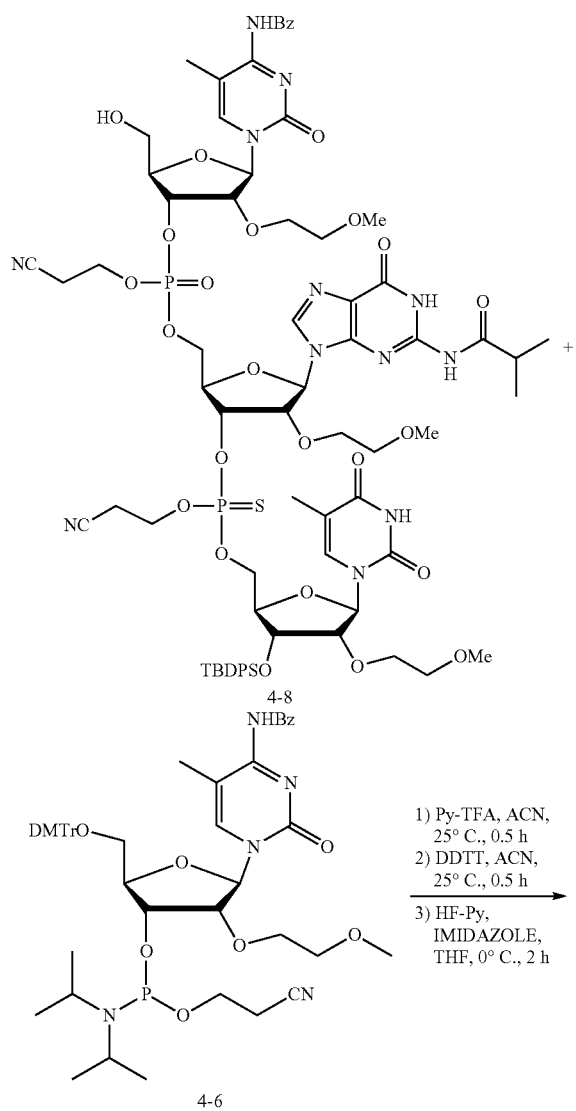

4-8

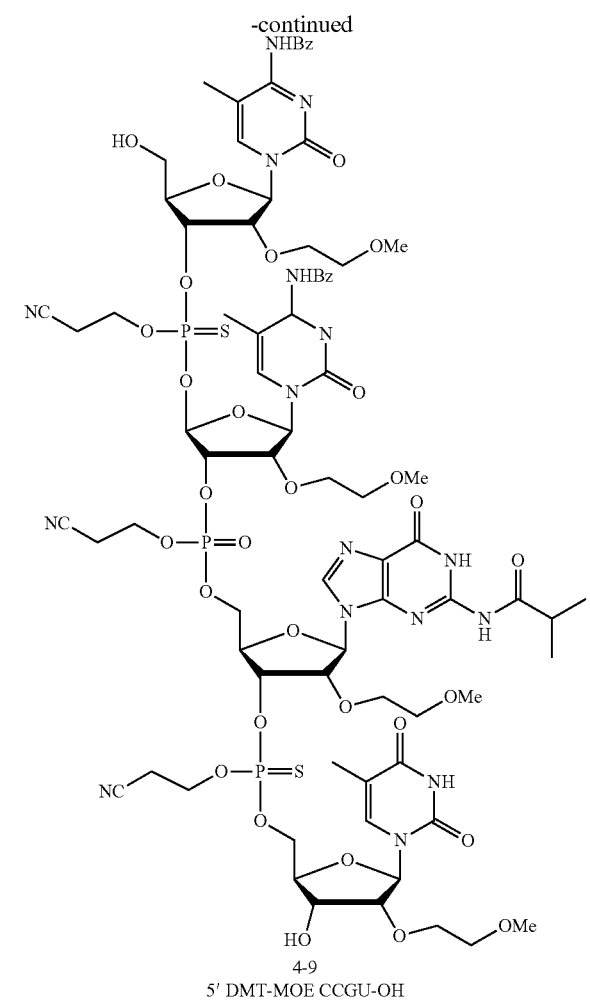

4-9
5' DMT-MOE CCGU-OH

Compound 4-8 (153 g, 92.8 mmol) and compound 4-6 (89.9 g, 97.5 mmol) were co-evaporated with ACN (400 mL×3) under $Ar_2$ in a 3000 mL single-necked round bottle, and 3A molecular sieve (45.0 g) were added to the single-necked bottle, under $Ar_2$ pressure ACN (928 mL) was added. The mixture was stirred at 25° C. for an hour, and then Py-TFA (1 M, 139 mL) was added to the mixture. HPLC showed the starting material was consumed completely.

After the coupling reaction finished DDTT (20.0 g, 97.5 mmol) was added to the mixture. The reaction mixture was stirred at 25° C. for 0.5 hr and changed from yellow cloudy to yellow homogenous solution which suggested the reaction went to completion and then cooled down to 0° C. in ice bath for 30 min.

At the same time, a 500 mL round bottom flask was charged with imidazole (127 g, 1.87 mol) and anhydrous THF (232 mL) and placed in the ice bath for 30 min. The HF-Py (24.3 mL, 70.0% purity) was slowly added and then stirred for another 15 min (A homogeneous solution was obtained from this step). The solution from the last step was slowly added to the reaction mixture from the last reaction mixture by the peristaltic pump (1 mL/5 min dropping rate) and stirred for 1-2 hours at 0° C. The completion of reaction can be monitored by HPLC. HPLC showed the starting material was consumed completely. The mixture was diluted with EA (4500 mL) and slowly neutralized by $NaHCO_3/H_2O$ (2500 mL) at 0° C. The organic layer was separated and washed with $NaHCO_3/H_2O$ (2500 mL), brine (2000 mL).

Figure 4:
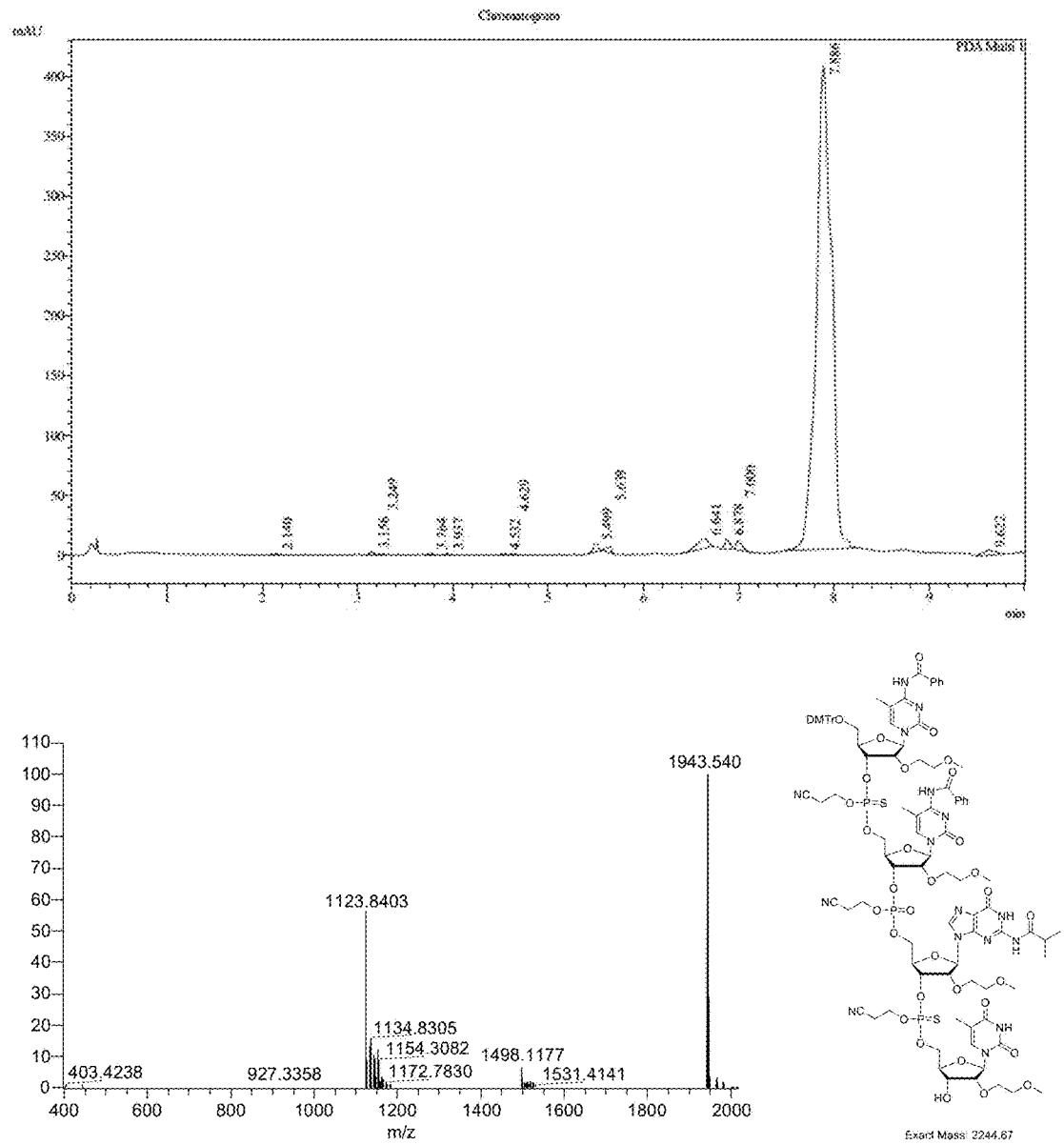
FIG. 4 shows HPLC and MS of product compound 4-9 obtained after precipitation.

The organic layer was dried and concentrated to dryness. The crude was re-dissolved in DCM (600 mL). The crude solvent was slowly dropped to a solvent of tBuOMe (6000 mL). Desired product was precipitated out. The product was collected as a light-yellow solid after filtration, and the solid cake was washed with tBuOMe (600 mL×2). 4-9 (5' DMT-MOE CCGU-OH) (190 g, 90.5% yield, 94.8% purity) was obtained as a light yellow solid. HPLC-MS for MOE-CCGU 4mer (4-9) is shown in FIG. 4.

HPLC-MS method for compound 4-9:
Column: ACQUITY UPLC BEH Shield RP18 Column, 130 Å, 1.7 µm, 2.1 mm×150 mm;
Column temperature: 60° C.;
MS analysis was done on the Thermo Orbitrap Fusion with 60k resolution and mass range from 400 to 2000;
MS polarity: positive
Mobile phase A: 20 mM Ammonium Acetate in ACN:Water=25:75; Mobile phase B: acetonitrile;
Gradient:

| Time min | A % | B % | Flow mL/min | Pressure bar |
|---|---|---|---|---|
| 0.00 | 60.00 | 40.00 | 0.50 | — |
| 1.00 | 60.00 | 40.00 | 0.50 | — |
| 28.0 | 40.00 | 60.00 | 0.50 | — |
| 30.0 | 10.00 | 90.00 | 0.50 | — |
| 31.0 | 10.00 | 90.00 | 0.50 | |
| 32.0 | 60.00 | 40.00 | 0.50 | |
| 35.0 | 60.00 | 40.00 | 0.50 | |
| 36.0 | 60.00 | 40.00 | 0.50 | |

C. Convergent Synthesis of Target Oligonucleotide
General Procedure for Preparation of Compound 5-1

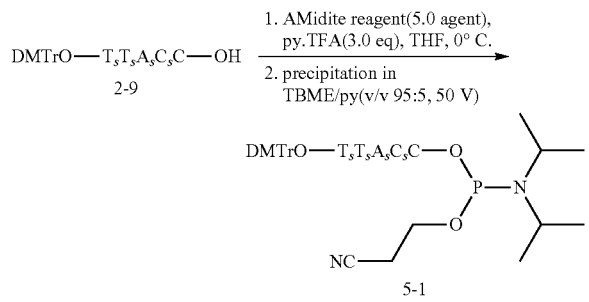

To a solution of Amidite Reagent (63.9 g, 212 mmol, 67.3 mL, 5.0 eq) and compound 2-9 (100 g, 42.4 mmol, 1.0 eq) in THF (400 mL) was added Py-TFA (24.5 g, 127 mmol, 15.9 mL, 3.0 eq) at 0° C. The mixture was stirred at 0° C. for 1 hr. HPLC showed the compound 2-9 was consumed completely.

The reaction mixture was transferred to 500 mL separation funnel (~20 mL after combining with DCM washing volume). To the solvent TBME/py (v/v 100:0.7, 15 L) was slowly dropped the solution of crude product from funnel to performance the precipitation process. This process took about 90 min. The pure product was collected as an off-white solid from the previous step, the cake of product was washed with pure TBME (1.0 L×3) and dried by vacuum. Compound 5-1 (106 g, 90.8% yield, 93% purity) was obtained as a white solid. Please note that anhydrous THF was used. Compound 2-9 and Py-TFA were co-evaporated with THF 3 times. Pyridine was added to maintain the basic environment to minimize the hydrolysis of amidite product.

General Procedure for Preparation of Compound 5-2

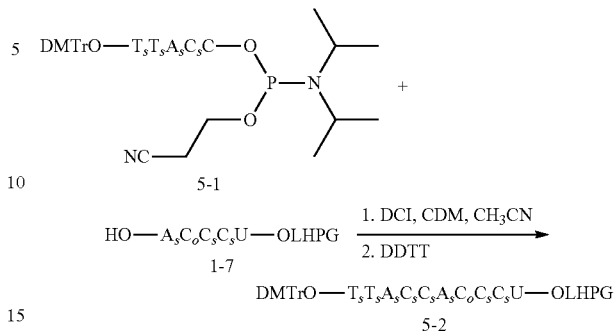

Compound 5-1 (122 g, 48.0 mmol, 1.5 eq), 3 Å molecular sieve (45.0 g) and Compound 1-7 (115 g, 32.0 mmol, 1.0 eq) was in DCM/ACN=2/1 (900 mL) was added DCI (9.46 g, 80.08 mmol, 2.5 eq). The mixture was stirred at 10° C. for 1h.

Monitor the reaction by TLC (60 min full conversion). After the coupling reaction finished DDTT (9.87 g, 48.05 mmol, 1.5 eq) was added to the mixture. The reaction mixture was stirred at 10° C. for 30 min. The reaction mixture was filtered and the filtrate was concentrated to 1/2 volume. The residue solution was added to ACN (5.0 L). Product was precipitated out. Filtered and the filter cake was collected. The filter cake was washed with ACN (1 L). and dried under vacuum. Compound 5-2 (194 g, 99.6% yield) was obtained as a light yellow solid. Please note that Acetonitrile and DCM were both redistilled freshly. The compound 5-1 and compound 1-7 were co-evaporated with DCM/ACN three times.

Figure 5:
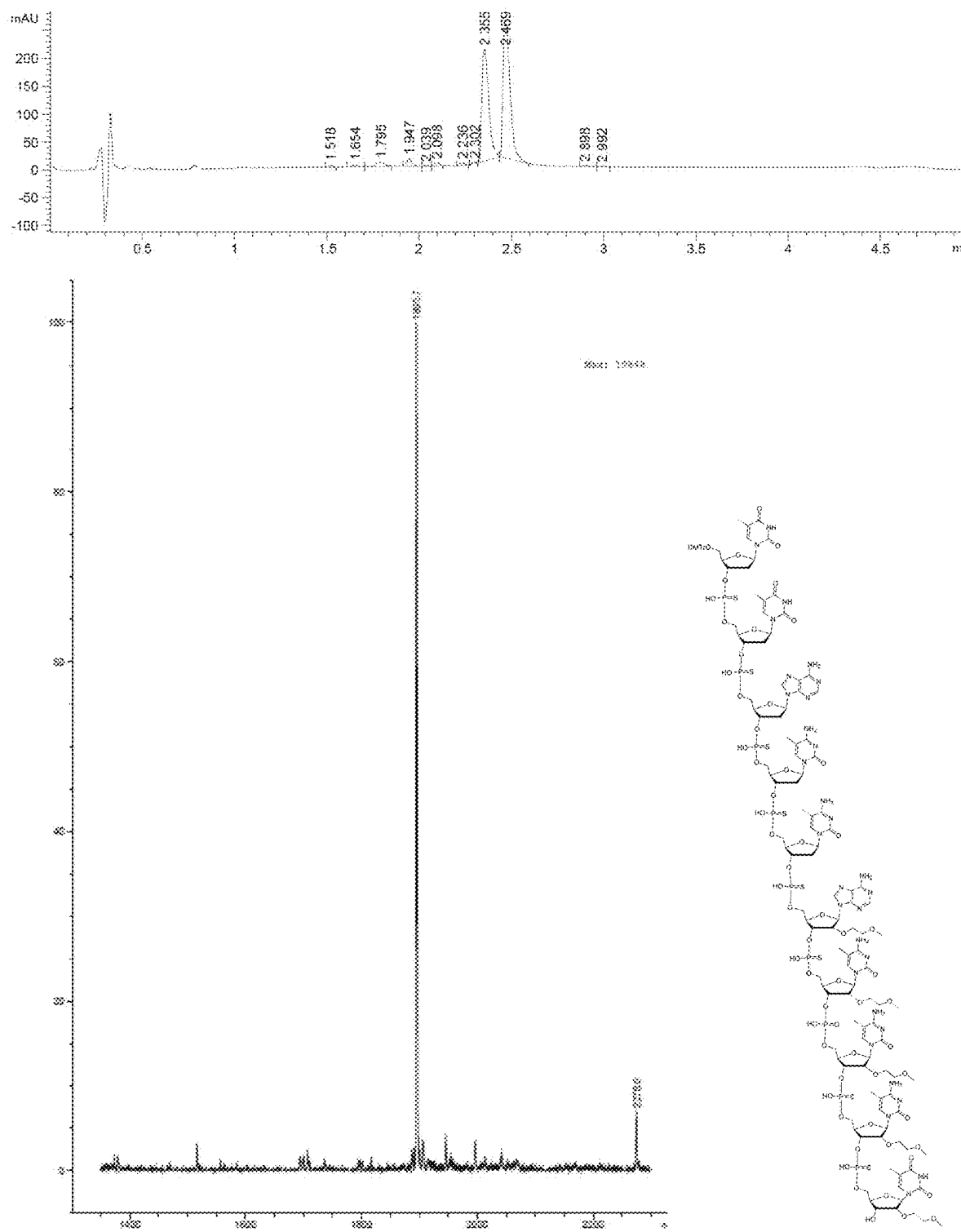
FIG. 5 shows HPLC and MS of compound 5-2-a obtained after ammonolysis of product compound 5-2.

For HPLC and LC-MS analyses of compound 5-2, it was deprotected using ammonolysis (NH$_3$/H$_2$O) procedure similar to the one used for compound 1 ammonolysis disclosed below to obtain 5-2-a (DMTrO-TsTsAsCsCsAsCoCsCsU-OH). HPLC and LC-MS of compound 5-2-a is shown in FIG. 5.

General Procedure for Preparation of Compound 5-3

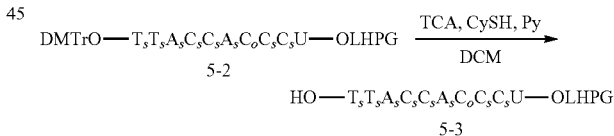

The compound 5-2 (194 g, 31.9 mmol, 1.0 eq) and 3 Å molecular sieve (65.0 g) were added to a round flask, under Ar pressure anhydrous DCM (1.3 L) was added. The mixture was stirred at 15° C. for 1 hour, and then CySH (7.42 g, 63.8 mmol, 7.81 mL, 2.0 eq) and TCA (52.1 g, 319 mmol, 32.1 mL, 10.0 eq) was added to the mixture at 0° C.

Figure 6:
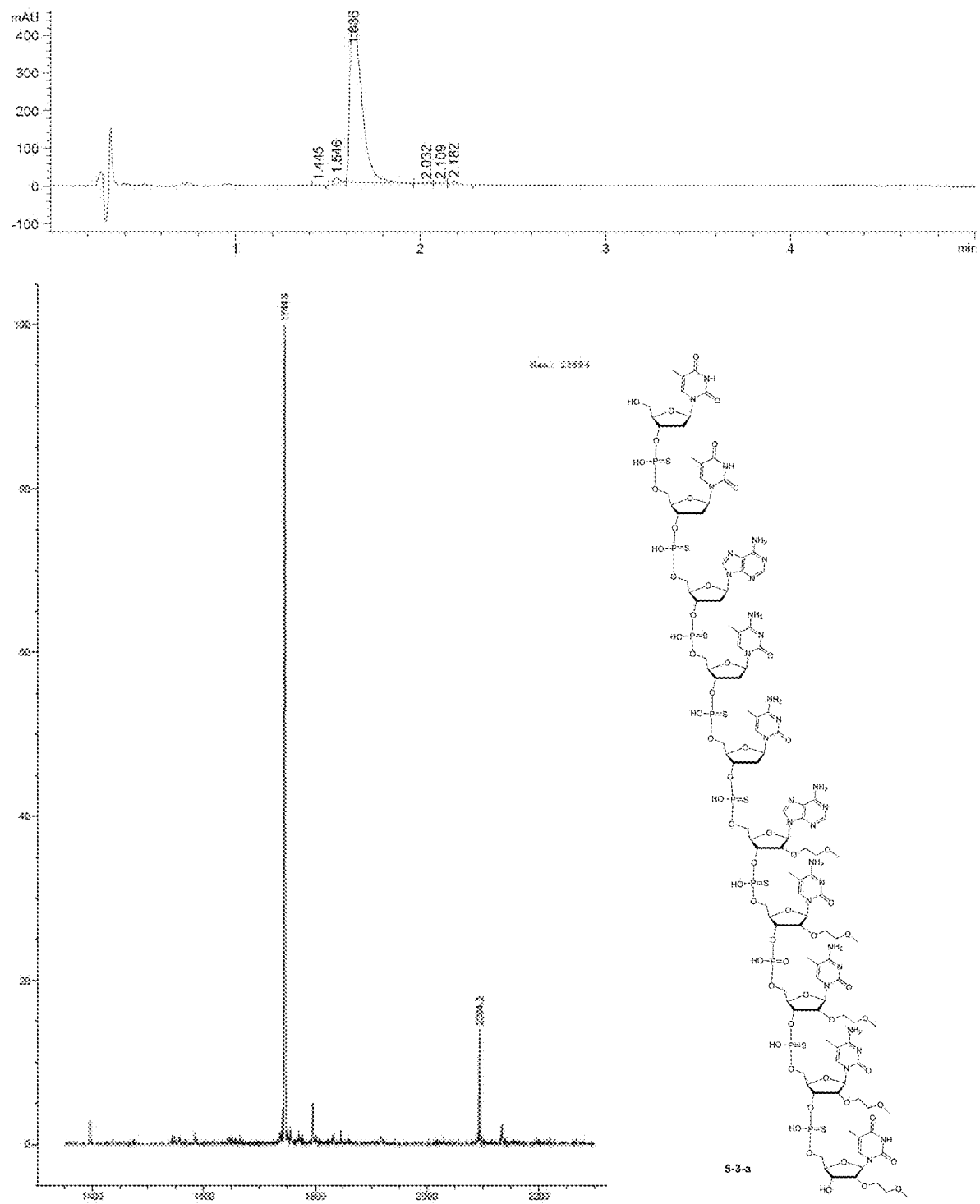
FIG. 6 shows HPLC and MS of compound 5-3-a obtained after ammonolysis of product compound 5-3

The reaction was stirred at 0° C. for 90 min (check reaction by TLC), and then Py (30.2 g, 382 mmol, 30.9 mL, 12.0 eq) was added to the mixture. The mixture was stirred at 15° C. for 5 min. 3A molecular sieves were removed by filtration. The DCM solvent was added to CH$_3$CN (7.0 L) slowly, light yellow solid precipitate out. Remove most of the DCM by rotavap, and the white precipitation was collected and washed with CH$_3$CN (500 ml×3). Compound 5-3 (180 g, 97.6% yield) was obtained as a light yellow solid. Please note that DCM was redistilled freshly. The compound 5-2 was co-evaporated with DCM 3 times. The product has good dissolvability in DCM, it's important to remove most of the DCM before filtration. For HPLC and LC-MS analyses of compound 5-3, it was deprotected using ammonolysis (NH$_3$/H2O) procedure similar to the one used for compound 1 ammonolysis disclosed below to obtain 5-3-a (HO-TsTsAsCsCsAsCoCsCsU-OH). HPLC and LC-MS of compound 5-3-a is shown in FIG. 6.

HPLC-MS method for 5-3-a
- Column: ACQUITY UPLC BEH C18 Column, 1.7 μm, 2.1 mm×50 mm;
- Column temperature: 50° C.;
- Ionization Mode: API-ES;
- mass range from 1350 to 2300;
- MS polarity: Negative;
- Mobile phase A: 5 mM TBuAA in 10% CH$_3$CN, 1 μm EDTA; Solution B: 5 mM TBuAA in 80% CH$_3$CN, 1 μm EDTA;
- Gradient

| Time min | A % | B % | Flow mL/min | Pressure bar |
|---|---|---|---|---|
| 0.14 | 60.00 | 40.00 | 0.51 | — |
| 3.70 | 20.00 | 80.00 | 0.51 | — |
| 4.00 | 10.00 | 90.00 | 0.51 | — |
| 4.20 | 60.00 | 40.00 | 0.51 | — |
| 5.00 | 60.00 | 40.00 | 0.51 | — |

General Procedure for Preparation of Compound 5-4

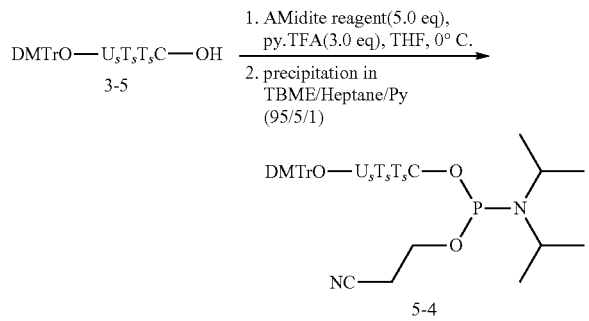

The compound 3-5 (102 g, 55.3 mmol, 1.0 eq) were co-evaporated with THF (300 mL×3). Py-TFA (32.0 g, 166 mmol, 3.0 eq) were co-evaporated with THF (300 mL×3). To a 2000 mL round bottom flask, compound 3-5 (102 g, 55.3 mmol, 1.0 eq) and AMidite reagent (83.4 g, 276 mmol, 87.9 mL, 5.0 eq) were added in anhydrous THF (400 mL) and cooled down to 0° C. in ice bath for 30 min. Activator Py-TFA (32.0 g, 166 mmol, 3.0 eq) was added and then the reaction mixture was stirred at 0° C. for 1 hour. HPLC showed the starting material was consumed completely.

To the solvent TBME/Heptane/Py (95/5/1, 15.8 L) was slowly dropped the solution of crude product from funnel to performance the precipitation process. This process took about 30 minutes. The pure product was collected as an off-white solid from the previous step, the cake of product was washed with pure TBME (500 mL×3) and dried by high vacuum for 3 hours.

Compound 5-4 (107 g, 52.4 mmol, 94.6% yield) was obtained as a white solid. Please note that THF was Anhydrous, and Compound 3-5 and Py-TFA were co-evaporated with anhydrous THF 3 times.

General Procedure for Preparation of Compound 5-5

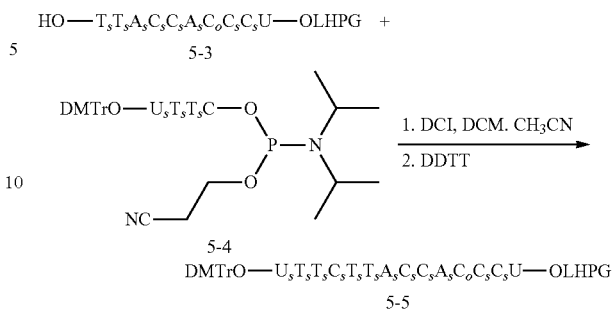

The compound 5-3 (177 g, 30.6 mmol, 1.0 eq), compound 5-4 (106 g, 52.0 mmol, 1.7 eq), and 3 Å molecular sieve (60 g) were added to a round flask, under Ar pressure in anhydrous DCM (850 mL, H$_2$O<50 ppm), ACN (425 mL, H$_2$O<50 PPM) were added. The mixture was stirred at 15° C. for 1 hour, and then DCI (9.05 g, 76.6 mmol, 2.5 eq) was added to the mixture. The mixture was stirred at 15° C. for 0.67 h. TLC (DCM:MeOH=10:1) indicated compound 5-3 was consumed completely.

After the coupling reaction finished, DDTT (10.7 g, 52.0 mmol, 1.7 eq) was added to the mixture. The reaction mixture was stirred at 15° C. for 10 min.

3 Å molecular sieve were removed by filtration, and the reaction was diluted with 6000 ml CH$_3$CN (white solid precipitate out). Remove DCM by rotovap, and the white solid was collected and washed with CH$_3$CN (500 mL×3). The light yellow solid was directly used for next step without any purification. Compound 5-5 (237 g, 99.6% yield) was obtained as a light yellow solid.

Figure 7:
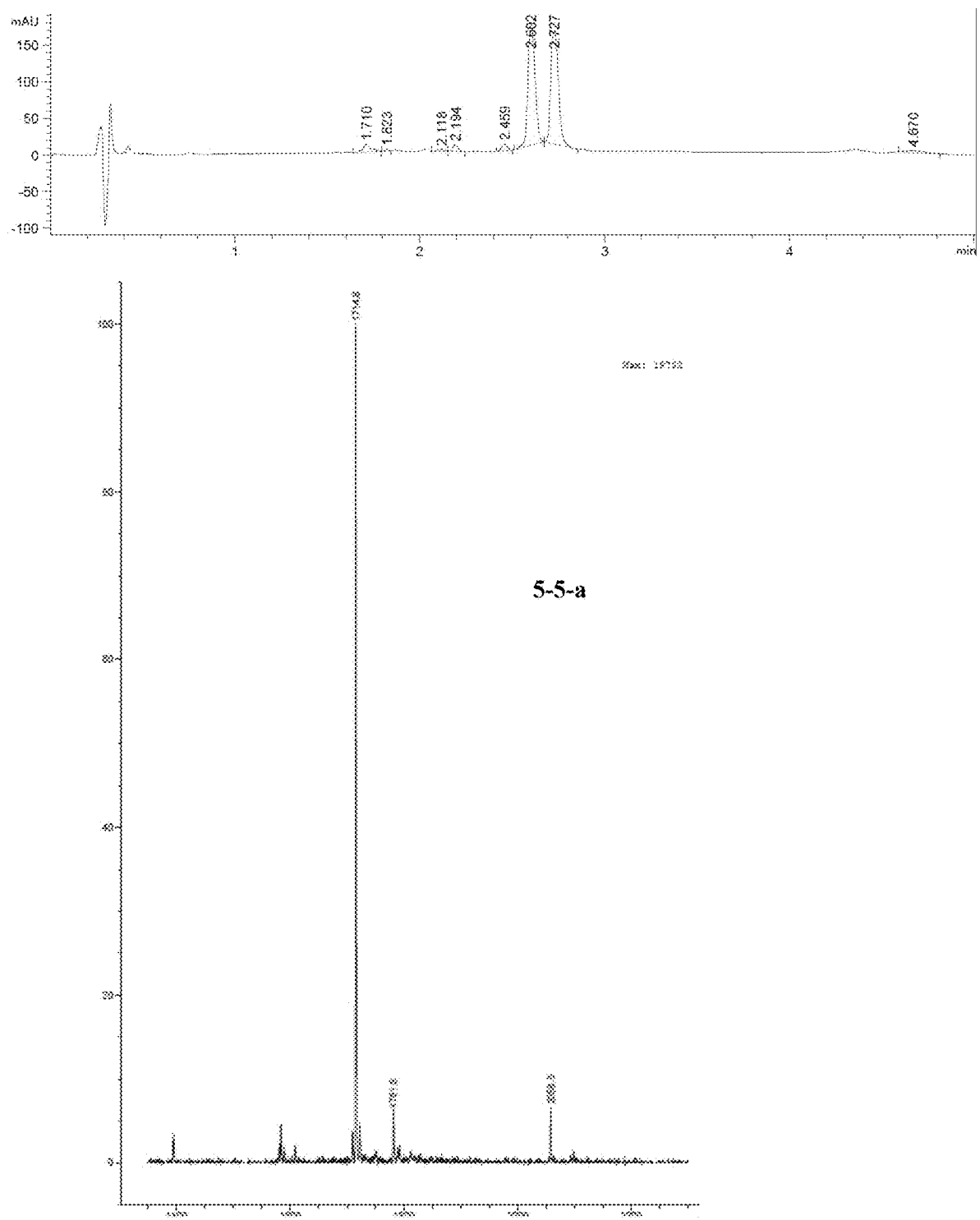
FIG. 7 shows HPLC and MS of compound 5-5-a obtained after ammonolysis of product compound 5-5.

For HPLC and LC-MS analyses of compound 5-5, it was deprotected using ammonolysis (NH3/H2O) procedure similar to the one used for compound 1 ammonolysis disclosed below to obtain 5-5-a (DMTrO-UsTsTsCsTsTsAsCsCsAsCoCsCsU-OH). HPLC and LC-MS of compound 5-5-a is shown in FIG. 7.

HPLC-MS method for 5-5-a
- Column: ACQUITY UPLC BEH C18 Column, 1.7 μm, 2.1 mm×50 mm;
- Column temperature: 50° C.;
- Ionization Mode: API-ES;
- mass range from 1350 to 2300;
- MS polarity: Negative;
- Mobile phase A: 5 mM TBuAA in 10% CH$_3$CN, 1 μm EDTA; Solution B: 5 mM TBuAA in 80% CH$_3$CN, 1 μm EDTA;
- Gradient:

| Time min | A % | B % | Flow mL/min | Pressure bar |
|---|---|---|---|---|
| 0.14 | 60.00 | 40.00 | 0.51 | — |
| 3.70 | 20.00 | 80.00 | 0.51 | — |
| 4.00 | 10.00 | 90.00 | 0.51 | — |
| 4.20 | 60.00 | 40.00 | 0.51 | — |
| 5.00 | 60.00 | 40.00 | 0.51 | — |

General Procedure for Preparation of Compound 5-6

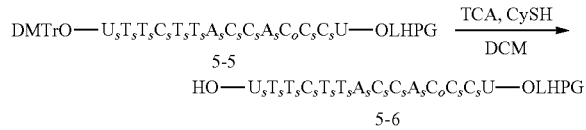

The compound 5-5 (234 g, 30.2 mmol, 1.0 eq), and 3 Å molecular sieve (12.5 g) were added to a round flask, under Ar pressure anhydrous DCM (1500 mL, $H_2O$<50 ppm) was added. The mixture was stirred at 15° C. for 1 hour, and then CySH (10.5 g, 90.5 mmol, 11.1 mL, 3.0 eq) and TCA (59.2 g, 362 mmol, 12.0 eq) was added to the mixture.

The reaction was stirred at 0° C. for 60 min (check reaction by TLC), and then Py (35.8 g, 452 mmol, 36.5 mL, 15.0 eq) was added to the mixture. The mixture stirred at 15° C. for 5 min, The 3 Å molecular sieves were removed by filtration. The DCM solvent was added to $CH_3CN$ 10 L slowly, light yellow solid precipitate out. Remove most of the DCM by rotavap, and the white precipitation was collected and washed with $CH_3CN$ (500 ml×3). Compound 5-6 (210 g, 93.3% yield) was obtained as a light yellow solid.

Figure 8:
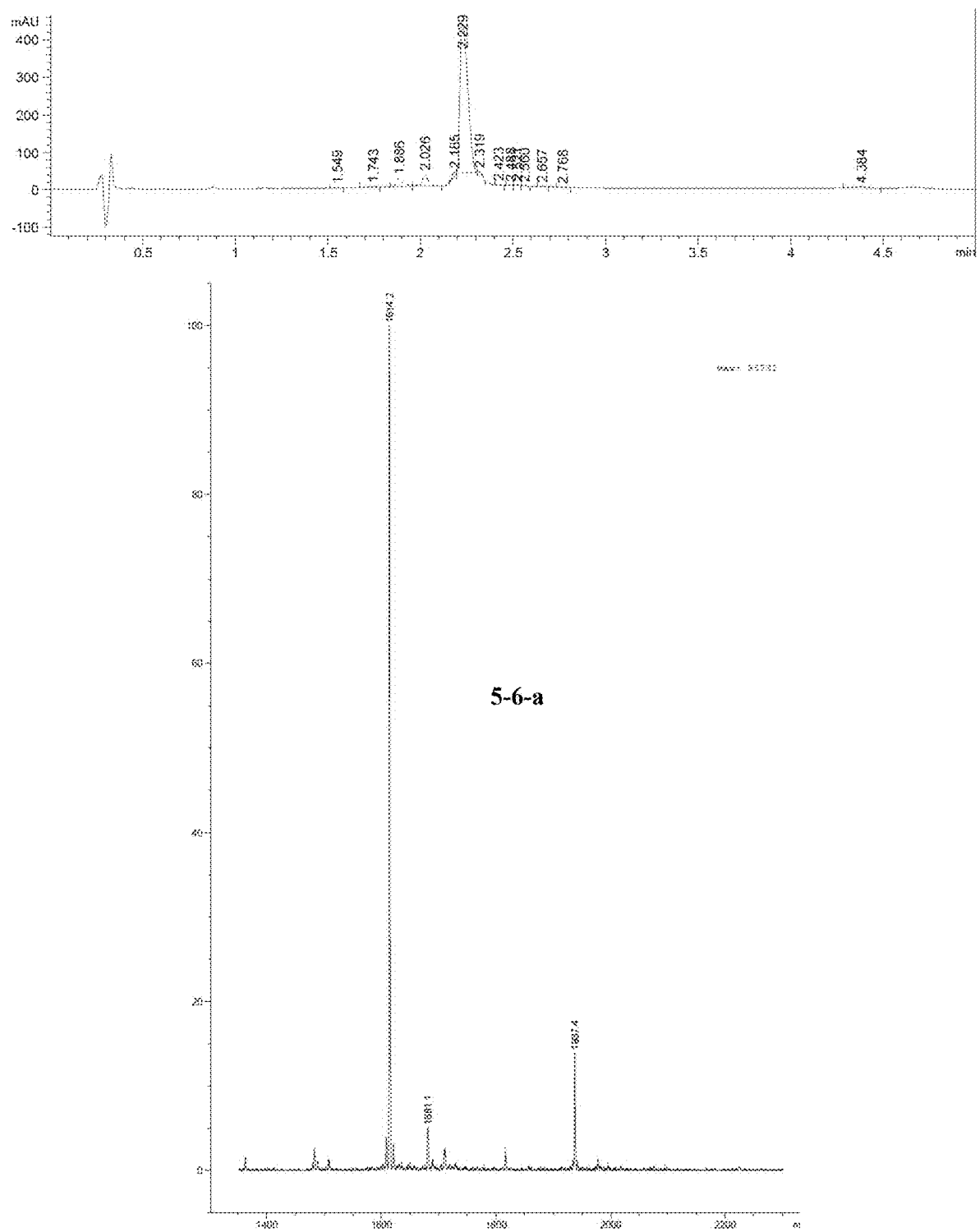
FIG. 8 shows HPLC and MS of compound 5-6-a obtained after ammonolysis of product compound 5-6.

For HPLC and LC-MS analyses of compound 5-6, it was deprotected using ammonolysis (NH3/H2O) procedure similar to the one used for compound 1 ammonolysis disclosed below to obtain 5-6-a (HO-UsTsTsCsTsTsAsCsCsAsCoCsCsU-OH). HPLC and LC-MS of compound 5-6-a is shown in FIG. 8.

HPLC-MS method for 5-6-a

Column: ACQUITY UPLC BEH C18 Column, 1.7 μm, 2.1 mm×50 mm;

Column temperature: 50° C.;

Ionization Mode: API-ES;

mass range from 1350 to 2300;

MS polarity: Negative;

Mobile phase A: 5 mM TBuAA in 10% $CH_3CN$, 1 μm EDTA; Solution B: 5 mM TBuAA in 80% $CH_3CN$, 1 μm EDTA;

Gradient:

| Time min | A % | B % | Flow mL/min | Pressure bar |
|---|---|---|---|---|
| 0.14 | 60.00 | 40.00 | 0.51 | — |
| 3.70 | 20.00 | 80.00 | 0.51 | — |
| 4.00 | 10.00 | 90.00 | 0.51 | — |
| 4.20 | 60.00 | 40.00 | 0.51 | — |
| 5.00 | 60.00 | 40.00 | 0.51 | — |

General Procedure for Preparation of Compound 5-7

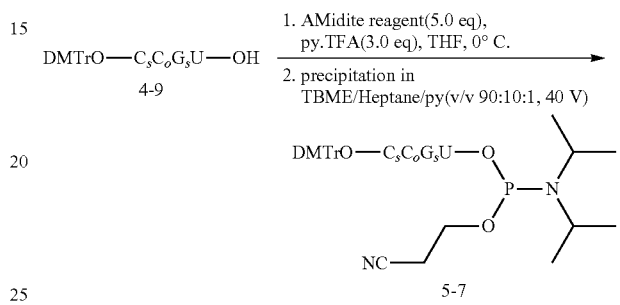

To a 2000 mL round bottom flask, compound 4-9 (130 g, 57.8 mmol, 1.0 eq), Amidite reagent (87.2 g, 289 mmol, 91.9 mL, 5.0 eq), were added in anhydrous THF (520 mL) and cooled down to 0° C. in ice bath for 30 min. Activator Py-TFA (33.5 g, 173 mmol, 34.2 mL, 3.0 eq) was added and then the reaction mixture was stirred at 0° C. for 1 hour. HPLC showed the starting material was consumed completely.

To the solvent TBME/HEPTANE/Py (95/5/1, 15850 mL) was slowly added to the solution of crude product from funnel to performance the precipitation process. This process took about 30 minutes. The pure product was collected as an off-white solid from the previous step, the cake of product was washed with pure TBME (500 mL×3) and dried under high vacuum for 3 hours.

Compound 5-7 (133 g, 93.9% yield) was obtained as a white solid.

General Procedure for Preparation of Compound 1, the Fully Protected ASO 9

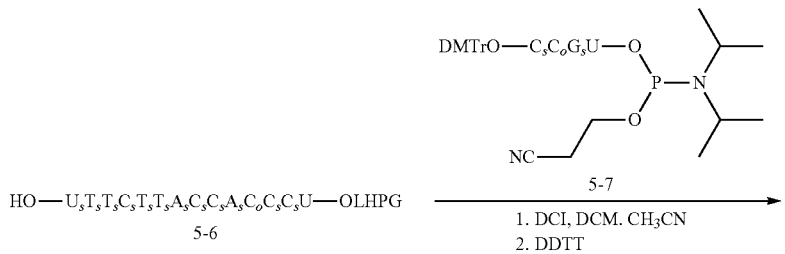

To compound 5-6 (242 g, 32.5 mmol, 1.0 eq), compound 5-7 (135 g, 55.2 eq) and 3 Å molecular sieve (80.0 g) in a round flask were added anhydrous DCM (1200 mL, $H_2O$<50 ppm) and ACN (600 mL, $H_2O$<50 PPM) under Ar pressure. The mixture was stirred at 15° C. for 1 hour, and then DCI (9.60 g, 81.2 mmol, 2.5 eq) was added to the mixture. The mixture was stirred at 15° C. for 1 h. The reaction completion was confirmed with TLC.

After the coupling reaction finished, DDTT (11.3 g, 55.2 mmol, 1.7 eq) was added to the mixture. The reaction mixture was stirred at 15° C. for 10 min. 3 Å molecular sieves were removed by filtration, and the reaction was diluted with 10 L $CH_3CN$ (light yellow solid precipitate out). DCM was removed by rotovap, and the light yellow solid was collected and washed with $CH_3CN$ (500 mL×3). Compound 1 (264 g, 82.8% yield) was obtained as a light yellow solid.

Figure 9:
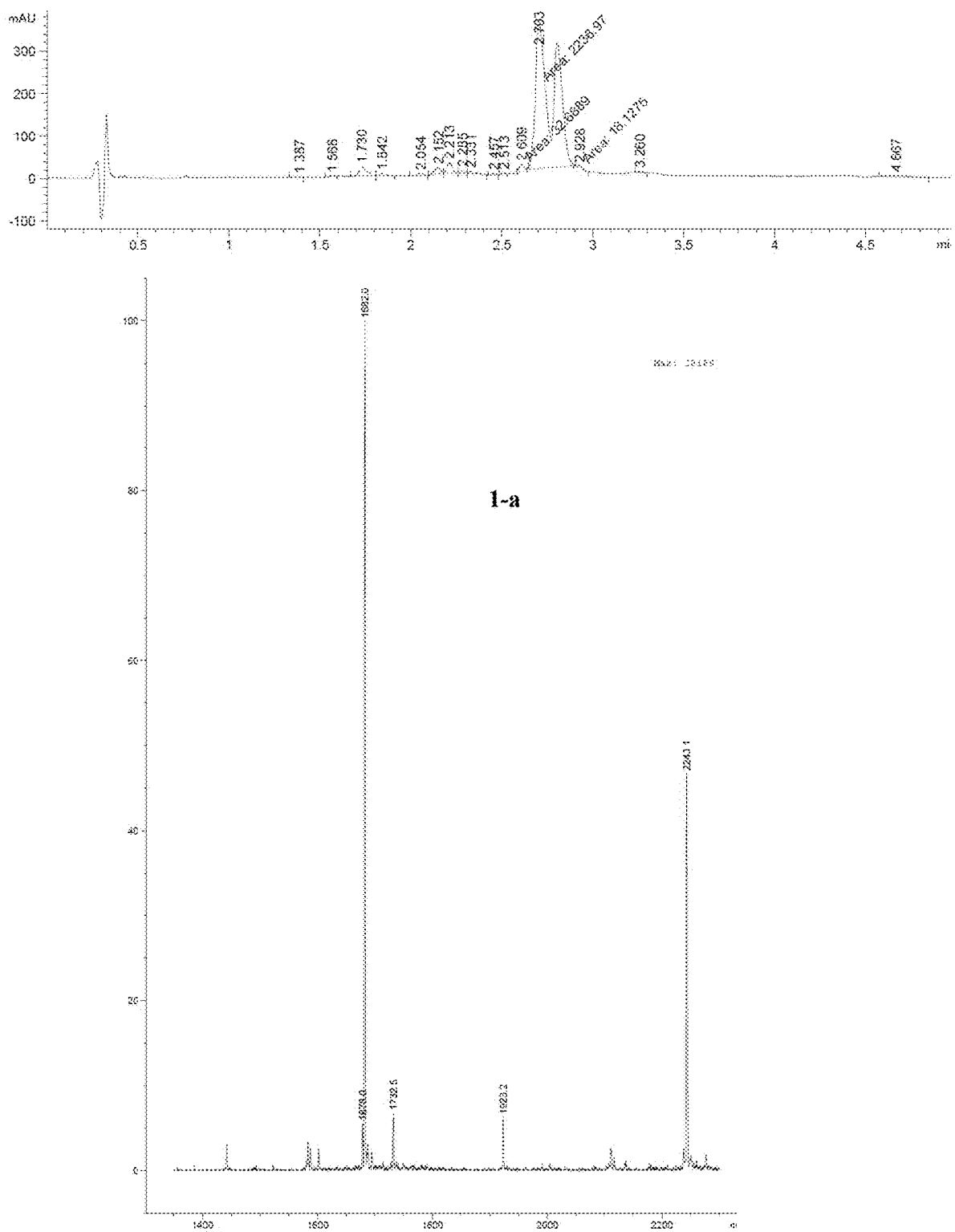
FIG. 9 shows HPLC and MS of compound 1-a obtained after ammonolysis of product compound 1.

HPLC and LC-MS analyses of compound 1, it was deprotected using ammonolysis ($NH_3/H_2O$) procedure described below to obtain 1-a (DMTrO-CsCoGsUsUsTsT-sCsTsTsAsCsCsAsCoCsCsU-OH). HPLC and LC-MS for compound 1-a is shown in FIG. 9.

HPLC-MS method for 1-a

Column: ACQUITY UPLC BEH C18 Column, 1.7 μm, 2.1 mm×50 mm;

Column temperature: 50° C.;

Ionization Mode: API-ES;

mass range from 1350 to 2300;

MS polarity: Negative;

Mobile phase A: 5 mM TBuAA in 10% $CH_3CN$, 1 μm EDTA; Solution B: 5 mM TBuAA in 80% $CH_3CN$, 1 μm EDTA;

Gradient:

| Time min | A % | B % | Flow mL/min | Pressure bar |
|---|---|---|---|---|
| 0.14 | 60.00 | 40.00 | 0.51 | — |
| 3.70 | 20.00 | 80.00 | 0.51 | — |
| 4.00 | 10.00 | 90.00 | 0.51 | — |
| 4.20 | 60.00 | 40.00 | 0.51 | — |
| 5.00 | 60.00 | 40.00 | 0.51 | — |

Figure 34:
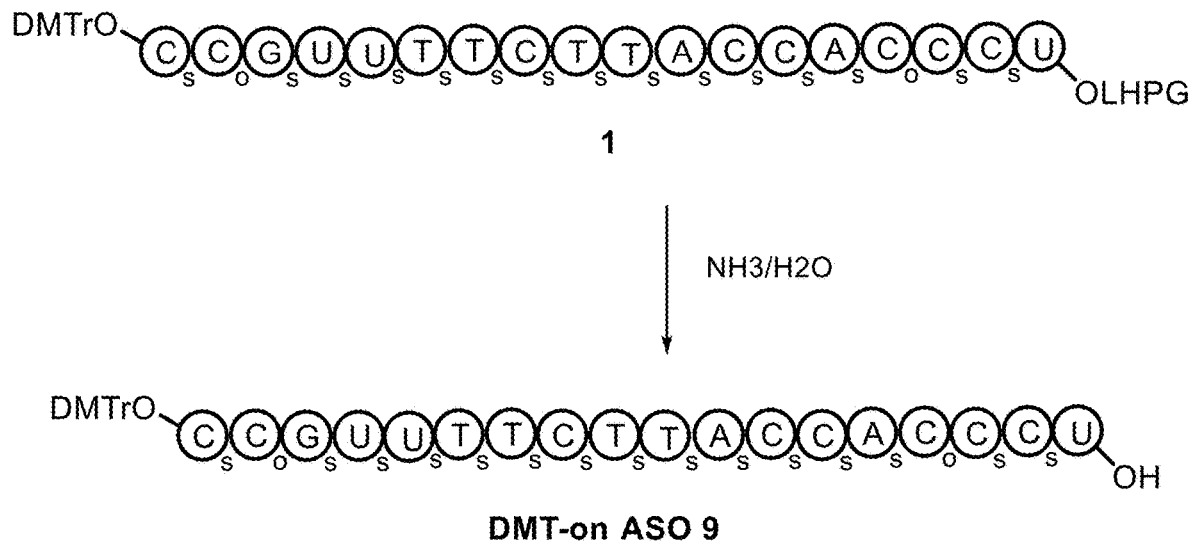
FIG. 34 shows a scheme for the deprotection and ammonolysis of Compound 1, full protected ASO 9.

Deprotection and Ammonolysis of Compound 1, Fully Protected ASO 9 (FIG. 34)

To a 1-L flask was added compound 1 (64 g) and $CH_3CN:Et_3N$ (640 ml, v/v). The mixture was stirred at 25° C. for two hours then solvents were removed by Rotovap. To the flask was added 500 ml $NH_4OH$ (~30% wt) and the mixture was stirred at 25° C. for ~30 min. The resultant solution was transferred into a 1-L glass pressure flask and the mixture was heated to 65° C. for 5 hours. The mixture was cooled to ambient temperature for downstream purification. ASO 9 Purification Process:

The DMT-on ASO 9 from ammonolysis (2L) was diluted with 1111 mM ammonium sulfate solution (18L) to final ammonium sulfate concentration ~1000 mM. The suspension was then filtered through a depth filter, which was wet, flushed, and equilibrated with 3 bed volumes of a solution (1000 mM ammonium sulfate, 50 mM tris, pH 8.5).

For the hydrophobic interaction chromatography (HIC) step, a 20 cm bed height (BH)×14 cm inner diameter (ID) HIC column was equilibrated with 4 column volumes (CVs) of equilibration buffer (1000 mM ammonium sulfate, 50 mM tris, pH 8.5). The filtrate from the depth filter was loaded onto the column. The column was chased with 4 CVs of buffer (1000 mM ammonium sulfate, 50 mM tris, pH 8.5), washed with buffer (800 mM ammonium sulfate, 50 mM tris, pH 8.5) at 100 cm/hr until UV gate (2 mm flowcell) hits 0.5 AU. Once the UV gate hit 0.5 AU, the column was washed with 2 more CVs of the same buffer (800 mM ammonium sulfate, 50 mM tris, pH 8.5). For the wash step, the flow rate was 100 cm/hr. The column was eluted with 8 CVs of buffer (50 mM ammonium sulfate, 50 mM tris, pH 8.5) to provide the DMT-on ASO 9. The column was stripped with 4 CVs of deionized water. The column was cleaned with 3 CVs of 1N sodium hydroxide and stored in 0.1N sodium hydroxide. The HIC process was run at 200 cm/hr with the exception of the wash which was run at 100 cm/hr.

The HIC eluate (~9 L) containing DMT-on ASO 9 was cooled to 10° C. and a solution (0.9 L) of 25% (w/w) citric acid was added to make pH of the mixture 2.7. This mixture was stirred at 10° C. for 4.5 hours and 5N sodium hydroxide (0.8 L) was added to make pH 8.5. The mixture was then filtered to remove DMT-OH byproduct using a 0.22 μm sterilizing filter. The filtrate was then purified by anion exchange chromatography.

Figure 12:
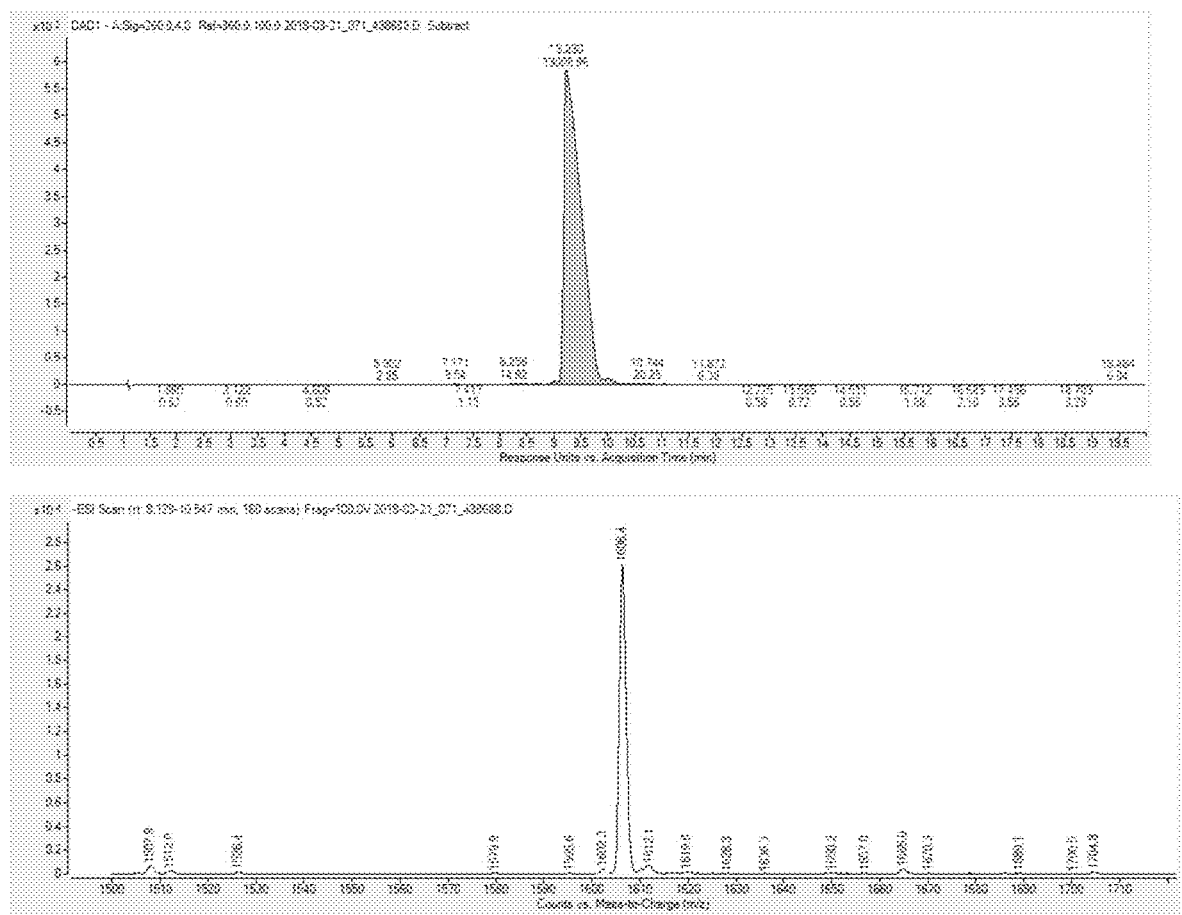
FIG. 12 shows HPLC-MS of product ASO 9.

For the anion exchange chromatography (AEX), a 15 cm BH×14 cm ID AEX column was charged with 2 CVs of a high salt buffer solution (2000 mM sodium chloride, 250 mM tris, pH 8.5) and equilibrated with 4 CVs of equilibration buffer solution (100 mM sodium chloride, 50 mM tris, pH 8.5). The filtrate from the detritylation step was diluted with water to the conductivity of ~20 mS and loaded to the column. The column was washed with buffer solution (300 mM sodium chloride, 50 mM tris, pH 8.5) until UV gate (2 mm flowcell) reaches 0.4 AU. The column was washed continuously with 4 more CVs of the same buffer (300 mM sodium chloride, 50 mM tris, pH 8.5). The column was eluted with 7 CVs of a buffer (525 mM sodium chloride, 50 mM tris, pH 8.5) to provide the ASO 9 solution. The column was stripped with 4 CVs of buffer (2000 mM sodium chloride, 250 mM tris, pH 8.5) and then cleaned with 3 CVs of 1N sodium hydroxide and stored in 0.1N sodium hydroxide. The AEX process was run at 200 cm/hr. HPLC-MS for ASO 9 is shown in FIG. 12.

Example 2. Synthesis of ASO Using 5' End to 3'End Elongation Strategy (10-mer)
1. General Synthesis of 5' P Amidite Fragment (5-mer)
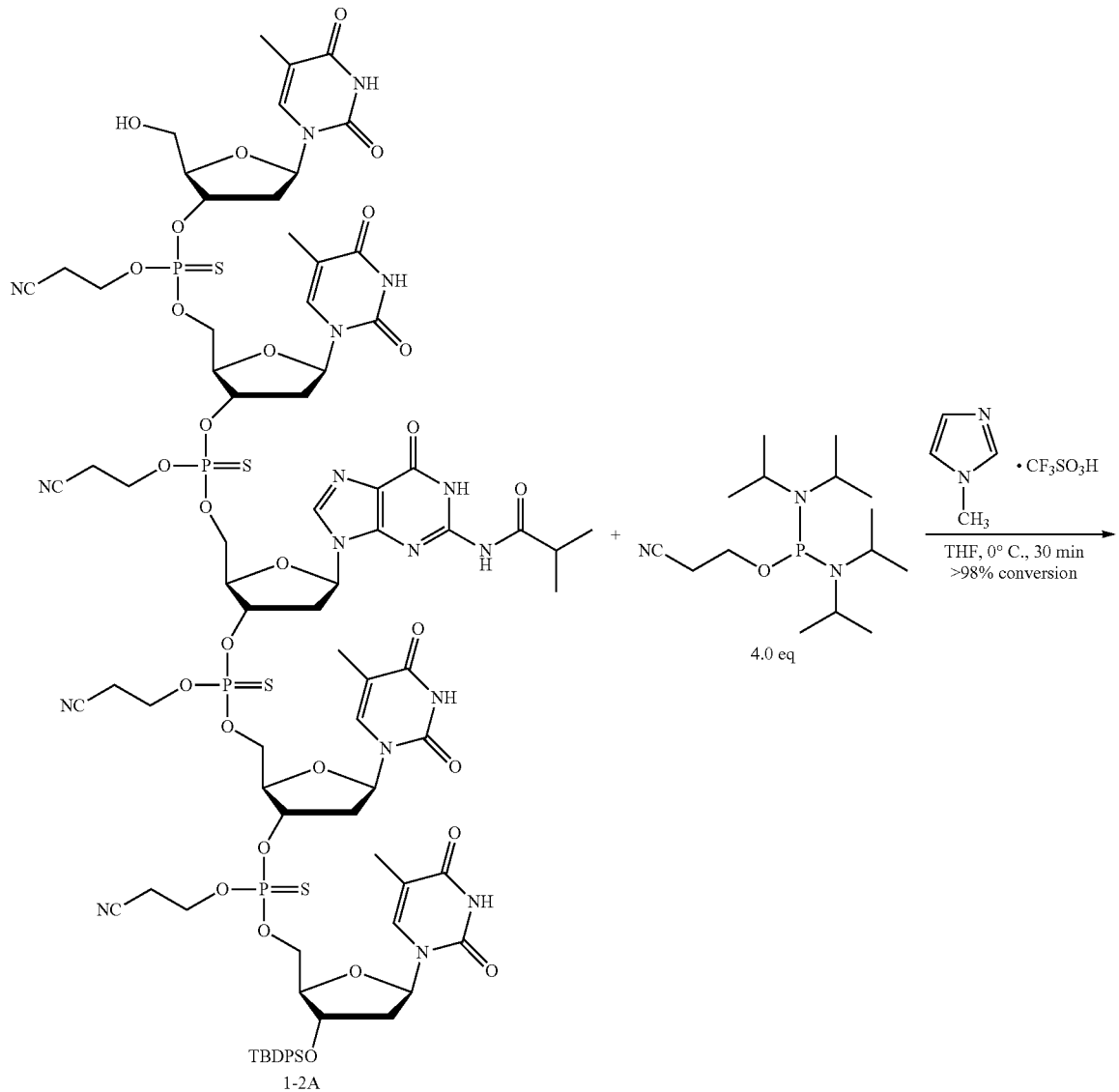

Figure 13:
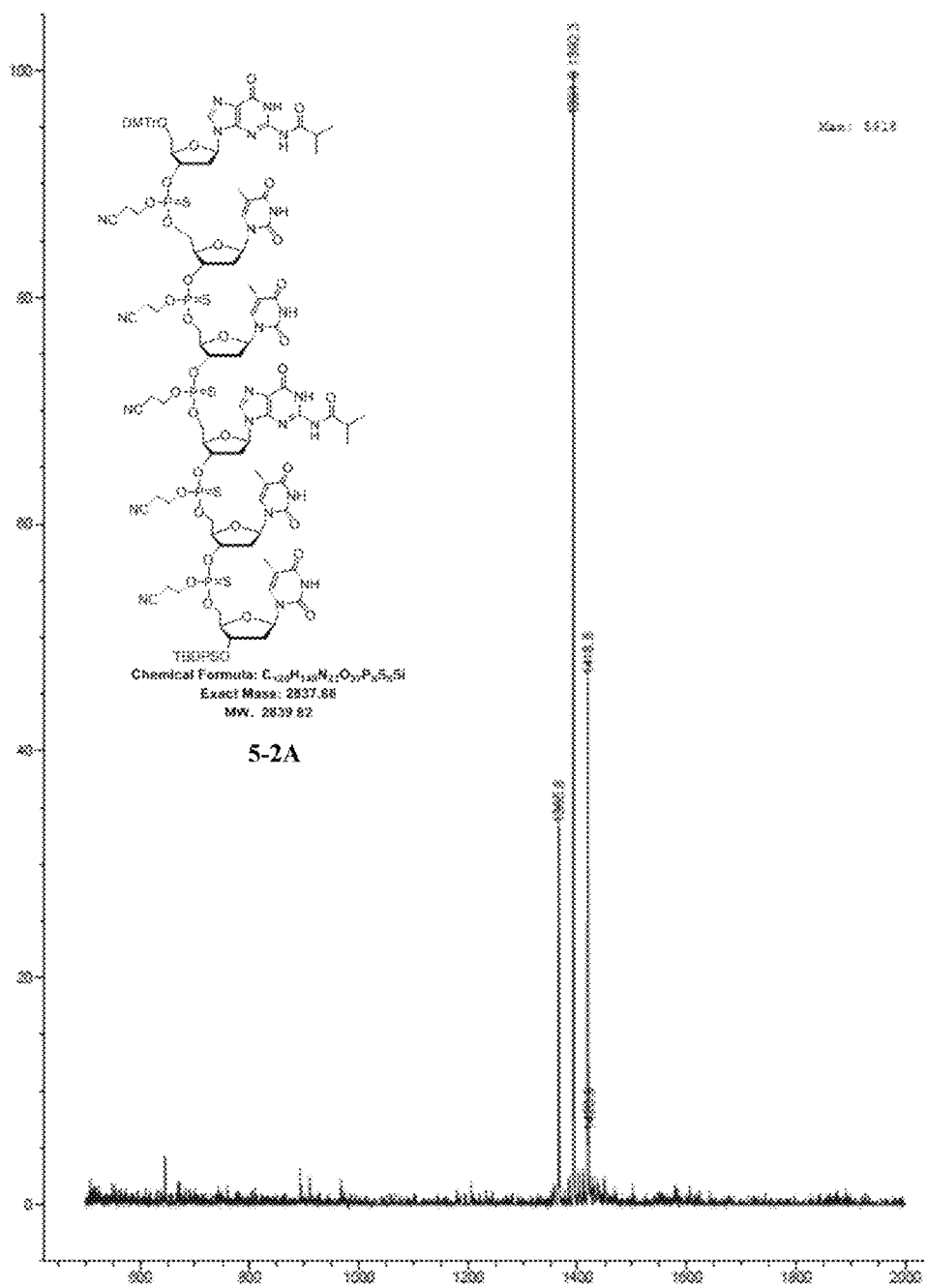
FIG. 13 shows MS of 6-mer DMT-dG-dT-dT-dG-dT-dT-OTBDPS.

-continued
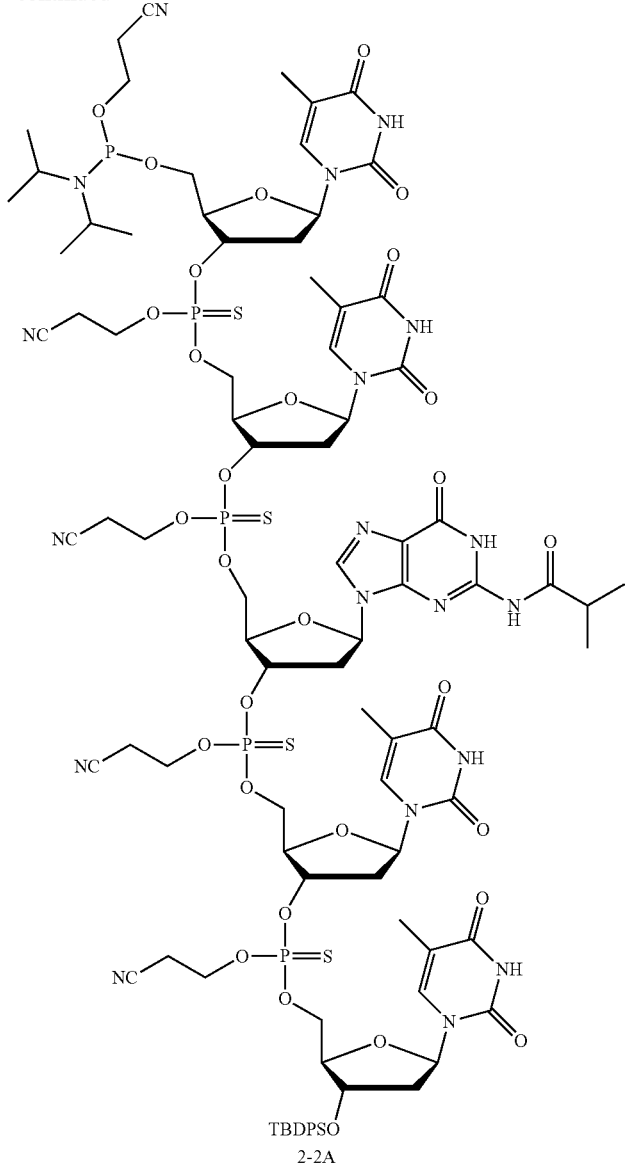
2-2A
Starting with 1-2A and phorphoramidite, compound 2-2A was obtained in >98% yield using similar procedure as described above for the synthesis of compound 1-8a.
2. Synthesis of an ASO 6-mer
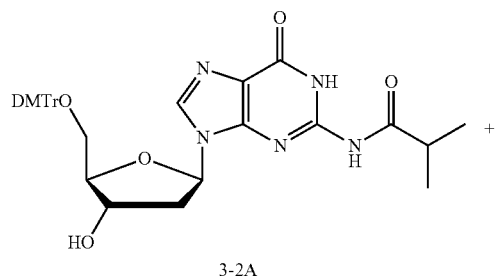
3-2A -continued
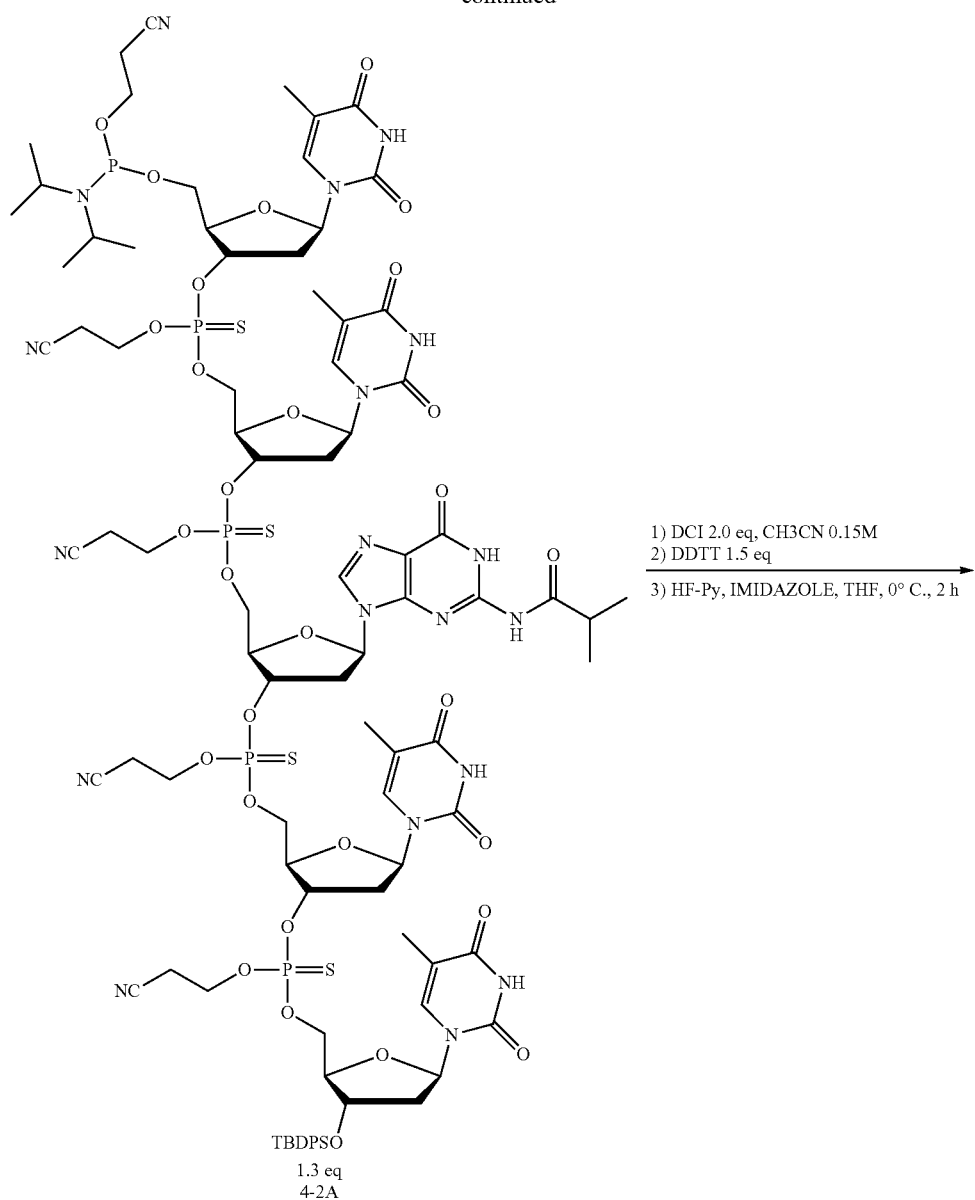
1) DCI 2.0 eq, CH3CN 0.15M
2) DDTT 1.5 eq
3) HF-Py, IMIDAZOLE, THF, 0° C., 2 h
1.3 eq
4-2A -continued
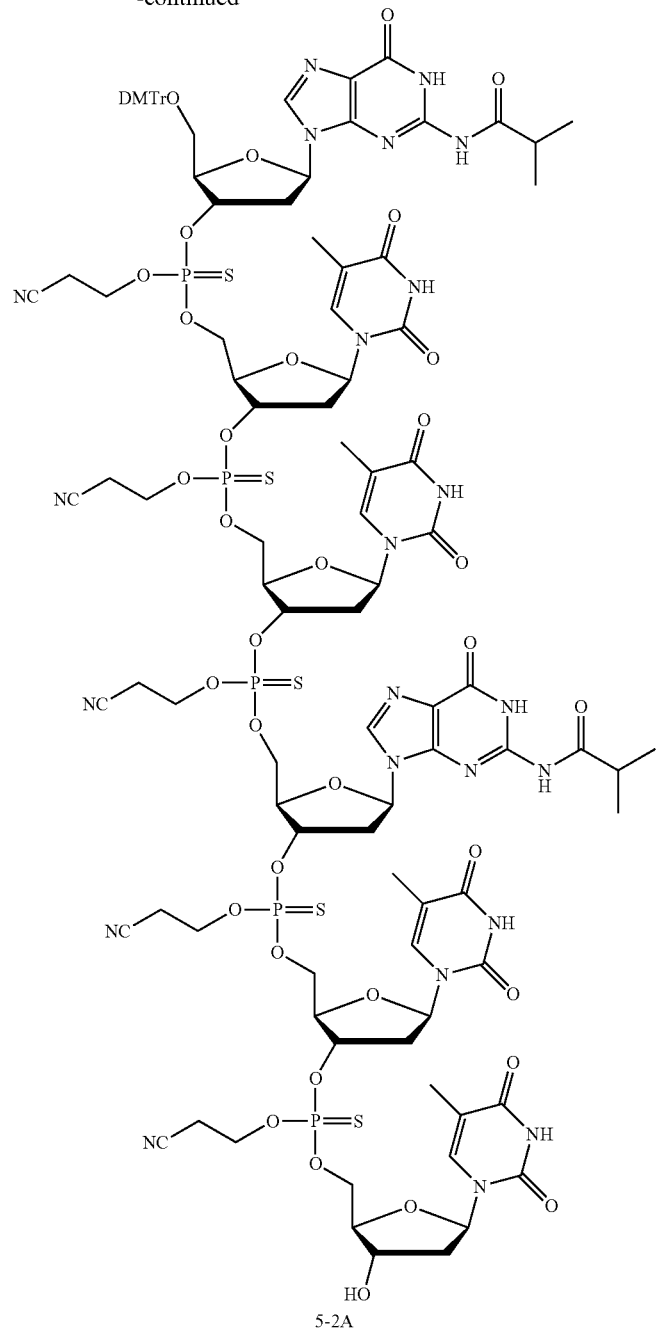
5-2A
Compound 4-2A was coupled with compound 3-2A to yield a 6-mer (compound 5-2A) in >98% yield, using a similar procedure as described above for the synthesis of fragment 1-9 followed by desilylation procedure described in step 3 of 4-9 synthesis. The mass spectrum of ASO 6-mer before desilylation is shown in FIG. 13.

3. Synthesis of an ASO 10-mer
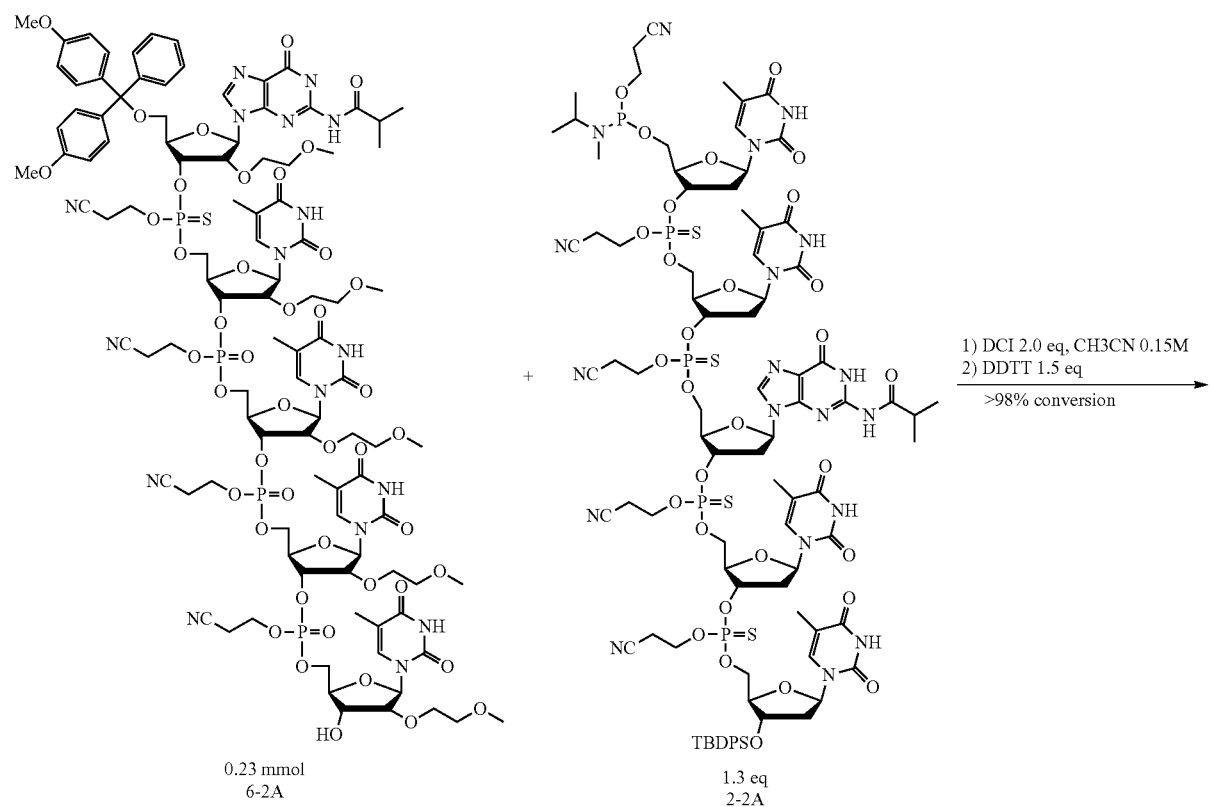

Figure 14:
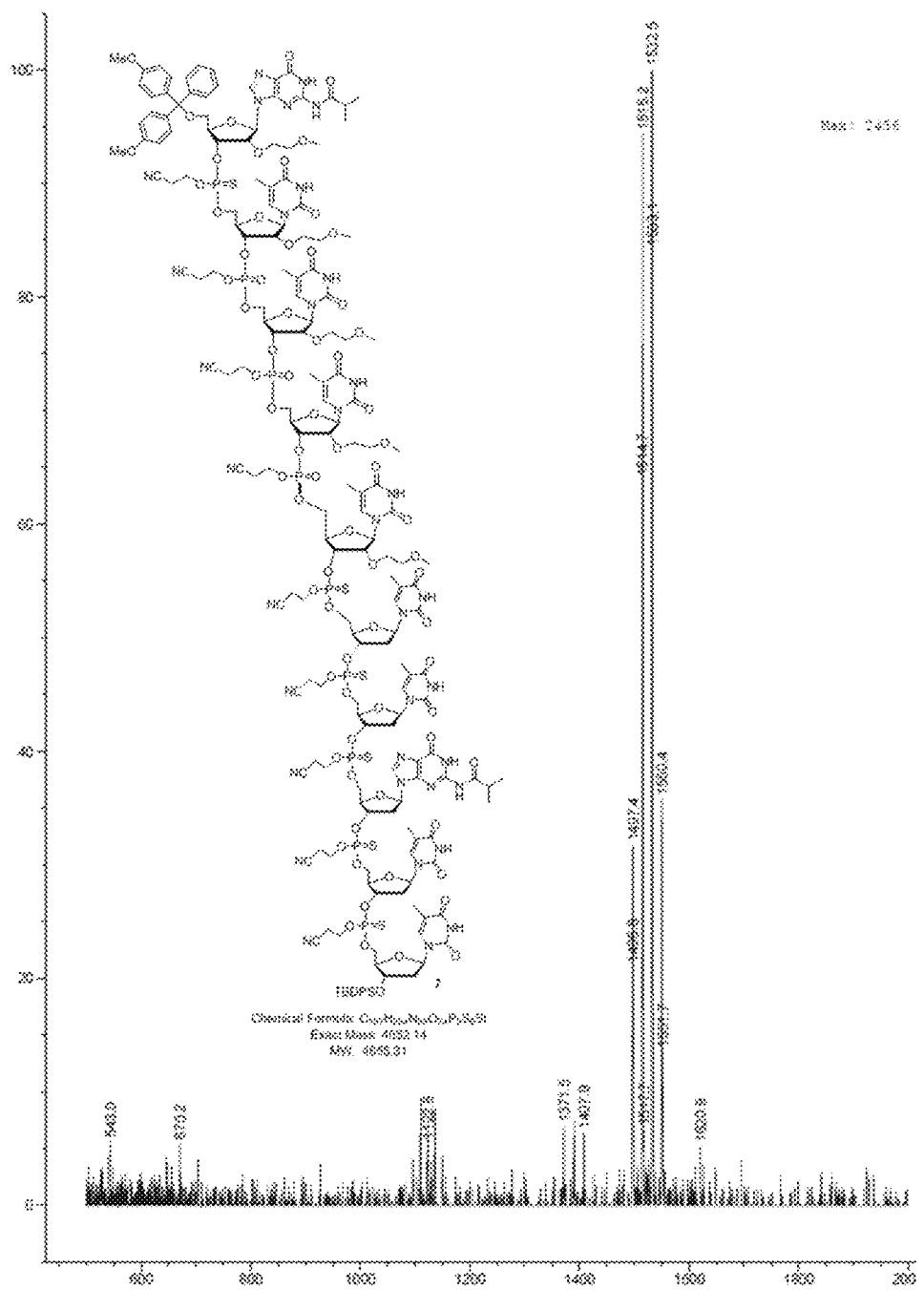
FIG. 14 shows MS of 10-mer DMT-Moe G-Moe U-Moe U-Moe U-Moe U-dT-dT-dG-dT-dT-OTBDPS.

-continued
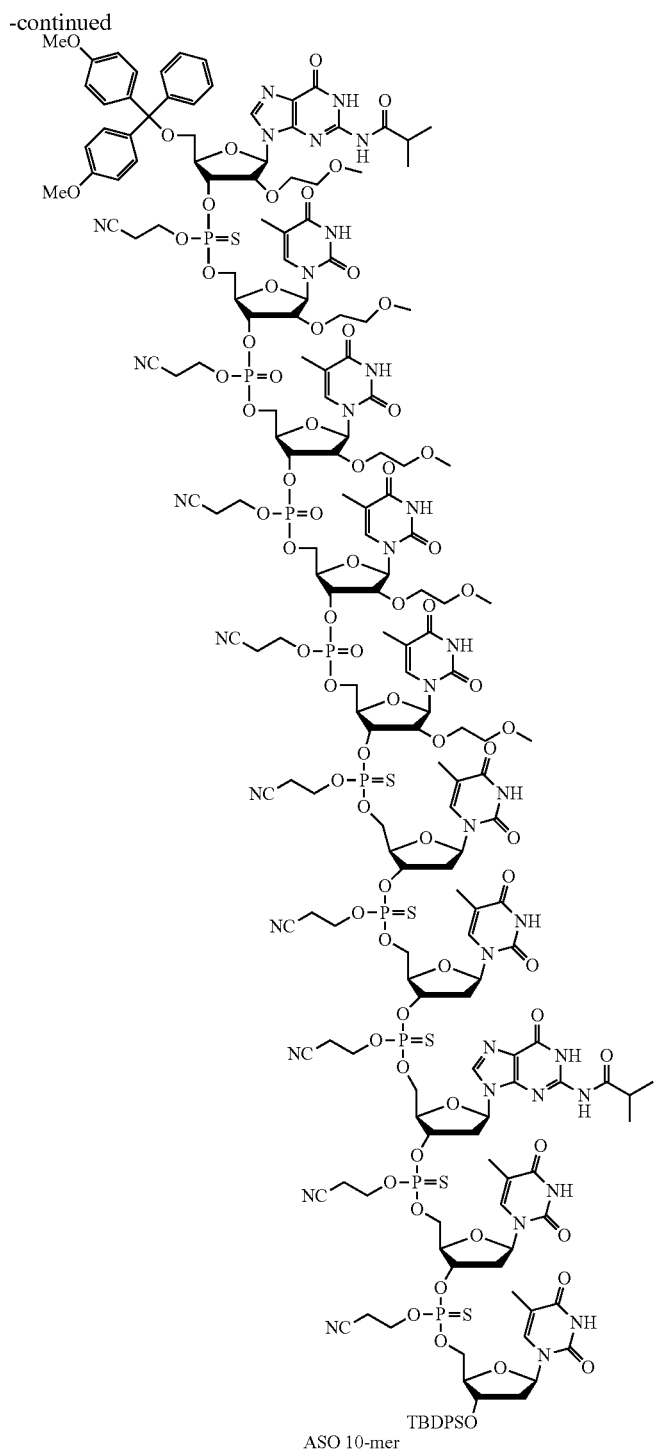
ASO 10-mer
The ASO 5-mer 6-2A was coupled with 5-mer fragment 2-2A to yield ASO 10-mer in >98% yield, using a similar procedure as described above for the synthesis of fragment 1-9. The mass spectrum of ASO 10-mer is shown in FIG. 14.

4. Convergent Synthesis of ASO 15-mer 5'-ACoAGATAT-TTTTGTT-3'-OH
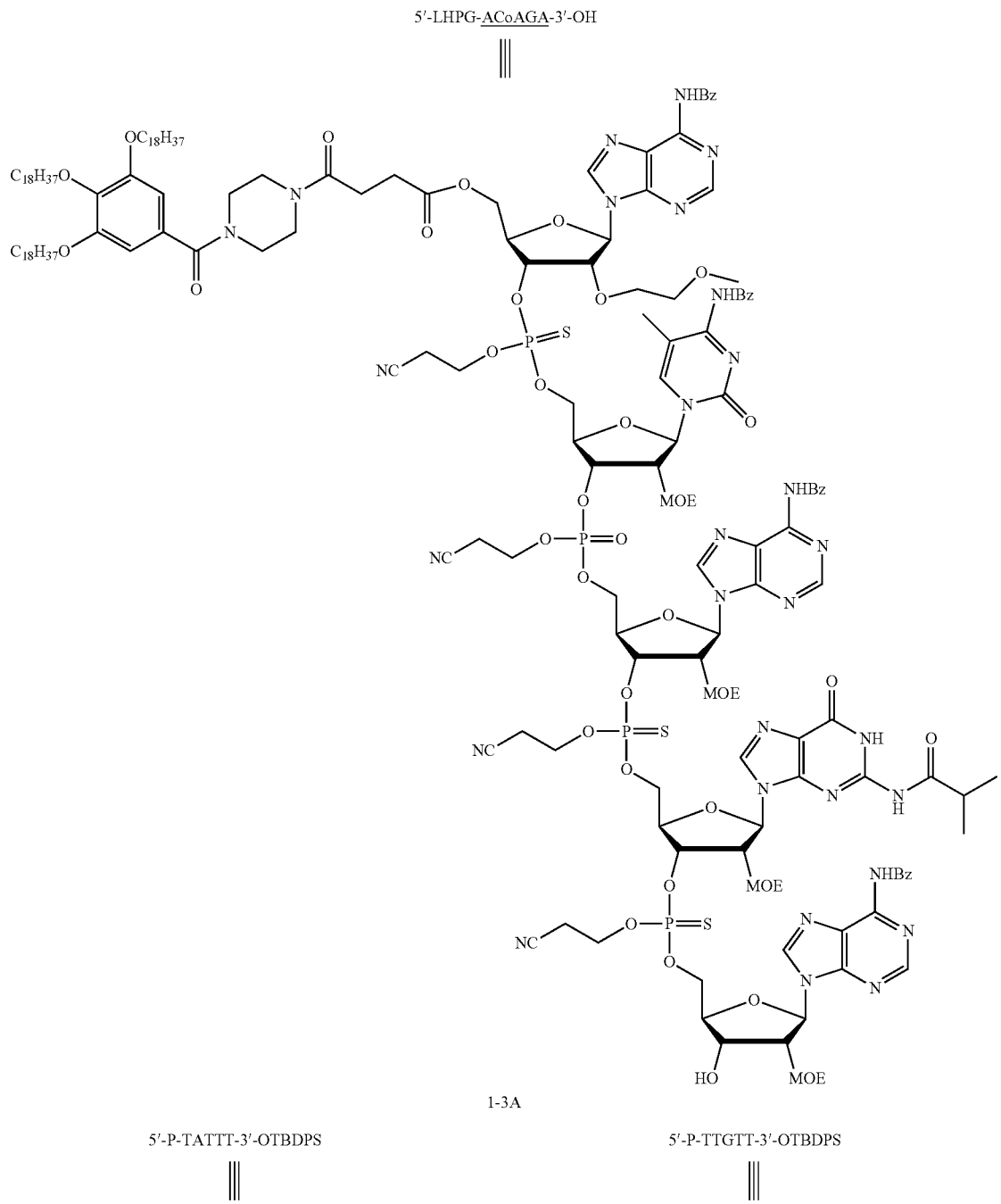

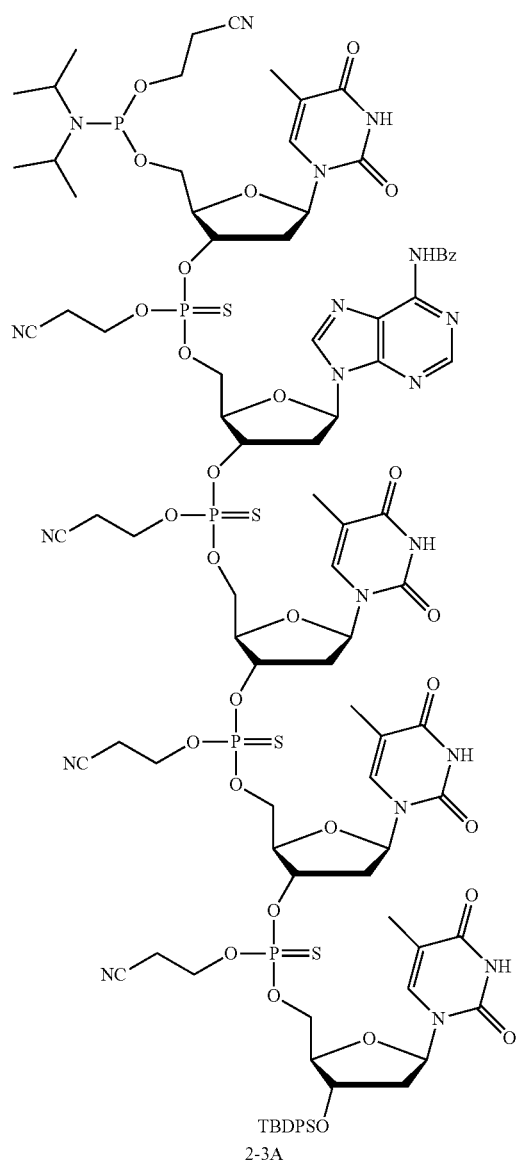

2-3A

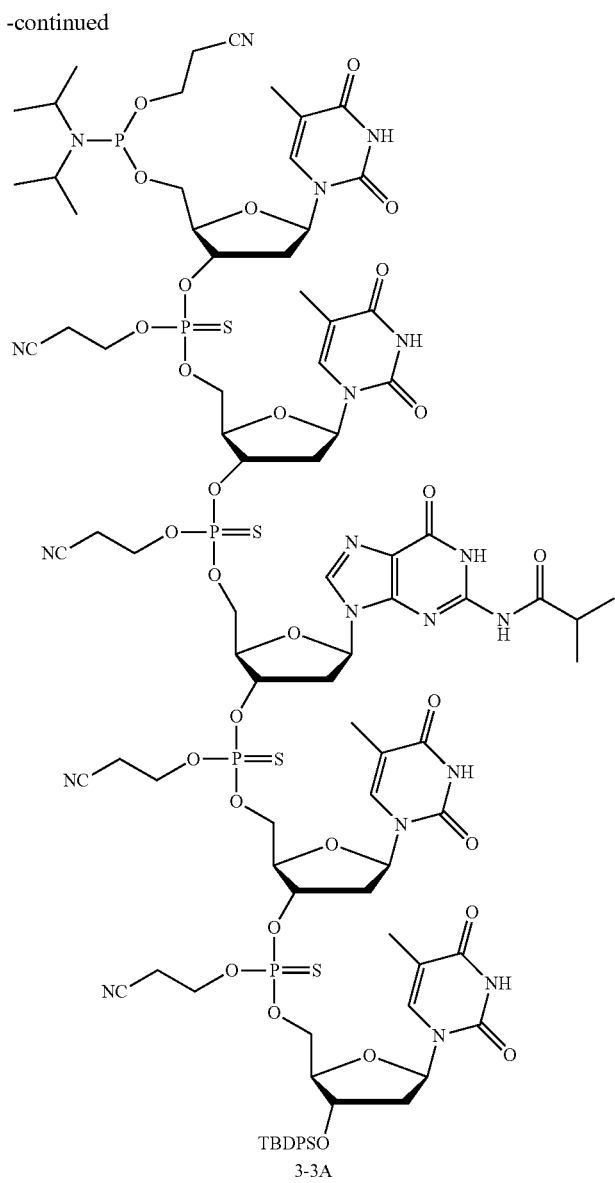

3-3A

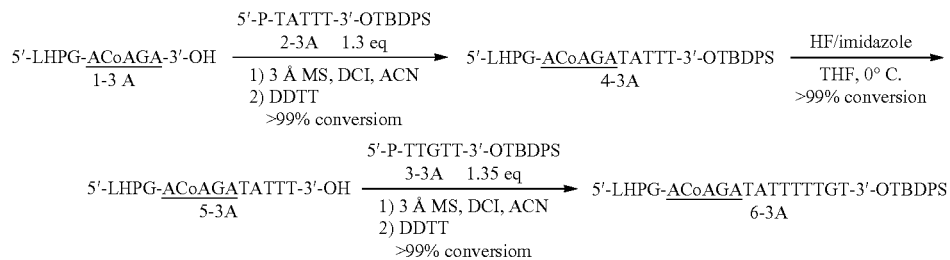

Underlined letters: MOE nucleotides, o is oxidation (phosphodiester linkage), All other phosphorus atoms are thiolated (phosphorothioate).

The ASO 15-mer was synthesized based on a convergent synthesis method shown in the scheme above using similar procedures as described above. The three fragments used in the convergent synthesis are: 5'-LHPG-ACoAGA-3'-OH (fragment 1); 5'-P-TATTT-3'-OTBDPS (fragment 2); and 5'-P-TTGTT-3'-OTBDPS (fragment 3).

1) Synthesis of Fragment 1: 5'-LHPG-ACoAGA-3'-OH(1-3AL)
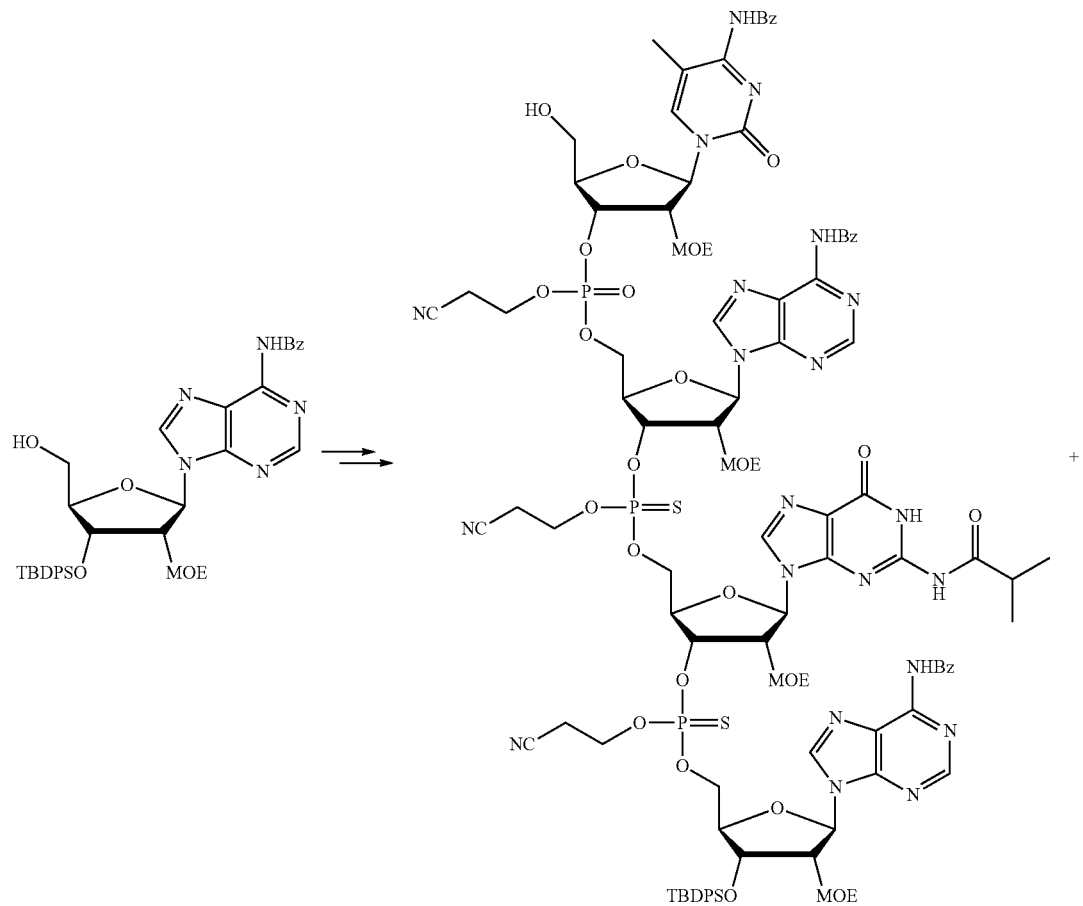

-continued
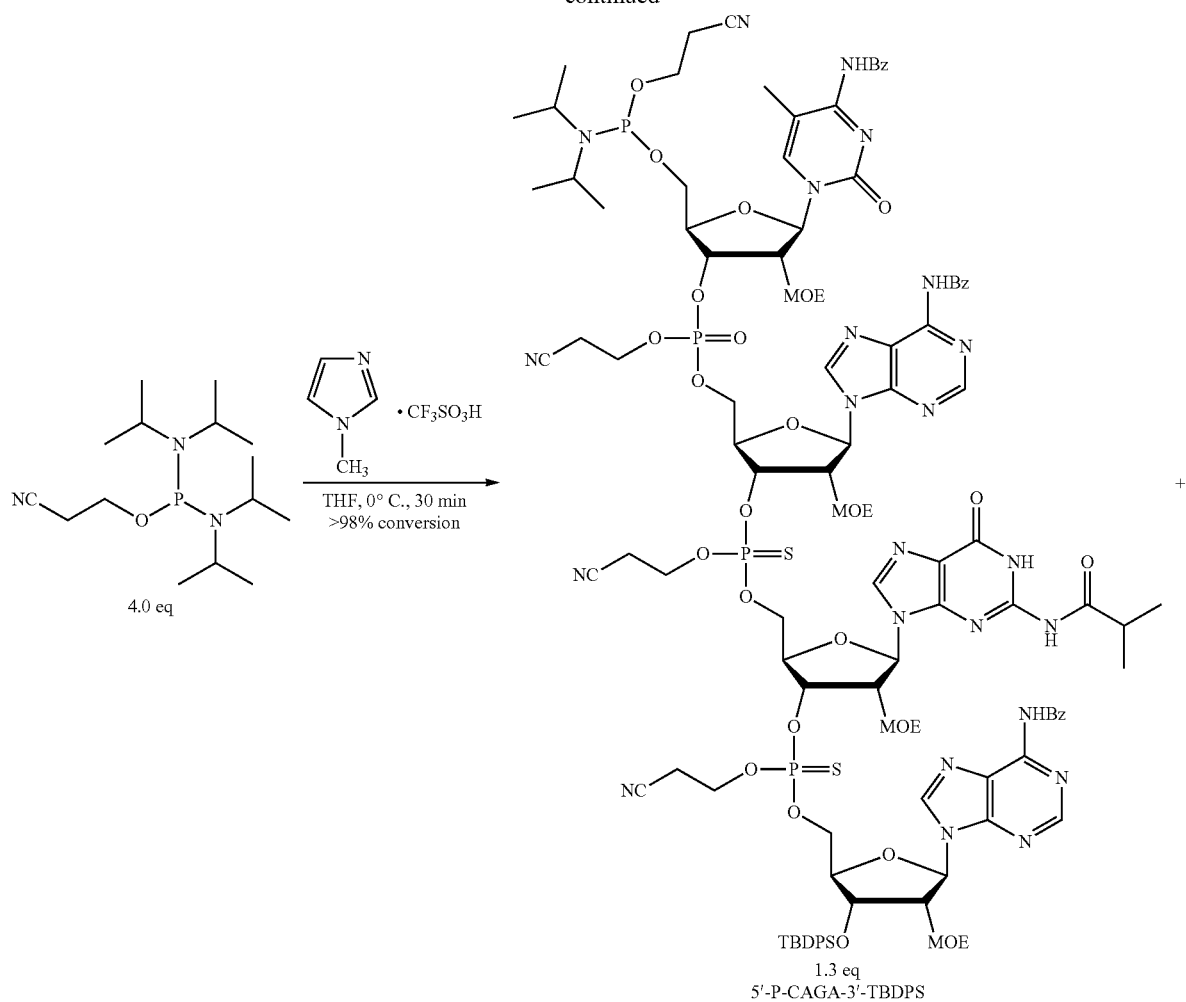
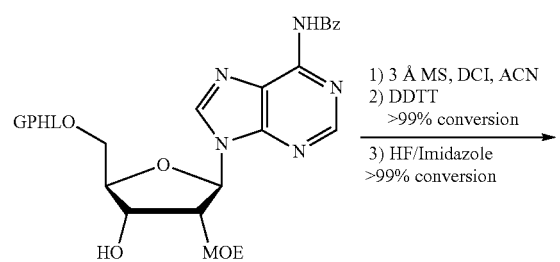

Figure 15:
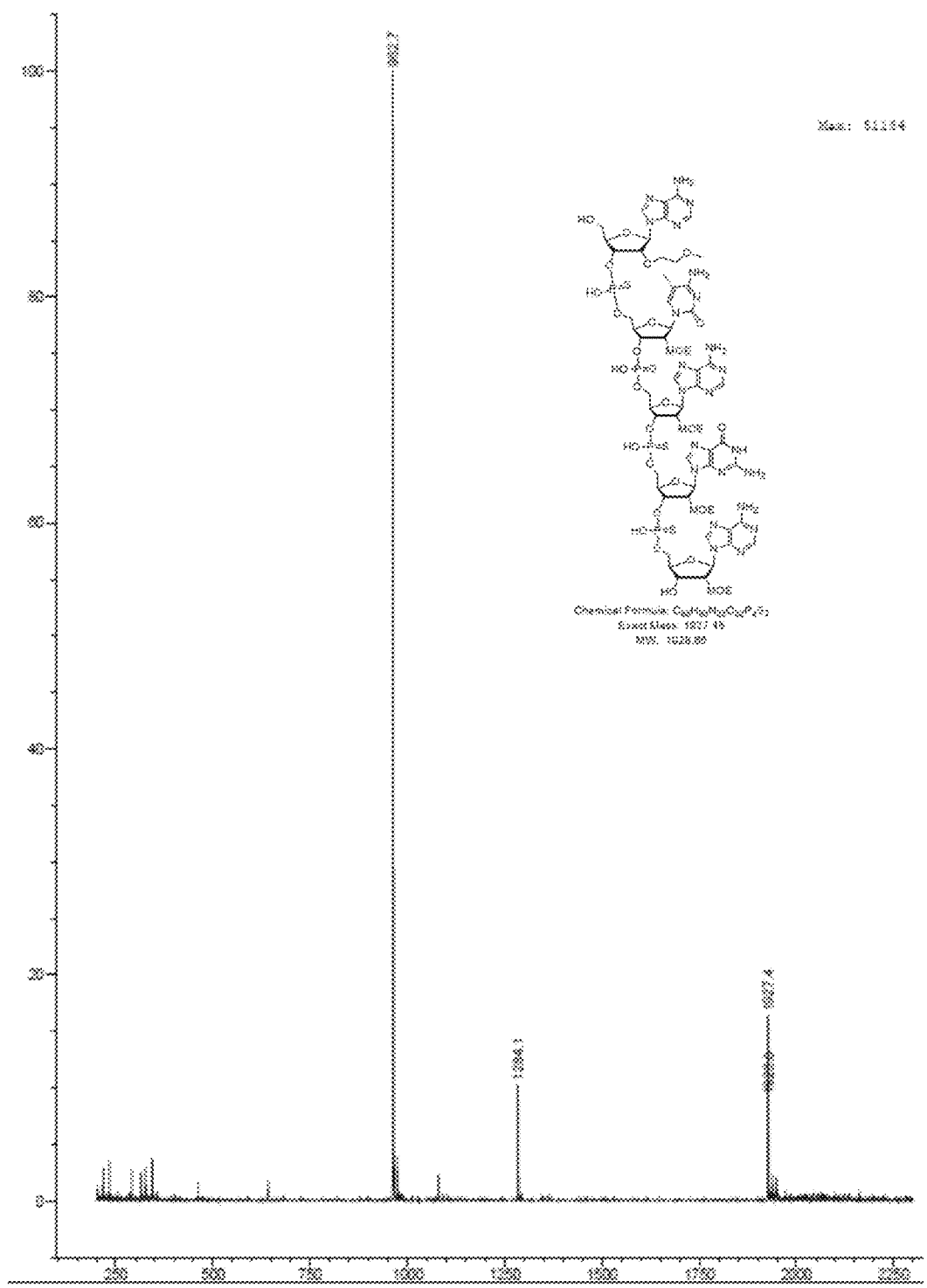
FIG. 15 shows MS of compound 1-3A-H.

-continued
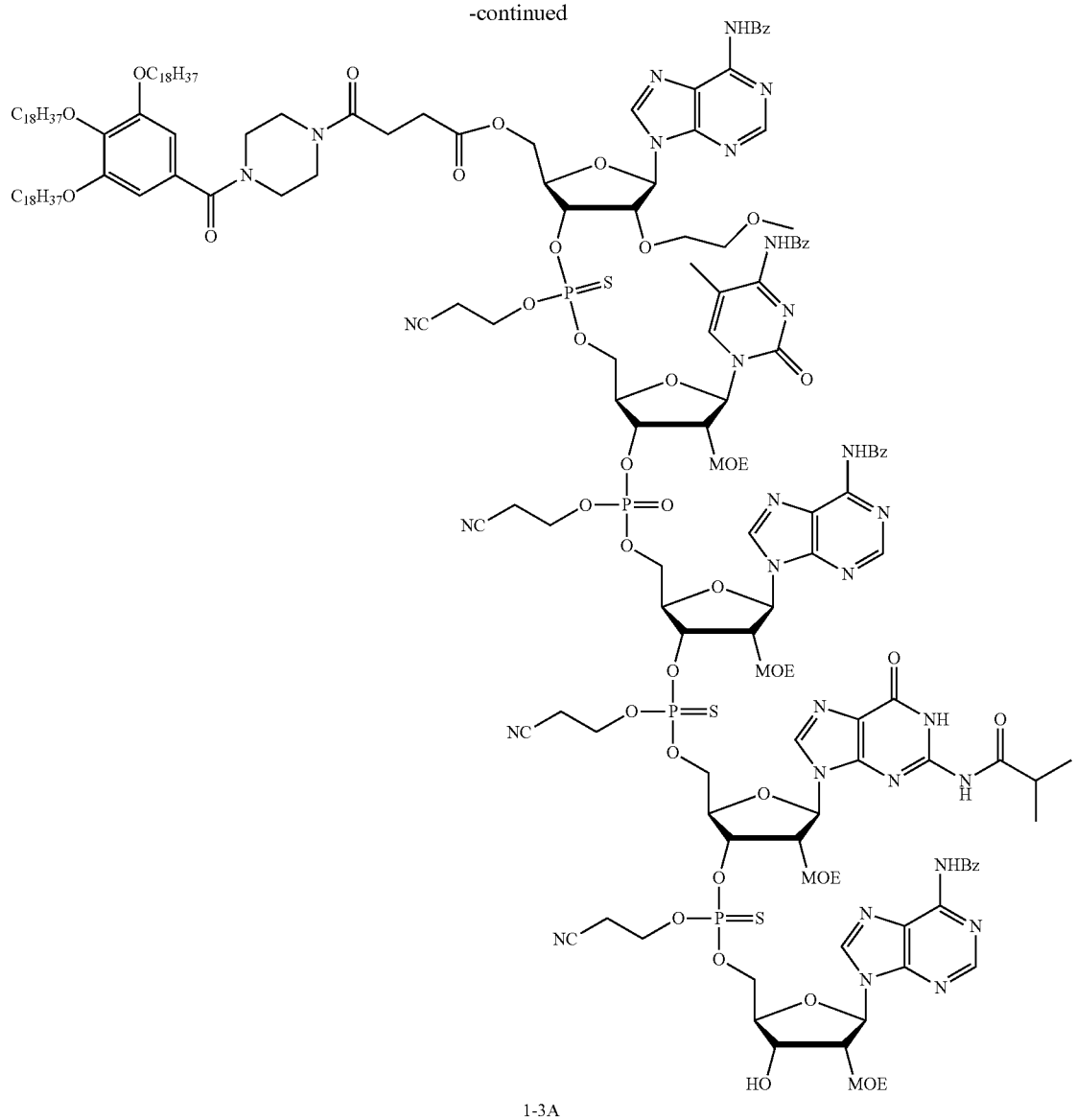
1-3A
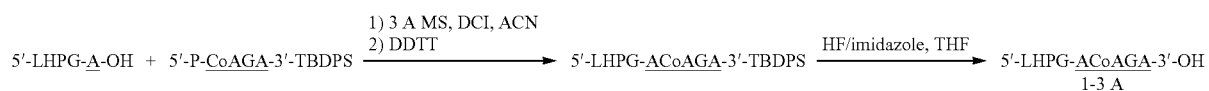
Fragment 1 (compound 1-3A) was synthesized as shown in the Scheme above using similar procedures as described above. Mass spectrum for deprotected fragment 1 (compound 1-3A-H) is shown in FIG. 15.

211 212
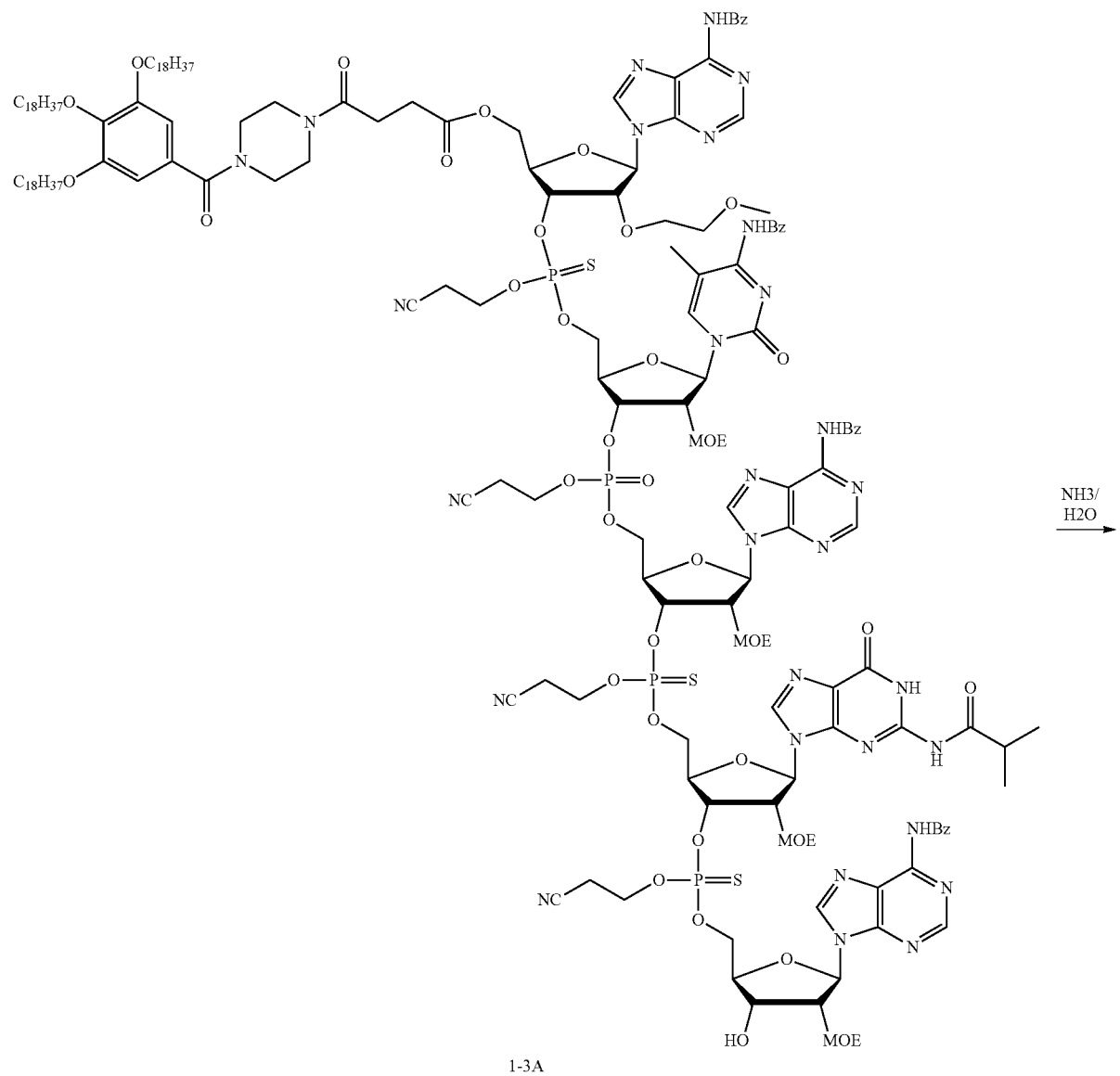
1-3A
$\xrightarrow{\text{NH3/ H2O}}$

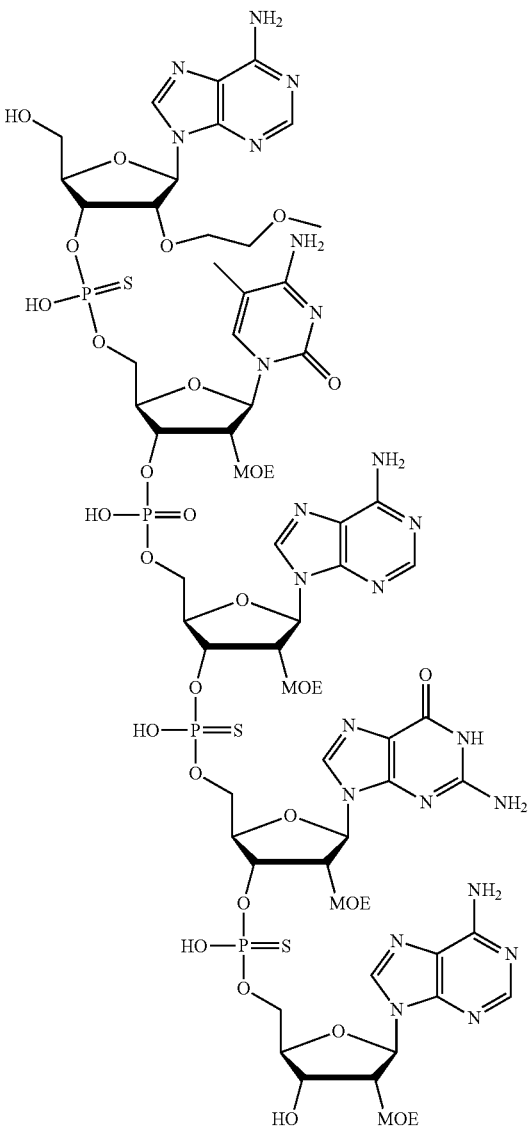

Chemical Formula: $C_{65}H_{93}N_{23}O_{32}P_4S_3$
Exact Mass: 1927.45
mw. 1928.66
1-3A-H 2) Synthesis of Fragment 2: 5'-P-TAT7T-3'-OTBDPS (compound 2-3A)

Fragment 2 was synthesized using similar procedure as described above for the 2-2A synthesis.

3) Synthesis of Fragment 3: 5'-P-TTGTT-3'-OTBDPS (compound 3-3A)

Fragment 3 was also synthesized using similar procedure as described above for the 2-2A synthesis.

Figure 16:
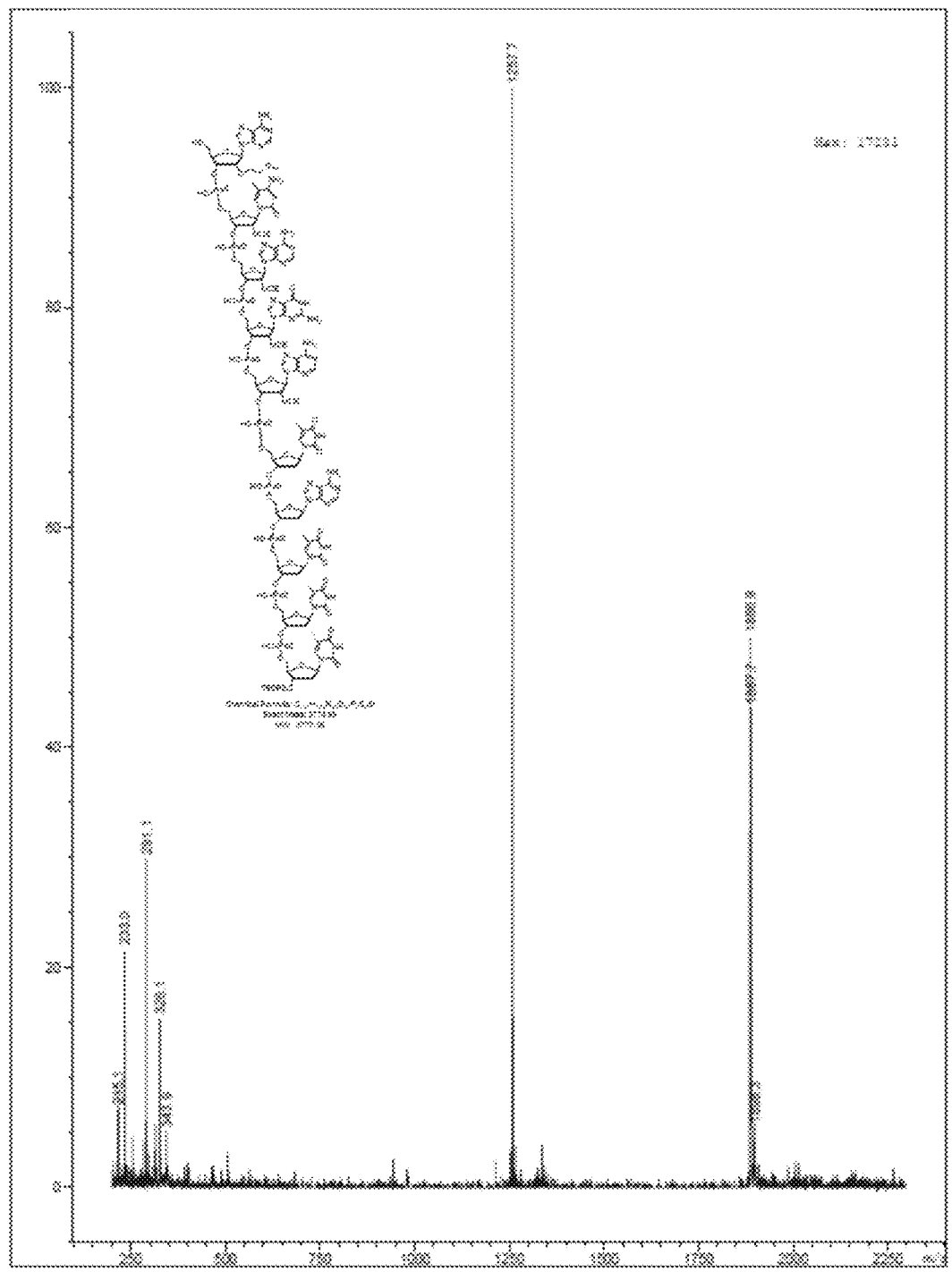
FIG. 16 shows MS of compound 4-3A-H.
Figure 17:
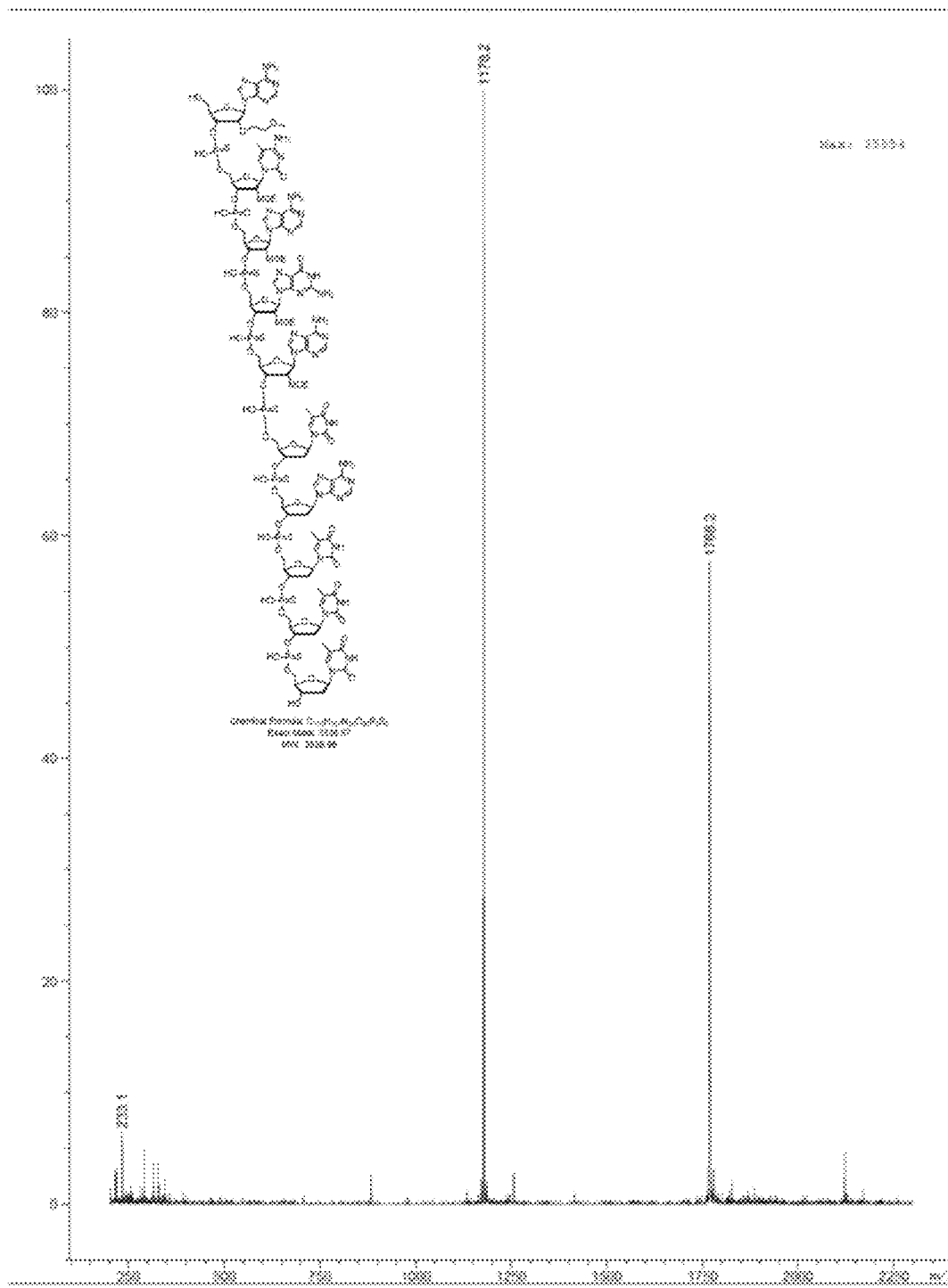
FIG. 17 shows MS of compound 5-3A-H.

4) Convergent Synthesis of ASO 15-mer:

The ASO 15-mer was synthesized using the liquid phase convergent synthesis method described herein. Fragment 1 and fragment 2 were coupled, followed by sulfurization to form compound 4-3A. Desilylation of compound 4-3A to remove 3'-TBDPS group yielded compound 5-3A, which was then coupled with fragment 3, followed by sulfurization to yield ASO 15-mer 6-3A. The formation of 4-3A and 5-3A was confirmed by the LC-MS analysis of the corresponding deprotected product 4-3A-H and 5-3A-H, which was formed by treating the compound 4-3A or 5-3A with $NH_3/H_2O$. Mass spectrum of compounds 4-3A-H and 5-3A-H are shown in FIG. 16 and FIG. 17, respectively. The ammonolysis reactions of compounds 4-3A and 5-3A are shown below:

215 216
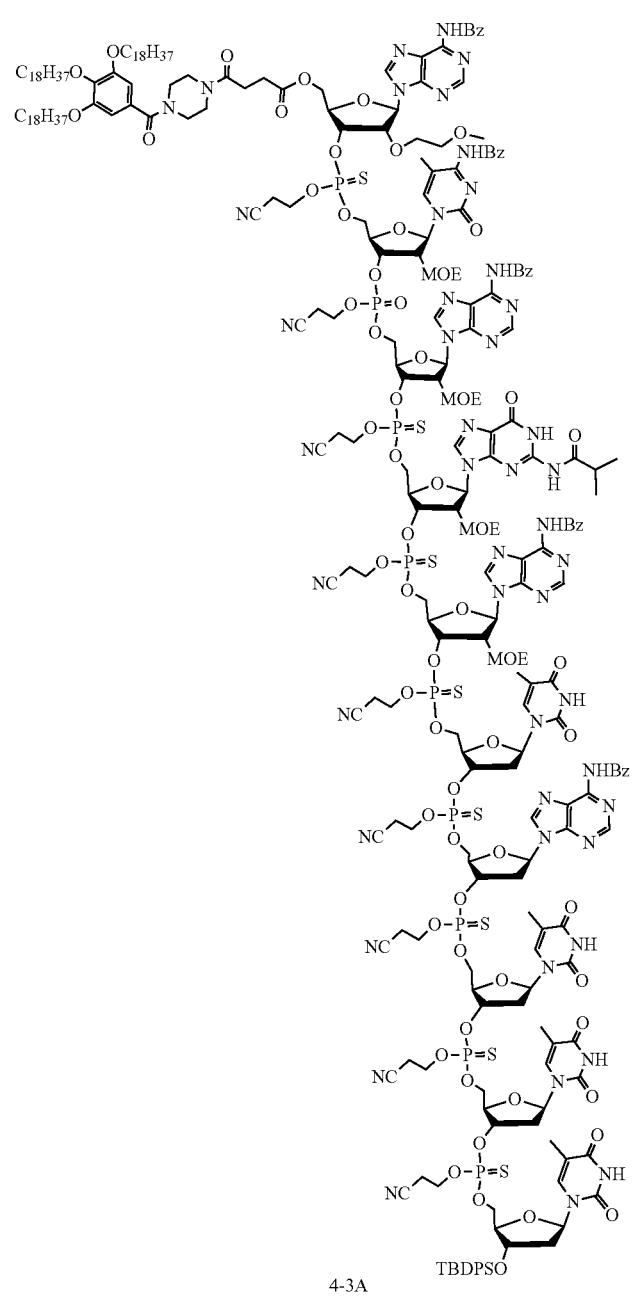
4-3A
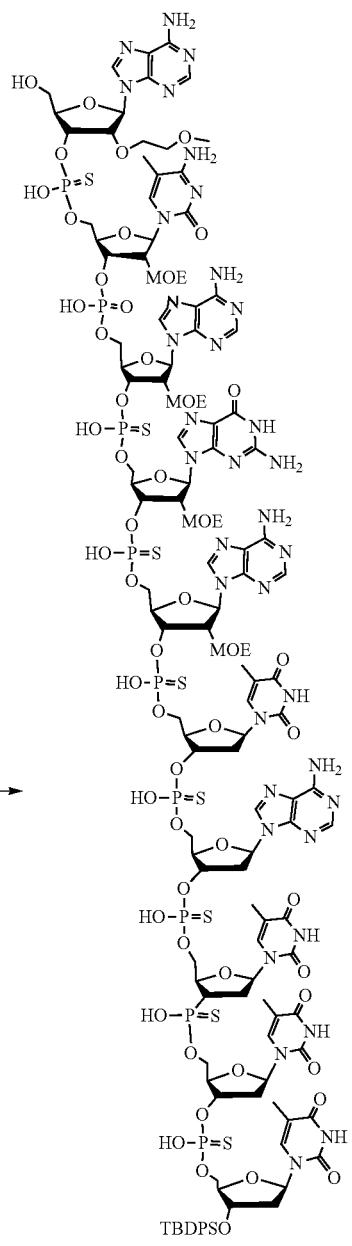
Chemical Formula $C_{131}H_{175}N_{36}O_{60}P_9S_8Si$
Exact Mass: 3774.69 Mw: 3777.36
4-3A-H
$NH_3/H_2O$ 217 218

-continued

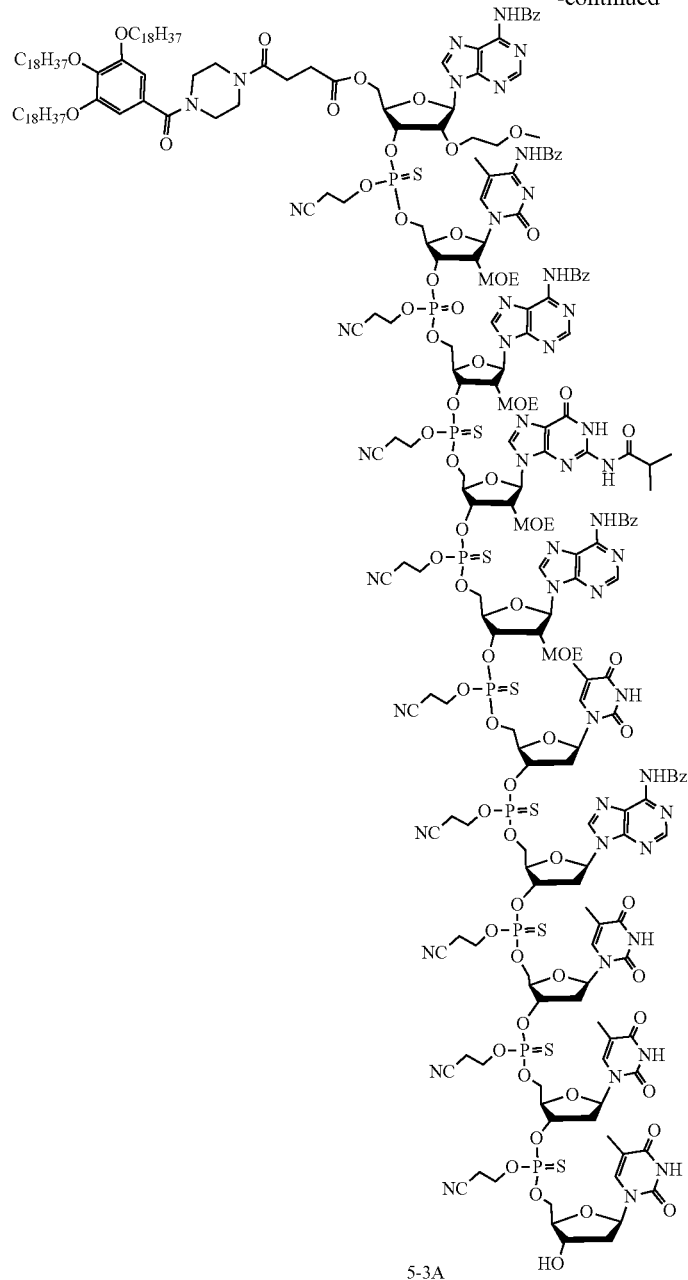

5-3A

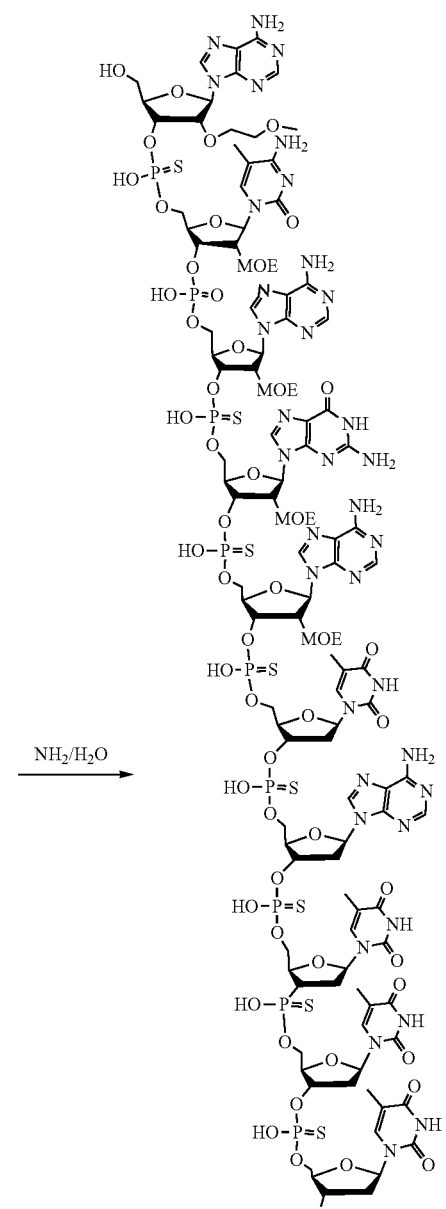

Chemical Formula C$_{115}$H$_{157}$N$_{36}$O$_{60}$P$_9$S$_8$
Exact Mass: 3536.57 Mw: 3538.96
5-3A-H 5) Deprotection and Ammonolysis of ASO 15-mer 6-3A

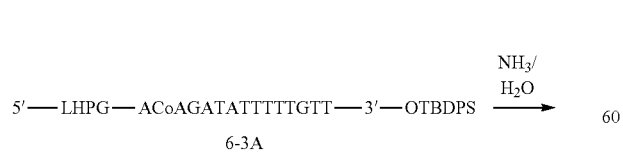

6-3A

-continued
5'—ACoAGATATTTTTGTT—3'—OTBDPS

6a

+

5'—ACoAGATATTTTTGTT—3'—OH

6b

Figure 18:
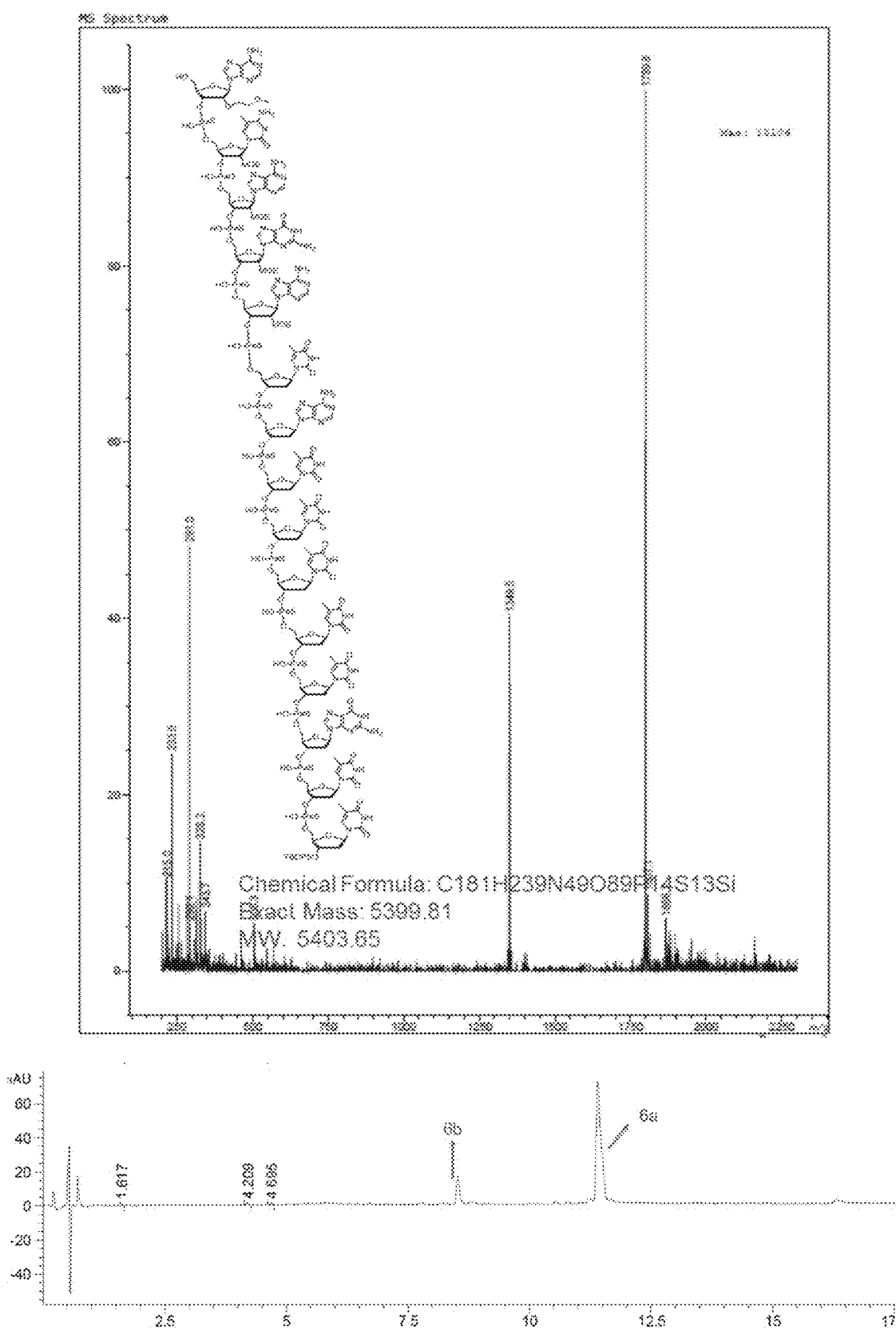
FIG. 18 shows HPLC and MS of 15-mer 5'-ACoAGAT-ATTTTTGTT-3'-OTBDPS.

Using a similar deprotection and ammonolysis procedure as described above for the DMT-on ASO 9 synthesis, treatment of ASO 15-mer 6-3A with NH$_4$OH resulted in a mixture of 6a and 6b, indicating the complete removal of 5'-LHPG protecting group and partial removal of the TBDPS group at the 3'-end (see FIG. 18).

Example 3: Deamination Study During 5'OH Deprotection

Detritylation Study of UCC Trimer and CC Dimer

1. UCC trimer deamination study:

Detritylation of UCC trimer was studied under different reaction conditions to find out the best conditions and reagents required to minimize deamination side reaction. Table 1 shows a comparison of different reaction conditions and the amount of undesired deamination product under those conditions. As can be seen in FIG. 9, use of 3 Å molecule sieves and quenching the reaction with pyridine resulted in <0.5% deamination as compared to 7% deamination with no sieves and 10% deamination with no sieves and no pyridine quench.

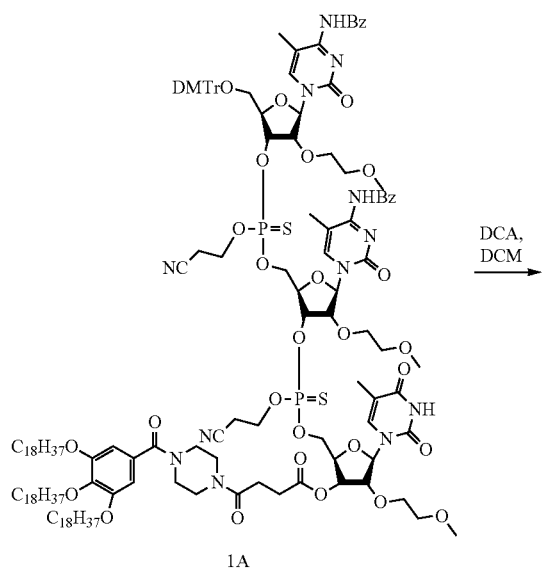

1A
5'—DMT—CCU—LHPG

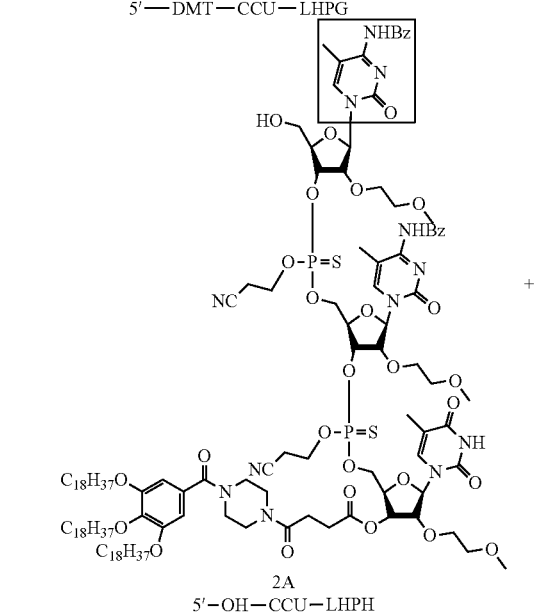

2A
5'—OH—CCU—LHPH

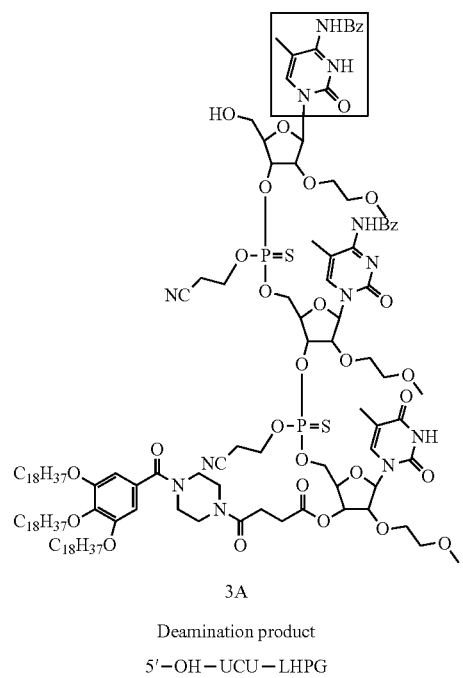

3A
Deamination product
5'—OH—UCU—LHPG

TABLE 1

Comparison of reaction conditions and deamination product for UCC trimer

Figure 10:
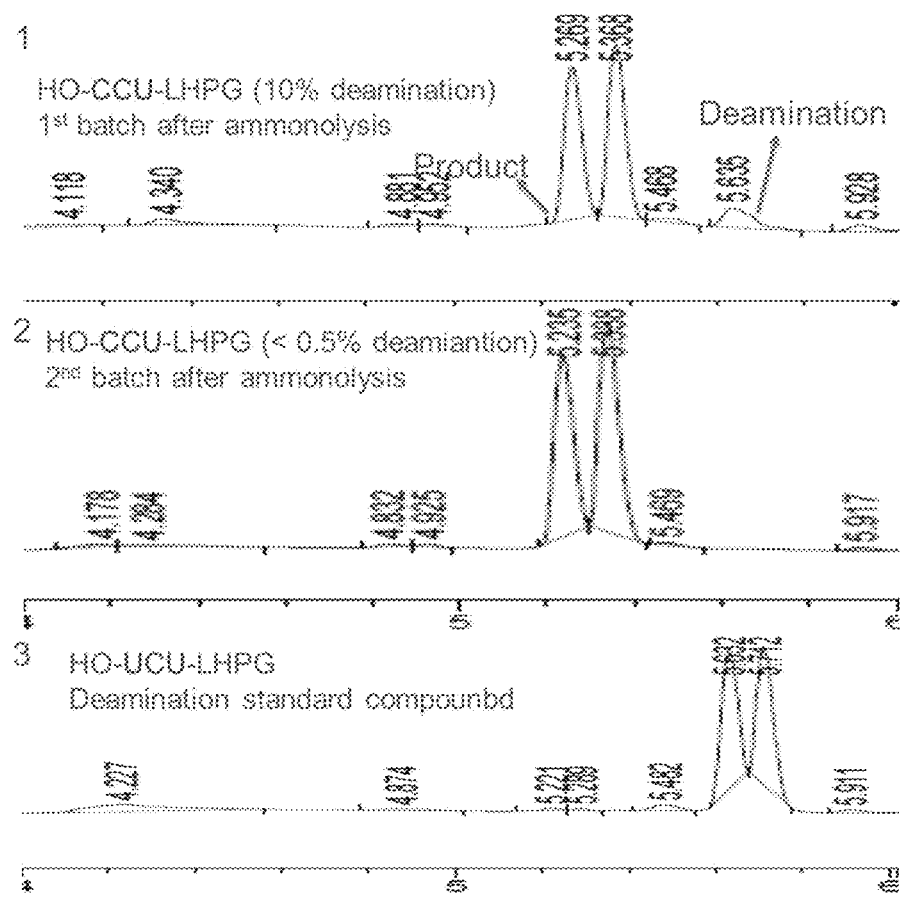
FIG. 10 shows HPLC comparison of deamination product obtained during UCC trimer detritylation reaction.

| | Reaction Conditions | Deamination Product |
|---|---|---|
| 5'-DMT-CCU-LHPG | 12 eq DCA, HPLC grade DCM, reaction at zero degree, NaHCO$_3$/H$_2$O quench | 10% deamination (FIG. 10, entry 1) |
| 5'-DMT-CCU-LHPG | 12 eq DCA, HPLC grade DCM, reaction at zero degree, pyridine quench | 7% deamination |
| 5'-DMT-CCU-LHPG | 12 eq DCA, anhydrous DCM, add 5% (v/v to DCM) 3Å molecule sieve, reaction at zero degree, pyridine quench | <0.5% deamination (FIG. 10, entry 2) |

Figure 11:
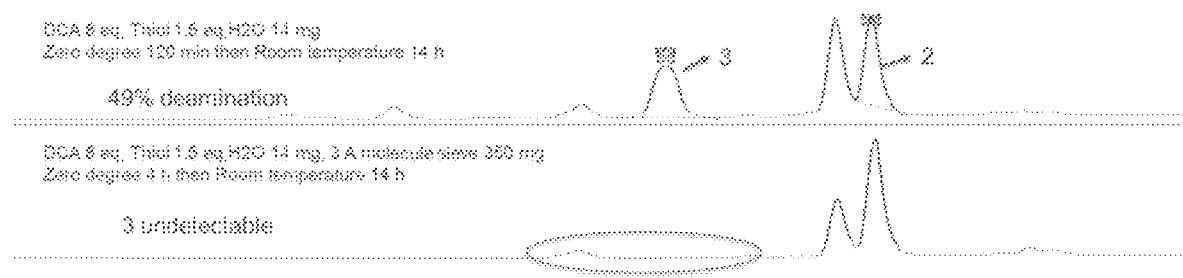
FIG. 11 shows HPLC comparison of deamination product obtained during CC dimer detritylation reaction.

2. CC Dimer Deamination Study:

Similar to the above study done for UCC trimer, detritylation was performed on CC dimer with various reagents and conditions to minimize or avoid the deamination reaction. As can be seen in table 2 and FIG. 11, no deamination product was detected after 14 hrs at room temperature even with addition of water when DCA, thiol and 3 Å molecule sieves were used. On the other hand 4.46% deamination product was obtained when no molecular sieves and no water were added and 49% deamination product with water but no molecular sieves with stirring for 14 hrs at room temperature

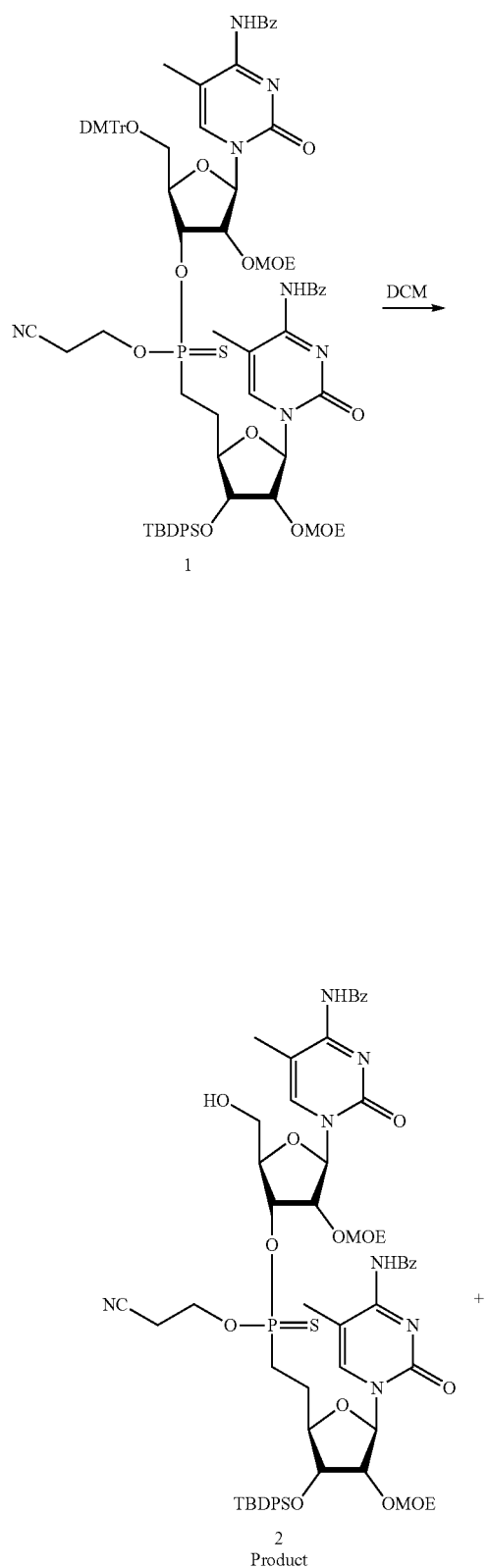

1

2
Product

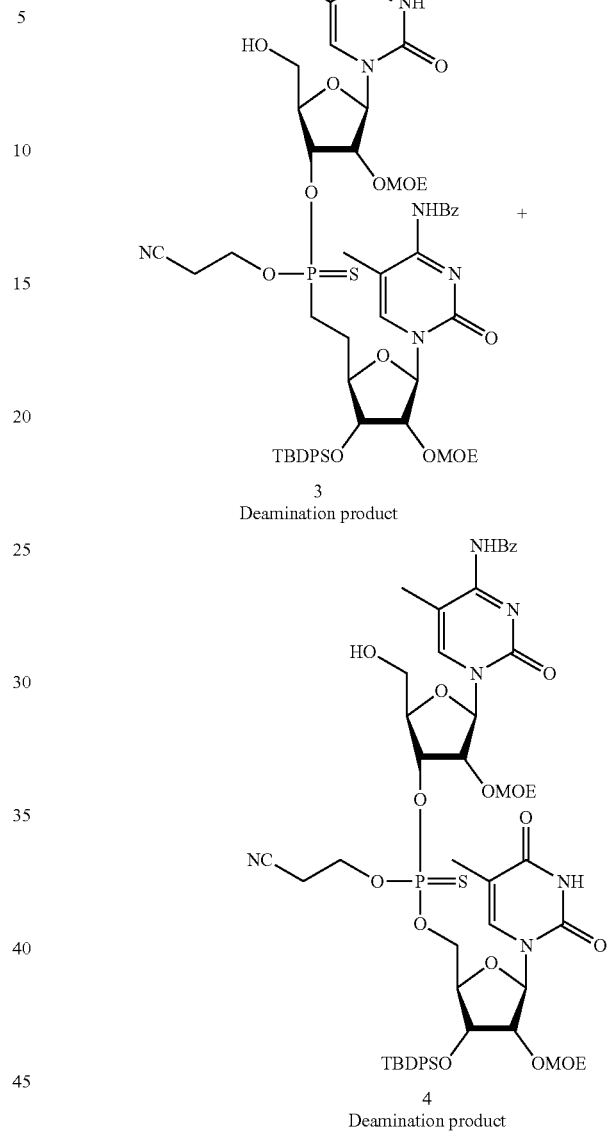

3
Deamination product

4
Deamination product

TABLE 2

Comparison of reaction conditions and deamination product for CC Dimer

| | DCA/DCM | Thiol/H₂O | 45 min 0° C. | 120 min 0° C. | rt 14 h |
|---|---|---|---|---|---|
| 5'-DMTr-Moe-CC-TBDPS | 14 ml DCA | 8 eq Thiol 1.5 eq | Deamination Not detected | Deamination Not detected | 4.46% Deamination |
| 500 mg 5'-DMTr-Moe-CC-TBDPS | 7 ml DCA | 8 eq, Thiol 1.5 eq H₂O 14 mg, (2.4 eq, 1500 ppm) | 0.47% (254 nm) Deamination | 1.31% (254 nm) Deamination | 49% (254 nm) Deamination |
| 500 mg 5'-DMTr-Moe- | 7 ml DCA | 8 eq, Thiol 1.5 eq H₂O | Deamination Not detected | Deamination Not | Deamination Not |

TABLE 2-continued

Comparison of reaction conditions and deamination product for CC Dimer

| | DCA/ DCM Thiol/H$_2$O | 45 min 0° C. | 120 min 0° C. | rt 14 h |
|---|---|---|---|---|
| CC-TBDPS | 14 mg, (2.4 eq, 1500 ppm), DCA 8 eq 3Å molecular sieves 350 mg | | detected | detected |

3. Deamination Study Results of Detritylation from Fragment Synthesis

Five-mer MOE DMTO-ACoCCU-OH (from DMTO-ACCCU-OLHPG) contained ~10% deamination impurities (Ia, Ib, and Ic combined, ratio has not been determined) (Scheme A).

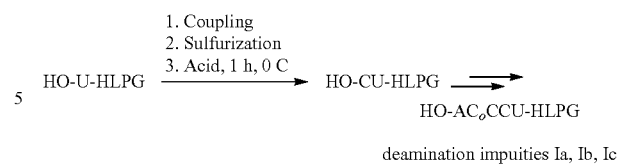

deamination impurities Ia, Ib, Ic

TABLE 3

Impact of Drying of on Deamination impurity in MOE DMTO-AC$_o$CCU-OH

| expt | Step 3. Treatment of detritylation reaction mixture before acid addition | Product (% UV area) | Ia + Ib + Ic (% UV area) |
|---|---|---|---|
| DMTO-AC$_o$CCU | Without 3Å MS drying | 90 | 10 |
| DMTO-AC$_o$CCU | Dried with 3 Å MS for 1 h | 100 | <0.5% |

Scheme A. High Levels of Deamination Impurities in DMTO-ACCCU-OLHPG

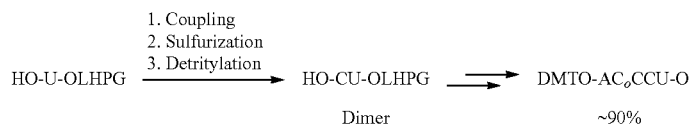

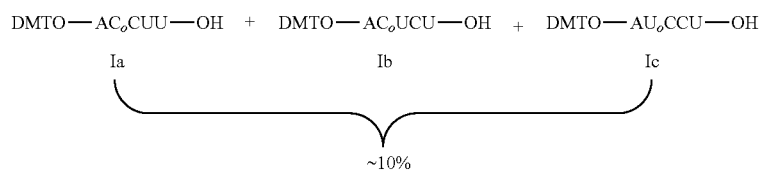

Synthesis of its analogue, HO-CCC-OTBDPS, was then completed using the same procedure and it was found that this trimer product contained at least 10% total deamination impurities (Scheme B).

Scheme B: High Levels of Deamination Impurities in HO-CCC-OTBDPS

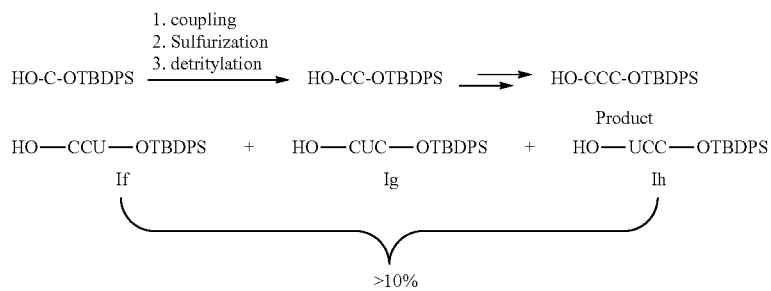

MOE Fragment-LHPG (I): with the above results, five-mer MOE DMTO-ACoCCU-OH, was repeated with modification of the procedure for detritylation. In this synthesis, the solutions were dried over 3 Å molecular sieves before the acid was added for every detritylation reaction. The deamination side products were completely suppressed (Table 3).

Example 4. Synthesis of ASO 8

The fully protected ASO 8 having DMT group at the 5'-end and the LHPS group at the 3'-end was prepared using similar procedures described in Example 1 for ASO 9. The oligonucleotide fragments used for the synthesis are shown in the schemes below.

Figure 35:
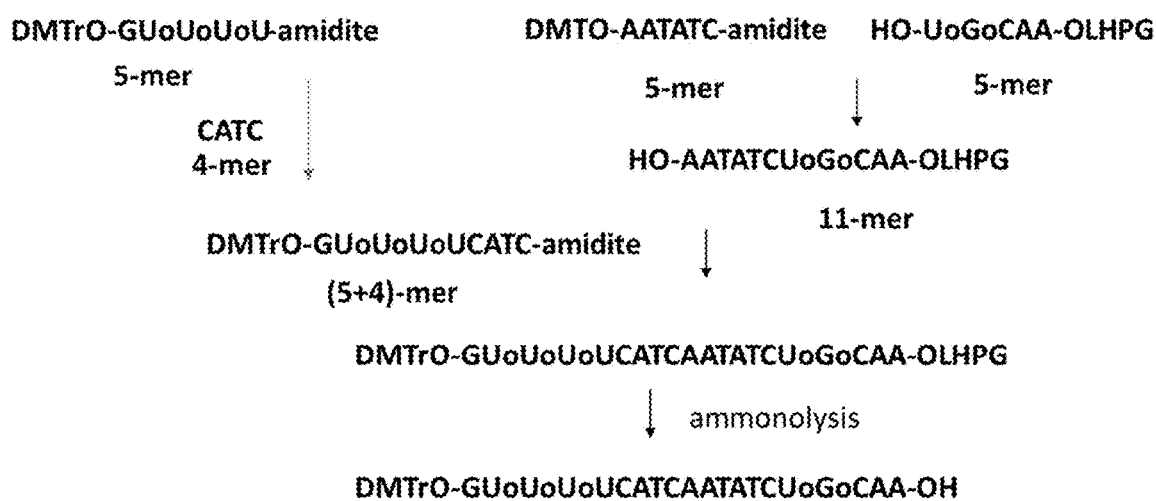
FIG. 35 shows a scheme for the synthesis of ASO 8 through 5+6+(4+5) coupling.
Figure 36:
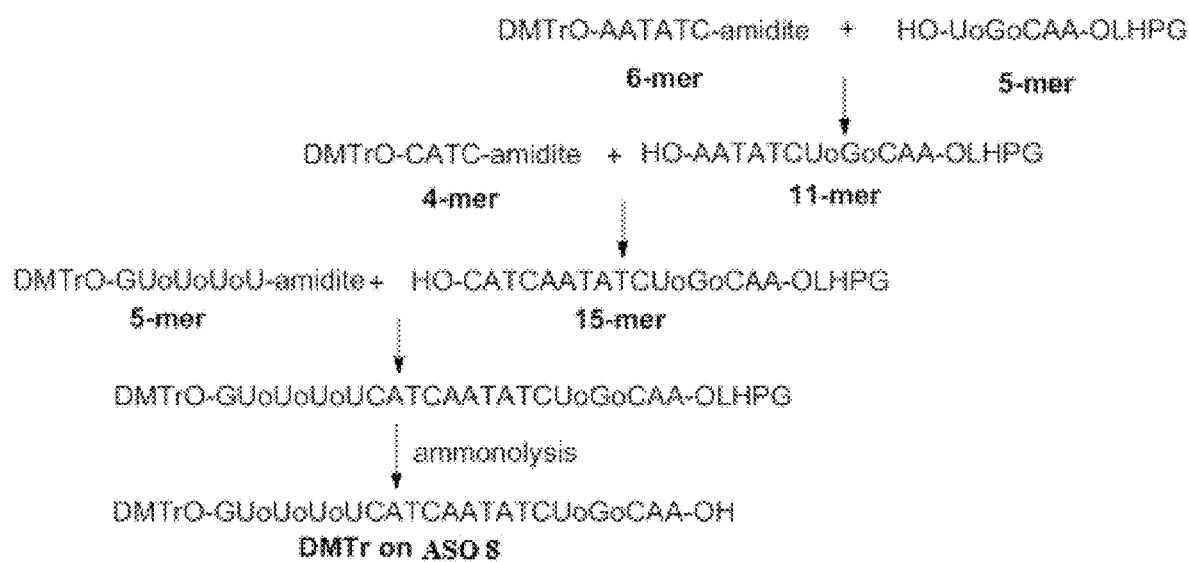
FIG. 36 shows a scheme for the synthesis of ASO 8 through 5+6+4+5 coupling.

1. Synthesis of ASO 8 through 5+6+(4+5) coupling (FIG. 35)
2. Synthesis of ASO 8 through 5+6+4+5 coupling (FIG. 36)

Figure 19:
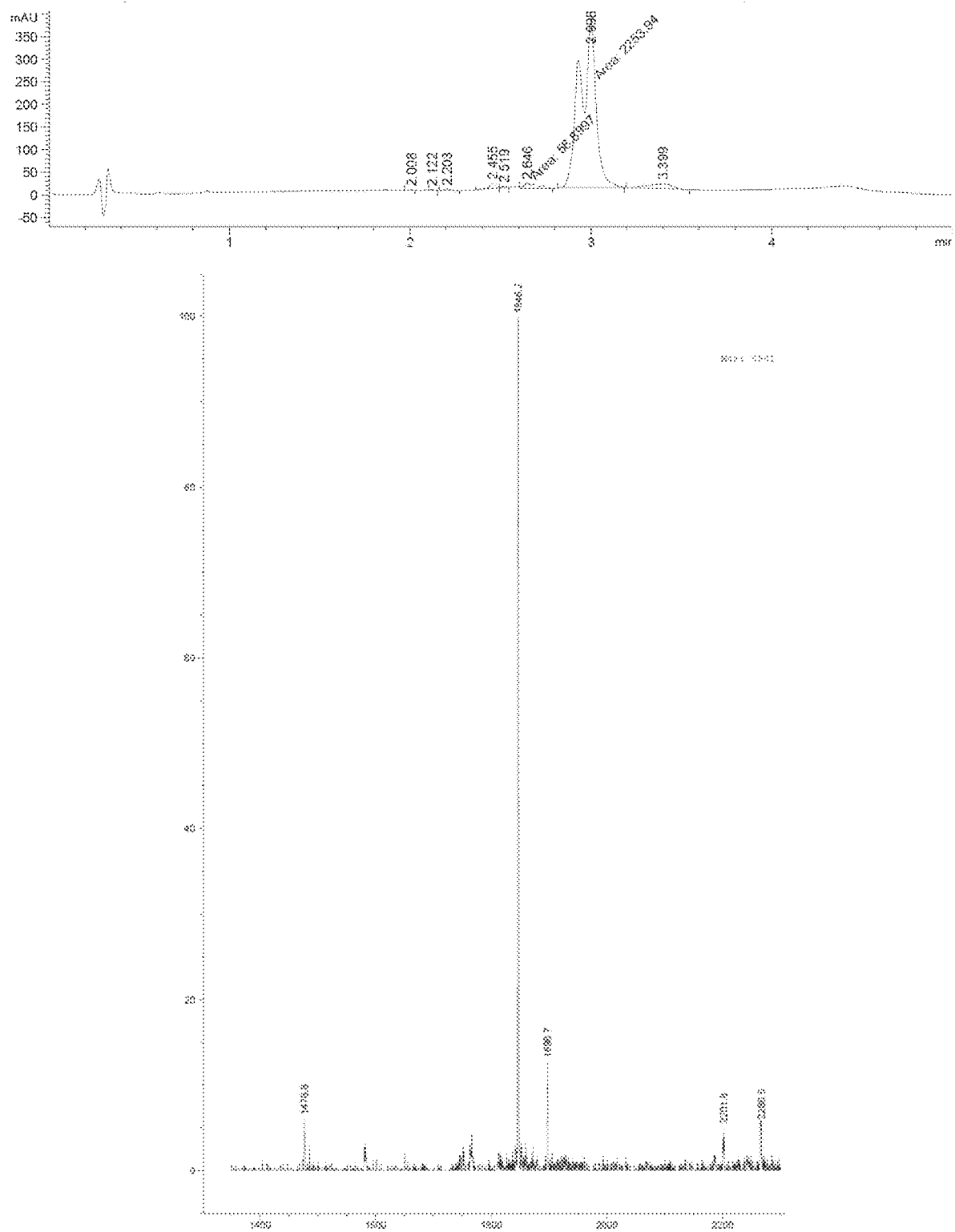
FIG. 19 shows HPLC and MS of product ASO 8.

The DMT-on ASO 8 was detritylated and purified using procedures similar to those described in Example 1 for ASO 9. HPLC-MS for ASO 8 is shown in FIG. 19.

HPLC-MS method for ASO 8:
Column: ACQUITY UPLC BEH C18 Column, 1.7 µm, 2.1 mm×50 mm;
Column temperature: 50° C.;
Ionization Mode: API-ES;
mass range from 1350 to 2300;
MS polarity: Negative;
Mobile phase A: 5 mM TBuAA in 10% $CH_3CN$, 1 µm EDTA; Solution B: 5 mM TBuAA in 80% $CH_3CN$, 1 µm EDTA;
Gradient:

| Time min | A % | B % | Flow mL/min | Pressure bar |
|---|---|---|---|---|
| 0.14 | 60.00 | 40.00 | 0.51 | — |
| 3.70 | 20.00 | 80.00 | 0.51 | — |
| 4.00 | 10.00 | 90.00 | 0.51 | — |
| 4.20 | 60.00 | 40.00 | 0.51 | — |
| 5.00 | 60.00 | 40.00 | 0.51 | — |

Example 5. Desilylation Study

Figure 37:
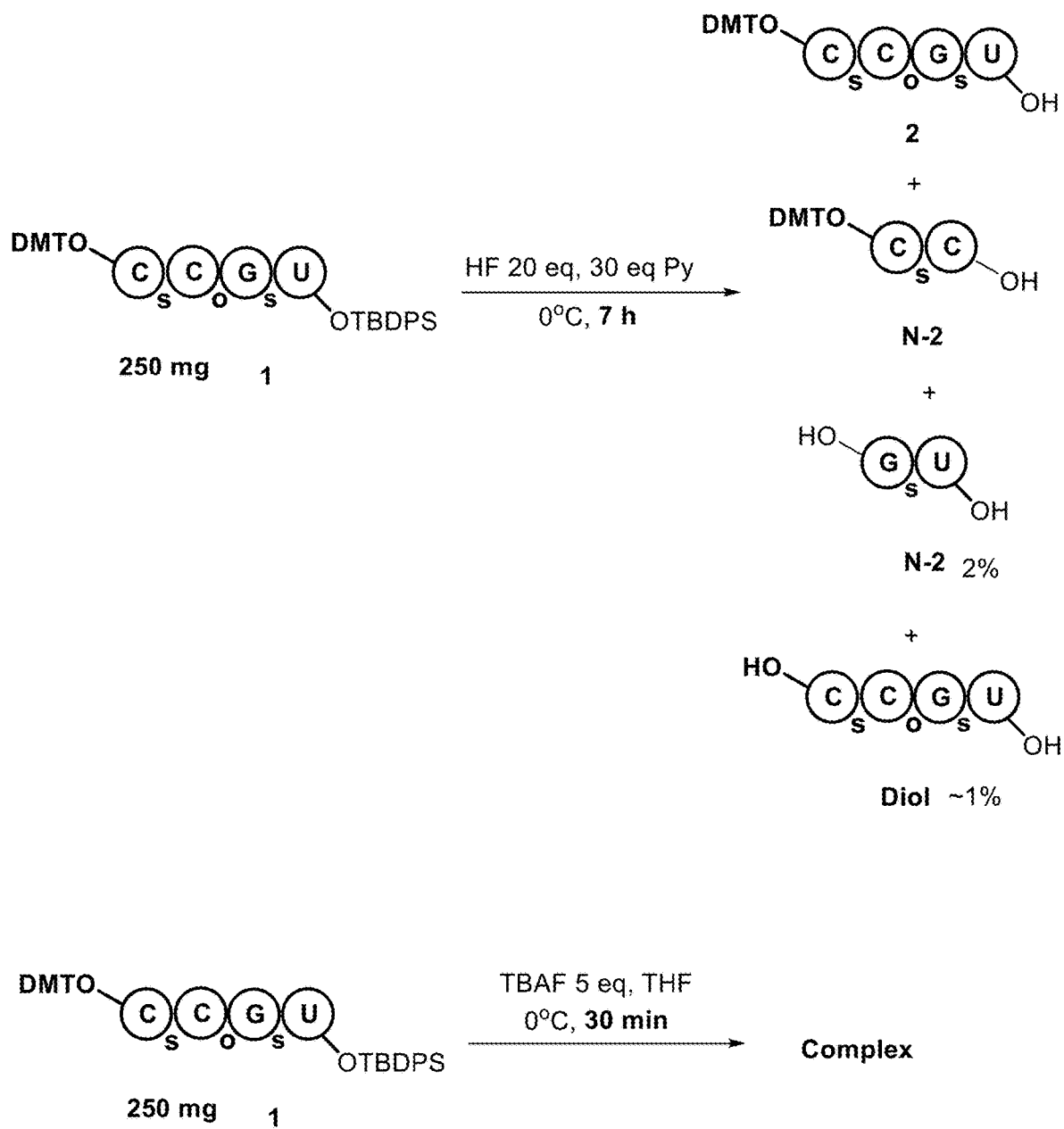
FIG. 37 shows a scheme for the desilylation of CCGU tetramer using known desilylation conditions.

A novel facile, mild, and clean deprotection method of 3'-OTBDPS was developed to minimize impurity formation. It was discovered that the presence of imidazole greatly accelerated the TBDPS deprotection and produces least amounts of impurities. A comparative study described below shows that desilylation using known conditions led to the formation of various by-products, such as N–2 and diol by-products. In contrast, the new desilylation method result in significant reduction of these by-products.

a. Desilylation of CCGU Tetramer Using Known Desilylation Conditions (FIG. 37):

250 mg of CCGU tetramer was treated with 20 eq. of HF and 30 eq. of pyridine at 0° C. for 7 hours. The N–2 and diol by-products were observed. Desilylation reactions with other known methods, such as TBAF or CsF lead to complex mixture.

Figure 38:
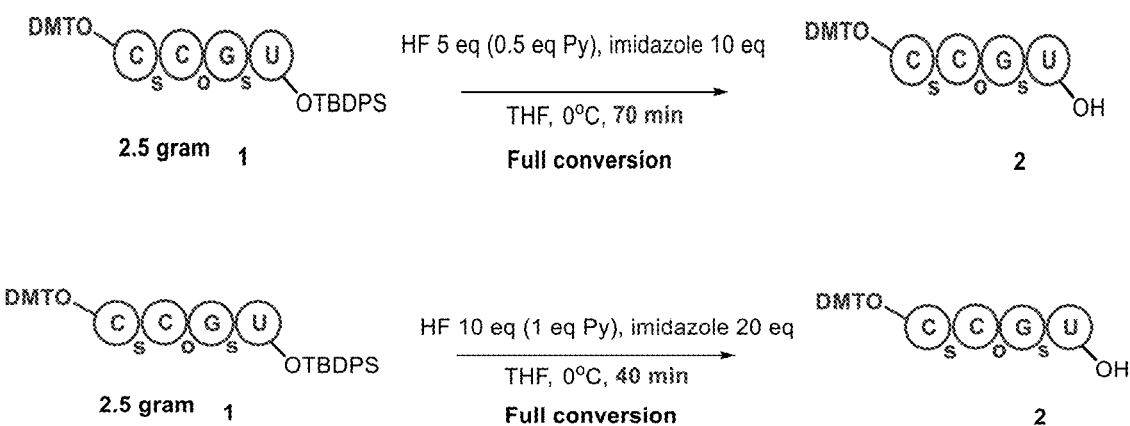
FIG. 38 shows a scheme for the desilylation of CCGU tetramer under HF/imidazole desilylation conditions.

The presence of the N–2 and diol by-products can significantly influence the purity of the final target oligonucleotides.

b. Desilylation of CCGU Tetramer Under HF/Imidazole Desilylation Condition (FIG. 38):

In contrast to the desilylation reactions carried out with known conditions described above, desilylation with HF/imidazole resulted in the completion of desilylation reaction in 2 hours with less than 0.5% diol and N-2 by-products observed. In addition, only 5 equivalents of HF was needed to achieve full conversion of the starting material, as compared to the 20 equivalents of HF needed with the known desilylation conditions.

Example 6. Synthesis of 5'-DMT-GUUUUUGCAA-$NO_2$-Benzoyl Through H Phosphonate Chemistry

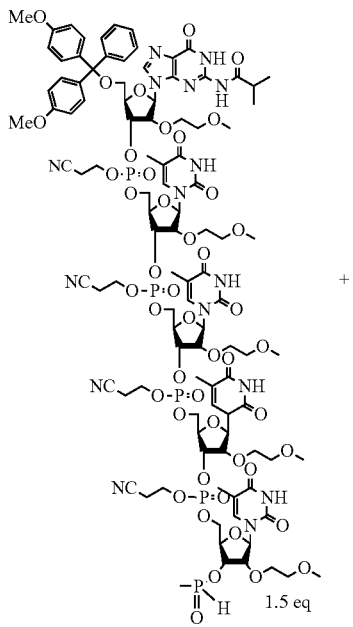

SM 1

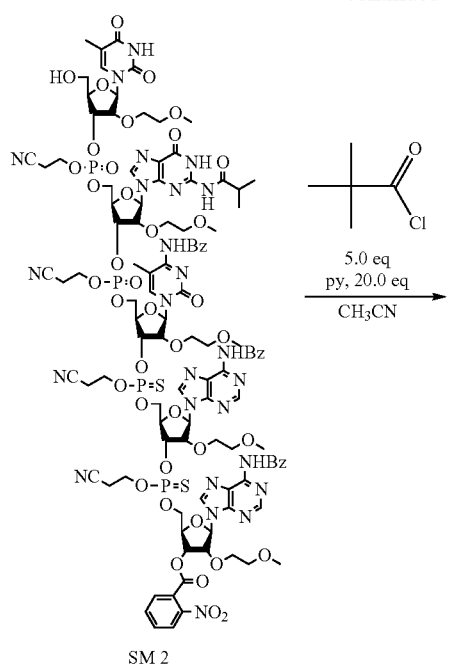
SM 2
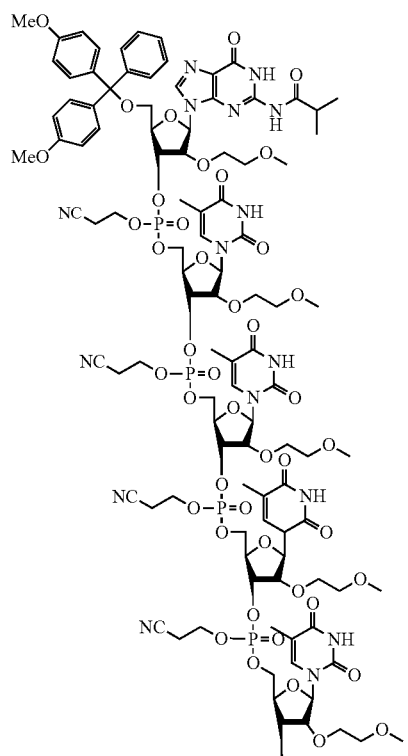

Figure 20:
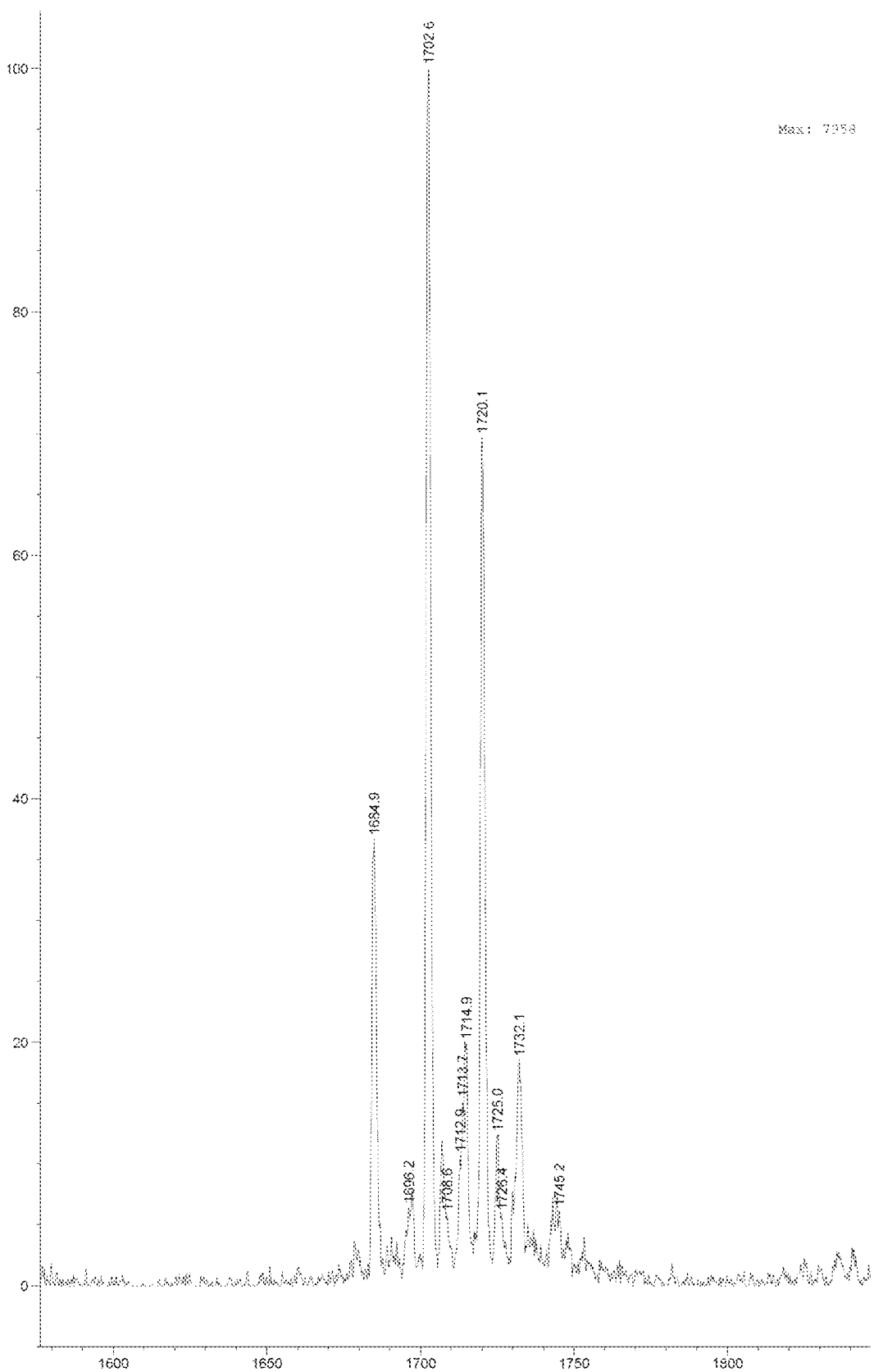
FIG. 20 shows MS of 5'-DMT-GUUUUUGCAA-NO$_2$—Benzoyl.

SM 1 (3.78 g) and SM 2 (2.64 g) were dissolved in 20 ml CH₃CN. At 0'C, pyridine 2.4 ml and pivaloyl chloride 0.62 ml were added to the mixture slowly. After stirred at 0° C. for 40 min, I₂/py (0.05 M 40 ml) was added to the mixture. After stirred at 0° C. for 30 min the reaction was quenched by Na₂S₂O₃/H₂O solution and 5'-DMT-GUUUUUGCAA-NO₂—Benzoyl was obtained as a light yellow solid. The structure of 5'-DMT-GUUUUUGCAA-NO₂—Benzoyl was confirmed by MS (see FIG. 20).

Example 7. Evaluation of Feasibility of Convergent Liquid-Phase Synthesis of ASO 9 Analogues with Various PO/PS Linkages HPLC method (A).

Column: Xbridge Shield RP18 5 μm, 2.1 mm×50 mm column.

Column temperature: 40° C.;

Mobile phases:

Solution A: 10 mM NH₄HCO₃ water solution

Solution B: 100% Acetonitrile

Gradient:

| Time min | A % | B % | Flow mL/min | Pressure bar |
|---|---|---|---|---|
| 0.01 | 90.00 | 10.00 | 0.80 | — |
| 8.00 | 20.00 | 80.00 | 0.80 | — |
| 9.00 | 20.00 | 80.00 | 0.80 | — |
| 9.01 | 90.00 | 10.00 | 1.20 | — |
| 10.00 | 90.00 | 10.00 | 1.20 | — |

HPLC method (B).

Column: Xbridge C18 3.5 μm, 4.6 mm×150 mm column.

Column temperature: 40° C.;

Mobile phases:

Solution A: 10 mM NH₄HCO₃ water solution

Solution B: 100% Acetonitrile

Gradient:

| Time min | A % | B % | Flow mL/min | Pressure bar |
|---|---|---|---|---|
| 0.00 | 50.00 | 50.00 | 1.00 | — |
| 15.00 | 0.00 | 100.00 | 1.00 | — |
| 15.01 | 50.00 | 50.00 | 1.00 | — |
| 20.00 | 50.00 | 50.00 | 1.00 | — |

HPLC method (C).

Column: Xbridge Shield RP18 5 μm, 2.1 mm×50 mm column.

Column temperature: 40° C.;

Mobile phases:
 Solution A: 10 mM NH$_4$HCO$_3$ water solution
 Solution B: 100% Acetonitrile
Gradient:

| Time min | A % | B % | Flow mL/min | Pressure bar |
|---|---|---|---|---|
| 0.01 | 100.00 | 0.00 | 0.80 | — |
| 4.50 | 70.00 | 30.00 | 0.80 | — |
| 5.30 | 70.00 | 30.00 | 0.80 | — |
| 5.31 | 100.00 | 0.00 | 1.20 | — |
| 6.00 | 100.00 | 0.00 | 1.20 | — |

HPLC-MS method (D).
Column: Xbridge Shield RP18 5 μm, 2.1 mm×50 mm column.
Column temperature: 40° C.;
Mass range from 100 to 1000;
MS polarity: Negative
Mobile phases:
 Solution A: 10 mM NH$_4$HCO$_3$ water solution
 Solution B: 100% Acetonitrile
Gradient:

| Time min | A % | B % | Flow mL/min | Pressure bar |
|---|---|---|---|---|
| 0.01 | 95.00 | 5.00 | 1.00 | — |
| 1.00 | 5.00 | 95.00 | 1.00 | — |
| 1.80 | 0.00 | 100.00 | 1.00 | — |
| 1.81 | 95.00 | 5.00 | 1.00 | — |
| 2.20 | 95.00 | 5.00 | 1.00 | — |

HPLC-MS method (E).
Column: Luna C18 3.0 μm, 2.0 mm×30 mm column.
Column temperature: 40° C.;
Mass range from 100 to 2000;
MS polarity: Positive
Mobile phases:
 Solution A: 0.037% TFA (v/v) water solution
 Solution B: 0.018% TFA (v/v) acetonitrile solution.
Gradient:

| Time min | A % | B % | Flow mL/min | Pressure bar |
|---|---|---|---|---|
| 0.01 | 95.00 | 5.00 | 1.00 | — |
| 1.00 | 5.00 | 95.00 | 1.00 | — |
| 1.80 | 0.00 | 100.00 | 1.00 | — |
| 1.81 | 95.00 | 5.00 | 1.20 | — |
| 2.00 | 95.00 | 5.00 | 1.20 | — |

HPLC-MS method (F).
Column: Xbridge Shield RP18 5 μm, 2.1 mm×50 mm column.
Column temperature: 40° C.;
Mass range from 100 to 1000;
MS polarity: Positive
Mobile phases:
 Solution A: 10 mM NH$_4$HCO$_3$ water solution
 Solution B: 100% Acetonitrile
Gradient:

| Time min | A % | B % | Flow mL/min | Pressure bar |
|---|---|---|---|---|
| 0.01 | 95.00 | 5.00 | 1.00 | — |
| 1.00 | 5.00 | 95.00 | 1.00 | — |
| 1.80 | 0.00 | 100.00 | 1.00 | — |
| 1.81 | 95.00 | 5.00 | 1.00 | — |
| 2.20 | 95.00 | 5.00 | 1.00 | — |

HPLC-MS method (G) for amidite compounds 7-1-6a, 7-3-10a and 7-4-8a.
Column: ACQUITY UPLC BEH C18 1.7 μm, 2.1 mm×50 mm column.
Column temperature: 50° C.;
Mass range from 500 to 2200;
MS polarity: Negative
Mobile phases:
 Solution A: 5 mM tributylamine acetate (TBuAA) in 10% CH$_3$CN, 1 μm EDTA;
 Solution B: 5 mM TBuAA in 80% CH$_3$CN, 1 μm EDTA
Gradient:

| Time min | A % | B % | Flow mL/min | Pressure bar |
|---|---|---|---|---|
| 0.20 | 92.50 | 7.50 | 0.51 | — |
| 9.00 | 5.00 | 95.00 | 0.51 | — |
| 10.00 | 5.00 | 95.00 | 0.51 | — |

Figure 39:
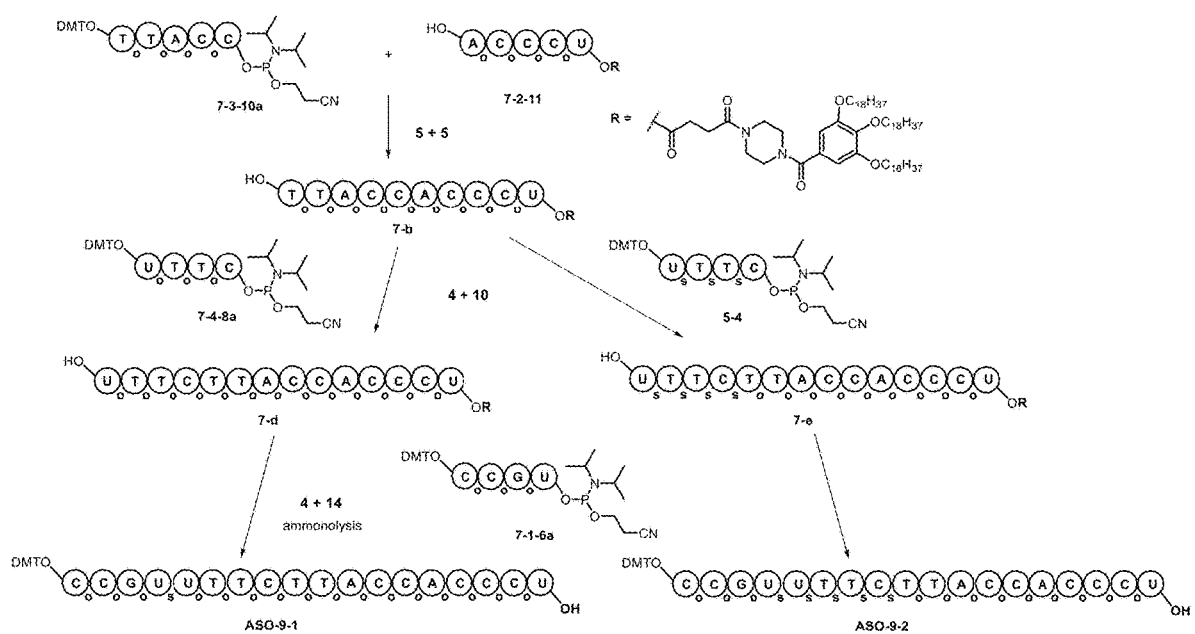
FIG. 39 shows a scheme for synthetic strategies for accessing ASO 9 analogues with different numbers of P=O/S linkages.

ASO 9 analogues with different numbers of P=O/S linkages were synthesized (FIG. 39).
A. Preparation of 5' Fragment
1. Preparation of 5'-DMTr-CCGU-OH or 5'-OH-CCGU-TBDPS 4mer (Fragment 4)
Synthesis of Compound 7-1-2

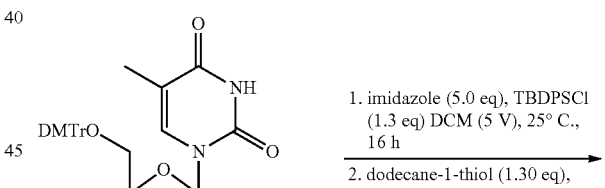

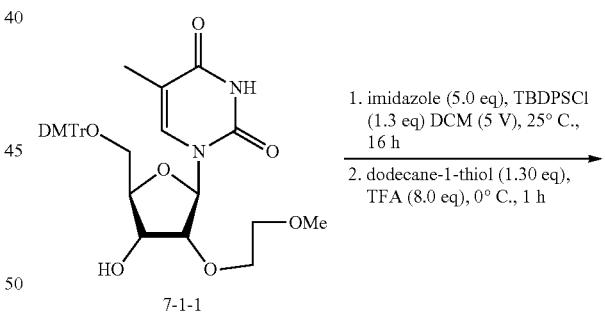

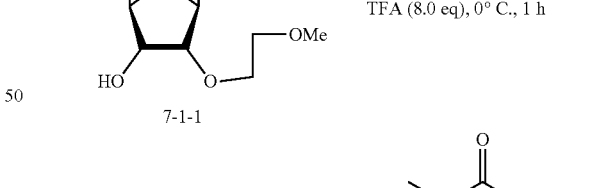

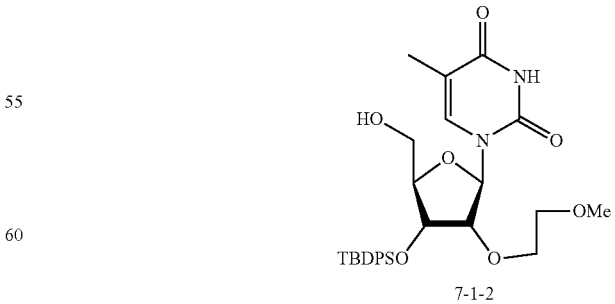

To a solution of compound 7-1-1 (8.50 g, 13.7 mmol, 1.00 eq) and imidazole (4.68 g, 68.7 mmol, 5.00 eq) in DCM (85 mL) was added TBDPSCl (4.15 g, 15.1 mmol, 3.88 mL, 1.10 eq). The mixture was stirred at 25° C. for 16 h. TLC (Petroleum ether:Ethyl acetate=1:2, Product: $R_f$=0.55) indicated compound 7-1-1 was consumed completely and one new spot formed. The reaction was clean according to TLC. Propan-2-ol (825 mg, 13.7 mmol, 1.00 eq) was added and the mixture was stirred at 25° C. for 0.5 h.

To the above solution was added dodecane-1-thiol (7.23 g, 35.7 mmol, 8.56 mL, 1.30 eq) cooled to 0° C., and then TFA (25.0 g, 219 mmol, 16.2 mL, 8.00 eq) was added the reaction mixture at 0° C. The mixture was stirred at 0° C. for 1 h. TLC (Petroleum ether:Ethyl acetate=1:2, Product: $R_f$=0.28) indicated that the starting material was consumed completely and one new spot formed. The reaction was clean according to TLC.

The reaction mixture was quenched by addition NaHCO$_3$ (500 mL), and then diluted with DCM (100 mL) and extracted with NaHCO$_3$ (200 mL). The combined organic layers were washed with brine 200 mL (100 mL×2), dried over MgSO$_4$, filtered and concentrated under reduced pressure to give a residue. The crude product was dissolved in DCM (600 mL) and loaded in a 1000 mL separation funnel.

The crude product was dissolved in ACN 100 mL and 50 mL DI water, the mixture was extracted by Heptane:TBME=4:1 (120 mL×4). (TLC indicated of the product was clean in the ACN and DI water). The product was in ACN and water. The mixture was extracted by TBME (100 mL) and the organic layer was dried and concentrated to dryness as a white solid. Compound 7-2 (14.0 g, 23.4 mmol, 85.1% yield, 92.7% purity) was obtained as a white foam. HPLC (Method A): RT=3.446 min; LCMS (Method F): RT=1.371 min; m/z: [M+H]$^+$=555.3 for compound 7-1-2.

Synthesis of Compound 7-1-3

Compound 7-1-2 (12.0 g, 21.6 mmol, 1.00 eq) and MOE G amidite (21.7 g, 23.8 mmol, 1.10 eq) were co-evaporated with ACN (10 mL×3) under Argon in a 250 mL single-necked round bottle, and 3 Å molecular sieves (3.00 g) were added to the single-necked bottle, under Argon pressure ACN (60 mL). The mixture was stirred at 25° C. for 1 h, and then DCI (3.83 g, 32.4 mmol, 1.50 eq) was added to the mixture. The reaction mixture was stirred at 25° C. for 1 h. TLC (Dichloromethane:Methanol=15:1, Product: $R_f$=0.39) indicated compound 7-1-2 was consumed completely and one new spot formed. The reaction was clean according to TLC. HPLC (product: RT=7.199 min; start material: RT=5.194 min) indicated compound 2 was consumed completely.

To the above solution was added BuOOH (3.90 g, 43.2 mmol, 4.15 mL, 2.00 eq). The mixture was stirred at 25° C. for 0.5 h. HPLC (7-1-3, Product: RT=6.869 min; start material: RT=7.199 min) indicated the reaction completed. The reaction mixture was poured into the NaHCO$_3$ and Na$_2$SO$_3$ solution (10.0 eq NaHCO$_3$ and 5.00 eq Na$_2$SO$_3$ in 400 mL DI water), and then dilute the mixture with DCM (100 mL) and two layers were separated, the organic layer was washed with NaHCO$_3$ (200 mL), brine (200 mL), dried filtered and concentrated.

Compound 7-1-3 (32.0 g, 18.9 mmol, 87.6% yield, 82.0% purity) was obtained as a light yellow foam.

HPLC (Method A): RT=6.868 min; LCMS (Method F): RT=1.501, 1.520 min; m/z: [M+H]+=1383.5 for compound 7-1-3.

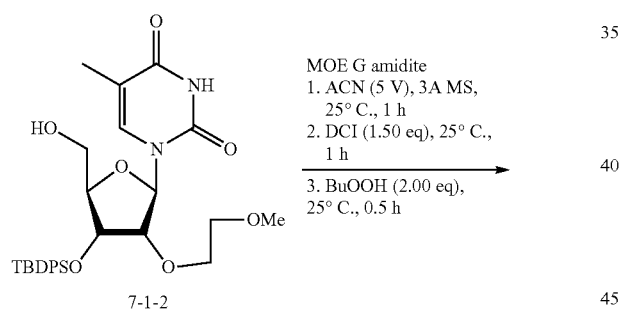

General procedure for preparation of compound 7-1-3a

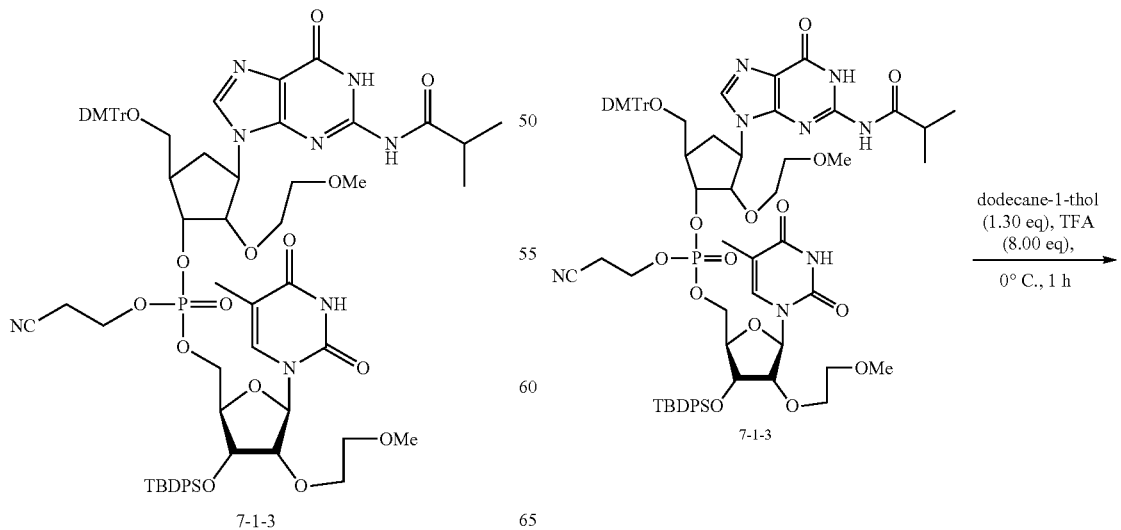

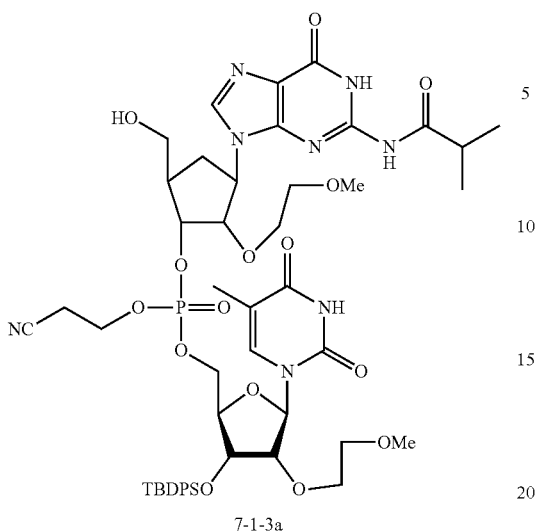

7-1-3a

Compound 7-1-3 (25.0 g, 18.0 mmol, 1.00 eq) in DCM (120 mL) Was added dodecane-1-thiol (4.75 g, 23.4 mmol, 5.63 mL, 1.30 eq) at 0° C., and then TFA (16.4 g, 144 mmol, 10.7 mL, 8.00 eq) was added the reaction mixture at 0° C. The mixture was stirred at 0° C. for 1 h. TLC (Dichloromethane:Methanol=10:1, Product: $R_f$=0.24) indicated compound 7-1-3 was consumed completely and one new spot formed. The reaction was clean according to TLC.

The reaction mixture was poured into the NaHCO$_3$ solution (10.0 eq NaHCO$_3$ in 300 mL DI water), and then dilute the mixture with DCM (100 mL) and two layers were separated, the organic layer was washed with NaHCO$_3$ (100 mL), brine (100 mL), dried filtered and concentrated.

The mixture was re-dissolved in CH$_3$CN:H$_2$O (2:1, 70 mL), and the CH$_3$CN/H$_2$O layer was washed by Heptane:MTBE=4:1 (100 mL×4), and then dilute the layer of CH$_3$CN and H$_2$O with EtOAc (100 mL), the organic layer was washed with brine (100 mL), dried filtered and concentrated. Compound 7-1-3a (17.0 g, 15.0 mmol, 83.3% yield, 95.8% purity) was obtained as a light yellow foam.

HPLC (Method A): RT=6.778 min; LCMS (Method F): RT=1.322 min; m/z: [M+H]+=1081.4 for compound 7-1-3a.

Synthesis of Compound 7-1-4

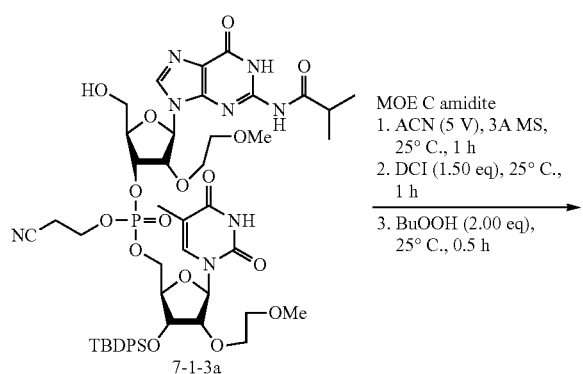

MOE C amidite
1. ACN (5 V), 3A MS, 25° C., 1 h
2. DCI (1.50 eq), 25° C., 1 h
3. BuOOH (2.00 eq), 25° C., 0.5 h

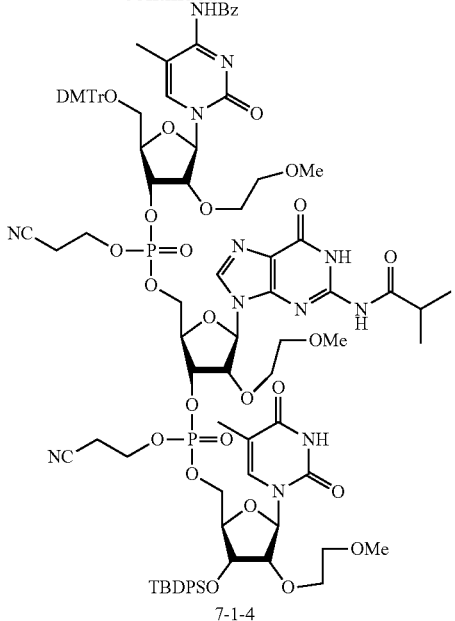

7-1-4

Compound 7-1-3a (17.0 g, 15.7 mmol, 1.00 eq) and MOE C amidite (15.9 g, 17.2 mmol, 1.10 eq) were co-evaporated with ACN (50 mL×3) under Ar in a 250 mL single-necked round bottle, and 3 Å molecular sieve (4.00 g) were added to the single-necked bottle, under Ar pressure ACN (85 mL) was added. The mixture was stirred at 25° C. for 1 h, and then DCI (2.78 g, 23.5 mmol, 1.50 eq) was added to the mixture. The reaction mixture was stirred at 25° C. for 1 h. HPLC (product: RT=7.932, 8.001 min; start material: RT=5.111, 5.169 min) showed the starting material was consumed completely.

To the above solution was added BuOOH (4.05 g, 31.4 mmol, 4.31 mL, 70.0% purity, 2.00 eq). The mixture was stirred at 25° C. for 0.5 h. HPLC (7-1-4, product: RT=7.746, 7.832, 7.916 min; start material: RT=7.932, 8.001 min) showed the starting material was consumed completely.

The reaction mixture was poured into the NaHCO$_3$ and Na$_2$SO$_3$ solution (10.0 eq NaHCO$_3$ and 5.00 eq Na$_2$SO$_3$ in 400 mL DI water), and then dilute the mixture with EtOAc (100 mL) and two layers were separated, the organic layer was washed with NaHCO$_3$ (200 mL), brine (200 mL), dried filtered and concentrated. Compound 7-1-4 (33.4 g, 12.7 mmol, 81.3% yield, 73.5% purity) was obtained as a white solid.

HPLC (Method A): RT=7.746, 7.832, 7.916 min; LCMS (Method F): RT=1.603 min; m/z: [M+H]+=1917.7 for compound 7-1-4.

Synthesis of Compound 7-1-4a

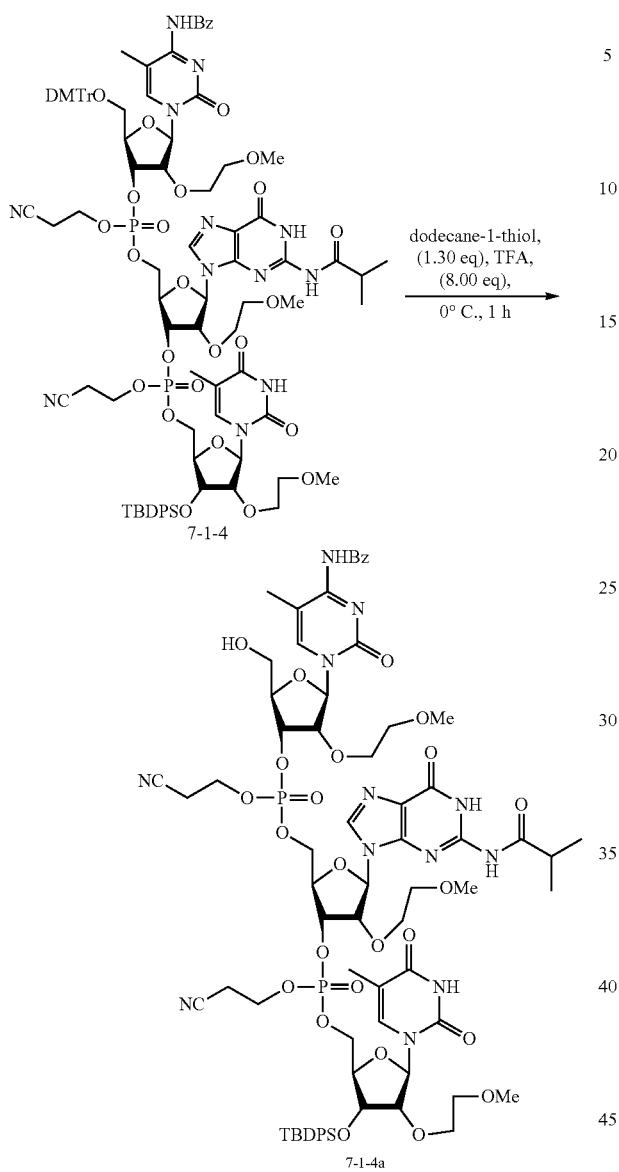

To Compound 7-1-4 (23.0 g, 11.9 mmol, 1.00 eq) in ACN (120 mL) was added dodecane-1-thiol (3.15 g, 15.5 mmol, 3.73 mL, 1.30 eq) at 0° C., and then TFA (10.9 g, 95.8 mmol, 7.10 mL, 8.00 eq) was added the reaction mixture at 0° C. The mixture was stirred at 0° C. for 1 h. TLC (Dichloromethane:Methanol=7:1, Product: $R_f$=0.40) indicated compound 7-1-4 was consumed completely and one new spot formed. The reaction was clean according to TLC.

The reaction mixture was poured into the $NaHCO_3$ (10.0 eq $NaHCO_3$ in 400 mL DI water), and then dilute the mixture with EtOAc (200 mL) and two layers were separated, the organic layer was washed with aq·$NaHCO_3$ (150 mL), brine (150 mL), dried filtered and concentrated. The crude was re-dissolve in DCM (50 mL). The crude solvent was slowly dropped to a solvent of isopropyl ether (500 mL). Desired product was precipitated out. The product was collected as a light-yellow solid after filtration, and the solid cake was washed with isopropyl ether (50 mL×2). Compound 7-1-4a (22.0 g, 11.1 mmol, 93.0% yield, 81.9% purity) was obtained as a light yellow solid.

Compound 7-1-4a (13.0 g, 8.04 mmol, 86.9% yield, 98.3% purity) was obtained as a white foam after HPLC purification. HPLC (Method A): RT=6.127, 6.193, 6.277 minutes, and LCMS (Method F): RT=1.431 min; m/z: $[M+H]^+$=1615.5.

Preparation of CCGU 4mer

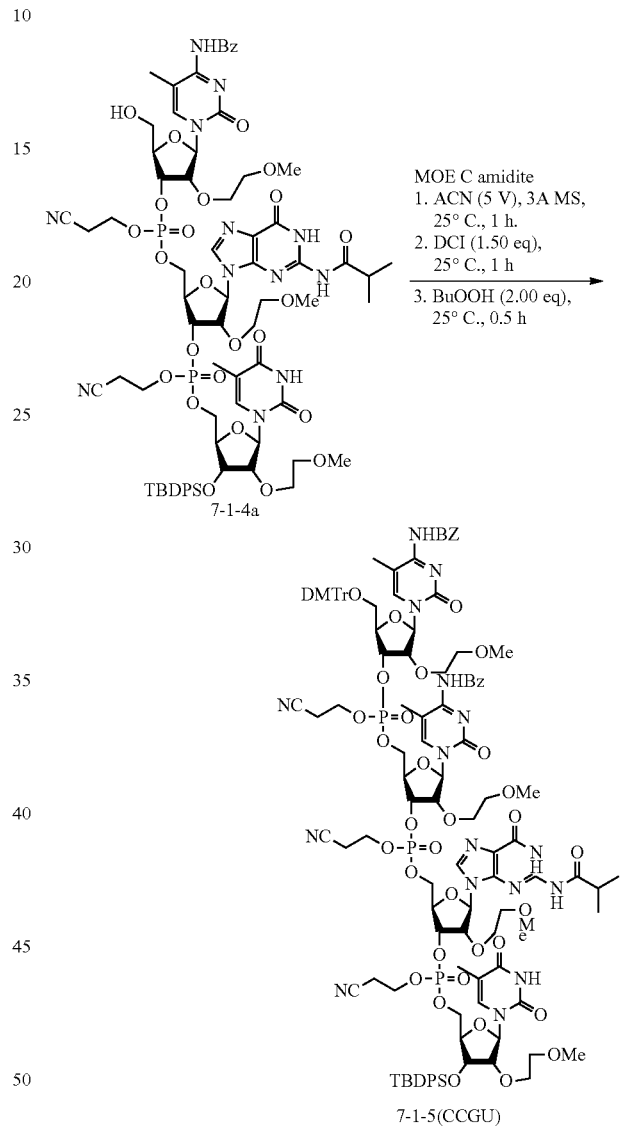

Compound 7-1-4a (13.0 g, 8.04 mmol, 1.00 eq) and MOE C amidite (8.17 g, 8.84 mmol, 1.10 eq) were co-evaporated with ACN (30 mL×3) under Ar in a 250 mL single-necked round bottle, and 3 Å molecular sieve (3.50 g) were added to the single-necked bottle, under Ar pressure ACN (65 mL) was added. The mixture was stir at 25° C. for 1 h, and then DCI (1.42 g, 12.0 mmol, 1.50 eq) was added to the mixture. The mixture was stirred at 25° C. for 1 h. HPLC (product: RT=8.547 min; starting material: RT=6.127, 6.193, 6.277 min) showed the starting material was consumed completely.

To the above solution was added BuOOH (2.07 g, 16.0 mmol, 2.20 mL, 70.0% purity, 2.00 eq) at 25° C. The mixture was stirred at 25° C. for 0.5 h. HPLC (7-5, product:

RT=8.400 min; starting material: RT=8.547 min) showed the starting material was consumed completely.

The reaction mixture was poured into the NaHCO₃ and Na₂SO₃ solution (10.0 eq NaHCO₃ and 5.00 eq Na₂SO₃ in 500 mL DI water), and then dilute the mixture with EtOAc (300 mL) and two layers were separated, the organic layer was washed with NaHCO₃ (200 mL), brine (200 mL), dried filtered and concentrated. The crude was re-dissolved in DCM (50 mL). The crude solvent was slowly dropped to a solvent of isopropyl ether (600 mL). Desired product was precipitated out. The product was collected as a light-yellow solid after filtration, and the solid cake was washed with isopropyl ether (50 mL×2). Compound 7-1-5 (CCGU) (15.0 g, 5.94 mmol, 73.9% yield, 97.3% purity) was obtained as a yellow solid after HPLC purification. HPLC (Method B): RT=8.400 min, and LCMS (Method F): RT=1.665 min; m/z: [M+2H]²⁺/2=1226.4

Preparation of DMTr-CCGU-OH (7-1-6)

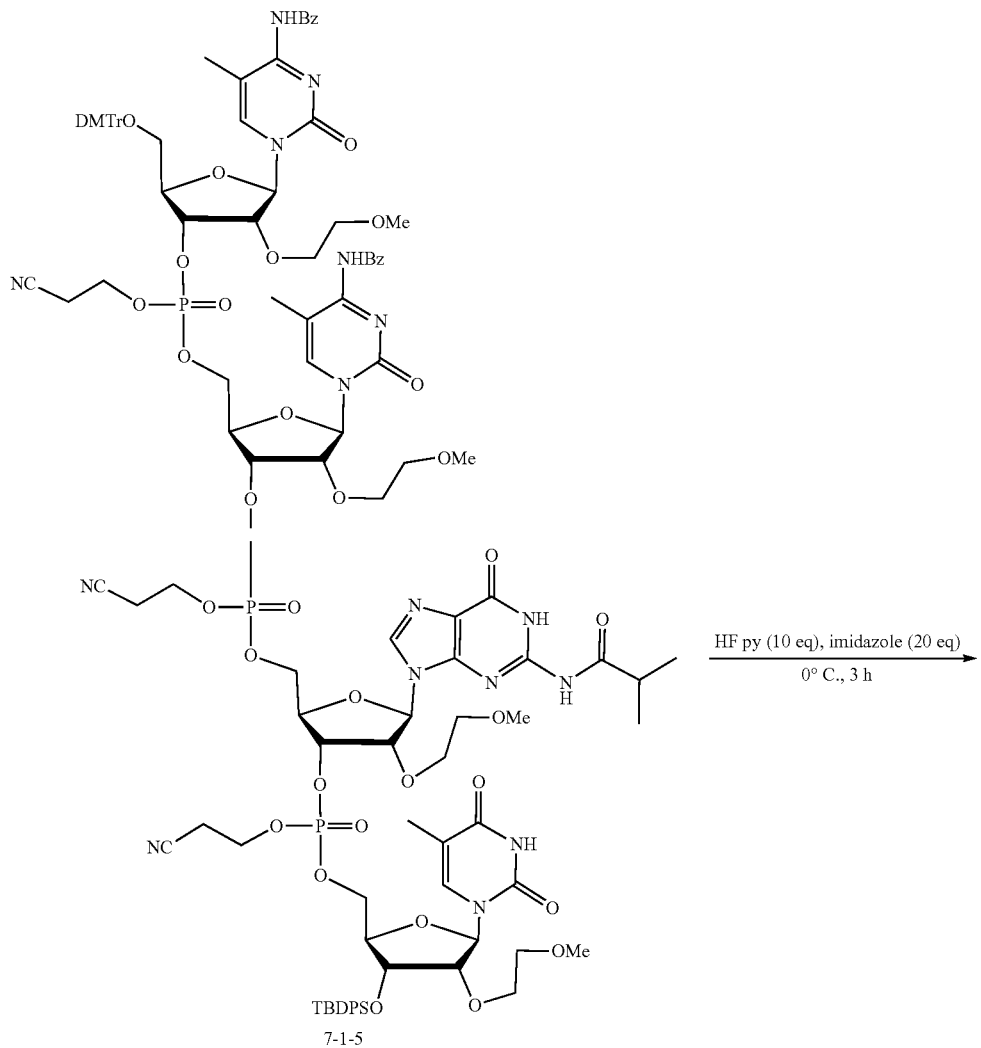

-continued
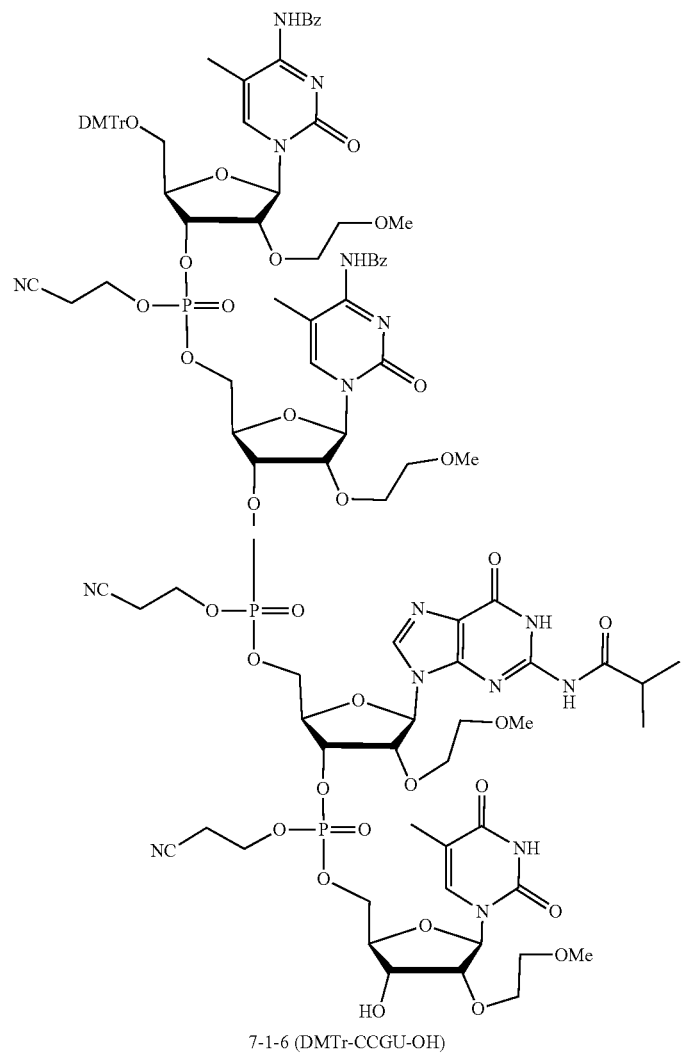
7-1-6 (DMTr-CCGU-OH)

To a solution of 7-1-5 (6.00 g, 2.44 mmol, 1.00 eq) in ACN (35 mL) and then pyridine; hydrofluoride (698 mg, 24.4 mmol, 634 μL, 70.0% purity, 10.0 eq) and imidazole (3.33 g, 48.8 mmol, 20.0 eq) in THF (8 mL) was added dropwise at 0° C. The mixture was stirred at 0° C. for 3 h. TLC (Dichloromethane:Methanol=10:1, Product: $R_f$=10:1) indicated compound 7-1-5 was consumed completely and two new spots formed. The reaction was messy according to TLC.

The reaction mixture was dissolved in the EtOAc (20 mL). The organic layer was washed with saturated aq·NaHCO$_3$ (20 mL×2), brine (20 mL) and dried by anhydrous Na$_2$SO$_4$, filtered and concentrated in vacuum. The crude was re-dissolved in DCM (5 mL). The crude solvent was slowly dropped to a solvent of MTBE (50 mL). Desired product was precipitated out. The product was collected as a white solid after filtration, and the solid cake was washed with isopropyl ether MTBE (50 mL×2). Compound 7-1-6 (4.90 g, 2.07 mmol, 84.5% yield, 93.5% purity) was obtained as a white solid. HPLC (Method B): RT=10.986, 11.182, 11.264 min, and LCMS (Method F): RT=1.502 min; m/z: [M+2H]2/2=1107.4.

Preparation of DMTr-CCGU-OH (7-1-6a)

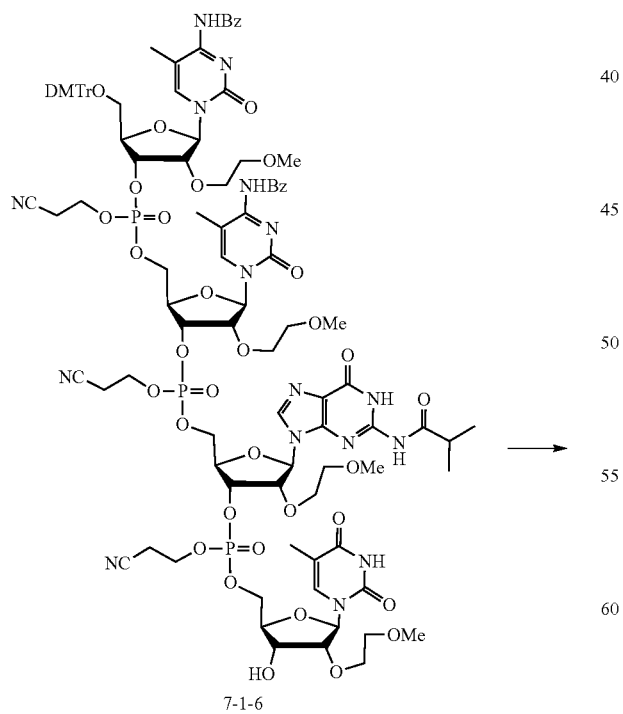

7-1-6

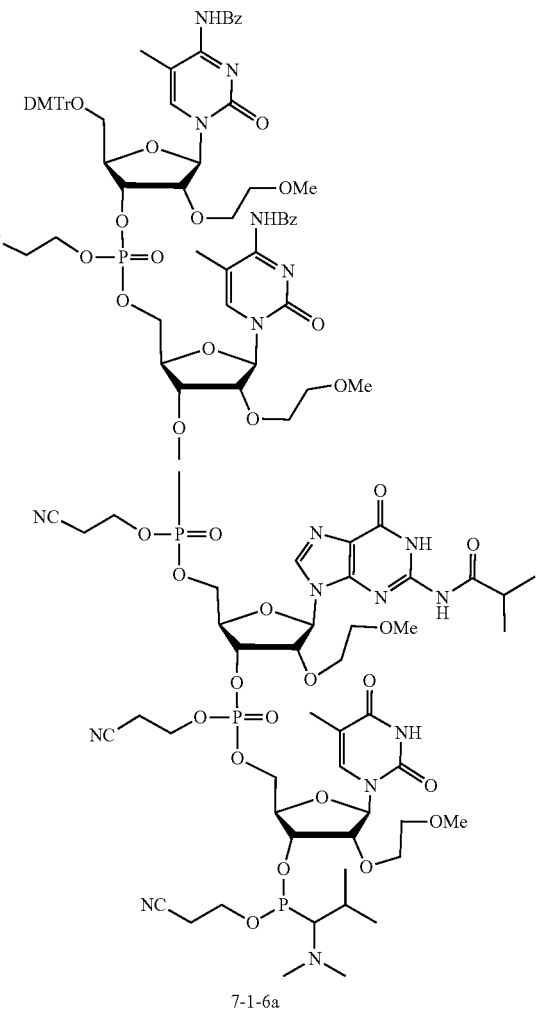

7-1-6a 7-1-6a was synthesized from 7-1-6 using similar procedure as described above for the phosphoramidite synthesis. HPLC-MS (Method G): RT=9.740, 9.843, 9.949 min; m/z: [M−2H]2/2=1205.8 for compound 7-1-6a.

Preparation of HO-CCGU-OTBDPS (7-1-7)
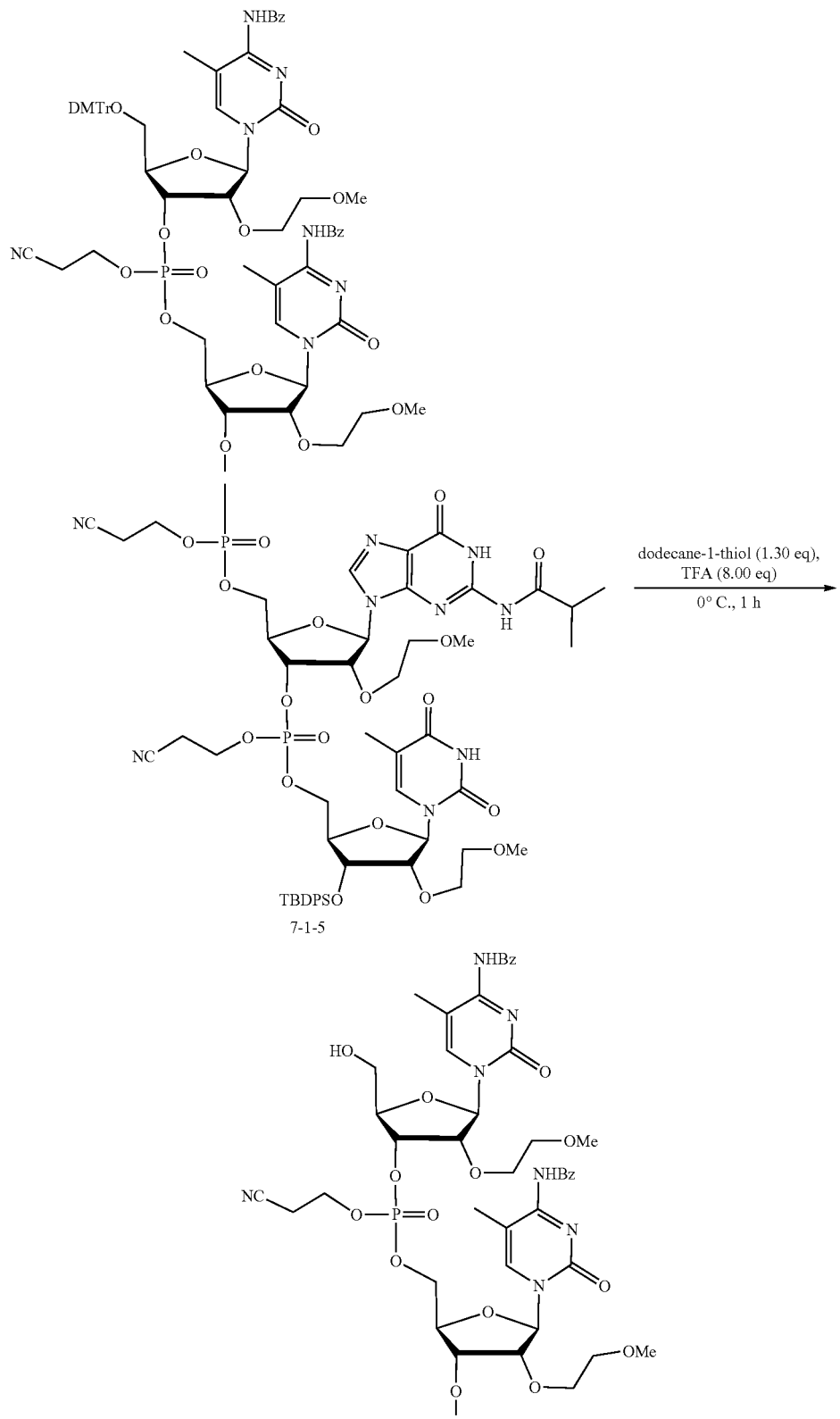

-continued

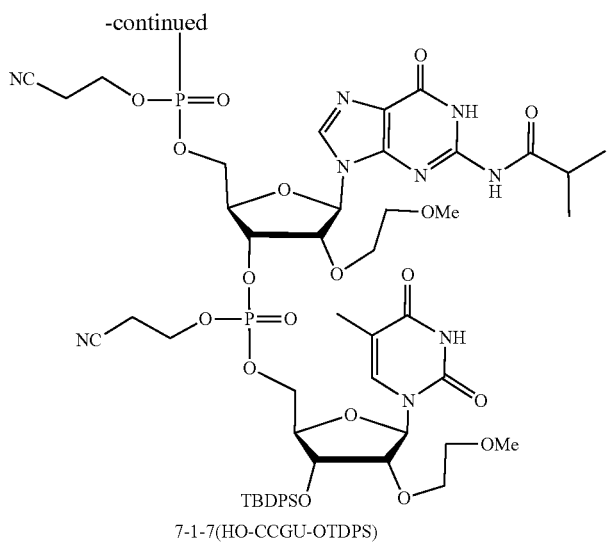

7-1-7(HO-CCGU-OTDPS)

To a solution of 7-1-5 (6.20 g, 2.52 mmol, 1.00 eq) in ACN (30 mL) was added dodecane-1-thiol (766 mg, 3.79 mmol, 906 µL, 1.50 eq) at 0° C., and then TFA (2.30 g, 20.1 mmol, 1.49 mL, 8.00 eq) was added dropwise at 0° C. The mixture was stirred at 0° C. for 1 h. TLC (DCM:MeOH=10: 1, Product: $R_f$=0.35) indicated compound 7-1-5 was consumed completely and two new spots formed. The reaction was messy according to TLC.

The reaction mixture was poured into the NaHCO$_3$ (10.0 eq NaHCO$_3$ in 100 mL DI water), and then diluted with EtOAc 50 mL and extracted with aq·NaHCO$_3$ 100 mL. The combined organic layers were washed with brine 200 mL (100 mL×2), dried over Na$_2$SO$_4$, filtered and concentrated under reduced pressure to give a residue. The crude was re-dissolved in DCM (80 mL). The crude solvent was slowly dropped to a solvent of MTBE (300 mL). Desired product was precipitated out. The product was collected as a white solid after filtration, and the solid cake was washed with isopropyl ether MTBE (50 mL×2).

Compound 7-1-7 (4.86 g, 2.18 mmol, 86.4% yield, 96.6% purity) was obtained as a white solid with HPLC purification. HPLC (Method B): RT=0.664, 10.794, 10.917 min, and LCMS (Method F): RT=1.431 min; m/z: [M+2H]$^2$+/ 2=1075.9.

B. Preparation of 3' fragment

1. General procedure for preparation of 5'-OH-ACCCU-LHPG 5mer (Fragment 1)

General procedure for preparation of compound 7-2-1

-continued

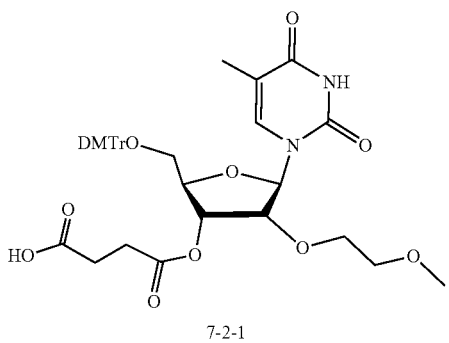

7-2-1

Compound 7-2-a was co-evaporated with toluene (60.0 ml×3). To a solution of compound 7-2-a (10.0 g, 16.1 mmol, 1.00 eq) in DCM (100 mL) was added N,N-diethylethanamine (8.18 g, 80.8 mmol, 11.2 mL, 5.00 eq) and tetrahydrofuran-2,5-dione (3.24 g, 32.3 mmol, 2.00 eq). The mixture was stirred at 25° C. for 4 hr. HPLC indicated compound 7-2-a was consumed completely. The reaction mixture washed with TEAB (0.5 M, 300 ml), dried over anhydrous Na$_2$SO$_4$, filtered and concentrated under reduced pressure to give a residue. Compound 7-2-1 (11.0 g, 15.3 mmol, 94.6% yield) was obtained as a brown solid. HPLC (Method A): RT=2.405 min General procedure for preparation of compound 7-2-2

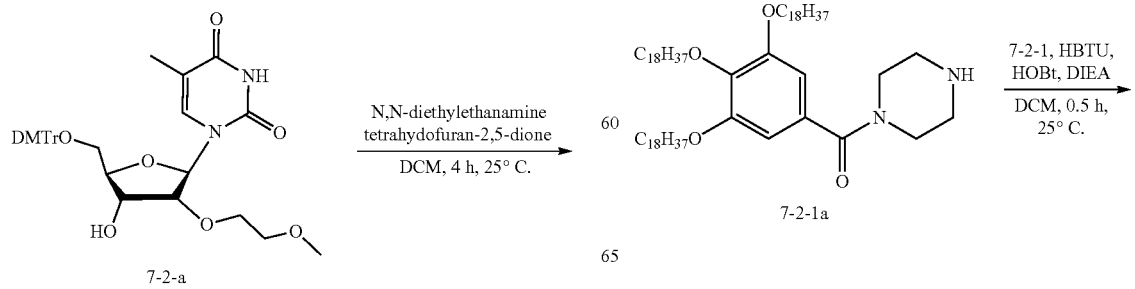

-continued

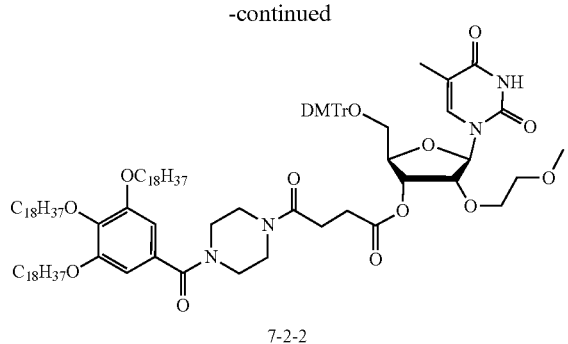

7-2-2

To a solution of compound 7-2-1a (10.1 g, 10.2 mmol, 1.00 eq) in DCM (300 mL) was added compound 7-2-2 (11.0 g, 14.5 mmol, 1.43 eq, HCl), HBTU (13.1 g, 34.6 mmol, 3.40 eq), HOBt (4.69 g, 34.6 mmol, 3.40 eq) and DIEA (4.48 g, 34.6 mmol, 6.04 mL, 3.40 eq). The mixture was stirred at 25° C. for 0.5 hr. TLC (start material, $R_f$=0.38, product, $R_f$=0.42) indicated compound 7-2-1a was consumed completely. The reaction mixture was concentrated under reduced pressure to remove solvent. The crude product was triturated with ACN (700 ml) at 25° C. for 15 min. Then filtered and washed with ACN (100 ml×2). Compound 7-2-2 (16.0 g, 9.43 mmol, 92.4% yield) was obtained as a brown solid.

General procedure for preparation of compound 7-2-3

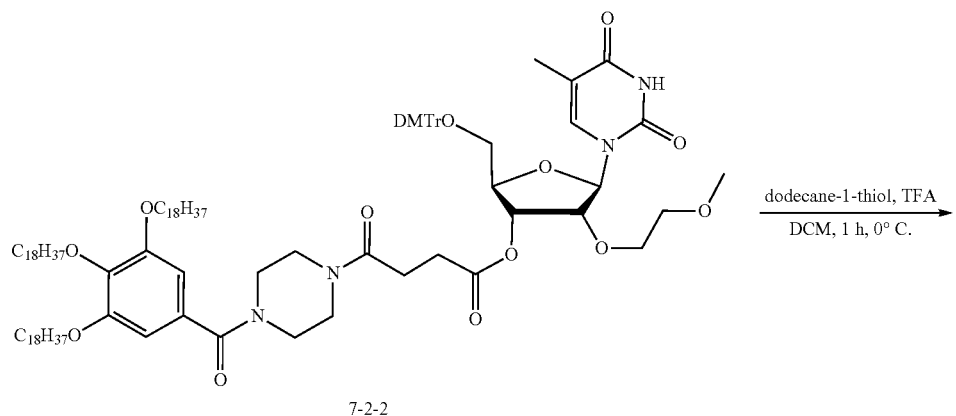

7-2-2

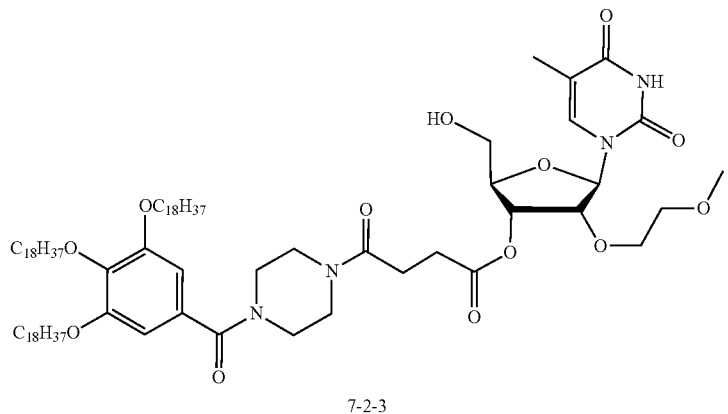

7-2-3

To a solution of compound 7-2-2 (16.0 g, 9.43 mmol, 1.00 eq) in DCM (160 mL) was added dodecane-1-thiol (5.73 g, 28.3 mmol, 6.78 mL, 3.00 eq) and TFA (10.7 g, 94.3 mmol, 6.98 mL, 10.0 eq). The mixture was stirred at 0° C. for 1 hr. TLC (DCM:MeOH=10:1, start material, $R_f$=0.50, product, $R_f$=0.43) indicated compound 7-2-2 was consumed completely. The reaction mixture was washed with aq. sat. NaHCO$_3$ until pH>7, extracted with Dichloromethane (300 mL), washed with brine (200 ml), dried over anhydrous Na$_2$SO$_4$, filtered and concentrated under reduced pressure to give a residue. The crude product was triturated with ACN (800 ml) at 25° C. for 30 min. Then filtered and washed with ACN (100 ml×2). Compound 7-2-3 (11.7 g, 8.39 mmol, 88.9% yield) was obtained as a white solid.

General procedure for preparation of compound 7-2-4

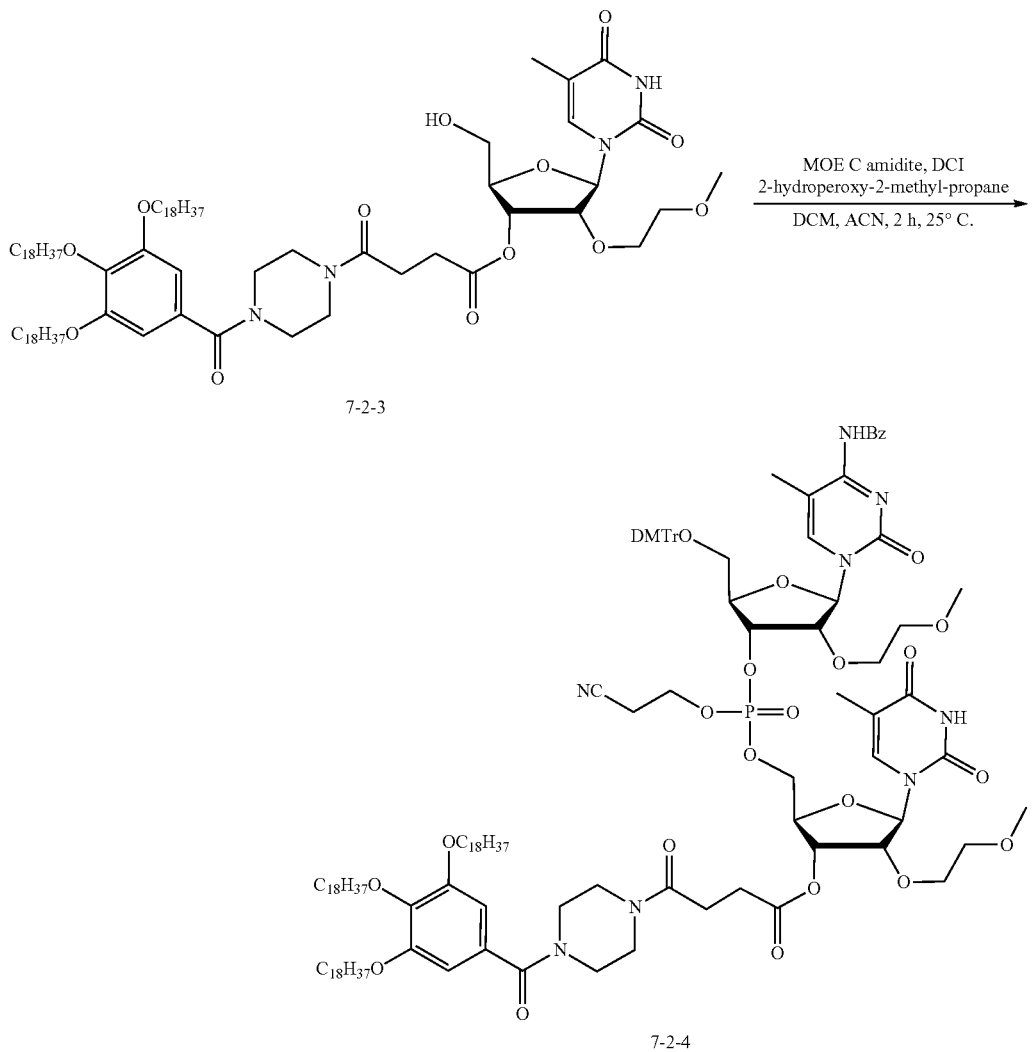

Compound 7-2-3 and MOE C amidite was co-evaporated with (ACN 60.0 ml×3) and (DCM 20.0 ml×3). To a solution of compound 7-2-3 (11.7 g, 8.39 mmol, 1.00 eq) and MOE C amidite (15.4 g, 16.7 mmol, 2.00 eq) was added in DCM (120 mL) and ACN (20 mL), then added 3A MS, the mixture was stirred for 1 h, then added DCI (2.98 g, 20.98 mmol, 2.50 eq) in the mixture, the mixture was stirred for 0.5 h, then added 2-hydroperoxy-2-methyl-propane (3.24 g, 25.1 mmol, 5.04 mL, 5M, 3.00 eq) in the mixture, the mixture was stirred for 0.5 h at 25° C. TLC (DCM:MeOH=20:1, start material, $R_f$=0.43, product, $R_f$=0.48) indicated compound 7-2-3 was consumed completely. The reaction mixture was washed with aqueous NaHCO$_3$ and aqueous Na$_2$SO$_3$ (200 ml), washed with brine (200 ml), filtered and concentrated under reduced pressure to give a residue. The crude product was triturated with ACN (350 ml) at 25° C. for 30 min. Then filtered and washed with ACN (100 ml×2). Compound 7-2-4 (17.1 g, 7.33 mmol, 87.2% yield) was obtained as a white solid.

General procedure for preparation of compound 7-2-5

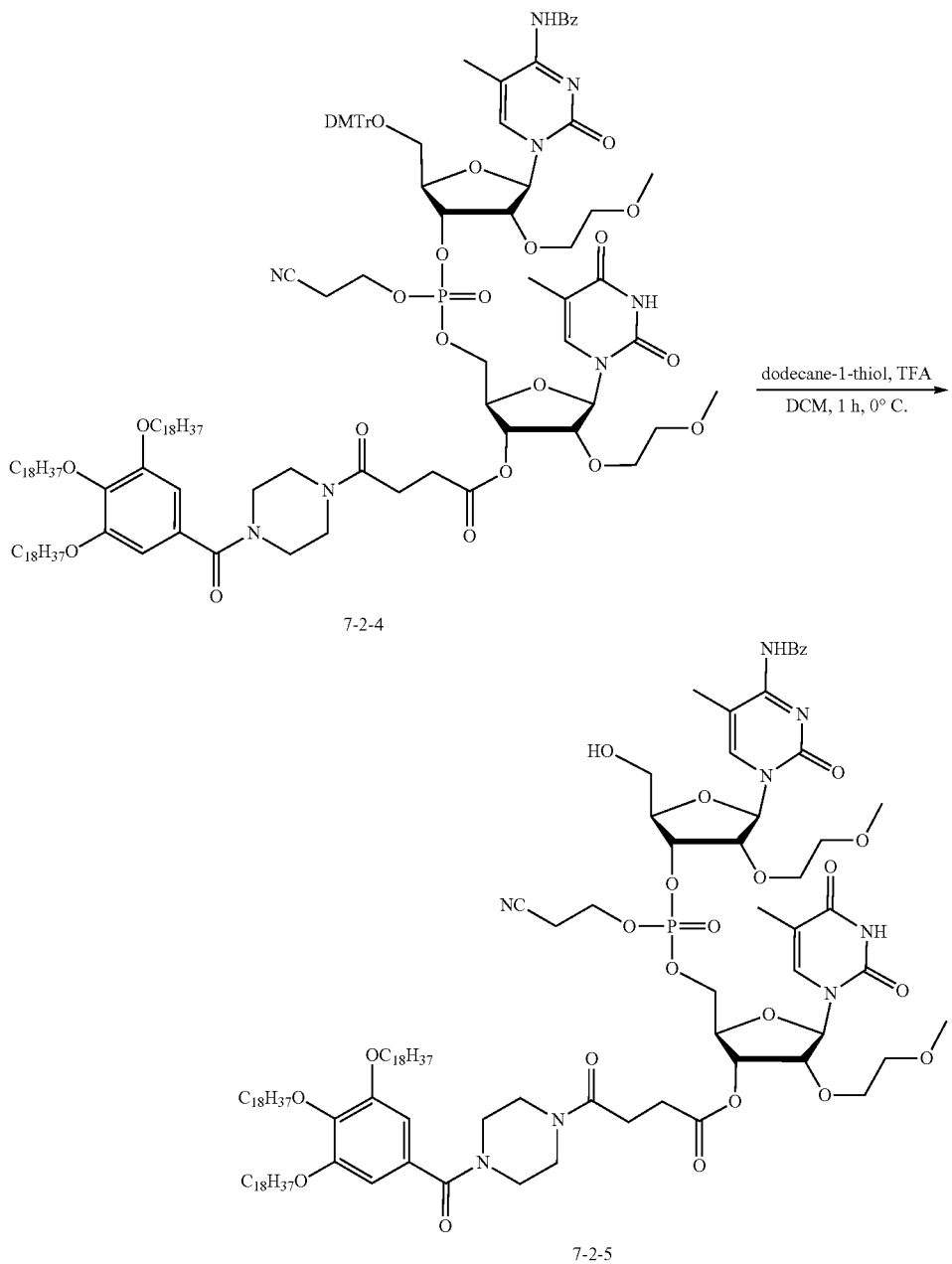

To a solution of compound 7-2-4 (17.1 g, 7.33 mmol, 1.00 eq) in DCM (170 mL) was added dodecane-1-thiol (4.45 g, 21.9 mmol, 5.26 mL, 3.00 eq) and TFA (8.35 g, 73.2 mmol, 5.42 mL, 10.0 eq). The mixture was stirred at 0° C. for 1 hr. TLC (DCM:MeOH=10:1, start material, $R_f$=0.43, product, $R_f$=0.48) indicated compound 7-2-4 was consumed completely. The reaction mixture was washed with aqueous saturated $NaHCO_3$ until pH>7, extracted with Dichloromethane (300 mL), washed with brine (200 ml), dried over anhydrous $Na_2SO_4$, filtered and concentrated under reduced pressure to give a residue. The crude product was triturated with ACN at 0° C. for 30 min. Then filtered and washed with ACN (100 ml×2). Compound 7-2-5 (13.7 g, 6.74 mmol, 92.0% yield) was obtained as a white solid.

General procedure for preparation of compound 7-2-6

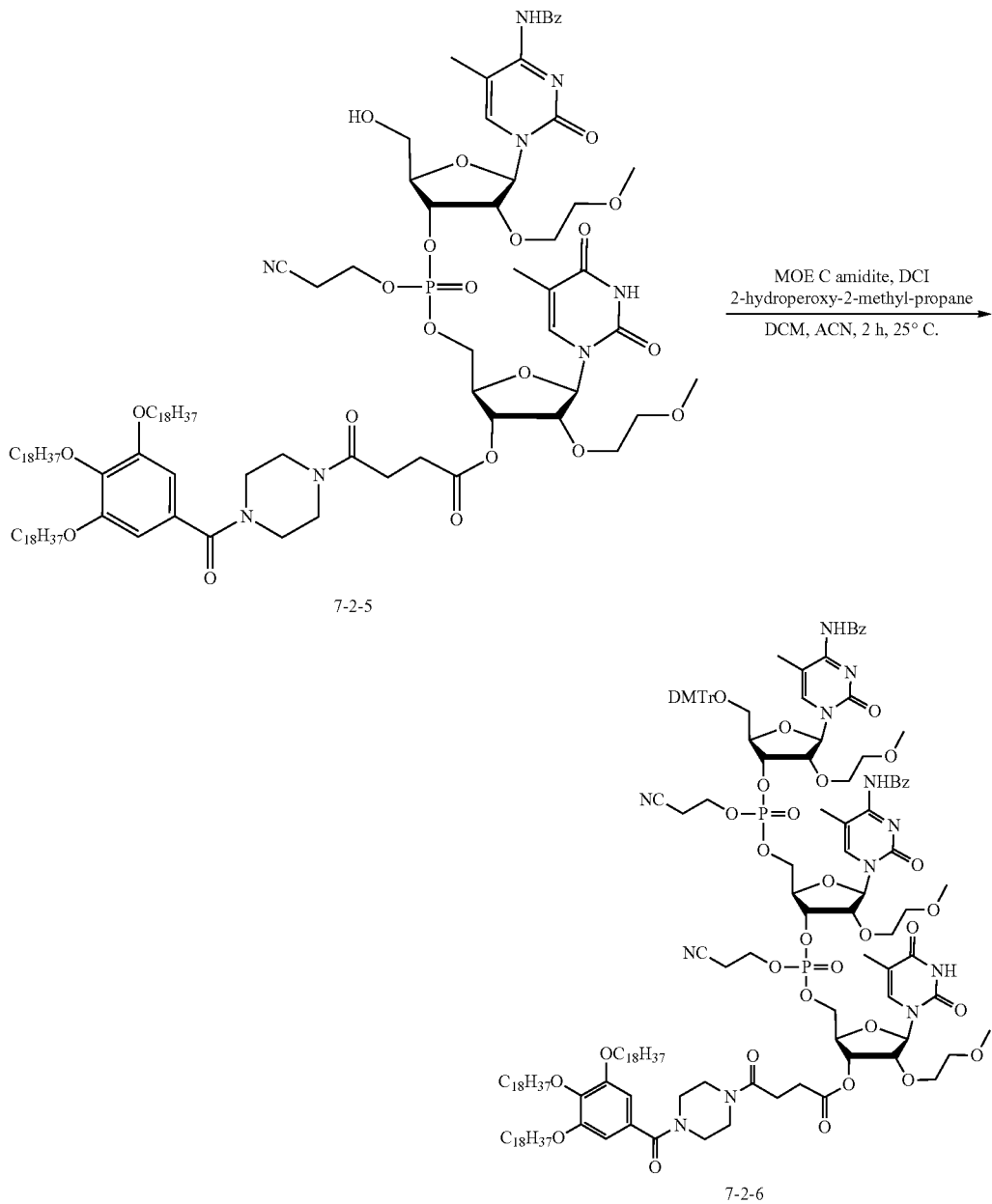

Compound 5 and MOE C amidite was co-evaporated with (ACN 80.0 ml×3) and (DCM 30.0 ml×3). To a solution of compound 7-2-5 (13.7 g, 6.74 mmol, 1.00 eq) and MOE C amidite (12.4 g, 13.4 mmol, 2.00 eq) was added in DCM (80.0 mL) and ACN (20.0 mL), then added 3 Å molecular sieves, the mixture was stirred for 1 h, then added DCI (2.39 g, 16.8 mmol, 2.50 eq) in the mixture, the mixture was stirred for 0.5 h, then added 2-hydroperoxy-2-methyl-propane (5 M, 4.05 mL, 3.00 eq) in the mixture, the mixture was stirred for 0.5 h at 25° C. TLC (DCM:MeOH=15:1, start material, $R_f$=0.43, product, $R_f$=0.50) indicated compound 7-2-5 was consumed completely. The reaction mixture was filtered. The filtrate was triturated with ACN at 25° C. for 30 min. Then filtered and washed with ACN (100 ml×2). Compound 7-2-6 (17.0 g, 6.15 mmol, 91.1% yield) was obtained as a white solid.

General procedure for preparation of compound 7-2-7
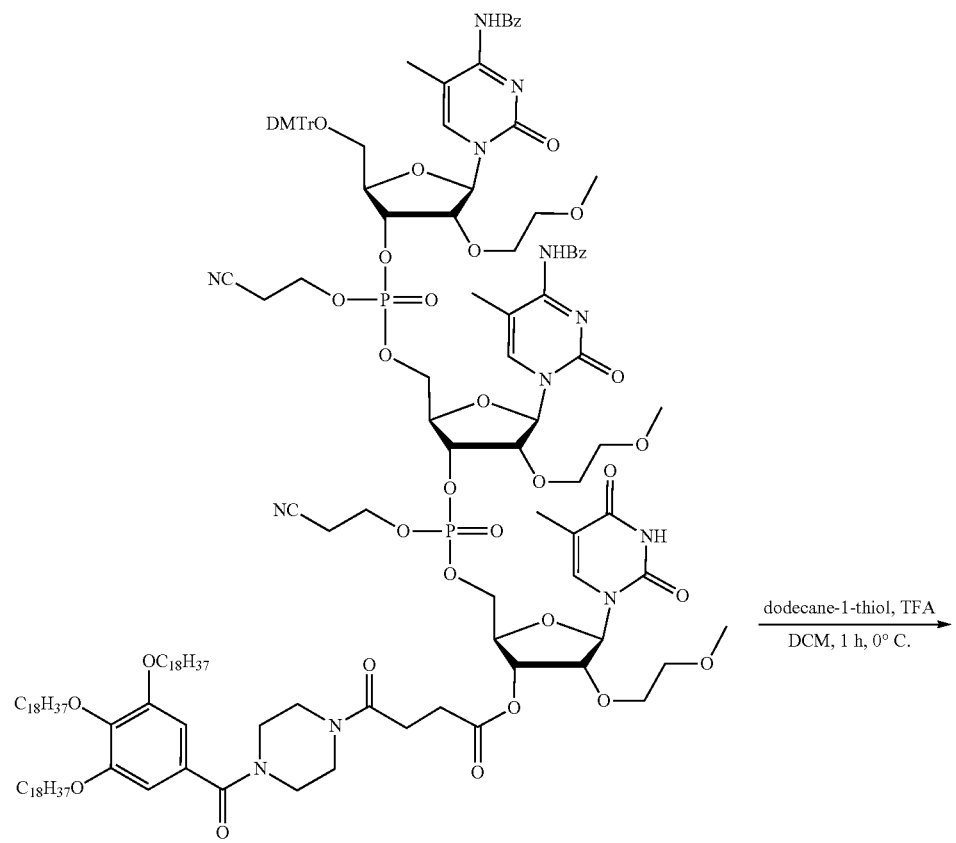
7-2-6

-continued

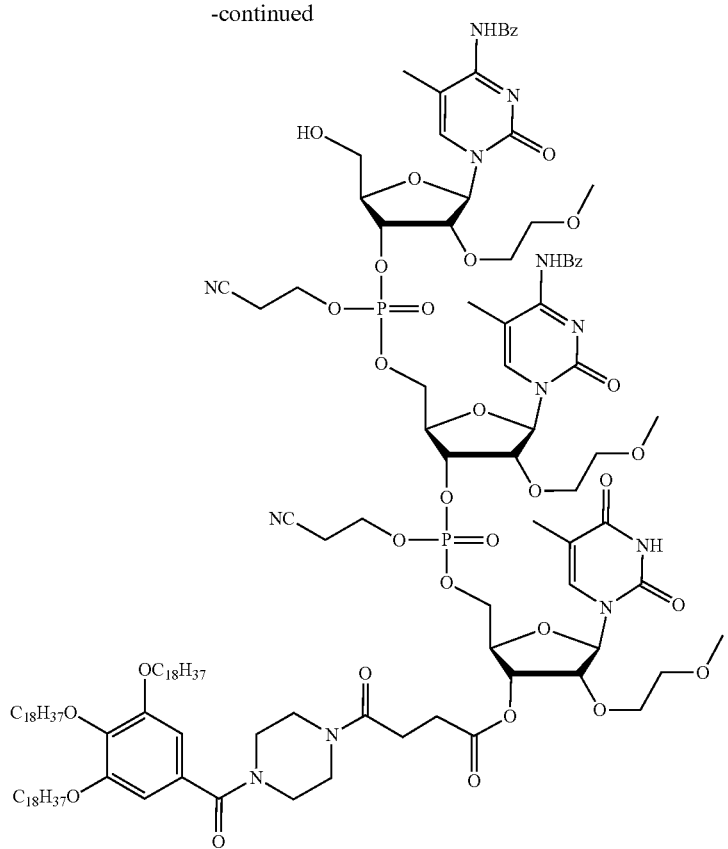

7-2-7

To a solution of compound 7-2-6 (17.0 g, 6.15 mmol, 1.00 eq) in DCM (190 mL) was added dodecane-1-thiol (3.73 g, 18.4 mmol, 4.42 mL, 3.00 eq) and TFA (7.01 g, 61.4 mmol, 4.55 mL, 10.0 eq). The mixture was stirred at 0° C. for 1 hr. TLC (DCM:MeOH=10:1, start material, $R_f$=0.43, product, $R_f$=0.38) indicated compound 7-2-6 was consumed completely. The reaction mixture was washed with aq. Saturated NaHCO$_3$ until pH>7, extracted with Dichloromethane (300 mL), washed with brine (200 ml), dried over anhydrous Na$_2$SO$_4$, filtered and concentrated under reduced pressure to give a residue. The crude product was triturated with ACN at 0° C. for 30 min. Then filtered and washed with ACN (100 ml×2). Compound 7-2-7 (14.7 g, 5.97 mmol, 97.0% yield) was obtained as a white solid.

General procedure for preparation of compound 7-2-8
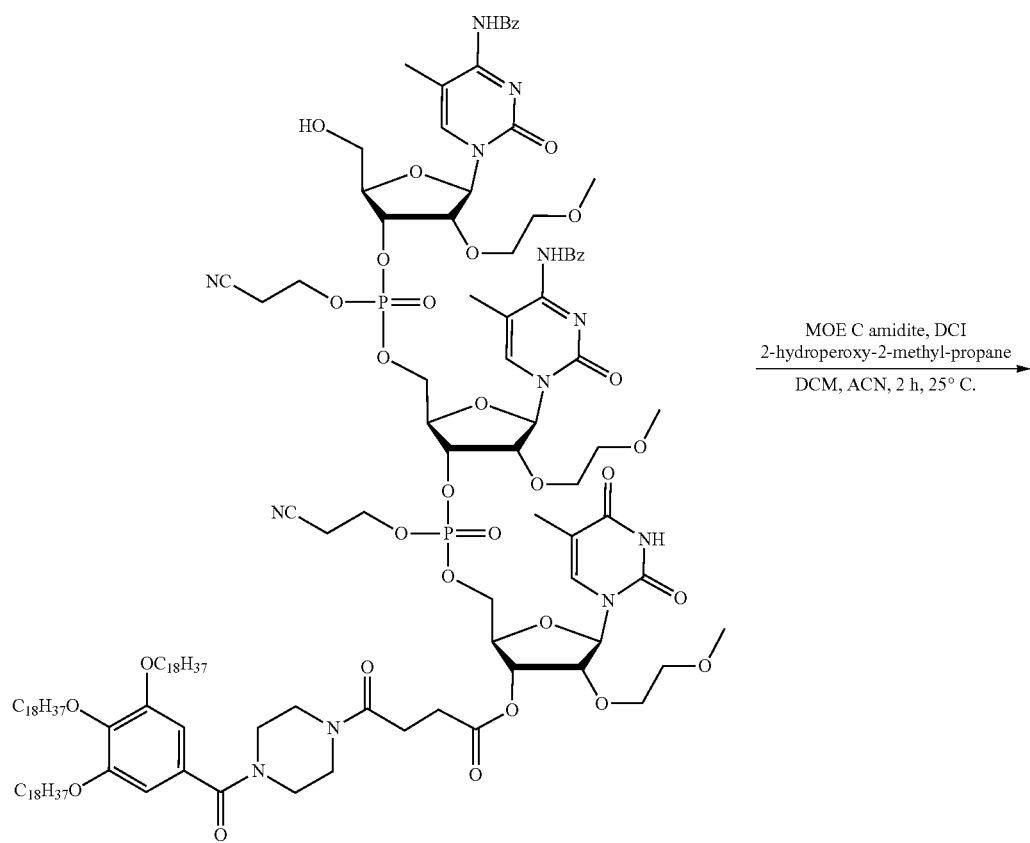

-continued

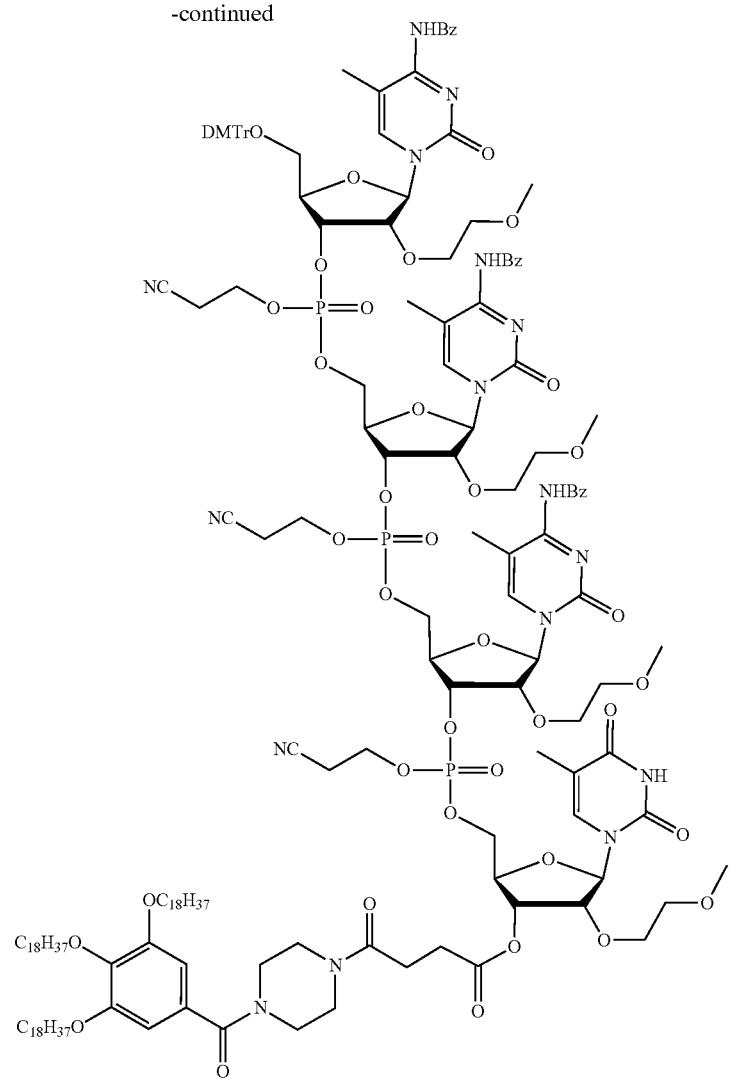

7-2-8

Compound 7-2-7 and MOE C amidite was co-evaporated with (ACN 60.0 ml×3) and (DCM 20.0 ml×3). To a solution of compound 7-2-7 (13.0 g, 5.31 mmol, 1.00 eq) and MOE C amidite (9.80 g, 10.6 mmol, 2.00 eq) was added in DCM (60.0 mL) and ACN (20.0 mL), then added 3 Å molecular sieves (MS), the mixture was stirred for 1 h, then added DCI (1.89 g, 13.2 mmol, 2.50 eq) in the mixture, the mixture was stirred for 0.5 h, then added 2-hydroperoxy-2-methyl-propane (5 M, 3.19 mL, 3.00 eq) in the mixture, the mixture was stirred for 0.5 h at 25° C. TLC (DCM:MeOH=15:1, start material, $R_f$=0.43, product, $R_f$=0.48) indicated compound 7-2-7 was consumed completely. The reaction mixture was filtered. The filtrate was triturated with ACN (800 ml) at 25° C. for 30 min. Then filtered and washed with ACN (100 ml×2). Compound 7-2-8 (14.4 g, 4.36 mmol, 82.1% yield) was obtained as a white solid.

General procedure for preparation of compound 7-2-9
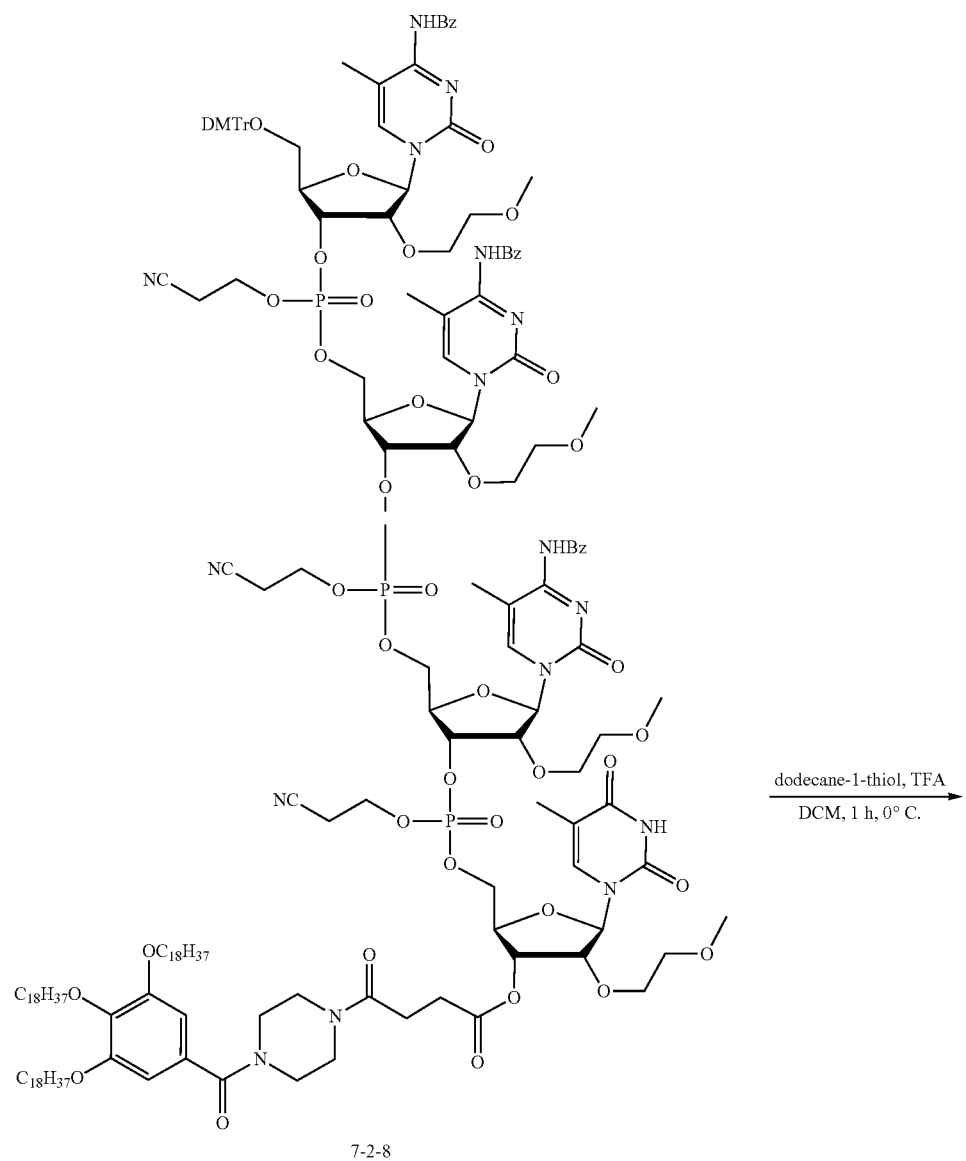
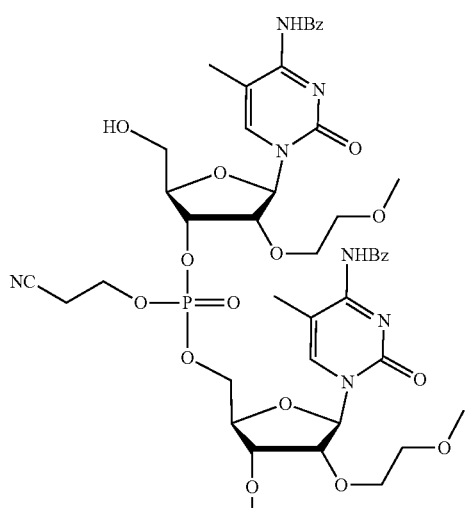

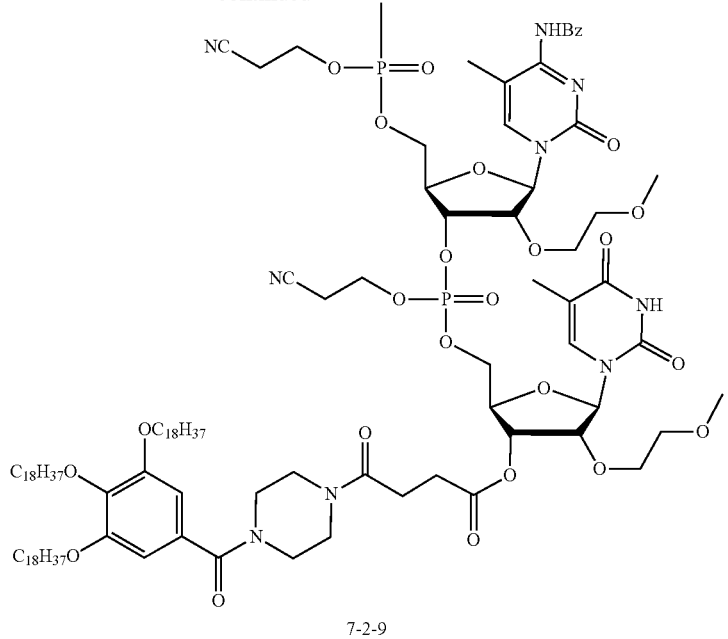

7-2-9

To a solution of compound 7-2-8 (14.47 g, 4.39 mmol, 1.00 eq) in DCM (70.0 mL) was added dodecane-1-thiol (2.66 g, 13.1 mmol, 3.15 mL, 3.00 eq) and TFA (5.00 g, 43.8 mmol, 3.25 mL, 10.0 eq). The mixture was stirred at 0° C. for 1 hr. TLC (DCM:MeOH=10:1, start material, $R_f$=0.43, product, $R_f$=0.38) indicated compound 7-2-8 was consumed completely. The reaction mixture was washed with aq. sat. NaHCO₃ until pH>7, extracted with Dichloromethane (300 mL), washed with brine (200 ml), dried over anhydrous Na₂SO₄, filtered and concentrated under reduced pressure to give a residue. The crude product was triturated with ACN (800 ml) at 25° C. for 30 min. Then filtered and washed with ACN (100 ml×2). Compound 7-2-9 (11.6 g, 3.88 mmol, 88.5% yield) was obtained as a white solid.

General procedure for preparation of compound 7-2-10

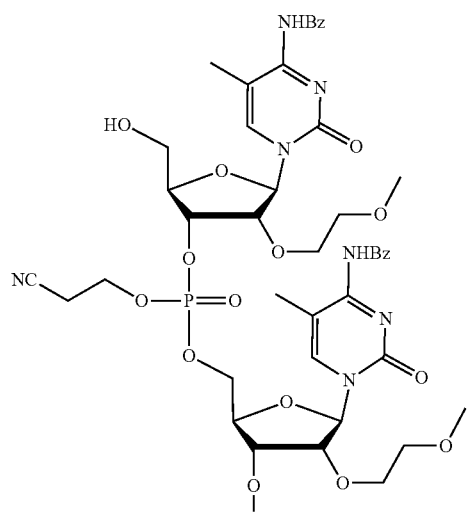

-continued
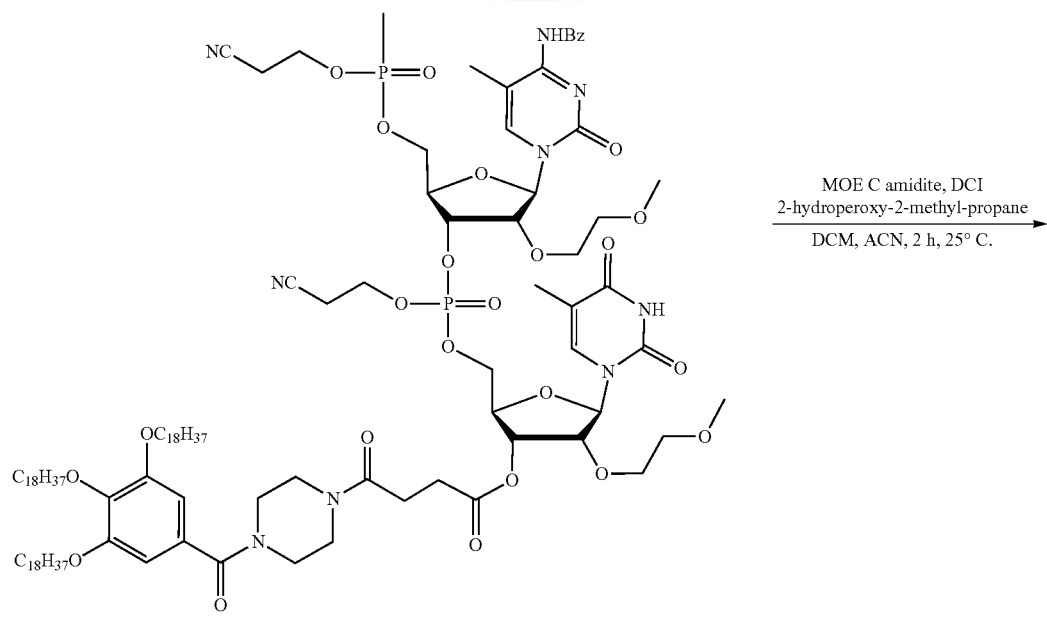
7-2-9
MOE C amidite, DCI
2-hydroperoxy-2-methyl-propane
―――――――――――――→
DCM, ACN, 2 h, 25° C.
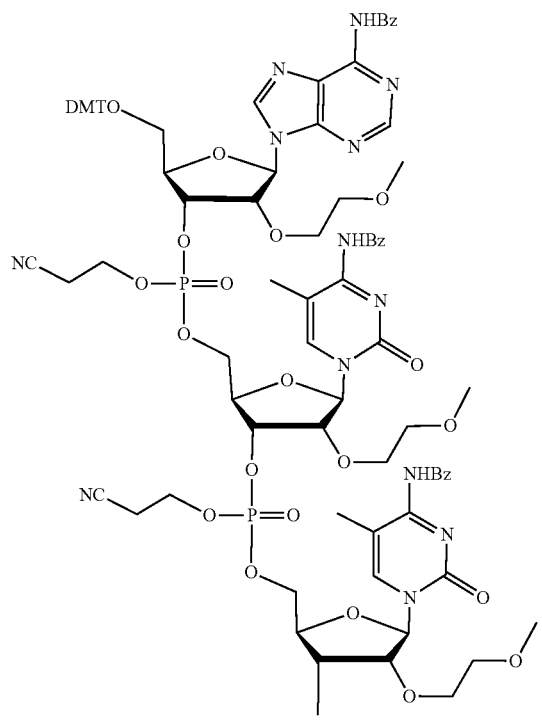

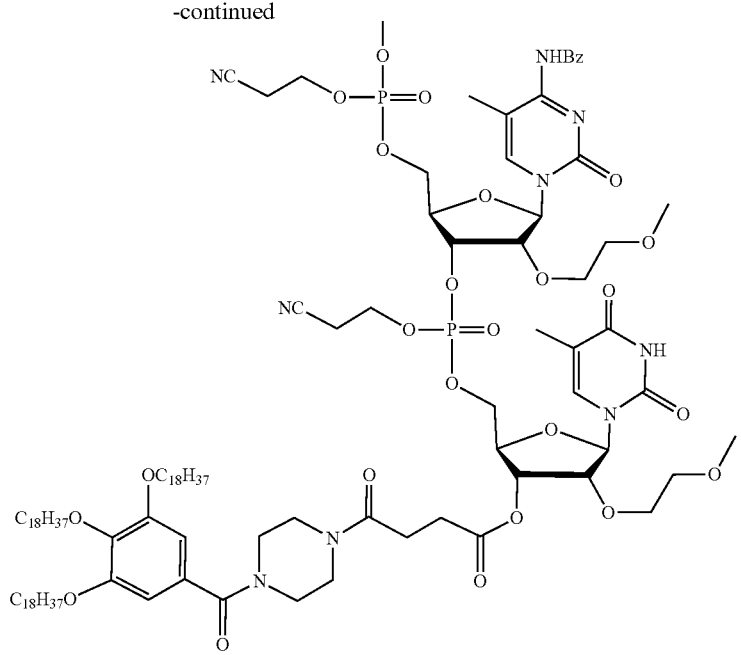

7-2-10

Compound 7-2-9 and MOE A amidite was co-evaporated with (ACN 60 ml×3) and (DCM 20 ml×3). To a solution of compound 7-2-9 (11.6 g, 3.87 mmol, 1.00 eq) and MOE A amidite (7.21 g, 7.74 mmol, 2.00 eq) was added in DCM (60.0 mL) and ACN (20.0 mL), then added 3 Å MS, the mixture was stirred for 1 h, then added DCI (1.37 g, 9.67 mmol, 2.50 eq) in the mixture, the mixture was stirred for 0.5 h, then added 2-hydroperoxy-2-methyl-propane (5 M, 2.32 mL, 3.00 eq) in the mixture, the mixture was stirred for 0.5 h at 25° C. TLC (DCM:MeOH=15:1, start material, $R_f$=0.43, product, $R_f$=0.47) indicated compound 7-2-9 was consumed completely. The reaction mixture was filtered. The filtrate was triturated with ACN (800 ml) at 25° C. for 30 min. Then filtered and washed with ACN (100 ml×2). Compound 7-2-10 (14.0 g, 3.64 mmol, 94.1% yield) was obtained as a white solid.

General procedure for preparation of Fragment 1

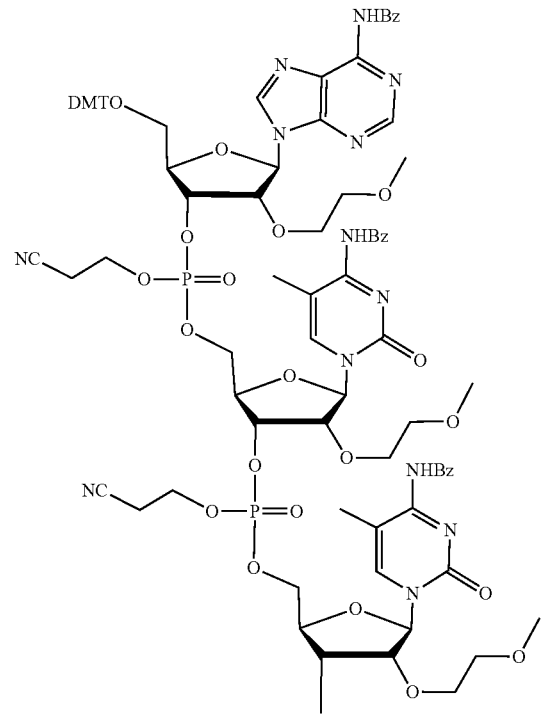

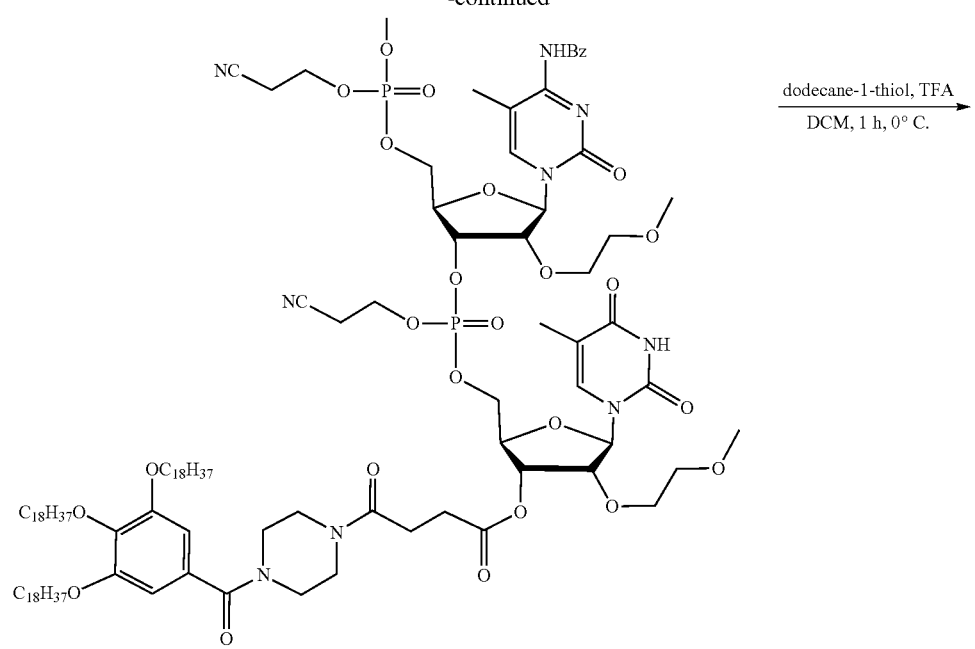
7-2-10
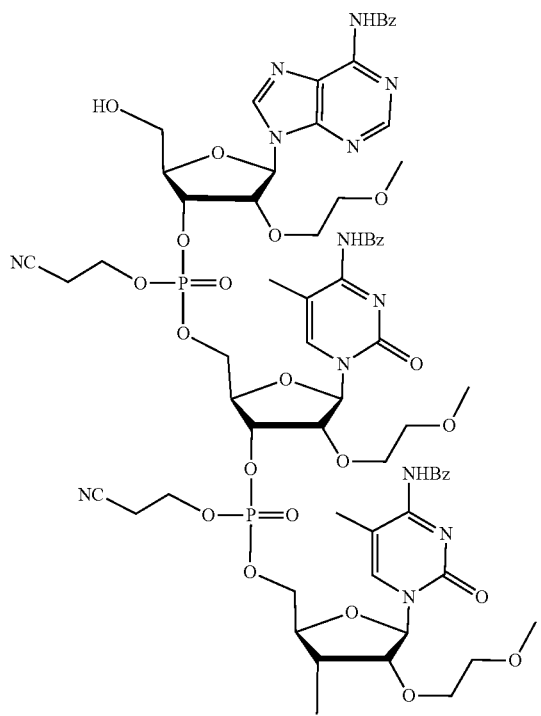

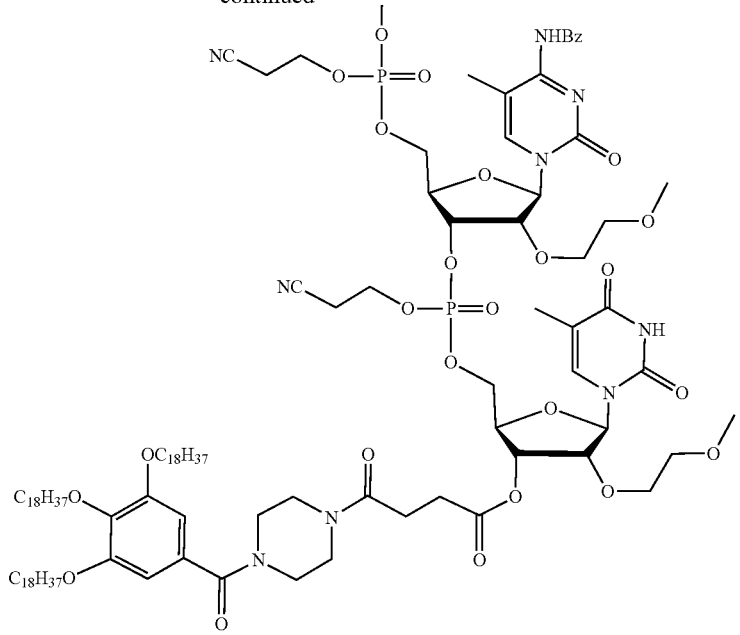

7-2-11(Fragment 1)

To a solution of compound 7-2-10 (14.0 g, 3.64 mmol, 1.00 eq) in DCM (70.0 mL) was added dodecane-1-thiol (2.21 g, 10.9 mmol, 2.62 mL, 3.00 eq). The mixture was stirred at 0° C. for 1 h. TLC (DCM:MeOH=15:1, start material, $R_f$=0.43, product, $R_f$=0.39) indicated compound 7-2-10 was consumed completely. The reaction mixture was washed with aq. sat. NaHCO$_3$ until pH>7, extracted with Dichloromethane (300 mL), washed with brine (200 ml), dried over anhydrous Na$_2$SO$_4$, filtered and concentrated under reduced pressure to give a residue. The crude product was triturated with ACN (800 ml) at 25° C. for 30 min. Then filtered and washed with ACN (100 ml×2). Compound 7-2-10 (Fragment 1) (10.0 g, 2.82 mmol, 77.5% yield) was obtained as a white solid. 7-2-10 (Fragment 1) was characterized by HPLC and Mass Spectrometry after deprotecting LHPG group using ammonolysis. HPLC (Method C): RT=2.11 min and LCMS (Method D): RT=0.219 min; m/z: [M−2H]2/2=916.6.

2. General procedure for preparation of 5'-Deoxy-TTACC 5mer or 5'-DMTr-TTACC-OH or 5'-OH-TTACC-TBDPS 5mer (Fragment 2)

General procedure for preparation of compound 7-3-2

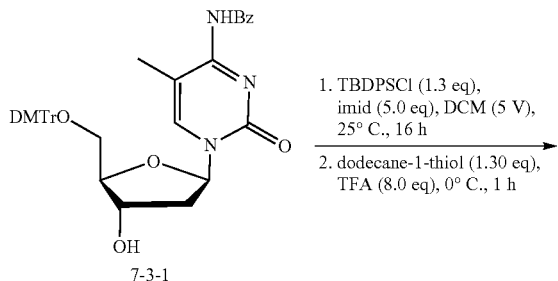

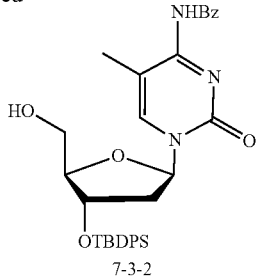

7-3-2

To a solution of compound 7-3-1 (40.0 g, 61.7 mmol, 1.00 eq) in DCM (200 mL) was added imidazole (21.0 g, 308 mmol, 5.00 eq). The mixture was light yellow homogenous solution. TBDPSCl (22.0 g, 80.2 mmol, 20.6 mL, 1.30 eq) was added. The mixture was stirred at 25° C. for 16 h. TLC (Petroleum ether:Ethyl acetate=2:1, Product: $R_f$=0.46) indicated compound 7-3-1 was consumed completely and one new spot formed. The reaction was clean according to TLC.

Propan-2-ol (4.73 mL, 1.00 eq) was added and the mixture was stirred at 0.5 h. The above mixture was cooled to 0° C. in ice water bath. Dodecane-1-thiol (16.2 g, 80.2 mmol, 19.2 mL, 1.30 eq) was added and the mixture was stirred at 0° C. for 15 min. TFA (56.3 g, 494 mmol, 36.5 mL, 8.00 eq) was added dropwise at 0° C. The mixture was stirred at 0° C. for 1 h. TLC (Petroleum ether:Ethyl acetate=2:1, $R_f$=0.24) indicated starting material was consumed completely and one new spot formed. The reaction was clean according to TLC. The reaction mixture was poured into the NaHCO$_3$ (10.0 eq NaHCO$_3$ in 500 mL DI water), and then diluted with DCM 100 mL and extracted with aq. NaHCO$_3$ 200 mL. The combined organic layers were washed with brine 200 mL (100 mL×2), dried over Na$_2$SO$_4$, filtered and concentrated under reduced pressure to give a residue.

The crude product was dissolved in DCM 100 mL, to the solvent mixture of Heptane/TBME (v/v 9:1, 1200 mL) was slowly dropped the solution of crude product from funnel to performance the precipitation process. This process took about 30 min. The pure product was collected as a white solid with buchner funnel, the cake of product was washed with the solvent mixture of Heptane (100 mL×2) and concentrated to dry.

Compound 7-3-2 (34.8 g, 56.1 mmol, 91.0% yield, 94.2% purity) was obtained as a white solid. HPLC (Method A): RT=7.136 min, and LCMS (Method F): RT=1.570 min; m/z: [M+H]+=584.2.

General procedure for preparation of compound 7-3-3

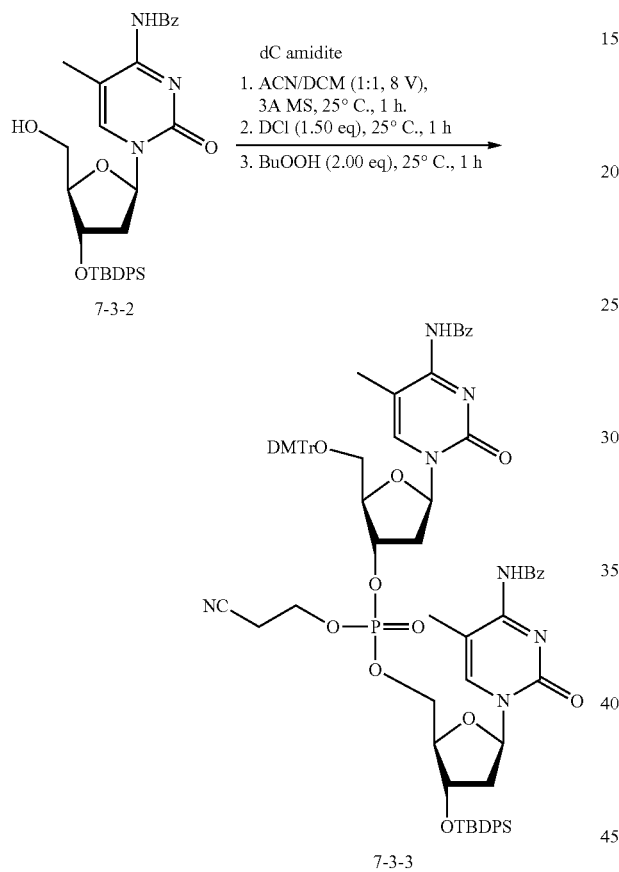

To a solution of compound 7-3-2 (13.0 g, 22.2 mmol, 1.00 eq) and dC amidite (20.7 g, 24.5 mmol, 1.10 eq) were co-evaporated with ACN (100 mL×3) under Ar in a 250 mL single-necked round bottle, and 3 Å molecular sieve (3.00 g) was added to the single-necked bottle, under Ar pressure ACN/DCM=1:1 (100 mL) was added. The mixture was stir at 25° C. for 1 h, and then DCI (3.94 g, 33.4 mmol, 1.50 eq) was added to the mixture. The mixture was stirred at 25° C. for 1 h. HPLC (product: RT=6.207 min; start material: RT=7.136 min) showed the starting material was consumed completely.

After the coupling reaction finished, to the above solution was added BuOOH (5.73 g, 44.5 mmol, 6.10 mL, 70.0% purity, 2.00 eq) at 25° C. The mixture was stirred at 25° C. for 1 h. HPLC (7-3-3, product: RT=9.028 min; start material: RT=6.027 min) showed the starting material was consumed completely. The reaction mixture was poured into the NaHCO₃ and Na₂SO₃ solution (10.0 eq NaHCO₃ and 5.00 eq Na₂SO₃ in 400 mL DI water), and then dilute the mixture with EtOAc (200 mL) and two layers were separated, the organic layer was washed with NaHCO₃ (200 mL), brine (100 mL), dried filtered and concentrated.

Compound 7-3-3 (33.0 g, 22.0 mmol, 98.7% yield, 89.7% purity) was obtained as a white foam.

HPLC (Method A): RT=5.518 min, and LCMS (Method D): RT=1.787 min; m/z: [M−H]⁻=1344.6.

General procedure for preparation of compound 7-3-4

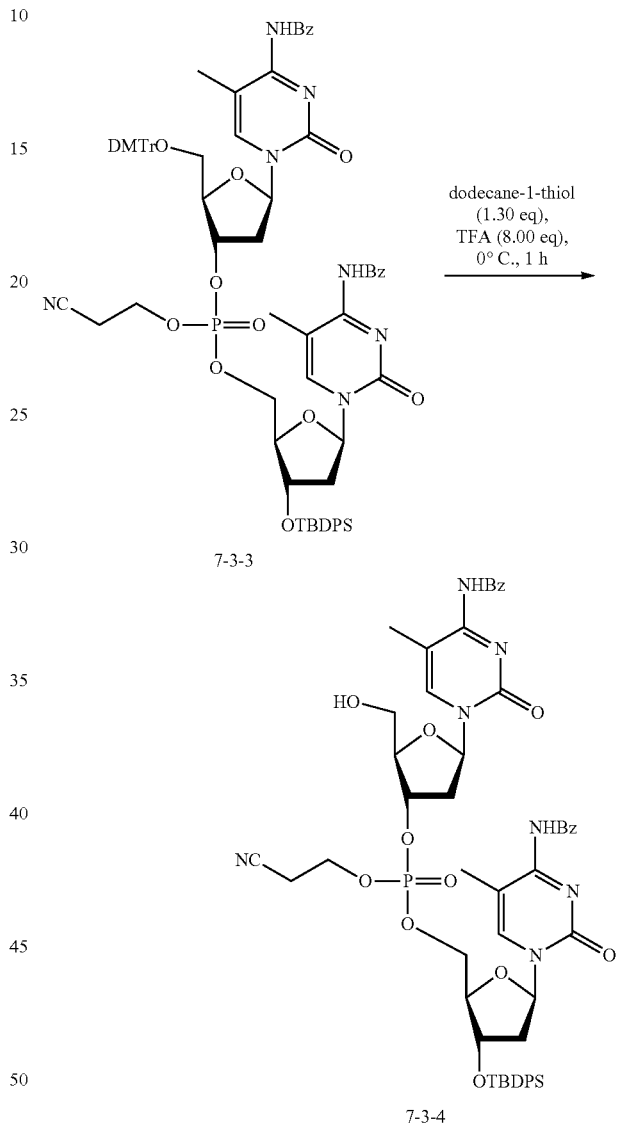

Compound 7-3-3 (24.0 g, 17.8 mmol, 1.00 eq) in ACN (120 mL) was added dodecane-1-thiol (4.69 g, 23.1 mmol, 5.55 mL, 1.30 eq) at 0° C., and then TFA (16.2 g, 142 mmol, 10.5 mL, 8.00 eq) was added dropwise at 0° C. The mixture was stirred at 0° C. for 1 h. TLC (Dichloromethane:Methanol=10:1, Product: $R_f$=0.55) indicated compound 7-3-3 was consumed completely and two new spots formed. The reaction was messy according to TLC. The reaction mixture was poured into the NaHCO₃ (10.0 eq NaHCO₃ in 300 mL DI water), and then diluted with EtOAc 100 mL and extracted with aq·NaHCO₃ 100 mL. The combined organic layers were washed with brine 200 mL (100 mL×2), dried over Na₂SO₄, filtered and concentrated under reduced pressure to give a residue.

The mixture was re-dissolved in CH₃CN:H₂O (2:1, 100 mL), and the CH₃CN/H₂O layer was washed by Heptane:tBuOMe=4:1 (200 mL×4), and then dilute the layer of CH₃CN and H₂O with EtOAc/MTBE (1/3, 120 mL). The organic layer was washed with DI water (100 mL) the organic layer was washed with brine (100 mL), dried over Na₂SO₄, filtered and concentrated under reduced pressure to give a residue. Compound 7-3-4 (16.4 g, 14.3 mmol, 80.4% yield, 91.2% purity) was obtained as a white solid. The crude product was purified by reversed-phase HPLC (pH=7 condition). Compound 7-3-4 (14.7 g, 13.4 mmol, 87.4% yield, 95.2% purity) was obtained as a white foam. HPLC (Method A): RT=7.344 min, and LCMS (Method E): RT=1.451 min; m/z: [M+H]⁺=1044.7.

General procedure for preparation of compound 7-3-5

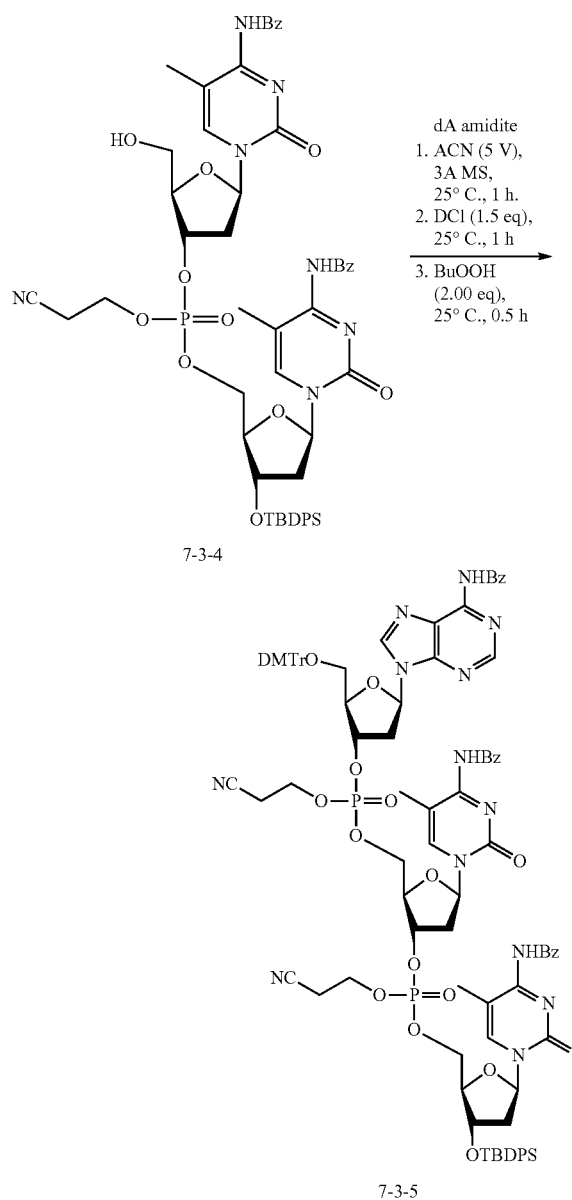

single-necked round bottle, and 3 Å molecular sieve (4.00 g) were added to the single-necked bottle, under Ar pressure ACN (75 mL) was added. The mixture was stir at 25° C. for 1 h, and then DCI (2.49 g, 21.1 mmol, 1.50 eq) was added to the mixture. The mixture was stirred at 25° C. for 1 h. HPLC (product: RT=7.344 min; start material: RT=8.501 min) showed the starting material was consumed completely.

After the coupling reaction finished, to the above solution was added BuOOH (3.62 g, 28.1 mmol, 3.86 mL, 70.0% purity, 2.00 eq) at 25° C. The mixture was stirred at 25° C. for 0.5 h. HPLC (7-3-5, product: RT=8.232 min; start material: RT=8.501 min) showed the starting material was consumed completely. The reaction mixture was poured into the NaHCO₃ and Na₂SO₃ solution (10.0 eq NaHCO₃ and 5.00 eq Na₂SO₃ in 500 mL DI water), and then dilute the mixture with EtOAc (200 mL) and two layers were separated, the organic layer was washed with NaHCO₃ (200 mL), brine (100 mL), dried filtered and concentrated.

The crude was re-dissolved in DCM (80 mL). The crude solvent was slowly dropped to a solvent of MTBE (1000 mL). Desired product was precipitated out. The product was collected as a white solid after filtration, and the solid cake was washed with isopropyl ether MTBE (50 mL×2). Compound 7-3-5 (30.0 g, 13.4 mmol, 95.7% yield, 81.6% purity) was obtained as a white solid. The crude product was purified by reversed-phase HPLC (pH=7 condition).

Compound 7-3-5 (24.0 g, 13.0 mmol, 96.9% yield, 98.8% purity) was obtained as a white solid. HPLC (Method A): RT=8.233 min.; LCMS (Method D): RT=1.622 min; m/z: [M−2H]²12=906.8.

General procedure for preparation of compound 7-3-6

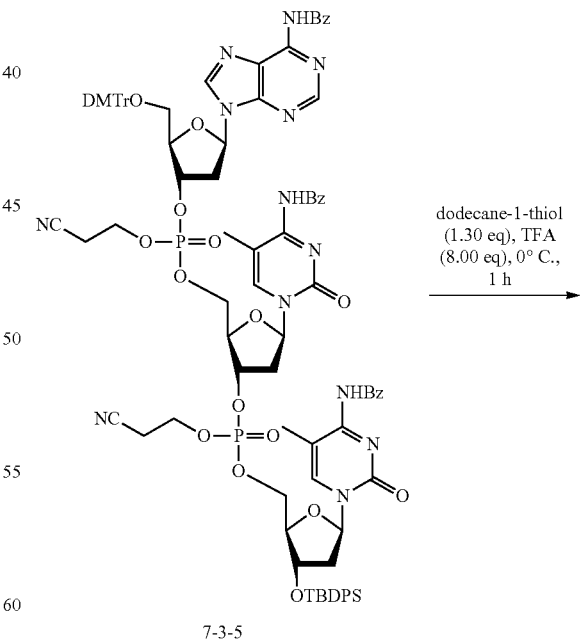

A solution of compound 7-3-4 (14.7 g, 14.0 mmol, 1.00 eq) and dA amidite (13.2 g, 15.4 mmol, 1.10 eq) were co-evaporated with ACN (100 mL×3) under Ar in a 250 mL -continued

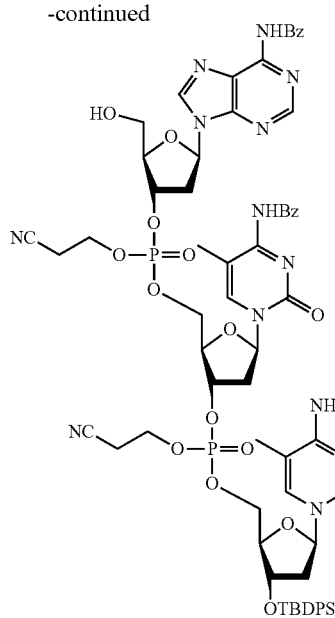

7-3-6

To a solution of compound 7-3-5 (18.3 g, 10.0 mmol, 1.00 eq) in ACN (90 mL) was added dodecane-1-thiol (2.65 g, 13.0 mmol, 3.14 mL, 1.30 eq) at 0° C., and then TFA (9.19 g, 80.5 mmol, 5.97 mL, 8.00 eq) was added dropwise at 0° C. The mixture was stirred at 0° C. for 1 h. TLC (DCM: MeOH=10:1, Product: $R_f$=0.43) indicated compound 7-3-5 was consumed completely and two spots formed. The reaction was messy according to TLC.

The reaction mixture was poured into the NaHCO$_3$ (10.0 eq NaHCO$_3$ in 300 mL DI water), and then diluted with EtOAc 100 mL and extracted with aq. NaHCO$_3$ 100 mL. The combined organic layers were washed with brine 200 mL (100 mL×2), dried over Na$_2$SO$_4$, filtered and concentrated under reduced pressure to give a residue. The crude was re-dissolved in DCM (80 mL). The crude solvent was slowly dropped to a solvent of MTBE (1000 mL). Desired product was precipitated out. The product was collected as a white solid after filtration, and the solid cake was washed with isopropyl ether Heptane (50 mL×2). Compound 7-3-6 (14.3 g, 9.34 mmol, 92.7% yield, 98.8% purity) was obtained as a white solid.

HPLC (Method A): RT=7.008 min.; LCMS (Method E): RT=1.444 min; m/z: [M+H]$^+$=1514.8.

General procedure for preparation of compound 7-3-7

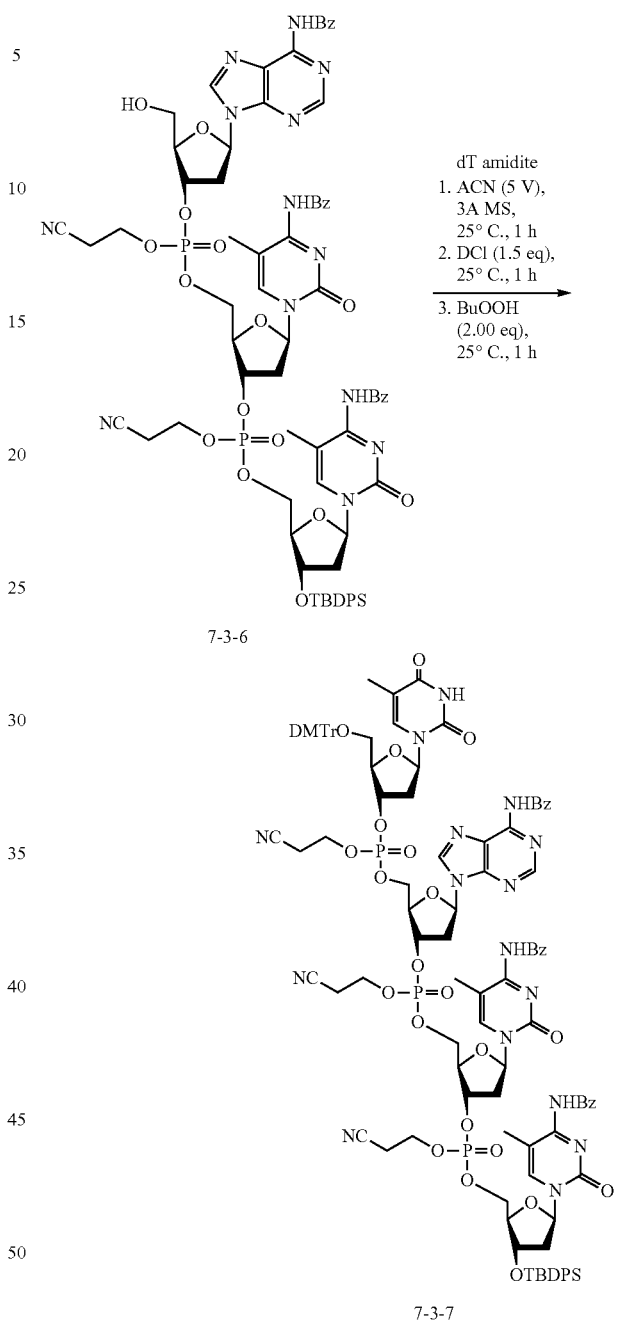

Compound 7-3-6 (14.3 g, 9.44 mmol, 1.00 eq) and dT amidite (7.73 g, 10.3 mmol, 1.10 eq) were co-evaporated with ACN (50 mL×3) under Ar in a 250 mL single-necked round bottle, and 3 Å molecular sieve (4.00 g) was added to the single-necked bottle, under Ar pressure ACN (75 mL) was added. The mixture was stirred at 25° C. for 1 h, and then DCI (1.67 g, 14.1 mmol, 1.50 eq) was added to the mixture. The mixture was stirred at 25° C. for 1 h. HPLC (Product: RT=8.061 min; start material: RT=7.008 min) showed the starting material was consumed completely.

After the coupling reaction finished, to the above solution was added BuOOH (2.43 g, 18.8 mmol, 2.59 mL, 70.0% purity, 2.00 eq) at 25° C. The mixture was stirred at 25° C.

for 1 h. HPLC (7-3-7, product: RT=7.856 min; start material: RT=8.061 min) showed the starting material was consumed completely. The reaction mixture was poured into the NaHCO$_3$ and Na$_2$SO$_3$ solution (10.0 eq NaHCO$_3$ and 5.00 eq Na$_2$SO$_3$ in 400 mL DI water), and then dilute the mixture with EtOAc (200 mL) and two layers were separated, the organic layer was washed with NaHCO$_3$ (200 mL), brine (100 mL), dried filtered and concentrated.

Compound 7-3-7 (21.9 g, 8.78 mmol, 93.0% yield, 87.1% purity) was obtained as a white solid. The crude product was purified by reversed-phase HPLC (pH=7 condition). Compound 7-3-7 (19.0 g, 8.57 mmol, 97.6% yield, 98.0% purity) was obtained as a white foam. HPLC (Method A): RT=7.848 min; LCMS (Method D): RT=1.569 min; m/z: [M−2H]$^{2-}$/2=1085.5.

General procedure for preparation of compound 7-3-8

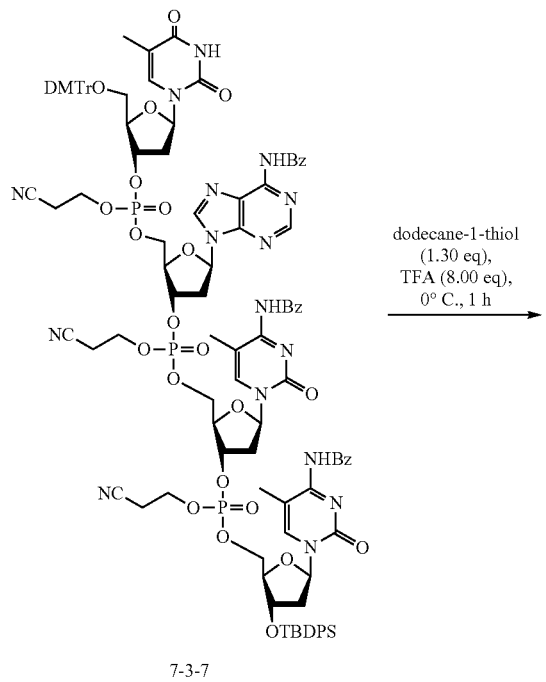

7-3-7 dodecane-1-thiol (1.30 eq), TFA (8.00 eq), 0° C., 1 h

To a solution of compound 7-3-7 (14.0 g, 6.44 mmol, 1.00 eq) in ACN (70 mL) was added dodecane-1-thiol (1.69 g, 8.37 mmol, 2.01 mL, 1.30 eq) at 0° C., and then TFA (5.87 g, 51.5 mmol, 3.81 mL, 8.00 eq) was added dropwise at 0° C. The mixture was stirred at 0° C. for 1 h. TLC (Methanol:Dichloromethane=10:1, Product: R$_f$=0.41) indicated compound 7-3-7 was consumed completely and two new spots formed. The reaction was messy according to TLC. The reaction mixture was poured into the NaHCO$_3$ (10.0 eq NaHCO$_3$ in 300 mL DeIonized (DI) water), and then diluted with EtOAc 100 mL and extracted with aq. NaHCO$_3$ 100 mL. The combined organic layers were washed with brine 200 mL (100 mL×2), dried over Na$_2$SO$_4$, filtered and concentrated under reduced pressure to give a residue.

The crude was re-dissolved in DCM (80 mL). The crude solvent was slowly dropped to a solvent of MTBE (1000 mL). Desired product was precipitated out. The product was collected as a white solid after filtration, and the solid cake was washed with isopropyl ether MTBE (50 mL×2). Compound 7-3-8 (11.5 g, 6.00 mmol, 93.1% yield, 97.6% purity) was obtained as a white solid.

HPLC (Method A): RT=6.705 min.

General procedure for preparation of deoxy-TTACC 5mer 7-3-9

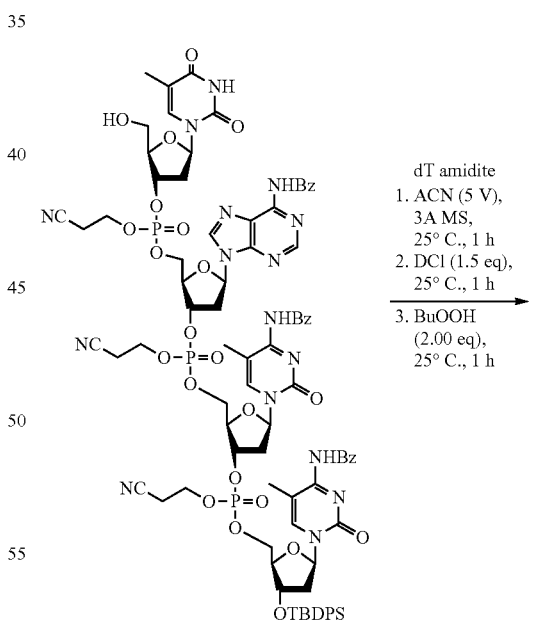

7-3-8 dT amidite
1. ACN (5 V), 3A MS, 25° C., 1 h
2. DCI (1.5 eq), 25° C., 1 h
3. BuOOH (2.00 eq), 25° C., 1 h -continued

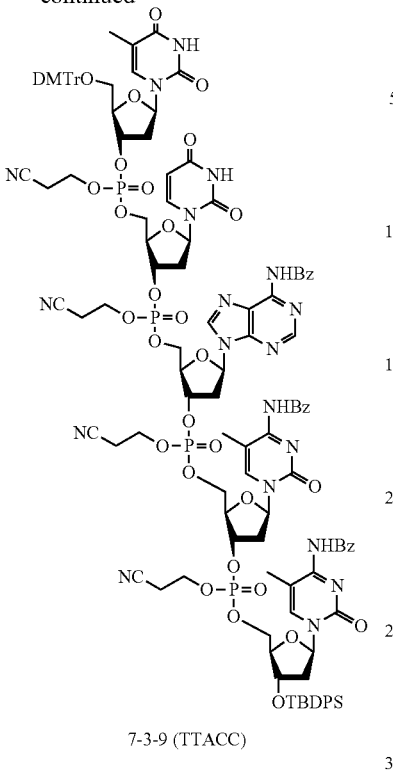

7-3-9 (TTACC)

To a solution of compound 7-3-8 (11.5 g, 6.14 mmol, 1.00 eq) and dT amidite (5.03 g, 6.76 mmol, 1.10 eq) were co-evaporated with ACN (50 mL×3) under Ar in a 250 mL single-necked round bottle, and 3 Å molecular sieve (4.00 g) were added to the single-necked bottle, under Ar pressure ACN (75 mL) was added. The mixture was stir at 25° C. for 1 h, and then DCI (1.67 g, 14.1 mmol, 1.50 eq) was added to the mixture. The mixture was stirred at 25° C. for 1 h. HPLC (product: RT=7.730 min; start material: RT=6.705 min) showed the starting material was consumed completely.

After the coupling reaction finished, to the above solution was added BuOOH (1.58 g, 12.2 mmol, 1.68 mL, 70.0% purity, 2.00 eq). The mixture was stirred at 25° C. for 1 h. HPLC (product: RT=7.517 min; start material: RT=7.730 min) showed the starting material was consumed completely. The reaction mixture was poured into the $NaHCO_3$ and $Na_2SO_3$ solution (10.0 eq $NaHCO_3$ and 5.00 eq $Na_2SO_3$ in 500 mL DI water), and then dilute the mixture with EtOAc (200 mL) and two layers were separated, the organic layer was washed with $NaHCO_3$ (200 mL), brine (100 mL), dried filtered and concentrated.

The crude was re-dissolved in DCM (80 mL). The crude solvent was slowly dropped to a solvent of MTBE (800 mL). Desired product was precipitated out. The product was collected as a white solid after filtration, and the solid cake was washed with isopropyl ether MTBE (50 mL×2). LCMS: product: RT=1.443 min.

The crude product was purified by reversed-phase HPLC (pH=7 condition). 7-3-9 (deoxy-TTACC 5mer) (14.3 g, 5.47 mmol, 89.3% yield, 96.8% purity) was obtained as a light yellow solid.

HPLC (Method B): RT=11.993, 12.120, 12.240 min; LCMS (Method D): RT=1.443 min; m/z: $[M-2H]^{2-}/2=1263.7$.

General procedure for preparation of DMTr-TTACC-OH 7-3-10

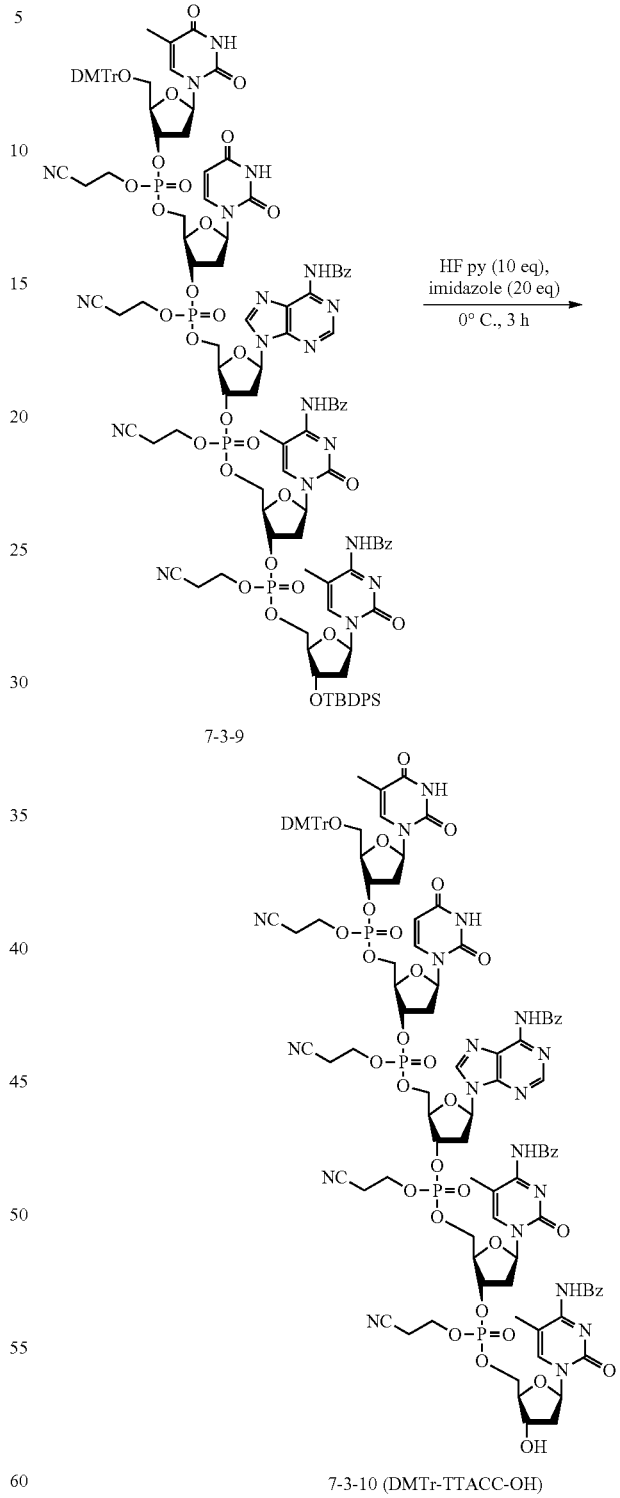

To a solution of compound 7-3-9 (7.20 g, 2.84 mmol, 1.00 eq) in ACN (35 mL) and then pyridine; hydrofluoride (813 mg, 28.4 mmol, 739 μL, 70.0% purity, 10.0 eq) and imidazole (3.87 g, 56.8 mmol, 20.0 eq) in THF (12 mL) was added dropwise at 0° C. The mixture was stirred at 0° C. for 3 h.

TLC (Dichloromethane:Methanol=10:1, Purity: $R_f$=0.30) indicated compound 7-3-9 was consumed completely and two new spots formed. The reaction was messy according to TLC.

The reaction mixture was dissolved in the EtOAc (50 mL). The organic layer was washed with sat. aq. NaHCO$_3$ (100 mL×2), brine (100 mL) and dried by anhydrous Na$_2$SO$_4$, filtered and concentrated in vacuum.

The crude was re-dissolved in DCM (5 mL). The crude solvent was slowly dropped to a solvent of MTBE (300 mL). Desired product was precipitated out. The product was collected as a white solid after filtration, and the solid cake was washed with isopropyl ether MTBE (50 mL×2). Compound 7-3-10 DMTr-TTACC-OH (6.00 g, 2.33 mmol, 82.0% yield, 89.1% purity) was obtained as a white solid.

HPLC (Method B): RT=6.449, 6.591 min.; LCMS (Method F): RT=1.312 min; m/z: $[M+2H]^{2+}/2$=1147.4.

Preparation of Compound 7-3-10a

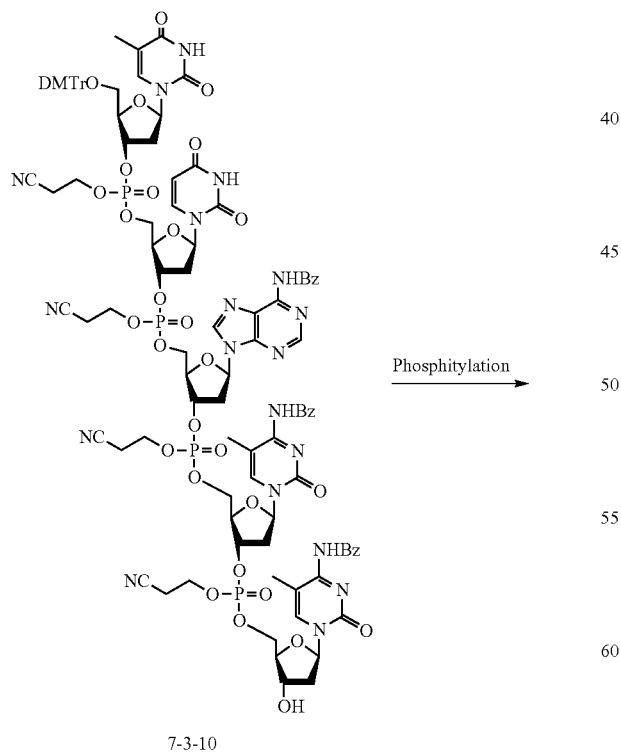

7-3-10

Phosphitylation →

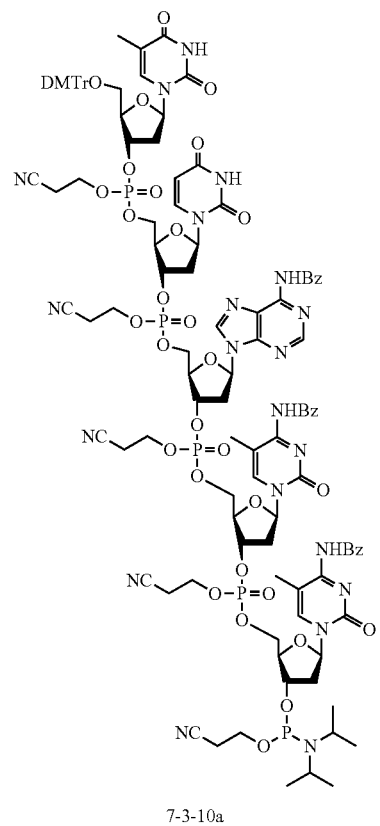

7-3-10a

Compound 7-3-10a was synthesized from 7-3-10 using similar procedure as described above for the phosphoramidite synthesis. HPLC-MS (Method G): RT=8.174, 8.251, 8.420, 8.494 min; m/z: $[M-2H]^{2-}/2$=1245.4 for compound 7-3-10a.

Preparation of HO-TTACC-OTBDPS 7-3-11

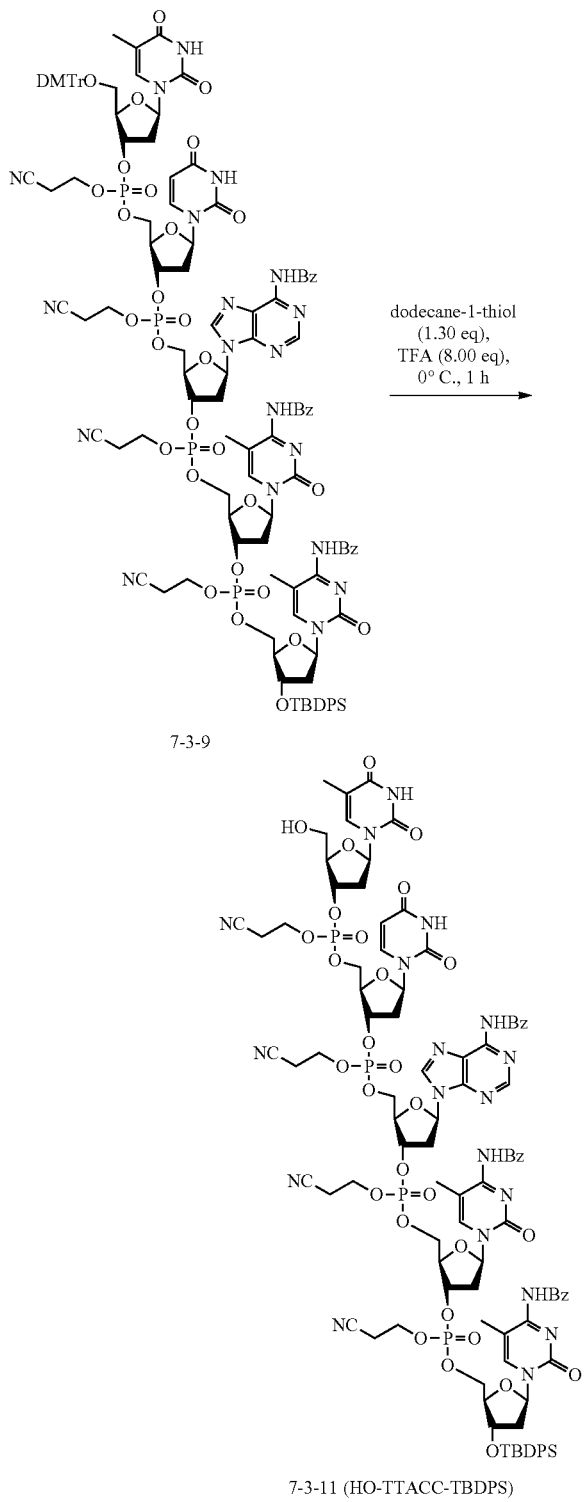

7-3-11 (HO-TTACC-TBDPS)

To a solution of compound 7-3-9 (6.60 g, 2.61 mmol, 1.00 eq) in ACN (35 mL) was added dodecane-1-thiol (791 mg, 3.91 mmol, 936 μL, 1.50 eq) at 0° C., and then TFA (2.38 g, 20.8 mmol, 1.54 mL, 8.00 eq) was added dropwise at 0° C. The mixture was stirred at 0° C. for 1 h. TLC (DCM:MeOH=10:1, Product: R$_f$=0.35) indicated compound 7-3-9 was consumed completely and two new spots formed. The reaction was messy according to TLC. The reaction mixture was poured into the NaHCO$_3$ (10.0 eq NaHCO$_3$ in 100 mL DI water), and then diluted with EtOAc 50 mL and extracted with aq·NaHCO$_3$ 100 mL. The combined organic layers were washed with brine 200 mL (100 mL×2), dried over Na$_2$SO$_4$, filtered and concentrated under reduced pressure to give a residue.

The crude was re-dissolved in DCM (80 mL). The crude solvent was slowly dropped to a solvent of MTBE (300 mL). Desired product was precipitated out. The product was collected as a white solid after filtration, and the solid cake was washed with isopropyl ether MTBE (50 mL×2). Compound 7-3-11 (HO-TTACC-OTBDPS) (5.35 g, 2.37 mmol, 90.7% yield, 98.6% purity) was obtained as a white solid.

HPLC (Method B): RT=9.508, 9.650 min.; LCMS (Method D): RT=1.444 min; m/z: [M−2H]$^{2-}$/2=1113.3.

3. General procedure for preparation of 5'-UTTC 4mer or 5'-DMTr-UTTC-OH or 5'-OH-UTTC-TBDPS 4mer (Fragment 3) General procedure for preparation of compound 7-4-2

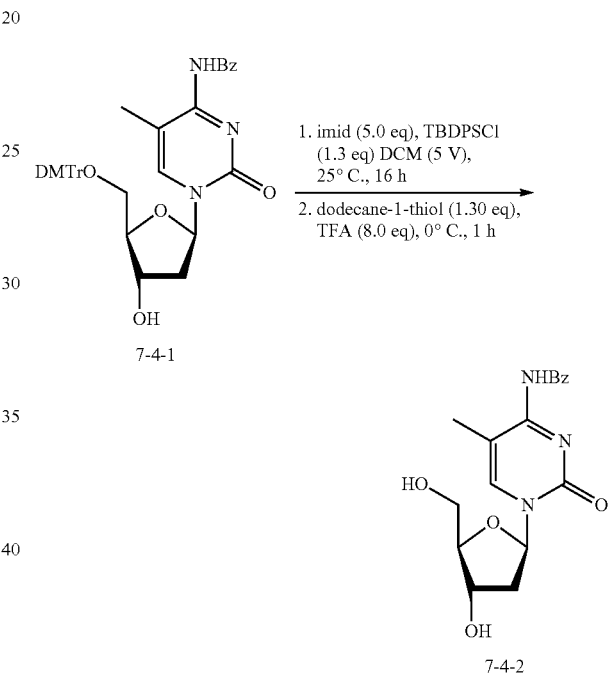

To a solution of compound 7-4-1 (40.0 g, 61.7 mmol, 1.00 eq) in DCM (200 mL) was added imidazole (21.0 g, 308 mmol, 5.00 eq). The mixture was light yellow homogenous solution. TBDPSCl (22.0 g, 80.2 mmol, 20.6 mL, 1.30 eq) was added. The mixture was stirred at 25° C. for 16 h. TLC (Petroleum ether:Ethyl acetate=2:1, Product: R$_f$=0.46) indicated compound 7-4-1 was consumed completely and one new spot formed. The reaction was clean according to TLC.

Propan-2-ol (4.73 mL, 1.00 eq) was added and the mixture was stirred at 0.5 h. The above mixture was cooled to 0° C. in ice water bath. Dodecane-1-thiol (16.2 g, 80.2 mmol, 19.2 mL, 1.30 eq) was added and the mixture was stirred at 0° C. for 15 min. TFA (56.3 g, 494 mmol, 36.5 mL, 8.00 eq) was added dropwise at 0° C. The mixture was stirred at 0° C. for 1 h. TLC (Petroleum ether:Ethyl acetate=2:1, R$_f$=0.24) indicated the starting mixture was consumed completely and one new spot formed. The reaction was clean according to TLC. The reaction mixture was poured into the NaHCO$_3$ (10.0 eq NaHCO$_3$ in 500 mL DI water), and then diluted with DCM 100 mL and extracted with aq·NaHCO$_3$ 200 mL. The combined organic layers were washed with brine 200 mL (100 mL×2), dried over Na$_2$SO$_4$, filtered and concentrated under reduced pressure to give a residue.

The crude product was dissolved in DCM 100 mL, to the solvent mixture of Heptane/TBME (v/v 9:1, 1200 mL) was slowly dropped the solution of crude product from funnel to performance the precipitation process. This process took about 0.5 h. The pure product was collected as a white solid with Buchner funnel, the cake of product was washed with the solvent mixture of Heptane (100 mL×2) and concentrated to dry. Compound 7-4-2 (34.8 g, 56.1 mmol, 91.0% yield, 94.2% purity) was obtained as a white solid.

HPLC (Method A): RT=7.136 min, and LCMS (Method F): RT=1.570 min; m/z: [M+H]$^+$=584.2

General procedure for preparation of compound 7-4-3 and 5.00 eq Na$_2$SO$_3$ in 400 mL DI water), and then dilute the mixture with DCM (200 mL) and two layers were separated, the organic layer was washed with NaHCO$_3$ (200 mL), brine (100 mL), dried filtered and concentrated.

Compound 7-4-3 (36.0 g, 24.9 mmol, 97.1% yield, 86.2% purity) was obtained as a white solid. HPLC: product: RT=7.764, 7.826 min.; LCMS: compound 7-4-3, RT=1.602 min. The crude compound 3 was used for the next step.

Compound 7-4-3 (10.0 g, 6.93 mmol, 86.2% purity) was purified by reversed-phase MPLC (pH=7 condition MeCN/water). Compound 7-4-3 (8.00 g, 6.19 mmol, 89.2% yield, 96.1% purity) was obtained as a white foam. HPLC (Method A): RT=7.792, 7.845 min, and LCMS (Method F): RT=1.602 min; m/z: [M+H]$^+$=1243.4.

General procedure for preparation of compound 7-4-4

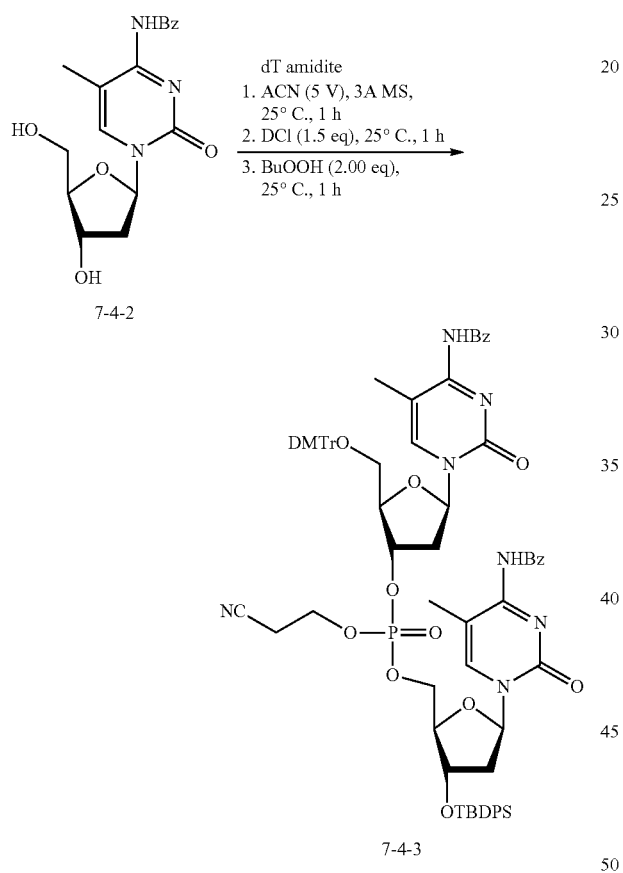

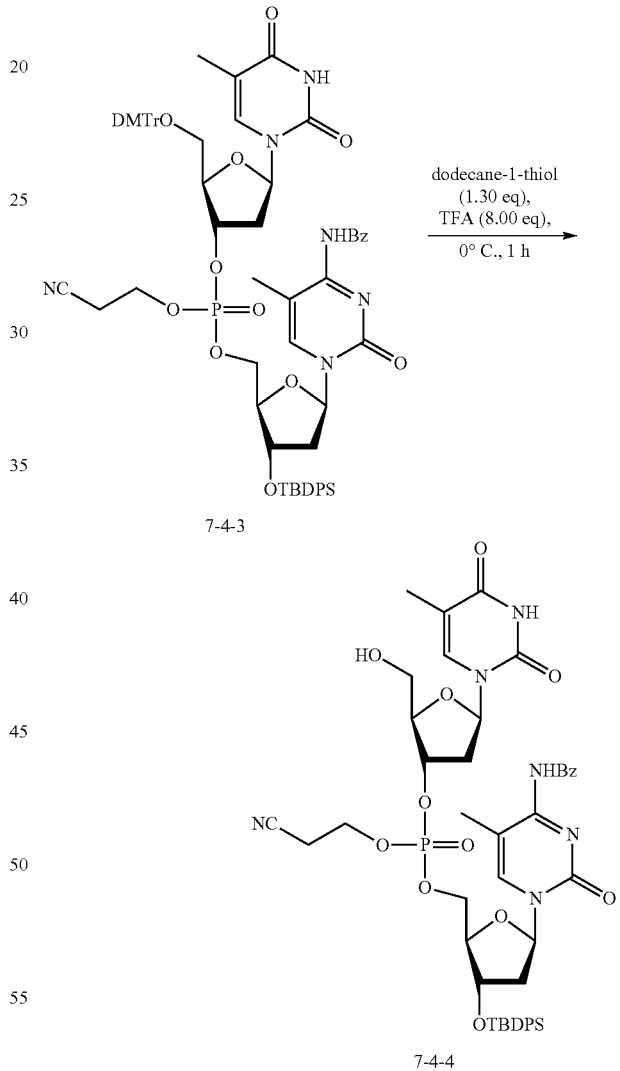

Compound 7-4-2 (15.0 g, 25.7 mmol, 1.00 eq) and dT amidite (21.0 g, 28.2 mmol, 1.10 eq) were co-evaporated with ACN/DCM (1/1, 100 mL×3) under Ar in a 250 mL single-necked round bottle, and 3 Å molecular sieve (6.50 g) were added to the single-necked bottle, under Ar pressure ACN (60 mL) and DCM (60 mL) was added. The mixture was stir at 25° C. for 1 h, and then DCI (4.55 g, 38.5 mmol, 1.50 eq) was added to the mixture. The mixture was stirred at 25° C. for 1 h. HPLC (product: RT=8.233 min) indicated compound 7-4-2 was consumed completely.

After the coupling reaction finished, to the above solution was added BuOOH (6.62 g, 51.3 mmol, 7.04 mL, 70.0% purity, 2.00 eq) at 25° C. The mixture was stirred at 25° C. for 0.5 h. HPLC (product: RT=7.764, 7.826 min) indicated the reaction completed. The reaction mixture was poured into the NaHCO$_3$ and Na$_2$SO$_3$ solution (10.0 eq NaHCO$_3$ To a solution of compound 7-4-3 (26.0 g, 20.9 mmol, 1.00 eq) in ACN (120 mL) was added dodecane-1-thiol (5.50 g, 27.18 mmol, 6.51 mL, 1.30 eq) cooled to 0° C., and then TFA (19.0 g, 167 mmol, 12.3 mL, 8.00 eq) was added dropwise at 0° C. The mixture was stirred at 0° C. for 1 h. TLC (Dichloromethane:Methanol=10:1, Product: R$_f$=0.46) indicated compound 7-4-3 was consumed completely and one new spot formed. The reaction was clean according to TLC. The reaction mixture was poured into the NaHCO$_3$ solution (10.0 eq NaHCO$_3$ in 400 mL DI water), and then dilute the mixture with EtOAc (300 mL) and two layers were separated, the organic layer was washed with NaHCO$_3$ (200 mL), brine (200 mL), dried over Na$_2$SO$_4$, filtered and concentrated under reduced pressure to give a residue.

The mixture was re-dissolved in CH$_3$CN:H$_2$O (2:1, 100 mL), and the CH$_3$CN/H$_2$O layer was washed by Heptane:tBuOMe=4:1 (200 mL×4), and then dilute the layer of CH$_3$CN and H$_2$O with EtOAc/MTBE (1/3, 120 mL). The organic layer was washed with DI water (100 mL) the organic layer was washed with brine (100 mL), dried over Na$_2$SO$_4$, filtered and concentrated under reduced pressure to give a residue.

Compound 7-4-4 (17.0 g, 16.7 mmol, 80.0% yield, 92.6% purity) was obtained as a white foam. HPLC (Method A): RT=5.977 min, and LCMS (Method E): RT=1.241 min; m/z: [M+H]$^+$=941.5.

General Procedure for Preparation of Compound 7-4-5

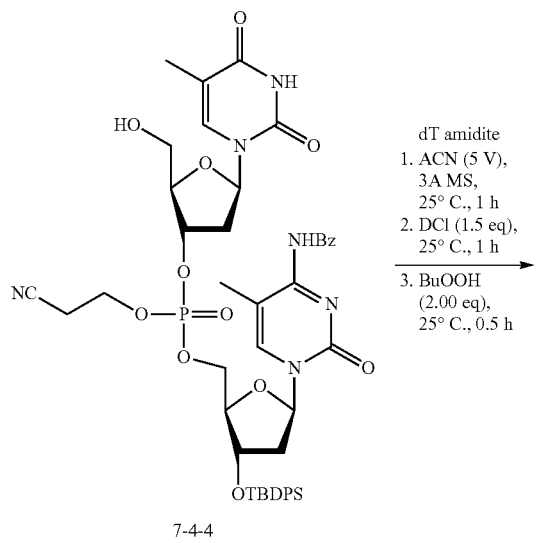

7-4-4

Compound 7-4-4 (17.0 g, 18.0 mmol, 1.00 eq) and dT amidite (14.8 g, 19.8 mmol, 1.10 eq) were co-evaporated with ACN (100 mL×3) under Ar in a 250 mL single-necked round bottle, and 3 Å molecular sieve (4.50 g) were added to the single-necked bottle, under Ar pressure ACN (85 mL) was added. The mixture was stir at 25° C. for 1 h, and then DCI (3.20 g, 27.1 mmol, 1.50 eq) was added to the mixture. The mixture was stirred at 25° C. for 1 h. HPLC (product: RT=7.451 min; start material: RT=5.977 min) showed the starting material was consumed completely.

After the coupling reaction finished, to the above solution was added BuOOH (4.65 g, 36.1 mmol, 4.95 mL, 70.0% purity, 2.00 eq). The mixture was stirred at 25° C. for 0.5 h. HPLC (product: RT=7.810 min; start material: RT=7.451 min) showed the starting material was consumed completely. The reaction mixture was poured into the NaHCO$_3$ and Na$_2$SO$_3$ solution (10.0 eq NaHCO$_3$ and 5.00 eq Na$_2$SO$_3$ in 400 mL DI water), and then dilute the mixture with EtOAc (200 mL) and two layers were separated, the organic layer was washed with NaHCO$_3$ (200 mL), brine (100 mL), dried filtered and concentrated. Compound 7-4-5 (34.0 g, 17.2 mmol, 95.2% yield, 81.0% purity) was obtained as a white foam.

Compound 7-4-5 (24.0 g, 15.0 mmol, 81.0% purity) was purified by reversed-phase

HPLC (pH=7 condition; MeCN/water). Compound 7-4-5 (17.8 g, 11.1 mmol, 89.7% yield, 98.2% purity) was obtained as a white foam.

HPLC (Method A): RT=7.179 min, and LCMS (Method D): RT=1.530 min; m/z: [M−H]$^-$=1599.6.

General procedure for preparation of compound 7-4-6

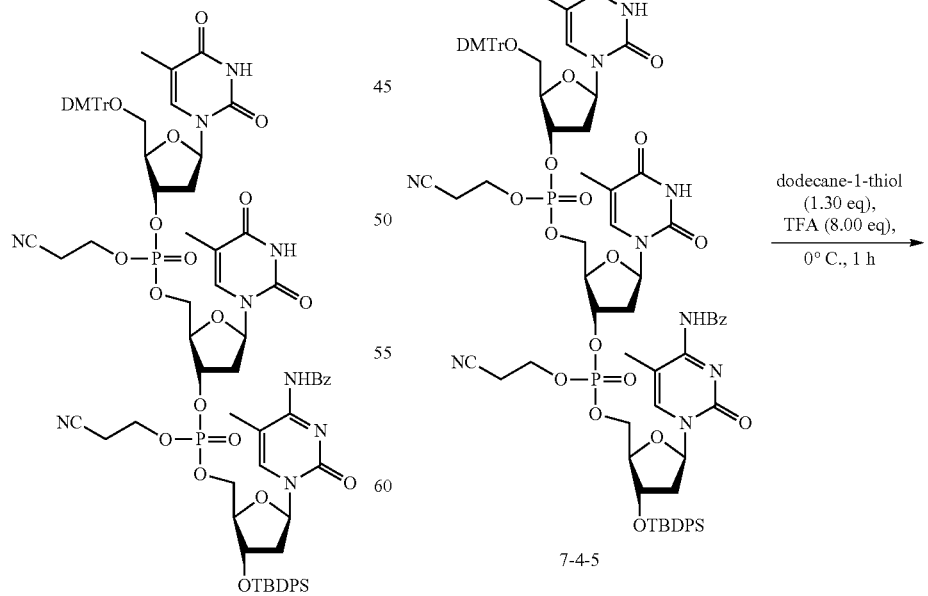

7-4-5

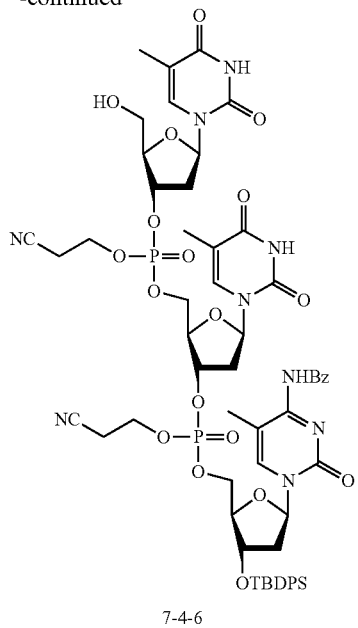

7-4-6

To a solution of compound 7-4-5 (12.6 g, 7.87 mmol, 1.00 eq) in ACN (65 mL) was added dodecane-1-thiol (2.07 g, 10.2 mmol, 2.45 mL, 1.30 eq) at 0° C., and then TFA (7.18 g, 62.9 mmol, 4.66 mL, 8.00 eq) was added dropwise at 0° C. The mixture was stirred at 0° C. for 1 h. TLC (Dichloromethane:Methanol=10:1, Product: $R_f$=0.36) indicated compound 7-4-5 was consumed completely and one new spot formed. The reaction was clean according to TLC. The reaction mixture was poured into the NaHCO$_3$ (10.0 eq NaHCO$_3$ in 200 mL DI water), and then diluted with EtOAc 100 mL and extracted with aq·NaHCO$_3$ 100 mL. The combined organic layers were washed with brine 200 mL (100 mL×2), dried over Na$_2$SO$_4$, filtered and concentrated under reduced pressure to give a residue.

The crude product was dissolved in DCM 100 mL, to the solvent mixture of Heptane/TBME (v/v 9:1, 500 mL) was slowly dropped the solution of crude product from funnel to performance the precipitation process. This process took about 0.5 h. The pure product was collected as a white solid with buchner funnel, the cake of product was washed with the solvent mixture of Heptane (100 mL×2) and concentrated to dry.

Compound 7-4-6 (11.0 g, 7.75 mmol, 98.4% yield, 91.4% purity) was obtained as a white solid. HPLC (Method A): RT=5.661 min, and LCMS (Method F): RT=1.365 min; m/z: [M+H]$^+$=1298.4.

General Procedure for Preparation of UTTC 4mer 7-4-7

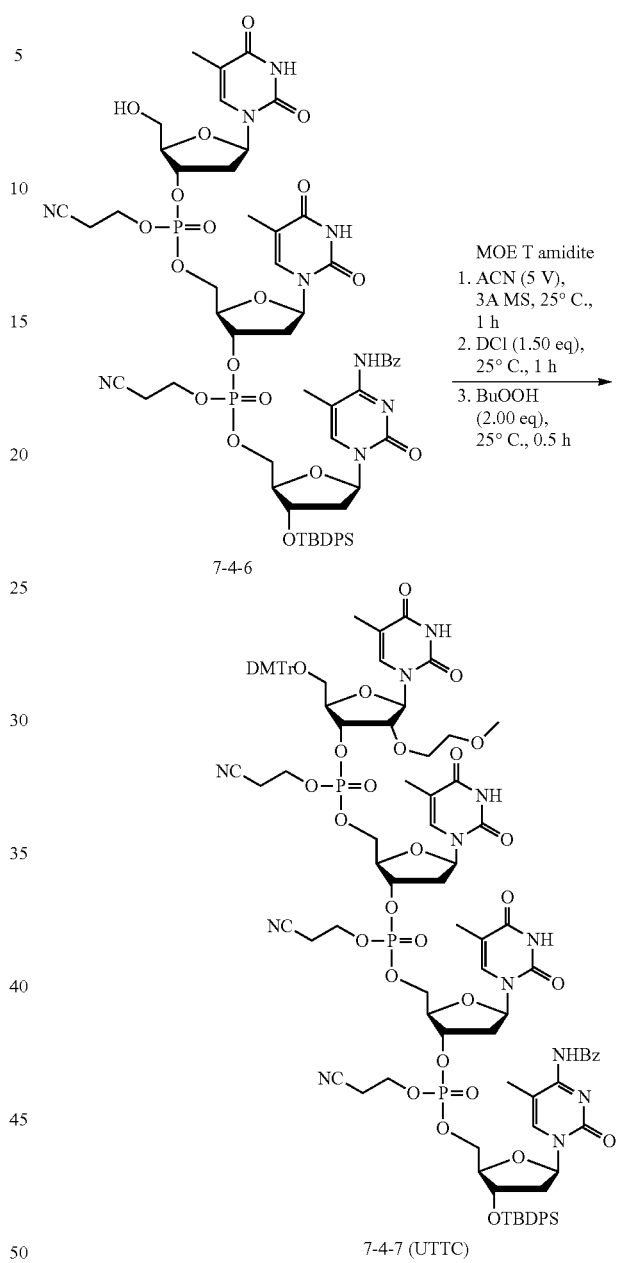

Compound 7-4-6 (11.0 g, 8.47 mmol, 1.00 eq) and MOE T amidite (7.63 g, 9.32 mmol, 1.10 eq) were co-evaporated with ACN (100 mL×3) under Ar in a 250 mL single-necked round bottle, and 3 Å molecular sieve (3.00 g) were added to the single-necked bottle, under Ar pressure ACN (55 mL) was added. The mixture was stir at 25° C. for 1 h, and then DCI (1.50 g, 12.7 mmol, 1.50 eq) was added to the mixture. The mixture was stirred at 25° C. for 1 h. HPLC (Product: RT=7.056, 7.180 min; start material: RT=5.661 min) showed the starting material was consumed completely.

After the coupling reaction finished, to the above solution was added BuOOH (2.18 g, 16.9 mmol, 2.32 mL, 70.0% purity, 2.00 eq). The mixture was stirred at 25° C. for 0.5 h. HPLC (product: RT=6.897, 6.961 min; start material: RT=7.056, 7.180 min) showed the starting material was consumed completely. The reaction mixture was poured into the NaHCO$_3$ and Na$_2$SO$_3$ solution (10.0 eq NaHCO$_3$ and 5.00 eq Na$_2$SO$_3$ in 500 mL DI water), and then dilute the mixture with EtOAc (200 mL) and two layers were separated, the organic layer was washed with NaHCO$_3$ (200 mL), brine (200 mL), dried filtered and concentrated.

The crude was re-dissolved in DCM (50 mL). The crude solvent was slowly dropped to a solvent of MTBE (600 mL). Desired product was precipitated out. The product was collected as a white solid after filtration, and the solid cake was washed with isopropyl ether MTBE (50 mL×2). The crude solid was purified by reversed-phase HPLC (pH=7 condition; MeCN/water).

Compound 7-4-7 (UTTC 4mer) (14.5 g, 7.06 mmol, 83.3% yield, 98.9% purity) was obtained as a white solid.

HPLC (Method B): RT=10.638, 10.822 min, and LCMS (Method D): RT=1.396 min; m/z: [M−H]$^-$=1014.3.

General Procedure for Preparation of 7-4-8 (DMTr-UTTC-OH)

To a solution of 7-4-7 (6.60 g, 3.25 mmol, 1.00 eq) in ACN (35 mL) and then pyridine; hydrofluoride (928 mg, 32.4 mmol, 844 μL, 70.0% purity, 10.0 eq) and imidazole (4.42 g, 64.9 mmol, 20.0 eq) in THF (8 mL) was added dropwise at 0° C. The mixture was stirred at 0° C. for 3 h. TLC (Dichloromethane:Methanol=10:1, Product: R$_f$=0.33) indicated compound 7-4-7 was consumed completely and two new spots formed. The reaction was messy according to TLC.

The reaction mixture was dissolved in the EtOAc (20 mL). The organic layer was washed with sat·aq·NaHCO$_3$ (50 mL×2), brine (20 mL) and dried by anhydrous Na$_2$SO$_4$, filtered and concentrated in vacuum. The crude was redissolve in DCM (5 mL). The crude solvent was slowly dropped to a solvent of MTBE (300 mL). Desired product was precipitated out. The product was collected as a white solid after filtration, and the solid cake was washed with isopropyl ether MTBE (50 mL×2).

Compound 7-4-8 (DMTr-UTTC-OH) (5.57 g, 2.90 mmol, 89.3% yield, 93.4% purity) was obtained as a white solid.
HPLC (Method B): RT=4.461, 4.761 min, and LCMS (Method D): RT=1.237 min; m/z: [M−H]-=1791.5.

General procedure for preparation of 7-4-8a (Fragment 3)

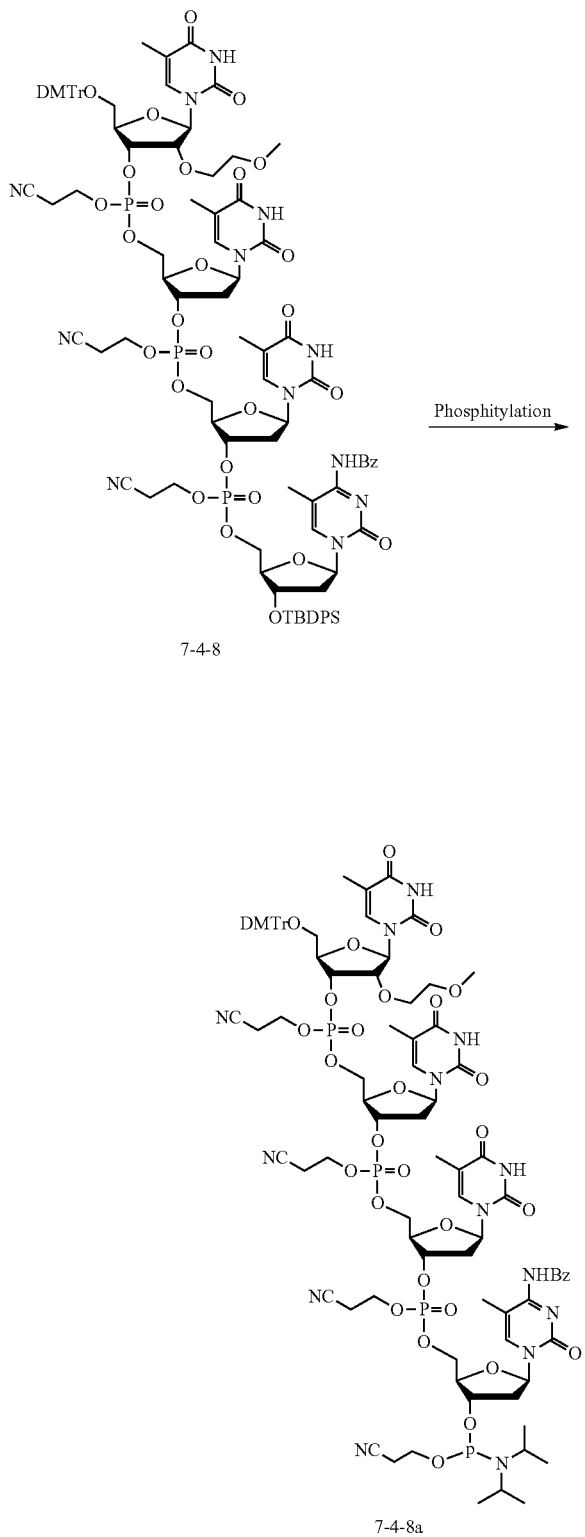

7-4-8

7-4-8a

Compound 7-4-8a was synthesized from 7-4-8 using similar procedure as described above for the phosphoramidite synthesis. HPLC-MS (Method G): RT=7.335, 7.446, 7.583, 7.637 min; m/z: [M–H]⁻=1991.6 for compound 7-4-8a.

General Procedure for Preparation of 7-4-9 (HO-UTTC-OTBDPS)

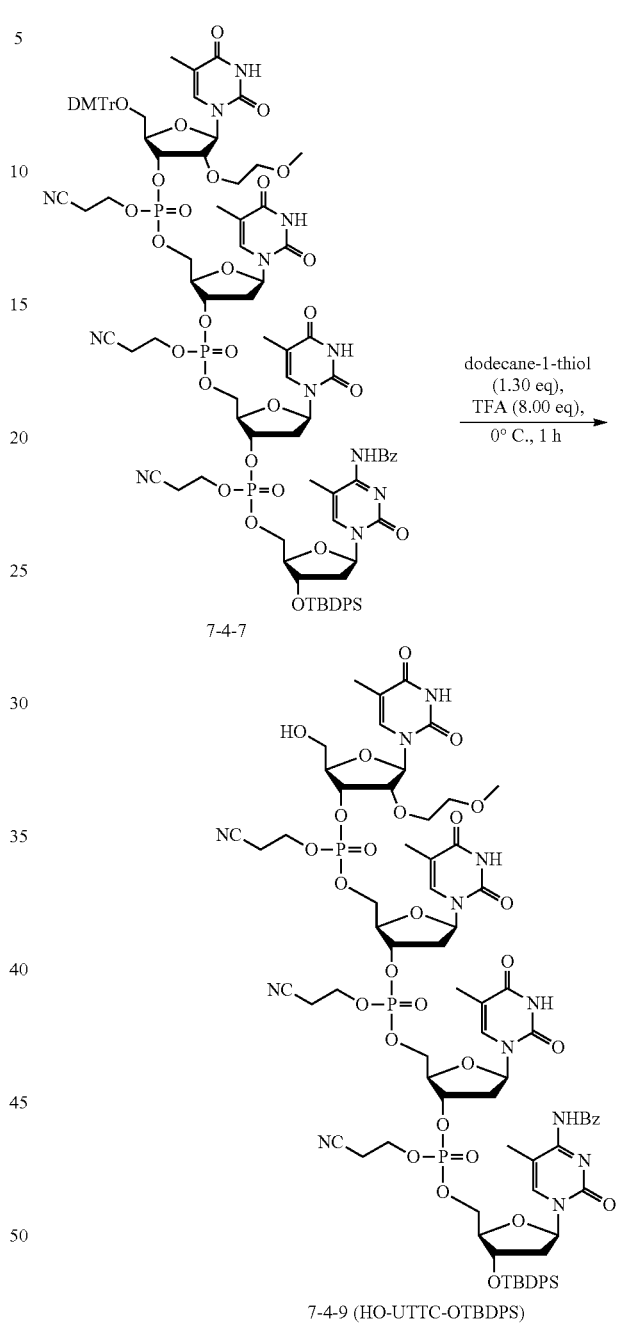

7-4-7 dodecane-1-thiol
(1.30 eq),
TFA (8.00 eq),
0° C., 1 h 7-4-9 (HO-UTTC-OTBDPS)

To a solution of 7-4-7 (6.00 g, 2.95 mmol, 1.00 eq) in ACN (30 mL) was added dodecane-1-thiol (896 mg, 4.43 mmol, 1.06 mL, 1.50 eq) and then TFA (2.69 g, 23.6 mmol, 1.75 mL, 8.00 eq) was added dropwise at 0° C. The mixture was stirred at 0° C. for 1 h. TLC (DCM: MeOH=10:1, Product: $R_f$=0.35) indicated 7-4-7 was consumed completely and two new spots formed. The reaction was messy according to TLC.

The reaction mixture was poured into the NaHCO₃ (10.0 eq NaHCO₃ in 100 mL DI water), and then diluted with EtOAc 50 mL and extracted with aq·NaHCO₃ 100 mL. The combined organic layers were washed with brine 200 mL (100 mL×2), dried over Na₂SO₄, filtered and concentrated under reduced pressure to give a residue.

The crude was re-dissolved in DCM (80 mL). The crude solvent was slowly dropped to a solvent of MTBE (300 mL). Desired product was precipitated out. The product was collected as a white solid after filtration, and the solid cake was washed with isopropyl ether MTBE (50 mL×2).

Compound 7-4-9 (HO-UTTC-OTBDPS) (4.97 g, 2.86 mmol, 96.6% yield, and 99.3% purity) was obtained as a white solid.

HPLC (Method B): RT=6.895 min.; LCMS (Method F): RT=1.323 min; m/z: [M+H]+=1729.6.

C. Convergent Synthesis of Target Oligonucleotide ASO 9-1

HPLC-MS method for synthesis of ASO 9-1 & 9-2 and their intermediates 7a-e.

Column: ACQUITY UPLC Oligonucleotide BEH C18 Column, 130 Å, 1.7 μm, 2.1 mm×150 mm;
Column temperature: 35° C.;
Mass range from 200 to 2300;
MS polarity: Negative
Mobile phases:
    Solution A: 5 mM tributylamine acetate (TBuAA) in 10% CH₃CN, 1 μm EDTA;
    Solution B: 5 mM TBuAA in 80% CH₃CN, 1 μm EDTA
Gradient:

| Time min | A % | B % | Flow mL/min | Pressure bar |
|---|---|---|---|---|
| 0.50 | 75.00 | 25.00 | 0.51 | — |
| 5.00 | 50.00 | 50.00 | 0.51 | — |
| 18.00 | 20.00 | 80.00 | 0.51 | — |
| 19.00 | 75.00 | 25.00 | 0.51 | — |
| 20.00 | 75.00 | 25.00 | 0.51 | — |

Figure 40:
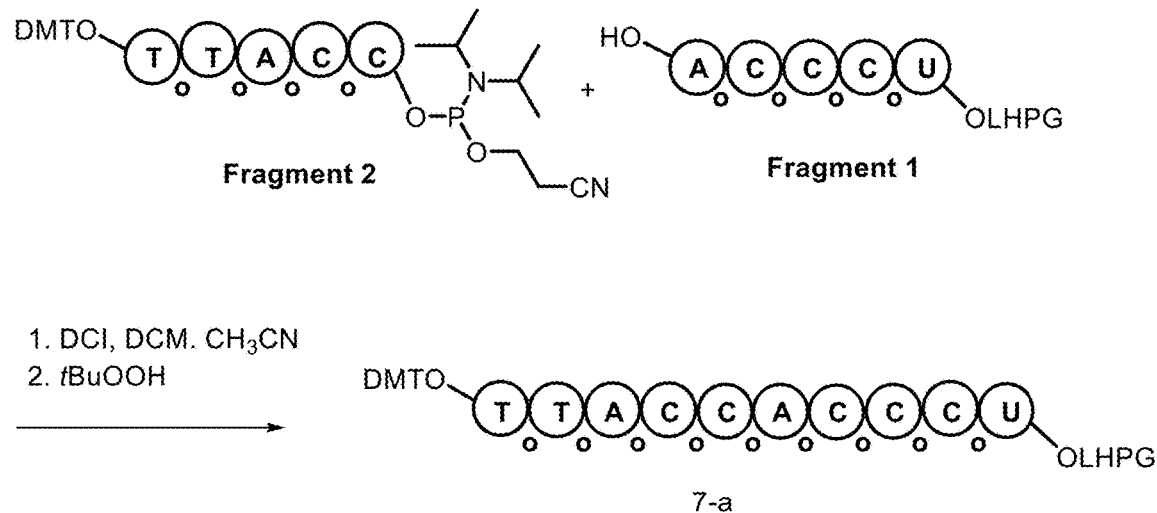
FIG. 40 shows a scheme for the general preparation of Compound 7-a.

ASO 9-1 was synthesized using the convergent synthesis procedure similar to the above disclosed method for ASO 9 synthesis General procedure for preparation of compound 7-a (FIG. 40)

Figure 21:
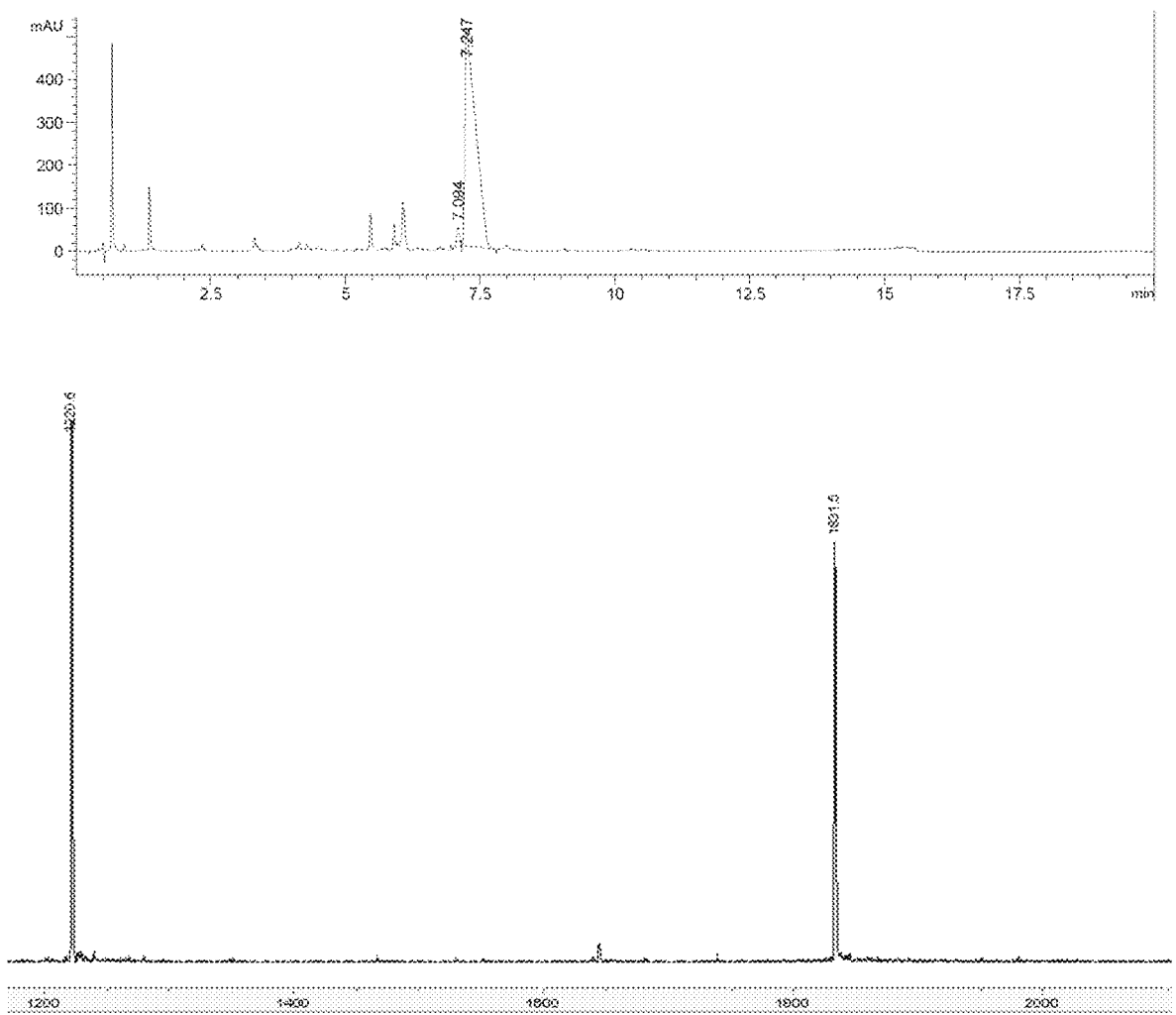
FIG. 21 shows HPLC and MS of LHPG deprotected compound 7-a.

Fragment 1 and 2 were coupled to synthesize 7-a using the similar procedure as disclosed above. 7-a was characterized by HPLC and mass spectrometry after deprotecting LHPG group using ammonolysis; HPLC-MS: RT=7.247 min and m/z=1831.5 (see FIG. 21).

Figure 41:
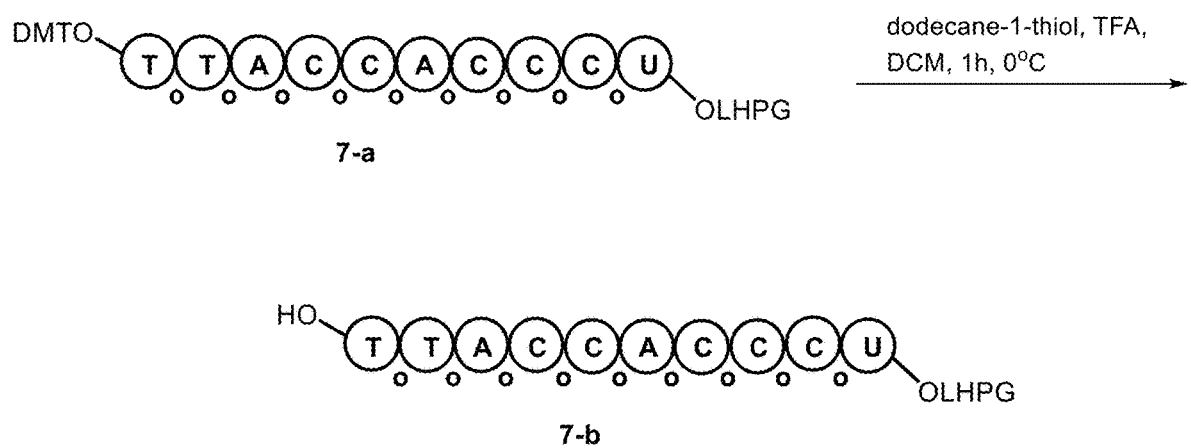
FIG. 41 shows a scheme for the general preparation of Compound 7-b.

General procedure for preparation of compound 7-b (FIG. 41)

Figure 22:
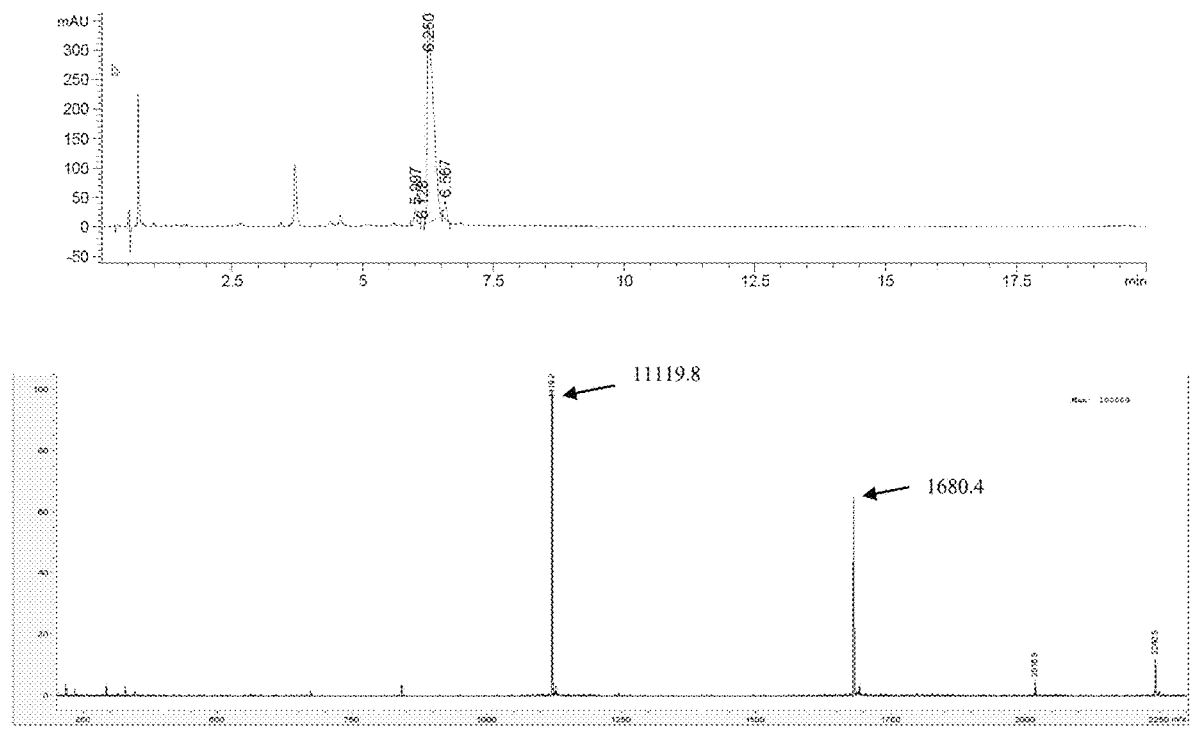
FIG. 22 shows HPLC and MS of LHPG deprotected compound 7-b.

Compound 7-b was synthesized from 7-a using the above-disclosed detritylation method. 7-b was characterized by HPLC and Mass Spectrometry after deprotecting LHPG group using ammonolysis HPLC-MS: RT=6.250 min and m/z=1680.4 (see FIG. 22)

Figure 42:
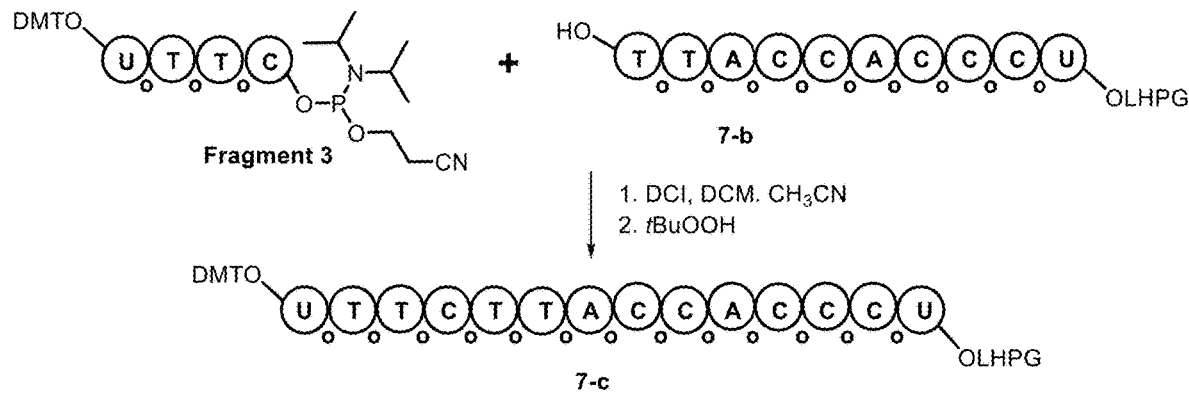
FIG. 42 shows a scheme for the general preparation of Compound 7-c.

General procedure for preparation of compound 7-c (FIG. 42)

Figure 23:
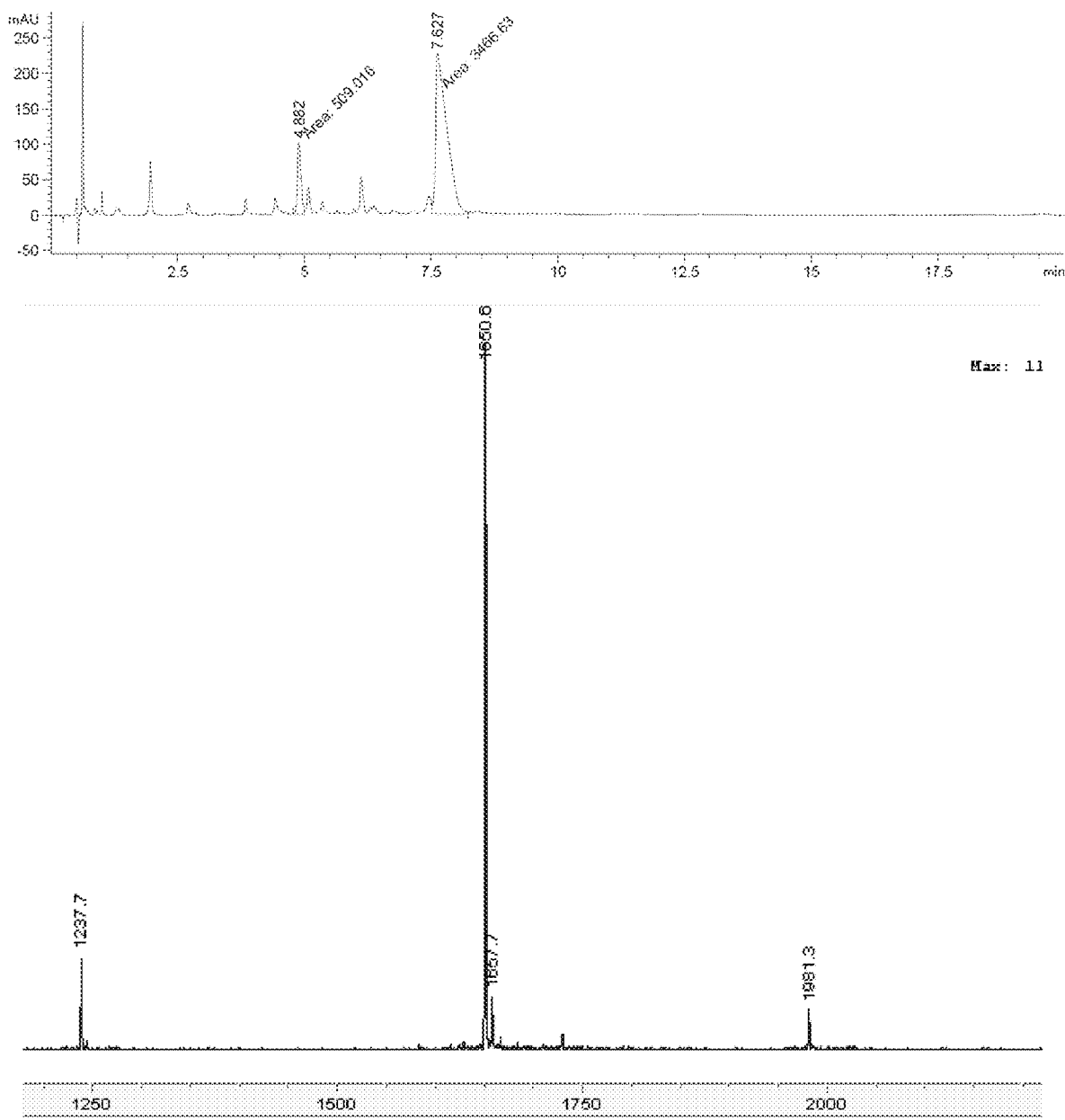
FIG. 23 shows HPLC and MS of LHPG deprotected compound 7-c.

Fragment 3 and 7-b were coupled to synthesize 7-c using the similar procedure as disclosed above. 7-c was characterized by HPLC and Mass Spectrometry after deprotecting LHPG group using ammonolysis HPLC-MS: RT=7.627 min and m/z=1650.6 (see FIG. 23)

Figure 43:
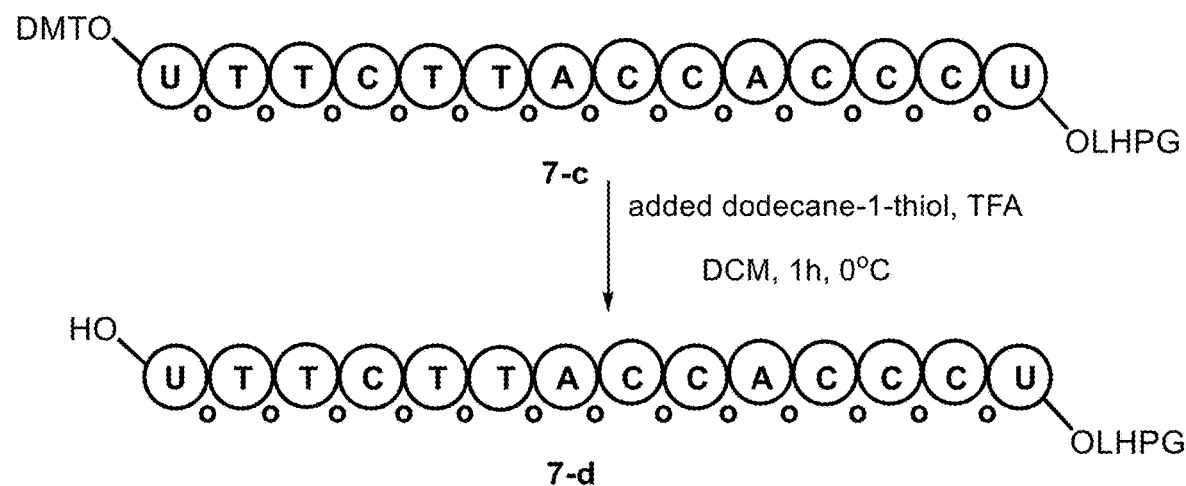
FIG. 43 shows a scheme for the general preparation of Compound 7-d.

General procedure for preparation of compound 7-d (FIG. 43)

Figure 24:
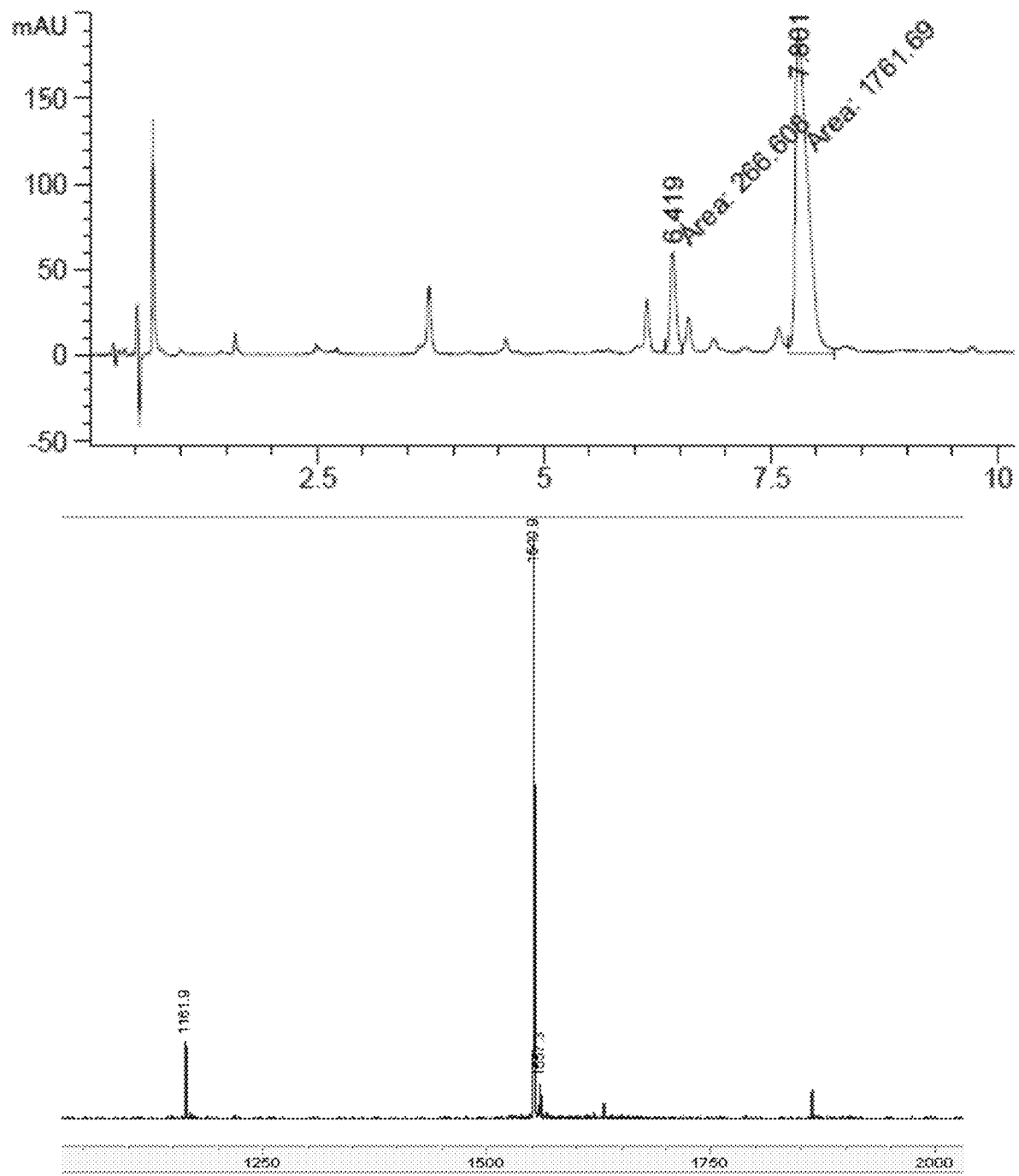
FIG. 24 shows HPLC and MS of LHPG deprotected 7-d compound.

Compound 7-d was synthesized from 7-c using the above-disclosed detritylation method. 7-d was characterized by HPLC and Mass Spectrometry after deprotecting LHPG group using ammonolysis; HPLC-MS: RT=7.801 min and m/z=1549.9 (see FIG. 24).

Figure 44:
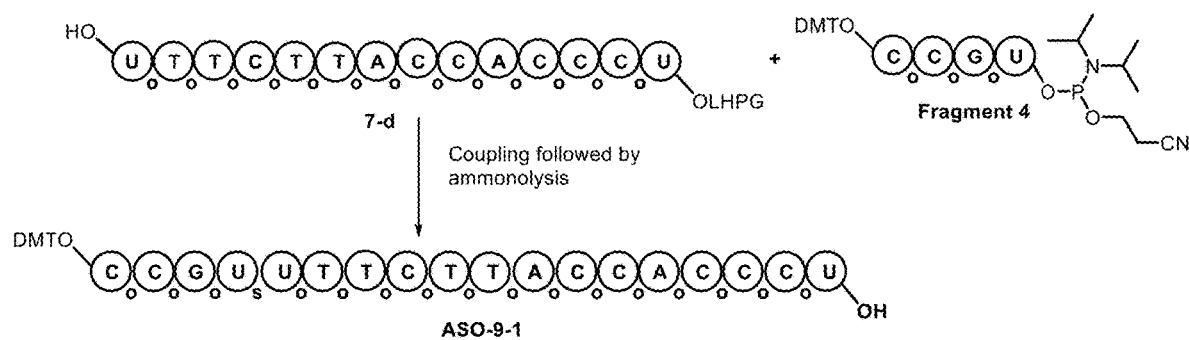
FIG. 44 shows a scheme for the general preparation of Compound ASO-9-1.

General procedure for preparation of compound ASO-9-1 (FIG. 44)

Figure 25:
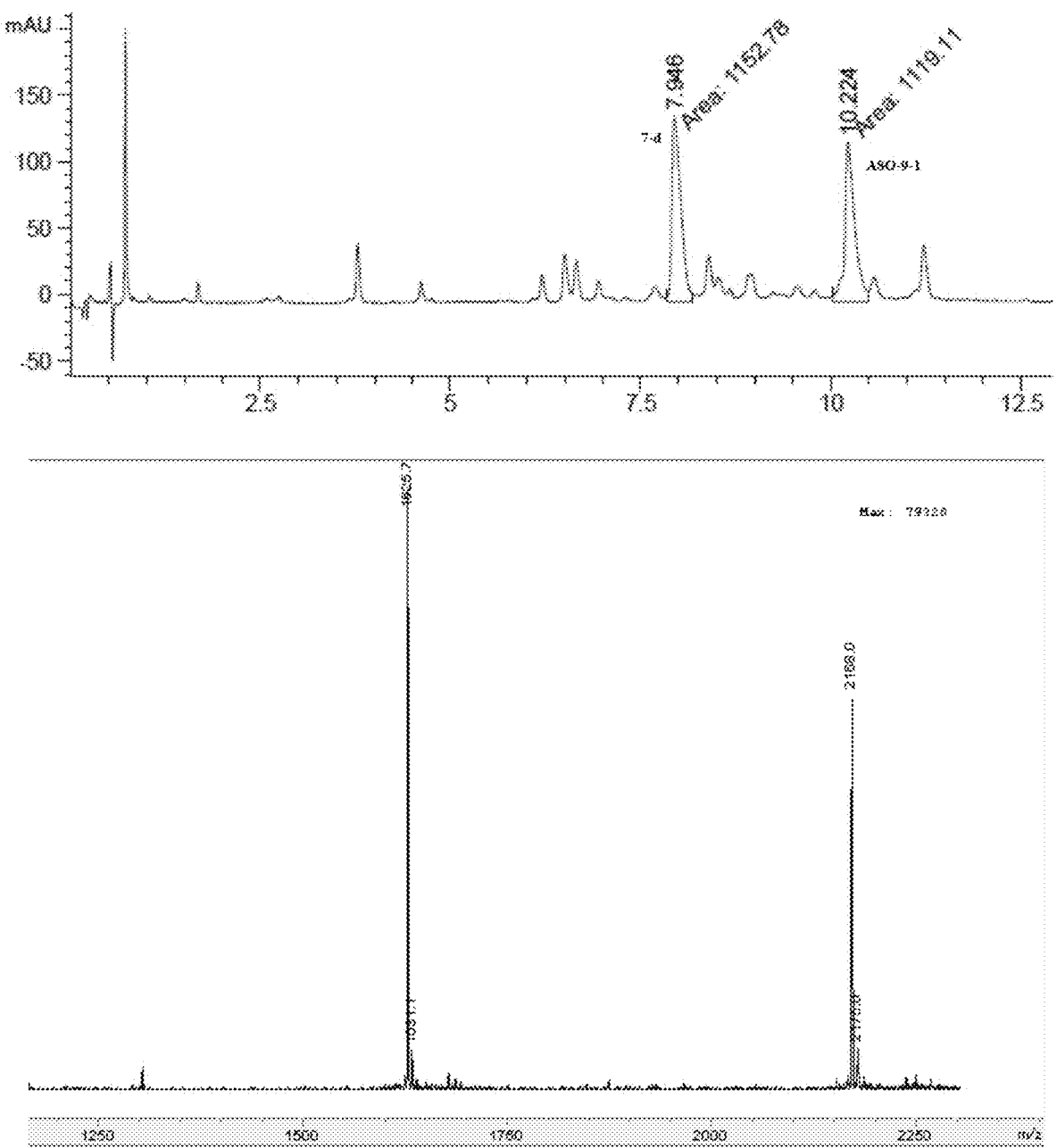
FIG. 25 shows HPLC and MS of ASO-9-1.

ASO-9-1 was synthesized by coupling fragment 7-d and fragment 4 using similar procedure as disclosed for the synthesis of ASO 9. ASO-9-1 was confirmed by HPLC-MS: RT=10.224 min and m/z: =2168.0 (see FIG. 25).

Figure 45:
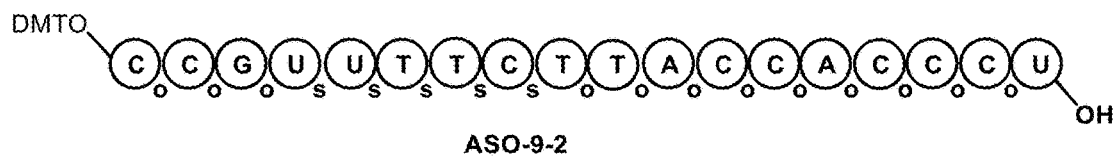
FIG. 45 shows a target oligonucleotide ASO-9-2.

D. Convergent Synthesis of Target Oligonucleotide ASO-9-2 (FIG. 45)

Figure 46:
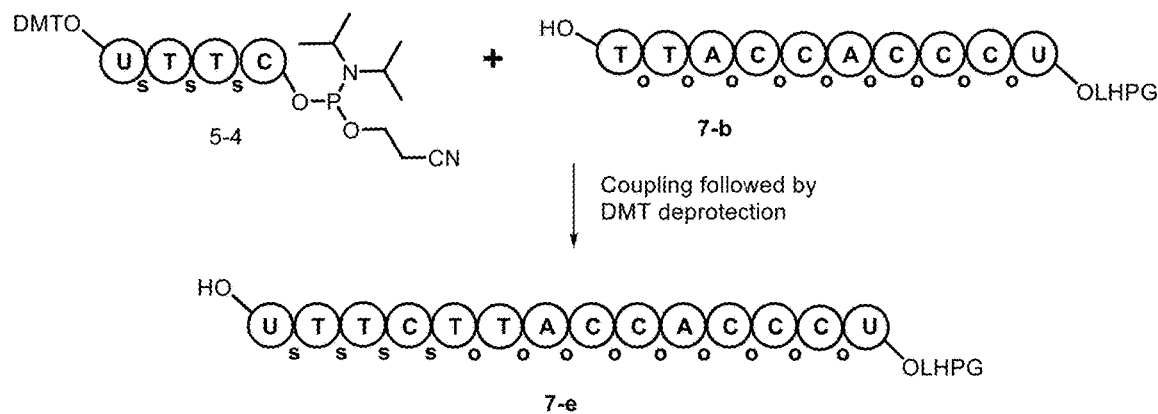
FIG. 46 shows a scheme for the convergent synthesis of target oligonucleotide ASO-9-2.

ASO 9-2 was synthesized using the convergent synthesis procedure similar to the above disclosed method for ASO 9 and ASO-9-1 synthesis. (FIG. 46)

Figure 26:
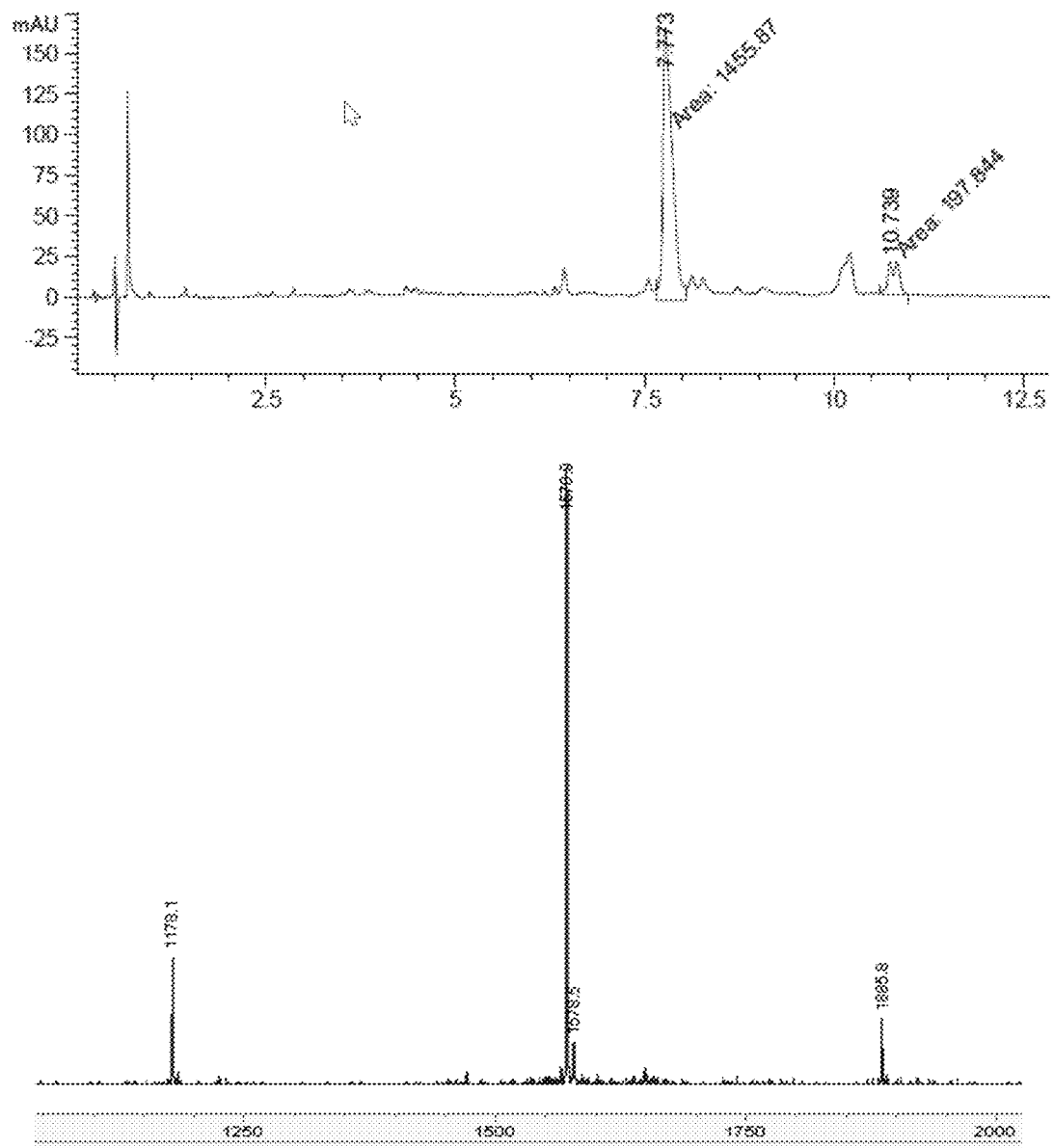
FIG. 26 shows HPLC and MS of LHPG deprotected 7-e compound.

Compound 7-e was synthesized by coupling fragment 5-4 and fragment 7-b using the above-disclosed coupling procedure followed by the above-disclosed detritylation method. 7-e was characterized by HPLC and Mass Spectrometry after deprotecting LHPG group using ammonolysis; HPLC-MS: RT=7.773 min and m/z=1570.9 (see FIG. 26)

Figure 47:
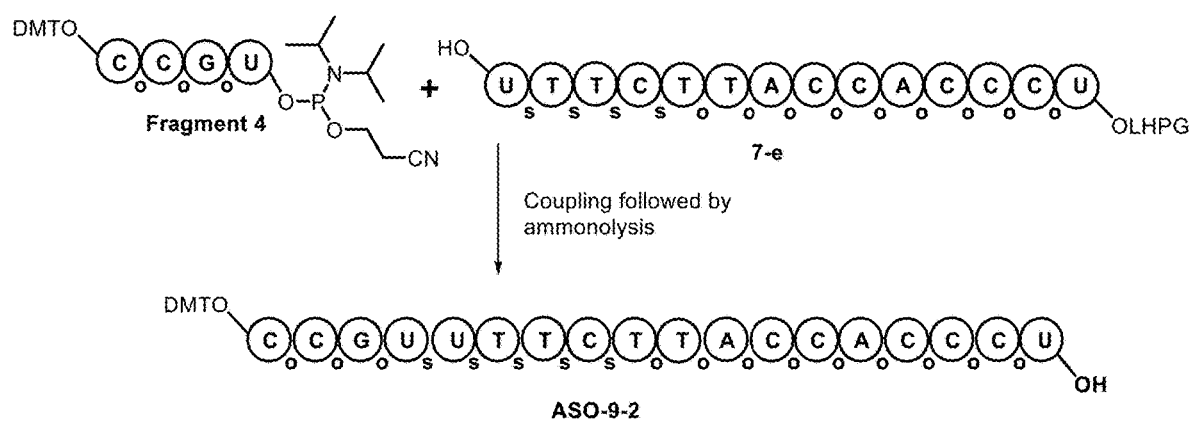
FIG. 47 shows a scheme for the general preparation of Compound ASO-9-2.

General procedure for preparation of compound ASO-9-2 (FIG. 47)

Figure 27:
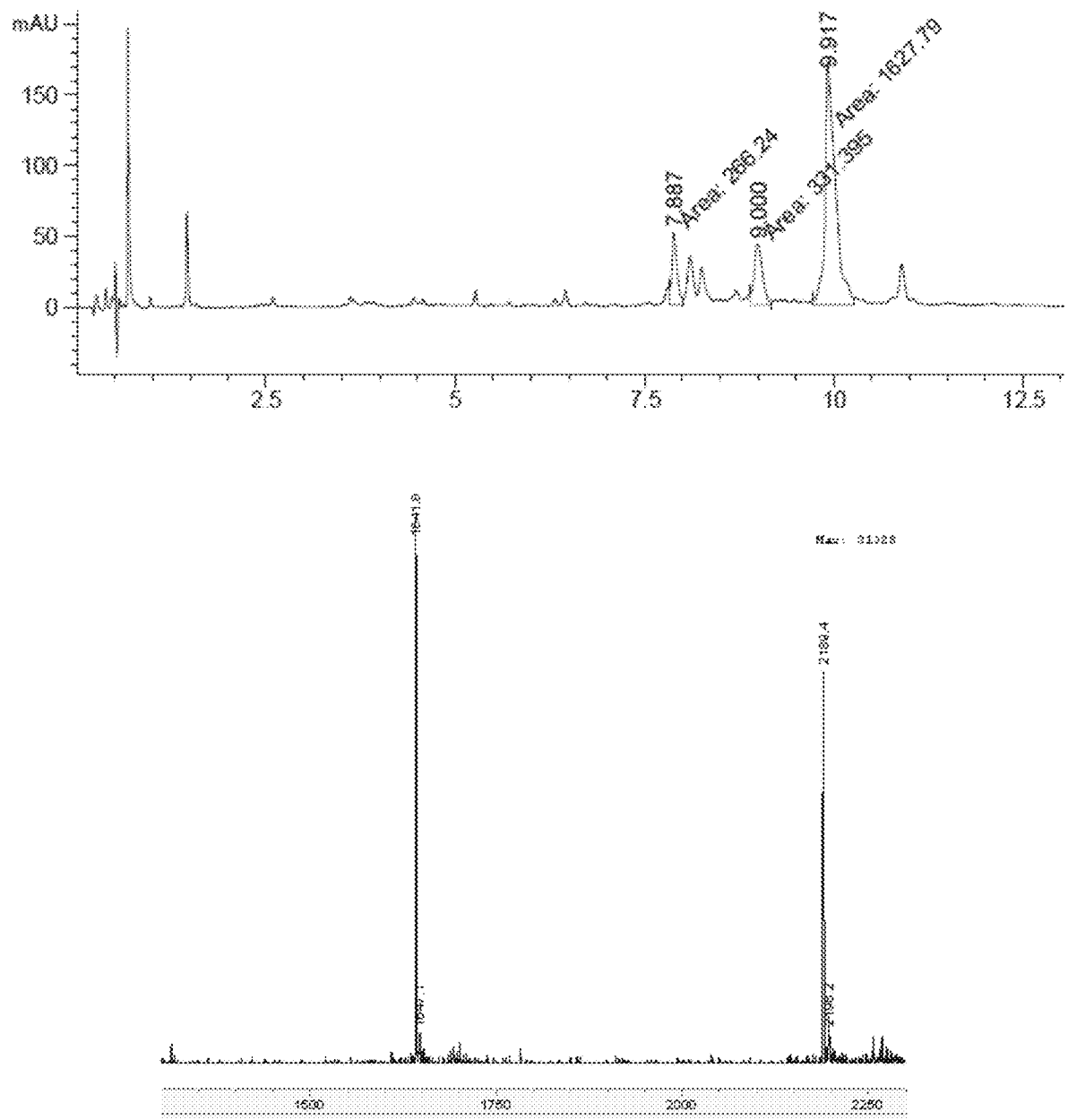
FIG. 27 shows HPLC and MS of ASO-9-2.

ASO-9-2 was synthesized by coupling fragment 7-e and fragment 4 using similar procedure as disclosed for the synthesis of ASO 9 and ASO-9-1. ASO-9-2 was confirmed by HPLC-MS: RT=9.917 min and m/z: =2189.4 (see FIG. 27).

Example 8. Synthesis of Stereospecific Oligonucleotides Using PSI Chemistry

For the Prep-HPLC method described below, mobile phase solvents are described in the format of [A-B], in which A refers to mobile phase A and B refers to mobile phase B. For example, mobile phase [TEAB(10 mM)-ACN] means that 10 mM TEAB was used as mobile phase A and HPLC grade acetonitrile was used as mobile phase B.

The following analytical methods were used for the synthesis of compounds and oligonucleotides described in Example 8.

HPLC method:

| Method name: | 10-80HPLC-CD-10min |
|---|---|
| Instrument: | Shimadzu LC-20AD |
| Column: | XBridge Shield RP18 2.1*50 mm, 5 um |
| Column temperature: | 40° C. |
| Mobile phase A (MPA) | H₂O + 10 mM NH₄HCO₃ |
| Mobile phase B (MPB) | HPLC grade acetonitrile |
| Flow rate: | 0.8 mL/min (0.01-9 min), 1.2 mL/min (9.01-10 min) |
| Gradient Ratio: | Time (min)  0.01  8  9  9.01  10 |
| | MPA (%)  90  20  20  90  90 |
| | MPB (%)  10  80  80  10  10 |
| Detection: | Diode array (DAD) 220 nm, 215 nm, 254 nm |

LC-MC method:
| | |
|---|---|
| Method name: | 5-95CD-MS2000_2min |
| Instrument: | Shimadzu LC-20AD & MS 2020 |
| Column: | Xbridge Shield RP18 2.1*50 mm, 5 um |
| Column temperature: | 40° C. |
| Mobile phase A (MPA) | H2O + 10 mM NH4HCO3 |
| Mobile phase B (MPB) | Acetonitrile |
| Flow rate: | 1.0 mL/min |
| Gradient Ratio: | Time (min)  0.01  1.00  1.80  1.81  2.2 |
| | MPA (%)     95    5     0     95    95 |
| | MPB (%)     5     95    100   5     5 |
| Detection: | 220 nm, 254 nm |
| STOP time: | 2.2 min |
| MS Mode: | Positive |
| MS Range: | 100-2000 |
1.1 Linear synthesis of dTdAdCdC Fragment
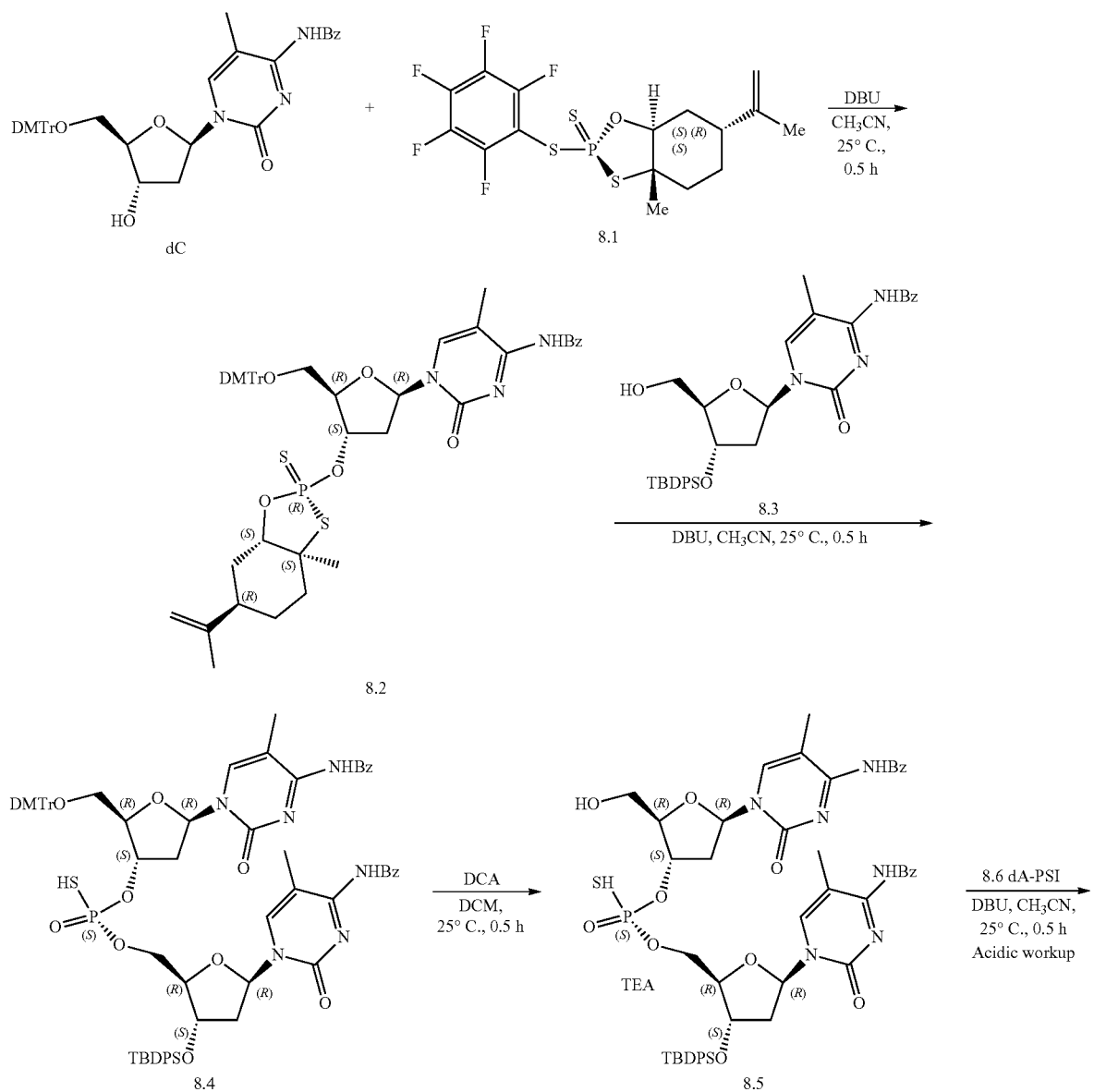

-continued

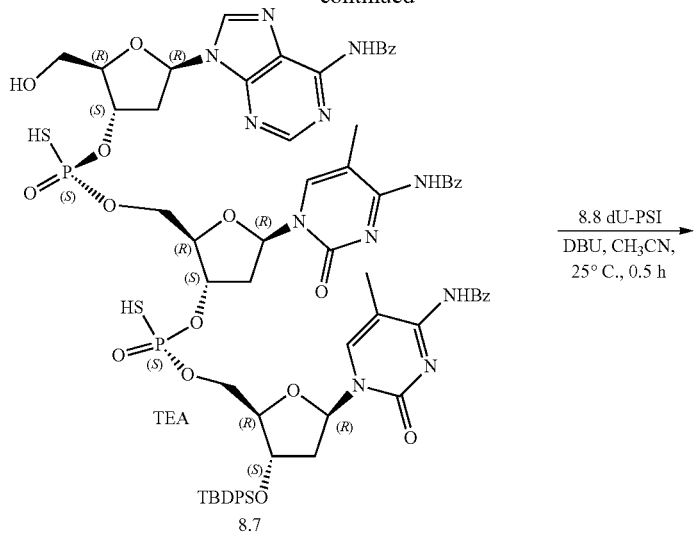

8.8 dU-PSI
DBU, CH₃CN,
25° C., 0.5 h

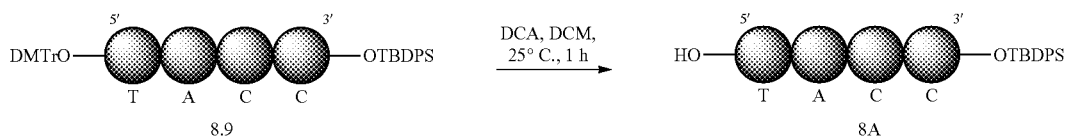

Preparation of compound 8.2

Compound dC (10 g, 15.44 mmol, 1 eq) was azeotropic with ACN (10 mL×2). To a solution of Compound dC (10 g, 15.44 mmol, 1 eq) and PSI reagent, compound 8.1, (8.96 g, 20.07 mmol, 1.3 eq) in ACN (60 mL) was added DBU (3.06 g, 20.07 mmol, 3.03 mL, 1.3 eq) at 0° C. under $N_2$. The mixture was stirred at 25° C. for 0.5 h. TLC (Petroleum ether/Ethyl acetate=2:1, $R_f$=0.54) indicated Compound dC was consumed completely. The mixture was filtered through a short pad of silica gel, then the silica gel was washed with BA (60 mL×2). The organic phase was washed with sat·$KH_2PO_4$ (30 mL), sat. $NaHCO_3$ (30 mL), brine (30 mL×2), dried over anhydrous $Na_2SO_4$, filtered and the solvent was removed in vacuum. The crude product was purified by chromatography ($SiO_2$, Petroleum ether/Ethyl acetate=50/1 to 1/1). Compound 8.2 (7.3 g, 8.00 mmol, 51.83% yield, 98% purity) was obtained as a white solid. IPC (in process control): TLC (Petroleum ether/Ethyl acetate=2:1, product ($R_f$)=0.54) HPLC shows RT 8.666.

Preparation of Compound 8.4

Compound 8.3 (4 g, 6.85 mmol, 1 eq) was azeotropic with ACN (10 mL×2). Compound 8.3 (3.5 g, 6.00 mmol, 1 eq) in ACN (24 mL) was added Molecular Sieve 3A (1 g, 1.00 eq) at 25° C. The mixture was stirred at 25° C. for 0.5 h. Then Compound 8.2 (5.90 g, 6.60 mmol, 1.1 eq) and DBU (2.74 g, 17.99 mmol, 2.71 mL, 3 eq) was added at 25° C. The mixture was stirred at 25° C. for 0.5h. LCMS (product: RT=1.469 min) indicated Compound 8.2 was consumed completely. The mixture was diluted with ethyl acetate (10 mL), 20% citric acid (10 mL). The organic phase was washed with $H_2O$ (10 mL), sat. $NaHCO_3$ (10 mL), brine (10 mL), dried over anhydrous $Na_2SO_4$, filtered and the solvent was removed in vacuo. The crude product was used without purification. Compound 8.4 [(m/z-H⁺)=1307.6, 9.48 g, crude] was obtained as a yellow solid.

Figure 28:
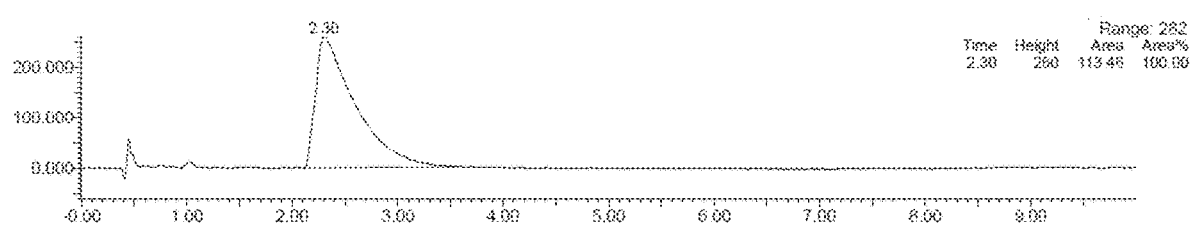
FIG. 28 shows chiral SFC-MS of compound 8.4.

Stereoselectivity of Compound 8.4 was tested by superfluid chromatograph (SFC) (described below). Compound 8.4 was demonstrated a single peak at RT=2.30 min (see FIG. 28). No other peaks are detected. The stereoselectivity is >99.5%.

Figure 29:
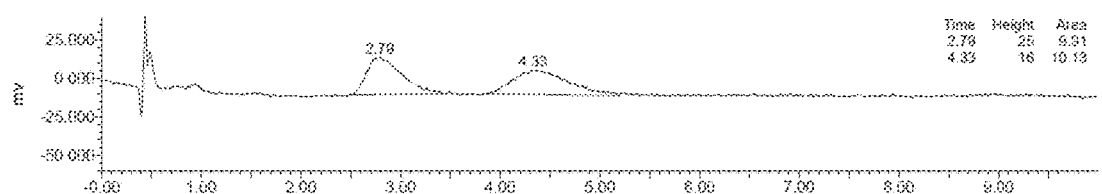
FIG. 29 shows SFC-MS of racemic mixture of compound 8.4.

SFC method:
Instrument: CAS-TJ-ANA-SFC-1 (Waters SFC-MS)
Column: chiralcel OD-3, 4.6*100 mm, 3 um
Mobile phase: A for SFC CO2 and B for EtOH (0.05% IPAm)
Gradient: B is 40% in 10 minutes
Flow rate: 4.0 mL/min
Column temperature: 35° C.
Wavelength: 220 nm
System Back Pressure: 100 bar For comparison, a racemic sample was synthesized by amidite chemistry as standard with 2 retention times: 2.79 min and 4.33 min (see FIG. 29).

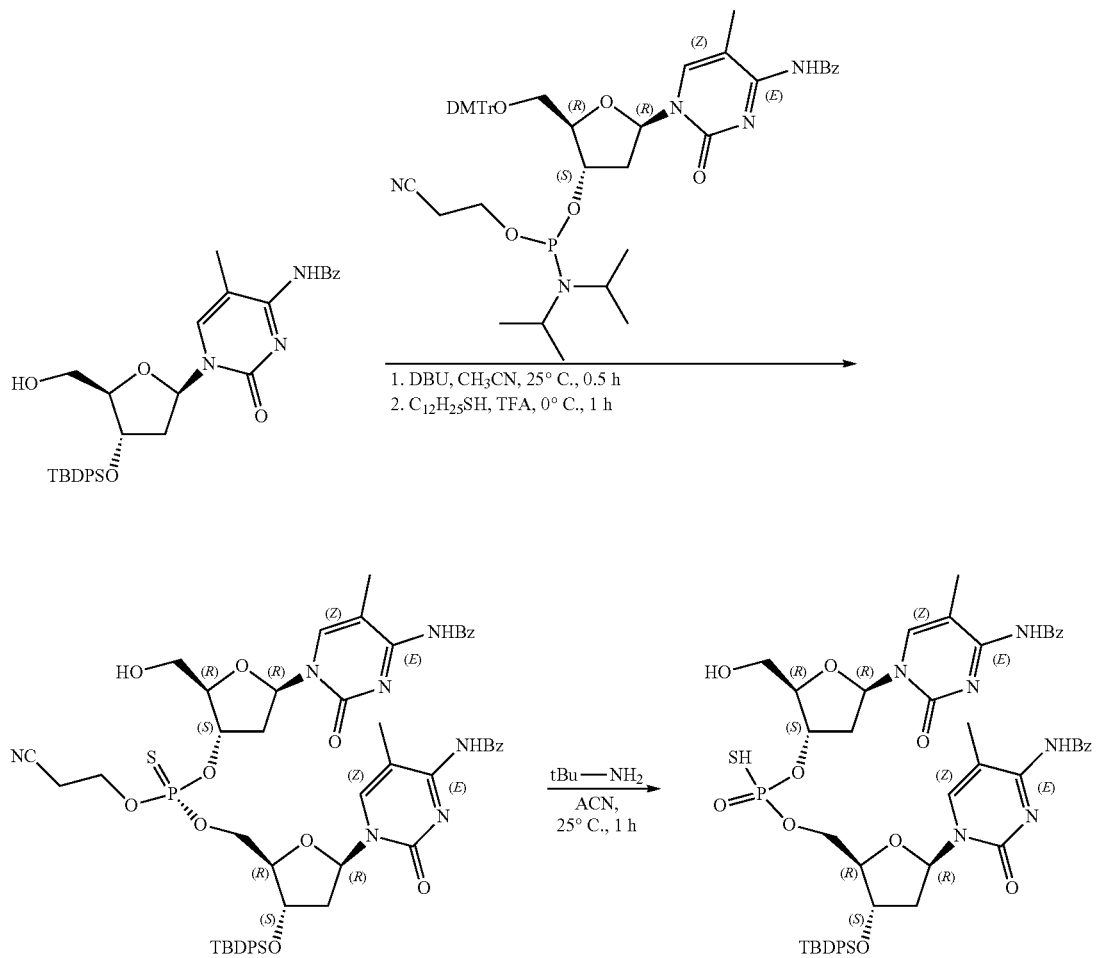

Preparation of Compound 8.5

To a solution of Compound 8.4 (7.85 g, 5.99 mmol, 1 eq) in DCM (55 mL) was added 2,2-dichloroacetic acid (5.18 g, 40.18 mmol, 3.3 mL, 6.70 eq) at 25° C. under $N_2$. The mixture was stirred at 25° C. for 1 h. LCMS (product: RT=1.352 min) indicated Compound 8.4 was consumed completely. The mixture was diluted with TEAB (10 mL), DCM (10 mL). The organic phase was washed with $H_2O$ (10 mL), sat. $NaHCO_3$ (10 mL), brine (10 mL×2), dried over anhydrous $Na_2SO_4$, filtered and the solvent was removed in vacuum. The residue was purified by prep-HPLC (neutral condition) (column: YMC-Triart Prep C18 250*50 mm*10 um; mobile phase: [TEAB(10 mM)-ACN]; B %: 45%-65%, 22 min). Compound 8.5 (3.8 g, 3.70 mmol, 61.68% yield, 98% purity) was obtained as a white solid. MS (m-H$^+$)/ z=1005.4, Preparation of compound 8.7

Compound 8.5 (3.5 g, 3.48 mmol, 1 eq) was azeotropic with ACN (10 mL×2). Compound 8.5 (3.5 g, 3.48 mmol, 1 eq) in ACN (25 mL) was added Molecular Sieve 3 Å (0.5 g, 3.48 mmol, 1.00 eq) at 25° C. The mixture was stirred at 25° C. for 0.5 h. Then Compound 8.6 (4.71 g, 5.21 mmol, 1.5 eq) and DBU (1.59 g, 10.43 mmol, 1.57 mL, 3 eq) was added at 25° C. The mixture was stirred at 25° C. for 0.5 h. LCMS (product: RT=1.314 min, (m-H$^+$)/z=1740.4) indicated Compound 8.5 was consumed completely. The mixture was diluted with DCM (10 mL), 20% citric acid (10 mL×2). The organic phase was washed with $H_2O$ (10 mL), $NaHCO_3$ (10 mL), brine (10 mL), dried over anhydrous $Na_2SO_4$, filtered and the solvent was removed in vacuo. The crude product was purified by prep-HPLC (Instrument: Shimadzu 20AP; column: YMC-Actus Triart C18 150*30 mm*5 um; mobile phase: [TEAB (10 mM)-ACN]; B %: 20%-60%, 12 min). Compound 8.7 (2.7 g, 53.79% yield, 97% purity) was obtained as a yellow solid.

Preparation of compound 8.9

Compound 8.7 (1 g, 694.20 umol, 1 eq) was azeotropic with ACN (5 mL×2). Compound 8.7 (1 g, 694.20 umol, 1 eq) in ACN (7 mL) was added Molecular Sieve 3 Å (0.5 g, 208.26 umol, 1.00 eq) at 25° C. The mixture was stirred at 25° C. for 0.5 h. Then Compound 8.8 (1.10 g, 1.39 mmol, 2 eq) and DBU (317.06 mg, 2.08 mmol, 313.92 uL, 3 eq) was added at 25° C. The mixture was stirred at 25° C. for 0.5 h. LCMS (product: RT=1.254 min) indicated Compound 8.7 was consumed completely. The mixture was diluted with DCM (30 mL), pH=3 citric acid (20 mL). The organic phase was washed with $H_2O$ (20 mL), TEAB (20 mL), brine (20 mL), dried over anhydrous $Na_2SO_4$, filtered and the solvent was removed in vacuo. The crude product was used without purification. Compound 8.9 was obtained as a yellow solid (MS (m−2H$^+$)/z=807.3, 2.1 g, 75.49% LCMS purity).

Preparation of Compound 8A

To a solution of Compound 8.9 (1.43 g, 693.12 umol, 1 eq) in DCM (12 mL) was added 2,2-dichloroacetic acid (1.13 g, 8.77 mmol, 720.00 uL, 12.65 eq) at 25° C. under $N_2$.

Figure 30:
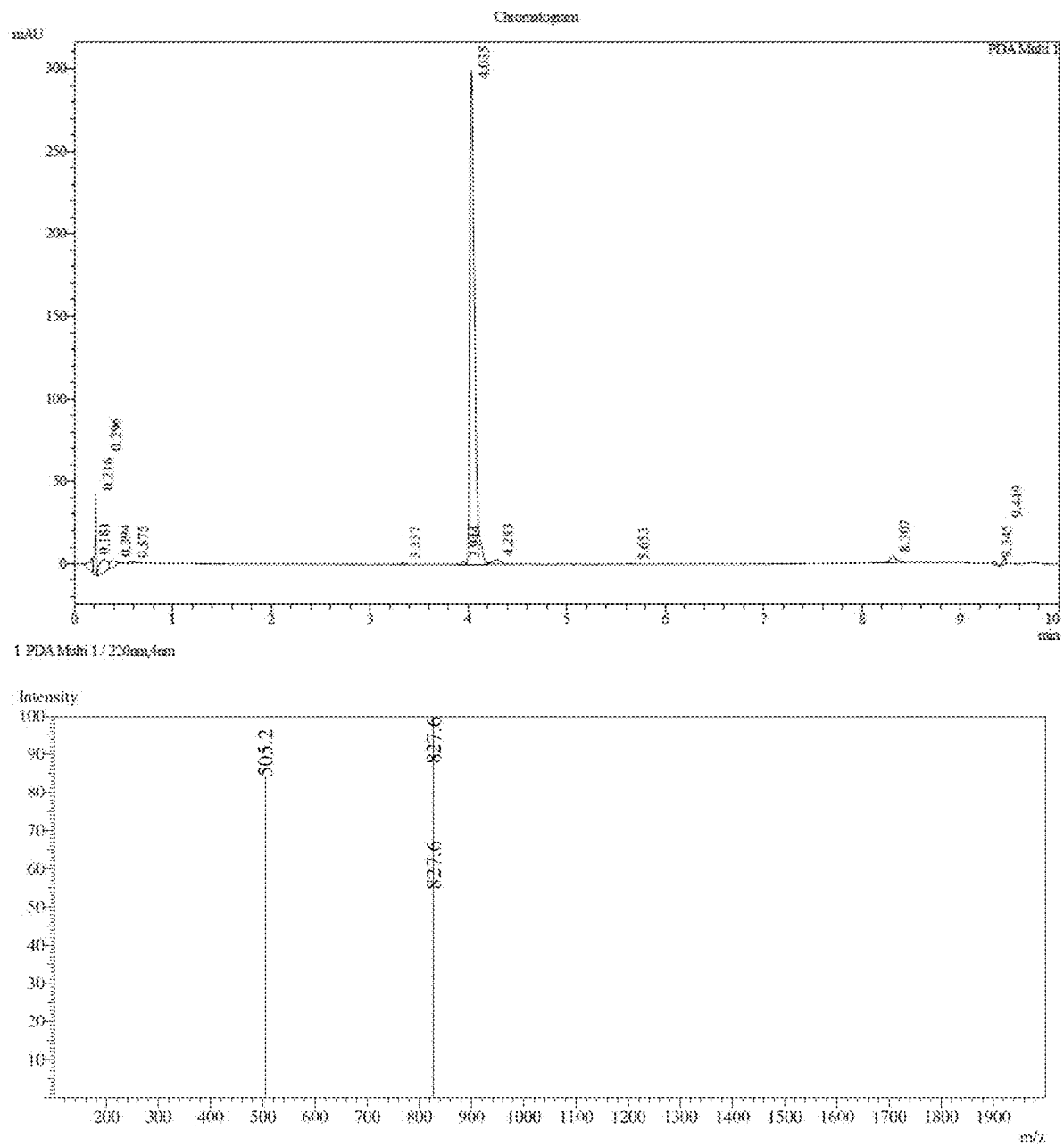
FIG. 30 shows HPLC and MS of compound 8A.

The mixture was stirred at 25° C. for 1 h. LCMS (product: RT=1.168 min) showed the starting material was consumed completely. The mixture was diluted with TEAB (15 mL), DCM (25 mL). The organic phase was washed with $H_2O$ (20 mL), brine (20 mL), dried over anhydrous $Na_2SO_4$, filtered and the solvent was removed in vacuum. The crude product was purified by prep-HPLC (neutral condition) (column: YMC-Actus Triart C18 150*30 mm*5 um; mobile phase: [TEAB(10 mM)-ACN]; B %: 10%-40%, 10 min. Compound 8A [(m−2H$^+$)/z=879.6, 522 mg, 41.0% yield for two steps, 97.6% purity) was obtained as a white solid and characterized by HPLC and MS (see FIG. 30). 1.1.1 Coupling conditions during TACC tetramer synthesis:

Based on the IPC after coupling reaction, the conversion of coupling steps went completion. The summarized coupling step conditions at different stages and the HPLC purities were as follows:

| Coupling Stage | Equivalent of PSI-amidite | Equivalent of DBU | Reaction time (h) | Reaction Temp (° C.) | Yield (%) | Purity (%) |
|---|---|---|---|---|---|---|
| Dimer | 1.1 | 3.0 | 0.5 | 25 | 61.68 | 98 |
| Trimer | 1.5 | 3.0 | 0.5 | 25 | 53.79 | 97 |
| Tetramer | 1.5 | 3.0 | 0.5 | 25 | 41.00 | 98 |

In conclusion, a tetramer oligonucleotide was synthesized using liquid phase linear elongation method with PSI-reagent. Detritylation with DCA caused a de-prunination of adenosine. De-tritylation of trimer was achieved by acidic work-up step using 20% citric acid. Coupling efficiency decreases as the oligonucleotide grows longer. Additional equivalent of PSI-amidite and DBU are necessary at later stage of the coupling. The presence of benzyl and isobutyryl protecting group are not disturbed under the coupling conditions, especially under the treatment of DBU.

1.2 Linear elongation of MOE-Fragment DMTO-AGUCU-OH by using PSI chemistry

Figure 48:
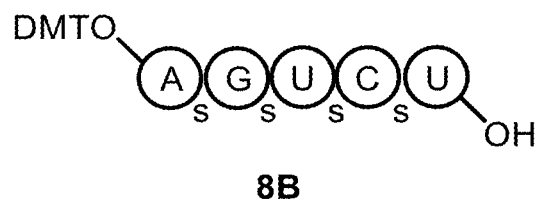
FIG. 48 shows oligonucleotide fragment 8B.

The synthesis of MOE-oligo by using PSI reagent is not reported. PSI chemistry was applied on the coupling reaction of 2' MOE nucleoside, and a liquid phase synthesis process for the elongation of 2' MOE oligo 8B was developed (FIG. 48).

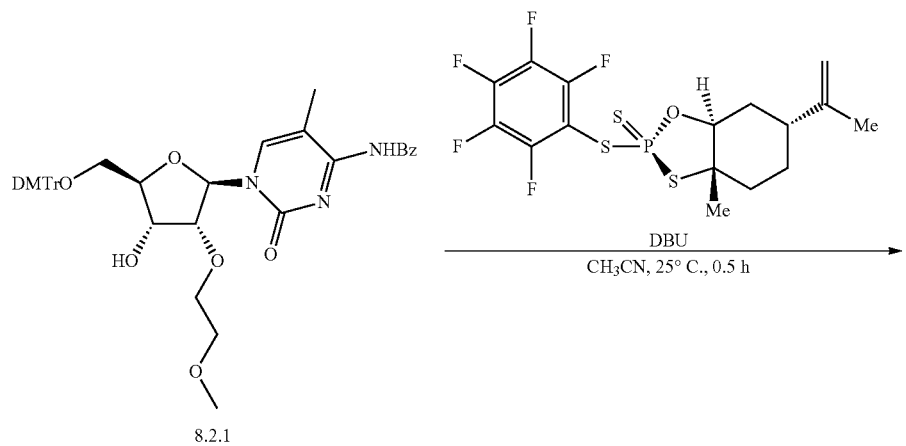

8.2.1

-continued
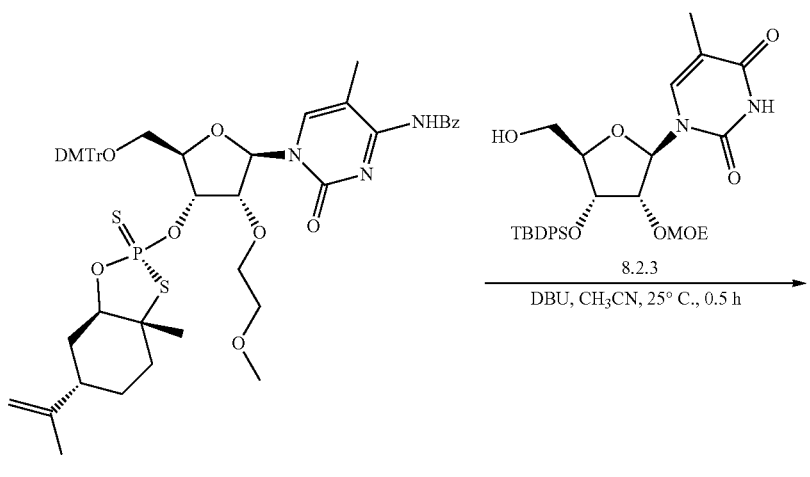
8.2.2
→ DBU, CH₃CN, 25° C., 0.5 h
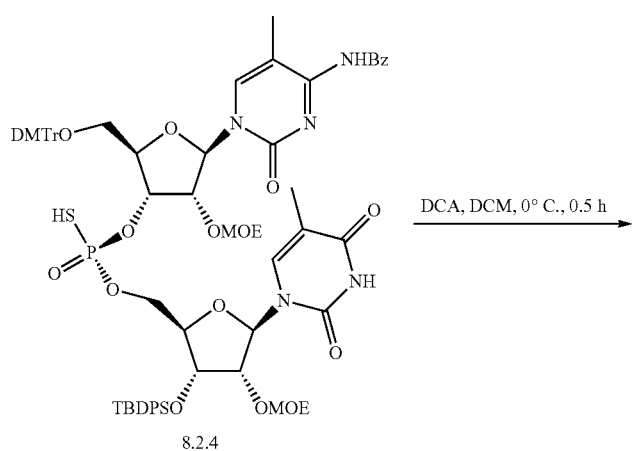
8.2.4
→ DCA, DCM, 0° C., 0.5 h
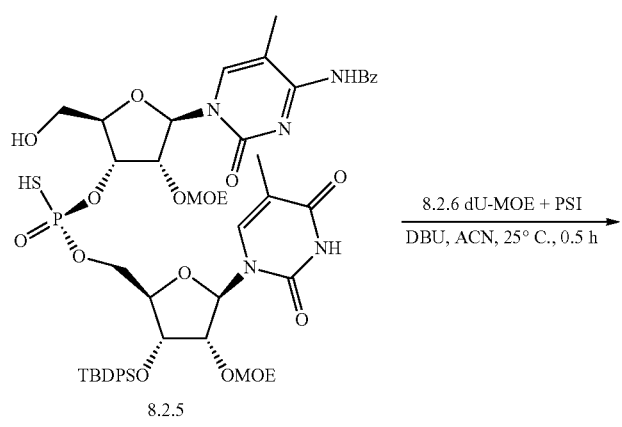
8.2.5
→ 8.2.6 dU-MOE + PSI
DBU, ACN, 25° C., 0.5 h

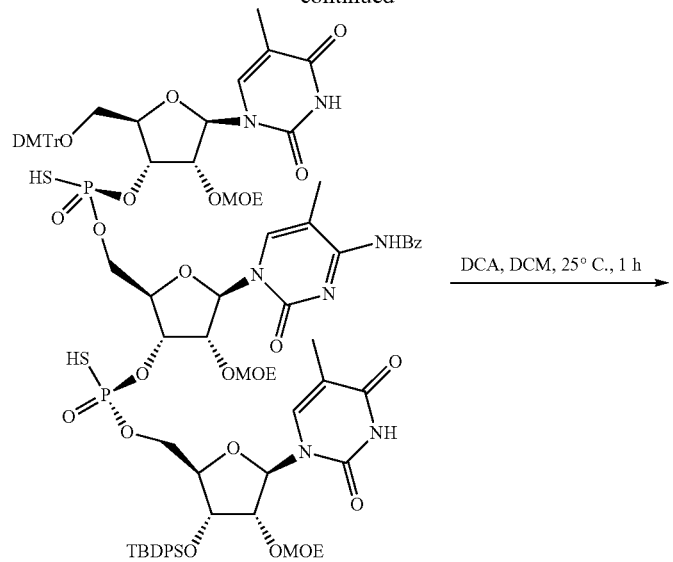
8.2.7
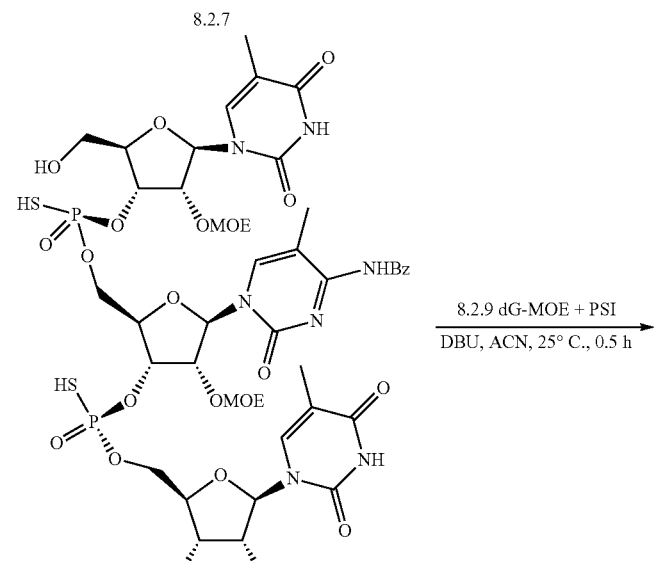
8.2.8
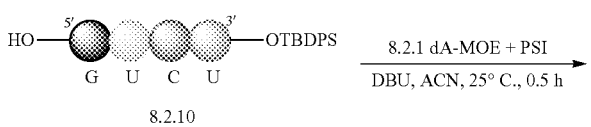
8.2.10
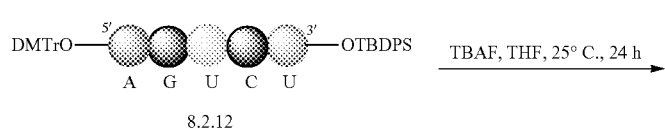
8.2.12
8B
Synthesis of Compound 8.2.2
To a solution of Compound 8.2.1 (5.00 g, 6.93 mmol, 1 eq) and PSI reagent (4.02 g, 9.01 mmol, 1.3 eq) in ACN (35 mL) was added DBU (1.37 g, 9.01 mmol, 1.36 mL, 1.3 eq) at 0° C. The mixture was stirred at 25° C. for 0.5 h. TLC (Petroleum ether:Ethyl acetate=0:1, Rf=0.82) indicated Reactant 8.2.1 was consumed completely. The mixture was filtered through a short pad of silica gel, then the silica gel was washed with EA (80 mL×2). The filtered was washed with sat·KH$_2$PO$_4$ (100 mL), sat. NaHCO$_3$ (100 mL), brine (100 mL), dried over anhydrous Na$_2$SO$_4$, filtered and concentrated. The residue was purified by chromatography (SiO$_2$, Petroleum ether/Ethyl acetate=30/1 to 0/1). Compound 8.2.2 [(m-H$^+$)/z=966.4, 5.5 g, 5.51 mmol, 79.55% yield, 97% purity] was obtained as a white solid.

Synthesis of Compound 8.2.4

Compound 8.2.2 (5.00 g, 9.01 mmol, 1 eq) was azeotropic with ACN (40 mL×2), Compound 8.2.3 (9.60 g, 9.92 mmol, 1.1 eq) was co-evaporated with ACN (40 mL×2). To a solution of Compound 8.2.2 (5 g, 9.01 mmol, 1 eq) and Compound 8.2.3 (9.60 g, 9.92 mmol, 1.1 eq) in ACN (35 mL) was added DBU (4.12 g, 27.04 mmol, 4.08 mL, 3 eq) at 25° C. The mixture was stirred at 25° C. for 0.5 h. LCMS indicated Compound 8.2.2 was consumed completely. The mixture was diluted with EA (150 mL), 20% citric acid (80 mL). The organic phase was washed with sat. NaHCO$_3$ (150 mL), H$_2$O (150 mL), brine (150 mL×2), dried over anhydrous Na$_2$SO$_4$, filtered and the solvent was removed in vacuo. The crude product was used for the next step without purification. Compound 8.2.4 [(m-H$^+$)/z=1353.6, 12.21 g, crude] was obtained as a yellow solid.

Synthesis of Compound 8.2.5

To a solution of Compound 8.2.4 (12.21 g, 9.01 mmol, 1 eq) in DCM (85 mL) was added 2,2-dichloroacetic acid (8.01 g, 62.10 mmol, 5.1 mL, 6.89 eq) at 25° C. The mixture was stirred at 25° C. for 1 h. LCMS indicated Compound 8.2.4 was consumed completely. The mixture was added TEAB (150 mL) slowly, extracted with DCM (150 mL). Then the organic phase was washed with sat. NaHCO$_3$ (150 mL), H$_2$O (150 mL), brine (150 mL), dried over anhydrous Na$_2$SO$_4$, filtered and the solvent was removed in vacuo. The crude product was purified by Prep-HPLC: column: Agela DuraShell C18 250*50 mm*10 um; mobile phase: [TEAB (10 mM)-ACN]; B %: 30%-53%, 22 min. Compound 8.2.5 [(m-H$^+$)/z=1050.5, 6.9 g, 6.36 mmol, 70.57% yield, 97% purity] was obtained as a white solid.

Synthesis of Compound 8.2.7

Compound 8.2.5 (4.50 g, 4.28 mmol, 1 eq) was azeotropic with ACN (40 mL×2), Compound 8.2.6 (5.55 g, 6.42 mmol, 1.5 eq) was co-evaporated with ACN (40 mL×2). To a solution of Compound 8.2.5 (4.5 g, 4.28 mmol, 1 eq) in ACN (30 mL) was added Molecular Sieve 3A (2.40 g, 4.28 mmol, 1.00 eq) at 25° C. The mixture was stirred at 25° C. for 0.5 h. Then Compound 8.2.6 (5.55 g, 6.42 mmol, 1.5 eq) was added at 25° C. DBU (1.95 g, 12.83 mmol, 1.93 mL, 3 eq) was added slowly at 25° C. The mixture was stirred at 25° C. for 0.5 h. LCMS indicated 8.2.5 was consumed completely. The mixture was diluted with DCM (200 mL), pH--3 citric acid (150 mL). The organic phase was washed with NaHCO$_3$ (200 mL), H$_2$O (200 mL), brine (200 mL), dried over anhydrous Na$_2$SO$_4$, filtered and the solvent was removed in vacuo. The crude product was used for the next step without purification. Compound 8.2.7 (9.3 g, crude) was obtained as yellow solid.

Synthesis of Compound 8.2.8

To a solution of Compound 8.2.7 (7.48 g, 4.28 mmol, 1 eq) in DCM (60 mL) was added 2,2-dichloroacetic acid (7.85 g, 60.88 mmol, 5 mL, 14.23 eq) at 25° C. The mixture was stirred at 25° C. for 1 h. LCMS indicated Compound 8.2.7 was consumed completely. The mixture was diluted with DCM (150 mL), quenched by TEAB (150 mL). The organic phase was washed with NaHCO$_3$ (150 mL), H$_2$O (150 mL), brine (150 mL), dried over anhydrous Na$_2$SO$_4$, filtered and the solvent was removed in vacuo. The crude product was triturated with TBME (250 mL), then filtered, the solid was washed with TEAB. The crude product was purified by Prep-HPLC: column: YMC-Triart Prep C18 250*50 mm*10 um; mobile phase: [TEAB(10 mM)-ACN]; B %: 25%-48%, 22 min. Compound 8.2.8 [(m-H$^+$)/z=1444.5, 3.3 g, 2.21 mmol, 51.74% yield, 97% purity] was obtained as a yellow solid.

Synthesis of Compound 8.2.10

Compound 2.18 (3.3 g, 2.28 mmol, 1 eq) was azeotropic with ACN (20 mL×2), Compound 8.2.9 (3.29 g, 3.42 mmol, 1.5 eq) was co-evaporated with ACN (20 mL×2). To a solution of Compound 8.2.8 (3.3 g, 2.28 mmol, 1 eq) in ACN (20 mL) was added Molecular Sieve 3A (1.6 g, 2.28 mmol, 1 eq) at 25° C. The mixture was stirred at 25° C. for 0.5 h. Then Compound 8.2.9 (3.29 g, 3.42 mmol, 1.5 eq) and DBU (1.74 g, 11.41 mmol, 1.72 mL, 5 eq) was added at 25° C. The mixture was stirred at 25° C. for 0.5 h. LCMS indicated Compound 8.2.8 was consumed completely. The mixture was diluted with DCM (50 mL), 20% citric acid (50 mL). The organic phase was washed with TEAB (50 mL), dried over anhydrous Na$_2$SO$_4$, filtered and the solvent was removed in vacuo. The crude product was purified by Prep-HPLC: column: Agela DuraShell C18 250*50 mm*10 um; mobile phase: [TEAB(10 mM)-ACN]; B %: 15%-45%, 22 min. Compound 8.2.10 [(m-2H$^+$)/z=967.1, 3.1 g, 1.54 mmol, 67.38% yield, 96% purity) was obtained as a white solid.

Synthesis of Compound 8.2.12

Figure 31:
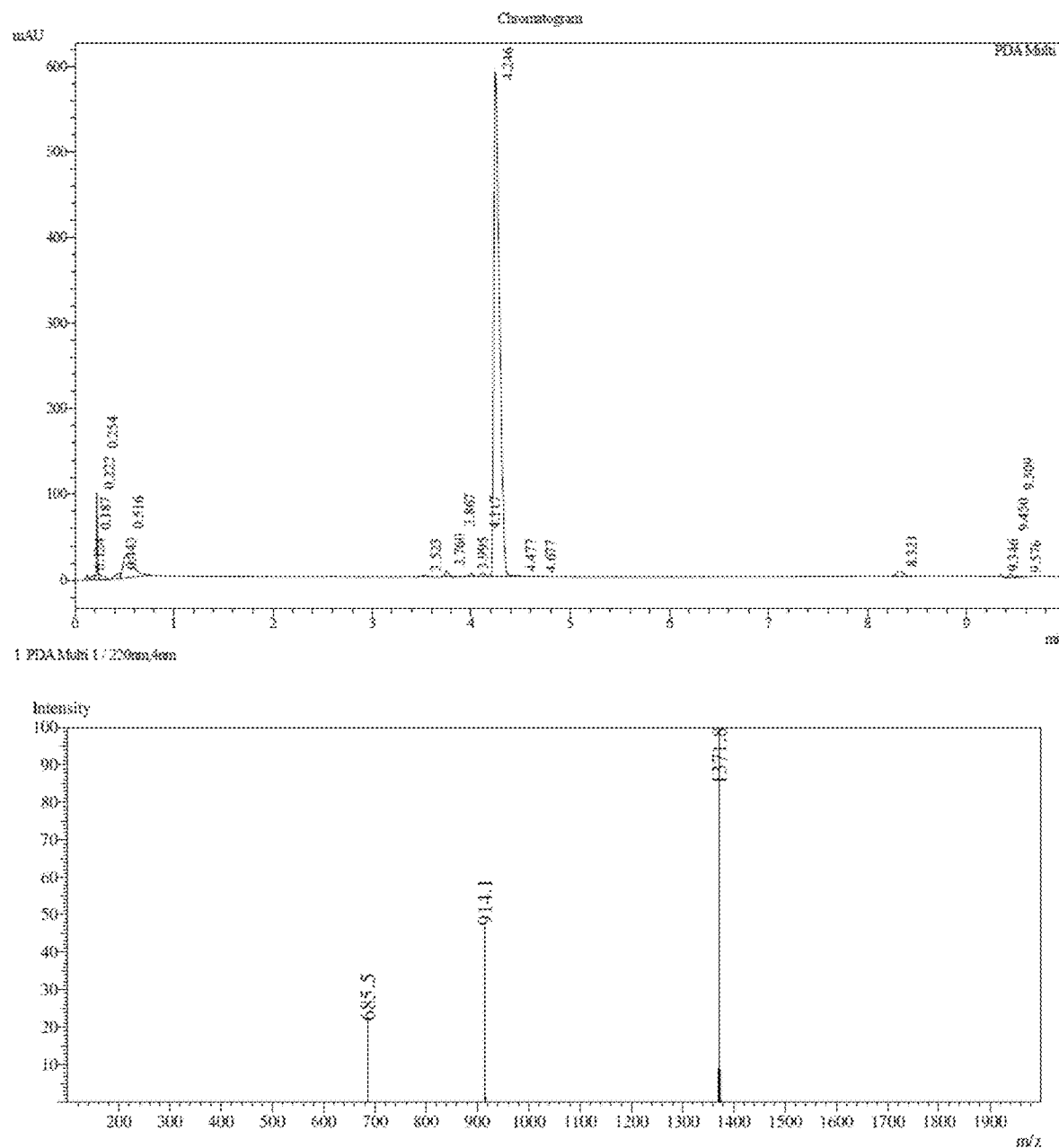
FIG. 31 shows HPLC and MS of compound 8.2.12.

Compound 8.2.10 (2.1 g, 1.08 mmol, 1 eq) was azeotropic with ACN (20 mL×2), Compound 8.2.11 (2.12 g, 2.17 mmol, 2 eq) was co-evaporated with ACN (20 mL×2). To a solution of Compound 8.2.10 (2.1 g, 1.08 mmol, 1 eq) in ACN (14 mL) was added Molecular sieve 3 Å (1.2 g, 1.08 mmol, 1.00 eq) at 25° C. The mixture was stirred at 25° C. for 0.5 h. Then Compound 8.2.11 (2.12 g, 2.17 mmol, 2 eq) and DBU (495.42 mg, 3.25 mmol, 490.51 uL, 3 eq) was added at 25° C. The mixture was stirred at 25° C. for 0.5 h. LCMS indicated Compound 8.2.10 was consumed completely. The mixture was filtered the 3A MS, the filter cake was washed with ACN (5 mL). The crude product was purified by Prep-HPLC (column: YMC-Triart Prep C18 250*50 mm*10 um; mobile phase: [TEAB(10 mM)-ACN]; B %: 18%-50%, 22 min. Compound 8.2.12 [(m-2H$^+$)/z=1371.8, 1.92 g, 678.28 umol, 62.53% yield, 97% purity] was obtained as a white solid, and characterized by HPLC and LCMS (see FIG. 31).

Synthesis of Compound 8B

Figure 32:
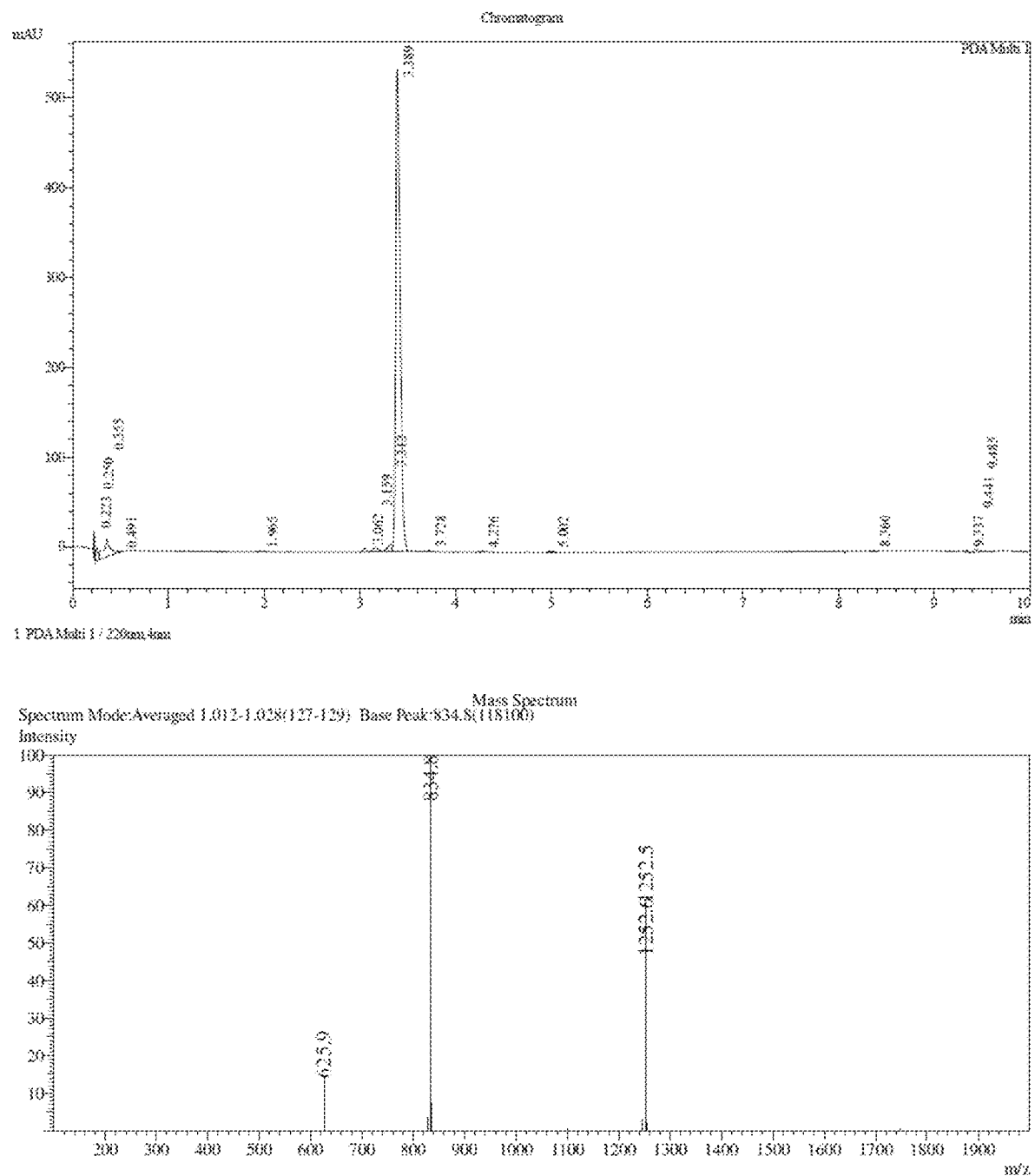
FIG. 32 shows HPLC and MS of compound 8B.

To a solution of Compound 8.2.12 (0.18 g, 65.56 umol, 1 eq) in THF (2 mL) was added TBAF (1 M, 196.67 uL, 3 eq) at 25° C. The mixture was stirred at 25° C. for 24 h. LCMS indicated Compound 8.2.12 was consumed completely. The mixture was washed with TEAB (10 mL), diluted with DCM (10 mL), dried over anhydrous Na$_2$SO$_4$, then filtered and concentrated. The crude product was purified by Prep-HPLC (column: YMC-Actus Triart C18 150*30 mm*5 um; mobile phase: [TEAB(10 mM)-ACN]; B %: 30%-60%, 12 min). Compound 8B [(m-3H$^+$)/z=834.8, 0.124 g, 47.48 umol, 72.42% yield, 96% purity) was obtained as a white solid, and characterized by HPLC and LCMS (see FIG. 32). 1.2.1 Coupling conditions for MOE Fragment Based on the IPC after coupling reaction, the conversion of coupling steps went completion. The summarized coupling step conditions at different stages and the HPLC purities were listed as follows:

| Coupling Stage | Equivalent of PSI-amidite | Equivalent of DBU | Reaction time (h) | Reaction Temp (° C.) | Yield (%) | Purity (%) |
|---|---|---|---|---|---|---|
| Dimer | 1.1 | 3.0 | 0.5 | 25 | 70.57 | 97 |
| Trimer | 1.5 | 3.0 | 0.5 | 25 | 51.74 | 97 |
| Tetramer | 1.5 | 5.0 | 0.5 | 25 | 67.38 | 96 |
| Pentamer | 2.0 | 3.0 | 0.5 | 25 | 62.53 | 97 |

In conclusion, a pentamer oligonucleotide was synthesized using liquid phase linear elongation of 2'-MOE amidite with PSI-reagent. Detritylation with DCA caused a de-prunination of adenosine. De-tritylation of trimer was achieved by acidic work-up step using 20% citric acid. Similar to the elongation of deoxy oligonucleotide, coupling efficiency decreases as the oligonucleotide grows longer. Additional equivalent of PSI-amidite and DBU are necessary at later stage of the coupling.

1.3 Convergent synthesis of fragments.

Figure 49:
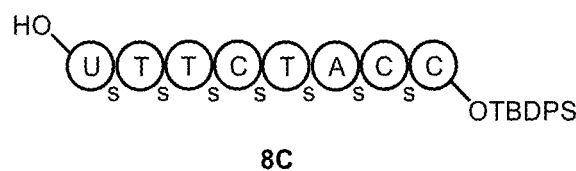
FIG. 49 shows oligonucleotide fragment 8C.
Figure 50:
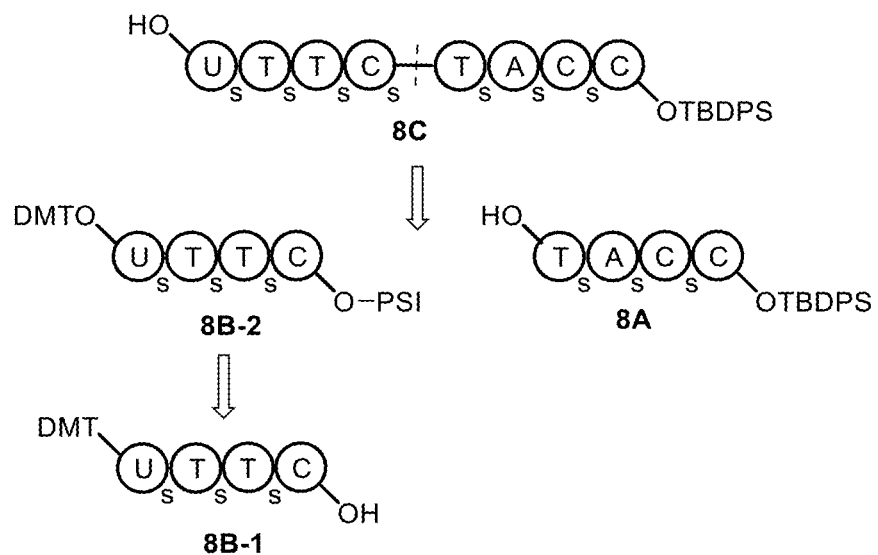
FIG. 50 shows a retrosynthetic scheme for the preparation of oligonucleotide fragment 8C.

Fragment 8C (FIG. 49) was synthesized by combining fragments 8A and 8B-2 (FIG. 50). The fragment 8B-2 was synthesized from 8B-1 and synthesis of the fragment 8A was described above.

Synthesis of UdTdTdC Fragment 8B-2

The formation of UdTdTdC fragment was provided by the cleavage of cyanoethyl group with the treatment of amine of the tetramer fragment obtained from the amidite chemistry during ASO 9 synthesis, and then coupled with PSI reagent (10 eq) in ACN at 0° C. The product 8B-2 is extremely sensitive to water. If the work up was exposed under air, the product will be hydrolyzed by moisture.

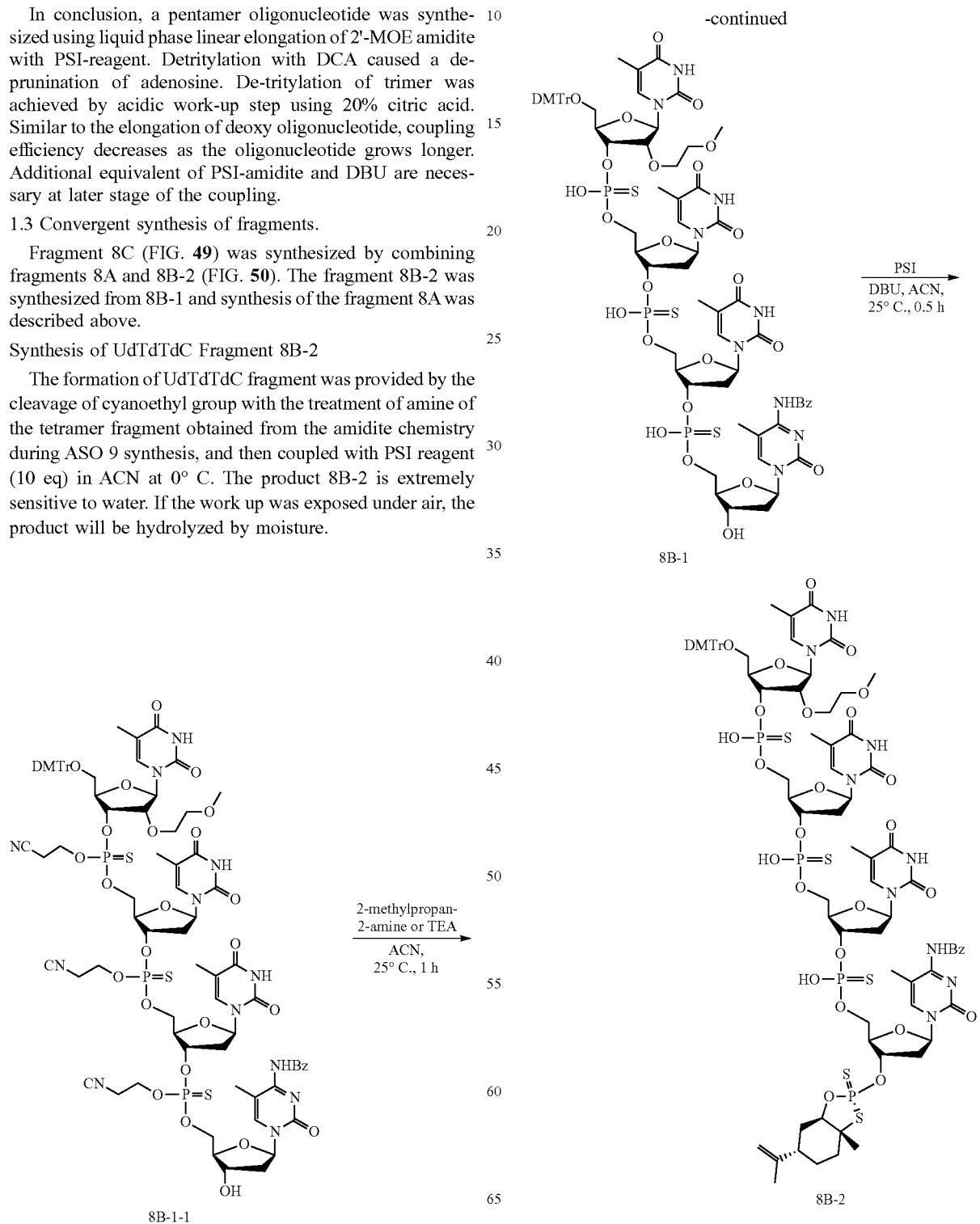

Two types of amine for the cleavage of cyanoethyl group were screened, 2-methylpropan-2-amine and TEA. The results are listed in the table below:

| Batch No. | Scale | Deprotection Condition | Result before work-up | Result After work-up |
|---|---|---|---|---|
| 1 | 3.3 g | 2-methyl-propan-2-amine | Product: hydrolysed = 14:1 | Product: hydrolysed = 1.1:1 |
| 2 | 200 mg | TEA | No hydrolyzed product | Product: hydrolysed = 2:1 |
| 3 | 500 mg | TEA | No hydrolyzed product | Product: hydrolyzed = 4.8:1 |
| 4 | 550 mg | TEA | No hydrolyzed product | Product: hydrolyzed = 5.4:1 |

Convergent synthesis of ASO 8C

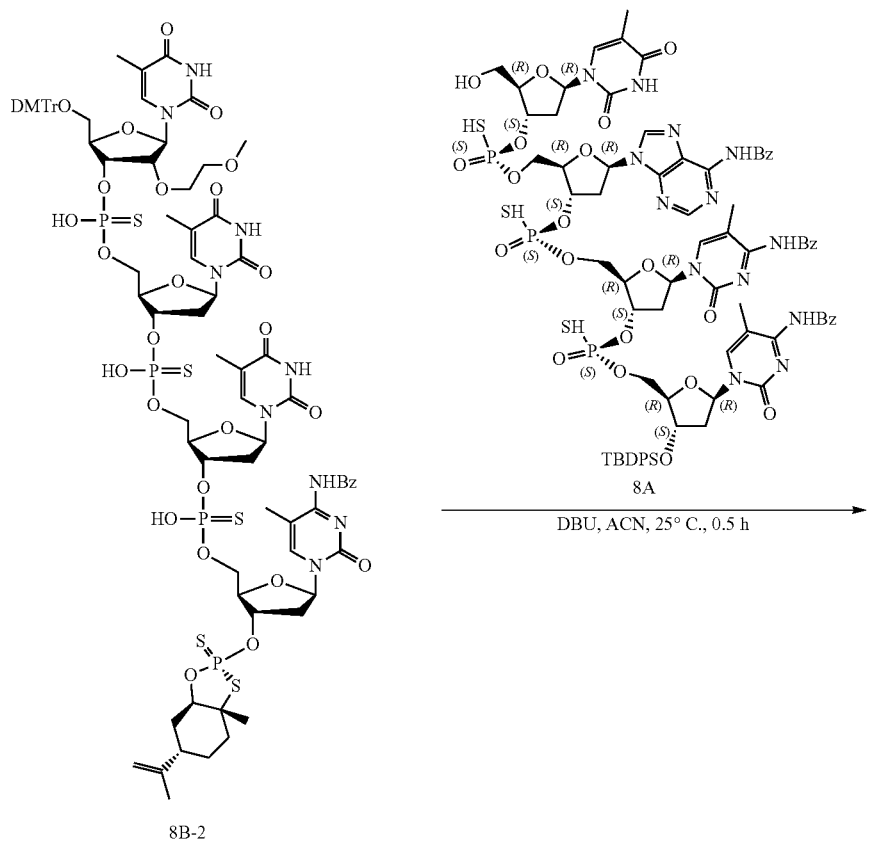

-continued

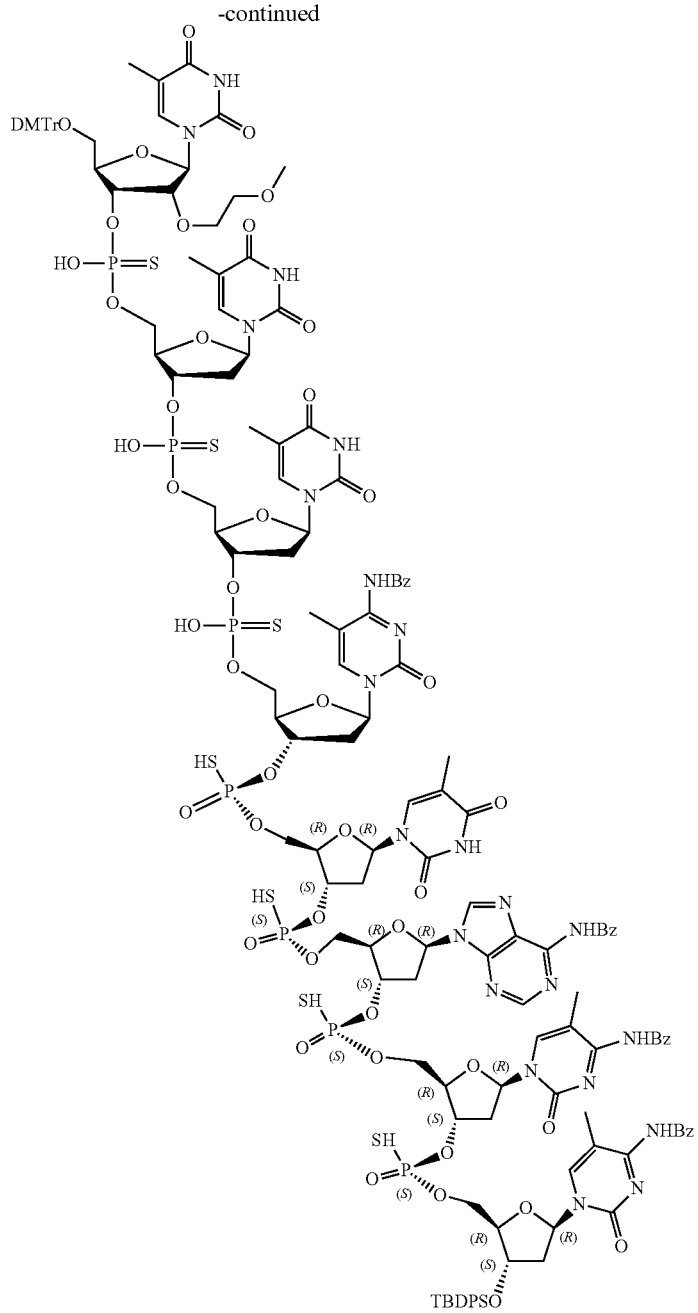

8C

Figure 33:
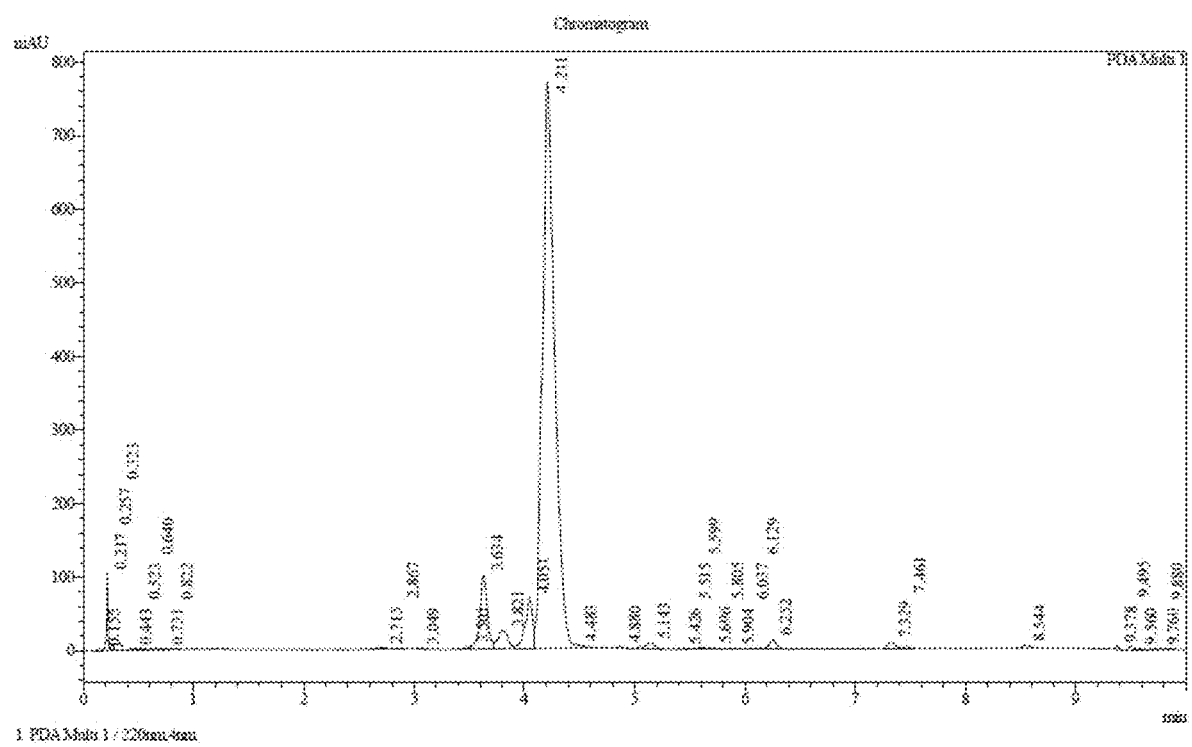
FIG. 33 shows HPLC and MS of compound 8C.
Figure 33:
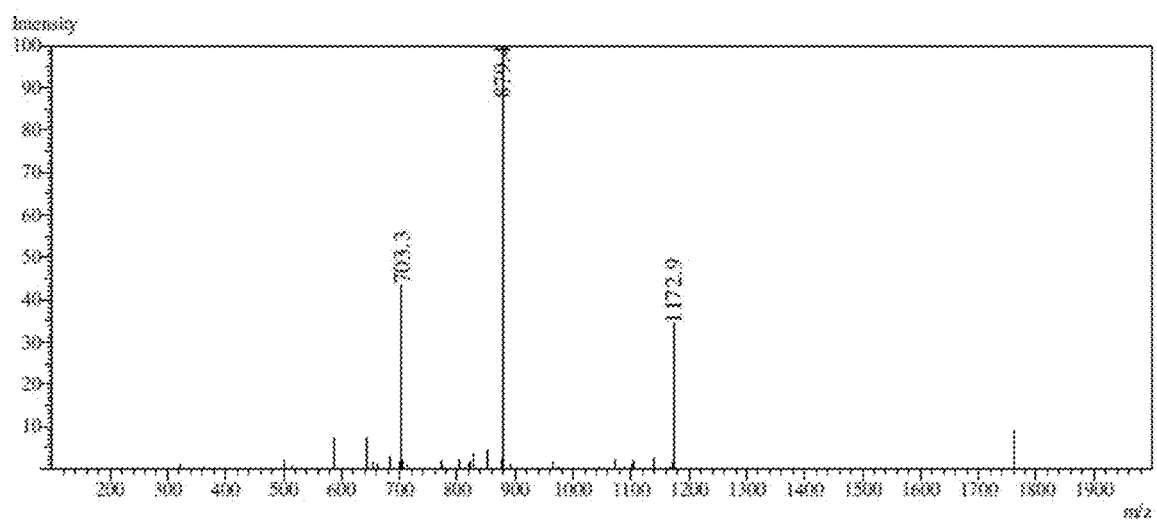

Compound 8A (0.05 g, 28.40 umol, 1 eq) was azeotropic with ACN (2 mL*2). Compound 8B-2 (164.32 mg, 85.19 umol, 3 eq) was azeotropic with ACN (2 mL*2). To compound 8B-2 in ACN (0.1 mL) was added molecular sieve 3 Å (0.015 g, 1.00 eq) at 25° C. The mixture was stirred at 25° C. for 0.5 h. Pre-mix the Compound 8A (0.05 g, 28.40 umol, 1 eq) with DBU (30.26 mg, 198.78 μmol, 29.96 μL, 7 eq) in ACN (0.2 mL) to make a mixture, then adding the above mixture dropwise to Compound 8B-2 (164.32 mg, 85.19 umol, 3 eq) in ACN (0.1 mL) at 25° C. under Ar. The mixture was stirred at 25° C. for 0.5 h. LCMS and HPLC showed the starting material was consumed for more than 90%. The reaction mixture was filtered. The mixture was purified by prep-HPLC (neutral condition, column: Phenomenex Gemini-NX 80*30 mm*3 um; mobile phase: [water (10 mM $NH_4HCO_3$)-ACN]; B %: 25%-55%, 7 min. Compound 8C [(m−4H$^+$)/z=879.4, 40.0 mg, 9.77 umol, 34.4% yield, 86% purity] was obtained as a white solid, and characterized by HPLC and LCMS (see FIG. 33).

In conclusion, PSI chemistry was successfully applied in the liquid phase synthesis of a deoxy tetramer and 2'-MOE pentamer, as well as in the convergent liquid phase synthesis of stereocontrolled ASOs. The convergent coupling reaction is very sensitive to moisture. Pre-azeotrope of $H_2O$ with ACN is necessary to ensure a high conversion rate of the reaction. In addition, concentration of DBU is crucial to conversion yield with 0.64 M (10% by volume of DBU to ACN) as recommended for a high conversion.

Figure 51:
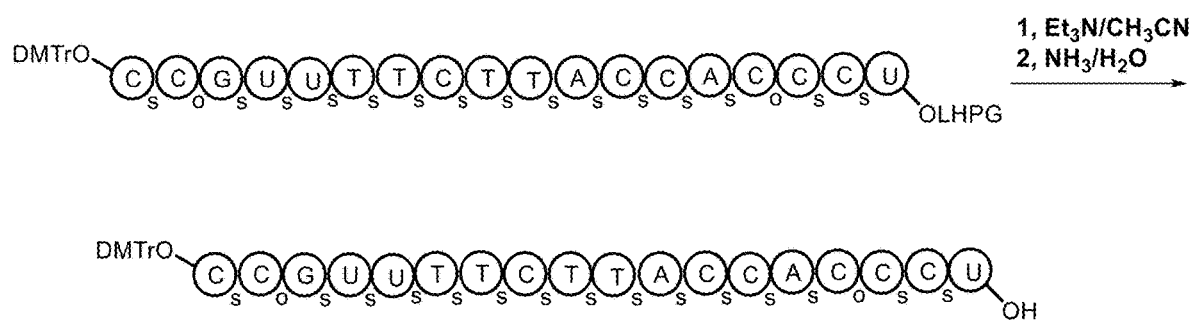
FIG. 51 shows a scheme for the deprotection of an ASO full length product.

Example 9. Deprotection of ASO Full Length Product (FIG. 51)

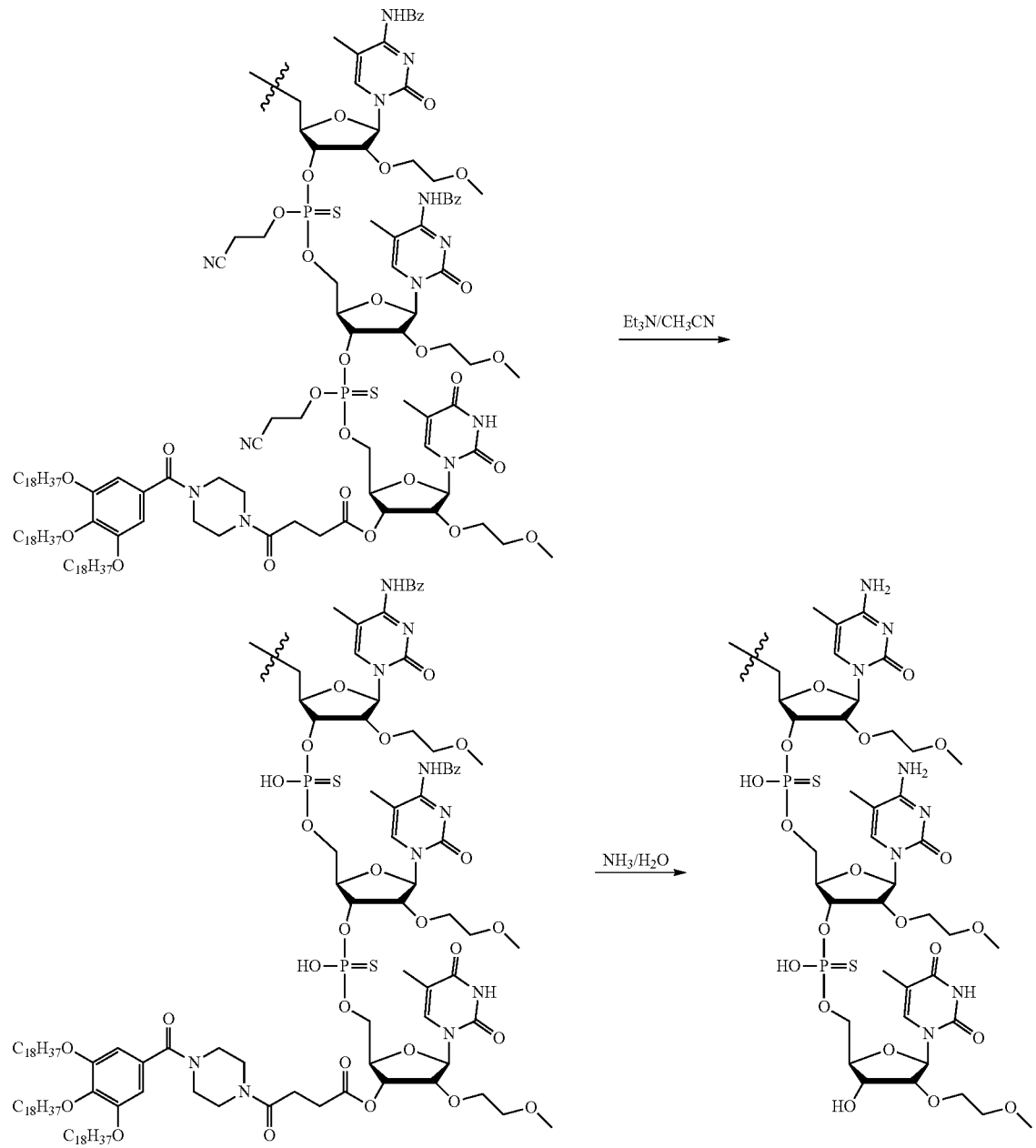

Firstly, the cyanoethyl group was de-protected by dissolving 64 gram protected ASO 9 in 640 ml of $CH_3CN:Et_3N=1:1$ solution. The solvents were removed by Rotovap after the mixture were stirred at 25° C. for two hours. The crude was taken to the next step for deprotecting LHPG and amine protecting groups. To the crude mixture was added 500 ml concentrate $NH_3/H_2O$ and the reaction mixture was stirred at 25° C. until the solid was totally dissolved (about 20-30 min). After the solid was dissolved in $NH_3/H_2O$, the mixture was transferred to a 1 L glass pressure flask and then heated at 65° C. for 5 hours. The reaction mixture was cooled down to room temperature and the deprotected ASO 9 was ready for downstream purification. All the protecting groups (except 5'-DMTr) on ASO 9 were deprotected in this operation. DMTr group was removed after downstream HIC purification.

The invention claimed is:

1. A liquid phase process for preparing a compound of formula (AI):

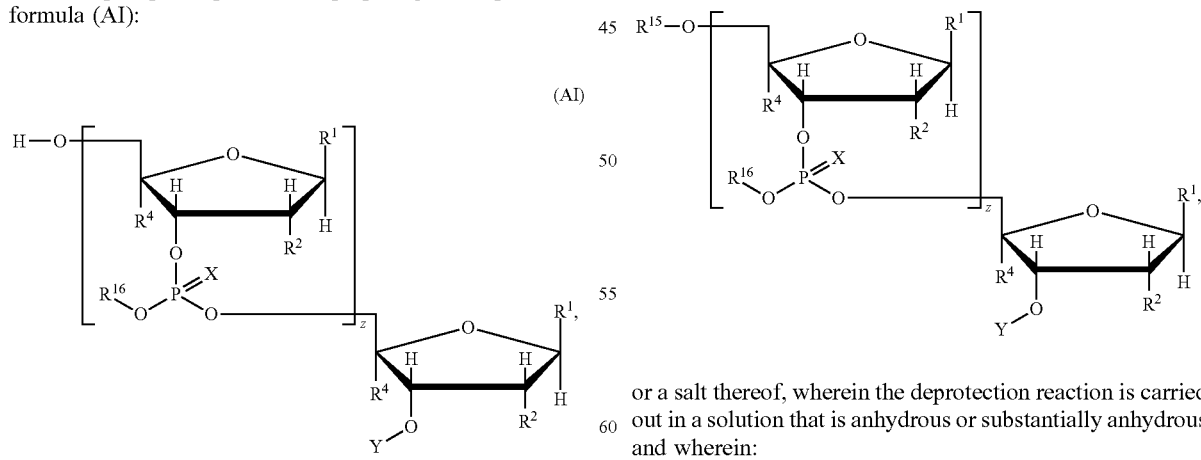

or a salt thereof, comprising deprotecting a compound of formula (AII):

or a salt thereof, wherein the deprotection reaction is carried out in a solution that is anhydrous or substantially anhydrous and wherein:

$R^1$, for each occurrence, is independently a nucleobase, wherein the $NH_2$ of the nucleobase, is protected by an amine protecting group;

$R^2$, for each occurrence, is independently selected from the group consisting of H, halo, and $C_{1-6}$alkoxy optionally substituted with $C_{1-6}$alkoxy;

R⁴, for each occurrence, is independently H or forms a ring with the alkoxy group of R²;

R¹⁵ is a hydroxyl protecting group;

R¹⁶, for each occurrence, is independently $C_{1-6}$alkyl group, $C_{2-6}$alkenyl group, phenyl or benzyl group, each of which is optionally substituted with —CN, —NO₂ or halogen; or R¹⁶ is

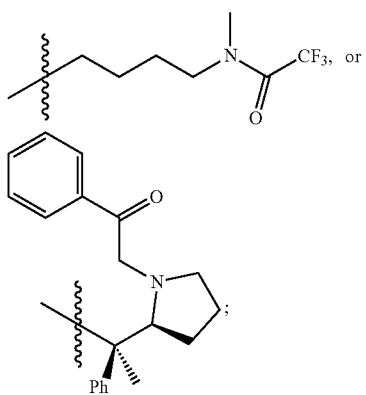

z is 0 or an integer from 1 to 200;

X, for each occurrence, is independently O or S; and

Y is a hydrophobic hydroxyl protecting group containing an alkyl chain.

2. The process of claim 1, wherein R¹⁵ is a 4,4'-dimethoxytrityl group.

3. The process of claim 1, wherein the deprotection reaction is carried out in the presence of a drying agent; optionally the drying agent is molecular sieves.

4. The process of claim 1, wherein the anhydrous or substantially anhydrous solution is obtained by removing water using azeotropic distillation prior to the deprotection reaction.

5. The process of claim 1, wherein the deprotection reaction is carried out in the presence of a cation scavenger comprising a-SH group, a silane group, a siloxane group, a polystyrene group, furan, pyrrole or indole; optionally the cation scavenger is a compound of formula RSH, wherein R is an alkyl, a cycloalkyl, a heterocycloalkyl, an aryl or a heteroaryl group, each of which is optionally substituted.

6. The process of claim 1, wherein the deprotection reaction is carried out by reacting the compound of formula (AII) with a detritylation reagent.

7. The process of claim 1, wherein Y is represented by the following formula:

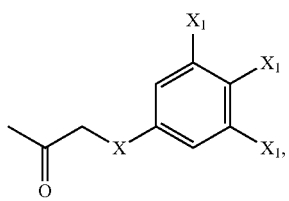

wherein X is $C_{1-10}$alkyl, wherein one or more CH₂ groups are independently replaced with C(O), C(O)NH2, cycloalkyl or $C_{1-6}$heterocylcyl group; and X₁ is $C_{1-25}$alkyl or $C_{1-25}$alkoxy; or wherein Y is represented by the following formula:

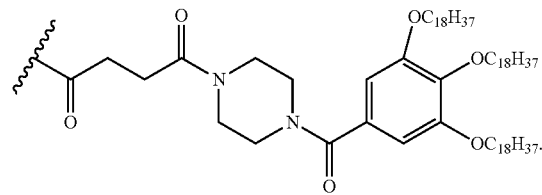

8. The process of claim 1, wherein:
each R₂ is independently H, F or $C_{1-4}$alkoxy optionally substituted with $C_{1-4}$alkoxy;
R⁴ is H; and
R¹⁶ is -CH₂CH₂CN.

9. The process of claim 1, wherein the compound of formula (AI) is not purified by chromatography; or wherein the compound of formula (AI) is purified by selective precipitation and/or extraction.

10. A liquid phase process for preparing a compound of formula (AI'):

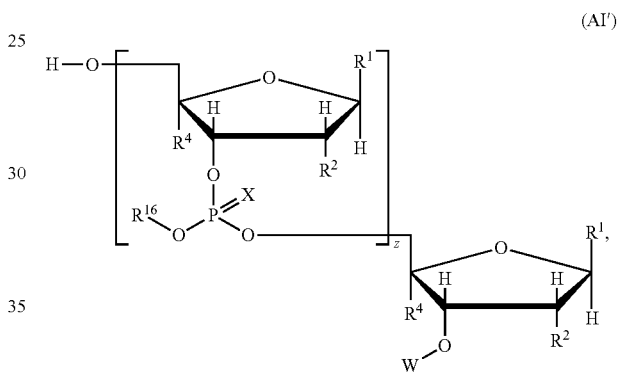

(AI')

or a salt thereof, comprising deprotecting a compound of formula (AII'):

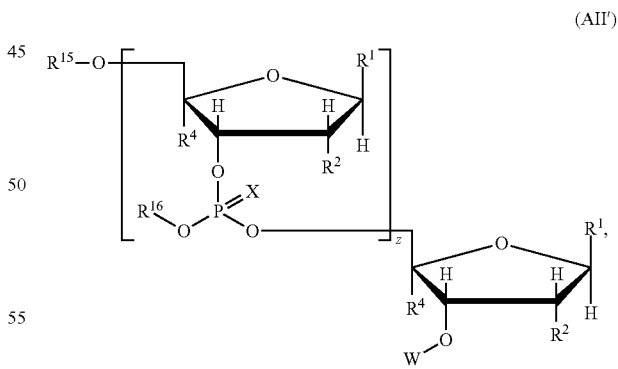

(AII')

or a salt thereof, wherein the deprotection reaction is carried out in a solution that is anhydrous or substantially anhydrous and wherein:

R¹, for each occurrence, is independently a nucleobase, wherein the NH₂ of the nucleobase, is protected by an amine protecting group;

R², for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

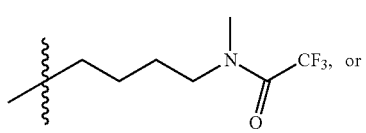

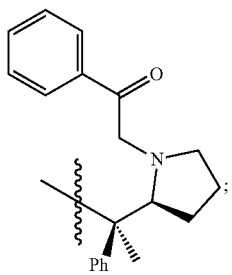

z is 0 or an integer from 1 to 200;

X, for each occurrence, is independently O or S;

W is H or Z; and

Z is a silyl hydroxyl protecting group.

11. A liquid process for preparing a compound of formula (BI):

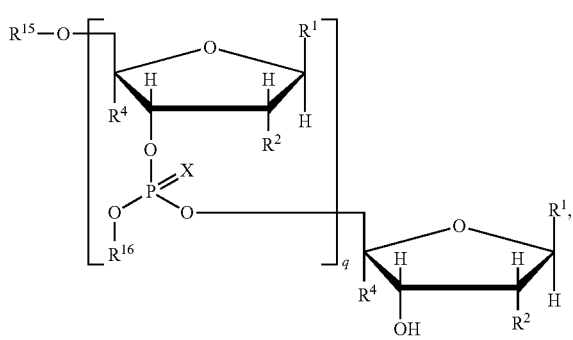

or a salt thereof, comprising deprotecting a compound of formula (BII):

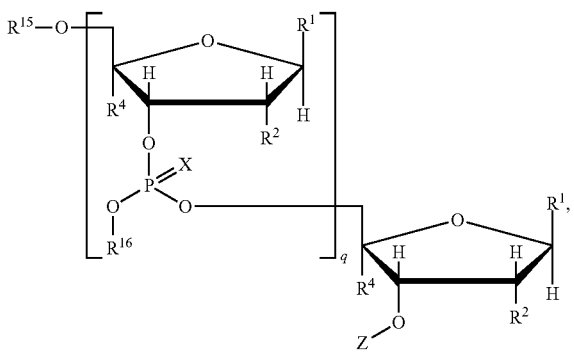

or a salt thereof, to form the compound of formula (BI), or a salt thereof, wherein:

$R^1$, for each occurrence, is independently a nucleobase, wherein the $NH_2$ of the nucleobase, is protected by an amine protecting group;

$R^2$, for each occurrence, is independently selected from the group consisting of H, halo, and $C_{1-6}$alkoxy optionally substituted with $C_{1-6}$alkoxy;

$R^4$, for each occurrence, is independently H or forms a ring with the alkoxy group of $R^2$;

$R^{15}$ is a hydroxyl protecting group;

$R^{16}$, for each occurrence, is independently $C_{1-6}$alkyl group, $C_{2-6}$alkenyl group, phenyl or benzyl group, each of which is optionally substituted with —CN, —$NO_2$ or halogen; or $R^{16}$ is

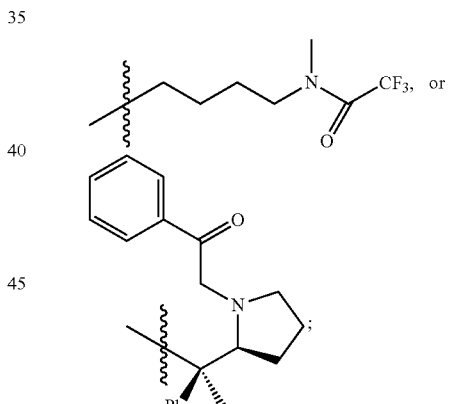

q is an integer from 1 to 200;

X, for each occurrence, is independently O or S; and

Z is a silyl hydroxyl protecting group.

12. The process of claim 3, wherein the size of molecular sieves is 3 Å.

13. The process of claim 5, wherein RSH is $CH_3(CH_2)_5SH$, $CH_3(CH_2)_{11}SH$, cyclohexanethiol, or $CH_3CH_2OC(=O)CH_2CH_2SH$.

14. The process of claim 6, wherein the detritylation reagent is a strong organic acid.

15. The process of claim 14, wherein the detritylation reagent is $CF_3COOH$, $CCl_3COOH$, $CHCl_2COOH$, $CH_2ClCOOH$, $H_3PO_4$, methanesulfonic acid, benzenesulfonic acid, $CClF_2COOH$, $CHF_2COOH$, or $PhSO_2H$.

16. The process of claim 14, wherein the detritylation reagent is $CH_2ClCOOH$.

17. The process of claim 14, wherein the detritylation reagent is $CF_3COOH$ or $CHCl_2COOH$.

\* \* \* \* \*

UNITED STATES PATENT AND TRADEMARK OFFICE
CERTIFICATE OF CORRECTION

PATENT NO. : 12,378,276 B2
APPLICATION NO. : 17/608802
DATED : August 5, 2025
INVENTOR(S) : Xianglin Shi et al.

Page 1 of 1

It is certified that error appears in the above-identified patent and that said Letters Patent is hereby corrected as shown below:

In the Claims

Column 332, Claim 1, Line 63, please replace "$NH_2$ of the nucleobase, is protected by" with -- $NH_2$ of the nucleobase is protected by --.

Column 334, Claim 10, Line 63, please replace "$NH_2$ of the nucleobase, is protected by" with -- $NH_2$ of the nucleobase is protected by --.

Column 336, Claim 11, Line 21, please replace "$NH_2$ of the nucleobase, is protected by" with -- $NH_2$ of the nucleobase, if present, is protected by --.

Signed and Sealed this
Eleventh Day of November, 2025

John A. Squires
*Director of the United States Patent and Trademark Office*